United States Patent
Gentles et al.

(10) Patent No.: US 11,964,973 B2
(45) Date of Patent: Apr. 23, 2024

(54) SUBSTITUTED BICYCLIC COMPOUNDS USEFUL AS T CELL ACTIVATORS

(71) Applicant: BRISTOL-MYERS SQUIBB COMPANY, Princeton, NJ (US)

(72) Inventors: Robert G. Gentles, Killingworth, CT (US); Upender Velaparthi, Princeton, NJ (US); Min Ding, Stow, MA (US); Richard E. Olson, Cambridge, MA (US); Scott W. Martin, Middletown, CT (US); Saumya Roy, Bangalore (IN); Prasada Rao Jalagam, Bangalore (IN); Jayakumar Sankara Warrier, Bangalore (IN); Louis S. Chupak, Old Saybrook, CT (US); Denise Christine Grunenfelder, Boston, MA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 97 days.

(21) Appl. No.: 17/130,022

(22) Filed: Dec. 22, 2020

(65) Prior Publication Data
US 2021/0188845 A1  Jun. 24, 2021

(30) Foreign Application Priority Data
Dec. 23, 2019  (IN) .............................. 201911053552

(51) Int. Cl.
C07D 471/04 (2006.01)
C07D 401/04 (2006.01)

(52) U.S. Cl.
CPC ......... *C07D 471/04* (2013.01); *C07D 401/04* (2013.01)

(58) Field of Classification Search
None
See application file for complete search history.

(56) References Cited

U.S. PATENT DOCUMENTS

| | | | |
|---|---|---|---|
| 4,324,893 A | 4/1982 | Scotese et al. |
| 6,943,169 B2 | 9/2005 | Repke et al. |
| 7,084,141 B2 | 8/2006 | Gaeta et al. |
| 7,173,036 B2 | 2/2007 | Sircar et al. |
| 7,220,856 B2 | 5/2007 | Dunning et al. |
| 7,279,481 B2 | 10/2007 | Falchi et al. |
| 7,381,401 B2 | 6/2008 | Gajewski |
| 9,050,334 B2 | 6/2015 | Gaweco et al. |
| 9,133,164 B2 | 9/2015 | Gaweco et al. |
| 10,532,042 B2 | 1/2020 | Lanman et al. |
| 10,669,272 B2 | 6/2020 | Velaparthi et al. |
| 2005/0124604 A1 | 6/2005 | Sircar et al. |
| 2005/0266510 A1 | 12/2005 | Gajewski |
| 2008/0139551 A1 | 6/2008 | Sircar et al. |
| 2010/0087649 A1 | 4/2010 | Kesteleyn et al. |
| 2011/0281908 A1 | 11/2011 | Sun et al. |
| 2015/0224142 A1 | 8/2015 | Albelda et al. |
| 2018/0334454 A1 | 11/2018 | Lanman et al. |
| 2020/0115384 A1 | 4/2020 | Wu et al. |
| 2021/0061802 A1 | 3/2021 | Velaparthi et al. |

FOREIGN PATENT DOCUMENTS

| | | |
|---|---|---|
| WO | 2004056824 A2 | 7/2004 |
| WO | 2004074218 A2 | 9/2004 |
| WO | 2004087880 A2 | 10/2004 |
| WO | 2005009967 A2 | 2/2005 |
| WO | 2005021546 A1 | 3/2005 |
| WO | 2007109251 A2 | 9/2007 |
| WO | 2007132948 A1 | 11/2007 |
| WO | 2007136125 A1 | 11/2007 |
| WO | 2010042489 A2 | 4/2010 |

(Continued)

OTHER PUBLICATIONS

Avila-Flores, A. et al., "Predominant Contribution of DGKζ over DGKα in the Control of PKC/PDK-1-Regulated Functions in T Cells", Immunology and Cell Biology (2017) 95: 549-563.

Barraza et al., "Discovery of Anthranilamides as a Novel Class of Inhyibitors of Neurotropic Alphavirus Replication", Bioorg. Med. Chem 23 (2015) 1569-1587.

Boroda et al., "Dual Activites of Ritanserin and R59022 as DGKα inhibitors and Serotonin Receptor Antagonists" Biochemical Pharmacology 123 (2017) 29-39.

Chen et al., "Diacylglycerol Kinases in T Cell Tolerance and Effector Function", Frontiers in Cell and Development Biology vol. 4 pp. 1-13, (2016).

(Continued)

*Primary Examiner* — Po-Chih Chen
(74) *Attorney, Agent, or Firm* — Gary Greenblatt

(57) ABSTRACT

Disclosed are compounds of Formula (I):

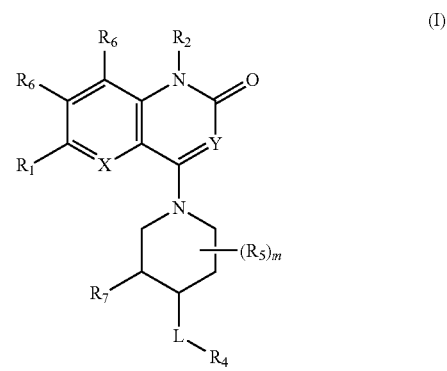

or a salt thereof, wherein: X is $CR_6$ or N; Y is $CR_3$ or N; $R_1$, $R_2$, $R_3$, $R_4$, $R_5$, $R_6$, $R_7$, and m are defined herein. Also disclosed are methods of using such compounds to inhibit the activity of one or both of diacylglycerol kinase alpha (DGKα) and diacylglycerol kinase zeta (DGKζ), and pharmaceutical compositions comprising such compounds. These compounds are useful in the treatment of viral infections and proliferative disorders, such as cancer.

11 Claims, 4 Drawing Sheets

Specification includes a Sequence Listing.

(56) References Cited

FOREIGN PATENT DOCUMENTS

| WO | 2010088408 A2 | 8/2010 |
|---|---|---|
| WO | 2012009649 A1 | 1/2012 |
| WO | 2012142498 A2 | 10/2012 |
| WO | 2013118071 A1 | 8/2013 |
| WO | 2016164675 A1 | 10/2016 |
| WO | 2017106607 A1 | 6/2017 |
| WO | 2017177037 A1 | 10/2017 |
| WO | 2018119183 A2 | 6/2018 |
| WO | 2018134685 A2 | 7/2018 |
| WO | 2019005883 A1 | 1/2019 |
| WO | 2020006016 A1 | 1/2020 |
| WO | 21105115 A1 | 6/2021 |
| WO | 21105116 A1 | 6/2021 |
| WO | 21105117 A1 | 6/2021 |

OTHER PUBLICATIONS

Dagia et al., "A fluorinated Analog of ISO-1 blocks the Recognition and Biological Function of MIF and is Orally Efficacious in a Murine Model of Colitis" Eur. J. Pharmacology 607 (2009) 201-212.

Database Registry Chemical Abstracts Service: Database RN 2249638-34-2 (Entered STN Nov. 19, 2018).

Facciabene, et al. "T-Regulartory Cells: Key Players in Tumor Immune Escape and Angiogenesis" Cancer Res. 72(9) 2162-2171 (2012).

Franks et al., "The Ligand Binding Landscape of Diacylglycerol Kinases" Cell Chem Bio 24, 870-880 (2017).

Ganesan et al., "Comprehensive in vitro Characterization of PD-L1 Small Molecule Inhibitors", Scientific Reports 9, Article No. 12392 (2019).

International Search Report for PCT/US2020/066507—dated Mar. 11, 2021.

Jing et al., "T Cells Deficient In Diacylglycerol Kinase ζ are Resistance to PD-1 Inhibition and Help Create Persistent Host Immunity to Leukemia" Cancer Res 77(20) 5676-5686 (2017).

Krishna et al., "Regulation of Lipid Signaling by Diacylglycerol Kinases During T Cell Development and Function" Front Immunolog. (2013) 4: Article 178.

Liu et al., "A Novel Diacylglycerol Kinase a-Selective Inhibitor CU-3, Induces Cancer Cell Apoptosis and Enhances Immune Response" J. Lipid Res. 57, 368-379 (2016).

McCloud et al., "Deconstructing Lipid Kinase Inhibitors By Chemical Proteomics" Biochem. 2018, 57, 231-236.

McLean et al., "Fragment Screening of Inhibitors for MIF Tautomerase Reveals a Cryptic Surface Binding Site" Bio. Med. Chem. Lett. 20 (2010) 1821-1824.

Mellman et al. "Cancer Immunotherapy Comes of Age" Nature 480 480-489 (2011).

Merida et al., "Redundant and Specialized Roles for Diacylglycerol Kinases α and ζ in the Control of T cell Functions" Science Signaling 8 (374), re6 (2015).

Merida I., Arranz-Nicolás J., et al., "Diacylglycerol Kinase Malfunction in Human Disease and the Search for Specific Inhibitors", Handbook of Experimental Pharmacology. Springer, Berlin, Heidelberg (2019). First Online: Jun. 22, 2019.

Mizoguchi et al., "Alterations in Signal Transduction Molecules in T Lumphocytes from Tumor-Bearing Mice" (1992) Science 258:1795-98.

Noessner, "DGK-α: A Checkpoint in Cancer-Mediated Immuno-Inhibition and Target for Immunotherapy" Front Cell Dev Bio 2017 5, Article 16.

Olenchock et al., "Disruption of the Diacylglycerol Metabolism Impairs the Induction of T cell Anergy", Nature Immunology 7(11) 1174-1181 (2006).

Prinz et al., "High DGK-α and Disabled MAPK Pathways Cause Dysfunction of Human Tumor-Infiltrating CD8+ T Cells that Is Reversible by Pharmacologic Intervention", J Immunology 188(12) 5990-6000 (2012).

Purow, B. "Molecular Pathways: Targeting Diacylglycerol Kinase Aplha in Cancer" Clin. Cancer Res. 21(22) 5008-5012 (2015).

Riese et al., "Decreased Diacylglycerol Metabolism Enhances ERK Activation and Augments DC8+ T Cell Functional Responses", J Bio Chem 286(7) 5254-5265 (2011).

Riese et al., "Diacylglycerol Kinases (DGKs): Novel Targets for Improving T Cell Activity in Cancer" Frontiers Cell Dev Bio (2016) 4, Article 108.

Santilli et al., "2-Oxo-1,8-naphthyridine-3-carboxylic Acid Derivaties with Potent Gastric Antisecretory Properties" J. Med. Chem. 1987, 30, 2270-2277.

Sjoblom et al. "The Consensus Coding Sequences of Human Breast and Colorectal Cancers" Science 314 268-274 (2006).

Topalian et al., "Targetomg the PD-1/B7-H1(PD-L1) Pathway to Activate Anti-tumor Immunity", Curr. Opin. Immunol. 2012, 24:207-212.

Velnati et al., "Identification of a Novel DGKα Inhibitor for XLP-1 Therapy by Virtual Screening", Eur J Med Chem 164 (2019) 378-390.

Wesley et al., "Diacylglycerol Kinase ζ (DGKζ) and Casitas b-Lineage Proto-Oncogene b-Deficient Mice Have Similar Functional Outcomes in T Cells but DGK ζ-Deficient Mice have Increased T Cell Activatin and Tumor Clearance" ImmunoHorizons 2018 2 94) 107-118.

Zha Y et al., "T Cell Anergy is Reversed by Active Ras and is Regulated by Diacylglycerol Kinase-α" Nature Immunology, (2006) 7(11) 1166-1173; Erratum 7(12) 1343.

STN: RN 2190960-90-6, Registry, Mar. 14, 2018.

STN: RN 2320855-98-7, Registry, May 30, 2019.

Method A:

Method B:

Method C:

Method D:

DADC = dialkyl diazodicarboxylate

Method A:

Method B:

Chiral HPLC Separation

SUBSTITUTED BICYCLIC COMPOUNDS USEFUL AS T CELL ACTIVATORS

CROSS REFERENCE

This application claims the benefit of Indian Provisional Application No. 201911053552 filed Dec. 23, 2019 which is incorporated herein in its entirety.

DESCRIPTION

The present invention generally relates to substituted bicyclic compounds that activate T cells, promote T cell proliferation, and/or exhibit antitumor activity. Provided herein are substituted bicyclic compounds, compositions comprising such compounds, and methods of their use. The invention further pertains to pharmaceutical compositions comprising at least one compound according to the invention that are useful for the treatment of proliferative disorders, such as cancer, and viral infections.

BACKGROUND OF THE INVENTION

Human cancers harbor numerous genetic and epigenetic alterations, generating neoantigens potentially recognizable by the immune system (Sjoblom et al. (2006) Science 314:268-74). The adaptive immune system, comprised of T and B lymphocytes, has powerful anti-cancer potential, with a broad capacity and exquisite specificity to respond to diverse tumor antigens. Further, the immune system demonstrates considerable plasticity and a memory component. The successful harnessing of all these attributes of the adaptive immune system would make immunotherapy unique among all cancer treatment modalities. However, although an endogenous immune response to cancer is observed in preclinical models and patients, this response is ineffective, and established cancers are viewed as "self" and tolerated by the immune system.

Contributing to this state of tolerance, tumors may exploit several distinct mechanisms to actively subvert anti-tumor immunity. These mechanisms include dysfunctional T-cell signaling (Mizoguchi et al., (1992) Science 258:1795-98), suppressive regulatory cells (Facciabene et al., (2012) Cancer Res. 72:2162-71), and the co-opting of endogenous "immune checkpoints", which serve to down-modulate the intensity of adaptive immune responses and protect normal tissues from collateral damage, by tumors to evade immune destruction (Topalian et al., (2012) Curr. Opin. Immunol. 24:1-6; Mellman et al. (2011) Nature 480:480-489).

Diacylglycerol kinases (DGKs) are lipid kinases that mediate the conversion of diacylglycerol to phosphatidic acid thereby terminating T cell functions propagated through the TCR signaling pathway. Thus, DGKs serve as intracellular checkpoints and inhibition of DGKs are expected to enhance T cell signaling pathways and T cell activation. Supporting evidence include knock-out mouse models of either DGKa or DGKζ which show a hyper-responsive T cell phenotype and improved anti-tumor immune activity (Riese M. J. et al., *Journal of Biological Chemistry*, (2011) 7: 5254-5265; Zha Y et al., *Nature Immunology*, (2006) 12:1343; Olenchock B. A. et al., (2006) 11: 1174-81). Furthermore tumor infiltrating lymphocytes isolated from human renal cell carcinoma patients were observed to over-express DGKα which resulted in inhibited T cell function (Prinz, P. U. et al., *J Immunology* (2012) 12:5990-6000). Thus, DGKα and DGKζ are viewed as targets for cancer immunotherapy (Riese M. J. et al., *Front Cell Dev Biol.* (2016) 4: 108; Chen, S. S. et al., *Front Cell Dev Biol.* (2016) 4: 130; Avila-Flores, A. et al., *Immunology and Cell Biology* (2017) 95: 549-563; Noessner, E., *Front Cell Dev Biol.* (2017) 5: 16; Krishna, S., et al., *Front Immunology* (2013) 4:178; Jing, W. et al., *Cancer Research* (2017) 77: 5676-5686.

There remains a need for compounds useful as inhibitors of one or both of DGKα and DGKζ. Additionally, there remains a need for compounds useful as inhibitors of one or both of DGKα and DGKζ that have selectivity over other diacylglycerol kinases, protein kinases, and/or other lipid kinases.

Accordingly, an agent that is safe and effective in restoring T cell activation, lowering antigen threshold, enhancing antitumor functionality, and/or overcoming the suppressive effects of one or more endogenous immune checkpoints, such as PD-1, LAG-3 and TGFβ, would be an important addition for the treatment of patients with proliferative disorders, such as cancer, as well as viral infections.

SUMMARY OF THE INVENTION

Applicants have found compounds that have activity as inhibitors of one or both of DGKα and DGKζ. Further, applicants have found compounds that have activity as inhibitors of one or both of DGKα and DGKζ and have selectivity over other diacylglycerol kinases, protein kinases, and/or other lipid kinases. These compounds are provided to be useful as pharmaceuticals with desirable stability, bioavailability, therapeutic index, and toxicity values that are important to their drugability.

The present invention provides substituted bicyclic compounds of Formula (I), which are useful as inhibitors of DGKα, DGKζ, or both DGKα and DGKζ, including salts and prodrugs thereof.

The present invention also provides pharmaceutical compositions comprising a compound of Formula (I) and/or a pharmaceutically acceptable salt thereof; and a pharmaceutically acceptable carrier.

The present invention also provides a method of treating a disease or disorder associated with the activity of DGKα, DGKζ, or both DGKα and DGKζ, the method comprising administering to a mammalian patient a compound of Formula (I) and/or a pharmaceutically acceptable salt thereof.

The present invention also provides processes and intermediates for making the compounds of Formula (I) and/or salts thereof.

The present invention also provides a compound of Formula (I) and/or a pharmaceutically acceptable salt thereof, for use in therapy.

The present invention also provides the use of the compounds of Formula (I) and/or pharmaceutically acceptable salts thereof, for the manufacture of a medicament for the treatment of proliferative disorders, such as cancer and viral infections.

The compounds of Formula (I) and compositions comprising the compounds of Formula (I) may be used in treating, preventing, or curing viral infections and various proliferative disorders, such as cancer. Pharmaceutical compositions comprising these compounds are useful in treating, preventing, or slowing the progression of diseases or disorders in a variety of therapeutic areas, such as viral infections and cancer.

These and other features of the invention will be set forth in expanded form as the disclosure continues.

BRIEF DESCRIPTION OF THE DRAWINGS

The invention is illustrated by reference to the accompanying drawings described below.

FIG. 3 shows a general synthesis schematic for the preparation of example compounds in Table 6.

DETAILED DESCRIPTION

Figure 1:
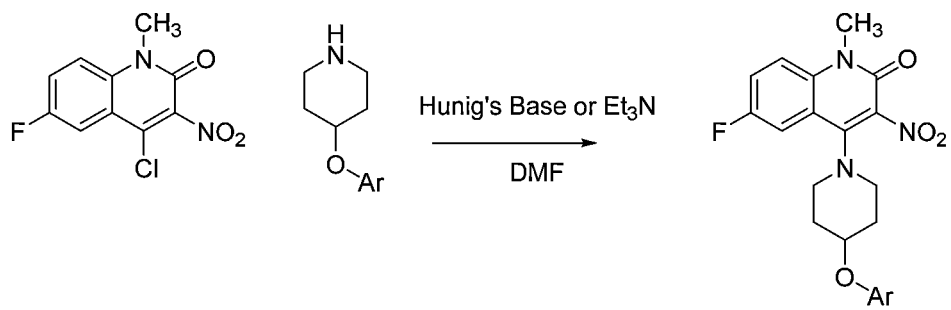
FIG. 1 shows general synthesis schematics for the preparation of example compounds in Table 2 according to Method A and Method B.
Figure 1:
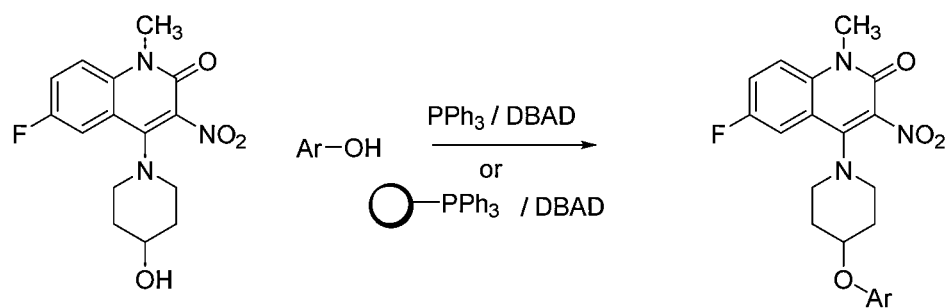
Figure 2:
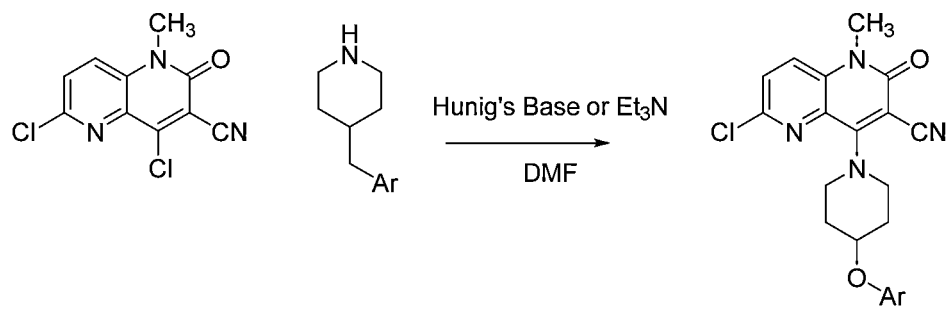
FIG. 2 shows general synthesis schematics for the preparation of example compounds in Table 3 according to Method C and Method D.
Figure 2:
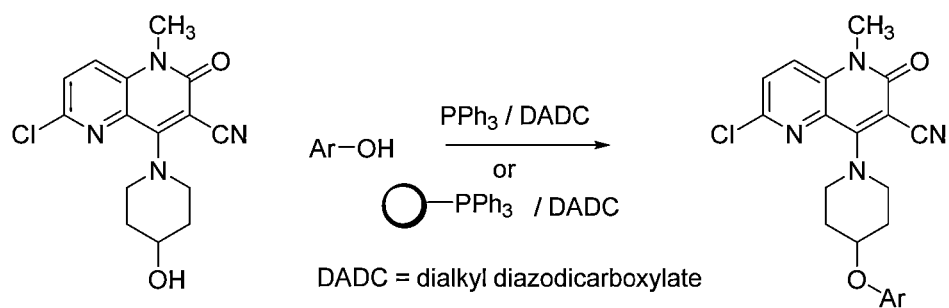
Figure 3:
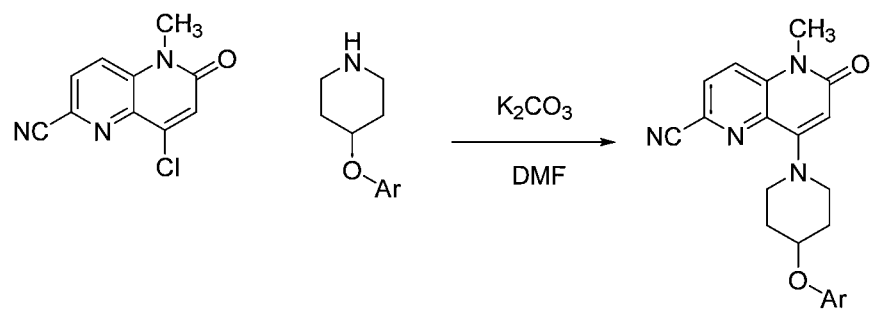
FIG. 3 shows general synthesis schematics for the preparation of example compounds in Table 4 according to Method A and Method B.
Figure 3:
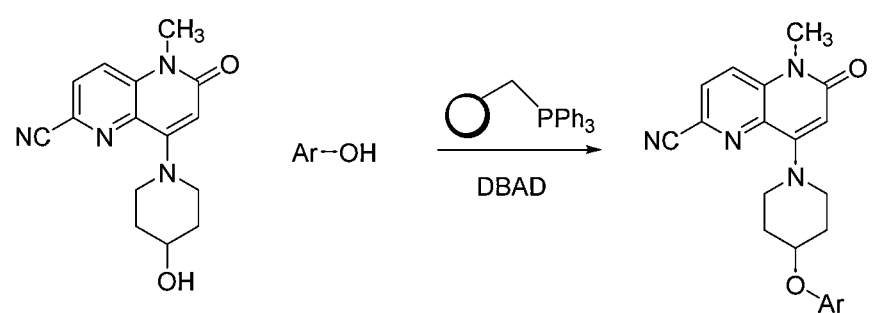
Figure 4:
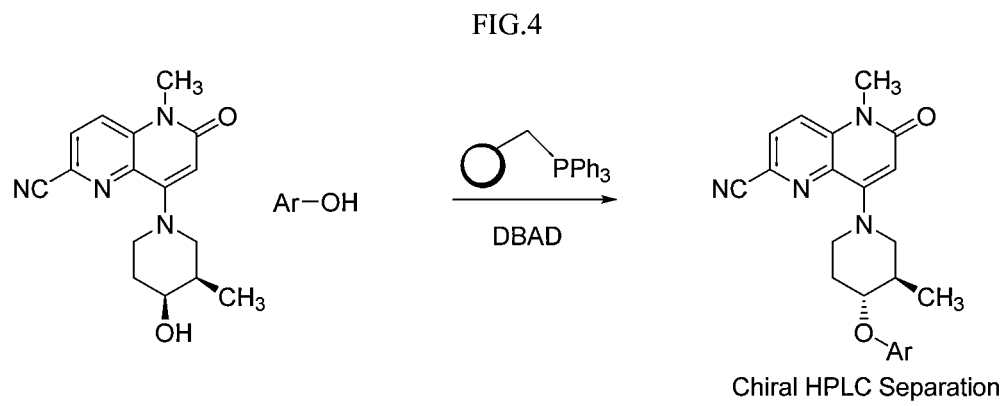

The first aspect of the present invention provides at least one compound of Formula (I):

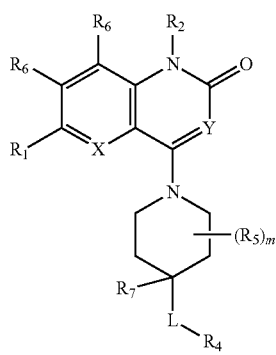

or a salt thereof, wherein:
X is $CR_6$ or N;
Y is $CR_3$ or N;
L is —O—, —S—, $S(O)_2$—, —$NR_{4c}$—, or —$NR_{4d}C(O)$—;
$R_1$ is H, F, Cl, Br, —CN, $C_{1-3}$ alkyl substituted with zero to 4 $R_{1a}$, $C_{3-4}$ cycloalkyl substituted with zero to 4 $R_{1a}$, $C_{1-3}$ alkoxy substituted with zero to 4 $R_{1a}$, —$C(O)NR_aR_a$, —$NR_aR_a$, —$S(O)_nR_e$, or —$P(O)R_eR_e$;
each $R_{1a}$ is independently F, Cl, —CN, —OH, —$OCH_3$, or —$NR_aR_a$;
each $R_a$ is independently H or $C_{1-3}$ alkyl;
each $R_e$ is independently $C_{3-4}$ cycloalkyl or $C_{1-3}$ alkyl substituted with zero to 4 $R_{1a}$;
$R_2$ is H, $C_{1-3}$ alkyl substituted with zero to 4 $R_{2a}$, $C_{2-3}$ alkenyl substituted with zero to 4 $R_{2a}$, or $C_{3-4}$ cycloalkyl substituted with zero to 4 $R_{2a}$;
each $R_{2a}$ is independently F, Cl, —CN, —OH, —$O(C_{1-2}$ alkyl), $C_{3-4}$ cycloalkyl, $C_{3-4}$ alkenyl, or $C_{3-4}$ alkynyl;
$R_3$ is H, F, Cl, Br, —CN, $C_{1-3}$ alkyl, $C_{1-2}$ fluoroalkyl, $C_{3-4}$ cycloalkyl, $C_{3-4}$ fluorocycloalkyl, —$NO_2$, or pyridinyl substituted with zero to 2 $R_{3a}$;
each $R_{3a}$ is halo, —CN, $C_{1-3}$ alkyl, or $C_{1-3}$ alkoxy;
$R_4$ is $R_{4a}$, —$CH_2R_{4a}$, or —$CH_2CH_2R_{4a}$;
$R_{4a}$ is $C_{3-6}$ cycloalkyl, $C_{5-14}$ heterocyclyl, $C_{6-10}$ aryl, or $C_{5-14}$ heteroaryl, each substituted with zero to 4 $R_{4b}$;
each $R_{4b}$ is independently F, Cl, Br, —CN, —OH, $C_{1-6}$ alkyl, $C_{1-3}$ fluoroalkyl, $C_{1-4}$ hydroxyalkyl, —$(CH_2)_{1-2}O(C_{1-3}$ alkyl), $C_{1-4}$ alkoxy, —$O(C_{1-4}$ hydroxyalkyl), —$O(CH)_{1-3}O(C_{1-3}$ alkyl), $C_{1-3}$ fluoroalkoxy, —$O(CH)_{1-3}NR_cR_c$, —$OCH_2CH=CH_2$, —$OCH_2C\equiv CH$, —$C(O)(C_{1-4}$ alkyl), —$C(O)OH$, —$C(O)O(C_{1-4}$ alkyl), —$C(O)NH_2$, —$C(O)NH(C_{1-4}$ alkyl), —$C(O)N(C_{1-4}$ alkyl)$_2$, —$NR_cR_c$, —$NR_aS(O)_2(C_{1-3}$ alkyl), —$NR_aC(O)(C_{1-3}$ alkyl), —$NR_aC(O)O(C_{1-4}$ alkyl), —$P(O)(C_{1-3}$ alkyl)$_2$, —$S(O)_2(C_{1-3}$ alkyl), —$O(CH_2)_{1-2}(C_{3-6}$ cycloalkyl), —$O(CH_2)_{1-2}$(morpholinyl), $C_{3-6}$ cycloalkyl, cyanocyclopropyl, methylazetidinyl, acetylazetidinyl, triazolyl, tetrahydropyranyl, morpholinyl, thiophenyl, methylpiperidinyl, or —$CR_cR_c$(phenyl);
each $R_c$ is independently H or $C_{1-2}$ alkyl;
$R_{4c}$ is H, $C_{1-6}$ alkyl, or $R_{4a}$;
$R_{4d}$ is H or $C_{1-6}$ alkyl;
each $R_5$ is independently F, Cl, —CN, —OH, $C_{1-6}$ alkyl substituted with zero to 4 $R_g$, $C_{1-3}$ alkoxy substituted with zero to 4 $R_g$, $C_{2-4}$ alkenyl substituted with zero to 4 $R_g$, $C_{2-4}$ alkynyl substituted with zero to 4 $R_g$, —$(CH_2)_{1-2}(C_{3-4}$ cycloalkyl substituted with zero to 4 $R_g$), phenyl substituted with zero to 4 $R_g$, oxadiazolyl substituted with zero to 3 $R_g$, pyridinyl substituted with zero to 4 $R_g$, —$(CH_2)_{1-2}$(heterocyclyl substituted with zero to 4 $R_g$), —$(CH_2)_{1-2}NR_cC(O)(C_{1-4}$ alkyl), —$(CH_2)_{1-2}NR_cC(O)O(C_{1-4}$ alkyl), —$O(CH_2)_{1-2}$(heterocyclyl substituted with zero to 4 $R_g$), —$(CH_2)_{1-2}NR_cS(O)_2(C_{1-4}$ alkyl), —$C(O)(C_{1-4}$ alkyl), —$C(O)OH$, —$C(O)O(C_{1-4}$ alkyl), —$C(O)O(C_{3-4}$ cycloalkyl), —$C(O)NR_aR_a$, or —$C(O)NR_a(C_{3-4}$ cycloalkyl), or two $R_5$ attached to the same carbon atom form =O;
each $R_g$ is independently F, Cl, —CN, —OH, $C_{1-3}$ alkoxy, $C_{1-3}$ fluoroalkoxy, —$O(CH_2)_{1-2}O(C_{1-2}$ alkyl), $C_{3-5}$ cycloalkyl, or —$NR_cR_c$;
each $R_6$ is H, F, Cl, —CN, —$CH_3$, —$CH_2F$, —$CHF_2$, —$CF_3$, or —$OCH_3$;
$R_7$ is H or —$CH_3$;
m is zero, 1, 2, or 3; and
n is zero, 1, or 2.

The second aspect of the present invention provides at least one compound of Formula (I):

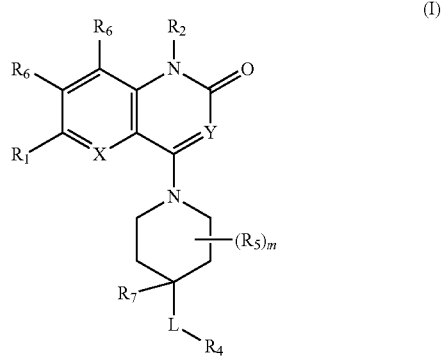

or a salt thereof, wherein:
X is $CR_6$ or N;
Y is $CR_3$ or N;
L is —O—, —S—, $S(O)_2$—, —$NR_{4c}$—, or —$NR_{4d}C(O)$—;
$R_1$ is H, F, Cl, Br, —CN, $C_{1-3}$ alkyl substituted with zero to 4 $R_{1a}$, $C_{3-4}$ cycloalkyl substituted with zero to 4 $R_{1a}$, $C_{1-3}$ alkoxy substituted with zero to 4 $R_{1a}$, —$C(O)NR_aR_a$, —$NR_aR_a$, —$S(O)_nR_e$, or —$P(O)R_eR_e$;
each $R_{1a}$ is independently F, Cl, —CN, —OH, —$OCH_3$, or —$NR_aR_a$;
each $R_a$ is independently H or $C_{1-3}$ alkyl;
each $R_e$ is independently $C_{3-4}$ cycloalkyl or $C_{1-3}$ alkyl substituted with zero to 4 $R_{1a}$;

$R_2$ is H, $C_{1-3}$ alkyl substituted with zero to 4 $R_{2a}$, $C_{2-3}$ alkenyl substituted with zero to 4 $R_{2a}$, or $C_{3-4}$ cycloalkyl substituted with zero to 4 $R_{2a}$;

each $R_{2a}$ is independently F, Cl, —CN, —OH, —O($C_{1-2}$ alkyl), $C_{3-4}$ cycloalkyl, $C_{3-4}$ alkenyl, or $C_{3-4}$ alkynyl;

$R_3$ is H, F, Cl, Br, —CN, $C_{1-3}$ alkyl, $C_{1-2}$ fluoroalkyl, $C_{3-4}$ cycloalkyl, $C_{3-4}$ fluorocycloalkyl, —NO$_2$, or pyridinyl substituted with zero to 2 $R_{3a}$;

each $R_{3a}$ is halo, —CN, $C_{1-3}$ alkyl, or $C_{1-3}$ alkoxy;

$R_4$ is $R_{4a}$, —CH$_2$R$_{4a}$, or —CH$_2$CH$_2$R$_{4a}$;

$R_{4a}$ is $C_{3-6}$ cycloalkyl, $C_{5-14}$ heterocyclyl, $C_{6-10}$ aryl, or $C_{5-14}$ heteroaryl, each substituted with zero to 4 $R_{4b}$;

each $R_{4b}$ is independently F, Cl, Br, —CN, —OH, $C_{1-6}$ alkyl, $C_{1-3}$ fluoroalkyl, $C_{1-4}$ hydroxyalkyl, —(CH$_2$)$_{1-2}$O(C$_{1-3}$ alkyl), $C_{1-4}$ alkoxy, —O(C$_{1-4}$ hydroxyalkyl), —O(CH)$_{1-3}$O(C$_{1-3}$ alkyl), $C_{1-3}$ fluoroalkoxy, —O(CH)$_{1-3}$NR$_c$R$_c$, —OCH$_2$CH=CH$_2$, —OCH$_2$C≡CH, —C(O)(C$_{1-4}$ alkyl), —C(O)OH, —C(O)O(C$_{1-4}$ alkyl), —C(O)NH$_2$, —C(O)NH(C$_{1-4}$ alkyl), —C(O)N(C$_{1-4}$ alkyl)$_2$, —NR$_c$R$_c$, —NR$_a$S(O)$_2$(C$_{1-3}$ alkyl), —NR$_a$C(O)(C$_{1-3}$ alkyl), —NR$_a$C(O)O(C$_{1-4}$ alkyl), —P(O)(C$_{1-3}$ alkyl)$_2$, —S(O)$_2$(C$_{1-3}$ alkyl), —O(CH$_2$)$_{1-2}$(C$_{3-6}$ cycloalkyl), —O(CH$_2$)$_{1-2}$(morpholinyl), $C_{3-6}$ cycloalkyl, cyanocyclopropyl, methylazetidinyl, acetylazetidinyl, triazolyl, tetrahydropyranyl, morpholinyl, thiophenyl, methylpiperidinyl, or —CR$_c$R$_c$(phenyl);

each $R_c$ is independently H or $C_{1-2}$ alkyl;

$R_{4c}$ is H, $C_{1-6}$ alkyl, or $R_{4a}$;

$R_{4d}$ is H or $C_{1-6}$ alkyl;

each $R_5$ is independently F, Cl, —CN, —OH, $C_{1-6}$ alkyl substituted with zero to 4 $R_g$, $C_{1-3}$ alkoxy substituted with zero to 4 $R_g$, $C_{2-4}$ alkenyl substituted with zero to 4 $R_g$, $C_{2-4}$ alkynyl substituted with zero to 4 $R_g$, $C_{3-4}$ cycloalkyl substituted with zero to 4 $R_g$, phenyl substituted with zero to 4 $R_g$, oxadiazolyl substituted with zero to 3 $R_g$, pyridinyl substituted with zero to 4 $R_g$, —(CH$_2$)$_{1-2}$(heterocyclyl substituted with zero to 4 $R_g$), —(CH$_2$)$_{1-2}$NR$_c$C(O)(C$_{1-4}$ alkyl), —(CH$_2$)$_{1-2}$NR$_c$C(O)O(C$_{1-4}$ alkyl), —(CH$_2$)$_{1-2}$NR$_c$S(O)$_2$(C$_{1-4}$ alkyl), —C(O)(C$_{1-4}$ alkyl), —C(O)OH, —C(O)O(C$_{1-4}$ alkyl), —C(O)O(C$_{3-4}$ cycloalkyl), —C(O)NR$_a$R$_a$, or —C(O)NR$_a$(C$_{3-4}$ cycloalkyl);

each $R_g$ is independently F, Cl, —CN, —OH, $C_{1-3}$ alkoxy, $C_{1-3}$ fluoroalkoxy, —O(CH$_2$)$_{1-2}$O(C$_{1-2}$ alkyl), $C_{3-5}$ cycloalkyl, or —NR$_c$R$_c$;

each $R_6$ is H, F, Cl, —CN, —CH$_3$, —CH$_2$F, —CHF$_2$, —CF$_3$, or —OCH$_3$;

$R_7$ is H or —CH$_3$;

m is zero, 1, 2, or 3; and n is zero, 1, or 2.

In one embodiment, a compound of Formula (I) or a salt thereof is provided wherein X is CR$_6$; and Y is CR$_3$ or N. Compounds of this embodiment have the structure of Formula (II):

(II)

In one embodiment, a compound of Formula (I) or a salt thereof is provided wherein X is CR$_6$ or N; and Y is CR$_3$. Compounds of this embodiment have the structure of Formula (III):

(III)

One embodiment provides a compound of Formula (I) or a salt thereof, wherein X is CR$_6$ and Y is CR$_3$. Compounds of this embodiment have the structure of Formula (IV):

(IV)

Included in this embodiment are compounds in which L is O. Also, included in this embodiment are compounds in which X is CH. Additionally, included in this embodiment are compounds in which each R$_6$ is H.

One embodiment provides a compound of Formula (I) or a salt thereof, wherein X is N and Y is CR$_3$. Compounds of this embodiment have the structure of Formula (V):

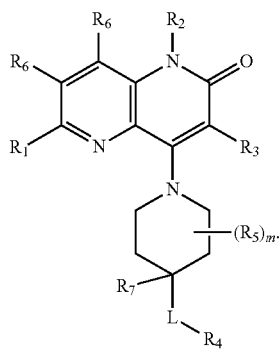

(V)

Included in this embodiment are compounds in which L is O. Also, included in this embodiment are compounds in which each $R_6$ is H.

One embodiment provides a compound of Formula (I) or a salt thereof, wherein X is $CR_6$ and Y is N. Compounds of this embodiment have the structure of Formula (VI):

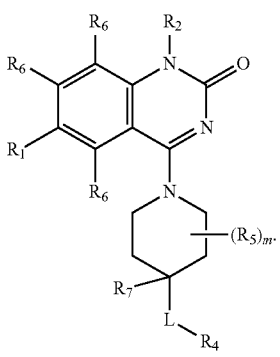

(VI)

Included in this embodiment are compounds in which L is O. Also, included in this embodiment are compounds in which X is CH. Additionally, included in this embodiment are compounds in which each $R_6$ is H.

One embodiment provides a compound of Formula (I) or a salt thereof, wherein X is N and Y is N. Compounds of this embodiment have the structure of Formula (VII):

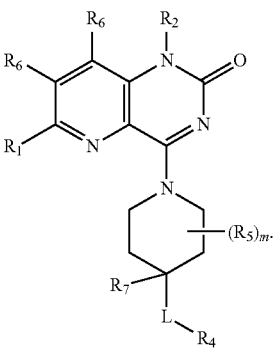

(VII)

Included in this embodiment are compounds in which L is O. Also, included in this embodiment are compounds in which each $R_6$ is H.

One embodiment provides a compound of Formula (I) or a salt thereof, wherein: $R_1$ is H, F, Cl, Br, —CN, $C_{1-3}$ alkyl substituted with zero to 4 $R_{1a}$, cyclopropyl substituted with zero to 3 $R_{1a}$, $C_{1-3}$ alkoxy substituted with zero to 3 $R_{1a}$, —C(O)$NR_aR_a$, —$NR_aR_a$, —S(O)$_n$CH$_3$, or —P(O)(CH$_3$)$_2$;
each $R_{1a}$ is independently F, Cl, or —CN;
each $R_a$ is independently H or $C_{1-3}$ alkyl;
$R_2$ is H, $C_{1-2}$ alkyl substituted with zero to 2 $R_{2a}$, or $C_{2-3}$ alkenyl substituted with zero to 2 $R_{2a}$;
each $R_{2a}$ is independently F, Cl, —CN, —OH, —O($C_{1-2}$ alkyl), cyclopropyl, $C_{3-4}$ alkenyl, or $C_{3-4}$ alkynyl;
$R_3$ is H, F, Cl, Br, —CN, $C_{1-2}$ alkyl, $C_{1-2}$ fluoroalkyl, $C_{3-4}$ cycloalkyl, —NO$_2$, or pyridinyl substituted with zero to 1 $R_{1a}$;
$R_{4a}$ is $C_{3-6}$ cycloalkyl, oxetanyl, tetrahydrofuranyl, tetrahydropyranyl, piperidinyl, piperazinyl, morpholinyl, phenyl, naphthalenyl, furanyl, pyranyl, pyrrolyl, pyrazolyl, imidazolyl, isoxazolyl, oxazolyl, oxadiazolyl, triazolyl, indolyl, indazolyl, phthalazinyl, pyridazinyl, pyridinyl, pyrimidinyl, pyrazinyl, triazinyl, benzoxazolyl, benzothiazolyl, benzoimidazolyl, quinolinyl, isoquinolinyl, quinoxalinyl, quinazolinyl, naphthyridinyl, or dihydrobenzo[b][1,4]dioxepinyl, each substituted with zero to 3 $R_{4b}$;
each $R_{4b}$ is independently F, Cl, Br, —CN, —OH, $C_{1-6}$ alkyl, $C_{1-2}$ fluoroalkyl, $C_{1-3}$ hydroxyalkyl, —(CH$_2$)$_{1-20}$ ($C_{1-3}$ alkyl), $C_{1-4}$ alkoxy, —O($C_{1-3}$ hydroxyalkyl), —O(CH)$_{1-3}$O($C_{1-3}$ alkyl), $C_{1-2}$ fluoroalkoxy, —O (CH)$_{1-2}$NR$_c$R$_c$, —C(O)($C_{1-3}$ alkyl), —C(O)OH, —C(O)O($C_{1-3}$ alkyl), —C(O)NH$_2$, —C(O)NH($C_{1-3}$ alkyl), —C(O)N($C_{1-3}$ alkyl)$_2$, —NR$_c$R$_c$, —S(O)$_2$($C_{1-2}$ alkyl), $C_{3-6}$ cycloalkyl, or —CR$_c$R$_c$(phenyl);
$R_{4c}$ is H, $C_{1-4}$ alkyl, or $R_{4a}$;
$R_{4d}$ is H or $C_{1-4}$ alkyl;
each $R_5$ is independently F, —CN, —OH, $C_{1-5}$ alkyl substituted with zero to 4 $R_g$, $C_{1-3}$ alkoxy substituted with zero to 3 $R_g$, $C_{2-3}$ alkenyl substituted with zero to 4 $R_g$, $C_{2-3}$ alkynyl substituted with zero to 4 $R_g$, —(CH$_2$)$_{1-2}$($C_{3-4}$ cycloalkyl substituted with zero to 4 $R_g$), phenyl substituted with zero to 3 $R_g$, oxadiazolyl substituted with zero to 3 $R_g$, pyridinyl substituted with zero to 3 $R_g$, —(CH$_2$)$_{1-2}$ (heterocyclyl substituted with zero to 4 $R_g$), —O(CH$_2$)$_{1-2}$(heterocyclyl substituted with zero to 4 $R_g$), —(CH$_2$)$_{1-2}$NR$_c$C(O)($C_{1-4}$ alkyl), —(CH$_2$)$_{1-2}$NR$_c$C(O)O($C_{1-4}$ alkyl), —(CH$_2$)$_{1-2}$NR$_c$S (O)$_2$($C_{1-4}$ alkyl), —C(O)($C_{1-4}$ alkyl), —C(O)OH, —C(O)O($C_{1-4}$ alkyl), —C(O)O($C_{3-4}$ cycloalkyl), —C(O)NR$_a$R$_a$, or —C(O)NR$_a$($C_{3-4}$ cycloalkyl);
each $R_6$ is H, F, or —CH$_3$; and
$R_7$ is H or —CH$_3$. Included in this embodiment are compounds in which $R_7$ is H, D, —CH$_3$, or —CD$_3$.

One embodiment provides a compound of Formula (I) or a salt thereof, wherein:
$R_1$ is H, F, Cl, Br, —CN, $C_{1-3}$ alkyl substituted with zero to 4 $R_{1a}$, cyclopropyl substituted with zero to 3 $R_{1a}$, $C_{1-3}$ alkoxy substituted with zero to 3 $R_{1a}$, —C(O) $NR_aR_a$, —$NR_aR_a$, —S(O)$_n$CH$_3$, or —P(O)(CH$_3$)$_2$;
each $R_{1a}$ is independently F, Cl, or —CN;
each $R_a$ is independently H or $C_{1-3}$ alkyl;
$R_2$ is H, $C_{1-2}$ alkyl substituted with zero to 2 $R_{2a}$, or $C_{2-3}$ alkenyl substituted with zero to 2 $R_{2a}$;
each $R_{2a}$ is independently F, Cl, —CN, —OH, —O($C_{1-2}$ alkyl), cyclopropyl, $C_{3-4}$ alkenyl, or $C_{3-4}$ alkynyl;
$R_3$ is H, F, Cl, Br, —CN, $C_{1-2}$ alkyl, $C_{1-2}$ fluoroalkyl, $C_{3-4}$ cycloalkyl, —NO$_2$, methylpyridinyl, or methoxypyridinyl;

$R_{4a}$ is $C_{3-6}$ cycloalkyl, oxetanyl, tetrahydrofuranyl, tetrahydropyranyl, piperidinyl, piperazinyl, morpholinyl, phenyl, naphthalenyl, furanyl, pyranyl, pyrrolyl, pyrazolyl, imidazolyl, isoxazolyl, oxazolyl, oxadiazolyl, triazolyl, indolyl, indazolyl, phthalazinyl, pyridazinyl, pyridinyl, pyrimidinyl, pyrazinyl, triazinyl, benzothiazolyl, benzoimidazolyl, quinolinyl, isoquinolinyl, quinoxalinyl, quinazolinyl, naphthyridinyl, or dihydrobenzo[b][1,4]dioxepinyl, each substituted with zero to 3 $R_{4b}$;

each $R_{4b}$ is independently F, Cl, Br, —CN, —OH, $C_{1-6}$ alkyl, $C_{1-2}$ fluoroalkyl, $C_{1-3}$ hydroxyalkyl, —$(CH_2)_{1-2}$O($C_{1-3}$ alkyl), $C_{1-4}$ alkoxy, —O($C_{1-3}$ hydroxyalkyl), —O($CH$)$_{1-3}$O($C_{1-3}$ alkyl), $C_{1-2}$ fluoroalkoxy, —O$(CH)_{1-2}NR_cR_c$, —C(O)($C_{1-3}$ alkyl), —C(O)OH, —C(O)O($C_{1-3}$ alkyl), —C(O)NH$_2$, —C(O)NH($C_{1-3}$ alkyl), —C(O)N($C_{1-3}$ alkyl)$_2$, —NR$_c$R$_c$, —S(O)$_2$($C_{1-2}$ alkyl), $C_{3-6}$ cycloalkyl, or —CR$_c$R$_c$(phenyl);

$R_{4c}$ is H, $C_{1-4}$ alkyl, or $R_{4a}$;

$R_{4d}$ is H or $C_{1-4}$ alkyl;

each $R_5$ is independently F, —CN, —OH, $C_{1-5}$ alkyl substituted with zero to 4 $R_g$, $C_{1-2}$ alkoxy substituted with zero to 3 $R_g$, $C_{2-3}$ alkenyl substituted with zero to 4 $R_g$, $C_{2-3}$ alkynyl substituted with zero to 4 $R_g$, $C_{3-4}$ cycloalkyl substituted with zero to 4 $R_g$, phenyl substituted with zero to 3 $R_g$, oxadiazolyl substituted with zero to 3 $R_g$, pyridinyl substituted with zero to 3 $R_g$, —$(CH_2)_{1-2}$(heterocyclyl substituted with zero to 4 $R_g$), —$(CH_2)_{1-2}NR_cC(O)(C_{1-4}$ alkyl), —$(CH_2)_{1-2}NR_cC(O)O(C_{1-4}$ alkyl), —$(CH_2)_{1-2}NR_cS(O)_2(C_{1-4}$ alkyl), —C(O)($C_{1-4}$ alkyl), —C(O)OH, —C(O)O($C_{1-4}$ alkyl), —C(O)O($C_{3-4}$ cycloalkyl), —C(O)NR$_a$R$_a$, or —C(O)NR$_a$($C_{3-4}$ cycloalkyl); and each $R_6$ is H, F, or —CH$_3$. Included in this embodiment are compounds in which $R_7$ is H, D, —CH$_3$, or —CD$_3$.

One embodiment provides a compound of Formula (I) or a salt thereof, wherein:

X is CH and Y is CR$_3$;
X is N and Y is CR$_3$; or
X is N and Y is N;
L is —O—, —NH—, —N(CH$_3$)—, or —N(CH$_3$)C(O)—;
$R_1$ is F, Cl, Br, —CN, —OCH$_3$, or —C(O)NH$_2$;
$R_2$ is —CH$_3$;
$R_3$ is H, F, Cl, Br, —CN, —CH$_3$, —NO$_2$, methylpyridinyl, or methoxypyridinyl;
$R_4$ is $R_{4a}$ or —CH$_2$R$_{4a}$;
$R_{4a}$ is cyclohexyl, phenyl, indazolyl, phthalazinyl, pyridazinyl, pyridinyl, pyrimidinyl, pyrazinyl, benzoxazolyl, benzothiazolyl, quinolinyl, quinoxalinyl, quinazolinyl, 1,7-naphthyridinyl, or dihydrobenzo[b][1,4]dioxepinyl, each substituted with zero to 3 $R_{4b}$;
each $R_{4b}$ is independently F, Cl, Br, —CN, —CH$_3$, —CH$_2$CH$_3$, —CH$_2$CH$_2$CH$_3$, —CH(CH$_3$)$_2$, —CH$_2$CH$_2$CH$_2$CH$_3$, —C(CH$_3$)$_3$, —CH$_2$CH$_2$CH$_2$CH$_2$CH$_3$, —C(CH$_3$)$_2$CH$_2$CH$_3$, —CHF$_2$, —CF$_3$, —OCH$_3$, —OCH(CH$_3$)$_2$, —OC(CH$_3$)$_3$, —OCF$_3$, —C(O)N(CH$_3$)$_2$, —S(O)$_2$CH$_3$, —CH$_2$(phenyl), —C(CH$_3$)$_2$(phenyl), cyclopropyl, cyclopentyl, or cyclohexyl;
each $R_5$ is independently hydrogen, F, —OH, $C_{1-2}$ alkyl, $C_{1-3}$ alkoxy, —CH$_2$CF$_3$, —OCH$_2$CH$_2$OCH$_3$, —OCH$_2$CH$_2$N(CH$_3$)$_2$, —OCH$_2$(cyclopropyl), or —OCH$_2$CH$_2$(morpholinyl); and
each $R_6$ is H.

One embodiment provides a compound of Formula (I) or a salt thereof, wherein:

X is CH and Y is CR$_3$;
X is N and Y is CR$_3$; or
X is N and Y is N;
L is —O— or —NH—;
$R_1$ is F, Cl, Br, —CN, —OCH$_3$, or —C(O)NH$_2$;
$R_2$ is —CH$_3$;
$R_3$ is H, F, Cl, Br, —CN, $C_{1-2}$ alkyl, $C_{1-2}$ fluoroalkyl, $C_{3-4}$ cycloalkyl, —NO$_2$, or pyridinyl substituted with zero to 1 $R_{1a}$;
$R_4$ is $R_{4a}$ or —CH$_2$R$_{4a}$;
$R_{4a}$ is phenyl, indazolyl, phthalazinyl, pyridazinyl, pyridinyl, pyrimidinyl, quinolinyl, quinoxalinyl, quinazolinyl, 1,7-naphthyridinyl, or dihydrobenzo[b][1,4]dioxepinyl, each substituted with zero to 2 $R_{4b}$;
each $R_{4b}$ is independently F, Cl, Br, —CN, —CH$_3$, —CH$_2$CH$_3$, —CH$_2$CH$_2$CH$_3$, —CH(CH$_3$)$_2$, —CH$_2$CH$_2$CH$_2$CH$_3$, —C(CH$_3$)$_3$, —CH$_2$CH$_2$CH$_2$CH$_2$CH$_3$, —C(CH$_3$)$_2$CH$_2$CH$_3$, —CF$_3$, —OCH$_3$, —OCH(CH$_3$)$_2$, —OC(CH$_3$)$_3$, —OCF$_3$, —C(O)N(CH$_3$)$_2$, —CH$_2$(phenyl), —C(CH$_3$)$_2$(phenyl), cyclopropyl, cyclopentyl, or cyclohexyl;
each $R_5$ is independently hydrogen, F, —OH, $C_{1-2}$ alkyl, or $C_{1-2}$ alkoxy;
each $R_6$ is H; and
$R_7$ is H. Included in this embodiment are compounds in which $R_7$ is D.

One embodiment provides a compound of Formula (I) or a salt thereof, wherein:

X is CH and Y is CR$_3$;
X is N and Y is CR$_3$; or
X is N and Y is N;
L is —O—;
$R_1$ is F, Cl, Br, —CN, —OCH$_3$, or —C(O)NH$_2$;
$R_2$ is —CH$_3$;
$R_3$ is H, F, Cl, Br, —CN, —CH$_3$, —NO$_2$, methylpyridinyl, or methoxypyridinyl;
$R_4$ is $R_{4a}$ or —CH$_2$R$_{4a}$;
$R_{4a}$ is cyclohexyl, phenyl, indazolyl, phthalazinyl, pyridazinyl, pyridinyl, pyrimidinyl, pyrazinyl, benzoxazolyl, benzothiazolyl, quinolinyl, quinoxalinyl, quinazolinyl, 1,7-naphthyridinyl, or dihydrobenzo[b][1,4]dioxepinyl, each substituted with zero to 3 $R_{4b}$;
each $R_{4b}$ is independently F, Cl, Br, —CN, —CH$_3$, —CH$_2$CH$_3$, —CH$_2$CH$_2$CH$_3$, —CH(CH$_3$)$_2$, —CH$_2$CH$_2$CH$_2$CH$_3$, —C(CH$_3$)$_3$, —CH$_2$CH$_2$CH$_2$CH$_2$CH$_3$, —C(CH$_3$)$_2$CH$_2$CH$_3$, —CHF$_2$, —CF$_3$, —OCH$_3$, —OCH(CH$_3$)$_2$, —OC(CH$_3$)$_3$, —OCF$_3$, —C(O)N(CH$_3$)$_2$, —S(O)$_2$CH$_2$(phenyl), —C(CH$_3$)$_2$(phenyl), cyclopropyl, cyclopentyl, or cyclohexyl;
each $R_5$ is independently hydrogen, F, —OH, $C_{1-2}$ alkyl, $C_{1-3}$ alkoxy, —CH$_2$CF$_3$, —OCH$_2$CH$_2$OCH$_3$, —OCH$_2$CH$_2$N(CH$_3$)$_2$, —OCH$_2$(cyclopropyl), or —OCH$_2$CH$_2$(morpholinyl); and
each $R_6$ is H; and
$R_7$ is H or —CH$_3$. Included in this embodiment are compounds in which $R_7$ is H, D, —CH$_3$, or —CD$_3$.

One embodiment provides a compound of Formula (I) or a salt thereof, wherein:

X is CH and Y is CR$_3$;
X is N and Y is CR$_3$; or
X is N and Y is N;
L is —O—;
$R_1$ is F, Cl, Br, —CN, —OCH$_3$, or —C(O)NH$_2$;
$R_2$ is —CH$_3$;
$R_3$ is H, F, Cl, Br, —CN, —CH$_3$, —NO$_2$, methylpyridinyl, or methoxypyridinyl;
$R_4$ is $R_{4a}$ or —CH$_2$R$_{4a}$;

$R_{4a}$ is phenyl, indazolyl, phthalazinyl, pyridazinyl, pyridinyl, pyrimidinyl, quinolinyl, quinoxalinyl, quinazolinyl, 1,7-naphthyridinyl, or dihydrobenzo[b][1,4]dioxepinyl, each substituted with zero to 2 $R_{4b}$;

each $R_{4b}$ is independently F, Cl, Br, —CN, —CH$_3$, —CH$_2$CH$_3$, —CH$_2$CH$_2$CH$_3$, —CH(CH$_3$)$_2$, —CH$_2$CH$_2$CH$_2$CH$_3$, —C(CH$_3$)$_3$, —CH$_2$CH$_2$CH$_2$CH$_2$CH$_3$, —C(CH$_3$)$_2$CH$_2$CH$_3$, —CF$_3$, —OCH$_3$, —OCH(CH$_3$)$_2$, —OC(CH$_3$)$_3$, —OCF$_3$, —C(O)N(CH$_3$)$_2$, —CH$_2$(phenyl), —C(CH$_3$)$_2$(phenyl), cyclopropyl, cyclopentyl, or cyclohexyl;

each $R_5$ is independently hydrogen, F, —OH, $C_{1-2}$ alkyl, or $C_{1-2}$ alkoxy;

each $R_6$ is H; and $R_7$ is H. Included in this embodiment are compounds in which $R_7$ is D.

One embodiment provides a compound of Formula (I) or a salt thereof, wherein: X is CH and Y is CR$_3$; L is —O—; $R_1$ is F, Cl, Br, —CN, —OCH$_3$, or —C(O)NH$_2$; $R_2$ is —CH$_3$; $R_3$ is H, F, Cl, Br, —CN, —CH$_3$, —NO$_2$, methylpyridinyl, or methoxypyridinyl; $R_4$ is $R_{4a}$ or —CH$_2$R$_{4a}$; $R_{4a}$ is cyclohexyl, phenyl, indazolyl, phthalazinyl, pyridazinyl, pyridinyl, pyrimidinyl, pyrazinyl, benzoxazolyl, benzothiazolyl, quinolinyl, quinoxalinyl, quinazolinyl, 1,7-naphthyridinyl, or dihydrobenzo[b][1,4]dioxepinyl, each substituted with zero to 3 $R_{4b}$; each $R_{4b}$ is independently F, Cl, Br, —CN, —CH$_3$, —CH$_2$CH$_3$, —CH$_2$CH$_2$CH$_3$, —CH(CH$_3$)$_2$, —CH$_2$CH$_2$CH$_2$CH$_3$, —C(CH$_3$)$_3$, —CH$_2$CH$_2$CH$_2$CH$_2$CH$_3$, —C(CH$_3$)$_2$CH$_2$CH$_3$, —CHF$_2$, —CF$_3$, —OCH$_3$, —OCH(CH$_3$)$_2$, —OC(CH$_3$)$_3$, —OCF$_3$, —C(O)N(CH$_3$)$_2$, —S(O)$_2$CH$_3$, —CH$_2$(phenyl), —C(CH$_3$)$_2$(phenyl), cyclopropyl, cyclopentyl, or cyclohexyl; each $R_5$ is independently hydrogen, F, —OH, $C_{1-2}$ alkyl, $C_{1-3}$ alkoxy, —CH$_2$CF$_3$, —OCH$_2$CH$_2$OCH$_3$, —OCH$_2$CH$_2$N(CH$_3$)$_2$, —OCH$_2$(cyclopropyl), or —OCH$_2$CH$_2$(morpholinyl); and $R_7$ is H. Included in this embodiment are compounds in which $R_7$ is D.

One embodiment provides a compound of Formula (I) or a salt thereof, wherein: X is CH and Y is CR$_3$; L is —O—; $R_1$ is F, Cl, Br, —CN, —OCH$_3$, or —C(O)NH$_2$; $R_2$ is —CH$_3$; $R_3$ is H, F, Cl, Br, —CN, —CH$_3$, —NO$_2$, methylpyridinyl, or methoxypyridinyl; $R_4$ is $R_{4a}$ or —CH$_2$R$_{4a}$; $R_{4a}$ is phenyl, indazolyl, phthalazinyl, pyridazinyl, pyridinyl, pyrimidinyl, quinolinyl, quinoxalinyl, quinazolinyl, 1,7-naphthyridinyl, or dihydrobenzo[b][1,4]dioxepinyl, each substituted with zero to 2 $R_{4b}$; each $R_{4b}$ is independently F, Cl, Br, —CN, —CH$_3$, —CH$_2$CH$_3$, —CH$_2$CH$_2$CH$_3$, —CH(CH$_3$)$_2$, —CH$_2$CH$_2$CH$_2$CH$_3$, —C(CH$_3$)$_3$, —CH$_2$CH$_2$, —C(CH$_3$)$_2$CH$_2$CH$_3$, —CF$_3$, —OCH$_3$, —OCH(CH$_3$)$_2$, —OC(CH$_3$)$_3$, —OCF$_3$, —C(O)N(CH$_3$)$_2$, —CH$_2$(phenyl), —C(CH$_3$)$_2$(phenyl), cyclopropyl, cyclopentyl, or cyclohexyl; each $R_5$ is independently hydrogen, F, —OH, $C_{1-2}$ alkyl, or $C_{1-2}$ alkoxy; each $R_6$ is H; and $R_7$ is H. Included in this embodiment are compounds in which $R_7$ is D.

One embodiment provides a compound of Formula (I) or a salt thereof, wherein: X is N and Y is CR$_3$; L is —O—; $R_1$ is F, Cl, Br, —CN, —OCH$_3$, or —C(O)NH$_2$; $R_2$ is —CH$_3$; $R_3$ is H, F, Cl, Br, —CN, —CH$_3$, —NO$_2$, methylpyridinyl, or methoxypyridinyl; $R_4$ is $R_{4a}$ or —CH$_2$R$_{4a}$; $R_{4a}$ is phenyl, indazolyl, phthalazinyl, pyridazinyl, pyridinyl, pyrimidinyl, quinolinyl, quinoxalinyl, quinazolinyl, 1,7-naphthyridinyl, or dihydrobenzo[b][1,4]dioxepinyl, each substituted with zero to 2 $R_{4b}$; each $R_{4b}$ is independently F, Cl, Br, —CN, —CH$_3$, —CH$_2$CH$_3$, —CH$_2$CH$_2$CH$_3$, —CH(CH$_3$)$_2$, —CH$_2$CH$_2$CH$_2$CH$_3$, —C(CH$_3$)$_3$, —CH$_2$CH$_2$CH$_2$CH$_2$CH$_3$, —C(CH$_3$)$_2$CH$_2$CH$_3$, —CF$_3$, —OCH$_3$, —OCH(CH$_3$)$_2$, —OC(CH$_3$)$_3$, —OCF$_3$, —C(O)N(CH$_3$)$_2$, —CH$_2$(phenyl), —C(CH$_3$)$_2$(phenyl), cyclopropyl, cyclopentyl, or cyclohexyl; each $R_5$ is independently hydrogen, F, —OH, $C_{1-2}$ alkyl, or $C_{1-2}$ alkoxy; each $R_6$ is H; and $R_7$ is H. Included in this embodiment are compounds in which $R_7$ is D.

One embodiment provides a compound of Formula (I) or a salt thereof, wherein: X is N and Y is N; L is —O—; $R_1$ is F, Cl, Br, —CN, —OCH$_3$, or —C(O)NH$_2$; $R_2$ is —CH$_3$; $R_3$ is H, F, Cl, Br, —CN, —CH$_3$, —NO$_2$, methylpyridinyl, or methoxypyridinyl; $R_4$ is $R_{4a}$ or —CH$_2$R$_{4a}$; $R_{4a}$ is phenyl, indazolyl, phthalazinyl, pyridazinyl, pyridinyl, pyrimidinyl, quinolinyl, quinoxalinyl, quinazolinyl, 1,7-naphthyridinyl, or dihydrobenzo[b][1,4]dioxepinyl, each substituted with zero to 2 $R_{4b}$; each $R_{4b}$ is independently F, Cl, Br, —CN, —CH$_3$, —CH$_2$CH$_3$, —CH$_2$CH$_2$CH$_3$, —CH(CH$_3$)$_2$, —CH$_2$CH$_2$CH$_2$CH$_3$, —C(CH$_3$)$_3$, —CH$_2$CH$_2$CH$_2$CH$_2$CH$_3$, —C(CH$_3$)$_2$CH$_2$CH$_3$, —CF$_3$, —OCH$_3$, —OCH(CH$_3$)$_2$, —OC(CH$_3$)$_3$, —OCF$_3$, —C(O)N(CH$_3$)$_2$, —CH$_2$(phenyl), —C(CH$_3$)$_2$(phenyl), cyclopropyl, cyclopentyl, or cyclohexyl; each $R_5$ is independently hydrogen, F, —OH, $C_{1-2}$ alkyl, or $C_{1-2}$ alkoxy; each $R_6$ is H; and $R_7$ is H. Included in this embodiment are compounds in which $R_7$ is D.

One embodiment provides a compound of Formula (I) or a salt thereof, wherein L is —O—.

One embodiment provides a compound of Formula (I) or a salt thereof, wherein L is —S— or —S(O)$_2$—.

One embodiment provides a compound of Formula (I) or a salt thereof, wherein L is —S—.

One embodiment provides a compound of Formula (I) or a salt thereof, wherein L is —S(O)$_2$—.

One embodiment provides a compound of Formula (I) or a salt thereof, wherein L is —NR$_{4c}$— or —NR$_{4d}$C(O)—.

One embodiment provides a compound of Formula (I) or a salt thereof, wherein L is —NR$_{4c}$—. Included in this embodiment are compounds in which $R_{4c}$ is H or $C_{1-4}$ alkyl. Also, included in this embodiment are compounds in which $R_{4c}$ is $R_{4a}$.

One embodiment provides a compound of Formula (I) or a salt thereof, wherein L is —NR$_{4d}$C(O)—. Included in this embodiment are compounds in which $R_{4d}$ is H or $C_{1-2}$ alkyl.

One embodiment provides a compound of Formula (I) or a salt thereof, wherein $R_1$ is H, F, Cl, Br, —CN, $C_{1-3}$ alkyl substituted with zero to 4 $R_{1a}$, $C_{3-4}$ cycloalkyl substituted with zero to 4 $R_{1a}$, $C_{1-3}$ alkoxy substituted with zero to 4 $R_{1a}$, —C(O)NR$_a$R$_a$, —NR$_a$R$_a$, —S(O)$_n$R$_e$, or —P(O)R$_e$R$_e$. Included in this embodiment are compounds in which $R_1$ is H, F, Cl, Br, —CN, $C_{1-3}$ alkyl substituted with zero to 4 $R_{1a}$, cyclopropyl substituted with zero to 3 $R_{1a}$, $C_{1-3}$ alkoxy substituted with zero to 3 $R_{1a}$, —C(O)NR$_a$R$_a$, —NR$_a$R$_a$, —S(O)$_n$CH$_3$, or —P(O)(CH$_3$)$_2$. Also, included in this embodiment are compounds in which $R_1$ is H, F, Cl, Br, —CN, $C_{1-2}$ alkyl substituted with zero to 4 $R_{1a}$, cyclopropyl substituted with zero to 1 $R_{1a}$, $C_{1-3}$ alkoxy substituted with zero to 3 $R_{1a}$, —C(O)NR$_a$R$_a$, —NR$_a$R$_a$, —S(O)$_n$CH$_3$, or —P(O)(CH$_3$)$_2$. Additionally, included in this embodiment are compounds in which $R_1$ is F, Cl, Br, —CN, —OCH$_3$, or —C(O)NH$_2$.

One embodiment provides a compound of Formula (I) or a salt thereof, wherein each $R_{1a}$ is independently F, Cl, —CN, —OH, or —OCH$_3$. Included in this embodiment are compounds in which each $R_{1a}$ is independently F, Cl, —CN, or —OCH$_3$. Also, included in this embodiment are compounds in which each $R_{1a}$ is independently F, Cl, or —CN.

One embodiment provides a compound of Formula (I) or a salt thereof, wherein each $R_a$ is independently H or $C_{1-2}$ alkyl. Included in this embodiment are compounds in which each $R_a$ is independently H or —CH$_3$.

One embodiment provides a compound of Formula (I) or a salt thereof, wherein $R_2$ is H, $C_{1-3}$ alkyl substituted with zero to 3 $R_{2a}$, or $C_{3-4}$ cycloalkyl substituted with zero to 2 $R_{2a}$. Included in this embodiment are compounds in which $R_2$ is H or $C_{1-2}$ alkyl substituted with zero to 2 $R_{2a}$. Also, included in this embodiment are compounds in which $R_2$ is H or —$CH_3$. Additionally, included in this embodiment are compounds in which $R_2$ is —$CH_3$.

One embodiment provides a compound of Formula (I) or a salt thereof, wherein each $R_{2a}$ is independently F, Cl, —CN, —OH, —O($C_{1-2}$ alkyl), cyclopropyl, $C_{3-4}$ alkenyl, or $C_{3-4}$ alkynyl. Included in this embodiment are compounds in which each $R_{2a}$ is independently F, Cl, —CN, —OH, —$OCH_3$, or cyclopropyl.

One embodiment provides a compound of Formula (I) or a salt thereof, wherein $R_3$ is H, F, Cl, Br, —CN, $C_{1-3}$ alkyl, $C_{1-2}$ fluoroalkyl, $C_{3-4}$ cycloalkyl, —$NO_2$, or pyridinyl substituted with zero to 2 $R_{3a}$. Included in this embodiment are compounds in which $R_3$ is H, F, Cl, Br, —CN, $C_{1-2}$ alkyl, $C_{1-2}$ fluoroalkyl, $C_{3-4}$ cycloalkyl, —$NO_2$, or pyridinyl substituted with zero to 1 $R_{3a}$. Also, included in this embodiment are compounds in which $R_3$ is H, F, Cl, Br, —CN, —$CH_3$, —$NO_2$, methylpyridinyl, or methoxypyridinyl. Additionally, included in this embodiment are compounds in which $R_3$ is H, F, Cl, Br, —CN, —$CH_3$, or —$NO_2$.

One embodiment provides a compound of Formula (I) or a salt thereof, wherein X is $CR_6$ or N; Y is $CR_3$; $R_1$ is $C_1$; and $R_3$ is —CN. Included in this embodiment are compounds in which X is $CR_6$ and Y is $CR_3$. Also, included in this embodiment are compounds in which X is N and Y is $CR_3$.

One embodiment provides a compound of Formula (I) or a salt thereof, wherein X is $CR_6$ or N; Y is $CR_3$; $R_1$ is Br; and $R_3$ is —CN. Included in this embodiment are compounds in which X is $CR_6$ and Y is $CR_3$. Also, included in this embodiment are compounds in which X is N and Y is $CR_3$.

One embodiment provides a compound of Formula (I) or a salt thereof, wherein X is $CR_6$ or N; Y is $CR_3$; $R_1$ is —CN; and $R_3$ is H. Included in this embodiment are compounds in which X is $CR_6$ and Y is $CR_3$. Also, included in this embodiment are compounds in which X is N and Y is $CR_3$.

One embodiment provides a compound of Formula (I) or a salt thereof, wherein X is $CR_6$ or N; Y is $CR_3$; $R_1$ is F; and $R_3$ is —$NO_2$. Included in this embodiment are compounds in which X is $CR_6$ and Y is $CR_3$. Also, included in this embodiment are compounds in which X is N and Y is $CR_3$.

One embodiment provides a compound of Formula (I) or a salt thereof, wherein X is $CR_6$ or N; Y is $CR_3$; $R_1$ is —$OCH_3$; and $R_3$ is —CN. Included in this embodiment are compounds in which X is $CR_6$ and Y is $CR_3$. Also, included in this embodiment are compounds in which X is N and Y is $CR_3$.

One embodiment provides a compound of Formula (I) or a salt thereof, wherein X is $CR_6$ or N; Y is $CR_3$; $R_1$ is —CN; and $R_3$ is —CN. Included in this embodiment are compounds in which X is $CR_6$ and Y is $CR_3$. Also, included in this embodiment are compounds in which X is N and Y is $CR_3$.

One embodiment provides a compound of Formula (I) or a salt thereof, wherein X is $CR_6$ or N; Y is $CR_3$; $R_1$ is —CN; and $R_3$ is —$NO_2$. Included in this embodiment are compounds in which X is $CR_6$ and Y is $CR_3$. Also, included in this embodiment are compounds in which X is N and Y is $CR_3$.

One embodiment provides a compound of Formula (I) or a salt thereof, wherein X is $CR_6$ or N; Y is $CR_3$; $R_1$ is —C(O)$NH_2$; and $R_3$ is H. Included in this embodiment are compounds in which X is $CR_6$ and Y is $CR_3$. Also, included in this embodiment are compounds in which X is N and Y is $CR_3$.

One embodiment provides a compound of Formula (I) or a salt thereof, wherein X is $CR_6$ or N; Y is $CR_3$; $R_1$ is —CN; and $R_3$ is —$CH_3$. Included in this embodiment are compounds in which X is $CR_6$ and Y is $CR_3$. Also, included in this embodiment are compounds in which X is N and Y is $CR_3$.

One embodiment provides a compound of Formula (I) or a salt thereof, wherein X is $CR_6$ or N; Y is $CR_3$; $R_1$ is —CN; and $R_3$ is F. Included in this embodiment are compounds in which X is $CR_6$ and Y is $CR_3$. Also, included in this embodiment are compounds in which X is N and Y is $CR_3$.

One embodiment provides a compound of Formula (I) or a salt thereof, wherein X is $CR_6$ or N; Y is $CR_3$; $R_1$ is —CN; and $R_3$ is $C_1$. Included in this embodiment are compounds in which X is $CR_6$ and Y is $CR_3$. Also, included in this embodiment are compounds in which X is N and Y is $CR_3$.

One embodiment provides a compound of Formula (I) or a salt thereof, wherein X is $CR_6$ or N; Y is $CR_3$; $R_1$ is —CN; and $R_3$ is Br. Included in this embodiment are compounds in which X is $CR_6$ and Y is $CR_3$. Also, included in this embodiment are compounds in which X is N and Y is $CR_3$.

One embodiment provides a compound of Formula (I) or a salt thereof, wherein X is $CR_6$ or N; Y is $CR_3$; $R_1$ is $C_1$; and $R_3$ is H. Included in this embodiment are compounds in which X is $CR_6$ and Y is $CR_3$. Also, included in this embodiment are compounds in which X is N and Y is $CR_3$.

One embodiment provides a compound of Formula (I) or a salt thereof, wherein $R_4$ is $R_{4a}$ or —$CH_2R_{4a}$. Included in this embodiment are compounds in which $R_4$ is $R_{4a}$. Also included in this embodiment are compounds in which $R_{4a}$ is $C_{3-6}$ cycloalkyl, oxetanyl, tetrahydrofuranyl, tetrahydropyranyl, piperidinyl, piperazinyl, morpholinyl, phenyl, naphthalenyl, furanyl, pyranyl, pyrrolyl, pyrazolyl, imidazolyl, isoxazolyl, oxazolyl, oxadiazolyl, triazolyl, indolyl, indazolyl, phthalazinyl, pyridazinyl, pyridinyl, pyrimidinyl, pyrazinyl, triazinyl, benzoxazolyl, benzothiazolyl, benzoimidazolyl, quinolinyl, isoquinolinyl, quinoxalinyl, quinazolinyl, naphthyridinyl, or dihydrobenzo[b][1,4]dioxepinyl, each substituted with zero to 3 $R_{4b}$.

One embodiment provides a compound of Formula (I) or a salt thereof, wherein $R_4$ is $R_{4a}$ or —$CH_2R_{4a}$. Included in this embodiment are compounds in which $R_4$ is $R_{4a}$. Also, included in this embodiment are compounds in which $R_4$ is —$CH_2R_{4a}$. Further, included in this embodiment are compounds in which $R_{4a}$ is $C_{3-6}$ cycloalkyl, oxetanyl, tetrahydrofuranyl, tetrahydropyranyl, piperidinyl, piperazinyl, morpholinyl, phenyl, naphthalenyl, furanyl, pyranyl, pyrrolyl, pyrazolyl, imidazolyl, isoxazolyl, oxazolyl, oxadiazolyl, triazolyl, indolyl, indazolyl, phthalazinyl, pyridazinyl, pyridinyl, pyrimidinyl, pyrazinyl, triazinyl, benzothiazolyl, benzoimidazolyl, quinolinyl, isoquinolinyl, quinoxalinyl, quinazolinyl, naphthyridinyl, or dihydrobenzo[b][1,4]dioxepinyl, each substituted with zero to 3 $R_{4b}$.

One embodiment provides a compound of Formula (I) or a salt thereof, wherein $R_4$ is $R_{4a}$; and $R_{4a}$ is $C_{3-6}$ cycloalkyl, oxetanyl, tetrahydrofuranyl, tetrahydropyranyl, piperidinyl, piperazinyl, morpholinyl, phenyl, naphthalenyl, furanyl, pyranyl, pyrrolyl, pyrazolyl, imidazolyl, isoxazolyl, oxazolyl, oxadiazolyl, triazolyl, indolyl, indazolyl, phthalazinyl, pyridazinyl, pyridinyl, pyrimidinyl, pyrazinyl, triazinyl, benzoxazolyl, benzothiazolyl, benzoimidazolyl, quinolinyl, isoquinolinyl, quinoxalinyl, quinazolinyl, naphthyridinyl, or dihydrobenzo[b][1,4]dioxepinyl, each substituted with zero to 3 $R_{4b}$. Included in this embodiment are compounds in which $R_{4a}$ is cyclohexyl, phenyl, indazolyl, phthalazinyl, pyridazinyl, pyridinyl, pyrimidinyl, pyrazinyl, benzoxazolyl, benzothiazolyl, quinolinyl, quinoxalinyl, quinazolinyl, 1,7-naphthyridinyl, or dihydrobenzo[b][1,4]dioxepinyl, each substituted with zero to 3 $R_{4b}$; and each $R_{4b}$ is independently F, Cl, Br, —CN, —CH$_3$, —CH$_2$CH$_3$, —CH$_2$CH$_2$CH$_3$, —CH(CH$_3$)$_2$, —CH$_2$CH$_2$CH$_2$CH$_3$, —C(CH$_3$)$_3$, —CH$_2$CH$_2$CH$_2$CH$_2$CH$_3$, —C(CH$_3$)$_2$CH$_2$CH$_3$, —CHF$_2$, —CF$_3$, —OCH$_3$, —OCH(CH$_3$)$_2$, —OC(CH$_3$)$_3$, —OCF$_3$, —C(O)N(CH$_3$)$_2$, —S(O)$_2$CH$_3$, —CH$_2$(phenyl), —C(CH$_3$)$_2$(phenyl), cyclopropyl, cyclopentyl, or cyclohexyl.

One embodiment provides a compound of Formula (I) or a salt thereof, wherein $R_4$ is $R_{4a}$; and $R_{4a}$ is $C_{3-6}$ cycloalkyl, oxetanyl, tetrahydrofuranyl, tetrahydropyranyl, piperidinyl, piperazinyl, morpholinyl, phenyl, naphthalenyl, furanyl, pyranyl, pyrrolyl, pyrazolyl, imidazolyl, isoxazolyl, oxazolyl, oxadiazolyl, triazolyl, indolyl, indazolyl, phthalazinyl, pyridazinyl, pyridinyl, pyrimidinyl, pyrazinyl, triazinyl, benzothiazolyl, benzoimidazolyl, quinolinyl, isoquinolinyl, quinoxalinyl, quinazolinyl, naphthyridinyl, or dihydrobenzo[b][1,4]dioxepinyl, each substituted with zero to 3 $R_{4b}$. Included in this embodiment are compounds in which $R_{4a}$ is phenyl, indazolyl, phthalazinyl, pyridazinyl, pyridinyl, pyrimidinyl, quinolinyl, quinoxalinyl, quinazolinyl, 1,7-naphthyridinyl, or dihydrobenzo[b][1,4]dioxepinyl, each substituted with zero to 2 $R_{4b}$; and each $R_{4b}$ is independently F, Cl, Br, —CN, —CH$_3$, —CH$_2$CH$_3$, —CH$_2$CH$_2$CH$_3$, —CH(CH$_3$)$_2$, —CH$_2$CH$_2$CH$_2$CH$_3$, —C(CH$_3$)$_3$, —CH$_2$CH$_2$CH$_2$CH$_2$CH$_3$, —C(CH$_3$)$_2$CH$_2$CH$_3$, —CF$_3$, —OCH$_3$, —OCH(CH$_3$)$_2$, —OC(CH$_3$)$_3$, —OCF$_3$, —C(O)N(CH$_3$)$_2$, —CH$_2$(phenyl), —C(CH$_3$)$_2$(phenyl), cyclopropyl, cyclopentyl, or cyclohexyl.

One embodiment provides a compound of Formula (I) or a salt thereof, wherein $R_4$ is $R_{4a}$, —CH$_2$R$_{4a}$, or —CH$_2$CH$_2$R$_{4a}$; and $R_{4a}$ is $C_{3-6}$ cycloalkyl, oxetanyl, tetrahydrofuranyl, tetrahydropyranyl, piperidinyl, piperazinyl, morpholinyl, phenyl, naphthalenyl, furanyl, pyranyl, pyrrolyl, pyrazolyl, imidazolyl, isoxazolyl, oxazolyl, oxadiazolyl, triazolyl, indolyl, indazolyl, phthalazinyl, pyridazinyl, pyridinyl, pyrimidinyl, pyrazinyl, triazinyl, benzoxazolyl, benzothiazolyl, benzoimidazolyl, quinolinyl, isoquinolinyl, quinoxalinyl, quinazolinyl, naphthyridinyl, or dihydrobenzo[b][1,4]dioxepinyl, each substituted with zero to 3 $R_{4b}$. Included in this embodiment are compounds in which $R_{4a}$ is $R_{4a}$ is cyclohexyl, phenyl, indazolyl, phthalazinyl, pyridazinyl, pyridinyl, pyrimidinyl, pyrazinyl, benzoxazolyl, benzothiazolyl, quinolinyl, quinoxalinyl, quinazolinyl, 1,7-naphthyridinyl, or dihydrobenzo[b][1,4]dioxepinyl, each substituted with zero to 3 $R_{4b}$; and each $R_{4b}$ is independently F, Cl, Br, —CN, —CH$_3$, —CH$_2$CH$_3$, —CH$_2$CH$_2$CH$_3$, —CH(CH$_3$)$_2$, —CH$_2$CH$_2$CH$_2$CH$_3$, —C(CH$_3$)$_3$, —CH$_2$CH$_2$CH$_2$CH$_3$, —CHF$_2$, —CF$_3$, —OCH$_3$, —OCH(CH$_3$)$_2$, —OC(CH$_3$)$_3$, —OCF$_3$, —C(O)N(CH$_3$)$_2$, —S(O)$_2$CH$_3$, —CH$_2$(phenyl), —C(CH$_3$)$_2$(phenyl), cyclopropyl, cyclopentyl, or cyclohexyl.

One embodiment provides a compound of Formula (I) or a salt thereof, wherein $R_4$ is $R_{4a}$, —CH$_2$R$_{4a}$, or —CH$_2$CH$_2$R$_{4a}$; and $R_{4a}$ is $C_{3-6}$ cycloalkyl, oxetanyl, tetrahydrofuranyl, tetrahydropyranyl, piperidinyl, piperazinyl, morpholinyl, phenyl, naphthalenyl, furanyl, pyranyl, pyrrolyl, pyrazolyl, imidazolyl, isoxazolyl, oxazolyl, oxadiazolyl, triazolyl, indolyl, indazolyl, phthalazinyl, pyridazinyl, pyridinyl, pyrimidinyl, pyrazinyl, triazinyl, benzothiazolyl, benzoimidazolyl, quinolinyl, isoquinolinyl, quinoxalinyl, quinazolinyl, naphthyridinyl, or dihydrobenzo[b][1,4]dioxepinyl, each substituted with zero to 3 $R_{4b}$. Included in this embodiment are compounds in which $R_{4a}$ is phenyl, indazolyl, phthalazinyl, pyridazinyl, pyridinyl, pyrimidinyl, quinolinyl, quinoxalinyl, quinazolinyl, 1,7-naphthyridinyl, or dihydrobenzo[b][1,4]dioxepinyl, each substituted with zero to 2 $R_{4b}$; and each $R_{4b}$ is independently F, Cl, Br, —CN, —CH$_3$, —CH$_2$CH$_3$, —CH$_2$CH$_2$CH$_3$, —CH(CH$_3$)$_2$, —CH$_2$CH$_2$CH$_2$CH$_3$, —C(CH$_3$)$_3$, —CH$_2$CH$_2$CH$_2$CH$_2$CH$_3$, —C(CH$_3$)$_2$CH$_2$CH$_3$, —CF$_3$, —OCH$_3$, —OCH(CH$_3$)$_2$, —OC(CH$_3$)$_3$, —OCF$_3$, —C(O)N(CH$_3$)$_2$, —CH$_2$(phenyl), —C(CH$_3$)$_2$(phenyl), cyclopropyl, cyclopentyl, or cyclohexyl.

One embodiment provides a compound of Formula (I) or a salt thereof, wherein $R_{4a}$ is cyclohexyl, phenyl, indazolyl, phthalazinyl, pyridazinyl, pyridinyl, pyrimidinyl, pyrazinyl, benzoxazolyl, benzothiazolyl, quinolinyl, quinoxalinyl, quinazolinyl, 1,7-naphthyridinyl, or dihydrobenzo[b][1,4]dioxepinyl, each substituted with zero to 3 $R_{4b}$; and each $R_{4b}$ is independently F, Cl, Br, —CN, —CH$_3$, —CH$_2$CH$_3$, —CH$_2$CH$_2$CH$_3$, —CH(CH$_3$)$_2$, —CH$_2$CH$_2$CH$_2$CH$_3$, —C(CH$_3$)$_3$, —CH$_2$CH$_2$CH$_2$CH$_2$CH$_3$, —C(CH$_3$)$_2$CH$_2$CH$_3$, —CHF$_2$, —CF$_3$, —OCH$_3$, —OCH(CH$_3$)$_2$, —OC(CH$_3$)$_3$, —OCF$_3$, —C(O)N(CH$_3$)$_2$, —S(O)$_2$CH$_3$, —CH$_2$(phenyl), —C(CH$_3$)$_2$(phenyl), cyclopropyl, cyclopentyl, or cyclohexyl.

One embodiment provides a compound of Formula (I) or a salt thereof, wherein $R_{4a}$ is phenyl, indazolyl, phthalazinyl, pyridazinyl, pyridinyl, pyrimidinyl, quinolinyl, quinoxalinyl, quinazolinyl, 1,7-naphthyridinyl, or dihydrobenzo[b][1,4]dioxepinyl, each substituted with zero to 2 $R_{4b}$; and each $R_{4b}$ is independently F, Cl, Br, —CN, —CH$_3$, —CH$_2$CH$_3$, —CH$_2$CH$_2$CH$_3$, —CH(CH$_3$)$_2$, —CH$_2$CH$_2$CH$_2$CH$_3$, —C(CH$_3$)$_3$, —CH$_2$CH$_2$CH$_2$CH$_2$CH$_3$, —C(CH$_3$)$_2$CH$_2$CH$_3$, —CF$_3$, —OCH$_3$, —OCH(CH$_3$)$_2$, —OC(CH$_3$)$_3$, —OCF$_3$, —C(O)N(CH$_3$)$_2$, —CH$_2$(phenyl), —C(CH$_3$)$_2$(phenyl), cyclopropyl, cyclopentyl, or cyclohexyl.

One embodiment provides a compound of Formula (I) or a salt thereof, wherein m is 1, 2 or 3. Included in this embodiment are compounds in which m is zero, 1 or 2. Also, included in this embodiment are compounds in which m is 1 or 2.

One embodiment provides a compound of Formula (I) or a salt thereof, wherein m is 1, 2 or 3; and each $R_5$ is independently F, —CN, —OH, $C_{1-5}$ alkyl substituted with zero to 4 $R_g$, $C_{1-3}$ alkoxy substituted with zero to 3 $R_g$, $C_{2-3}$ alkenyl substituted with zero to 4 $R_g$, $C_{2-3}$ alkynyl substituted with zero to 4 $R_g$, —(CH$_2$)$_{1-2}$($C_{3-4}$ cycloalkyl substituted with zero to 4 $R_g$), phenyl substituted with zero to 3 $R_g$, oxadiazolyl substituted with zero to 3 $R_g$, pyridinyl substituted with zero to 3 $R_g$, —(CH$_2$)$_{1-2}$(heterocyclyl substituted with zero to 4 $R_g$), —O(CH$_2$)$_{1-2}$(heterocyclyl substituted with zero to 4 $R_g$), —(CH$_2$)$_{1-2}$NR$_c$C(O)(C$_{1-4}$ alkyl), —(CH$_2$)$_{1-2}$NR$_c$C(O)O(C$_{1-4}$ alkyl), —(CH$_2$)$_{1-2}$NR$_c$S(O)$_2$(C$_{1-4}$ alkyl), —C(O)(C$_{1-4}$ alkyl), —C(O)OH, —C(O)O(C$_{1-4}$ alkyl), —C(O)O(C$_{3-4}$ cycloalkyl), —C(O)NR$_a$R$_a$, or —C(O)NR$_a$(C$_{3-4}$ cycloalkyl). Included in this embodiment are compounds in which each $R_5$ is independently hydrogen, F, —OH, $C_{1-2}$ alkyl, $C_{1-3}$ alkoxy, —CH$_2$CF$_3$, —OCH$_2$CH$_2$OCH$_3$, —OCH$_2$CH$_2$N(CH$_3$)$_2$, —OCH$_2$(cyclopropyl), or —OCH$_2$CH$_2$(morpholinyl).

One embodiment provides a compound of Formula (I) or a salt thereof, wherein m is 1, 2 or 3; and each $R_5$ is independently F, —CN, —OH, $C_{1-5}$ alkyl substituted with zero to 4 $R_g$, $C_{1-2}$ alkoxy substituted with zero to 3 $R_g$, $C_{2-3}$ alkenyl substituted with zero to 4 $R_g$, $C_{2-3}$ alkynyl substituted with zero to 4 $R_g$, $C_{3-4}$ cycloalkyl substituted with zero to 4 $R_g$, phenyl substituted with zero to 3 $R_g$, oxadiazolyl substituted with zero to 3 $R_g$, pyridinyl substituted with zero to 3 $R_g$, —$(CH_2)_{1-2}$(heterocyclyl substituted with zero to 4 $R_g$), —$(CH_2)_{1-2}NR_cC(O)(C_{1-4}$ alkyl), —$(CH_2)_{1-2}NR_cC(O)O(C_{1-4}$ alkyl), —$(CH_2)_{1-2}NR_cS(O)_2(C_{1-4}$ alkyl), —C(O)($C_{1-4}$ alkyl), —C(O)OH, —C(O)O($C_{1-4}$ alkyl), —C(O)O($C_{3-4}$ cycloalkyl), —C(O)$NR_aR_a$, or —C(O)$NR_a(C_{3-4}$ cycloalkyl). Included in this embodiment are compounds in which each $R_5$ is independently hydrogen, F, —CN, —OH, $C_{1-2}$ alkyl substituted with zero to 4 $R_g$, or $C_{1-2}$ alkoxy. Also, included in this embodiment are compounds in which each $R_5$ is independently hydrogen, F, —OH, $C_{1-2}$ alkyl, or $C_{1-2}$ alkoxy.

One embodiment provides a compound of Formula (I) or a salt thereof, wherein m is 1 or 2; and each $R_5$ is independently hydrogen, F, —OH, $C_{1-2}$ alkyl, $C_{1-3}$ alkoxy, —$CH_2CF_3$, —$OCH_2CH_2OCH_3$, —$OCH_2CH_2N(CH_3)_2$, —$OCH_2$(cyclopropyl), or —$OCH_2CH_2$(morpholinyl). Included in this embodiment are compounds in which each $R_5$ is independently F, —OH, $C_{1-2}$ alkyl, $C_{1-3}$ alkoxy, —$CH_2CF_3$, —$OCH_2CH_2OCH_3$, —$OCH_2CH_2N(CH_3)_2$, —$OCH_2$(cyclopropyl), or —$OCH_2CH_2$(morpholinyl).

One embodiment provides a compound of Formula (I) or a salt thereof, wherein m is 1; and $R_5$ is hydrogen, F, —OH, $C_{1-2}$ alkyl, $C_{1-3}$ alkoxy, —$CH_2CF_3$, —$OCH_2CH_2OCH_3$, —$OCH_2CH_2N(CH_3)_2$, —$OCH_2$(cyclopropyl), or —$OCH_2CH_2$(morpholinyl). Included in this embodiment are compounds in which each $R_5$ is independently F, —OH, $C_{1-2}$ alkyl, $C_{1-3}$ alkoxy, —$CH_2CF_3$, —$OCH_2CH_2OCH_3$, —$OCH_2CH_2N(CH_3)_2$, —$OCH_2$(cyclopropyl), or —$OCH_2CH_2$(morpholinyl).

One embodiment provides a compound of Formula (I) or a salt thereof, wherein m is 1 or 2; and each $R_5$ is independently hydrogen, F, —OH, $C_{1-2}$ alkyl, or $C_{1-2}$ alkoxy. Included in this embodiment are compounds in which each $R_5$ is independently F, —OH, $C_{1-2}$ alkyl, or $C_{1-2}$ alkoxy.

One embodiment provides a compound of Formula (I) or a salt thereof, wherein m is 1; and $R_5$ hydrogen, F, —OH, $C_{1-2}$ alkyl, or $C_{1-2}$ alkoxy. Included in this embodiment are compounds in which $R_5$ is F, —OH, $C_{1-2}$ alkyl, or $C_{1-2}$ alkoxy.

One embodiment provides a compound of Formula (I) or a salt thereof, having a structure selected from:

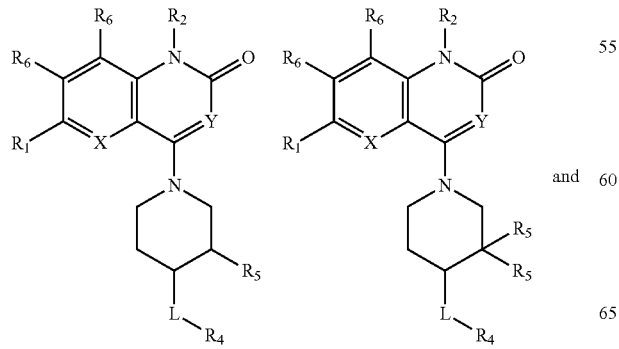

One embodiment provides a compound of Formula (I) or a salt thereof, having a structure selected from:

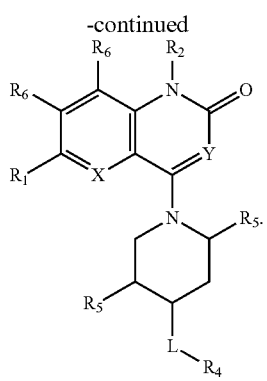

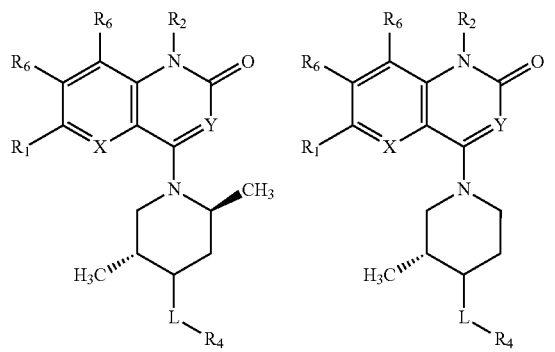

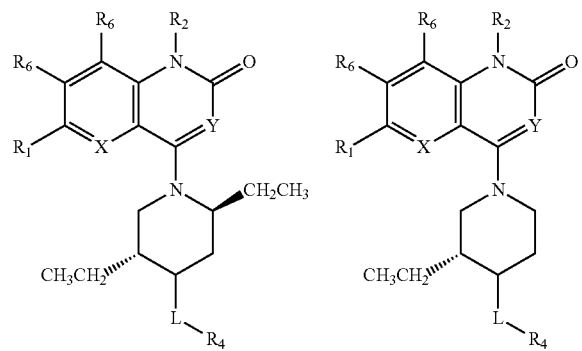

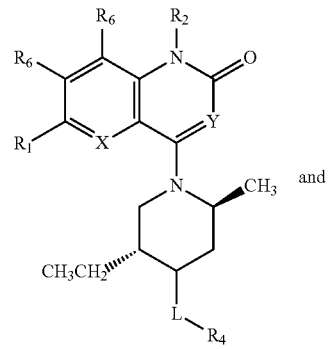

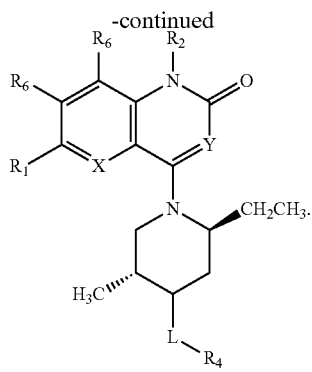

One embodiment provides a compound of Formula (I) or a salt thereof, wherein said compound is: 6-fluoro-4-(4-(3-fluoro-5-methylphenoxy)piperidin-1-yl)-1-methyl-3-nitroquinolin-2(1H)-one (1); 6-fluoro-4-(4-(4-isopropylphenoxy)piperidin-1-yl)-1-methyl-3-nitroquinolin-2(1H)-one (2); 6-fluoro-1-methyl-3-nitro-4-(4-(4-(trifluoromethoxy)phenoxy) piperidin-1-yl)quinolin-2(1H)-one (3); 6-fluoro-1-methyl-3-nitro-4-(4-(m-tolyloxy)piperidin-1-yl)quinolin-2 (1H)-one (4); 4-(4-((1H-indazol-4-yl)oxy)piperidin-1-yl)-6-fluoro-1-methyl-3-nitroquinolin-2(1H)-one (5); 3-((1-(6-fluoro-1-methyl-3-nitro-2-oxo-1,2-dihydroquinolin-4-yl) piperidin-4-yl)oxy)benzonitrile (6); 4-(4-(3-chlorophenoxy)piperidin-1-yl)-6-fluoro-1-methyl-3-nitroquinolin-2(1H)-one (7); 6-fluoro-4-(4-(2-methoxy-5-(trifluoromethyl) phenoxy)piperidin-1-yl)-1-methyl-3-nitroquinolin-2(1H)-one (8); 6-fluoro-4-(4-(3-fluorophenoxy)piperidin-1-yl)-1-methyl-3-nitroquinolin-2(1H)-one (9); or 4-(4-(4-(tert-butyl)phenoxy)piperidin-1-yl)-1-methyl-2-oxo-1,2-dihydroquinoline-6-carbonitrile (53).

One embodiment provides a compound of Formula (I) or a salt thereof, wherein said compound is: 4-((2S,5S)-4-((5-isopropoxypyridin-2-yl)oxy)-2,5-dimethylpiperidin-1-yl)-1-methyl-2-oxo-1,2-dihydropyrido[3,2-d]pyrimidine-6-carbonitrile (243 and 246); 4-((2R,5R)-4-((5-isopropoxypyridin-2-yl)oxy)-2,5-dimethylpiperidin-1-yl)-1-methyl-2-oxo-1,2-dihydropyrido[3,2-d]pyrimidine-6-carbonitrile (244-245); 4-((2R,5S)-4-((5-isopropoxypyridin-2-yl)oxy)-2,5-dimethylpiperidin-1-yl)-1-methyl-2-oxo-1,2-dihydropyrido[3,2-d]pyrimidine-6-carbonitrile (248-249); 4-((2S,5R)-4-((5-isopropoxypyridin-2-yl)oxy)-2,5-dimethylpiperidin-1-yl)-1-methyl-2-oxo-1,2-dihydropyrido[3,2-d] pyrimidine-6-carbonitrile (247 and 250); 4-((2R,5S)-2,5-dimethyl-4-(3-(trifluoromethyl)phenoxy)piperidin-1-yl)-1-methyl-2-oxo-1,2-dihydropyrido[3,2-d]pyrimidine-6-carbonitrile (251 and 253); 4-((2S,5R)-2,5-dimethyl-4-(3-(trifluoromethyl) phenoxy)piperidin-1-yl)-1-methyl-2-oxo-1,2-dihydropyrido[3,2-d]pyrimidine-6-carbonitrile (252 and 254); 4-((2R,5R)-2,5-dimethyl-4-(3-(trifluoromethyl)phenoxy)piperidin-1-yl)-1-methyl-2-oxo-1,2-dihydropyrido[3,2-d]pyrimidine-6-carbonitrile (256-257); 4-((2S,5S)-2,5-dimethyl-4-(3-(trifluoromethyl)phenoxy)piperidin-1-yl)-1-methyl-2-oxo-1,2-dihydropyrido[3,2-d]pyrimidine-6-carbonitrile (255 and 258); (±)-trans-6-chloro-4-(3-hydroxy-4-(3-(trifluoromethyl)phenoxy)piperidin-1-yl)-1-methylpyrido[3,2-d]pyrimidin-2(1H)-one (271-272); (±)-trans-4-(3-hydroxy-4-(3-(trifluoromethyl)phenoxy) piperidin-1-yl)-1-methyl-2-oxo-1,2-dihydropyrido[3,2-d] pyrimidine-6-carbonitrile (273-274); 6-chloro-4-((3R,4R)-3-methoxy-4-(3-(trifluoromethyl)phenoxy)piperidin-1-yl)-1-methylpyrido[3,2-d]pyrimidin-2(1H)-one (275); (±)-trans-4-(3-hydroxy-4-(3-(trifluoromethyl)phenoxy) piperidin-1-yl)-1-methyl-2-oxo-1,2-dihydropyrido[3,2-d] pyrimidine-6-carbonitrile (276-277); 4-((3R,4R)-3-ethoxy-4-(3-(trifluoromethyl)phenoxy)piperidin-1-yl)-1-methyl-2-oxo-1,2-dihydropyrido[3,2-d]pyrimidine-6-carbonitrile (278-279); 6-chloro-4-((2S,4R,5R)-5-ethyl-4-((5-isopropoxypyridin-2-yl)oxy)-2-methylpiperidin-1-yl)-1-methylpyrido[3,2-d]pyrimidin-2(1H)-one (300); 4-((2S,4R,5R)-5-ethyl-4-((5-isopropoxypyridin-2-yl)oxy)-2-methylpiperidin-1-yl)-1-methyl-2-oxo-1,2-dihydropyrido[3,2-d]pyrimidine-6-carbonitrile (301); 6-chloro-4-((2R,4R,5R)-5-ethyl-4-((5-isopropoxypyridin-2-yl)oxy)-2-methylpiperidin-1-yl)-1-methylpyrido[3,2-d]pyrimidin-2 (1H)-one (302); 4-((2R,4R,5R)-5-ethyl-4-((5-isopropoxypyridin-2-yl)oxy)-2-methylpiperidin-1-yl)-1-methyl-2-oxo-1,2-dihydropyrido[3,2-d]pyrimidine-6-carbonitrile (303); 6-chloro-4-((2R,4S,5R)-5-ethyl-4-((5-isopropoxypyridin-2-yl)oxy)-2-methylpiperidin-1-yl)-1-methylpyrido[3,2-d]pyrimidin-2(1H)-one (304); 4-((2R,4S,5R)-5-ethyl-4-((5-isopropoxypyridin-2-yl)oxy)-2-methylpiperidin-1-yl)-1-methyl-2-oxo-1,2-dihydropyrido[3,2-d]pyrimidine-6-carbonitrile (305); 6-chloro-4-((2S,4S,5R)-5-ethyl-4-((5-isopropoxypyridin-2-yl)oxy)-2-methylpiperidin-1-yl)-1-methylpyrido[3,2-d]pyrimidin-2 (1H)-one (306); 4-((2S,4S,5R)-5-ethyl-4-((5-isopropoxypyridin-2-yl)oxy)-2-methylpiperidin-1-yl)-1-methyl-2-oxo-1,2-dihydropyrido[3,2-d]pyrimidine-6-carbonitrile (307); 1-methyl-2-oxo-4-((2S,5S)-2,4,5-trimethyl-4-(3-(trifluoromethyl)phenoxy)piperidin-1-yl)-1,2-dihydropyrido[3,2-d]pyrimidine-6-carbonitrile (339-340); (±)-trans-6-chloro-4-(3-ethoxy-4-((5-isopropoxypyridin-2-yl)oxy)piperidin-1-yl)-1-methylpyrido[3,2-d]pyrimidin-2 (1H)-one (399); trans-4-(3-ethoxy-4-((5-isopropoxypyridin-2-yl)oxy)piperidin-1-yl)-1-methyl-2-oxo-1,2-dihydropyrido [3,2-d]pyrimidine-6-carbonitrile (400-401); trans-4-(3-ethoxy-4-phenoxypiperidin-1-yl)-1-methyl-2-oxo-1,2-dihydropyrido[3,2-d]pyrimidine-6-carbonitrile (402-403); or 4-((3S,4S)-3-ethoxy-4-(4-(trifluoromethyl)phenoxy)piperidin-1-yl)-1-methyl-2-oxo-1,2-dihydropyrido[3,2-d]pyrimidine-6-carbonitrile (404-405).

One embodiment provides a compound of Formula (I) or a salt thereof, wherein said compound is: 6-chloro-4-(4-(3-methoxyphenoxy)piperidin-1-yl)-1-methyl-2-oxo-1,2-dihydro-1,5-naphthyridine-3-carbonitrile (10); 6-chloro-1-methyl-2-oxo-4-(4-(2-(trifluoromethyl)phenoxy)piperidin-1-yl)-1,2-dihydro-1,5-naphthyridine-3-carbonitrile (11); 6-chloro-4-(4-(3,4-difluorophenoxy)piperidin-1-yl)-1-methyl-2-oxo-1,2-dihydro-1,5-naphthyridine-3-carbonitrile (12); 6-chloro-1-methyl-2-oxo-4-(4-(3-(trifluoromethoxy) phenoxy)piperidin-1-yl)-1,2-dihydro-1,5-naphthyridine-3-carbonitrile (13); 6-chloro-4-(4-(4-methoxyphenoxy)piperidin-1-yl)-1-methyl-2-oxo-1,2-dihydro-1,5-naphthyridine-3-carbonitrile (14); 4-(4-(4-(tert-butyl)phenoxy)piperidin-1-yl)-6-chloro-1-methyl-2-oxo-1,2-dihydro-1,5-naphthyridine-3-carbonitrile (15); 6-chloro-4-(4-(4-chlorophenoxy)piperidin-1-yl)-1-methyl-2-oxo-1,2-dihydro-1,5-naphthyridine-3-carbonitrile (16); 6-chloro-4-(4-(3-fluoro-4-(trifluoromethoxy)phenoxy)piperidin-1-yl)-1-methyl-2-oxo-1,2-dihydro-1,5-naphthyridine-3-carbonitrile (17); 6-chloro-4-(4-(2-chlorophenoxy) piperidin-1-yl)-1-methyl-2-oxo-1,2-dihydro-1,5-naphthyridine-3-carbonitrile (18); 6-chloro-1-methyl-2-oxo-4-(4-(4-(trifluoromethoxy)phenoxy)piperidin-1-yl)-1,2-dihydro-1,5-naphthyridine-3-carbonitrile (19); 6-chloro-4-(4-(4-fluorophenoxy)piperidin-1-yl)-1-methyl-2-oxo-1,2-dihydro-1,5-naphthyridine-3-carbonitrile (20); 6-chloro-1-methyl-2-oxo-4-(4-(p-tolyloxy)piperidin-1-yl)-1,2-dihydro-1,5-naphthyridine-3-carbonitrile (21); 6-chloro-1-methyl-2- oxo-4-(4-(m-tolyloxy)piperidin-1-yl)-1,2-dihydro-1,5-naphthyridine-3-carbonitrile (22); 6-chloro-4-(4-(2-chloro-5-fluorophenoxy)piperidin-1-yl)-1-methyl-2-oxo-1,2-dihydro-1,5-naphthyridine-3-carbonitrile (23); 6-chloro-1-methyl-2-oxo-4-(4-(3-(trifluoromethyl)phenoxy)piperidin-1-yl)-1,2-dihydro-1,5-naphthyridine-3-carbonitrile (24); 4-((1-(6-chloro-3-cyano-1-methyl-2-oxo-1,2-dihydro-1,5-naphthyridin-4-yl)piperidin-4-yl)oxy)-N,N-dimethylbenzamide (25); 4-(4-(4-bromo-2-methylphenoxy)piperidin-1-yl)-6-chloro-1-methyl-2-oxo-1,2-dihydro-1,5-naphthyridine-3-carbonitrile (26); 6-chloro-4-(4-(3-chlorophenoxy)piperidin-1-yl)-1-methyl-2-oxo-1,2-dihydro-1,5-naphthyridine-3-carbonitrile (27); 6-chloro-4-(4-(3-chloro-5-fluorophenoxy)piperidin-1-yl)-1-methyl-2-oxo-1,2-dihydro-1,5-naphthyridine-3-carbonitrile (28); -chloro-1-methyl-4-(4-(2-methyl-4-(trifluoromethoxy)phenoxy)piperidin-1-yl)-2-oxo-1,2-dihydro-1,5-naphthyridine-3-carbonitrile (29); 6-chloro-1-methyl-2-oxo-4-(4-(4-(trifluoromethyl)phenoxy)piperidin-1-yl)-1,2-dihydro-1,5-naphthyridine-3-carbonitrile (30); 4-(4-(4-(tert-butoxy)phenoxy)piperidin-1-yl)-6-chloro-1-methyl-2-oxo-1,2-dihydro-1,5-naphthyridine-3-carbonitrile (31); 6-chloro-4-(4-(4-cyanophenoxy)piperidin-1-yl)-1-methyl-2-oxo-1,2-dihydro-1,5-naphthyridine-3-carbonitrile (32); 6-chloro-1-methyl-2-oxo-4-(4-(2-(trifluoromethoxy)phenoxy)piperidin-1-yl)-1,2-dihydro-1,5-naphthyridine-3-carbonitrile (33); 6-chloro-4-(4-(3-cyanophenoxy)piperidin-1-yl)-1-methyl-2-oxo-1,2-dihydro-1,5-naphthyridine-3-carbonitrile (34); 6-chloro-4-(4-(2-methoxyphenoxy)piperidin-1-yl)-1-methyl-2-oxo-1,2-dihydro-1,5-naphthyridine-3-carbonitrile (35); 6-chloro-4-(4-(4-fluoro-2-methoxyphenoxy)piperidin-1-yl)-1-methyl-2-oxo-1,2-dihydro-1,5-naphthyridine-3-carbonitrile (36); 6-chloro-4-(4-(4-isopropylphenoxy)piperidin-1-yl)-1-methyl-2-oxo-1,2-dihydro-1,5-naphthyridine-3-carbonitrile (37); 6-chloro-4-(4-(3-chloro-4-cyanophenoxy) piperidin-1-yl)-1-methyl-2-oxo-1,2-dihydro-1,5-naphthyridine-3-carbonitrile (38); 6-chloro-4-(4-(4-chloro-3-methoxyphenoxy)piperidin-1-yl)-1-methyl-2-oxo-1,2-dihydro-1,5-naphthyridine-3-carbonitrile (39); 6-chloro-4-(4-(3-chloro-4-methylphenoxy)piperidin-1-yl)-1-methyl-2-oxo-1,2-dihydro-1,5-naphthyridine-3-carbonitrile (40); 6-chloro-4-(4-(2-chloro-4-(trifluoromethoxy)phenoxy)piperidin-1-yl)-1-methyl-2-oxo-1,2-dihydro-1,5-naphthyridine-3-carbonitrile (41); 6-chloro-4-(4-(3-chloro-4-(trifluoromethoxy)phenoxy)piperidin-1-yl)-1-methyl-2-oxo-1,2-dihydro-1,5-naphthyridine-3-carbonitrile (42); 6-chloro-4-(4-(2-cyanophenoxy)piperidin-1-yl)-1-methyl-2-oxo-1,2-dihydro-1,5-naphthyridine-3-carbonitrile (43); 6-chloro-4-(4-(2-fluorophenoxy)piperidin-1-yl)-1-methyl-2-oxo-1,2-dihydro-1,5-naphthyridine-3-carbonitrile (44); 6-chloro-4-(4-(3-fluorophenoxy)piperidin-1-yl)-1-methyl-2-oxo-1,2-dihydro-1,5-naphthyridine-3-carbonitrile (45); 6-chloro-1-methyl-2-oxo-4-(4-phenoxypiperidin-1-yl)-1,2-dihydro-1,5-naphthyridine-3-carbonitrile (46); 6-bromo-1-methyl-2-oxo-4-(4-(4-(trifluoromethoxy)phenoxy)piperidin-1-yl)-1,2-dihydro-1,5-naphthyridine-3-carbonitrile (47); 6-methoxy-1-methyl-2-oxo-4-(4-(4-(trifluoromethoxy) phenoxy)piperidin-1-yl)-1,2-dihydro-1,5-naphthyridine-3-carbonitrile (48); 1-methyl-2,6-dioxo-4-(4-(4-(trifluoromethoxy)phenoxy)piperidin-1-yl)-1,2,5,6-tetrahydro-1,5-naphthyridine-3-carbonitrile (49); 5-methyl-6-oxo-8-(4-(4-(trifluoromethoxy)phenoxy) piperidin-1-yl)-5,6-dihydro-1,5-naphthyridine-2,7-dicarbonitrile (50); 5-methyl-7-nitro-6-oxo-8-(4-(4-(trifluoromethoxy)phenoxy)piperidin-1-yl)-5,6-dihydro-1,5-naphthyridine-2-carbonitrile (51); 5-methyl-6-oxo-8-(4-(4-(trifluoromethoxy)phenoxy)piperidin-1-yl)-5,6-dihydro-1,5-naphthyridine-2-carbonitrile (52); 5-methyl-6-oxo-8-(4-(4-(tert-pentyl)phenoxy) piperidin-1-yl)-5,6-dihydro-1,5-naphthyridine-2-carbonitrile (54); 8-(4-(4-benzylphenoxy) piperidin-1-yl)-5-methyl-6-oxo-5,6-dihydro-1,5-naphthyridine-2-carbonitrile (55); 8-(4-(4-butylphenoxy)piperidin-1-yl)-5-methyl-6-oxo-5,6-dihydro-1,5-naphthyridine-2-carbonitrile (56); 5-methyl-6-oxo-8-(4-(4-propylphenoxy)piperidin-1-yl)-5,6-dihydro-1,5-naphthyridine-2-carbonitrile (57); 8-(4-(4-cyclopentylphenoxy)piperidin-1-yl)-5-methyl-6-oxo-5,6-dihydro-1,5-naphthyridine-2-carbonitrile (58); 8-(4-(4-cyclopropylphenoxy)piperidin-1-yl)-5-methyl-6-oxo-5,6-dihydro-1,5-naphthyridine-2-carbonitrile (59); 8-(4-(4-isopropyl-3-methylphenoxy)piperidin-1-yl)-5-methyl-6-oxo-5,6-dihydro-1,5-naphthyridine-2-carbonitrile (60); 5-methyl-6-oxo-8-(4-((5,6,7,8-tetrahydronaphthalen-2-yl)oxy)piperidin-1-yl)-5,6-dihydro-1,5-naphthyridine-2-carbonitrile (61); 5-methyl-6-oxo-8-(4-(4-pentylphenoxy) piperidin-1-yl)-5,6-dihydro-1,5-naphthyridine-2-carbonitrile (62); 8-(4-(4-cyclohexylphenoxy)piperidin-1-yl)-5-methyl-6-oxo-5,6-dihydro-1,5-naphthyridine-2-carbonitrile (63); 8-(4-(4-(2-cyclohexylpropan-2-yl)phenoxy)piperidin-1-yl)-5-methyl-6-oxo-5,6-dihydro-1,5-naphthyridine-2-carbonitrile (64); 8-(4-(4-(tert-butoxy)phenoxy)piperidin-1-yl)-5-methyl-6-oxo-5,6-dihydro-1,5-naphthyridine-2-carbonitrile (65); 8-(4-((5-isopropoxypyridin-2-yl)oxy)piperidin-1-yl)-5-methyl-6-oxo-5,6-dihydro-1,5-naphthyridine-2-carbonitrile (66); 8-(4-((5-chloropyridin-2-yl)oxy)piperidin-1-yl)-5-methyl-6-oxo-5,6-dihydro-1,5-naphthyridine-2-carbonitrile (67); 8-(4-((6-(tert-butyl)pyridazin-3-yl)oxy)piperidin-1-yl)-5-methyl-6-oxo-5,6-dihydro-1,5-naphthyridine-2-carbonitrile (68); 5-methyl-6-oxo-8-(4-(quinoxalin-2-yloxy)piperidin-1-yl)-5,6-dihydro-1,5-naphthyridine-2-carbonitrile (69); 8-(4-((2,6-dimethylpyrimidin-4-yl)oxy) piperidin-1-yl)-5-methyl-6-oxo-5,6-dihydro-1,5-naphthyridine-2-carbonitrile (70); 5-methyl-6-oxo-8-(4-(quinazolin-4-yloxy)piperidin-1-yl)-5,6-dihydro-1,5-naphthyridine-2-carbonitrile (71); 5-methyl-8-(4-((2-methylpyrimidin-4-yl) oxy)piperidin-1-yl)-6-oxo-5,6-dihydro-1,5-naphthyridine-2-carbonitrile (72); 8-(4-((7-chloro-4-methoxyquinolin-2-yl)oxy)piperidin-1-yl)-5-methyl-6-oxo-5,6-dihydro-1,5-naphthyridine-2-carbonitrile (73); 8-(4-((1,7-naphthyridin-8-yl)oxy)piperidin-1-yl)-5-methyl-6-oxo-5,6-dihydro-1,5-naphthyridine-2-carbonitrile (74); 5-methyl-6-oxo-8-(4-(phthalazin-1-yloxy) piperidin-1-yl)-5,6-dihydro-1,5-naphthyridine-2-carbonitrile (75); 5-methyl-6-oxo-8-(4-((2-(trifluoromethyl)pyrimidin-4-yl)oxy)piperidin-1-yl)-5,6-dihydro-1,5-naphthyridine-2-carbonitrile (76); 5-methyl-6-oxo-8-(4-((5-(trifluoromethyl)pyridin-2-yl)oxy)piperidin-1-yl)-5,6-dihydro-1,5-naphthyridine-2-carbonitrile (77); 8-(4-((2-isopropyl-6-methylpyrimidin-4-yl)oxy)piperidin-1-yl)-5-methyl-6-oxo-5,6-dihydro-1,5-naphthyridine-2-carbonitrile (78); (+/−) 6-cyano-1-methyl-4-((3R,4R)-3-methyl-4-(4-(trifluoromethoxy)phenoxy)piperidin-1-yl)-1,5-naphthyridin-2 (1H)-one (79); 6-cyano-1-methyl-4-((3R,4R)-3-methyl-4-(4-(trifluoromethoxy)phenoxy)piperidin-1-yl)-1,5-naphthyridin-2(1H)-one (80); 6-cyano-1-methyl-4-(3R,4R)-3-methyl-4-(4-(trifluoromethoxy)phenoxy)piperidin-1-yl)-1,5-naphthyridin-2(1H)-one (81); 5-methyl-8-((3R,4R)-3-methyl-4-(4-(tert-pentyl)phenoxy) piperidin-1-yl)-6-oxo-5,6-dihydro-1,5-naphthyridine-2-carbonitrile (82-84); 8-((3R,4R)-4-(4-(tert-butoxy)phenoxy)-3-methylpiperidin-1-yl)-5-methyl-6-oxo-5,6-dihydro-1,5-naphthyridine-2-carbonitrile (85-87); 8-((3R,4R)-4-(4-(tert-butyl)phenoxy)-3-methylpiperidin-1-yl)-5-methyl-6-oxo-5,6-dihydro-1,5-naphthyridine-2-carbonitrile (88-90); 8-((3R,4R)-4-(3-cyclopropylphenoxy)-3-methylpiperidin-1-yl)-5-methyl-6-oxo-5,6-dihydro-1,5-naphthyridine-2-carbonitrile (91-93); 8-((3R,4R)-4-(4-isopropylphenoxy)-3-methylpiperidin-1-yl)-5-methyl-6-oxo-5,6-dihydro-1,5-naphthyridine-2-carbonitrile (94-96); 5-methyl-8-((3R,4R)-3-methyl-4-(4-(trifluoromethyl)phenoxy)piperidin-1-yl)-6-oxo-5,6-dihydro-1,5-naphthyridine-2-carbonitrile (97-99); 8-((3R,4R)-4-(4-cyclopentylphenoxy)-3-methylpiperidin-1-yl)-5-methyl-6-oxo-5,6-dihydro-1,5-naphthyridine-2-carbonitrile (100-102); 8-((3R,4R)-4-(3,4-difluorophenoxy)-3-methylpiperidin-1-yl)-5-methyl-6-oxo-5,6-dihydro-1,5-naphthyridine-2-carbonitrile (103-105); 8-((3R,4R)-4-(4-cyclohexylphenoxy)-3-methylpiperidin-1-yl)-5-methyl-6-oxo-5,6-dihydro-1,5-naphthyridine-2-carbonitrile (106); 5-methyl-8-((3R,4R)-3-methyl-4-(m-tolyloxy)piperidin-1-yl)-6-oxo-5,6-dihydro-1,5-naphthyridine-2-carbonitrile (107-109); 8-((3R,4R)-4-(4-ethylphenoxy)-3-methylpiperidin-1-yl)-5-methyl-6-oxo-5,6-dihydro-1,5-naphthyridine-2-carbonitrile (110); 8-((3R,4R)-4-(4-cyclopropylphenoxy)-3-methylpiperidin-1-yl)-5-methyl-6-oxo-5,6-dihydro-1,5-naphthyridine-2-carbonitrile (111); 8-((3R,4R)-4-(2-fluoro-4-(trifluoromethyl)phenoxy)-3-methylpiperidin-1-yl)-5-methyl-6-oxo-5,6-dihydro-1,5-naphthyridine-2-carbonitrile (112); 8-((3R,4R)-4-(2,4-difluorophenoxy)-3-methylpiperidin-1-yl)-5-methyl-6-oxo-5,6-dihydro-1,5-naphthyridine-2-carbonitrile (113-115); 8-((3R,4R)-4-(4-fluoro-2-(trifluoromethyl)phenoxy)-3-methylpiperidin-1-yl)-5-methyl-6-oxo-5,6-dihydro-1,5-naphthyridine-2-carbonitrile (116-118); 5-methyl-8-((3R,4R)-3-methyl-4-(p-tolyloxy)piperidin-1-yl)-6-oxo-5,6-dihydro-1,5-naphthyridine-2-carbonitrile (119-121); 8-((3R,4R)-4-(3-isopropylphenoxy)-3-methylpiperidin-1-yl)-5-methyl-6-oxo-5,6-dihydro-1,5-naphthyridine-2-carbonitrile (122); 8-((3R,4R)-4-(3-(tert-(123); 8-((3R,4R)-4-(2-fluoro-6-(trifluoromethyl)phenoxy)-3-methylpiperidin-1-yl)-5-methyl-6-oxo-5,6-dihydro-1,5-naphthyridine-2-carbonitrile (124); 8-((3R,4R)-4-(2,6-difluorophenoxy)-3-methylpiperidin-1-yl)-5-methyl-6-oxo-5,6-dihydro-1,5-naphthyridine-2-carbonitrile (125-127); 8-((3R,4R)-4-(4-fluorophenoxy)-3-methylpiperidin-1-yl)-5-methyl-6-oxo-5,6-dihydro-1,5-naphthyridine-2-carbonitrile (128-130); 5-methyl-8-((3R,4R)-3-methyl-4-(2,4,6-trifluorophenoxy)piperidin-1-yl)-6-oxo-5,6-dihydro-1,5-naphthyridine-2-carbonitrile (131); 8-((3R,4R)-4-((3,4-dihydro-2H-benzo[b][1,4]dioxepin-6-yl)oxy)-3-methylpiperidin-1-yl)-5-methyl-6-oxo-5,6-dihydro-1,5-naphthyridine-2-carbonitrile (132); 5-methyl-8-((3R,4R)-3-methyl-4-(4-(trifluoromethoxy)phenoxy)piperidin-1-yl)-6-oxo-5,6-dihydro-1,5-naphthyridine-2-carbonitrile (133-135); 5-methyl-8-((3R,4R)-3-methyl-4-(m-tolyloxy)piperidin-1-yl)-6-oxo-5,6-dihydro-1,5-naphthyridine-2,7-dicarbonitrile (136); 8-((3R,4R)-3-ethyl-4-(3-isopropylphenoxy)piperidin-1-yl)-5-methyl-6-oxo-5,6-dihydro-1,5-naphthyridine-2-carbonitrile (137-139); 8-((3R,4R)-3-ethyl-4-(3-(trifluoromethyl)phenoxy)piperidin-1-yl)-5-methyl-6-oxo-5,6-dihydro-1,5-naphthyridine-2-carbonitrile (140-142); 8-((3R,4R)-3-ethyl-4-(4-isopropylphenoxy)piperidin-1-yl)-5-methyl-6-oxo-5,6-dihydro-1,5-naphthyridine-2-carbonitrile (143-145); 8-((3R,4R)-3-ethyl-4-(4-(trifluoromethyl)phenoxy)piperidin-1-yl)-5-methyl-6-oxo-5,6-dihydro-1,5-naphthyridine-2-carbonitrile (146-148); 8-((3R,4R)-3-ethyl-4-(4-(tert-pentyl)phenoxy)piperidin-1-yl)-5-methyl-6-oxo-5,6-dihydro-1,5-naphthyridine-2-carbonitrile (149-151); 8-((3R,4R)-4-(4-(tert-butyl)phenoxy)-3-ethylpiperidin-1-yl)-5-methyl-6-oxo-5,6-dihydro-1,5-naphthyridine-2-carbonitrile (152-154); 8-((3R,4R)-4-(3-cyclopropylphenoxy)-3-ethylpiperidin-1-yl)-5-methyl-6-oxo-5,6-dihydro-1,5-naphthyridine-2-carbonitrile (155-157); 8-((3R,4R)-4-(4-(tert-butoxy)phenoxy)-3-ethylpiperidin-1-yl)-5-methyl-6-oxo-5,6-dihydro-1,5-naphthyridine-2-carbonitrile (158-160); 8-((3R,4R)-3-ethyl-4-(4-isopropoxyphenoxy)piperidin-1-yl)-5-methyl-6-oxo-5,6-dihydro-1,5-naphthyridine-2-carbonitrile (161); 8-((3R,4R)-3-ethyl-4-(3-(trifluoromethoxy)phenoxy)piperidin-1-yl)-5-methyl-6-oxo-5,6-dihydro-1,5-naphthyridine-2-carbonitrile (162-163); 8-((3R,4S)-3-ethyl-4-(3-isopropylphenoxy)piperidin-1-yl)-5-methyl-6-oxo-5,6-dihydro-1,5-naphthyridine-2-carbonitrile (164); 8-((3R,4S)-4-(3-(tert-butyl) phenoxy)-3-ethylpiperidin-1-yl)-5-methyl-6-oxo-5,6-dihydro-1,5-naphthyridine-2-carbonitrile (165-167); 5-methyl-8-((3R,4S)-3-methyl-4-(4-(tert-pentyl)phenoxy)piperidin-1-yl)-6-oxo-5,6-dihydro-1,5-naphthyridine-2-carbonitrile (169-171); 8-((3R,4S)-4-(4-(tert-butoxy)phenoxy)-3-methylpiperidin-1-yl)-5-methyl-6-oxo-5,6-dihydro-1,5-naphthyridine-2-carbonitrile (172-174); 8-((3R,4S)-4-(4-(tert-butyl)phenoxy)-3-methylpiperidin-1-yl)-5-methyl-6-oxo-5,6-dihydro-1,5-naphthyridine-2-carbonitrile (175); 8-((3R,4S)-4-(4-isopropylphenoxy)-3-methylpiperidin-1-yl)-5-methyl-6-oxo-5,6-dihydro-1,5-naphthyridine-2-carbonitrile (176-178); 8-((3R,4S)-4-(3-cyclopropylphenoxy)-3-methylpiperidin-1-yl)-5-methyl-6-oxo-5,6-dihydro-1,5-naphthyridine-2-carbonitrile (179-181); 8-((3R,4S)-4-(4-isopropylphenoxy)-3-methylpiperidin-1-yl)-5-methyl-6-oxo-5,6-dihydro-1,5-naphthyridine-2-carbonitrile (182-184); (+/−) 5-methyl-8-((3R,4S)-3-methyl-4-(4-(trifluoromethyl)phenoxy) piperidin-1-yl)-6-oxo-5,6-dihydro-1,5-naphthyridine-2-carboxamide (185); (+/−) 5-methyl-8-((3R,4S)-3-methyl-4-(4-(trifluoromethyl)phenoxy)piperidin-1-yl)-6-oxo-5,6-dihydro-1,5-naphthyridine-2-carbonitrile (186); 5-methyl-8-((3R,4S)-3-methyl-4-(4-(trifluoromethyl) phenoxy)piperidin-1-yl)-6-oxo-5,6-dihydro-1,5-naphthyridine-2-carbonitrile (187); 5-methyl-8-((3R,4S)-3-methyl-4-(4-(trifluoromethyl)phenoxy) piperidin-1-yl)-6-oxo-5,6-dihydro-1,5-naphthyridine-2-carbonitrile (188); 5-methyl-8-((3R,4S)-3-methyl-4-(4-(trifluoromethyl) phenoxy)piperidin-1-yl)-6-oxo-5,6-dihydro-1,5-naphthyridine-2,7-dicarbonitrile (189-191); 8-((3R,4R)-3-ethyl-4-((5-isopropoxypyridin-2-yl)oxy)piperidin-1-yl)-5-methyl-6-oxo-5,6-dihydro-1,5-naphthyridine-2-carbonitrile (192-194); 8-((3R,4R)-3-ethyl-4-(4-fluoro-3-propylphenoxy)piperidin-1-yl)-5-methyl-6-oxo-5,6-dihydro-1,5-naphthyridine-2-carbonitrile (195); 8-((3R,4R)-4-(3-(tert-butyl)phenoxy)-3-ethylpiperidin-1-yl)-5-methyl-6-oxo-5,6-dihydro-1,5-naphthyridine-2-carbonitrile (196-198); 8-((3R,4R)-4-((5-isopropoxypyridin-2-yl)oxy)-3-methylpiperidin-1-yl)-5-methyl-6-oxo-5,6-dihydro-1,5-naphthyridine-2-carbonitrile (199-201); 8-((3R,4S)-3-ethyl-4-((5-isopropoxypyridin-2-yl)oxy)piperidin-1-yl)-5-methyl-6-oxo-5,6-dihydro-1,5-naphthyridine-2-carbonitrile (202-204); 8-((3R,4S)-4-((5-isopropylpyridin-2-yl)oxy)-3-methylpiperidin-1-yl)-5-methyl-6-oxo-5,6-dihydro-1,5-naphthyridine-2-carbonitrile (205-207); 8-((3R,4S)-4-((5-(difluoromethyl)pyridin-2-yl)oxy)-3-methylpiperidin-1-yl)-5-methyl-6-oxo-5,6-dihydro-1,5-naphthyridine-2-carbonitrile (208-210); 8-((3R,4S)-4-((4-isopropylpyridin-2-yl)oxy)-3-methylpiperidin-1-yl)-5-methyl-6-oxo-5,6-dihydro-1,5-naphthyridine-2-carbonitrile (211-213); 8-((3R,4S)-4-((6-isopropylpyridin-2-yl)oxy)-3-methylpiperidin-1-yl)-5-methyl-6-oxo-5,6-dihydro-1,5-naphthyridine-2-carbonitrile (214-216); 5-methyl-8-((3R,4S)-3-methyl-4-(pyrimidin-2-yloxy)piperidin-1-yl)-6-oxo-5,6-dihydro-1,5-naphthyridine-2-carbonitrile (217); 8-((3R,4S)-4-((4-methoxypyrimidin-2-yl)oxy)-3-methylpiperidin-1-yl)-5-methyl-6-oxo-5,6-dihydro-1,5-naphthyridine-2-carbonitrile (218); 5-methyl-8-((3R,4S)-3-methyl-4-((5-propylpyrimidin-2-yl)oxy)piperidin-1-yl)-6-oxo-5,6-dihydro-1,5-naphthyridine-2-carbonitrile (219); 5-methyl-8-((3R,4S)-3-methyl-4-((2-methylpyrimidin-4-yl)oxy)piperidin-1-yl)-6-oxo-5,6-dihydro-1,5-naphthyridine-2-carbonitrile (220); 8-((3R,4S)-4-((5-ethylpyrimidin-2-yl)oxy)-3-methylpiperidin-1-yl)-5-methyl-6-oxo-5,6-dihydro-1,5-naphthyridine-2-carbonitrile (221); 5-methyl-8-((3R,4S)-3-methyl-4-((5-(trifluoromethyl)pyrimidin-2-yl)oxy)piperidin-1-yl)-6-oxo-5,6-dihydro-1,5-naphthyridine-2-carbonitrile (222); 8-((3R,4S)-4-((5-cyclopropylpyrimidin-2-yl)oxy)-3-methylpiperidin-1-yl)-5-methyl-6-oxo-5,6-dihydro-1,5-naphthyridine-2-carbonitrile (223); 8-((3R,4S)-4-((5-cyclopropylpyridin-2-yl)oxy)-3-methylpiperidin-1-yl)-5-methyl-6-oxo-5,6-dihydro-1,5-naphthyridine-2-carbonitrile (224); 5-methyl-8-((3R,4S)-3-methyl-4-((5-(trifluoromethyl)pyridin-2-yl)oxy)piperidin-1-yl)-6-oxo-5,6-dihydro-1,5-naphthyridine-2-carbonitrile (225-227); (+/−) 8-((3R,4S)-4-((5-isopropoxypyridin-2-yl)oxy)-3-methylpiperidin-1-yl)-5-methyl-6-oxo-5,6-dihydro-1,5-naphthyridine-2-carbonitrile (228); (+/−) 5-methyl-8-((3R,4R)-3-methyl-4-(4-(tert-pentyl)phenoxy)piperidin-1-yl)-6-oxo-5,6-dihydro-1,5-naphthyridine-2,7-dicarbonitrile (229); 5-methyl-8-((3R,4R)-3-methyl-4-(4-(tert-pentyl)phenoxy)piperidin-1-yl)-6-oxo-5,6-dihydro-1,5-naphthyridine-2,7-dicarbonitrile (230); 5-methyl-8-((3R,4R)-3-methyl-4-(4-(tert-pentyl)phenoxy)piperidin-1-yl)-6-oxo-5,6-dihydro-1,5-naphthyridine-2,7-dicarbonitrile (231); (+/−) 8-(4-((5-isopropoxypyridin-2-yl)oxy)-3,3-dimethylpiperidin-1-yl)-5-methyl-6-oxo-5,6-dihydro-1,5-naphthyridine-2-carbonitrile (232); 8-(4-((5-isopropoxypyridin-2-yl) oxy)-3,3-dimethylpiperidin-1-yl)-5-methyl-6-oxo-5,6-dihydro-1,5-naphthyridine-2-carbonitrile (233); 8-(4-((5-isopropoxypyridin-2-yl)oxy)-3,3-dimethylpiperidin-1-yl)-5-methyl-6-oxo-5,6-dihydro-1,5-naphthyridine-2-carbonitrile (234); (+/−) 5-methyl-8-((3R,4S)-3-methyl-4-((4-(trifluoromethoxy)benzyl)oxy)piperidin-1-yl)-6-oxo-5,6-dihydro-1,5-naphthyridine-2-carbonitrile (235); (+/−) 5-methyl-8-((3R,4S)-3-methyl-4-((4-(trifluoromethoxy)benzyl)oxy)piperidin-1-yl)-6-oxo-5,6-dihydro-1,5-naphthyridine-2-carboxamide (236); 7-fluoro-5-methyl-6-oxo-8-(4-(4-(trifluoromethoxy)phenoxy)piperidin-1-yl)-5,6-dihydro-1,5-naphthyridine-2-carbonitrile (237); 7-chloro-5-methyl-6-oxo-8-(4-(4-(trifluoromethoxy)phenoxy)piperidin-1-yl)-5,6-dihydro-1,5-naphthyridine-2-carbonitrile (238); 7-bromo-5-methyl-6-oxo-8-(4-(4-(trifluoromethoxy)phenoxy)piperidin-1-yl)-5,6-dihydro-1,5-naphthyridine-2-carbonitrile (239); 7-(6-methoxypyridin-3-yl)-5-methyl-6-oxo-8-(4-(4-(trifluoromethoxy)phenoxy)piperidin-1-yl)-5,6-dihydro-1,5-naphthyridine-2-carbonitrile (240); 7-(2-methoxypyridin-4-yl)-5-methyl-6-oxo-8-(4-(4-(trifluoromethoxy) phenoxy) piperidin-1-yl)-5,6-dihydro-1,5-naphthyridine-2-carbonitrile (241); (+/−) 6-bromo-1-methyl-4-((3R,4R)-3-methyl-4-(4-(tert-pentyl)phenoxy)piperidin-1-yl)-2-oxo-1,2-dihydro-1,5-naphthyridine-3-carbonitrile (242); 8-((2S,5S)-4-((5-isopropoxypyridin-2-yl)oxy)-2,5-dimethylpiperidin-1-yl)-5-methyl-6-oxo-5,6-dihydro-1,5-naphthyridine-2-carbonitrile (243 and 246); 8-((2R,5R)-4-((5-isopropoxypyridin-2-yl)oxy)-2,5-dimethylpiperidin-1-yl)-5-methyl-6-oxo-5,6-dihydro-1,5-naphthyridine-2-carbonitrile (244-245); 4-((2R,5S)-4-((5-isopropoxypyridin-2-yl)oxy)-2,5-dimethylpiperidin-1-yl)-1-methyl-2-oxo-1,2-dihydropyrido[3,2-d]pyrimidine-6-carbonitrile (248-249); 4-((2S,5R)-4-((5-isopropoxypyridin-2-yl)oxy)-2,5-dimethylpiperidin-1-yl)-1-methyl-2-oxo-1,2-dihydropyrido[3,2-d]pyrimidine-6-carbonitrile (247 and 250); 4-((2R,5S)-2,5-dimethyl-4-(3-(trifluoromethyl)phenoxy)piperidin-1-yl)-1-methyl-2-oxo-1,2-dihydropyrido[3,2-d]pyrimidine-6-carbonitrile (251 and 253); 4-((2S,5R)-2,5-dimethyl-4-(3-(trifluoromethyl) phenoxy)piperidin-1-yl)-1-methyl-2-oxo-1,2-dihydropyrido[3,2-d]pyrimidine-6-carbonitrile (252 and 254); 4-((2R,5R)-2,5-dimethyl-4-(3-(trifluoromethyl)phenoxy)piperidin-1-yl)-1-methyl-2-oxo-1,2-dihydropyrido[3,2-d]pyrimidine-6-carbonitrile (256-257); 8-((2S,5S)-2,5-dimethyl-4-(3-(trifluoromethyl)phenoxy)piperidin-1-yl)-5-methyl-6-oxo-5,6-dihydro-1,5-naphthyridine-2-carbonitrile (255 and 258); (±)-trans-8-(3-hydroxy-4-(3-(trifluoromethyl) phenoxy)piperidin-1-yl)-5-methyl-6-oxo-5,6-dihydro-1,5-naphthyridine-2-carbonitrile (259-260); (±)-trans-8-(3-methoxy-4-(3-(trifluoromethyl)phenoxy)piperidin-1-yl)-5-methyl-6-oxo-5,6-dihydro-1,5-naphthyridine-2-carbonitrile (261-262); 8-((3R,4R)-3-ethoxy-4-(3-(trifluoromethyl)phenoxy)piperidin-1-yl)-5-methyl-6-oxo-5,6-dihydro-1,5-naphthyridine-2-carbonitrile (263-264); (±)-cis-8-(3-fluoro-4-(3-(trifluoromethyl)phenoxy)piperidin-1-yl)-5-methyl-6-oxo-5,6-dihydro-1,5-naphthyridine-2-carbonitrile (265-266); (±)-trans-8-(3-hydroxy-4-((5-isopropoxypyridin-2-yl)oxy)piperidin-1-yl)-5-methyl-6-oxo-5,6-dihydro-1,5-naphthyridine-2-carbonitrile (267-268); (±)-trans-8-(4-((5-isopropoxypyridin-2-yl)oxy)-3-methoxypiperidin-1-yl)-5-methyl-6-oxo-5,6-dihydro-1,5-naphthyridine-2-carbonitrile (269-270); 8-((2S,5R)-4-((5-methoxypyridin-2-yl)amino)-2,5-dimethylpiperidin-1-yl)-5-methyl-6-oxo-5,6-dihydro-1,5-naphthyridine-2-carbonitrile (280-281); N-((2S,5R)-1-(6-cyano-1-methyl-2-oxo-1,2-dihydro-1,5-naphthyridin-4-yl)-2,5-dimethylpiperidin-4-yl)-4-fluoro-N-methylbenzamide (282-283); N-(1-(6-cyano-1-methyl-2-oxo-1,2-dihydro-1,5-naphthyridin-4-yl)-3-methylpiperidin-4-yl)-4-fluoro-N-methylbenzamide (284-287); N-(1-(3,6-dicyano-1-methyl-2-oxo-1,2-dihydro-1,5-naphthyridin-4-yl)-3-methylpiperidin-4-yl)-N-methyl-4-(trifluoromethyl) benzamide (288-293). 8-((2S,4S,5S)-5-ethyl-4-((5-isopropoxypyridin-2-yl) oxy)-2-methylpiperidin-1-yl)-5-methyl-6-oxo-5,6-dihydro-1,5-naphthyridine-2-carbonitrile (294); 8-((2R,4S,5S)-5-ethyl-4-((5-isopropoxypyridin-2-yl)oxy)-2-methylpiperidin-1-yl)-5-methyl-6-oxo-5,6-dihydro-1,5-naphthyridine-2-carbonitrile (295); 8-((2S,4R,5R)-5-ethyl-4-((5-isopropoxypyridin-2-yl)oxy)-2-methylpiperidin-1-yl)-5-methyl-6-oxo-5,6-dihydro-1,5-naphthyridine-2-carbonitrile (296); 8-((2R,4R,5R)-5-ethyl-4-((5-isopropoxypyridin-2-yl) oxy)-2-methylpiperidin-1-yl)-5-methyl-6-oxo-5,6-dihydro-1,5-naphthyridine-2-carbonitrile (297); 8-((2R,4S,5R)-5-ethyl-4-((5-isopropoxypyridin-2-yl)oxy)-2-methylpiperidin-1-yl)-5-methyl-6-oxo-5,6-dihydro-1,5-naphthyridine-2-carbonitrile (298); 8-((2S,4S,5R)-5-ethyl-4-((5-isopropoxypyridin-2-yl) oxy)-2-methylpiperidin-1-yl)-5-methyl-6-oxo-5,6-dihydro-1,5-naphthyridine-2-carbonitrile (299); 8-((2S,4S,5R)-5-ethyl-2-methyl-4-(3-(trifluoromethyl) phenoxy)piperidin-1-yl)-5-methyl-6-oxo-5,6-dihydro-1,5-naphthyridine-2-carbonitrile (308); 8-((2R,4S,5R)-5-ethyl-2-methyl-4-(3-(trifluoromethyl)phenoxy)piperidin-1-yl)-5-methyl-6-oxo-5,6-dihydro-1,5-naphthyridine-2-carbonitrile (309); 8-((2R,4R,5R)-5-ethyl-2-methyl-4-(3-(trifluoromethyl)phenoxy) piperidin-1-yl)-5-methyl-6-oxo-5,6-dihydro-1,5-naphthyridine-2-carbonitrile (310); 8-((2R,4S,5R)-2,5-dimethyl-4-(3-(trifluoromethyl)phenoxy)piperidin-1-yl)-5-methyl-6-oxo-5,6-dihydro-1,5-naphthyridine-2-carbonitrile (311); 8-((2S,4R,5S)-2,5-dimethyl-4-(p-tolyloxy)piperidin-1-yl)-5-methyl-6-oxo-5,6-dihydro-1,5-naphthyridine-2-carbonitrile (312); 8-((2S,4R,5S)-4-(3-chlorophenoxy)-2,5-dimethylpiperidin-1-yl)-5-methyl-6-oxo-5,6-dihydro-1,5-naphthyridine-2-carbonitrile (313); 8-((2S,4R,5S)-4-(3-cyanophenoxy)-2,5-dimethylpiperidin-1-yl)-5-methyl-6- oxo-5,6-dihydro-1,5-naphthyridine-2-carbonitrile (314); 8-((2S,4R,5S)-4-(4-fluorophenoxy)-2,5-dimethylpiperidin-1-yl)-5-methyl-6-oxo-5,6-dihydro-1,5-naphthyridine-2-carbonitrile (315); 8-((2S,5S)-2,5-dimethyl-4-((4-(trifluoromethyl)phenyl)amino)piperidin-1-yl)-5-methyl-6-oxo-5,6-dihydro-1,5-naphthyridine-2-carbonitrile (316A); 8-(2,5)-dimethyl-4-(methyl(4-(trifluoromethyl)phenyl) amino) piperidin-1-yl)-5-methyl-6-oxo-5,6-dihydro-1,5-naphthyridine-2-carbonitrile (316-319); 8-((2S,5S)-2,5-dimethyl-4-(methyl(3-(trifluoromethyl)phenyl)amino) piperidin-1-yl)-5-methyl-6-oxo-5,6-dihydro-1,5-naphthyridine-2-carbonitrile (320-321); 8-(4-((4-fluorobenzyl) (methyl)amino)-3-methylpiperidin-1-yl)-5-methyl-6-oxo-5,6-dihydro-1,5-naphthyridine-2,7-dicarbonitrile (322-325); -(4-((4-fluorobenzyl)(methyl) amino)-3-methylpiperidin-1-yl)-5-methyl-6-oxo-5,6-dihydro-1,5-naphthyridine-2-carbonitrile (326-328); 8444 (4,4-difluorocyclohexyl)(methyl)amino)-3-methylpiperidin-1-yl)-5-methyl-6-oxo-5,6-dihydro-1,5-naphthyridine-2,7-dicarbonitrile (329-330); 8-((2S,5R)-4-((4-fluorobenzyl)(methyl) amino)-2,5-dimethylpiperidin-1-yl)-5-methyl-6-oxo-5,6-dihydro-1,5-naphthyridine-2-carbonitrile (331-332); 8-((2S,5S)-4-((4-fluorobenzyl) (methyl)amino)-2,5-dimethylpiperidin-1-yl)-5-methyl-6-oxo-5,6-dihydro-1,5-naphthyridine-2-carbonitrile (333-334); 8-((2S,5S)-4-((5-Isopropoxypyridin-2-yl)oxy)-2,4,5-trimethylpiperidin-1-yl)-5-methyl-6-oxo-5,6-dihydro-1,5-naphthyridine-2-carbonitrile (335-336); 5-methyl-6-oxo-8-((2S,5S)-2,4,5-trimethyl-4-(3-(trifluoromethyl)phenoxy) piperidin-1-yl)-5,6-dihydro-1,5-naphthyridine-2-carbonitrile (337-338); trans-8-(3-ethoxy-4-phenoxypiperidin-1-yl)-5-methyl-6-oxo-5,6-dihydro-1,5-naphthyridine-2-carbonitrile (341-342); 8-((3S,4S)-3-ethoxy-4-(4-(trifluoromethyl)phenoxy) piperidin-1-yl)-5-methyl-6-oxo-5,6-dihydro-1,5-naphthyridine-2-carbonitrile (343-344); 8-((3S,4S)-3-ethoxy-4-(2-(trifluoromethyl)phenoxy)piperidin-1-yl)-5-methyl-6-oxo-5,6-dihydro-1,5-naphthyridine-2-carbonitrile (345-346); 8-((3S,4S)-3-ethoxy-4-(4-isopropoxyphenoxy)piperidin-1-yl)-5-methyl-6-oxo-5,6-dihydro-1,5-naphthyridine-2-carbonitrile (347-348); 8-((3S,4S)-3-ethoxy-4-(4-(trifluoromethoxy)phenoxy) piperidin-1-yl)-5-methyl-6-oxo-5,6-dihydro-1,5-naphthyridine-2-carbonitrile (349-350); 8-((3S,4S)-3-ethoxy-4-(3-(trifluoromethoxy)phenoxy)piperidin-1-yl)-5-methyl-6-oxo-5,6-dihydro-1,5-naphthyridine-2-carbonitrile (351-352); 8-((3S,4S)-3-ethoxy-4-(4-(methyl sulfonyl)phenoxy) piperidin-1-yl)-5-methyl-6-oxo-5,6-dihydro-1,5-naphthyridine-2-carbonitrile (353-354); 8-((3S,4S)-3-ethoxy-4-((2-methylbenzo[d]oxazol-5-yl)oxy)piperidin-1-yl)-5-methyl-6-oxo-5,6-dihydro-1,5-naphthyridine-2-carbonitrile (355-356); 8-((3S,4S)-4-(4-chloro-3-fluorophenoxy)-3-ethoxypiperidin-1-yl)-5-methyl-6-oxo-5,6-dihydro-1,5-naphthyridine-2-carbonitrile (357-358); 8-((3S,4S)-3-ethoxy-4-((2-(trifluoromethyl)pyridin-4-yl) oxy) piperidin-1-yl)-5-methyl-6-oxo-5,6-dihydro-1,5-naphthyridine-2-carbonitrile (359-362); trans-8-(3-ethoxy-4-((6-(trifluoromethyl)pyridin-2-yl)oxy)piperidin-1-yl)-5-methyl-6-oxo-5,6-dihydro-1,5-naphthyridine-2-carbonitrile (363-364); 8-((3S,4S)-3-ethoxy-4-((4-(trifluoromethyl)pyridin-2-yl)oxy)piperidin-1-yl)-5-methyl-6-oxo-5,6-dihydro-1,5-naphthyridine-2-carbonitrile (365-366); trans-8-(3-ethoxy-4-((5-(trifluoromethyl)pyridin-2-yl)oxy)piperidin-1-yl)-5-methyl-6-oxo-5,6-dihydro-1,5-naphthyridine-2-carbonitrile (367-368); cis-8-(3-ethoxy-4-(3-(trifluoromethyl)phenoxy) piperidin-1-yl)-5-methyl-6-oxo-5,6-dihydro-1,5-naphthyridine-2-carbonitrile (369-370); cis-8-(3-ethoxy-4-((5-isopropoxypyridin-2-yl)oxy)piperidin-1-yl)-5-methyl-6-oxo-5,6-dihydro-1,5-naphthyridine-2-carbonitrile (371-372); trans-8-4-(benzo[d]thiazol-2-yloxy)-3-ethoxypiperidin-1-yl)-5-methyl-6-oxo-5,6-dihydro-1,5-naphthyridine-2-carbonitrile (373-374); 8-((3S,4S)-3-ethoxy-4-((6-isopropoxypyridazin-3-yl)oxy)piperidin-1-yl)-5-methyl-6-oxo-5,6-dihydro-1,5-naphthyridine-2-carbonitrile (375-376); 8-((3S,4S)-3-ethoxy-4-((5-isopropoxypyrazin-2-yl) oxy)piperidin-1-yl)-5-methyl-6-oxo-5,6-dihydro-1,5-naphthyridine-2-carbonitrile (377-378); 8-((3S,4S)-3-ethoxy-4-((5-isopropoxypyrimidin-2-yl)oxy)piperidin-1-yl)-5-methyl-6-oxo-5,6-dihydro-1,5-naphthyridine-2-carbonitrile (379-380); 8-((3S,4S)-3-ethoxy-4-((3-(trifluoromethyl)benzyl) oxy)piperidin-1-yl)-5-methyl-6-oxo-5,6-dihydro-1,5-naphthyridine-2-carbonitrile (381-382); 8-((3S,4S)-3-ethoxy-4-((5-isopropoxypyridin-2-yl)methoxy) piperidin-1-yl)-5-methyl-6-oxo-5,6-dihydro-1,5-naphthyridine-2-carbonitrile (383-384); 8-((3R,4R)-3-(2-(dimethylamino) ethoxy)-4-(3-(trifluoromethyl)phenoxy)piperidin-1-yl)-5-methyl-6-oxo-5,6-dihydro-1,5-naphthyridine-2-carbonitrile (385-386); 8-((3R,4R)-3-(cyclopropylmethoxy)-4-(3-(trifluoromethyl)phenoxy)piperidin-1-yl)-5-methyl-6-oxo-5,6-dihydro-1,5-naphthyridine-2-carbonitrile (387-388); 8-((3R,4R)-3-(2-methoxyethoxy)-4-(3-(trifluoromethyl)phenoxy) piperidin-1-yl)-5-methyl-6-oxo-5,6-dihydro-1,5-naphthyridine-2-carbonitrile (389-390); 5-methyl-8-((3R,4R)-3-(2-morpholinoethoxy)-4-(3-(trifluoromethyl) phenoxy)piperidin-1-yl)-6-oxo-5,6-dihydro-1,5-naphthyridine-2-carbonitrile (391-392); 5-methyl-6-oxo-8-((3R,4R)-3-(2,2,2-trifluoroethoxy)-4-(3-(trifluoromethyl)phenoxy) piperidin-1-yl)-5,6-dihydro-1,5-naphthyridine-2-carbonitrile (393-394); trans-8-(3-isopropoxy-4-(3-(trifluoromethyl)phenoxy)piperidin-1-yl)-5-methyl-6-oxo-5,6-dihydro-1,5-naphthyridine-2-carbonitrile (395-396); or trans-8-(4-((5-isopropoxypyridin-2-yl)oxy)-3-ethoxypiperidin-1-yl)-5-methyl-6-oxo-5,6-dihydro-1,5-naphthyridine-2-carbonitrile (397-398).

The present invention may be embodied in other specific forms without departing from the spirit or essential attributes thereof. This invention encompasses all combinations of the aspects and/or embodiments of the invention noted herein. It is understood that any and all embodiments of the present invention may be taken in conjunction with any other embodiment or embodiments to describe additional embodiments. It is also to be understood that each individual element of the embodiments is meant to be combined with any and all other elements from any embodiment to describe an additional embodiment.

Definitions

The features and advantages of the invention may be more readily understood by those of ordinary skill in the art upon reading the following detailed description. It is to be appreciated that certain features of the invention that are, for clarity reasons, described above and below in the context of separate embodiments, may also be combined to form a single embodiment. Conversely, various features of the invention that are, for brevity reasons, described in the context of a single embodiment, may also be combined so as to form sub-combinations thereof. Embodiments identified herein as exemplary or preferred are intended to be illustrative and not limiting.

Unless specifically stated otherwise herein, references made in the singular may also include the plural. For example, "a" and "an" may refer to either one, or one or more.

As used herein, the phrase "compounds and/or salts thereof" refers to at least one compound, at least one salt of the compounds, or a combination thereof. For example, compounds of Formula (I) and/or salts thereof includes a compound of Formula (I); two compounds of Formula (I); a salt of a compound of Formula (I); a compound of Formula (I) and one or more salts of the compound of Formula (I); and two or more salts of a compound of Formula (I).

Unless otherwise indicated, any atom with unsatisfied valences is assumed to have hydrogen atoms sufficient to satisfy the valences.

The definitions set forth herein take precedence over definitions set forth in any patent, patent application, and/or patent application publication incorporated herein by reference.

Listed below are definitions of various terms used to describe the present invention. These definitions apply to the terms as they are used throughout the specification (unless they are otherwise limited in specific instances) either individually or as part of a larger group.

Throughout the specification, groups and substituents thereof may be chosen by one skilled in the field to provide stable moieties and compounds.

In accordance with a convention used in the art,

is used in structural formulas herein to depict the bond that is the point of attachment of the moiety or substituent to the core or backbone structure.

The terms "halo" and "halogen," as used herein, refer to F, Cl, Br, and I.

The term "cyano" refers to the group —CN.

The term "amino" refers to the group —NH$_2$.

The term "oxo" refers to the group =O.

The term "alkyl" as used herein, refers to both branched and straight-chain saturated aliphatic hydrocarbon groups containing, for example, from 1 to 12 carbon atoms, from 1 to 6 carbon atoms, and from 1 to 4 carbon atoms. Examples of alkyl groups include, but are not limited to, methyl (Me), ethyl (Et), propyl (e.g., n-propyl and i-propyl), butyl (e.g., n-butyl, i-butyl, sec-butyl, and t-butyl), and pentyl (e.g., n-pentyl, isopentyl, neopentyl), n-hexyl, 2-methylpentyl, 2-ethylbutyl, 3-methylpentyl, and 4-methylpentyl. When numbers appear in a subscript after the symbol "C", the subscript defines with more specificity the number of carbon atoms that a particular group may contain. For example, "$C_{1-4}$ alkyl" denotes straight and branched chain alkyl groups with one to four carbon atoms.

The term "fluoroalkyl" as used herein is intended to include both branched and straight-chain saturated aliphatic hydrocarbon groups substituted with one or more fluorine atoms. For example, "$C_{1-4}$ fluoroalkyl" is intended to include $C_1$, $C_2$, $C_3$, and $C_4$ alkyl groups substituted with one or more fluorine atoms. Representative examples of fluoroalkyl groups include, but are not limited to, —CF$_3$ and —CH$_2$CF$_3$.

The term "hydroxyalkyl" includes both branched and straight-chain saturated alkyl groups substituted with one or more hydroxyl groups. For example, "hydroxyalkyl" includes —CH$_2$OH, —CH$_2$CH$_2$OH, and $C_{1-4}$ hydroxyalkyl.

The term "alkenyl" refers to a straight or branched chain hydrocarbon radical containing from 2 to 12 carbon atoms and at least one carbon-carbon double bond. Exemplary such groups include ethenyl or allyl. For example, "$C_{2-6}$ alkenyl" denotes straight and branched chain alkenyl groups with two to six carbon atoms.

The term "alkynyl" refers to a straight or branched chain hydrocarbon radical containing from 2 to 12 carbon atoms and at least one carbon to carbon triple bond. Exemplary such groups include ethynyl. For example, "$C_{2-6}$ alkynyl" denotes straight and branched chain alkynyl groups with two to six carbon atoms.

The term "cycloalkyl," as used herein, refers to a group derived from a non-aromatic monocyclic or polycyclic hydrocarbon molecule by removal of one hydrogen atom from a saturated ring carbon atom. Representative examples of cycloalkyl groups include, but are not limited to, cyclopropyl, cyclopentyl, and cyclohexyl. When numbers appear in a subscript after the symbol "C", the subscript defines with more specificity the number of carbon atoms that a particular cycloalkyl group may contain. For example, "$C_{3-6}$ cycloalkyl" denotes cycloalkyl groups with three to six carbon atoms.

The term "fluorocycloalkyl" as used herein is intended to include a cycloalkyl group substituted with one or more fluorine atoms.

The term "alkoxy," as used herein, refers to an alkyl group attached to the parent molecular moiety through an oxygen atom, for example, methoxy group (—OCH$_3$). For example, "$C_{1-3}$ alkoxy" denotes alkoxy groups with one to three carbon atoms.

The terms "fluoroalkoxy" and "—O(fluoroalkyl)" represent a fluoroalkyl group as defined above attached through an oxygen linkage (—O—). For example, "$C_{1-4}$ fluoroalkoxy" is intended to include $C_1$, $C_2$, $C_3$, and $C_4$ fluoroalkoxy groups.

The terms "carbocyclo", "carbocyclic" or "carbocyclyl" may be used interchangeably and refer to cyclic groups having at least one saturated or partially saturated non-aromatic ring wherein all atoms of all rings are carbon. The carbocyclyl ring may be unsubstituted or may contain one or more substituents as valence allows.

Thus, the term includes nonaromatic rings such as for example, cycloalkyl, cycloalkenyl, and cycloalkynyl rings. Exemplary bicyclic carbocyclyl groups include, indanyl, indenyl, dihydronaphthalenyl, tetrahydronaphthenyl, hexahydronaphthalenyl, octahydronaphthalenyl, decahydronaphthalenyl, bicycloheptanyl, bicyclooctanyl, and bicyclononanyl.

The term "aryl" as used herein, refers to a group of atoms derived from a molecule containing aromatic ring(s) by removing one hydrogen that is bonded to the aromatic ring(s). Representative examples of aryl groups include, but are not limited to, phenyl and naphthalenyl. The aryl ring may be unsubstituted or may contain one or more substituents as valence allows.

The term "benzyl," as used herein, refers to a methyl group in which one of the hydrogen atoms is replaced by a phenyl group. The phenyl ring may be unsubstituted or may contain one or more substituents as valence allows.

The term "heteroatom" refers to oxygen (O), sulfur (S), and nitrogen (N).

The terms "heterocyclo", "heterocyclic", or "heterocyclyl" may be used interchangeably and refer to cyclic groups having at least one saturated or partially saturated non-aromatic ring and wherein one or more of the rings have at least one heteroatom (O, S or N), said heteroatom containing ring preferably having 1 to 3 heteroatoms independently selected from O, S, and/or N. The ring of such a group containing a heteroatom can contain one or two oxygen or sulfur atoms and/or from one to four nitrogen atoms provided that the total number of heteroatoms in each ring is four or less, and further provided that the ring contains at least one carbon atom. The nitrogen and sulfur atoms may optionally be oxidized and the nitrogen atoms may optionally be quaternized. The heterocyclo group may be attached at any available nitrogen or carbon atom. The heterocyclo ring may be unsubstituted or may contain one or more substituents as valence allows.

Exemplary monocyclic heterocyclyl groups include pyrrolidinyl, imidazolinyl, oxazolidinyl, isoxazolinyl, thiazolidinyl, isothiazolidinyl, tetrahydrofuranyl, piperidinyl, piperazinyl, 2-oxopiperazinyl, 2-oxopiperidinyl, 2-oxopyrrolodinyl, 2-oxoazepinyl, azepinyl, 4-piperidonyl, tetrahydropyranyl, morpholinyl, thiamorpholinyl, thiamorpholinyl sulfoxide, thiamorpholinyl sulfone, 1,3-dioxolane, tetrahydro-1,1-dioxothienyl, dihydroisoindolyl, and tetrahydroquinolinyl The term "heteroaryl" refers to unsubstituted and substituted aromatic groups that have at least one heteroatom (O, S or N) in at least one of the rings, said heteroatom-containing ring preferably having 1, 2, or 3 heteroatoms independently selected from O, S, and/or N. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. The 5- to 14-membered heteroaryl groups include 5- or 6-membered monocyclic heteroaryl groups, 9- or 10-membered bicyclic heteroaryl groups, and 11 to 14-membered tricyclic heteroaryl groups. The fused rings completing the bicyclic group and the tricyclic heteroaryl group are aromatic and may contain only carbon atoms. The nitrogen and sulfur atoms may optionally be oxidized and the nitrogen atoms may optionally be quaternized. Bicyclic and tricyclic heteroaryl groups must include only aromatic rings. The heteroaryl group may be attached at any available nitrogen or carbon atom of any ring. The heteroaryl ring system may be unsubstituted or may contain one or more substituents.

Exemplary monocyclic heteroaryl groups include pyrrolyl, pyrazolyl, pyrazolinyl, imidazolyl, oxazolyl, isoxazolyl, thiazolyl, thiadiazolyl, isothiazolyl, furanyl, thiophenyl, oxadiazolyl, pyridinyl, pyrazinyl, pyrimidinyl, pyridazinyl, and triazinyl.

Exemplary bicyclic heteroaryl groups include indolyl, benzothiazolyl, benzodioxolyl, benzoxazolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, and pyrrolopyridyl.

Exemplary tricyclic heteroaryl groups include acridinyl, benzoquinolinyl, benzoisoquinolinyl, and benzonaphthyridinyl.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The compounds of Formula (I) can form salts which are also within the scope of this invention. Unless otherwise indicated, reference to an inventive compound is understood to include reference to one or more salts thereof. The term "salt(s)" denotes acidic and/or basic salts formed with inorganic and/or organic acids and bases. In addition, the term "salt(s) may include zwitterions (inner salts), e.g., when a compound of Formula (I) contains both a basic moiety, such as an amine or a pyridine or imidazole ring, and an acidic moiety, such as a carboxylic acid. Pharmaceutically acceptable (i.e., non-toxic, physiologically acceptable) salts are preferred, such as, for example, acceptable metal and amine salts in which the cation does not contribute significantly to the toxicity or biological activity of the salt. However, other salts may be useful, e.g., in isolation or purification steps which may be employed during preparation, and thus, are contemplated within the scope of the invention. Salts of the compounds of the formula (I) may be formed, for example, by reacting a compound of the Formula (I) with an amount of acid or base, such as an equivalent amount, in a medium such as one in which the salt precipitates or in an aqueous medium followed by lyophilization.

Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecyl sulfates, ethanesulfonates, fumarates, glucoheptanoates, glycerophosphates, hemi sulfates, heptanoates, hexanoates, hydrochlorides (formed with hydrochloric acid), hydrobromides (formed with hydrogen bromide), hydroiodides, maleates (formed with maleic acid), 2-hydroxyethanesulfonates, lactates, methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

Exemplary basic salts include ammonium salts, alkali metal salts such as sodium, lithium, and potassium salts; alkaline earth metal salts such as calcium and magnesium salts; barium, zinc, and aluminum salts; salts with organic bases (for example, organic amines) such as trialkylamines such as triethylamine, procaine, dibenzylamine, N-benzyl-β-phenethylamine, 1-ephenamine, N,N'-dibenzylethylenediamine, dehydroabietylamine, N-ethylpiperidine, benzylamine, dicyclohexylamine or similar pharmaceutically acceptable amines and salts with amino acids such as arginine, lysine and the like. Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others. Preferred salts include monohydrochloride, hydrogensulfate, methanesulfonate, phosphate or nitrate salts.

The compounds of Formula (I) can be provided as amorphous solids or crystalline solids. Lyophilization can be employed to provide the compounds of Formula (I) as a solid.

It should further be understood that solvates (e.g., hydrates) of the Compounds of Formula (I) are also within the scope of the present invention. The term "solvate" means a physical association of a compound of Formula (I) with one or more solvent molecules, whether organic or inorganic. This physical association includes hydrogen bonding. In certain instances the solvate will be capable of isolation, for example when one or more solvent molecules are incorporated in the crystal lattice of the crystalline solid. "Solvate" encompasses both solution-phase and isolable solvates. Exemplary solvates include hydrates, ethanolates, methanolates, isopropanolates, acetonitrile solvates, and ethyl acetate solvates. Methods of solvation are known in the art.

Various forms of prodrugs are well known in the art and are described in Rautio, J. et al., *Nature Review Drug Discovery*, 17, 559-587 (2018).

In addition, compounds of Formula (I), subsequent to their preparation, can be isolated and purified to obtain a composition containing an amount by weight equal to or greater than 99% of a compound of Formula (I) ("substantially pure"), which is then used or formulated as described herein. Such "substantially pure" compounds of Formula (I) are also contemplated herein as part of the present invention.

"Stable compound" and "stable structure" are meant to indicate a compound that is sufficiently robust to survive isolation to a useful degree of purity from a reaction mixture, and formulation into an efficacious therapeutic agent. The present invention is intended to embody stable compounds.

"Therapeutically effective amount" is intended to include an amount of a compound of the present invention alone or an amount of the combination of compounds claimed or an amount of a compound of the present invention in combination with other active ingredients effective to act as an inhibitor of DGKα and/or DGKζ, or effective to treat or prevent viral infections and proliferative disorders, such as cancer.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting its development; and/or (c) relieving the disease-state, i.e., causing regression of the disease state.

The compounds of the present invention are intended to include all isotopes of atoms occurring in the present compounds. Isotopes include those atoms having the same atomic number but different mass numbers. By way of general example and without limitation, isotopes of hydrogen include deuterium (D) and tritium (T). Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

Compounds in accordance with Formula (I) and/or pharmaceutically acceptable salts thereof can be administered by any means suitable for the condition to be treated, which can depend on the need for site-specific treatment or quantity of Formula (I) compound to be delivered.

Also embraced within this invention is a class of pharmaceutical compositions comprising a compound of Formula (I) and/or pharmaceutically acceptable salts thereof; and one or more non-toxic, pharmaceutically-acceptable carriers and/or diluents and/or adjuvants (collectively referred to herein as "carrier" materials) and, if desired, other active ingredients. The compounds of Formula (I) may be administered by any suitable route, preferably in the form of a pharmaceutical composition adapted to such a route, and in a dose effective for the treatment intended. The compounds and compositions of the present invention may, for example, be administered orally, mucosally, or parentally including intravascularly, intravenously, intraperitoneally, subcutaneously, intramuscularly, and intrasternally in dosage unit formulations containing conventional pharmaceutically acceptable carriers, adjuvants, and vehicles. For example, the pharmaceutical carrier may contain a mixture of mannitol or lactose and microcrystalline cellulose. The mixture may contain additional components such as a lubricating agent, e.g. magnesium stearate and a disintegrating agent such as crospovidone. The carrier mixture may be filled into a gelatin capsule or compressed as a tablet. The pharmaceutical composition may be administered as an oral dosage form or an infusion, for example.

For oral administration, the pharmaceutical composition may be in the form of, for example, a tablet, capsule, liquid capsule, suspension, or liquid. The pharmaceutical composition is preferably made in the form of a dosage unit containing a particular amount of the active ingredient. For example, the pharmaceutical composition may be provided as a tablet or capsule comprising an amount of active ingredient in the range of from about 0.1 to 1000 mg, preferably from about 0.25 to 250 mg, and more preferably from about 0.5 to 100 mg. A suitable daily dose for a human or other mammal may vary widely depending on the condition of the patient and other factors, but, can be determined using routine methods.

Any pharmaceutical composition contemplated herein can, for example, be delivered orally via any acceptable and suitable oral preparations. Exemplary oral preparations, include, but are not limited to, for example, tablets, troches, lozenges, aqueous and oily suspensions, dispersible powders or granules, emulsions, hard and soft capsules, liquid capsules, syrups, and elixirs. Pharmaceutical compositions intended for oral administration can be prepared according to any methods known in the art for manufacturing pharmaceutical compositions intended for oral administration. In order to provide pharmaceutically palatable preparations, a pharmaceutical composition in accordance with the invention can contain at least one agent selected from sweetening agents, flavoring agents, coloring agents, demulcents, antioxidants, and preserving agents.

A tablet can, for example, be prepared by admixing at least one compound of Formula (I) and/or at least one pharmaceutically acceptable salt thereof with at least one non-toxic pharmaceutically acceptable excipient suitable for the manufacture of tablets. Exemplary excipients include, but are not limited to, for example, inert diluents, such as, for example, calcium carbonate, sodium carbonate, lactose, calcium phosphate, and sodium phosphate; granulating and disintegrating agents, such as, for example, microcrystalline cellulose, sodium croscarmellose, corn starch, and alginic acid; binding agents, such as, for example, starch, gelatin, polyvinyl-pyrrolidone, and acacia; and lubricating agents, such as, for example, magnesium stearate, stearic acid, and talc. Additionally, a tablet can either be uncoated, or coated by known techniques to either mask the bad taste of an unpleasant tasting drug, or delay disintegration and absorption of the active ingredient in the gastrointestinal tract thereby sustaining the effects of the active ingredient for a longer period. Exemplary water soluble taste masking materials, include, but are not limited to, hydroxypropyl-methylcellulose and hydroxypropyl-cellulose. Exemplary time delay materials, include, but are not limited to, ethyl cellulose and cellulose acetate butyrate.

Hard gelatin capsules can, for example, be prepared by mixing at least one compound of Formula (I) and/or at least one salt thereof with at least one inert solid diluent, such as, for example, calcium carbonate; calcium phosphate; and kaolin.

Soft gelatin capsules can, for example, be prepared by mixing at least one compound of Formula (I) and/or at least one pharmaceutically acceptable salt thereof with at least one water soluble carrier, such as, for example, polyethylene glycol; and at least one oil medium, such as, for example, peanut oil, liquid paraffin, and olive oil.

An aqueous suspension can be prepared, for example, by admixing at least one compound of Formula (I) and/or at least one pharmaceutically acceptable salt thereof with at least one excipient suitable for the manufacture of an aqueous suspension. Exemplary excipients suitable for the manufacture of an aqueous suspension, include, but are not limited to, for example, suspending agents, such as, for example, sodium carboxymethylcellulose, methylcellulose, hydroxypropylmethyl-cellulose, sodium alginate, alginic acid, polyvinyl-pyrrolidone, gum tragacanth, and gum acacia; dispersing or wetting agents, such as, for example, a naturally-occurring phosphatide, e.g., lecithin; condensation products of alkylene oxide with fatty acids, such as, for example, polyoxyethylene stearate; condensation products of ethylene oxide with long chain aliphatic alcohols, such as, for example heptadecaethylene-oxycetanol; condensation products of ethylene oxide with partial esters derived from fatty acids and hexitol, such as, for example, polyoxyethylene sorbitol monooleate; and condensation products of ethylene oxide with partial esters derived from fatty acids and hexitol anhydrides, such as, for example, polyethylene sorbitan monooleate. An aqueous suspension can also contain at least one preservative, such as, for example, ethyl and n-propyl p-hydroxybenzoate; at least one coloring agent; at least one flavoring agent; and/or at least one sweetening agent, including but not limited to, for example, sucrose, saccharin, and aspartame.

Oily suspensions can, for example, be prepared by suspending at least one compound of Formula (I) and/or at least one pharmaceutically acceptable salt thereof in either a vegetable oil, such as, for example, arachis oil; olive oil; sesame oil; and coconut oil; or in mineral oil, such as, for example, liquid paraffin. An oily suspension can also contain at least one thickening agent, such as, for example, beeswax; hard paraffin; and cetyl alcohol. In order to provide a palatable oily suspension, at least one of the sweetening agents already described hereinabove, and/or at least one flavoring agent can be added to the oily suspension. An oily suspension can further contain at least one preservative, including, but not limited to, for example, an anti-oxidant, such as, for example, butylated hydroxyanisol, and alpha-tocopherol.

Dispersible powders and granules can, for example, be prepared by admixing at least one compound of Formula (I) and/or at least one pharmaceutically acceptable salt thereof with at least one dispersing and/or wetting agent; at least one suspending agent; and/or at least one preservative. Suitable dispersing agents, wetting agents, and suspending agents are as already described above. Exemplary preservatives include, but are not limited to, for example, anti-oxidants, e.g., ascorbic acid. In addition, dispersible powders and granules can also contain at least one excipient, including, but not limited to, for example, sweetening agents; flavoring agents; and coloring agents.

An emulsion of at least one compound of Formula (I) and/or at least one pharmaceutically acceptable salt thereof can, for example, be prepared as an oil-in-water emulsion. The oily phase of the emulsions comprising compounds of Formula (I) may be constituted from known ingredients in a known manner. The oil phase can be provided by, but is not limited to, for example, a vegetable oil, such as, for example, olive oil and arachis oil; a mineral oil, such as, for example, liquid paraffin; and mixtures thereof. While the phase may comprise merely an emulsifier, it may comprise a mixture of at least one emulsifier with a fat or an oil or with both a fat and an oil. Suitable emulsifying agents include, but are not limited to, for example, naturally-occurring phosphatides, e.g., soy bean lecithin; esters or partial esters derived from fatty acids and hexitol anhydrides, such as, for example, sorbitan monooleate; and condensation products of partial esters with ethylene oxide, such as, for example, polyoxyethylene sorbitan monooleate. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. An emulsion can also contain a sweetening agent, a flavoring agent, a preservative, and/or an antioxidant. Emulsifiers and emulsion stabilizers suitable for use in the formulation of the present invention include Tween 60, Span 80, cetostearyl alcohol, myristyl alcohol, glyceryl monostearate, sodium lauryl sulfate, glyceryl distearate alone or with a wax, or other materials well known in the art.

The compounds of Formula (I) and/or at least one pharmaceutically acceptable salt thereof can, for example, also be delivered intravenously, subcutaneously, and/or intramuscularly via any pharmaceutically acceptable and suitable injectable form. Exemplary injectable forms include, but are not limited to, for example, sterile aqueous solutions comprising acceptable vehicles and solvents, such as, for example, water, Ringer's solution, and isotonic sodium chloride solution; sterile oil-in-water microemulsions; and aqueous or oleaginous suspensions.

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (i.e. Captisol), cosolvent solubilization (i.e. propylene glycol) or micellar solubilization (i.e. Tween 80).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

A sterile injectable oil-in-water microemulsion can, for example, be prepared by 1) dissolving at least one compound of Formula (I) in an oily phase, such as, for example, a mixture of soybean oil and lecithin; 2) combining the Formula (I) containing oil phase with a water and glycerol mixture; and 3) processing the combination to form a microemulsion.

A sterile aqueous or oleaginous suspension can be prepared in accordance with methods already known in the art. For example, a sterile aqueous solution or suspension can be prepared with a non-toxic parenterally-acceptable diluent or solvent, such as, for example, 1,3-butane diol; and a sterile oleaginous suspension can be prepared with a sterile non-toxic acceptable solvent or suspending medium, such as, for example, sterile fixed oils, e.g., synthetic mono- or diglycerides; and fatty acids, such as, for example, oleic acid.

Pharmaceutically acceptable carriers, adjuvants, and vehicles that may be used in the pharmaceutical compositions of this invention include, but are not limited to, ion exchangers, alumina, aluminum stearate, lecithin, self-emulsifying drug delivery systems (SEDDS) such as d-alpha-tocopherol polyethyleneglycol 1000 succinate, surfactants used in pharmaceutical dosage forms such as Tweens, polyethoxylated castor oil such as CREMOPHOR surfactant (BASF), or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium tri silicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as alpha-, beta-, and gamma-cyclodextrin, or chemically modified derivatives such as hydroxyalkylcyclodextrins, including 2- and 3-hydroxypropyl-cyclodextrins, or other solubilized derivatives may also be advantageously used to enhance delivery of compounds of the formulae described herein.

The pharmaceutically active compounds of this invention can be processed in accordance with conventional methods of pharmacy to produce medicinal agents for administration to patients, including humans and other mammals. The pharmaceutical compositions may be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents.

The amounts of compounds that are administered and the dosage regimen for treating a disease condition with the compounds and/or compositions of this invention depends on a variety of factors, including the age, weight, sex, the medical condition of the subject, the type of disease, the severity of the disease, the route and frequency of administration, and the particular compound employed. Thus, the dosage regimen may vary widely, but can be determined routinely using standard methods. A daily dose of about 0.001 to 100 mg/kg body weight, preferably between about 0.0025 and about 50 mg/kg body weight and most preferably between about 0.005 to 10 mg/kg body weight, may be appropriate. The daily dose can be administered in one to four doses per day. Other dosing schedules include one dose per week and one dose per two day cycle.

For therapeutic purposes, the active compounds of this invention are ordinarily combined with one or more adjuvants appropriate to the indicated route of administration. If administered orally, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose.

Pharmaceutical compositions of this invention comprise at least one compound of Formula (I) and/or at least one pharmaceutically acceptable salt thereof, and optionally an additional agent selected from any pharmaceutically acceptable carrier, adjuvant, and vehicle. Alternate compositions of this invention comprise a compound of the Formula (I) described herein, or a prodrug thereof, and a pharmaceutically acceptable carrier, adjuvant, or vehicle.

UTILITY

The compounds of Formula (I) are useful for the treatment of cancer.

In another embodiment, the present invention provides a combined preparation of a compound of Formula (I), and/or a pharmaceutically acceptable salt thereof, a stereoisomer thereof or a tautomer thereof, and additional therapeutic agent(s) for simultaneous, separate or sequential use in the treatment and/or prophylaxis of multiple diseases or disorders associated with DGK target inhibition in T cells.

In another aspect, the invention provides a method of treating a patient suffering from or susceptible to a medical condition that is associated with DGK target inhibition in T cells. A number of medical conditions can be treated. The method comprises administering to the patient a therapeutically effective amount of a composition comprising a compound of Formula (I) and/or a pharmaceutically acceptable salt thereof, a stereoisomer thereof or a tautomer thereof. For example, the compounds described herein may be used to treat or prevent viral infections and proliferative diseases such as cancer.

The compounds for Formula (I) and pharmaceutical compositions comprising at least one compound of Formula (I) are useful in treating or preventing any disease or conditions that are associated with DGK target inhibition in T cells. These include viral and other infections (e.g., skin infections, GI infection, urinary tract infections, genito-urinary infections, systemic infections), and proliferative diseases (e.g., cancer). The compounds of Formula (I) and pharmaceutical compositions comprising in at least one compound of Formula (I) may be administered to animals, preferably mammals (e.g., domesticated animals, cats, dogs, mice, rats), and more preferably humans. Any method of administration may be used to deliver the compound or pharmaceutical composition to the patient. In certain embodiments, the compound of Formula (I) or pharmaceutical composition comprising at least compound of Formula (I) is administered orally. In other embodiments, the Formula (I) or pharmaceutical composition comprising at least compound of Formula (I) is administered parenterally.

The compounds of Formula (I) can inhibit activity of the diacylglycerol kinase alpha and zeta (DGKα/ζ). For example, the compounds of Formula (I) can be used to inhibit activity of DGKα and DGKζ in a cell or in an individual in need of modulation of DGKα and DGKζ by administering an inhibiting amount of a compound of Formula (I) or a salt thereof.

The present invention further provides methods of treating diseases associated with activity or expression, including abnormal activity and/or overexpression, of DGKα and DGKζ in an individual (e.g., patient) by administering to the individual in need of such treatment a therapeutically effective amount or dose of a compound of Formula (I) or a pharmaceutical composition thereof. Example diseases can include any disease, disorder or condition that is directly or indirectly linked to expression or activity of DGKα and DGKζ enzyme, such as over expression or abnormal activity. A DGKα and DGKζ-associated disease can also include any disease, disorder or condition that can be prevented, ameliorated, or cured by modulating DGKα and DGKζ enzyme activity. Examples of DGKα and DGKζ associated diseases include cancer and viral infections such as HIV infection, hepatitis B, and hepatitis C.

In one aspect, the compound(s) of Formula (I) are sequentially administered prior to administration of the immuno-oncology agent. In another aspect, compound(s) of Formula (I) are administered concurrently with the immuno-oncology agent. In yet another aspect, compound(s) of Formula (I) are sequentially administered after administration of the immuno-oncology agent.

In another aspect, compounds of Formula (I) may be co-formulated with an immuno-oncology agent.

Immuno-oncology agents include, for example, a small molecule drug, antibody, or other biologic or small molecule. Examples of biologic immuno-oncology agents include, but are not limited to, cancer vaccines, antibodies, and cytokines. In one aspect, the antibody is a monoclonal antibody. In another aspect, the monoclonal antibody is humanized or human.

In one aspect, the immuno-oncology agent is (i) an agonist of a stimulatory (including a co-stimulatory) receptor or (ii) an antagonist of an inhibitory (including a co-inhibitory) signal on T cells, both of which result in amplifying antigen-specific T cell responses (often referred to as immune checkpoint regulators).

Certain of the stimulatory and inhibitory molecules are members of the immunoglobulin super family (IgSF). One important family of membrane-bound ligands that bind to co-stimulatory or co-inhibitory receptors is the B7 family, which includes B7-1, B7-2, B7-H1 (PD-L1), B7-DC (PD-L2), B7-H2 (ICOS-L), B7-H3, B7-H4, B7-H5 (VISTA), and B7-H6. Another family of membrane bound ligands that bind to co-stimulatory or co-inhibitory receptors is the TNF family of molecules that bind to cognate TNF receptor family members, which includes CD40 and CD40L, OX-40, OX-40L, CD70, CD27L, CD30, CD30L, 4-1BBL, CD137 (4-1BB), TRAIL/Apo2-L, TRAILR1/DR4, TRAILR2/DR5, TRAILR3, TRAILR4, OPG, RANK, RANKL, TWEAKR/Fn14, TWEAK, BAFFR, EDAR, XEDAR, TACI, APRIL, BCMA, LTβR, LIGHT, DcR3, HVEM, VEGI/TL1A, TRAMP/DR3, EDAR, EDA1, XEDAR, EDA2, TNFR1, Lymphotoxin α/TNFβ, TNFR2, TNFα, LTβR, Lymphotoxin α 1β2, FAS, FASL, RELT, DR6, TROY, NGFR.

In one aspect, T cell responses can be stimulated by a combination of a compound of Formula (I) and one or more of (i) an antagonist of a protein that inhibits T cell activation (e.g., immune checkpoint inhibitors) such as CTLA-4, PD-1, PD-L1, PD-L2, LAG-3, TIM-3, Galectin 9, CEACAM-1, BTLA, CD69, Galectin-1, TIGIT, CD113, GPR56, VISTA, 2B4, CD48, GARP, PD1H, LAIR1, TIM-1, and TIM-4, and (ii) an agonist of a protein that stimulates T cell activation such as B7-1, B7-2, CD28, 4-1BB (CD137), 4-1BBL, ICOS, ICOS-L, OX40, OX40L, GITR, GITRL, CD70, CD27, CD40, DR3 and CD28H.

Other agents that can be combined with compounds of Formula (I) for the treatment of cancer include antagonists of inhibitory receptors on NK cells or agonists of activating receptors on NK cells. For example, compounds of Formula (I) can be combined with antagonists of KIR, such as lirilumab.

Yet other agents for combination therapies include agents that inhibit or deplete macrophages or monocytes, including but not limited to CSF-1R antagonists such as CSF-1R antagonist antibodies including RG7155 (WO11/70024, WO11/107553, WO11/131407, WO13/87699, WO13/119716, WO13/132044) or FPA-008 (WO11/140249; WO13169264; WO14/036357).

In another aspect, compounds of Formula (I) can be used with one or more of agonistic agents that ligate positive costimulatory receptors, blocking agents that attenuate signaling through inhibitory receptors, antagonists, and one or more agents that increase systemically the frequency of anti-tumor T cells, agents that overcome distinct immune suppressive pathways within the tumor microenvironment (e.g., block inhibitory receptor engagement (e.g., PD-L1/PD-1 interactions), deplete or inhibit Tregs (e.g., using an anti-CD25 monoclonal antibody (e.g., daclizumab) or by ex vivo anti-CD25 bead depletion), inhibit metabolic enzymes such as IDO, or reverse/prevent T cell anergy or exhaustion) and agents that trigger innate immune activation and/or inflammation at tumor sites.

In one aspect, the immuno-oncology agent is a CTLA-4 antagonist, such as an antagonistic CTLA-4 antibody. Suitable CTLA-4 antibodies include, for example, YERVOY (ipilimumab) or tremelimumab.

In another aspect, the immuno-oncology agent is a PD-1 antagonist, such as an antagonistic PD-1 antibody. Suitable PD-1 antibodies include, for example, OPDIVO (nivolumab), KEYTRUDA (pembrolizumab), or MEDI-0680 (AMP-514; WO2012/145493). The immuno-oncology agent may also include pidilizumab (CT-011), though its specificity for PD-1 binding has been questioned. Another approach to target the PD-1 receptor is the recombinant protein composed of the extracellular domain of PD-L2 (B7-DC) fused to the Fc portion of IgG1, called AMP-224

In another aspect, the immuno-oncology agent is a PD-L1 antagonist, such as an antagonistic PD-L1 antibody. Suitable PD-L1 antibodies include, for example, MPDL3280A (RG7446; WO2010/077634), durvalumab (MEDI4736), BMS-936559 (WO2007/005874), and MSB0010718C (WO2013/79174).

In another aspect, the immuno-oncology agent is a LAG-3 antagonist, such as an antagonistic LAG-3 antibody. Suitable LAG3 antibodies include, for example, BMS-986016 (WO10/19570, WO14/08218), or IMP-731 or IMP-321 (WO08/132601, WO09/44273).

In another aspect, the immuno-oncology agent is a CD137 (4-1BB) agonist, such as an agonistic CD137 antibody. Suitable CD137 antibodies include, for example, urelumab and PF-05082566 (WO12/32433).

In another aspect, the immuno-oncology agent is a GITR agonist, such as an agonistic GITR antibody. Suitable GITR antibodies include, for example, BMS-986153, BMS-986156, TRX-518 (WO06/105021, WO09/009116) and MK-4166 (WO11/028683).

In another aspect, the immuno-oncology agent is an IDO antagonist. Suitable IDO antagonists include, for example, INCB-024360 (WO2006/122150, WO07/75598, WO08/36653, WO08/36642), indoximod, BMS-986205, or NLG-919 (WO09/73620, WO09/1156652, WO11/56652, WO12/142237).

In another aspect, the immuno-oncology agent is an OX40 agonist, such as an agonistic OX40 antibody. Suitable OX40 antibodies include, for example, MEDI-6383 or MEDI-6469.

In another aspect, the immuno-oncology agent is an OX40L antagonist, such as an antagonistic OX40 antibody. Suitable OX40L antagonists include, for example, RG-7888 (WO06/029879).

In another aspect, the immuno-oncology agent is a CD40 agonist, such as an agonistic CD40 antibody. In yet another embodiment, the immuno-oncology agent is a CD40 antagonist, such as an antagonistic CD40 antibody. Suitable CD40 antibodies include, for example, lucatumumab or dacetuzumab.

In another aspect, the immuno-oncology agent is a CD27 agonist, such as an agonistic CD27 antibody. Suitable CD27 antibodies include, for example, varlilumab.

In another aspect, the immuno-oncology agent is MGA271 (to B7H3) (WO11/109400).

The combination therapy is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single dosage form having a fixed ratio of each therapeutic agent or in multiple, single dosage forms for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. Combination therapy also can embrace the administration of the therapeutic agents as described above in further combination with other biologically active ingredients and non-drug therapies (e.g., surgery or radiation treatment.) Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal.

As used herein, the term "contacting" refers to the bringing together of indicated moieties in an in vitro system or an in vivo system. For example, "contacting" the DGKα and DGKζ enzyme with a compound of Formula (I) includes the administration of a compound of the present invention to an individual or patient, such as a human, having DGKα and DGKζ, as well as, for example, introducing a compound of Formula (I) into a sample containing a cellular or purified preparation containing DGKα and DGKζ enzyme.

The term "DGKα and DGKζ inhibitor" refers to an agent capable of inhibiting the activity of diacylglycerol kinase alpha and/or diacylglycerol kinase zeta (DGKα and DGKζ) in T cells resulting in T cell stimulation. The DGKα and DGKζ inhibitor may be a reversible or irreversible DGKα and DGKζ inhibitor. "A reversible DGKα and DGKζ inhibitor" is a compound that reversibly inhibits DGKα and DGKζ enzyme activity either at the catalytic site or at a non-catalytic site and "an irreversible DGKα and DGKζ inhibitor" is a compound that irreversibly destroys DGKα and DGKζ enzyme activity by forming a covalent bond with the enzyme.

Types of cancers that may be treated with the compound of Formula (I) include, but are not limited to, brain cancers, skin cancers, bladder cancers, ovarian cancers, breast cancers, gastric cancers, pancreatic cancers, prostate cancers, colon cancers, blood cancers, lung cancers and bone cancers. Examples of such cancer types include neuroblastoma, intestine carcinoma such as rectum carcinoma, colon carcinoma, familiar adenomatous polyposis carcinoma and hereditary non-polyposis colorectal cancer, esophageal carcinoma, labial carcinoma, larynx carcinoma, hypopharynx carcinoma, tongue carcinoma, salivary gland carcinoma, gastric carcinoma, adenocarcinoma, medullary thyroid carcinoma, papillary thyroid carcinoma, renal carcinoma, kidney parenchymal carcinoma, ovarian carcinoma, cervix carcinoma, uterine corpus carcinoma, endometrium carcinoma, chorion carcinoma, pancreatic carcinoma, prostate carcinoma, testis carcinoma, breast carcinoma, urinary carcinoma, melanoma, brain tumors such as glioblastoma, astrocytoma, meningioma, medulloblastoma and peripheral neuroectodermal tumors, Hodgkin lymphoma, non-Hodgkin lymphoma, Burkitt lymphoma, acute lymphatic leukemia (ALL), chronic lymphatic leukemia (CLL), acute myeloid leukemia (AML), chronic myeloid leukemia (CML), adult T-cell leukemia lymphoma, diffuse large B-cell lymphoma (DLBCL), hepatocellular carcinoma, gall bladder carcinoma, bronchial carcinoma, small cell lung carcinoma, non-small cell lung carcinoma, multiple myeloma, basalioma, teratoma, retinoblastoma, choroid melanoma, seminoma, rhabdomyosarcoma, craniopharyngioma, osteosarcoma, chondrosarcoma, myosarcoma, liposarcoma, fibrosarcoma, Ewing sarcoma and plasmocytoma.

One or more additional pharmaceutical agents or treatment methods such as, for example, anti-viral agents, chemotherapeutics or other anti-cancer agents, immune enhancers, immunosuppressants, radiation, anti-tumor and anti-viral vaccines, cytokine therapy (e.g., IL2 and GM-CSF), and/or tyrosine kinase inhibitors can be optionally used in combination with the compounds of Formula (I) for treatment of DGKα and DGKζ associated diseases, disorders or conditions. The agents can be combined with the present compounds in a single dosage form, or the agents can be administered simultaneously or sequentially as separate dosage forms.

Suitable chemotherapeutic or other anti-cancer agents include, for example, alkylating agents (including, without limitation, nitrogen mustards, ethylenimine derivatives, alkyl sulfonates, nitrosoureas and triazenes) such as uracil mustard, chlormethine, cyclophosphamide (CYTOXAN®), ifosfamide, melphalan, chlorambucil, pipobroman, triethylene-melamine, triethylenethiophosphoramine, busulfan, carmustine, lomustine, streptozocin, dacarbazine, and temozolomide.

In the treatment of melanoma, suitable agents for use in combination with the compounds of Formula (I) include: dacarbazine (DTIC), optionally, along with other chemotherapy drugs such as carmustine (BCNU) and cisplatin; the "Dartmouth regimen", which consists of DTIC, BCNU, cisplatin and tamoxifen; a combination of cisplatin, vinblastine, and DTIC, temozolomide or YERVOY™. Compounds of Formula (I) may also be combined with immunotherapy drugs, including cytokines such as interferon alpha, interleukin 2, and tumor necrosis factor (TNF) in the treatment of melanoma.

Compounds of Formula (I) may also be used in combination with vaccine therapy in the treatment of melanoma. Antimelanoma vaccines are, in some ways, similar to the anti-virus vaccines which are used to prevent diseases caused by viruses such as polio, measles, and mumps. Weakened melanoma cells or parts of melanoma cells called antigens may be injected into a patient to stimulate the body's immune system to destroy melanoma cells.

Melanomas that are confined to the arms or legs may also be treated with a combination of agents including one or more compounds of Formula (I), using a hyperthermic isolated limb perfusion technique. This treatment protocol temporarily separates the circulation of the involved limb from the rest of the body and injects high doses of chemotherapy into the artery feeding the limb, thus providing high doses to the area of the tumor without exposing internal organs to these doses that might otherwise cause severe side effects. Usually the fluid is warmed to 38.9° C. to 40° C. Melphalan is the drug most often used in this chemotherapy procedure. This can be given with another agent called tumor necrosis factor (TNF).

Suitable chemotherapeutic or other anti-cancer agents include, for example, antimetabolites (including, without limitation, folic acid antagonists, pyrimidine analogs, purine analogs and adenosine deaminase inhibitors) such as methotrexate, 5-fluorouracil, floxuridine, cytarabine, 6-mercaptopurine, 6-thioguanine, fludarabine phosphate, pentostatine, and gemcitabine.

Suitable chemotherapeutic or other anti-cancer agents further include, for example, certain natural products and their derivatives (for example, *vinca* alkaloids, antitumor antibiotics, enzymes, lymphokines and epipodophyllotoxins) such as vinblastine, vincristine, vindesine, bleomycin, dactinomycin, daunorubicin, doxorubicin, epirubicin, idarubicin, ara-C, paclitaxel (Taxol), mithramycin, deoxycoformycin, mitomycin-C, L-asparaginase, interferons (especially IFN-α), etoposide, and teniposide.

Other cytotoxic agents include navelbene, CPT-11, anastrazole, letrazole, capecitabine, reloxafine, and droloxafine.

Also suitable are cytotoxic agents such as epidophyllotoxin; an antineoplastic enzyme; a topoisomerase inhibitor; procarbazine; mitoxantrone; platinum coordination complexes such as cisplatin and carboplatin; biological response modifiers; growth inhibitors; antihormonal therapeutic agents; leucovorin; tegafur; and haematopoietic growth factors.

Other anti-cancer agent(s) include antibody therapeutics such as trastuzumab (HERCEPTIN®), antibodies to costimulatory molecules such as CTLA-4, 4-1BB and PD-1, or antibodies to cytokines (IL-1O or TGF-β).

Other anti-cancer agents also include those that block immune cell migration such as antagonists to chemokine receptors, including CCR2 and CCR4.

Other anti-cancer agents also include those that augment the immune system such as adjuvants or adoptive T cell transfer.

Anti-cancer vaccines include dendritic cells, synthetic peptides, DNA vaccines and recombinant viruses.

The pharmaceutical composition of the invention may optionally include at least one signal transduction inhibitor (STI). A "signal transduction inhibitor" is an agent that selectively inhibits one or more vital steps in signaling pathways, in the normal function of cancer cells, thereby leading to apoptosis. Suitable STIs include, but are not limited to: (i) bcr/abl kinase inhibitors such as, for example, STI 571 (GLEEVEC®); (ii) epidermal growth factor (EGF) receptor inhibitors such as, for example, kinase inhibitors (IRESSA®, SSI-774) and antibodies (Imclone: C225 [Goldstein et al., *Clin. Cancer Res.,* 1:1311-1318 (1995)], and Abgenix: ABX-EGF); (iii) her-2/neu receptor inhibitors such as farnesyl transferase inhibitors (FTI) such as, for example, L-744,832 (Kohl et al., *Nat. Med.,* 1(8):792-797 (1995)); (iv) inhibitors of Akt family kinases or the Akt pathway, such as, for example, rapamycin (see, for example, Sekulic et al., *Cancer Res.,* 60:3504-3513 (2000)); (v) cell cycle kinase inhibitors such as, for example, flavopiridol and UCN-O1 (see, for example, Sausville, *Curr. Med. Chem. Anti-Canc. Agents,* 3:47-56 (2003)); and (vi) phosphatidyl inositol kinase inhibitors such as, for example, LY294002 (see, for example, Vlahos et al., *J. Biol. Chem.,* 269:5241-5248 (1994)). Alternatively, at least one STI and at least one compound of Formula (I) may be in separate pharmaceutical compositions. In a specific embodiment of the present invention, at least one compound of Formula (I) and at least one STI may be administered to the patient concurrently or sequentially. In other words, at least one compound of Formula (I) may be administered first, at least one STI may be administered first, or at least one compound of Formula (I) and at least one STI may be administered at the same time. Additionally, when more than one compound of Formula (I) and/or STI is used, the compounds may be administered in any order.

The present invention further provides a pharmaceutical composition for the treatment of a chronic viral infection in a patient comprising at least one compound of Formula (I), optionally, at least one chemotherapeutic drug, and, optionally, at least one antiviral agent, in a pharmaceutically acceptable carrier.

Also provided is a method for treating a chronic viral infection in a patient by administering an effective amount of the above pharmaceutical composition.

In a specific embodiment of the present invention, at least one compound of Formula (I) and at least one chemotherapeutic agent are administered to the patient concurrently or sequentially. In other words, at least one compound of Formula (I) may be administered first, at least one chemotherapeutic agent may be administered first, or at least one compound of Formula (I) and the at least one STI may be administered at the same time. Additionally, when more than one compound of Formula (I) and/or chemotherapeutic agent is used, the compounds may be administered in any order. Similarly, any antiviral agent or STI may also be administered at any point in comparison to the administration of the compound of Formula (I).

Chronic viral infections that may be treated using the present combinatorial treatment include, but are not limited to, diseases caused by: hepatitis C virus (HCV), human papilloma virus (HPV), cytomegalovirus (CMV), herpes simplex virus (HSV), Epstein-Barr virus (EBV), varicella zoster virus, coxsackie virus, human immunodeficiency virus (HIV). Notably, parasitic infections (e.g., malaria) may also be treated by the above methods wherein compounds known to treat the parasitic conditions are optionally added in place of the antiviral agents.

Suitable antiviral agents contemplated for use in combination with the compound of Formula (I) can comprise nucleoside and nucleotide reverse transcriptase inhibitors (NRTIs), non-nucleoside reverse transcriptase inhibitors (NNRTIs), protease inhibitors and other antiviral drugs.

Examples of suitable NRTIs include zidovudine (AZT); didanosine (ddI); zalcitabine (ddC); stavudine (d4T); lamivudine (3TC); abacavir (1592U89); adefovir dipivoxil [bis(POM)-PMEA]; lobucavir; BCH-I0652; emitricitabine [(−)-FTC]; beta-L-FD4 (also called beta-L-D4C and named beta-L-2',3'-dideoxy-5-fluoro-cytidene); DAPD, ((−)-beta-D-2,6-diamino-purine dioxolane); and lodenosine (FddA). Typical suitable NNRTIs include nevirapine (BI-RG-587); delaviradine (BHAP, U-90152); efavirenz (DMP-266); PNU-142721; AG-1549; MKC-4-((2 (1-(ethoxy-methyl)-5-(1-methylethyl)-6-(phenylmethyl)-(2,4(1H,3H)-pyrimidinedione); and (+)-calanolide A (NSC-675451) and B. Typical suitable protease inhibitors include saquinavir (Ro 31-8959); ritonavir (ABT-538); indinavir (MK-639); nelfnavir (AG-1343); amprenavir (141W94); lasinavir; DMP-450; BMS-2322623; ABT-378; and AG-1549. Other antiviral agents include hydroxyurea, ribavirin, IL-2, IL-12, pentafuside and Yissum Project No. 11607.

The present invention also includes pharmaceutical kits useful, for example, in the treatment or prevention of DGKα and DGKζ-associated diseases or disorders, and other diseases referred to herein which include one or more containers containing a pharmaceutical composition comprising a therapeutically effective amount of a compound of Formula (I). Such kits can further include, if desired, one or more of various conventional pharmaceutical kit components, such as, for example, containers with one or more pharmaceutically acceptable carriers, additional containers, as will be readily apparent to those skilled in the art. Instructions, either as inserts or as labels, indicating quantities of the components to be administered, guidelines for administration, and/or guidelines for mixing the components, can also be included in the kit.

The combination therapy is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single dosage form having a fixed ratio of each therapeutic agent or in multiple, single dosage forms for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. Combination therapy also can embrace the administration of the therapeutic agents as described above in further combination with other biologically active ingredients and non-drug therapies (e.g., surgery or radiation treatment). Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

The invention also provides pharmaceutically acceptable compositions which comprise a therapeutically effective amount of one or more of the compounds of Formula (I), formulated together with one or more pharmaceutically acceptable carriers (additives) and/or diluents, and optionally, one or more additional therapeutic agents described above.

The compounds of this invention can be administered for any of the uses described herein by any suitable means, for example, orally, such as tablets, capsules (each of which includes sustained release or timed release formulations), pills, powders, granules, elixirs, tinctures, suspensions (including nanosuspensions, microsuspensions, spray-dried dispersions), syrups, and emulsions; sublingually; bucally; parenterally, such as by subcutaneous, intravenous, intramuscular, or intrasternal injection, or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories. They can be administered alone, but generally will be administered with a pharmaceutical carrier selected on the basis of the chosen route of administration and standard pharmaceutical practice.

The phrase "pharmaceutically acceptable carrier" as used herein means a pharmaceutically acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation, including, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms; and not injurious to the patient.

The term "pharmaceutical composition" means a composition comprising a compound of the invention in combination with at least one additional pharmaceutically acceptable carrier.

Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, Allen, L. V. Jr. et al. Remington: The Science and Practice of Pharmacy (2 Volumes), 22nd Edition (2012), Pharmaceutical Press.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired.

By way of general guidance, the daily oral dosage of each active ingredient, when used for the indicated effects, will range between about 0.001 to about 5000 mg per day, preferably between about 0.01 to about 1000 mg per day, and most preferably between about 0.1 to about 250 mg per day. Intravenously, the most preferred doses will range from about 0.01 to about 10 mg/kg/minute during a constant rate infusion. Compounds of this invention may be administered in a single daily dose, or the total daily dosage may be administered in divided doses of two, three, or four times daily.

The compounds are typically administered in admixture with suitable pharmaceutical diluents, excipients, or carriers (collectively referred to herein as pharmaceutical carriers) suitably selected with respect to the intended form of administration, e.g., oral tablets, capsules, elixirs, and syrups, and consistent with conventional pharmaceutical practices.

Dosage forms (pharmaceutical compositions) suitable for administration may contain from about 1 milligram to about 2000 milligrams of active ingredient per dosage unit. In these pharmaceutical compositions the active ingredient will ordinarily be present in an amount of about 0.1-95% by weight based on the total weight of the composition.

A typical capsule for oral administration contains at least one of the compounds of the present invention (250 mg), lactose (75 mg), and magnesium stearate (15 mg). The mixture is passed through a 60 mesh sieve and packed into a No. L gelatin capsule.

A typical injectable preparation is produced by aseptically placing at least one of the compounds of the present invention (250 mg) into a vial, aseptically freeze-drying and sealing. For use, the contents of the vial are mixed with 2 mL of physiological saline, to produce an injectable preparation.

The present invention includes within its scope pharmaceutical compositions comprising, as an active ingredient, a therapeutically effective amount of at least one of the compounds of the present invention, alone or in combination with a pharmaceutical carrier. Optionally, compounds of the present invention can be used alone, in combination with other compounds of the invention, or in combination with one or more other therapeutic agent(s), e.g., an anticancer agent or other pharmaceutically active material.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of this invention may be varied so as to obtain an amount of the active ingredient which is effective to achieve the therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the therapeutic effect and gradually increase the dosage until the effect is achieved.

In general, a suitable daily dose of a compound of the invention will be that amount of the compound which is the lowest dose effective to produce a therapeutic effect. Such an effective dose will generally depend upon the factors described above. Generally, oral, intravenous, intracerebroventricular and subcutaneous doses of the compounds of this invention for a patient will range from about 0.01 to about 50 mg per kilogram of body weight per day.

If desired, the effective daily dose of the active compound may be administered as two, three, four, five, six or more sub-doses administered separately at appropriate intervals throughout the day, optionally, in unit dosage forms. In certain aspects of the invention, dosing is one administration per day.

While it is possible for a compound of the present invention to be administered alone, it is preferable to administer the compound as a pharmaceutical formulation (composition).

The above other therapeutic agents, when employed in combination with the compounds of the present invention, may be used, for example, in those amounts indicated in the Physicians' Desk Reference (PDR) or as otherwise determined by one of ordinary skill in the art. In the methods of the present invention, such other therapeutic agent(s) may be administered prior to, simultaneously with, or following the administration of the inventive compounds.

Methods of Preparation

The compounds of the present invention may be synthesized by many methods available to those skilled in the art of organic chemistry. General synthetic schemes for preparing compounds of the present invention are described below. These schemes are illustrative and are not meant to limit the possible techniques one skilled in the art may use to prepare the compounds disclosed herein. Different methods to prepare the compounds of the present invention will be evident to those skilled in the art. Examples of compounds of the present invention prepared by methods described in the general schemes are given in the Examples section set out hereinafter. Preparation of homochiral examples may be carried out by techniques known to one skilled in the art. For example, homochiral compounds may be prepared by separation of racemic products or diastereomers by chiral phase preparative HPLC. Alternatively, the example compounds may be prepared by methods known to give enantiomerically or diastereomerically enriched products.

The reactions and techniques described in this section are performed in solvents appropriate to the reagents and materials employed and are suitable for the transformations being effected. Also, in the description of the synthetic methods given below, it is to be understood that all proposed reaction conditions, including choice of solvent, reaction atmosphere, reaction temperature, duration of the experiment and work up procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents that are compatible with the reaction conditions will be readily apparent to one skilled in the art, with alternatives required when incompatible substituents are present. This will sometimes require a judgment to modify the order of the synthetic steps or to select one particular process scheme over another in order to obtain a compound of the invention. It will also be recognized that another major consideration in the planning of any synthetic route in this field is the judicious choice of a protecting group used for protection of reactive functional groups present in the compounds described in this invention. An authoritative account describing the many alternatives to the trained practitioner is Wuts and Greene, *Greene's Protective Groups in Organic Synthesis*, Fourth Edition, Wiley and Sons (2007).

In a further enablement, intermediates and examples of the current invention may be prepared using stereoselective methodologies know in the art, examples of which are shown in the following schemes.

SCHEME 1

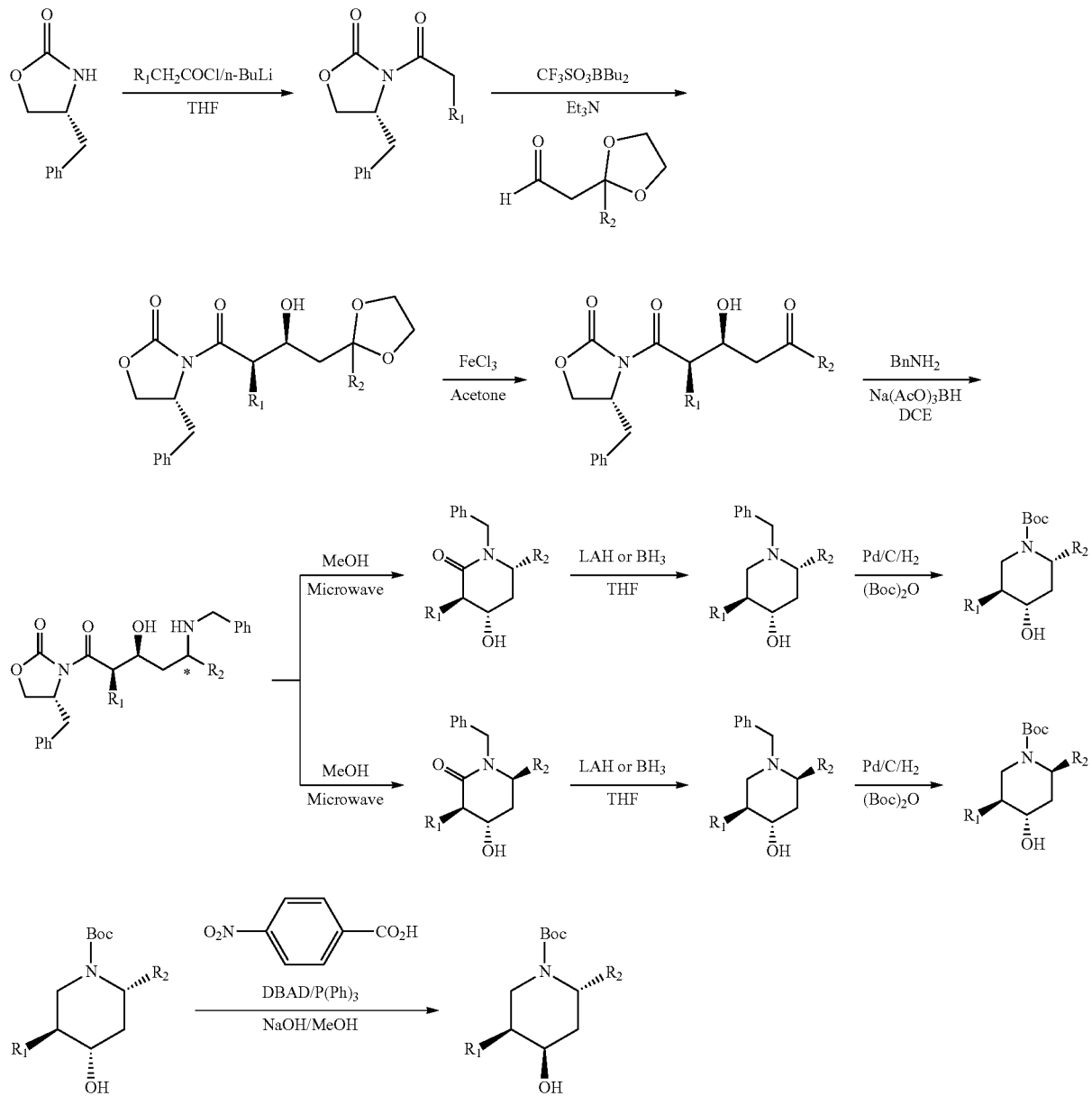

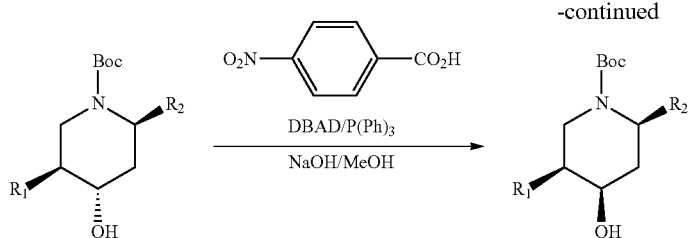

Both antipodes of chiral oxazolidinones of the type depicted can be reacted with acyl chlorides at low temperature to yield N-acyl derivatives. These can be converted into the related boron enolates and condensed with 2-(2-alkyl-1,3-dioxolan-2-yl)acetaldehydes to yield 4-benzyl-3-(2-alkyl-3-hydroxy-4-(2-alkyl-1,3-dioxolan-2-yl)butanoyl)oxazolidinones of known stereochemistry. Deprotection of the product dioxolanes using for example, ferric chloride in acetone can yield 1-(4-benzyl-2-oxooxazolidin-3-yl)-2-alkyl-3-hydroxyalkyl-1,5-diones. Subsequent reductive amination using benzylamine with for example, sodium triacetoxyborohydride can provide diastereomeric mixutures of 4-benzyl-3-(5-(benzylamino)-2-alkyl-3-hydroxyalkanoyl) oxazolidinones. The resultant amines may be intramolecularly cyclized by heating in MeOH under microwave conditions to provide chromatographically separable 1-benzyl-3-alkyl-4-hydroxy-6-alkylpiperidin-2-ones. Succeeding reduction of the product piperidinones with for example, borane or LAH can yield N-benyl-2-alkyl-4-hydoxy-5-alkylpiperidines. Removal of the benzyl moiety under hydrogenolysis conditions in the presence of di-tert-butyl dicarbonate can allow access to tert-butyl 4-hydroxy-2,5-dialkylpiperidine-1-carboxylates that are useful intermediates in the syntheses of examples of the current invention. In a further step, the stereochemistry of the 4-hydroxy moiety in these and related intermediates may be inverted using standard Mitsunobu conditions employing p-nitrobenzoic acid to yield esters from which the desired alcohols can be liberated by base catalyzed hydrolysis. Employing these methodologies with appropriately functionalized oxazolidinones and aldehydes can yield intermediates of known stereochemistry. An example of the utilization of such compounds to access additional embodiments of the current invention is shown in the methodologies outlined in the following scheme.

SCHEME 2

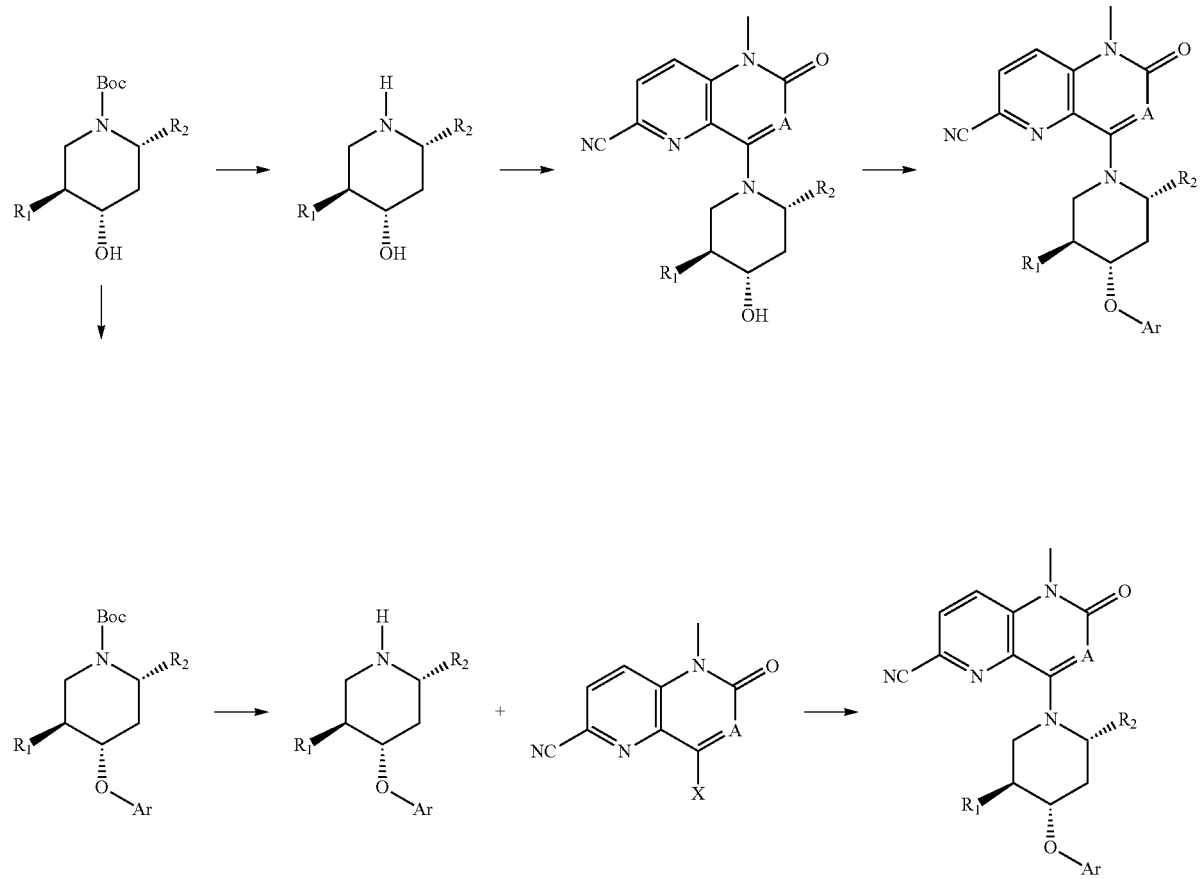

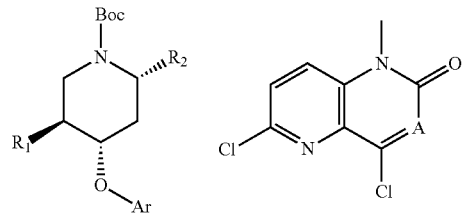
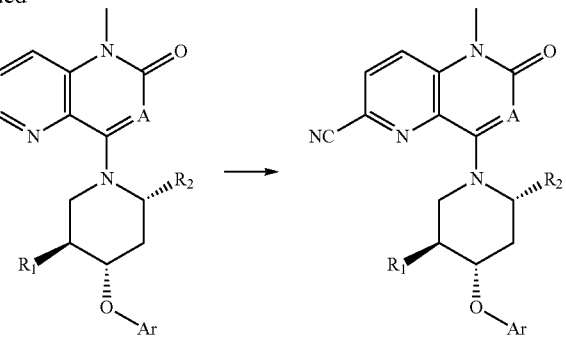

A = CH or N  Ar = aryl or heteroaryl  X = Cl or Triflate

In these instances, N-boc protected 2,5-dialkyl-4 hydroxypiperidines can first be deprotected under standard conditions and then reacted with suitably derivatized 1-alkylpyrido[3,2-d]pyrimidin-2(1H)-ones or 1-alkyl-1,5-naphthyridin-2(1H)-ones to give product alcohols that can subsequently be reacted under either Mitsunobu conditions, or with selected heterocycles under SNAr conditions to give examples of the current invention. Alternatively, the N-boc protected 2,5-dialkyl-4 hydroxypiperidines may first be reacted under Mitsunobu conditions with appropriately functionalized phenols, or with selected heterocycles under SNAr conditions to give additional intermediates of the type depicted above. Subsequent reaction with suitably functionalized pyrido[3,2-d]pyrimidin-2(1H)-ones or naphthyridin-2(1H)-ones can provide access to additional examples. In some cases, the 2,5-dialkyl-4-hydroxypiperidines or their related ethers can be reacted with 4,6-dichloro-1-alkylpyrido[3,2-d]pyrimidin-2(1H)-ones or 4,6-dichloro-1-alkyl-1,5-naphthyridin-2(1H)-ones to access the related 4-N-piperidinyl derivatives, thus facilitating the introduction of additional functionality at the 6-position of the bicyclic heterocycle, for example a nitrile group, which are further embodiments of the current invention.

EXAMPLES

The following examples illustrate the particular and preferred embodiments of the present invention and do not limit the scope of the present invention. Chemical abbreviations and symbols as well as scientific abbreviations and symbols have their usual and customary meanings unless otherwise specified. Additional abbreviations employed in the Examples and elsewhere in this application are defined above. Common intermediates are generally useful for the preparation of more than one Example and are identified sequentially (e.g., Intermediate 1, Intermediate 2, etc.) and are abbreviated as Int. 1 or I1, Int. 2 or I2, etc. Compounds of the Examples are identified by the example and step in which they were prepared (e.g., "1-A" denotes the Example 1, step A), or by the example only where the compound is the title compound of the example (for example, "1" denotes the title compound of Example 1). In some instances alternate preparations of intermediates or examples are described. Frequently chemists skilled in the art of synthesis may devise alternative preparations which may be desirable based on one or more considerations such as shorter reaction time, less expensive starting materials, ease of operation or isolation, improved yield, amenable to catalysis, avoidance of toxic reagents, accessibility of specialized instrumentation, and decreased number of linear steps, etc. The intent of describing alternative preparations is to further enable the preparation of the examples of this invention. In some instances some functional groups in the outlined examples and claims may be replaced by well-known bioisosteric replacements known in the art, for example, replacement of a carboxylic acid group with a tetrazole or a phosphate moiety. $^1$H NMR data collected in deuterated dimethyl sulfoxide used water suppression in the data processing. The reported spectra are uncorrected for the effects of water suppression. Protons adjacent to the water suppression frequency of 3.35 ppm exhibit diminished signal intensity.

In the examples, the use of hashed wedge bonds imply relative stereochemistry. The "(+/−)" designation preceding the name of a compound indicates a racemic mixture. The "(rel)" designation indicates that all stereochemical designations for the compound are relative and not absolute. The use of a non-hashed bond at a chiral center implies unknown relative stereochemistry. In the tables below, the stereochemistry of the example is shown in the column labeled "Stereo. Chem." wherein the designation "A" represents "achiral", the designation "R" represents a racemic mixture, and the designation "H" represents a homochiral material.

| ABBREVIATIONS | |
|---|---|
| Ac | acetyl |
| anhyd. | anhydrous |
| aq. | aqueous |
| BOP | benzotriazol-1-yloxytris-(dimethylamino)-phosphonium hexafluorophosphate |
| Bu | butyl |
| DCM | dichloromethane |
| DEA | diethylamine |
| DIEA or DIPEA | diisopropylethylamine |
| DMF | dimethylformamide |
| DMSO | dimethyl sulfoxide |
| dppf | 1,1'-bis(diphenylphosphino)ferrocene |
| Et | ethyl |
| EtOAc | ethyl acetate |
| EtOH | ethanol |
| h, hours or hrs | hour(s) |
| HCl | hydrochloric acid |
| HPLC | high pressure liquid chromatography |
| LC | liquid chromatography |
| LCMS | liquid chromatography-mass spectrometry |
| M | molar |
| mM | millimolar |
| Me | methyl |
| MeOH | methanol |
| Mesyl-Cl | methanesulfonyl chloride |
| MHz | megahertz |
| mins | minute(s) |

-continued

| ABBREVIATIONS | |
|---|---|
| M+1 | (M + H)+ |
| MS | mass spectrometry |
| n or N | normal |
| NH4OAc | ammonium acetate |
| nM | nanomolar |
| NMP | N-methylpyrrolidinone |
| Pd2(dba)3 | tris-(dibenzylideneacetone)dipalladium |
| pet ether | petroleum ether |
| Ph | phenyl |
| POCl3 | phosphorous oxychloride |
| rt or Ret time | retention time |
| sat | saturated |
| TEA | triethylamine |
| TFA | trifluoroacetic acid |
| THF | tetrahydrofuran |

Methodologies that can be employed in the syntheses of intermediates useful in the preparation of examples of the current invention are shown in the scheme below.

Benzooxazine-2,4(1H)-diones of the type shown can be treated with strong base and a methylating reagent such as methyl iodide to afford 1-methyl-2H-benzo[d][1,3]oxazine-2,4(1H)-diones. These can be treated with, for example, nitro acetates to generate 1-methyl-3-nitroquinoline-2,4(1H,3H)-diones. Such compounds can in turn be converted to the related 4-chloro derivatives that can be reacted with a diversity of functionalized piperidines to afford examples of the current invention.

In other methodologies, picolinic acids may be esterified under standard conditions and then treated with, for example, acetic anhydride to give ethyl 3-acetamidopicolinates. These may be alkylated under standard conditions and subsequently treated with a mixture of hydrogen peroxide and trifluoroacetic anhydride to access the related N-oxides, for example, 2-(ethoxycarbonyl)-3-(N-methylacetamido) pyridine 1-oxide. Under conditions known in the art, these intermediates can be converted to 6-cyano-3-(N-methylacetamido)picolinates that on treatment with base can cyclize to give 1,5-naphthyridine-2,4(1H,3H)-diones.

Compounds of this type can be derivatized in a plurality of ways to access a number of useful intermediates. For example, treatment under standard nitration conditions can generate the related 1-methyl-3-nitro-1,5-naphthyridine-2,4 (1H,3H)-diones that can be converted under standard conditions to the 4-chloro- or 4-trifluoromethanesulfonate intermediates that can be reacted with a variety of functionalized piperidines to afford additional examples of the current invention. Alternatively, treatment under bromination conditions, for example, N-bromosuccinimide in DMF, can give the related 3-bromo derivatives, which when derivatized as described above allow both the introduction of a diversity of piperidines at the 4-position of the heterocycle, as well as further derivatization at the 3-position of the naphthyridine. For example, aromatic and heteroaromatic moieties may be introduced at this vector through coupling chemistries that are known in the art.

In additional methodology, ethyl 3-amino-6-bromopicolinates generated from the related ethyl 3-amino-picolinates can be treated as described above to give 6-bromo-1-methyl-1,5-naphthyridine-2,4(1H,3H)-diones that allow the introduction of a diversity of moieties at the 6-position of the naphthyridine heterocycle, one instance being the introduction of the cyano function at this position as shown in Scheme 1.

SCHEME 1

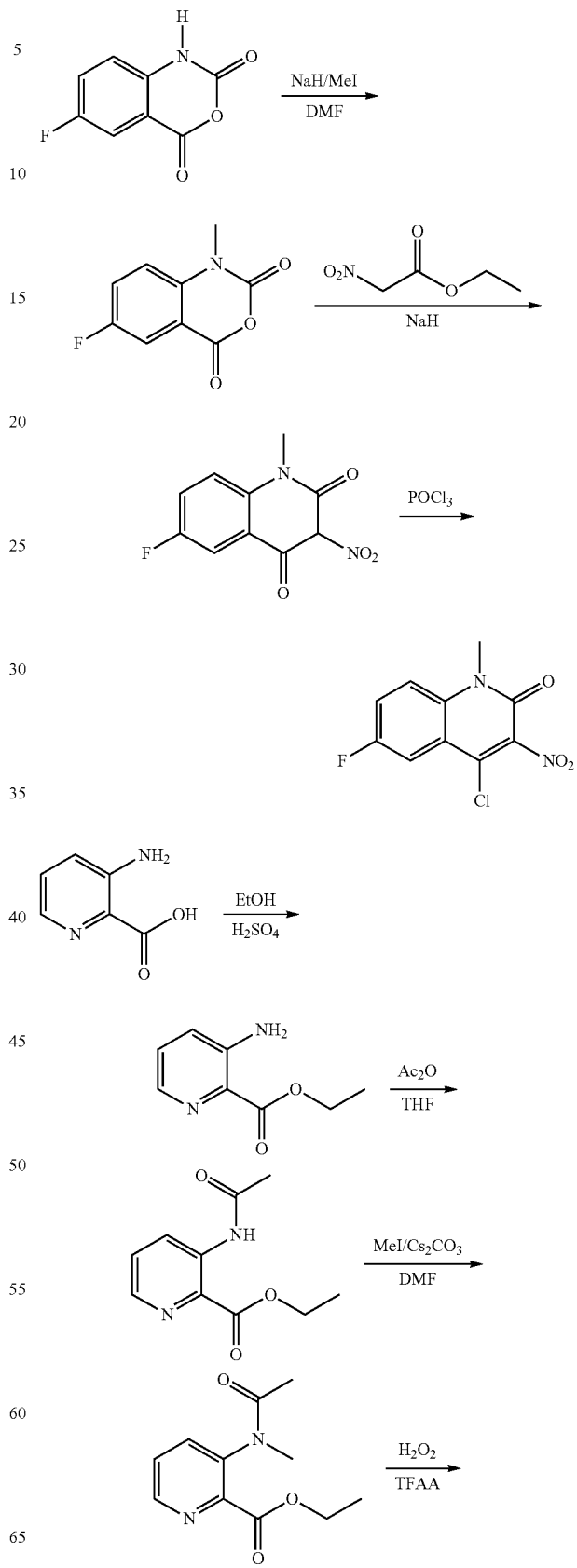

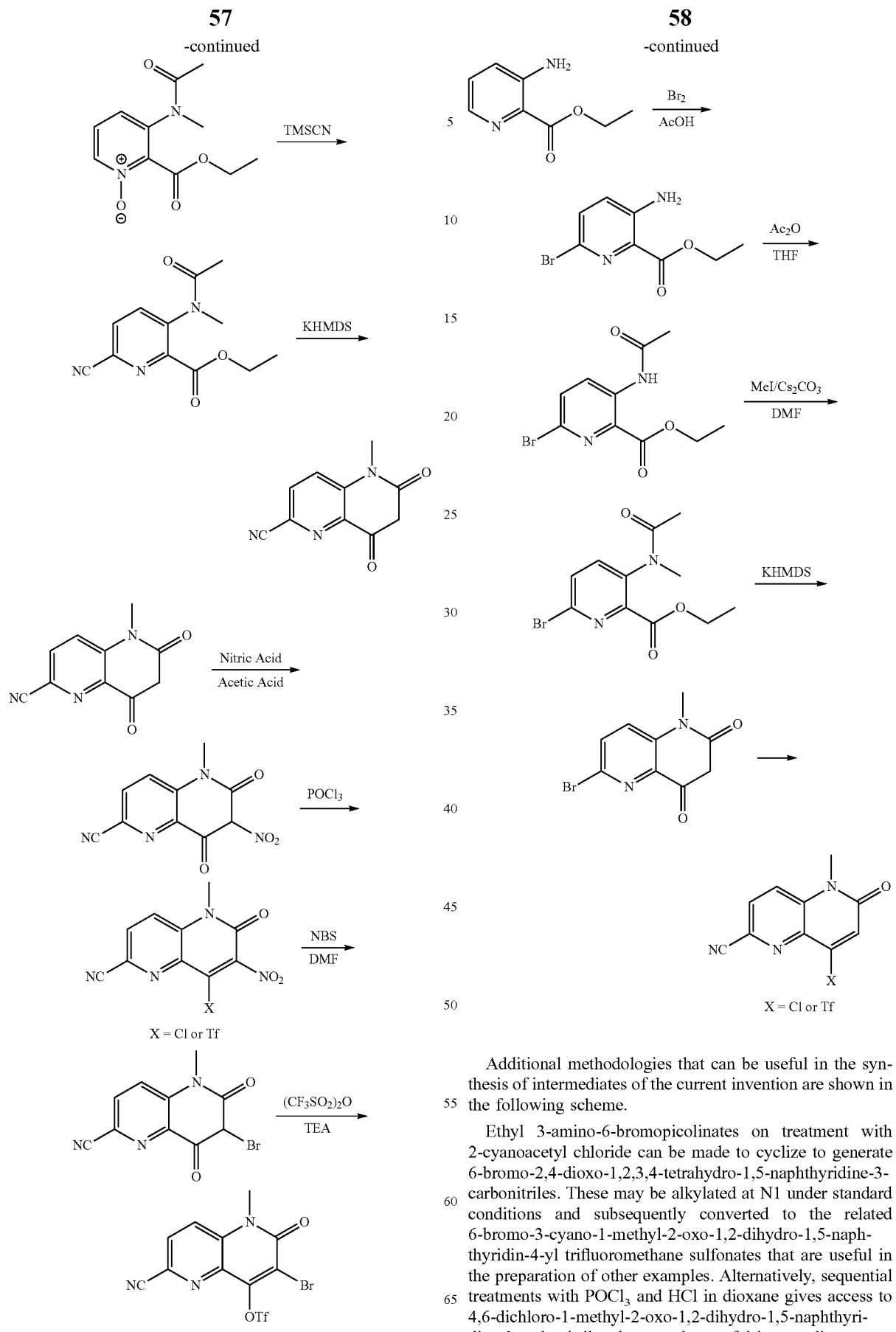

Additional methodologies that can be useful in the synthesis of intermediates of the current invention are shown in the following scheme.

Ethyl 3-amino-6-bromopicolinates on treatment with 2-cyanoacetyl chloride can be made to cyclize to generate 6-bromo-2,4-dioxo-1,2,3,4-tetrahydro-1,5-naphthyridine-3-carbonitriles. These may be alkylated at N1 under standard conditions and subsequently converted to the related 6-bromo-3-cyano-1-methyl-2-oxo-1,2-dihydro-1,5-naphthyridin-4-yl trifluoromethane sulfonates that are useful in the preparation of other examples. Alternatively, sequential treatments with POCl₃ and HCl in dioxane gives access to 4,6-dichloro-1-methyl-2-oxo-1,2-dihydro-1,5-naphthyridine-3-carbonitriles that are also useful intermediates.

SCHEME 2

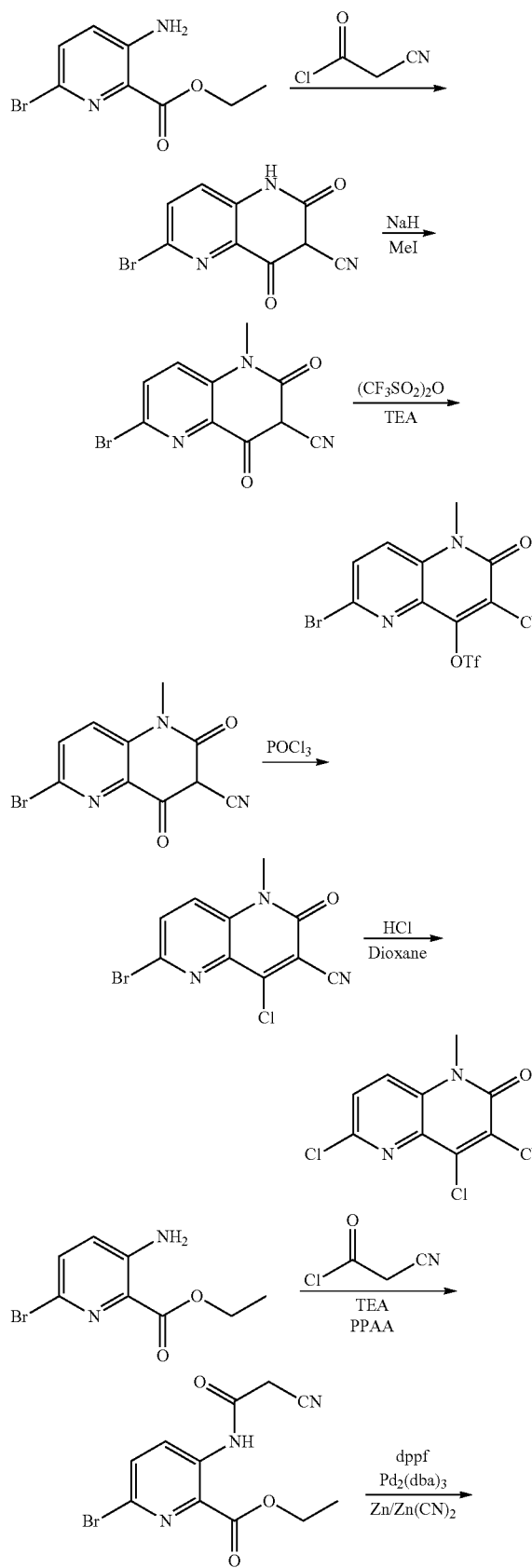

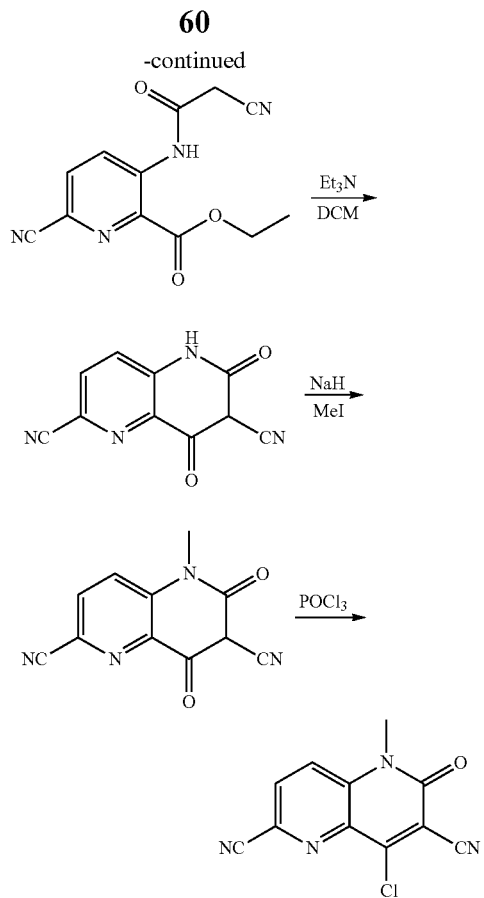

Other synthetic methods that may be useful for the introduction of a cyano motif at the 6-position of examples of the current invention can involve treatment of ethyl 6-bromo-3-(2-cyanoacetamido)picolinate intermediates with zinc and zinc cyanide under palladium catalyzed conditions to generate ethyl 3-(2-cyanoacetamido)-6-cyanopicolinates. These can be derivatized using methodologies as previously described to access 4-chloro-6-isocyano-1-methyl-2-oxo-1,2-dihydro-1,5-naphthyridine-3-carbonitriles that can be reacted with diversely functionalized piperidines to generate a number of examples of the current invention.

Additional useful intermediates can be prepared by condensing suitably functionalized naphthyridinone and quinolone heterocycles with variously functionalized piperidines as indicated in the scheme below. Such intermediates may be converted to examples of the current invention by further elaboration using, for example, Mitsunobu or SNAr reactions with appropriately functionalized aromatic or heteroaromatic coupling partners.

SCHEME 3

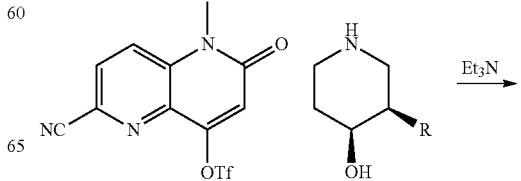

61
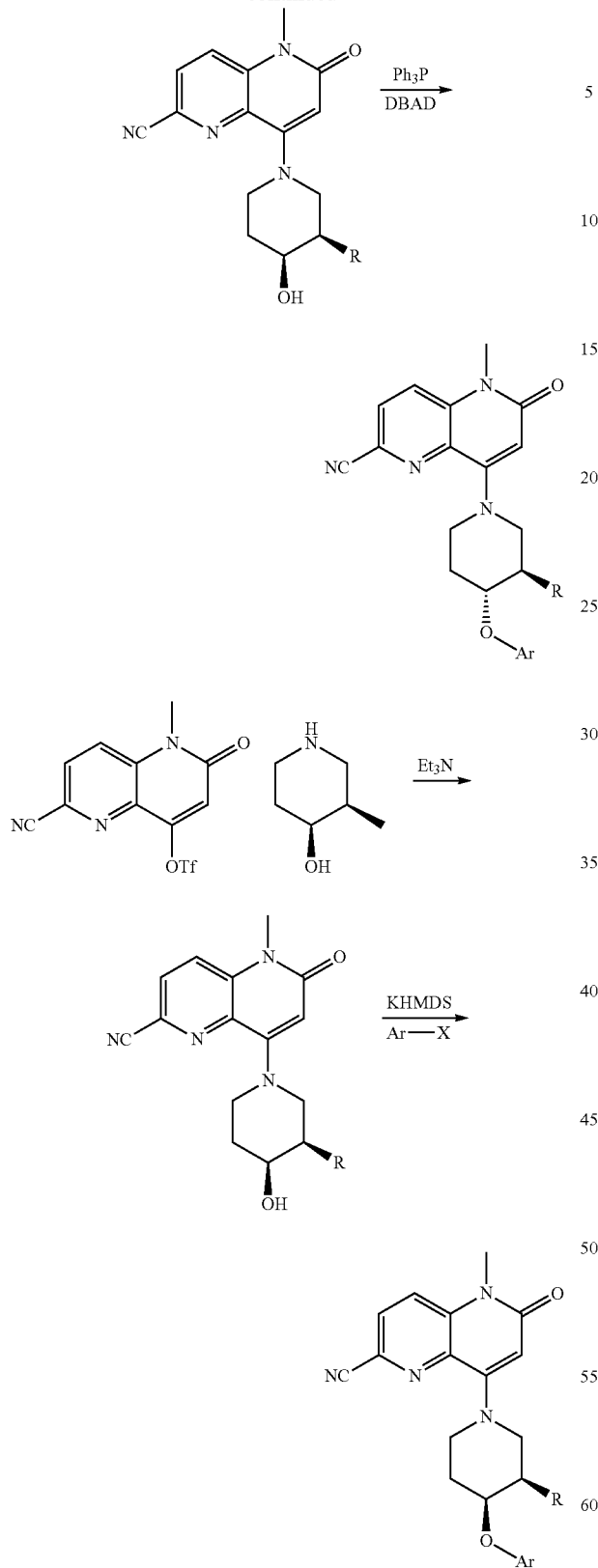
Methodology for the preparation of useful piperidine intermediates and additional examples is shown in the scheme below.
62
SCHEME 4
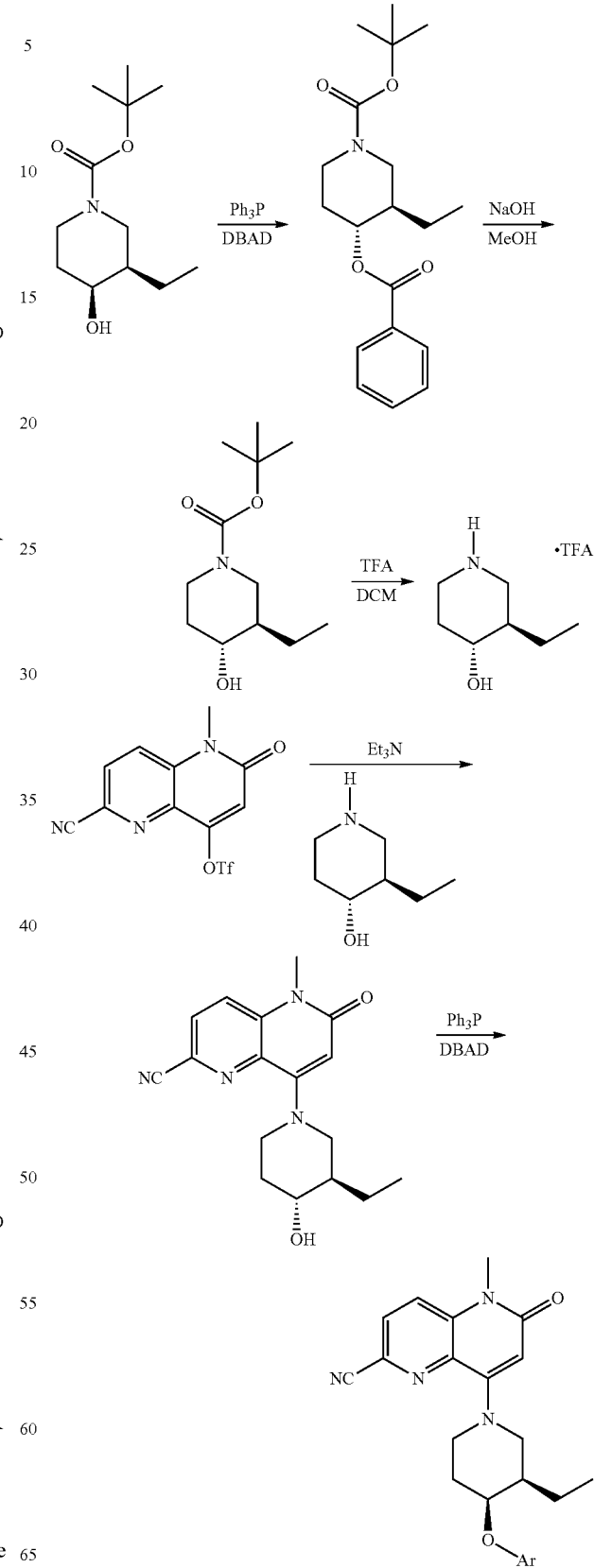

In these instances N-protected cis-4-hydroxy-3-alkylpiperidines can be treated with carboxylic acids, for example under Mitsunobu conditions, to provide trans-4-benzoyloxy-3-alkylpiperidines. These may be subsequently hydrolyzed to access the related trans-4-hydroxy-3-alkylpiperidines that can be utilized in methodology analogous to that discussed previously, whereby subsequent deprotection and condensation of the intermediate trans 4-hydroxy-3-alkylpiperidines with suitably functionalized naphthyridinones or quinolones generates trans-4-hydroxy-3-alkylpiperidin-1-yl)-5-methyl-6-oxo-5,6-dihydro-1,5-naphthyridine or related quinolone intermediates that can again be reacted under Mitsunobu or SN$_{Ar}$ conditions to provide further examples of the current invention.

In other instances, it may be preferable to prepare intermediate piperidine ethers that can subsequently be reacted with appropriately functionalized naphthyridinones and quinolones to provide additional examples. Some illustrative examples are shown in the following schemes. In this methodology N-protected alkylpiperidin-4-ones of the type shown can be reduced by methods known in the art to provide access to N-protected 3-alklpiperidin-4-ols.

SCHEME 5

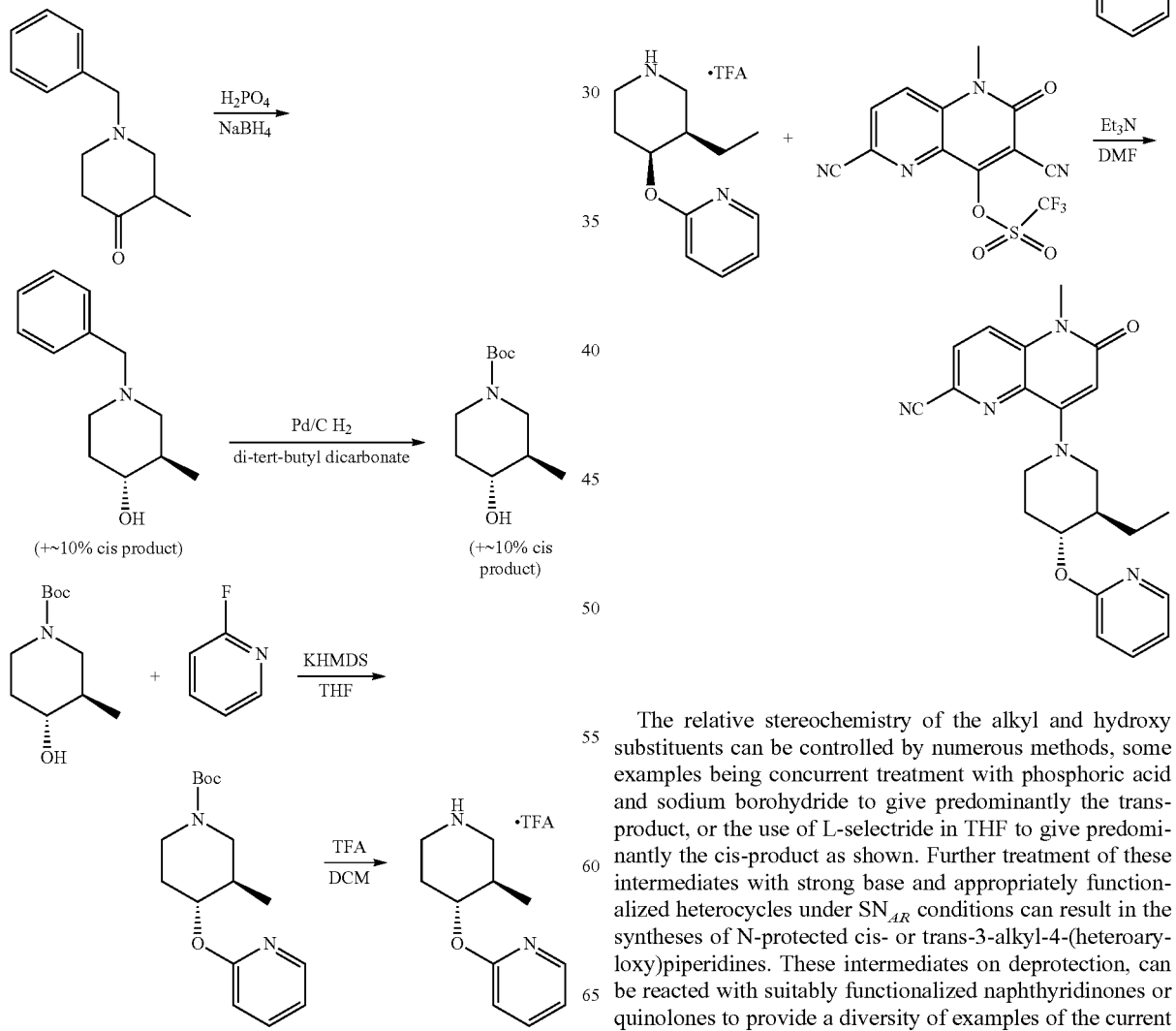

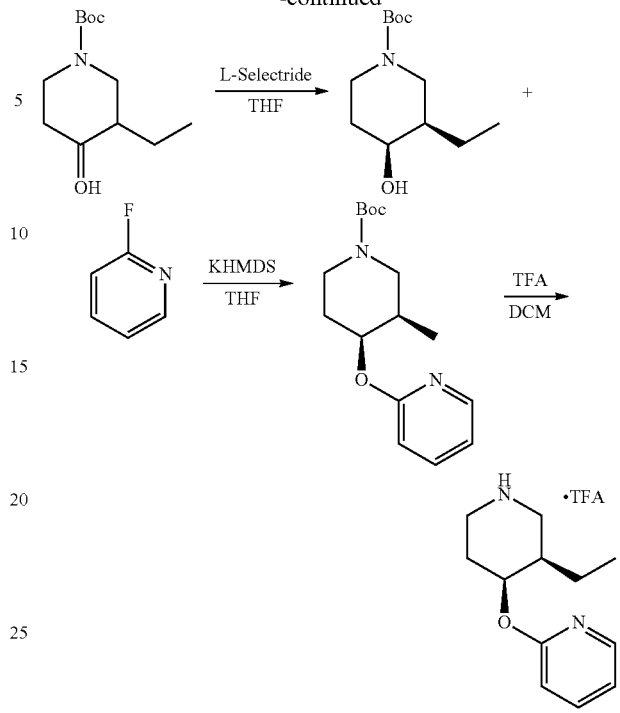

The relative stereochemistry of the alkyl and hydroxy substituents can be controlled by numerous methods, some examples being concurrent treatment with phosphoric acid and sodium borohydride to give predominantly the trans-product, or the use of L-selectride in THF to give predominantly the cis-product as shown. Further treatment of these intermediates with strong base and appropriately functionalized heterocycles under SN$_{AR}$ conditions can result in the syntheses of N-protected cis- or trans-3-alkyl-4-(heteroaryloxy)piperidines. These intermediates on deprotection, can be reacted with suitably functionalized naphthyridinones or quinolones to provide a diversity of examples of the current invention.

Intermediate 1

(+/−) trans-1-benzyl-3-methylpiperidin-4-ol

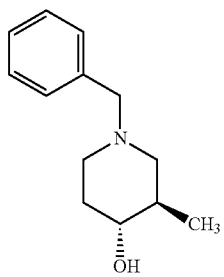

(I-1)

Phosphoric acid (85%, 4.25 g, 36.9 mmol) was added dropwise to a solution of 1-benzyl-3-methylpiperidin-4-one (7.5 g, 36.9 mmol) in water (50 mL) and methanol (25 mL) at −10° C. Sodium borohydride (2.79 g, 73.8 mmol) was then added in portions, and on addition the resulting mixture was allowed to warm to room temperature and stirring was continued overnight. The pH of the solution was adjusted to ~9 by the addition of 5 M sodium hydroxide solution. The resultant mixture was extracted with ethyl acetate (3×15 mL), and the combined extracts were washed with brine, dried over MgSO$_4$, filtered and concentrated in vacuo to give the product as a viscous yellow oil, (4.65 g, 22.65 mmol, 61.4% yield). LCMS (m/z): (M+H)$^+$=206.3, $^1$H NMR (500 MHz, CHLOROFORM-d) δ 7.52-7.12 (m, 5H), 3.71-3.40 (m, 2H), 3.22-3.10 (m, 1H), 2.93-2.86 (m, 1H), 2.85-2.79 (m, 1H), 2.11-1.99 (m, 1H), 1.97-1.87 (m, 1H), 1.76-1.56 (m, 3H), 1.54-1.39 (m, 1H), 1.05-0.86 (m, 3H).

Intermediate 2

(+/−) tert-butyl trans-4-hydroxy-3-methylpiperidine-1-carboxylate

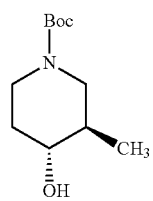

(I-2)

A solution of (+/−) (trans)-1-benzyl-3-methylpiperidin-4-ol (2.5 g, 12.18 mmol) and Boc-anhydride (3.11 mL, 13.39 mmol) in methanol (50 mL) was degassed and flushed with nitrogen (2×). Next, 10% Pd—C (1.2 g, 1.128 mmol) was added and the mixture again evacuated and flushed with nitrogen (2×) before being evacuated and filled with hydrogen at 1 atmosphere (balloon). The reaction mixture was stirred vigorously under the hydrogen atmosphere for 2 days. It was then filtered through celite, and the filtrate was washed with methanol and the washings combined with the original filtrate. The combined solutions were concentrated under vacuum to give the product as a viscous, yellow-colored oil, (1.71 g, 7.94 mmol, 65.2% yield). LCMS: (m/z) (M-tBu+ACN+H)$^+$=201.2. $^1$H NMR (500 MHz, CHLOROFORM-d) δ 4.10-3.85 (m, 2H), 3.40-3.24 (m, 1H), 2.93-2.71 (m, 1H), 2.62-2.34 (m, 1H), 1.99-1.87 (m, 1H), 1.50-1.46 (m, 11H), 1.57-1.40 (m, 12H), 1.06-0.99 (m, 3H).

Intermediate 3

(+/−) 5-isopropoxy-2-((trans-3-methylpiperidin-4-yl)oxy)pyridine, TFA

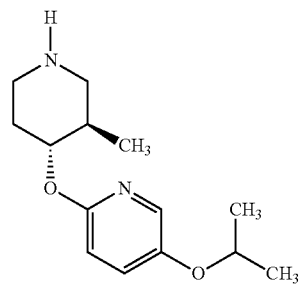

(I-3)

A 1.0 M solution of potassium bis(trimethylsilyl)amide (1.393 mL, 1.393 mmol) in THF was added dropwise to a solution of (+/−) tert-butyl trans-4-hydroxy-3-methylpiperidine-1-carboxylate (120 mg, 0.557 mmol) in THF (4 mL). The reaction mixture was stirred at room temperature for 30 min, then 2-fluoro-5-isopropoxypyridine (0.100 mL, 0.836 mmol) was added. The reaction mixture was then heated at 60° C. overnight. The reaction was then quenched by the addition of water and the resultant mixture was extracted with ethyl acetate. The organic layer was separated, washed with brine, dried over MgSO$_4$, filtered and evaporated under reduced pressure to give the crude product as a yellow-colored oil. This material was purified by preparative reverse phase HPLC using a CH$_3$CN—H$_2$O-TFA system as eluent. Homogeneous fractions were combined and concentrated under reduced pressure. The residual material was then treated a mixture of TFA (0.5 mL) in DCM (2 mL) for 3 h at room temperature. The resultant mixture was then concentrated in vacuo to give the product as a brown oil, (40 mg, 0.110 mmol, 19.70% yield).

Intermediate 4

(+/−) 2-((trans-3-ethylpiperidin-4-yl)oxy)-5-isopropoxypyridine (I-4)

A 1.0 M solution of potassium bis(trimethylsilyl)amide (1.090 mL, 1.090 mmol) in THF was added dropwise to a solution of (+/−) tert-butyl trans-3-ethyl-4-hydroxypiperidine-1-carboxylate (100 mg, 0.436 mmol) in THF (2 mL). The mixture was stirred at room temperature for 30 min, then 2-fluoro-5-isopropoxypyridine (0.078 mL, 0.654 mmol) in THF (1 mL) and the reaction mixture was heated at 60° C. for 5 hr under nitrogen. The reaction mixture was cooled to room temperature, water was added and the resultant mixture was extracted with ethyl acetate (3×). The organic layers were combined, washed with brine and then dried over $MgSO_4$, filtered and evaporated under reduced pressure to give the crude product as a yellow, viscous oil. This material was purified by flash chromatography on silica get using 20% ethyl acetate in hexanes as eluent. Homogeneous fractions were combined and evaporated in vacuo to give the product as a viscous, colorless oil. This was treated directly with TFA (1 mL) in DCM (3 mL) at room temperature overnight. The resultant mixture was then concentrated in vacuo to give the TFA salt of the title compound as a brown colored oil, (153 mg, 0.311 mmol, 71.3% yield). LCMS: (m/z) 265: $(M+H)^+=265.25$.

Intermediate 5

(+/−) 5-isopropyl-2-((cis-3-methylpiperidin-4-yl)oxy)pyridine

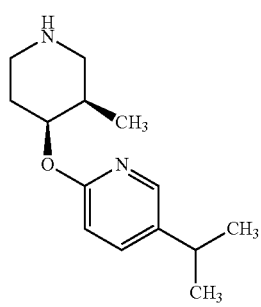

(I-5)

Sodium hydride (60% in mineral oil) (69.7 mg, 1.742 mmol) was added in portions to a solution of (+/−) tert-butyl cis-4-hydroxy-3-methylpiperidine-1-carboxylate (150 mg, 0.697 mmol) in THF (2 mL). The reaction mixture was stirred at room temperature for 10 min, then 2-chloro-5-isopropylpyridine (163 mg, 1.045 mmol) in THF (1 mL) was added. The reaction mixture was then heated at 60° C. overnight. The reaction was then quenched by the addition of water and the resultant mixture was extracted with ethyl acetate (3×). The organic layers were collected, washed with brine, dried over $MgSO_4$, filtered and evaporated under reduced pressure to give a brown, viscous oil. The crude product was purified by preparative reverse phase HPLC using $CH_3CN$—$H_2O$-TFA system. Homogeneous fractions were combined and evaporated in vacuo and the residue treated with TFA (1 mL) in DCM (2 mL) for 3 h at room temperature. The resultant solution was reduced in vacuo to give the bis-TFA salt of the title compound as a yellow-colored oil, (58.3 mg, 0.126 mmol, 18.10% yield). LCMS: (m/z): 235.1: $(M+H)^+$.

Intermediate 6

(+/−) 5-isopropoxy-2-((cis-3-methylpiperidin-4-yl)oxy)pyridine

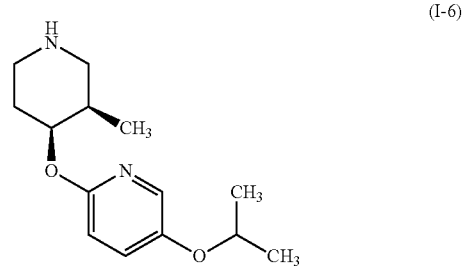 [SMILES: CC(C)Oc1ccc(O[C@H]2CCNC[C@H]2C)nc1]

(I-6)

A 1.0 M solution of potassium bis(trimethylsilyl)amide (1.393 mL, 1.393 mmol) in THF was added dropwise to a solution of a 9:1 mixture of cis- and trans-tert-butyl-4-hydroxy-3-methylpiperidine-1-carboxylate (120 mg, 0.557 mmol) in THF (4 mL). The mixture was stirred at room temperature for 30 min, then 2-fluoro-5-isopropoxypyridine (0.100 mL, 0.836 mmol) was added and the reaction mixture was heated at 60° C. overnight. The reaction was then quenched by the addition of water and the resultant mixture extracted with ethyl acetate (3×). The extracts were combined, washed with brine, dried over $MgSO_4$, filtered and evaporated under reduced pressure to give the crude product as a yellow oil. The crude product was purified by reverse phase preparative HPLC using $CH_3CN$—$H_2O$-TFA system. Homogeneous fractions were combined and concentrated under reduced pressure overnight. The residue was then dissolved in dichloromethane (2 mL) and TFA 0.5 mL was added. The solution was stirred at room temperature for 3 hr. The mixture was then evaporated in vacuo to give the TFA salt of the title compound as a brown, viscous oil, (40 mg, 0.110 mmol, 19.70% yield). LCMS: (m/z): $(M+H)^+=251.3$.

Intermediate 7

(+/−) 2-((3,3-dimethylpiperidin-4-yl)oxy)-5-isopropoxypyridine

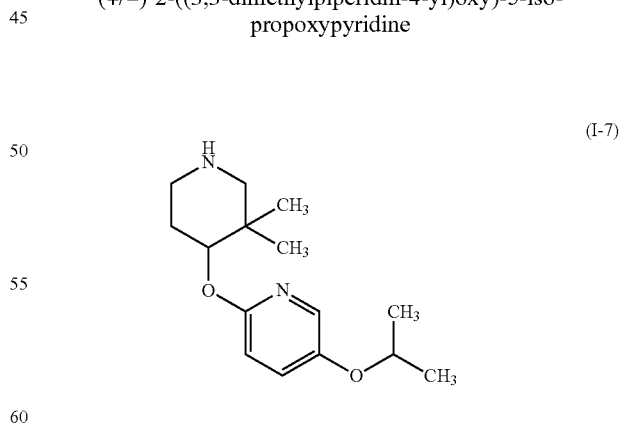

(I-7)

A 1.0 M solution of potassium bis(trimethylsilyl)amide (0.872 mL, 0.872 mmol) in THF was added dropwise to a solution of tert-butyl 4-hydroxy-3,3-dimethylpiperidine-1-carboxylate (80 mg, 0.349 mmol) in THF (2 mL). The reaction mixture was stirred at room temperature for 30 min, then 2-fluoro-5-isopropoxypyridine (0.062 mL, 0.523 mmol) was added. The reaction mixture was stirred at room temperature overnight, and was then quenched by the addition of water. The resultant mixture was extracted with ethyl acetate (3×) and the combined extracts were washed with brine, dried over MgSO₄, filtered and evaporated in vacuo to give the crude product as a brown oil. The product was purified by reverse phase preparative HPLC using $CH_3CN$—$H_2O$-TFA system. Homogeneous fractions were collected and concentrated under reduced pressure. The residue was then dissolved in DCM (3 mL) and treated with TFA (1 mL) at room temperature for 4 hr. The solution was then concentrated in vacuo to give the TFA salt of the title compound as a viscous, brown-colored oil, (24 mg, 0.063 mmol, 18.18% yield). (m/z): $(M+H)^+=251.3$.

Intermediate 8

(+/−) 5-(difluoromethyl)-2-((cis-3-methylpiperidin-4-yl)oxy)pyridine

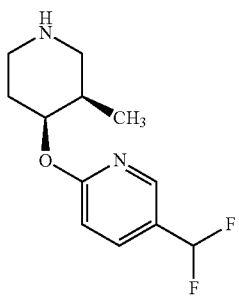

(I-8)

A 1.0 M solution of potassium bis(trimethylsilyl)amide (1.393 mL, 1.393 mmol) in THF was added dropwise to a solution of tert-butyl cis-4-hydroxy-3-methylpiperidine-1-carboxylate (120 mg, 0.557 mmol) in THF (2 mL). The reaction mixture was stirred at room temperature for 30 min, then 2-chloro-5-(trifluoromethyl)pyridine (137 mg, 0.836 mmol) in THF (1 mL) was added and the mixture heated at 60° C. overnight. The reaction was quenched by the addition of water, and the resultant mixture was extracted with ethyl acetate. The combined extracts were washed with brine, dried over MgSO₄, filtered and concentrated in vacuo to give the crude product as a yellow oil. The crude product was then purified by reverse phase preparative HPLC using $CH_3CN$—$H_2O$-TFA system. Homogeneous fractions were combined and concentrated under reduced pressure. The residue was then dissolved in dichloromethane (1 mL) and treated with TFA (0.5 mL) for 3 h at room temperature. The mixture was then evaporated in vacuo to give the TFA salt of the title compound as a brown, viscous oil, (160 mg, 0.340 mmol, 61.0% yield). LCMS: (m/z): $(M+H)^+=243.3$.

Intermediate 9

(+/−) 2-isopropyl-6-((cis-3-methylpiperidin-4-yl)oxy)pyridine

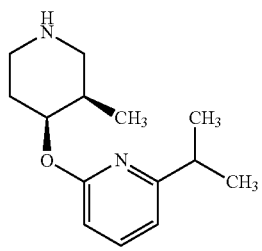

(I-9)

Sodium hydride (69.7 mg, 1.742 mmol) (60% in mineral oil) was added in portions to a solution of (+/−) tert-butyl cis-4-hydroxy-3-methylpiperidine-1-carboxylate (150 mg, 0.697 mmol) in anhydrous THF (2 mL). On addition, the reaction mixture was stirred at room temperature for 10 min., then 2-chloro-6-isopropylpyridine (163 mg, 1.045 mmol) in THF (1 mL) was added and the mixture heated at 60° C. under nitrogen overnight. The reaction was then quenched by the addition of water and the resultant mixture was extracted with ethyl acetate (3×). The extracts were combined, washed with brine, dried over MgSO₄, filtered and evaporated under reduced pressure to give the crude product as a brown, viscous oil. The product was purified by preparative reverse phase. HPLC using $CH_3CN$—$H_2O$-TFA system. Homogeneous fractions were combined and concentrated under reduced pressure. The residue was dissolved in DCM (2 mL) and TFA (1 mL) was added and the ensuing mixture was stirred at room temperature for 3 hr before being concentrated in vacuo to give the TFA salt of the title compound as a yellow-colored viscous oil, (53 mg, 0.115 mmol, 16.45% yield). LCMS: (m/z): $(M+H)^+=235.1$.

Intermediate 10

(+/−) 2-((cis-3-methylpiperidin-4-yl)oxy)-5-(trifluoromethyl)pyridine

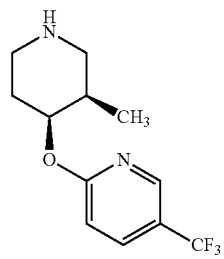

(I-10)

Sodium hydride (69.7 mg, 1.742 mmol) (60% in mineral oil) was added to a solution of (+/−) tert-butyl cis-4-hydroxy-3-methylpiperidine-1-carboxylate (150 mg, 0.697 mmol) in anhydrous THF (2 mL). The mixture was stirred at room temperature for 10 min, then 2-chloro-5-(trifluoromethyl)pyridine (190 mg, 1.045 mmol) in THF (1 mL) was added and the reaction mixture was heated at 60° C. for 3 h, before being quenched by the addition of water. The mixture was then extracted using ethyl acetate (3×), the extracts combined and washed with brine, dried over MgSO₄, filtered and evaporated under reduced pressure to give the crude product as a viscous brown oil. The product was purified using reverse phase preparative HPLC using a CH₃CN—H₂O-TFA system. Homogeneous fractions were combined and concentrated in vacuo. The residue was then dissolved in dichloromethane (2 mL) TFA (1 mL) was added, and the resultant mixture was stirred at room temperature for 3 h before being concentrated under vacuum to give the TFA salt of the title compound as a white solid, (157 mg, 0.419 mmol, 60.2% yield). LCMS: (m/z): (M+H)$^+$ =260.9.

Intermediate 11

(+/−) 4-isopropyl-2-((cis-3-methylpiperidin-4-yl)oxy)pyridine

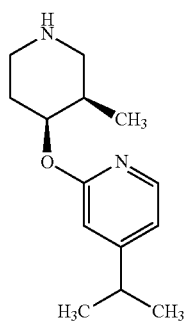

(I-11)

A 1.0 M solution of potassium bis(trimethylsilyl)amide (1.742 mL, 1.742 mmol) in THF was added dropwise to a solution of (+/−) tert-butyl cis-4-hydroxy-3-methylpiperidine-1-carboxylate (150 mg, 0.697 mmol) in THF (2 mL). The reaction mixture was stirred at room temperature for 30 min, then 2-chloro-4-isopropylpyridine (163 mg, 1.045 mmol) in THF (1 mL) was added and the ensuing mixture was heated at 60° C., under nitrogen overnight. The reaction was then quenched by the addition of water. The mixture was then extracted using ethyl acetate (3×), the extracts combined and washed with brine, dried over MgSO₄, filtered and evaporated under reduced pressure to give the crude product as a viscous brown oil. The product was purified using reverse phase preparative HPLC using a CH₃CN—H₂O-TFA system. Homogeneous fractions were combined and concentrated in vacuo. The residue was then dissolved in dichloromethane (1 mL) TFA (0.5 mL) was added, and the resultant mixture was stirred at room temperature for 3 h before being concentrated under vacuum to give the TFA salt of the title compound as a viscous, yellow-colored oil, (42 mg, 0.091 mmol, 13.04% yield). LCMS: (m/z): (M+H)$^+$=235.0.

Intermediate 12

(+/−) 5-cyclopropyl-2-((cis-3-methylpiperidin-4-yl)oxy)pyridine

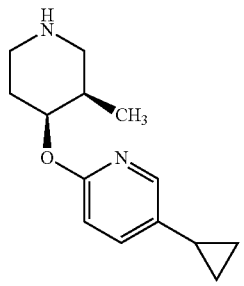 [SMILES: C[C@@H]1CNCC[C@@H]1Oc1ncc(C2CC2)cn1]

(I-12)

A 1.0 M solution of potassium bis(trimethylsilyl)amide (1.161 mL, 1.161 mmol) in THF was added dropwise to a solution of (+/−) tert-butyl cis-4-hydroxy-3-methylpiperidine-1-carboxylate (100 mg, 0.464 mmol) in anhydrous THF (2 mL). The mixture was stirred at room temperature for 30 min. Next, 2-chloro-5-cyclopropylpyridine (107 mg, 0.697 mmol) in THF (1 mL) was then added and the reaction mixture was heated at 60° C. overnight. The reaction was quenched by the addition of water. The resultant mixture was extracted with ethyl acetate (3×), and the extracts were combined, washed with brine, dried over MgSO₄, filtered and evaporated under reduced pressure to give the crude product as a viscous yellow oil. The product was purified using reverse phase preparative HPLC using a CH₃CN—H₂O-TFA system. Homogeneous fractions were combined and concentrated in vacuo. The residue was then dissolved in dichloromethane (1 mL) TFA (0.5 mL) was added, and the resultant mixture was stirred at room temperature for 3 h before being concentrated under vacuum to give the TFA salt of the title compound as a viscous yellow oil, (10 mg, 0.043 mmol, 9.27% yield). LCMS: (m/z): (M+H)$^+$=232.55.

Other related intermediates could be prepared by the methodology shown in the scheme below, which involved the reaction of a potassium alkoxide salt of an unprotected hydroxypiperidine with a chloro-pyrimidine.

Intermediate 13

(+/−) 2-((cis-3-methylpiperidin-4-yl)oxy)pyrimidine

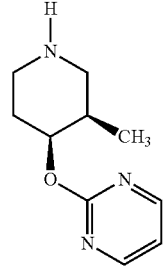

(I-13)

Potassium bis(trimethylsilyl)amide (0.901 mL, 0.901 mmol) was added to a solution of (+/−) cis-3-methylpiperidin-4-ol (104 mg, 0.901 mmol) in THF (2 mL) and the mixture was stirred at room temperature for 30 min. The amino alcohol did not completely dissolve in THF, and a suspension was always observed, even on addition of the base. A solution of 2-chloropyrimidine (86 mg, 0.751 mmol) in THF (1 mL) was then added and the mixture was left to stir at 60° C. overnight. The reaction mixture was then evaporated to dryness and the crude residue was used in subsequent experiments. LCMS: Start % B: 0, Final % B: 100. Gradient Time: 3.00 min. Stop Time: 3.50 min. Flow Rate: 1.0 mL/min. Wavelength 1: 220 nm. Solvent Pair: AA S174/S175. Solvent A: A1=10 mM NH$_4$OAc in CH$_3$CN: Water (5:95) S174. Solvent B: B1=10 mM NH$_4$OAc in CH$_3$CN:water (95:5) 5175. Column, Id: 3, Name: 3 (AA SCP 3 min) Acquity BEH C18 1.7 μm 2.1×50 mm. Retention Time=1.213 min. (m/z): (M+H)$^+$=194.2.

In a similar fashion, the following intermediates were prepared.

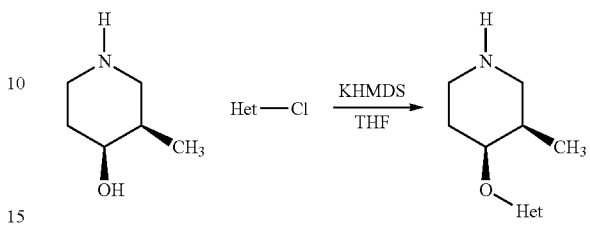

TABLE 1

| Intermediate No. | Heterocycle | Intermediate | LCMS R$_T$ (min.) | (m/z): (M + H)$^+$ |
|---|---|---|---|---|
| I-14 | 2-chloro-5-propylpyrimidine | piperidine-pyrimidine-propyl | 1.63 | 236.3 |
| I-15 | 2-chloro-4-methoxypyrimidine | piperidine-pyrimidine-OCH$_3$ | 0.92 | 224.0 |
| I-16 | 2-chloro-5-cyclopropylpyrimidine | piperidine-pyrimidine-cyclopropyl | 1.02 | 234.0 |
| I-17 | 2-chloro-5-trifluoromethylpyrimidine | piperidine-pyrimidine-CF$_3$ | 1.08 | 302.9 [+ACN] |

TABLE 1-continued

| Intermediate No. | Heterocycle | Intermediate | LCMS $R_T$ (min.) | (m/z): $(M + H)^+$ |
|---|---|---|---|---|
| I-18 | 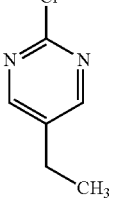 | | 0.98 | 222.0 |
| I-19 | 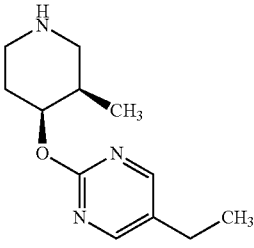 [SMILES: CCc1cnc(O[C@H]2CCNC[C@H]2C)nc1] | | 0.88 | 208.0 |

Intermediate 20

6-fluoro-1-methyl-2H-benzo[d][1,3]oxazine-2,4(1H)-dione

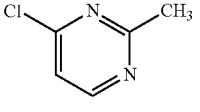
(I-20)

A 60% dispersion of sodium hydride (0.530 g, 13.25 mmol) in mineral oil was added in portions to a solution of 6-fluoro-1H-benzo[d][1,3]oxazine-2,4-dione (2 g, 11.04 mmol) in DMF (10 mL). The reaction mixture was stirred at room temperature for 30 min, then methyl iodide (0.829 mL, 13.25 mmol) was added dropwise. The reaction mixture was stirred at room temperature overnight. The reaction was quenched by the addition of water and a yellow solid separated that was collected by filtration. The solid was suspended in ethyl acetate, and the resultant mixture was filtered and the filtrate concentrated in vacuo to give the product as a yellow colored solid, (395 mg, 2.024 mmol, 18.33% yield). LCMS: (m/z): (M+H)$^+$=196. $^1$H NMR (400 MHz, DMSO-d$_6$) δ 7.83-7.74 (m, 2H), 7.55-7.46 (m, 1H).

Intermediate 21

6-fluoro-1-methyl-3-nitroquinoline-2,4(1H,3H)-dione

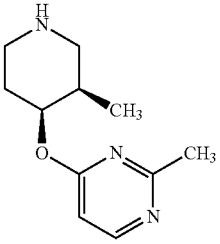
(I-21)

To a solution of ethyl 2-nitroacetate (293 mg, 2.198 mmol) in NMP (5 ml) in a round-bottomed flask at 0° C., a 60% dispersion of sodium hydride (96 mg, 2.398 mmol) in mineral oil was added in portions. The reaction mixture was stirred 5 minutes at 0° C., then 15 minutes at room temperature. Then 6-fluoro-1-methyl-1H-benzo[d][1,3]oxazine-2,4-dione (390 mg, 1.998 mmol) was added and the reaction mixture was heated at 120° C. for 2 hr. LC/MS shown completion of reaction. The reaction was quenched with the addition of ice-water. The mixture was acidified with 1 N HCl solution. Ethyl ether was added and 6-fluoro-1-methyl-3-nitroquinoline-2,4(1H,3H)-dione (140 mg, 0.588 mmol, 29.4% yield) as a yellow solid. LCMS: (m/z): (M+H)$^+$=239.

Intermediate 22

4-chloro-6-fluoro-1-methyl-3-nitroquinolin-2(1H)-one

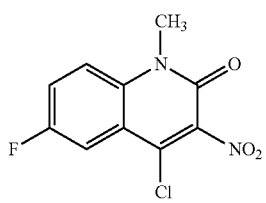
(I-22)

In a sealed tube, 6-fluoro-1-methyl-3-nitroquinoline-2,4(1H,3H)-dione (140 mg, 0.588 mmol) and phosphorus oxychloride (3 mL, 32.2 mmol) were added. The reaction mixture was heated at 95° C. for 4 hr. The mixture was poured into ice-water, neutralized with saturated NaHCO$_3$ solution, and extracted with dichloromethane (2×20 mL). The organic layers were combined, dried (MgSO$_4$) and concentrated to give 4-chloro-6-fluoro-1-methyl-3-nitroquinolin-2(1H)-one (140 mg, 0.546 mmol, 93% yield) as an orange solid. LCMS: (m/z) 257 (MH$^+$).

Intermediate 23

Ethyl 3-aminopicolinate

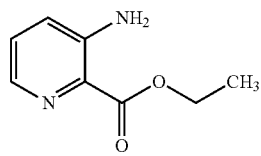
(I-23)

To a stirred suspension of 3-aminopicolinic acid (150 g, 1086 mmol) in ethanol (1500 mL) at 0-5° C. was added H2SO4 (463 mL, 8688 mmol) through a 1 L addition funnel over 60 min. After completion of the addition, the clear brown solution was refluxed at 90° C. for 24 h. The reaction mixture was then cooled to room temperature before being poured onto ice pellets in a 10 L beaker with overhead stirring. The mixture was basified using NH$_4$OH solution (~2 L required) to pH ~9, and stirred at room temperature for a further 60 min. Solid material was observed in the beaker which was filtered through Buchner funnel, washed with water (1 L) and dried under line vacuum to yield 60 g of product as an off-yellow solid. The filtrate was extracted using DCM (3×1000 mL), and the combined extracts were washed with brine (1×1.5 L), dried over Na$_2$SO$_4$, filtered and concentrated under reduced pressure to yield ethyl 3-aminopicolinate (116 g, 691 mmol, 63.6% yield). LCMS: m/z=167.2 (m/z): (M+H); RT 0.78 min; Method: Column-KINETEX-XB-C18 (75×3 mm-2.6 μm); Mobile phase A: 10 mM ammonium formate in water:acetonitrile (98:2); Mobile phase B: 10 mM ammonium formate in water:acetonitrile (2:98); Gradient: 20-100% B over 4 minutes, flow rate 1.0 mL/min, then a 0.6 minute hold at 100% B flow rate 1.5 mL/min; then Gradient: 100-20% B over 0.1 minutes, flow rate 1.5 mL/min.

Intermediate 24

Ethyl 3-acetamidopicolinate

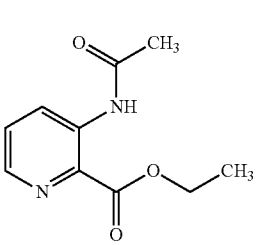
(I-24)

To a stirred solution of ethyl 3-aminopicolinate (115 g, 692 mmol) in THF (1000 mL) was added Ac$_2$O (588 mL, 6228 mmol) at room temperature. The reaction mixture was heated to 60° C. under a nitrogen atmosphere for ~7-8 h. The reaction mixture was cooled to room temperature and the volatiles were evaporated at water bath temperature (~50° C.) under line vacuum, followed by acetic acid removal under high vacuum at 50° C. to yield an off-white solid. The solid was triturated with petroleum ether (500 mL), stirred for 30 min at room temperature, then filtered through a Buchner funnel and washed with petroleum ether (500 mL). The filtrate was dried under vacuum at room temperature for 3 h to yield ethyl 3-acetamidopicolinate (139 g, 641 mmol, 93% yield) as an off-white solid; LCMS: m/z=209.3 (m/z): (M+H); rt 0.76 min; LC-MS Method: Column-KINETEX-XB-C18 (75×3 mm-2.6 μm); Mobile phase A: 10 mM ammonium formate in water:acetonitrile (98:2); Mobile phase B: 10 mM ammonium formate in water:acetonitrile (2:98); Gradient: 20-100% B over 4 minutes, flow rate 1.0 mL/min, then a 0.6 minute hold at 100% B flow rate 1.5 mL/min; then Gradient: 100-20% B over 0.1 minutes, flow rate 1.5 mL/min.

Intermediate 25

Ethyl 3-(N-methylacetamido)picolinate

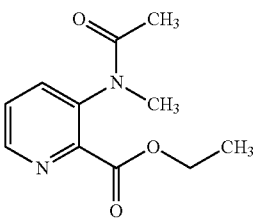
(I-25)

To a stirred light brown suspension of ethyl 3-acetamidopicolinate (75 g, 360 mmol) and cesium carbonate (176 g, 540 mmol) in DMF (750 mL) was added methyl iodide (36.0 mL, 576 mmol) at room temperature (slight exotherm observed). The resulting partial brown mixture was stirred at room temperature for ~8 h. The reaction was quenched with water (1500 mL) [slight exotherm observed] and extracted with DCM (3×1000 mL). The combined extracts were washed with water (2×1000 mL) and the aqueous layer re-extracted with DCM (2×500 mL). The combined organic solutions were washed with brine (2×1000 mL), dried over Na₂SO₄, filtered and concentrated at ~50° C., and then dried under vacuum at ~60° C. to yield a brown colored solution (contains some DMF). The material was dried under high vacuum to remove DMF at 58° C. for 25 min to yield a brown solid, which was dissolved in petroleum ether (1000 mL), stirred for 30 min at room temperature, filtered through a Buchner funnel, washed with petroleum ether (500 mL) upon filtration, dried under line vacuum for 8 h to yield ethyl 3-(N-methylacetamido)picolinate (70 g, 302 mmol, 84% yield) as a brown solid; LCMS: m/z=223.2 (m/z): (M+H); rt 0.64 min; LC-MS Method: Column-KINETEX-XB-C18 (75×3 mm-2.6 μm); Mobile phase A: 10 mM ammonium formate in water:acetonitrile (98:2); Mobile phase B: 10 mM ammonium formate in water:acetonitrile (2:98); Gradient: 20-100% B over 4 minutes, flow rate 1.0 mL/min, then a 0.6 minute hold at 100% B flow rate 1.5 mL/min; then Gradient: 100-20% B over 0.1 minutes, flow rate 1.5 mL/min.

Intermediate 26

2-(ethoxycarbonyl)-3-(N-methylacetamido)pyridine 1-oxide

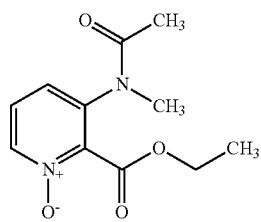

(I-26)

To a stirred brown clear solution of ethyl 3-(N-methyl-acetamido)picolinate (70 g, 315 mmol) in DCM (700 mL) at 0-5° C. was added urea hydrogen peroxide (44.4 g, 472 mmol), followed by trifluoroacetic anhydride (66.7 mL, 472 mmol) slowly over 40 min through a 100 mL addition funnel. The reaction mixture solidified during the trifluoroacetic anhydride addition. After completion of the addition, the reaction mixture was stirred at room temperature for ~2 h. The reaction was quenched with 10% NaHCO₃ solution (700 mL). The reaction mixture was extracted with DCM (3×500 mL). The combined organic layer was washed with brine solution (2×500 mL), dried over Na₂SO₄ and concentrated to yield 2-(ethoxycarbonyl)-3-(N-methylacetamido) pyridine 1-oxide (70 g, 285 mmol, 90% yield) as a light yellow solid; LCMS: m/z=239.0 (m/z): (M+H); rt 0.48 min; LC-MS Method: Column-KINETEX-XB-C18 (75×3 mm-2.6 μm); Mobile phase A: 10 mM ammonium formate in water:acetonitrile (98:2); Mobile phase B: 10 mM ammonium formate in water:acetonitrile (2:98); Gradient: 20-100% B over 4 minutes, flow rate 1.0 mL/min, then a 0.6 minute hold at 100% B flow rate 1.5 mL/min; then Gradient: 100-20% B over 0.1 minutes, flow rate 1.5 mL/min.

Intermediate 27

Ethyl 6-cyano-3-(N-methylacetamido)picolinate

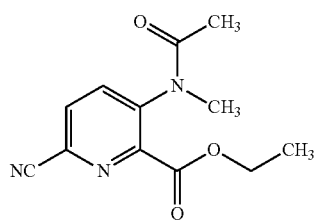

(I-27)

To a stirred pale yellow solution of 2-(ethoxycarbonyl)-3-(N-methylacetamido) pyridine 1-oxide (50 g, 210 mmol) in DCM (500 mL) at room temperature was added trimethylsilyl cyanide (39.4 mL, 294 mmol). The reaction mixture was stirred for 10 min and then cooled to −10° C. Benzoyl chloride (34.1 mL, 294 mmol) was added through a 50 mL addition funnel over 15 min followed by TEA (41.0 mL, 294 mmol) through a 50 mL addition funnel slowly over 20 min. An exothermic reaction was observed during TEA addition. The reaction mixture turned turbid (TEA salt) and stirring was continued for 2.5 h at the same temperature. The reaction was quenched with the addition of 10% NaHCO₃ solution (500 mL). The mixture was extracted with DCM (3×300 mL). The combined organic solution was washed with brine (2×250 mL), then dried over Na₂SO₄ and concentrated to yield a light yellow crude material. The crude material was purified through normal phase RediSep silica column on ISCO® using EA/petroleum ether as eluent. The product was isolated by 65-70% EA/petroleum ether, fractions were concentrated to afford ethyl 6-cyano-3-(N-methylacetamido)picolinate (43 g, 83% yield) as a light brown liquid; LCMS: m/z=248.0 (m/z): (M+H); rt 1.26 min; LC-MS Method: Column-KINETEX-XB-C18 (75×3 mm-2.6 μm); Mobile phase A: 10 mM ammonium formate in water:acetonitrile (98:2); Mobile phase B: 10 mM ammonium formate in water:acetonitrile (2:98); Gradient: 20-100% B over 4 minutes, flow rate 1.0 mL/min, then a 0.6 minute hold at 100% B flow rate 1.5 mL/min; then Gradient: 100-20% B over 0.1 minutes, flow rate 1.5 mL/min.

Intermediate 28

8-Hydroxy-5-methyl-6-oxo-5,6-dihydro-1,5-naphthyridine-2-carbonitrile

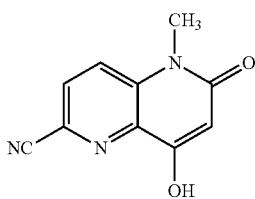

(I-28)

To a stirred solution of ethyl 6-cyano-3-(N-methylacetamido)picolinate (0.9 g, 3.64 mmol) in tetrahydrofuran (10 mL) was added KHMDS (4.80 mL, 4.37 mmol) at −78° C. over 10 min. The reaction mixture was stirred for 15 min.

The reaction mixture was slowly warmed to room temperature over 30 min and then stirred for another 90 min. The reaction mixture was cooled to 0° C. The reaction was quenched with the addition of saturated sodium bicarbonate solution (70 mL). The mixture was diluted with ethyl acetate (2×100 mL). The aqueous layer was collected and acidified with 1.5 N HCL to adjust the pH to ~3.0. The mixture was stirred for 15 min to form a solid mass, which was filtered through a Buchner funnel to yield 8-hydroxy-5-methyl-6-oxo-5,6-dihydro-1,5-naphthyridine-2-carbonitrile 550 mg, 75% yield) as a brown solid. LCMS: m/z=202.0 (m/z): (M+H); rt 0.36 min; LC-MS Method: Column-KINETEX-XB-C18 (75×3 mm-2.6 µm); Mobile phase A: 10 mM ammonium formate in water:acetonitrile (98:2); Mobile phase B: 10 mM ammonium formate in water:acetonitrile (2:98); Gradient: 20-100% B over 4 minutes, flow rate 1.0 mL/min, then a 0.6 minute hold at 100% B flow rate 1.5 mL/min; then Gradient: 100-20% B over 0.1 minutes, flow rate 1.5 mL/min.

Intermediate 29

8-Chloro-5-methyl-6-oxo-5,6-dihydro-1,5-naphthyridine-2-carbonitrile

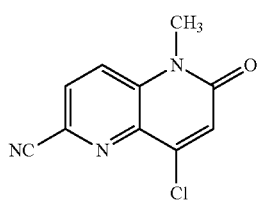

(I-29)

To a stirred solution of 8-hydroxy-5-methyl-6-oxo-5,6-dihydro-1,5-naphthyridine-2-carbonitrile (0.55 g, 2.73 mmol) in acetonitrile (10 mL) was added POCl$_3$ (1.53 mL, 16.4 mmol). The reaction mixture was heated to 85° C. over 5 min and then stirred for 16 h. The reaction mixture was concentrated under reduced pressure to yield the crude product. The reaction mixture was cooled to 0° C. The reaction was quenched by the addition of saturated sodium bicarbonate solution (50 mL). The resultant mixture was extracted with DCM (3×100 mL) and the combined organic layers were dried over anhydrous sodium sulfate, filtered, and evaporated under reduced pressure to yield 8-chloro-5-methyl-6-oxo-5,6-dihydro-1,5-naphthyridine-2-carbonitrile (0.25 g, 29.1% yield) as a brown solid. LCMS: m/z=220.2 (m/z): (M+H); rt 1.53 min; LC-MS Method: Column-KI-NETEX-XB-C18 (75×3 mm-2.6 µm); Mobile phase A: 10 mM ammonium formate in water:acetonitrile (98:2); Mobile phase B: 10 mM ammonium formate in water:acetonitrile (2:98); Gradient: 20-100% B over 4 minutes, flow rate 1.0 mL/min, then a 0.6 minute hold at 100% B flow rate 1.5 mL/min; then Gradient: 100-20% B over 0.1 minutes, flow rate 1.5 mL/min.

Intermediate 30

6-Cyano-1-methyl-2-oxo-1,2-dihydro-1,5-naphthyridin-4-yl trifluoromethanesulfonate

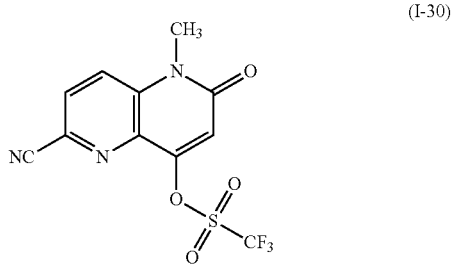 [SMILES: Cn1c(=O)cc(OS(=O)(=O)C(F)(F)F)c2nc(C#N)ccc21]

(I-30)

To a mixture of 8-hydroxy-5-methyl-6-oxo-5,6-dihydro-1,5-naphthyridine-2-carbonitrile (0.3 g, 1.49 mmol), DMAP (0.018 g, 0.15 mmol) and TEA (0.312 mL, 2.24 mmol) in DCM (30 mL) was added dropwise trifluoromethanesulfonic anhydride (0.269 mL, 1.640 mmol) in DCM (3 mL) at 0° C. The reaction mixture was stirred for 3 h. The reaction mixture was diluted with DCM, washed with water, the organic layer was dried over Na$_2$SO$_4$, filtered and evaporated under reduced pressure to yield 6-cyano-1-methyl-2-oxo-1,2-dihydro-1,5-naphthyridin-4-yl trifluoromethanesulfonate (0.45 g, 81% yield) as a pale yellow solid; LCMS: m/z=334.2 (m/z): (M+H); rt 1.40 min. LC-MS Method: Column-AQUITY UPLC BEH C18 (3.0×50 mm) 1.7 µm; Mobile phase A: Buffer:acetonitrile (95:5); Mobile phase B: Buffer:acetonitrile (5:95), Buffer: 10 mM ammonium acetate; Gradient: 20-100% B over 2.0 minutes, then a 0.2 minute hold at 100% B, flow rate 0.7 mL/min.

Intermediate 31

8-Hydroxy-5-methyl-7-nitro-6-oxo-5,6-dihydro-1,5-naphthyridine-2-carbonitrile

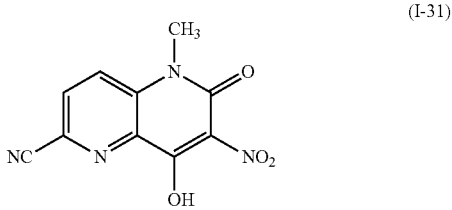 [SMILES: Cn1c(=O)c([N+](=O)[O-])c(O)c2nc(C#N)ccc21]

(I-31)

To a stirred solution of 8-hydroxy-5-methyl-6-oxo-5,6-dihydro-1,5-naphthyridine-2-carbonitrile (1 g, 4.97 mmol) in acetic acid (10 mL) was added nitric acid (0.666 mL, 14.91 mmol). The mixture was heated to 80° C. for 1 h. The reaction mixture was cooled to room temperature and diluted with water, stirred for 10 min and the resulting solid was filtered to yield 8-hydroxy-5-methyl-7-nitro-6-oxo-5,6-dihydro-1,5-naphthyridine-2-carbonitrile (0.805 g, 65.1% yield) as pale yellow solid; LCMS: m/z=247.2: (M+H); rt 1.19 min. LC-MS Method: Column-KINETEX-XB-C18 (75×3 mm-2.6 µm); Mobile phase A: 10 mM ammonium formate in water:acetonitrile (98:2); Mobile phase B: 10 mM ammonium formate in water:acetonitrile (2:98); Gradient: 20-100% B over 4 minutes, flow rate 1.0 mL/min, then a 0.6 minute hold at 100% B flow rate 1.5 mL/min; then Gradient: 100-20% B over 0.1 minutes, flow rate 1.5 mL/min.

Intermediate 32

8-chloro-5-methyl-7-nitro-6-oxo-5,6-dihydro-1,5-naphthyridine-2-carbonitrile

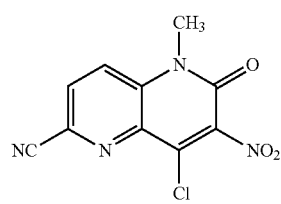

(I-32)

8-Hydroxy-5-methyl-7-nitro-6-oxo-5,6-dihydro-1,5-naphthyridine-2-carbonitrile (192 mg, 0.780 mmol) was dissolved in a mixture of acetonitrile (3.1 mL) and DIEA (0.272 ml, 1.560 mmol) to give a yellow colored solution. POCl$_3$ (0.131 ml, 1.404 mmol) was then added and the mixture stirred under nitrogen at room temperature for 1 h. Benzyltriethylammonium chloride (200 mg, 0.878 mmol) was added and the mixture was heated at 65° C. for 1 h. The mixture was concentrated in vacuo, and the residue dissolved in ethyl acetate and the resultant solution poured onto ice. This was left for approximately 1 h, before being transferred to a separatory funnel. The organic layer was collected and the aqueous solution was extracted with additional ethyl acetate. The combined organic layers were washed sequentially with 1.5M K$_2$HPO$_4$ solution, saturated NaHCO$_3$ solution and then brine. The mixture was then dried over MgSO$_4$, filtered and then evaporated in vacuo to give a brown crystalline solid (204 mg, 90% yield). LCMS: (m/z): (M+H)$^+$=264.9. $^1$H NMR (CHLOROFORM-d) δ 8.03 (d, J=8.8 Hz, 1H), 7.89-7.97 (m, 1H), 3.82 (s, 3H).

Intermediate 33

6-Cyano-1-methyl-3-nitro-2-oxo-1,2-dihydro-1,5-naphthyridin-4-yl trifluoromethanesulfonate

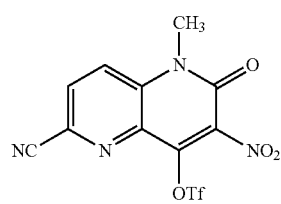

(I-33)

To a suspension of 8-hydroxy-5-methyl-7-nitro-6-oxo-5,6-dihydro-1,5-naphthyridine-2-carbonitrile (0.25 g, 1.016 mmol) in dry DCM (10 mL) was added TEA (0.212 mL, 1.523 mmol) followed by trifluoromethanesulfonic anhydride (0.183 mL, 1.117 mmol) under nitrogen atmosphere at 0° C. The reaction mixture was stirred for 3 h. The reaction mixture was diluted with DCM, washed with water, the organic layer was dried over Na$_2$SO$_4$, filtered and evaporated under reduced pressure to yield 6-cyano-1-methyl-3-nitro-2-oxo-1,2-dihydro-1,5-naphthyridin-4-yl trifluoromethanesulfonate (0.25 g, 48.8% yield) as a light brown solid; LCMS: m/z=379.2 (m/z): (M+H); rt 1.66 min. LC-MS Method: Column-AQUITY UPLC BEH C18 (3.0×50 mm) 1.7 μm; Mobile phase A: Buffer:acetonitrile (95:5); Mobile phase B: Buffer:acetonitrile (5:95), Buffer: 10 mM ammonium acetate; Gradient: 20-100% B over 2.0 minutes, then a 0.2 minute hold at 100% B, flow rate 0.7 mL/min.

Intermediate 34

7-bromo-8-hydroxy-5-methyl-6-oxo-5,6-dihydro-1,5-naphthyridine-2-carbonitrile

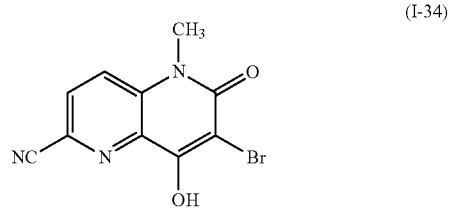 [SMILES: Cn1c(=O)c(Br)c(O)c2nc(C#N)ccc21]

(I-34)

To a stirred solution of 8-hydroxy-5-methyl-6-oxo-5,6-dihydro-1,5-naphthyridine-2-carbonitrile (1000 mg, 4.97 mmol) in dry DMF (10 mL) was added NBS (973 mg, 5.47 mmol). The reaction mixture was stirred at room temperature for 3 h. The solvent was removed under reduced pressure to yield residue. The residue was dissolved in water and stirred for 10 min. The solid material was filtered and washed with petroleum ether to yield 7-bromo-8-hydroxy-5-methyl-6-oxo-5,6-dihydro-1,5-naphthyridine-2-carbonitrile (0.8 g, 56.9% yield) as an off-white solid; LCMS: m/z=282: (M+H); rt 1.60 min. Method: Column-KINETEX-XB-C18 (75×3 mm-2.6 μm); Mobile phase A: 10 mM ammonium formate in water:acetonitrile (98:2); Mobile phase B: 10 mM ammonium formate in water:acetonitrile (2:98); Gradient: 20-100% B over 4 minutes, flow rate 1.0 mL/min, then a 0.6 minute hold at 100% B flow rate 1.5 mL/min; then gradient: 100-20% B over 0.1 minutes, flow rate 1.5 mL/min.

Intermediate 35

3-bromo-6-cyano-1-methyl-2-oxo-1,2-dihydro-1,5-naphthyridin-4-yl trifluoromethanesulfonate

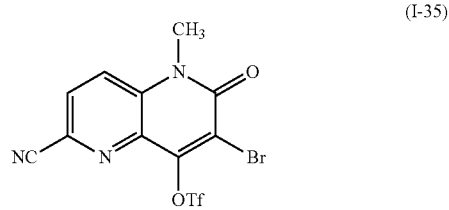 [SMILES: Cn1c(=O)c(Br)c(OS(=O)(=O)C(F)(F)F)c2nc(C#N)ccc21]

(I-35)

To a stirred solution of 7-bromo-8-hydroxy-5-methyl-6-oxo-5,6-dihydro-1,5-naphthyridine-2-carbonitrile (0.175 g, 0.625 mmol) and TEA (0.131 mL, 0.937 mmol) in dry DCM (10 mL) was added trifluoromethanesulfonic anhydride (0.137 mL, 0.812 mmol) at 0° C. The reaction mixture was stirred at room temperature for 3 h. The reaction mixture was diluted with DCM and washed with water, followed by brine wash, the organic layer was dried over anhydrous Na₂SO₄, filtered and evaporated under reduced pressure to yield 3-bromo-6-cyano-1-methyl-2-oxo-1,2-dihydro-1,5-naphthyridin-4-yl trifluoromethanesulfonate (190 mg, 53.9% yield) as a pale yellow solid; LCMS: m/z=414 (m/z): (M+H); rt 1.61 min. Method: Column-AQUITY UPLC BEH C18 (3.0×50 mm) 1.7 μm; Mobile phase A: Buffer:acetonitrile (95:5); Mobile phase B: Buffer:acetonitrile (5:95), Buffer: 10 mM ammonium acetate; Gradient: 20-100% B over 2.0 minutes, then a 0.3 minute hold at 100% B, flow rate 0.7 mL/min.

Intermediate 36

Ethyl 3-amino-6-bromopicolinate

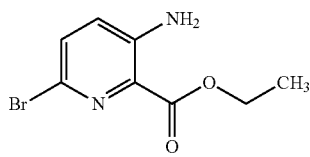
(I-36)

Ethyl 3-aminopicolinate (8.0 g, 48.1 mmol) was suspended in water (66 mL) in a 250 mL three neck round bottom flask equipped with a mechanical stirrer, addition funnel and thermocouple temperature probe. Sulfuric acid (1.7 mL, 31.9 mmol) and acetic acid (3.31 mL, 57.8 mmol) were added slowly while the flask was immersed in a room temperature water bath to control temperature. To the reaction mixture, a solution of bromine (2.5 mL, 48.5 mmol) in acetic acid (17.5 mL, 306 mmol) was added over 15 minutes at ambient temperature with vigorous stirring while maintaining the internal temperature of the reaction mixture below 23° C. The water bath was removed and the reaction mixture was stirred at ambient temperature for 2 hours. The reaction suspension was filtered and rinsed with a small amount of water, and then dried in vacuo at room temperature to yield ethyl 3-amino-6-bromopicolinate (9.305 g) as a yellow solid. LCMS: Column: Waters Acquity UPLC BEH C18, 2.1×50 mm, 1.7 μm particles; Mobile Phase A: 100% water with 0.05% trifluoroacetic acid; Mobile Phase B: 100% acetonitrile with 0.05% trifluoroacetic acid; Temperature: 40° C.; Gradient: 2-98% B over 1.5 minutes, then a 0.5 minute hold at 98% B; Flow: 0.8 mL/min; Detection: UV at 220 nm. Retention Time 0.94 min.; Obs. Adducts: [M+H]; Obs. Masses: 245.0. ¹H NMR (DMSO-d₆) δ 7.44 (d, J=8.8 Hz, 1H), 7.21 (d, J=8.7 Hz, 1H), 6.88 (br. s., 2H), 4.29 (q, J=7.1 Hz, 2H), 1.31 (t, J=7.1 Hz, 3H).

Intermediate 37

Ethyl 3-acetamido-6-bromopicolinate

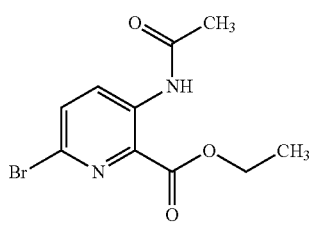
(I-37)

Ethyl 3-amino-6-bromopicolinate (1.31 g, 5.35 mmol) was dissolved in THF (6 mL) followed by the addition of acetic anhydride (1.6 mL, 16.96 mmol). The reaction mixture was a suspension/partial solution. The reaction mixture was placed under a nitrogen atmosphere and heated to reflux. The reaction mixture became homogeneous within 15 minutes. The reaction mixture was refluxed for 4 hrs. The reaction volatiles were removed in vacuo using a rotary evaporator. A small amount of ethyl acetate was added to the reaction residue and a nearly colorless solid was filtered off and dried in vacuo to yield ethyl 3-acetamido-6-bromopicolinate (787 mg). LCMS: Column: Waters Acquity UPLC BEH C18, 2.1×50 mm, 1.7 μm particles; Mobile Phase A: 100% water with 0.05% trifluoroacetic acid; Mobile Phase B: 100% acetonitrile with 0.05% trifluoroacetic acid; Temperature: 40° C.; Gradient: 2-98% B over 1.5 minutes, then a 0.5 minute hold at 98% B; Flow: 0.8 mL/min; Detection: UV at 220 nm. Retention Time 0.98 min.; Obs. Adducts: [M+H]; Obs. Masses: 287.0. ¹H NMR (DMSO-d₆) δ 10.40 (s, 1H), 8.32 (d, J=8.7 Hz, 1H), 7.83 (d, J=8.8 Hz, 1H), 4.33 (q, J=7.1 Hz, 2H), 2.12 (s, 3H), 1.32 (t, J=7.2 Hz, 3H). Removal of solvent from the filtrate provided an additional 695 mg of product (87% pure).

Intermediate 38

Ethyl 6-bromo-3-(N-methylacetamido)picolinate

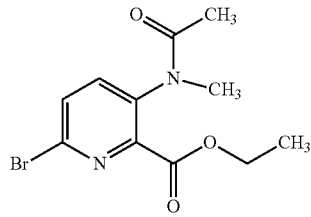
(I-38)

A solution was prepared by dissolving ethyl 3-acetamido-6-bromopicolinate (5 g, 17.41 mmol) into DMF (100 mL). Next, cesium carbonate (8.15 g, 25.01 mmol) and methyl iodide (1.75 mL, 28.0 mmol) were added. The reaction mixture was placed under a nitrogen atmosphere and stirred at room temperature for 2 hours and 40 minutes. Solvent was removed in vacuo using a rotary evaporator/vacuum pump combination. Ethyl acetate and DCM were added to the reaction residue along with chloroform and toluene. The mixture was filtered through a celite pad to remove salts. Solvents were again removed in vacuo using a rotary evaporator. The reaction residue was again dissolved in chloroform and toluene and filtered through a celite bed to remove trace insolubles still present. Removal of solvents in vacuo yielded 5.35 g of the product as an orange oil. LCMS; Column: Waters Acquity BEH 2.1 mm×50 mm, 1.7 μm particles; Mobile Phase A: 10:90 acetonitrile:water with 0.1% TFA; Mobile Phase B: 90:10 acetonitrile:water with 0.1% TFA; Temperature: 40° C.; Gradient 0% B to 100% B over 2 minutes, then 1 min hold at 100% B; Flow: 1 mL/min; Detection: MS and UV (220 nm). Injection volume: 1 μL. Retention Time 1.07 min.; Obs. Adducts: [M+H]; Obs. Masses: 301.1. Proton NMR shows characteristics of restricted rotation (rotamers); ¹H NMR (500 MHz, CHLOROFORM-d) δ 7.72 (d, J=8.4 Hz, 0.8H), 7.66 (d, J=8.4 Hz, 0.2H), 7.51 (d, J=8.4 Hz, 0.8H), 7.45 (d, J=8.4 Hz, 0.2H), 4.50-4.36 (m, 2.0H), 3.37 (s, 0.6H), 3.19 (s, 2.4H), 2.24 (s, 0.6H), 1.82 (s, 2.5H), 1.43-1.36 (m, 3.1H).

Intermediate 39

6-Bromo-4-hydroxy-1-methyl-1,5-naphthyridin-2(1H)-one

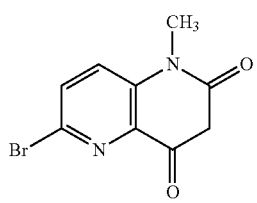

(I-39)

A 25 mL round bottom flask was charged with KHMDS (4.3 mL, 2.150 mmol) (0.5 M in toluene), placed under nitrogen and cooled to −78° C. To the solution of KHMDS was slowly added a solution of ethyl 6-bromo-3-(N-methylacetamido)picolinate (215 mg, 0.714 mmol) in THF (2.5 mL) over approximately 3 minutes. The reaction mixture was warmed to room temperature and a 1:1 mixture of ethyl acetate and water were added to fill the 60 mL separatory funnel. The phases were allowed to separate. The aqueous phase was acidified with 2.5 mL of 1 N hydrochloric acid and concentrated on the rotary evaporator using a vacuum pump. The crude residue was swirled in an Erlenmeyer flask with 7 mL of water. A yellow solid collected and dried under vacuum to give the title compound (130.2 mg, 72%). LCMS; Column: Waters Acquity UPLC BEH C18 2.1 mm×50 mm, 1.7 μm particles; Mobile Phase A: 100 water with 0.05% TFA; Mobile Phase B: 100 acetonitrile 0.05% TFA; Temperature: 40° C.; Gradient 2% B to 98% B over 1.5 minutes, then 1 min hold at 100% B; Flow: 0.8 mL/min; Detection: MS and UV (220 nm). Injection volume: 3 μL. Retention Time 0.8 min.; Obs. Adducts: [M+H]; Obs. Masses: 254.9, 256.9.

Intermediate 40

6-Bromo-1-methyl-2-oxo-1,2-dihydro-1,5-naphthyridin-4-yl trifluoromethanesulfonate

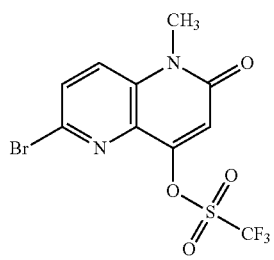

(I-40)

In a round bottom flask, 6-bromo-1-methyl-1,5-naphthyridine-2,4(1H,3H)-dione (200 mg, 0.784 mmol) was combined with DMAP (9.58 mg, 0.078 mmol), DIPEA (0.205 mL, 1.176 mmol) and DCM (20 mL). To the resulting suspension, a solution of trifluoromethanesulfonic anhydride (0.141 mL, 0.863 mmol) in dichloromethane (2 mL) was added dropwise at 0° C. The solution was stirred for 3 hours. LC/MS analysis indicated the reaction was complete. The solvent was removed under reduced pressure and the crude was purified by chromatography with 1:1 hexane:ethyl acetate on a 24 g silica gel column to afford the product as white solid (260 mg, 86%). Analytical LC\MS conditions: Injection Vol=1 μL, Start % B 0, Final % B 100, Gradient Time 2 Minutes, Flow Rate 1 mL/min, Wavelength 220 nm, Solvent Pair acetonitrile/water/TFA, Solvent A 10% Acetonitrile/90% Water/0.1% TFA, Solvent B 90% Acetonitrile/10% Water/0.1% TFA, Column Acquity BEH C18 21.×50 mm 1.7 μm, Oven Temp=40° C. LC\MS results; retention time 1.5 minutes, observed mass 386.7, 388.7 (M+).

Intermediate 41

2-cyanoacetyl chloride

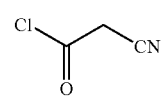

(I-41)

A few drops of DMF were added to a solution of 2-cyanoacetic acid (500 mg, 5.88 mmol) in CH$_2$Cl$_2$ (5 mL). Then a solution of 2 M oxalyl chloride (3.23 mL, 6.47 mmol) in methylene chloride was added dropwise. The reaction mixture was stirred at room temperature for 2 hr. and concentrated.

Intermediate 42

6-bromo-2,4-dioxo-1,2,3,4-tetrahydro-1,5-naphthyridine-3-carbonitrile

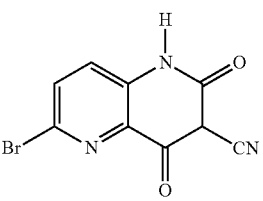

(I-42)

To a solution of ethyl 3-amino-6-bromopicolinate (1.3 g, 5.30 mmol) in DCM (10 mL), DIPEA (2.78 mL, 15.91 mmol) was added. Then 2-cyanoacetyl chloride (0.609 g, 5.88 mmol) in DCM (10 mL) was added slowly. The reaction mixture was stirred at room temperature for 10 min. LC/MS shown formation of ethyl 6-bromo-3-(2-cyanoacetamido)picolinate (MS at 312). The reaction was quenched with water and the resultant mixture was extracted with dichloromethane. The organic layer was separated, washed with brine, dried (MgSO$_4$) and concentrated to give a brownish thick oil as crude product. The crude product was triturated with ethyl acetate/hexanes to give a yellow solid. $^1$H NMR confirms its structure as the cyclized product with DIPEA. The product was washed with 1 N HCl solution and 6-bromo-2,4-dioxo-1,2,3,4-tetrahydro-1,5-naphthyridine-3- carbonitrile (650 mg, 2.443 mmol, 46.1% yield) as an off-white solid. $^1$H NMR (DMSO-$d_6$). LCMS: (m/z) >90% pure, 266, 268 (MW).

Intermediate 43

6-bromo-1-methyl-2,4-dioxo-1,2,3,4-tetrahydro-1,5-naphthyridine-3-carbonitrile

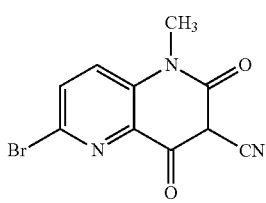

(I-43)

To a solution of 6-bromo-2,4-dioxo-1,2,3,4-tetrahydro-1,5-naphthyridine-3-carbonitrile (250 mg, 0.940 mmol) in DMF (5 mL), 60% sodium hydride (113 mg, 2.82 mmol) in mineral oil was added in portions. The reaction mixture was stirred at room temperature for 30 min., and iodomethane (0.176 mL, 2.82 mmol) was added. The reaction mixture was stirred at room temperature for overnight.

Intermediate 44

6-Bromo-3-cyano-1-methyl-2-oxo-1,2-dihydro-1,5-naphthyridin-4-yl trifluoromethanesulfonate

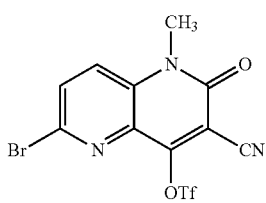

(I-44)

To a stirred solution of 6-bromo-1-methyl-2,4-dioxo-1,2,3,4-tetrahydro-1,5-naphthyridine-3-carbonitrile (0.6 g, 2.14 mmol) in DCM (8 mL) were added TEA (0.896 mL, 6.43 mmol) and DMAP (0.026 g, 0.214 mmol) at 0° C., followed by the addition of trifluoromethanesulfonic anhydride (0.724 mL, 4.28 mmol). The reaction mixture was slowly warmed to room temperature and was stirred for 3 h. The reaction was quenched with the addition of water (50 mL). The reaction mixture was diluted with DCM (3×100 mL). The combined organic layer was dried over anhydrous sodium sulfate, filtered and evaporated under reduced pressure to yield a brown solid. The crude compound was triturated with DCM and hexane (1:4) to yield 6-bromo-3-cyano-1-methyl-2-oxo-1,2-dihydro-1,5-naphthyridin-4-yl trifluoromethanesulfonate (700 mg, 79% yield) as a brown solid; LCMS: m/z=414.1 (m/z): (M+H); rt 0.65 min. LC-MS Method: Column-AQUITY UPLC BEH C18 (3.0×50 mm) 1.7 µm; Mobile phase A: Buffer:acetonitrile (95:5); Mobile phase B: Buffer:acetonitrile (5:95), Buffer: 10 mM ammonium acetate; Gradient: 20-100% B over 2.0 minutes, then a 0.3 minute hold at 100% B, flow rate 0.7 mL/min.

Intermediate 45

6-bromo-4-chloro-1-methyl-2-oxo-1,2-dihydro-1,5-naphthyridine-3-carbonitrile

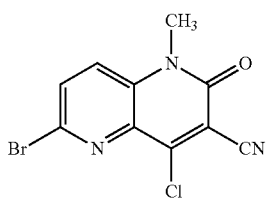

(I-45)

To a 500 mL round-bottom flask charged with 6-bromo-1-methyl-2,4-dioxo-1,2,3,4-tetrahydro-1,5-naphthyridine-3-carbonitrile (2.50 g, 8.93 mmol) in acetonitrile (89 ml), DIEA (9.4 ml, 53.8 mmol) was added and the mixture was stirred for 2 min during which time it became homogeneous. POCl$_3$ (3.3 ml, 35.4 mmol) was then added, followed by benzyltriethylammonium chloride (2.68 g, 11.77 mmol) and the reaction mixture was stirred under nitrogen at room temperature overnight. The mixture was then concentrated under line vacuum initially, then under high vacuum. The residue was then poured onto a mixture of ice and 1.5 M K$_2$HPO$_4$ solution. After 30 min the mixture was extracted using chloroform (3×). The combined extracts were washed sequentially with K$_2$HPO$_4$ solution, 1 N HCl solution and then brine. The organic solution was then dried over Na$_2$SO$_4$, filtered and concentrated in vacuo to give the crude product as a brown solid (3.1 g). The product was purified by flash chromatography on silica gel using 2% ethyl acetate in DCM as eluent. Homogeneous fractions were combined and evaporated under reduced pressure to give the product as a yellow colored solid, 1.922 g (yield 72%). LCMS: (m/z): (M+H)$^+$=298.05. $^1$H NMR (500 MHz, CHLOROFORM-d) δ 7.83 (d, J=8.8 Hz, 1H), 7.68 (d, J=9.0 Hz, 1H).

Intermediate 46

4,6-dichloro-1-methyl-2-oxo-1,2-dihydro-1,5-naphthyridine-3-carbonitrile

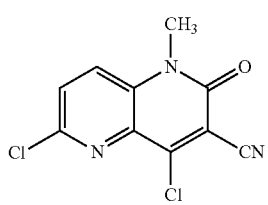

(I-46)

A 4 M solution of HCl in dioxane (20 mL, 80 mmol) was added to 6-bromo-4-chloro-1-methyl-2-oxo-1,2-dihydro-1,5-naphthyridine-3-carbonitrile (1 g, 3.35 mmol) in a dry glass pressure tube. The reaction mixture was sealed and heated at 85° C. for 4 days. The mixture was then cooled and concentrated under vacuum. The residue was triturated with methanol and a solid was collected by filtration and dried in vacuo to give the hydrochloride salt of the title compound as a brown colored solid, (0.78 g, 2.68 mmol, 80% yield).

Intermediate 47

Ethyl 6-bromo-3-(2-cyanoacetamido)picolinate

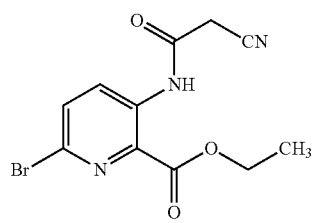
(I-47)

To a stirred solution of ethyl 3-amino-6-bromopicolinate (2.0 g, 8.16 mmol) in DMF (15 mL) were added 2-cyanoacetic acid (1.388 g, 16.32 mmol) and TEA (2.84 mL, 20.40 mmol) followed by 1-propanephosphonic anhydride (10.78 mL, 17.95 mmol). The reaction mixture was stirred at room temperature for 16 hours and was then quenched by the careful addition of water (100 mL). The resultant mixture was stirred for 15 min during which time a solid separated that was collected by filtration to give the product as a yellow colored solid, (2.45 g, 7.85 mmol, 96% yield).

Intermediate 48

Ethyl 6-cyano-3-(2-cyanoacetamido)picolinate

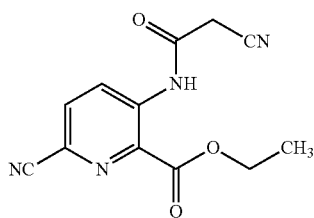
(I-48)

To a stirred solution of ethyl 6-bromo-3-(2-cyanoacetamido)picolinate (200 mg, 0.641 mmol) in NMP (8 mL) were added zinc (8.38 mg, 0.128 mmol) and zinc cyanide (150 mg, 1.282 mmol) under nitrogen. The mixture was purged with nitrogen for 3 min, after which dppf (21.31 mg, 0.038 mmol) and $Pd_2(dba)_3$ (58.7 mg, 0.064 mmol) were added and purging was continued for a further 3 min. The reaction mixture was then heated to 80° C. over 5 min and the mixture was stirred for an additional hour before being allowed to cool to room temperature. The reaction was then quenched by the addition of water, and the resultant mixture was filtered through a bed of celite. The filtrate was extracted using ethyl acetate (3×100 mL) and the combined extracts were washed with brine solution (50 mL), dried over $Na_2SO_4$, filtered and concentrated under reduced pressure to give a brown oil. The crude product was purified by flash chromatography on silica gel using 34%-39% ethyl acetate/pet.ether as eluant. Homogeneous fractions were combined and evaporated in vacuo to give the product as a as brown solid, (70 mg, 0.271 mmol, 42.3% yield) LCMS Method; Buffer: 10 mM Ammonium Acetate pH −5 adjusted with HCOOH Mobile phase A: Buffer:ACN (95:5) Mobile phase B: Buffer:ACN (5:95) Description: Method: % B: 0 min-5%:1.1 min-95%:1.7 min-95% Column Name: Acquity BEH C18 (2.1×50 mm) 1.7 um Method: C: \MassLynx\BMS_2013. Flow: 0.8 ml/min LCMS RT=1.10 min $(M-H)^-=257.2$).

Intermediate 49

6,8-dioxo-5,6,7,8-tetrahydro-1,5-naphthyridine-2,7-dicarbonitrile

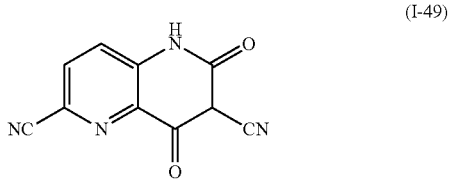 [SMILES: N#Cc1ccc2c(n1)C(=O)C(C#N)C(=O)N2]
(I-49)

To a stirred solution of ethyl 6-cyano-3-(2-cyanoacetamido)picolinate (70 mg, 0.271 mmol) in DCM (5 mL) was added triethylamine (0.113 mL, 0.813 mmol). The reaction mixture was warmed to 45° C. and then stirred for 3 hours. The mixture was concentrated under reduced pressure and the residue triturated with ethyl acetate for 15 min. The resultant suspension was filtered and the filtrand dried under reduced pressure to give the product as a brown colored solid, (54 mg, 0.255 mmol, 94% yield). LCMS: (m/z): $(M+H)^+=213.2$ Intermediate 50

5-methyl-6,8-dioxo-5,6,7,8-tetrahydro-1,5-naphthyridine-2,7-dicarbonitrile

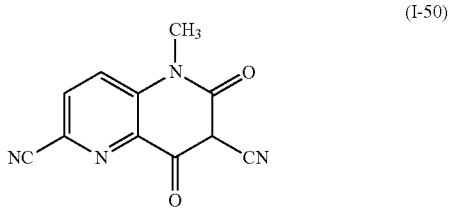 [SMILES: CN1C(=O)C(C#N)C(=O)c2nc(C#N)ccc21]
(I-50)

NaH (28.3 mg, 0.707 mmol was added to a stirred solution of 6,8-dioxo-5,6,7,8-tetrahydro-1,5-naphthyridine-2,7-dicarbonitrile (50 mg, 0.236 mmol) in DMF (3 mL) at 0° C. The stirred mixture was then allowed to warm to room temperature. Methyl iodide (0.044 mL, 0.707 mmol) was added and stirring was continued under a nitrogen atmosphere for 3 h. The reaction was quenched by the addition of water (10 mL). The pH of the mixture was adjusted to −6 using 1.5 N HCl. The resultant mixture was stirred for 15 min during which time a solid separated that was collected by filtration and then dried under reduced pressure to give the product as a brown colored solid, (20 mg, 0.088 mmol, 37.5% yield). LC-MS: Method info: Column-Ascentis Express $C_8$ (50×2.1 mm-2.7 μm), M phase A: (2% ACN-98% $H_2O$-10 mM $NH_4COOH$), M phase B: (98% ACN-2%

H₂O-10 mM NH₄COOH), Flow=1 mL/min, Time % B (0.0 0.0), (1.5 100.0), (3.2 100.0). LC-MS RT=1.301 min (m/z): (M+H)⁺=225.0.

Intermediate 51

8-chloro-5-methyl-6-oxo-5,6-dihydro-1,5-naphthyridine-2,7-dicarbonitrile

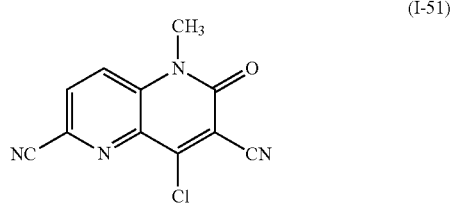 [SMILES: Cn1c(=O)c(C#N)c(Cl)c2nc(C#N)ccc21]

(I-51)

The starting material, the hydrochloride salt of 5-methyl-6,8-dioxo-5,6,7,8-tetrahydro-1,5-naphthyridine-2,7-dicarbonitrile, was dried overnight at 90° C. under vacuum before performing the reaction. To a stirred suspension of the hydrochloride salt of 5-methyl-6,8-dioxo-5,6,7,8-tetrahydro-1,5-naphthyridine-2,7-dicarbonitrile (10 g, 38.1 mmol) in acetonitrile (100 mL) was added DIPEA (19.95 mL, 114 mmol). The resulting turbid brown solution was cooled to 0-5° C. and POCl₃ (40.8 mL, 438 mmol) was added slowly over ~20 min, after which the mixture was heated to 90° C. for ~1 h. The reaction mixture was cooled to room temperature and then concentrated under high vacuum to afford a pale brown colored residue. Ice pellets were added and the slurry was stirred for ~15 min, during which time a free flowing solid formed. The mixture was neutralized by the addition of saturated NaHCO₃ solution, and the product extracted using DCM (4×500 mL). The combined extracts were washed with brine (1×500 mL), dried over Na₂SO₄, filtered and concentrated in vacuo to give the crude product as a brown colored solid. This was triturated with acetone (50 mL), and the product was collected by filtration and dried in vacuo to give 6 g of a solid. The filtrate was concentrated and the residue again triturated with acetone to give an additional 2.4 g of a solid. The solids were combined to give the title compound as a brown colored solid, (8.4 g, 33.8 mmol, 89% yield).

Intermediate 52

6-chloro-4-(4-hydroxypiperidin-1-yl)-1-methyl-2-oxo-1,2-dihydro-1,5-naphthyridine-3-carbonitrile

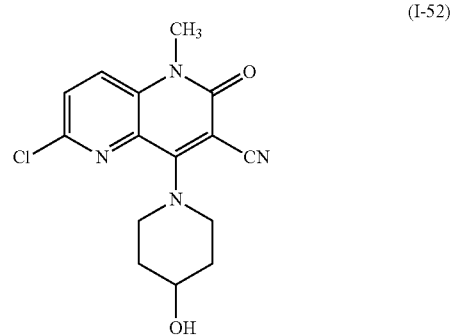 [SMILES: Cn1c(=O)c(C#N)c(N2CCC(O)CC2)c2nc(Cl)ccc21]

(I-52)

Piperidin-4-ol (110 mg, 1.084 mmol) was added to a solution of 4,6-dichloro-1-methyl-2-oxo-1,2-dihydro-1,5-naphthyridine-3-carbonitrile hydrochloride (300 mg, 1.033 mmol) and triethylamine (0.720 mL, 5.16 mmol) in DMF (5 mL). The reaction mixture was stirred at room temperature overnight before being quenched by the addition of water. On stirring, a yellow colored solid separated and was collected by filtration and then dried in vacuo to give the title compound as a yellow solid, (325 mg, 1.020 mmol, 99% yield). LCMS: (m/z): (M+H)⁺=319.08, ¹H NMR (500 MHz, DMSO-d₆) δ 8.04 (d, J=9.2 Hz, 1H), 7.77 (d, J=9.2 Hz, 1H), 4.72 (d, J=4.4 Hz, 1H), 4.14-3.99 (m, 2H), 3.87 (br dd, J=8.1, 4.0 Hz, 1H), 3.59 (ddd, J=13.0, 9.4, 3.3 Hz, 2H), 3.53 (s, 3H), 1.98 (ddd, J=9.4, 5.7, 2.9 Hz, 2H), 1.70 (td, J=8.4, 4.4 Hz, 2H).

Intermediate 53

(+/−) 6-bromo-4-(cis-4-hydroxy-3-methylpiperidin-1-yl)-1-methyl-2-oxo-1,2-dihydro-1,5-naphthyridine-3-carbonitrile

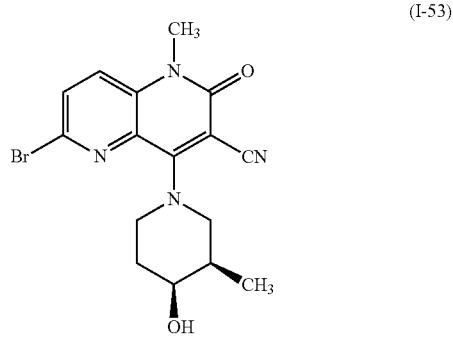 [SMILES: C[C@@H]1CN(c2c(C#N)c(=O)n(C)c3ccc(Br)nc23)CC[C@@H]1O]

(I-53)

To a solution of 6-bromo-4-chloro-1-methyl-2-oxo-1,2-dihydro-1,5-naphthyridine-3-carbonitrile (1.0 g, 3.35 mmol) in DMF (8 mL), (+/−) cis-3-methylpiperidin-4-ol (0.405 g, 3.52 mmol) and triethylamine (1.167 mL, 8.37 mmol) were added. The reaction mixture was stirred at room temperature for 2 h. Water was then added and an orange solid separated that was collected by filtration. The crude product was triturated with methanol/dichloromethane and the final product was obtained by filtration as a yellow-colored solid, (0.82 g, 2.174 mmol, 64.9% yield). LCMS: (m/z): (M+H)⁺= 376.9. ¹H NMR (400 MHz, DMSO-d₆) δ 7.97-7.87 (m, 1H), 8.02-7.79 (m, 1H), 4.79-4.64 (m, 1H), 3.91-3.71 (m, 4H), 3.51 (s, 3H), 3.45 (br dd, J=12.3, 10.1 Hz, 1H), 2.06 (ddd, J=9.7, 6.5, 3.2 Hz, 1H), 1.87 (br d, J=3.9 Hz, 2H), 0.91 (d, J=6.8 Hz, 3H).

Example 49

(+/−) 6-bromo-1-methyl-4-(trans-3-methyl-4-(4-(tert-pentyl)phenoxy)piperidin-1-yl)-2-oxo-1,2-dihydro-1,5-naphthyridine-3-carbonitrile

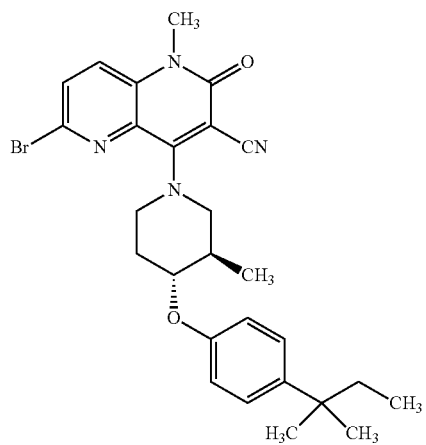

(49)

To a solution of 4-(tert-pentyl)phenol (65.3 mg, 0.398 mmol) in THF (8 mL), triphenylphosphine (194 mg, 0.583 mmol) on solid support was added. The reaction mixture was stirred at room temperature for 5 min. Then, di-tert-butyl (E)-diazene-1,2-dicarboxylate (98 mg, 0.424 mmol) and (+/−) 6-bromo-4-(cis-4-hydroxy-3-methylpiperidin-1-yl)-1-methyl-2-oxo-1,2-dihydro-1,5-naphthyridine-3-carbonitrile (100 mg, 0.265 mmol) were added. The reaction mixture was stirred at room temperature for 6 days. The reaction mixture was then filtered and the filtrate concentrated under vacuum to give a yellow solid. The product was purified using reverse phase preparative HPLC column using a $CH_3CN$—$H_2O$-TFA solvent system as eluent. Homogeneous fractions were collected and concentrated in vacuo to give the TFA salt of the title compound as a light-yellow colored solid, (31 mg, 0.049 mmol, 18.34% yield). LCMS: (m/z): $(M+H)^+$=523.0. $^1$H NMR (400 MHz, Acetone) δ 7.98 (d, J=9.0 Hz, 1H), 7.86 (d, J=9.0 Hz, 1H), 7.30 (d, J=8.8 Hz, 2H), 7.01 (d, J=8.8 Hz, 2H), 4.40-4.32 (m, 2H), 4.31-4.23 (m, 1H), 3.77 (ddd, J=13.4, 10.9, 2.8 Hz, 1H), 3.63 (s, 3H), 3.35 (dd, J=13.2, 9.8 Hz, 1H), 2.54-2.42 (m, 1H), 2.37 (ddd, J=12.6, 6.2, 2.9 Hz, 1H), 1.97-1.78 (m, 1H), 1.15 (d, J=6.6 Hz, 3H), 0.69 (t, J=7.5 Hz, 3H). A full assignment was not made due to obfuscation of certain compound associated peaks by solvent impurities.

Intermediate 55

8-chloro-5-methyl-6-oxo-5,6-dihydro-1,5-naphthyridine-2,7-dicarbonitrile

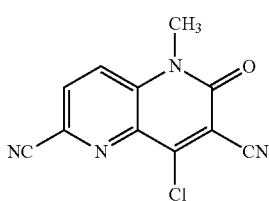

(I-55)

To a stirred suspension of 8-hydroxy-5-methyl-6-oxo-5,6-dihydro-1,5-naphthyridine-2,7-dicarbonitrile hydrochloride (10 g, 38.1 mmol) in acetonitrile (100 mL) was added DIPEA (19.95 mL, 114 mmol). The turbid brown colored solution was cooled to 0-5° C. $POCl_3$ (40.8 mL, 438 mmol) was then added slowly over ~20 min through a dropping funnel. The resulting mixture was heated to 90° C. for 1 min and then allowed to cool to room temperature. The mixture was concentrated under high vacuum to give a pale brown colored residue. Ice pellets were added and the resulting mixture was stirred for ~15 min during which time a free flowing solid formed. The mixture was neutralized using saturated $NaHCO_3$ solution and then extracted with DCM (4×500 mL). The combined extracts were washed with brine solution (1×500 mL), dried over $Na_2SO_4$, filtered and then concentrated to provide a brown colored material. The product was triturated with acetone (50 mL), and a solid was collected by filtration which was dried in vacuo to give the title compound as a brown solid (6 g). The filtrates were evaporated and the residue again triturated with acetone and additional product was obtained. The combined filtrates were dried in vacuo to give a the title compound as a brown solid, (8.4 g, 33.8 mmol, 89% yield). LCMS: $(M+H+H_2O)^+$= 262.0. $^1$H NMR (300 MHz, DMSO-$d_6$) δ 8.49-8.37 (m, 2H), 3.72-3.61 (m, 3H).

Intermediate 56

8-(4-hydroxypiperidin-1-yl)-5-methyl-6-oxo-5,6-dihydro-1,5-naphthyridine-2-carbonitrile

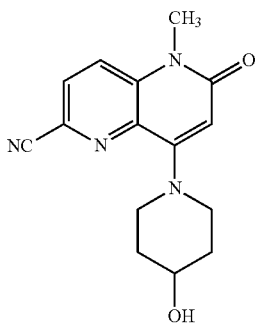

(I-56)

6-cyano-1-methyl-2-oxo-1,2-dihydro-1,5-naphthyridin-4-yl trifluoromethanesulfonate (0.600 g, 1.800 mmol) and 4-hydroxypiperidine (0.266 g, 2.63 mmol) were added to a mixture of acetonitrile (18.00 ml) and N-ethyl-N-isopropylpropan-2-amine (0.95 ml, 5.45 mmol) in a 50 mL round bottom flask. The mixture was heated at 80° C. for 1 h. The heterogeneous mixture was then cooled in an ice-bath at 0° C., and the resultant yellow precipitate was collected by filtration and then dried under vacuum to give the product as a yellow solid (473 mg, 92%). $^1$H NMR (500 MHz, CHLOROFORM-d) δ 7.80 (d, J=8.7 Hz, 0.9H), 7.70 (d, J=8.7 Hz, 0.9H), 6.23 (s, 0.9H), 4.02 (br s, 1.0H), 3.94-3.85 (m, 2.0H), 3.64 (s, 3.0H), 3.27 (ddd, J=12.5, 9.1, 3.3 Hz, 2.0H), 2.15-2.07 (m, 1.9H), 1.87-1.76 (m, 2.0H).

Intermediate 57

(+/−) 4-(cis-4-hydroxy-3-methylpiperidin-1-yl)-6-cyano-1-methyl-1,5-naphthyridin-2(1H)-one

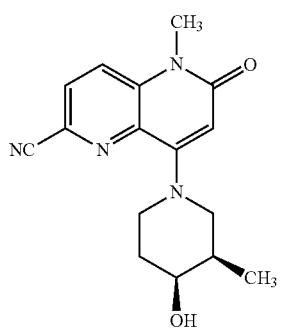

(I-57)

cis-3-methylpiperidin-4-ol (34.6 mg, 0.300 mmol) was added to a solution of 6-cyano-1-methyl-2-oxo-1,2-dihydro-1,5-naphthyridin-4-yl trifluoromethanesulfonate (100 mg, 0.300 mmol) and Hunig's base (0.105 mL, 0.600 mmol) in DMF (4 mL). The mixture was heated at 85° C. overnight. The solvent was removed under high vacuum and residue dissolved in EtOAc. The resultant solution was washed with water (2×) and once with brine. The mixture was then dried over MgSO$_4$, filtered and concentrated in vacuo to give 89 mg of a yellow solid, (100%). LCMS: RT=1.01 (m/z): (M+H)$^+$=299.03. $^1$H NMR (400 MHz) δ 8.02 (d, J=7.8 Hz, 1H), 7.85 (d, J=7.8 Hz, 1H), 5.88 (s, 1H), 3.72 (dddd, J=4.5, 4.2, 3.5, 3.4 Hz, 1H), 3.65 (s, 3H), 3.36 (dd, J=3.1, −12.2 Hz, 1H), 3.35 (ddd, J=12.1, 3.1, −12.2 Hz, 1H), 2.88 (dd, J=12.2, 4.5 Hz, 1H), 2.88 (dd, J=12.2, 11.8 Hz, 1H), 2.12 (dqt, J=11.8, 6.6, 4.5 Hz, 1H), 1.78 (dddd, J=12.1, 3.4, 3.1, −13.5 Hz, 1H), 1.72 (ddd, J=3.5, 3.1, −13.5 Hz, 1H), 0.98 (d, J=6.6 Hz, 3H).

Intermediate 58

(+/−) tert-butyl cis-4-hydroxy-3-methylpiperidine-1-carboxylate

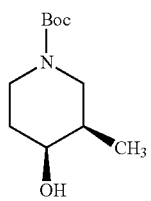

(I-58)

To a suspension of (+/−) cis-3-methylpiperidin-4-ol (1 g, 8.68 mmol) and triethylamine (1.452 mL, 10.42 mmol) in DCM (15 mL), Boc-anhydride (2.419 mL, 10.42 mmol) was added. The reaction mixture was stirred at room temperature overnight, and then diluted with DCM and acidified with 1 N HCl solution to pH-6. The organic layer was separated, washed with brine, dried over MgSO$_4$, filtered and evaporated under reduced pressure of solvent gave a yellowish oil. The crude product was then purified by flash chromatography using ethyl acetate/hexanes to (10-40%) as eluent. Homogeneous fractions were collected and evaporated under reduced pressure to give the product as a colorless, viscous oil, (1.35 g, 6.27 mmol, 72.2% yield). LCMS: 216 (m/z): (M+H)$^+$=216. $^1$H NMR (500 MHz, CHLOROFORM-d) δ 3.98-3.81 (m, 1H), 3.69-3.52 (m, 2H), 3.42-3.25 (m, 1H), 3.16-2.96 (m, 1H), 1.86-1.64 (m, 3H), 1.48 (s, 9H), 0.96 (d, J=7.0 Hz, 3H).

Intermediate 59

(+/−) tert-butyl trans-4-(benzoyloxy)-3-methylpiperidine-1-carboxylate

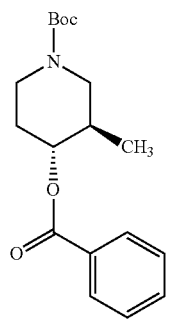

(I-59)

To a solution of (+/−) tert-butyl cis-4-hydroxy-3-methylpiperidine-1-carboxylate (0.982 g, 4.56 mmol) in THF (8 mL), triphenylphosphine (1.675 g, 6.39 mmol) and benzoic acid (0.780 g, 6.39 mmol) were added. Next, di-tert-butyl (E)-diazene-1,2-dicarboxylate (1.470 g, 6.39 mmol) in THF was added dropwise at 0° C. and the mixture was warmed and stirred at room temperature overnight. The reaction mixture was then concentrated under reduced pressure and the residue purified by flash chromatography using ethyl acetate in hexanes (10-30%) as eluent. Homogeneous fractions were combined and evaporated under vacuum to give the product as a viscous, colorless oil, (0.77 g, 2.411 mmol, 52.9% yield). $^1$H NMR (500 MHz, CHLOROFORM-d) δ 8.07 (d, J=7.6 Hz, 2H), 7.66-7.53 (m, 1H), 7.51-7.40 (m, 2H), 4.94-4.73 (m, 1H), 4.10-3.94 (m, 2H), 3.21-2.99 (m, 1H), 2.89-2.58 (m, br, 1H), 2.22-2.03 (m, 1H), 1.99-1.86 (m, 1H), 1.69-1.60 (m, 1H), 1.50 (s, 9H), 1.01 (d, J=6.6 Hz, 3H).

Intermediate 60

(+/−) tert-butyl trans-4-hydroxy-3-methylpiperidine-1-carboxylate

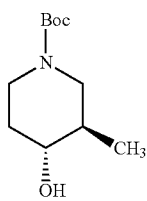

(I-60)

To a solution of (+/−) tert-butyl trans-4-(benzoyloxy)-3-methylpiperidine-1-carboxylate (0.761 g, 2.383 mmol) in MeOH (10 mL), sodium hydroxide (0.476 g, 11.91 mmol)

was added and the reaction mixture was stirred at room temperature for 2 h. The mixture was then concentrated under reduced pressure and the residue was partitioned between ethyl acetate and water. The organic layer was then separated, washed sequentially with water and brine, then dried over MgSO$_4$, filtered and evaporated under vacuum to give the product as a viscous, colorless oil, (446 mg, 2.072 mmol, 87% yield). $^1$H NMR (500 MHz, CHLOROFORM-d) δ 4.16-3.88 (m, 2H), 3.37-3.19 (m, 1H), 2.93-2.75 (m, 1H), 2.67-2.34 (m, br, 1H), 2.00-1.84 (m, 1H), 1.55-1.40 (m, 11H), 1.02 (d, J=6.6 Hz, 3H).

Intermediate 61

(+/−) trans-3-methylpiperidin-4-ol

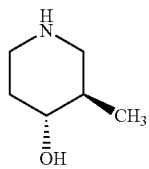
(I-61)

To a solution of (+/−) tert-butyl trans-4-hydroxy-3-methylpiperidine-1-carboxylate (440 mg, 2.044 mmol) in DCM (3 mL), TFA (1 mL, 12.98 mmol) was added and the reaction mixture was stirred at room temperature overnight. The mixture was concentrated in vacuo to give the TFA salt of the title compound as a colorless, viscous oil.

Intermediate 62

(+/−) 8-(trans-4-hydroxy-3-methylpiperidin-1-yl)-5-methyl-6-oxo-5,6-dihydro-1,5-naphthyridine-2-carbonitrile

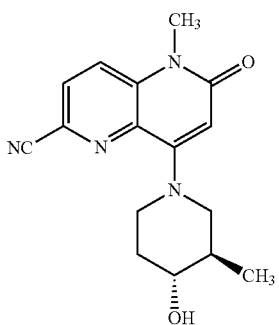
(I-62)

(+/−) trans-3-methylpiperidin-4-ol, trifluoroacetate (468 mg, 2.044 mmol) was added to a solution of 6-cyano-1-methyl-2-oxo-1,2-dihydro-1,5-naphthyridin-4-yl trifluoromethanesulfonate (487 mg, 1.460 mmol) and Hunig's base (1.275 mL, 7.30 mmol) in DMF (5 mL). The reaction mixture was heated at 85° C. overnight. The mixture was diluted with water and a yellow solid separated that was collected by filtration and dried under vacuum to give the product as a solid, (385 mg, 1.290 mmol, 88% yield). LCMS: (m/z): (M+H)$^+$=299. $^1$H NMR (500 MHz, DMSO-d$_6$) δ 8.16 (d, J=8.9 Hz, 1H), 8.07 (d, J=8.9 Hz, 1H), 6.07 (s, 1H), 4.72 (d, J=5.5 Hz, 1H), 4.08-3.96 (m, 1H), 3.94-3.85 (m, 1H), 3.53 (s, 3H), 3.25-3.14 (m, 1H), 3.00-2.88 (m, 1H), 2.72-2.62 (m, 1H), 1.97-1.83 (m, 1H), 1.70-1.49 (m, 2H), 0.98 (d, J=6.6 Hz, 3H).

Intermediate 63

6-cyano-1-methyl-4-(5-methyl-3,6-dihydropyridin-1(2H)-yl)-1,5-naphthyridin-2(1H)-one

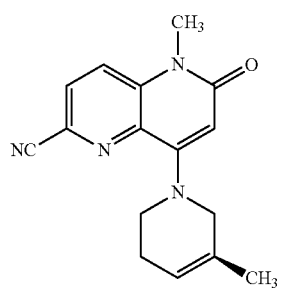
(I-63)

A dry 20 mL scintillation vial fitted with a septum was charged with triphenylphosphane (polymer supported) 3 mmol/g (2.212 mL, 0.664 mmol) and then evacuated and flushed with nitrogen. THF (2 mL) was then added, followed after ~1 min. by 4-(trifluoromethoxy)phenol (0.039 mL, 0.302 mmol). The resultant mixture was mixed briefly, after which a solution of di-tert-butyl (E)-diazene-1,2-dicarboxylate (111 mg, 0.483 mmol) in THF (1 mL) was added via syringe in a single portion. The mixture was agitated on an orbital shaker for 3 min., after which a solution of 8-(trans-4-hydroxy-3-methylpiperidin-1-yl)-5-methyl-6-oxo-5,6-dihydro-1,5-naphthyridine-2-carbonitrile (90 mg, 0.302 mmol)) in THF (2 mL) was added in a single portion. The vial was then shaken at room temperature overnight. The reaction mixture was subsequently filtered and evaporated to dryness. The residue was dissolved in 2 mL of DMF and the resultant solution fractionated via preparative LC/MS with the following conditions: Column: XBridge C18, 200 mm×19 mm, 5-μm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 31% B, 31-71% B over 25 minutes, then a 5-minute hold at 100% B; Flow Rate: 20 mL/min; Column Temperature: 25° C. Fraction collection was triggered by UV signals. Fractions containing the product were combined and dried via centrifugal evaporation. The yield of the product was 32.9 mg, and its estimated purity by LCMS analysis was 100%. Analytical LC/MS was used to determine purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min; Detection: MS and UV (220 nm). Injection 1 results: Purity: 100.0%; Observed Mass: 281.11; Retention Time: 1.86 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100%

B; Flow: 1 mL/min; Detection: MS and UV (220 nm). Injection 2 results: Purity: 100.0%; Observed Mass: 281.11; Retention Time: 1.69 min. $^1$H NMR (500 MHz, DMSO-$d_6$) δ 8.19-8.12 (m, 1H), 8.10-8.02 (m, 1H), 6.08-6.02 (m, 1H), 5.65-5.56 (m, 1H), 3.77-3.73 (m, 2H), 3.69-3.64 (m, 2H), 3.56-3.51 (m, 2H), 2.32-2.22 (m, 2H), 1.76-1.66 (m, 3H).

Intermediate 64

(+/−) tert-butyl cis-3-ethyl-4-hydroxypiperidine-1-carboxylate

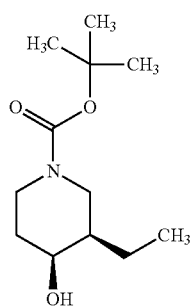

(I-64)

A 1 M solution of L-Selectride (16.50 mL, 16.50 mmol) in THF was added dropwise to a solution of tert-butyl 3-ethyl-4-oxopiperidine-1-carboxylate (2.5 g, 11.00 mmol) in THF (10 mL) at −78° C. The reaction mixture was stirred under nitrogen for 2 h., followed by the sequential addition of EtOH (2 mL), water (5 mL) and 1 M NaOH solution (5 mL) at the same temperature. The reaction mixture was then warmed to 0° C. and 30% aq. $H_2O_2$ (5 mL) was added dropwise. The cold bath was removed and the reaction mixture was stirred at room temperature for 2 h after which it was diluted with EtOAc. An insoluble white solid precipitated which was removed by filtration. The filtrate was collected, washed sequentially with saturated $NaHCO_3$ solution and brine, and then dried over $MgSO_4$, filtered and evaporated under reduced pressure to give a colorless, viscous oil. This mixture was fractionated using flash chromatography on silica gel using 10-30% EtOAc in Hexanes as eluent. Homogeneous fractions were collected and evaporated in vacuo to give the product as a colorless oil, (1.6 g, 6.98 mmol, 63.4% yield). LCMS: (M-(t-Bu)+ACN+H)$^+$= 215.35. $^1$H NMR (500 MHz, CHLOROFORM-d). All signals were very broad.

Intermediate 65

(+/−) cis-3-ethylpiperidin-4-ol, TFA Salt

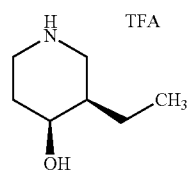

(I-65)

TFA (2 mL, 26.0 mmol) was added to a solution of tert-butyl cis-3-ethyl-4-hydroxypiperidine-1-carboxylate (1.6 g, 6.98 mmol) in DCM (5 mL). The reaction mixture was stirred at room temperature overnight, after which it was concentrated under reduced pressure to afford the product as a viscous, pale-yellow oil, TFA salt (1.65 g, 6.78 mmol, 97% yield). $^1$H NMR (500 MHz, CHLOROFORM-d) δ 9.03-8.82 (m, 1H), 8.82-8.60 (m, 1H), 4.19-4.02 (m, 1H), 3.38-3.20 (m, 2H), 3.17-2.99 (m, 2H), 2.08-1.97 (m, 2H), 1.90-1.80 (m, 1H), 1.52-1.40 (m, 1H), 1.40-1.29 (m, 1H), 1.02-0.94 (m, 3H).

Intermediate 66

(+/−) tert-butyl trans-4-(benzoyloxy)-3-ethylpiperidine-1-carboxylate

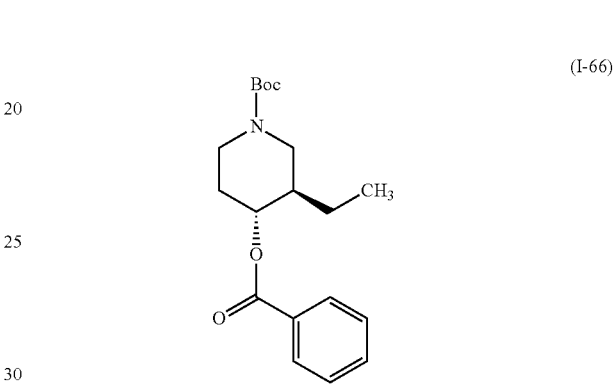

(I-66)

To a solution of (+/−) tert-butyl cis-3-ethyl-4-hydroxypiperidine-1-carboxylate (1.5 g, 6.54 mmol) in THF (10 mL), triphenylphosphine (2.402 g, 9.16 mmol) and benzoic acid (1.118 g, 9.16 mmol) were added. Di-tert-butyl (E)-diazene-1,2-dicarboxylate (2.109 g, 9.16 mmol) was added in portions at 0° C. The reaction mixture was warmed to room temperature and stirred under nitrogen overnight. The reaction mixture was then concentrated under reduced pressure and the residue purified by flash chromatography using ethyl acetate in hexanes (0-20%) as eluent. Homogeneous fractions were combined and evaporated under vacuum to give the product as a viscous, colorless oil, (1.70 g, 5.10 mmol, 78% yield).

Intermediate 67

(+/−) tert-butyl trans-3-ethyl-4-hydroxypiperidine-1-carboxylate

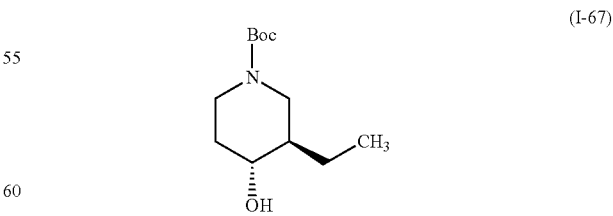

(I-67)

To a solution of (+/−) tert-butyl trans-4-(benzoyloxy)-3-ethylpiperidine-1-carboxylate (1.7 g, 5.10 mmol) in MeOH (15 mL), sodium hydroxide (1.020 g, 25.5 mmol) was added. The reaction mixture was stirred at room temperature for 3 h. The mixture was then concentrated under reduced pressure and the residue was partitioned between ethyl acetate and water. The organic layer was then separated, washed sequentially with water and brine, then dried over MgSO$_4$, filtered and evaporated under vacuum to give the crude product as a viscous oil. The mixture was fractionated using flash chromatography on silica gel using 10-30% ethyl acetate in hexanes as eluent. Homogeneous fractions were combined and evaporated under reduced pressure to afford tert-butyl trans-3-ethyl-4-hydroxypiperidine-1-carboxylate (0.68 g, 2.97 mmol, 58.2% yield) as a viscous colorless oil. $^1$H NMR (500 MHz, CHLOROFORM-d) δ 3.95 (br d, J=12.6 Hz, 1H), 3.46 (br d, J=0.9 Hz, 1H), 3.05-2.87 (m, 1H), 1.97-1.87 (m, 1H), 1.75 (br d, J=1.6 Hz, 1H), 1.51-1.40 (m, 11H), 1.40-1.30 (m, 1H), 1.25-1.15 (m, 1H), 0.99 (t, J=7.4 Hz, 3H). Spectrum was broad and could not be fully assigned.

Intermediate 68

(+/−) trans-3-ethylpiperidin-4-ol, TFA

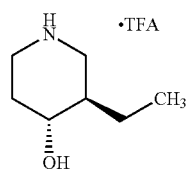

(I-68)

To a solution of (+/−) tert-butyl trans-3-ethyl-4-hydroxypiperidine-1-carboxylate (0.3 g, 1.308 mmol) in dichloromethane (3 mL), 1 mL TFA was added. The reaction mixture was stirred at room temperature for 3 h. The mixture was concentrated in vacuo.

Intermediate 69

(+/−) 8-(cis-3-ethyl-4-hydroxypiperidin-1-yl)-5-methyl-6-oxo-5,6-dihydro-1,5-naphthyridine-2-carbonitrile

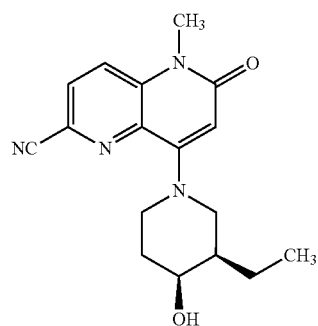

(I-69)

(+/−) cis-3-ethylpiperidin-4-ol TFA salt (1.2 g, 4.93 mmol) was added to a solution of 6-cyano-1-methyl-2-oxo-1,2-dihydro-1,5-naphthyridin-4-yl trifluoromethanesulfonate (1.370 g, 4.11 mmol) and Hunig's base (2.87 mL, 16.45 mmol) in DMF (8 mL). The reaction mixture was heated at 85° C. overnight under nitrogen. The resultant mixture was diluted with water and then extracted with ethyl acetate. The organic layers were combined, washed with brine and then dried over MgSO$_4$, filtered and evaporated under reduced pressure to give the crude product as an orange-colored solid. The product was triturated with methanol and the residual solid was collected by filtration, and air dried to give the product as a light-yellow colored solid (520 mg, 1.665 mmol, 40.5% yield). A portion of the filtrate was then purified under the following conditions: Column: XBridge C18, 200 mm×19 mm, 5-µm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 10% B, 10-50% B over 22 minutes, then a 4-minute hold at 100% B; Flow Rate: 20 mL/min; Column Temperature: 25° C. Fraction collection was triggered by MS and UV signals. Fractions containing the product were combined and dried via centrifugal evaporation. Analytical LC/MS was used to determine the final purity. Injection 1 conditions: Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min; Detection: MS and UV (220 nm). Injection 1 results: Purity: 98.5%; Observed Mass: 313.15; Retention Time: 1.17 min. Injection 2 conditions: Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). Injection 2 results: Purity: 99.3%; Observed Mass: 313.13; Retention Time: 1.22 min. $^1$H NMR (500 MHz, DMSO-d$_6$) δ 8.17-8.10 (m, 1H), 8.10-8.02 (m, 1H), 6.11-6.01 (m, 1H), 4.70-4.62 (m, 1H), 3.91-3.84 (m, 1H), 3.75-3.66 (m, 1H), 3.31-3.22 (m, 1H), 3.14-3.05 (m, 1H), 1.87-1.71 (m, 2H), 1.71-1.60 (m, 1H), 1.49-1.36 (m, 1H), 1.34-1.21 (m, 1H), 1.00-0.86 (m, 3H). The complete spectrum was not fully assigned due to the water suppression technique used.

Intermediate 70

4-(3-chlorophenoxy)piperidine

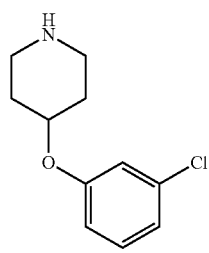

(70)

Triphenylphosphine (156 mg, 0.596 mmol) was added to a solution of tert-butyl 4-hydroxypiperidine-1-carboxylate (100 mg, 0.497 mmol) and 3-chlorophenol (63.9 mg, 0.497 mmol) in THF (5 mL). The reaction mixture was stirred at 0° C. for 15 min after which DIAD (0.116 mL, 0.596 mmol) was added dropwise. The reaction mixture was then warmed to room temperature and stirred under nitrogen overnight. The reaction was quenched by the addition of water and the resultant mixture was extracted with ethyl acetate (2×20 mL). The organic layers were combined, dried (MgSO$_4$), filtered and concentrated in vacuo to give the crude product as a yellow solid. This material was dissolved in DCM (5 mL) and 3 mL of TFA was added. The mixture was stirred at room temperature for 2 h and was then concentrated to give a yellow viscous oil. The mixture was purified using reverse phase preparative HPLC using a CH$_3$OH—H$_2$O-TFA buffer system. Homogeneous fractions were combined and evaporated under reduced pressure to give the TFA salt of the title compound as a white solid (101.5 mg, 0.312 mmol, 62.7% yield). LCMS: (m/z): (M+H)$^+$=212.0. $^1$H NMR (400 MHz, METHANOL-d$_4$) δ 7.30 (t, J=8.2 Hz, 1H), 7.08-7.06 (m, 1H), 7.03-6.99 (m, 1H), 6.98-6.94 (m, 1H), 4.96-4.87 (m, 1H), 4.79-4.66 (m, 1H), 3.48-3.37 (m, 2H), 3.28-3.15 (m, 2H), 2.25-2.11 (m, 2H), 2.11-1.96 (m, 2H).

Intermediate 71

4-(3-fluoro-5-methylphenoxy)piperidine

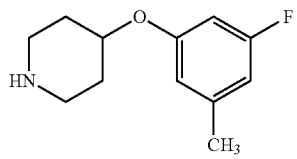

(I-71)

Triphenylphosphine on solid support (3 mmol/g) (289 mg, 1.1 mmol) was added to a dried 20 mL scintillation vial that was then capped and flushed with nitrogen. The resin was suspended in DCM (3 mL) and the reaction vial was placed on an orbital shaker for 2 min. 3-Fluoro-5-methylphenol (0.081 mL, 0.745 mmol) was then added in a single portion and the mixture further agitated briefly, after which di-tert-butyl (E)-diazene-1,2-dicarboxylate (183 mg, 0.795 mmol) was added. The mixture was then shaken for a further 3 min, and tert-butyl 4-hydroxypiperidine-1-carboxylate (100 mg, 0.497 mmol) was then, and the resultant mixture was agitated at room temperature overnight. The suspension was filtered, and the resin was washed with DCM. The washings and the filtrates were combined and evaporated under reduced pressure. The residue was treated with 6 mL of a mixture of DCM and TFA, 1:1 for 30 min, and the ensuing mixture was evaporated to dryness. The residue was dissolved in DCM and 5 N NaOH solution was added. The mixture was extracted using DCM. The extracts were combined, dried over MgSO$_4$, filtered and concentrated in vacuo to give the product as a colorless oil (63 mg, 61%). LCMS: (m/z): (M+H)$^+$=210.10.

Intermediate 72

(+/−) cis-3-methyl-4-(4-(trifluoromethyl)phenoxy)piperidine, TFA

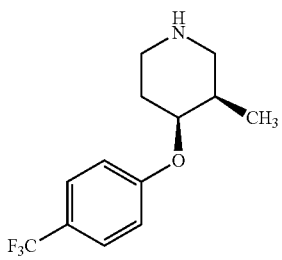

(I-72)

To a solution of tert-butyl cis-4-hydroxy-3-methylpiperidine-1-carboxylate (100 mg, 0.464 mmol) in THF (2 mL), 1.0 M solution of potassium bis(trimethylsilyl)amide (1.161 mL, 1.161 mmol) in THF was added. The reaction mixture was stirred at room temperature for 30 min, then 1-fluoro-4-(trifluoromethyl)benzene (114 mg, 0.697 mmol) in THF (1 mL) was added. The reaction mixture was then heated at 60° C. for 4 h. The reaction was then quenched with water. The resultant mixture was extracted with ethyl acetate. The organic layer was separated, washed with brine, dried over MgSO$_4$, filtered and evaporated under reduced pressure to give an oil. The product was fractionated using preparative HPLC using a CH$_3$CN—H$_2$O-TFA system as eluent. Homogeneous fractions were combined and concentrated under reduced pressure for 24 h. The residue was dissolved in DCM (3 mL) and 1 mL TFA was added. The reaction mixture was stirred at room temperature overnight, and then concentrated under vacuum to give the TFA salt of the title compound as a white solid (120 mg, 0.321 mmol, 69.2% yield). LCMS: (m/z): (M+H)$^+$=260. $^1$H NMR (CD$_3$OD): $^1$H NMR (500 MHz, METHANOL-d$_4$) δ 7.63 (br d, J=8.5 Hz, 2H), 7.19 (d, J=8.5 Hz, 2H), 4.77-4.73 (m, 1H), 3.28-3.12 (m, 4H), 2.33-2.18 (m, 2H), 2.08-1.93 (m, 1H), 1.11 (d, J=6.9 Hz, 3H).

The following method (Method A) was used to prepare a number of the following examples of the current invention.

Example 1

6-fluoro-4-(4-(3-fluoro-5-methylphenoxy)piperidin-1-yl)-1-methyl-3-nitroquinolin-2(1H)-one

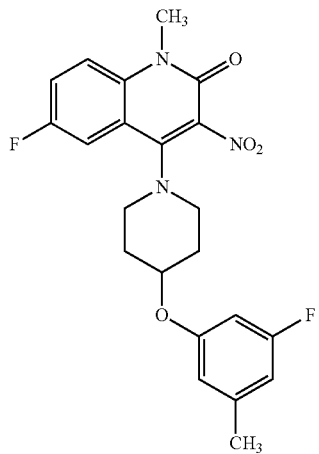

(1)

4-(3-Fluoro-5-methylphenoxy)piperidine (20 mg, 0.096 mmol) was added to a solution of 4-chloro-6-fluoro-1-methyl-3-nitroquinolin-2(1H)-one (20.44 mg, 0.080 mmol) and Hunig's Base (0.028 mL, 0.159 mmol) in DMF and the resultant mixture was stirred at room temperature overnight. The crude reaction mixture was then filtered, subsequently purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 41-81% B over 25 minutes, then a 6-minute hold at 100% B; Flow: 20 mL/min. Fractions containing the product were combined and dried via centrifugal evaporation. The yield of the product was 22.1 mg, and its estimated purity by LCMS analysis was 100%. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 429.94; Retention Time: 2.34 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 429.95; Retention Time: 2.33 min. $^1$H NMR (500 MHz, DMSO-$d_6$) δ 7.76-7.57 (m, 3H), 6.75-6.62 (m, 2H), 6.64-6.55 (m, 1H), 4.68 (dt, J=7.7, 3.9 Hz, 1H), 3.66 (s, 3H), 3.45-3.31 (m, 2H), 2.30 (s, 3H), 2.22-2.10 (m, 2H), 1.97-1.81 (m, 2H). A full assignment of all peaks in the spectrum was not accomplished due to the water suppression technique employed in the NMR experiment.

The following examples were prepared according to Method B.

Example 2

6-fluoro-4-(4-(4-isopropylphenoxy)piperidin-1-yl)-1-methyl-3-nitroquinolin-2(1H)-one

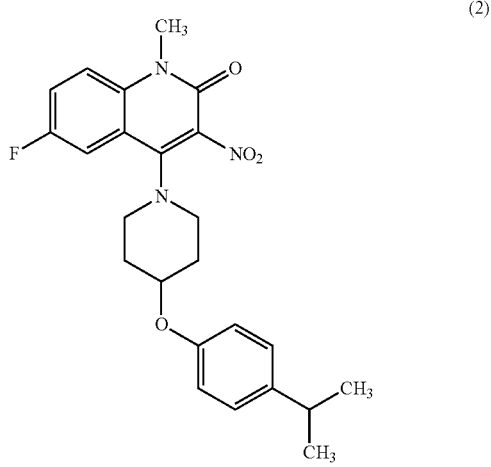 [SMILES: CC(C)c1ccc(OC2CCN(c3c([N+](=O)[O-])c(=O)n(C)c4ccc(F)cc34)CC2)cc1]

(2)

Triphenylphosphane on solid support 3 mmol/g (82.0 mg, 0.313 mmol) was added to a dried 20 mL scintillation vial. The resin was suspended in anhydrous DCM (3 mL) for a period of 2 min under nitrogen. 4-Isopropylphenol (12.72 mg, 0.093 mmol) was the added, followed after 5 min by the addition of di-tert-butyl (E)-diazene-1,2-dicarboxylate (22.93 mg, 0.100 mmol). The resultant suspension was agitated on an orbital shaker for 3 min., and 6-fluoro-4-(4-hydroxypiperidin-1-yl)-1-methyl-3-nitroquinolin-2(1H)-one (20 mg, 0.062 mmol) was added in a single portion. Shaking was continued at room temperature overnight. The reaction mixture was then concentrated in vacuo, and the residue triturated with 2 mL of DMF. The suspension was then filtered and the crude product fractionated using preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 53-93% B over 20 minutes, then a 6-minute hold at 100% B; Flow: 20 mL/min. Fractions containing the product were combined and dried via centrifugal evaporation. The yield of the product was 8.8 mg, and its estimated purity by LCMS analysis was 100%. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 440.16; Retention Time: 2.56 min. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 440.18; Retention Time: 2.54 min. $^1$H NMR (600 MHz, DMSO-$d_6$) δ 7.74-7.67 (m, 2H), 7.63 (dd, J=9.4, 2.0 Hz, 1H), 7.16 (br d, J=8.4 Hz, 2H), 6.93 (br d, J=8.8 Hz, 2H), 4.62 (br s, 1H), 3.64 (s, 3H), 3.14-3.07 (m, 1H), 2.87-2.77 (m, 1H), 2.19-2.07 (m, 2H), 1.93-1.83 (m, 2H), 1.17 (d, J=7.0 Hz, 6H). Some peaks associated with the piperazine ring were obscured by the water suppression techniques used in the acquisition of the spectrum.

In similar fashions, the following examples were prepared.

TABLE 2

| Ex. No. | Ar Structure | Stereo. Chem. | LCMS Method | LCMS RT | (m/z): (M + H)$^+$ | Synth. Method |
|---|---|---|---|---|---|---|
| 3 | ![p-OCF3 phenyl] | A | 1 | 2.40 | 482.0 | B |
| 4 | ![m-methylphenyl] | A | 1 | 2.34 | 412.1 | B |

TABLE 2-continued

| Ex. No. | Ar Structure | Stereo. Chem. | LCMS Method | LCMS RT | (m/z): (M + H)+ | Synth. Method |
|---|---|---|---|---|---|---|
| 5 | 4-(1H-indazolyl) | A | 1 | 1.76 | 438.1 | B |
| 6 | 3-cyanophenyl | A | 1 | 2.10 | 423.1 | B |
| 7 | 3-chlorophenyl | A | 1 | 2.39 | 432.1 | B |
| 8 | 2-OCH3-5-CF3-phenyl | A | 1 | 2.32 | 496.1 | B |
| 9 | 3-fluorophenyl | A | 1 | 2.26 | 416.1 | B |

Method A was used to prepare a number of the following examples.

Example 10

6-chloro-4-(4-(3-methoxyphenoxy)piperidin-1-yl)-1-methyl-2-oxo-1,2-dihydro-1,5-naphthyridine-3-carbonitrile

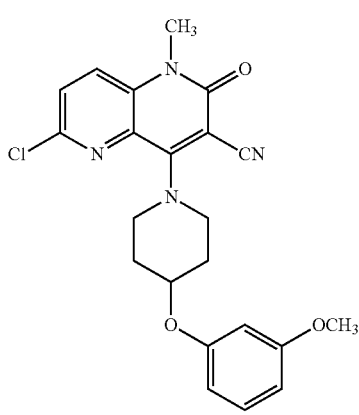

(10)

To a solution of 4,6-dichloro-1-methyl-2-oxo-1,2-dihydro-1,5-naphthyridine-3-carbonitrile hydrochloride (15 mg, 0.052 mmol) in DMF (1.5 mL), 4-(3-methoxyphenoxy)piperidine hydrochloride (13.84 mg, 0.057 mmol) and triethylamine (0.036 mL, 0.258 mmol) were added. The reaction mixture was stirred at room temperature for 2 h. It was then diluted with methanol (2 mL), filtered and the crude mixture was purified via preparative LC/MS with the following conditions: Column: XBridge C18, 19×200 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 38-78% B over 20 minutes, then a 4-minute hold at 100% B; Flow: 20 mL/min. Fractions containing the product were combined and dried via centrifugal evaporation. The yield of the product was 16.5 mg, and its estimated purity by LCMS analysis was 100%. Analytical LC/MS was used to determine the final purity. Injection 1 conditions: Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 425.06; Retention Time: 2.05 min. Injection 2 conditions: Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 425.1; Retention Time: 2.09 min. $^1$H NMR (600 MHz, DMSO-$d_6$) δ 8.07 (br d, J=8.8 Hz, 1H), 7.81 (br d, J=8.8 Hz, 1H), 7.20 (t, J=8.3 Hz, 1H), 6.65-6.49 (m, 3H), 4.78 (dt, J=7.4, 3.8 Hz, 1H), 4.09-3.97 (m, 2H), 3.77-3.69 (m, 4H), 2.19 (td, J=6.1, 2.9 Hz, 2H), 1.99-1.79 (m, 2H). The full spectrum was not assigned due to the water suppression technique used in the acquisition of the spectrum.

The following method (Method B) was used to prepare a number of the following examples of the current invention.

Example 11

6-chloro-1-methyl-2-oxo-4-(4-(2-(trifluoromethyl)phenoxy)piperidin-1-yl)-1,2-dihydro-1,5-naphthyridine-3-carbonitrile

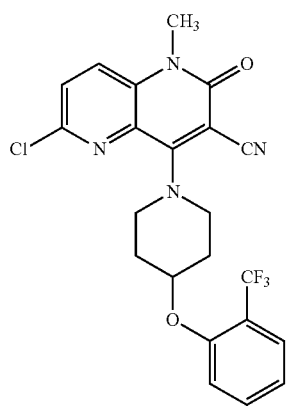

(11)

To a solution of 2-(trifluoromethyl)phenol (30.5 mg, 0.188 mmol) in DCM (2 mL), triphenylphosphane (49.4 mg, 0.188 mmol) was added. The mixture was stirred at room temperature for 5 min, then 6-chloro-4-(4-hydroxypiperidin-1-yl)-1-methyl-2-oxo-1,2-dihydro-1,5-naphthyridine-3-carbonitrile (15 mg, 0.047 mmol) was added and the reaction mixture was stirred for 15 min before DIAD (0.037 mL, 0.188 mmol) was added in a single portion. The resultant mixture was stirred at room temperature under nitrogen overnight. It was then concentrated in vacuo, and the residue dissolve in a 1:1 mixture of CAN and DMF (1.8 mL). This crude mixture was then purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 41-81% B over 20 minutes, then a 5-minute hold at 100% B; Flow: 20 mL/min. Fractions containing the product were combined and dried via centrifugal evaporation. The yield of the product was 8.0 mg, and its estimated purity by LCMS analysis was 100%. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 463.02; Retention Time: 2.20 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 463.01; Retention Time: 2.24 min. $^1$H NMR (500 MHz, DMSO-$d_6$) δ 8.08 (d, J=8.8 Hz, 1H), 7.82 (d, J=8.9 Hz, 1H), 7.65 (br d, J=7.0 Hz, 2H), 7.42 (br d, J=8.5 Hz, 1H), 7.11 (t, J=7.6 Hz, 1H), 5.03 (br s, 1H), 4.01-3.94 (m, 2H), 3.86-3.79 (m, 2H), 3.54 (s, 3H), 2.24 (br d, J=12.2 Hz, 2H), 1.96 (br d, J=6.4 Hz, 2H).

In a similar fashion to the preceding two methods, the following examples can be prepared.

TABLE 3

| Ex. No. | Ar Structure | Stereo. Chem. | LCMS Method | LCMS RT | (m/z): (M + H)+ | Method |
|---|---|---|---|---|---|---|
| 12 | 3,4-difluorophenyl | A | 1 | 2.14 | 431.1 | B |
| 13 | 3-OCF$_3$ phenyl | A | 1 | 2.31 | 479.0 | B |
| 14 | 4-OCH$_3$ phenyl | A | 1 | 2.00 | 425.1 | B |

TABLE 3-continued
| Ex. No. | Ar Structure | Stereo. Chem. | LCMS Method | LCMS RT | (m/z): (M + H)+ | Method |
|---|---|---|---|---|---|---|
| 15 | 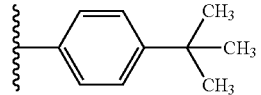 | A | 1 | 2.53 | 451.0 | A |
| 16 |  | A | 2 | 4.22 | 428.9 | A |
| 17 | 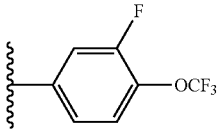 [SMILES: *c1ccc(OC(F)(F)F)c(F)c1] | A | 1 | 2.38 | 497.1 | B |
| 18 | 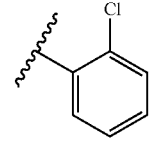 [SMILES: *c1ccccc1Cl] | A | 1 | 2.16 | 429.1 | A |
| 19 | 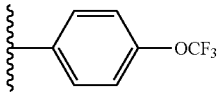 | A | 1 | 2.30 | 478.9 | A |
| 20 | 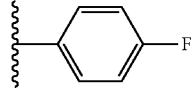 | A | 1 | 2.10 | 413.1 | B |
| 21 | 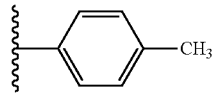 [SMILES: *c1ccc(C)cc1] | A | 2 | 4.11 | 408.9 | A |
| 22 | 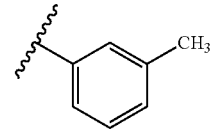 [SMILES: *c1cccc(C)c1] | A | 1 | 2.21 | 409.1 | B |
| 23 | 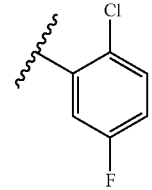 [SMILES: *c1cc(F)ccc1Cl] | A | 2 | 4.12 | 446.9 | A |
| 24 | 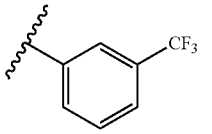 | A | 1 | 2.30 | 463.1 | B |
| 25 | 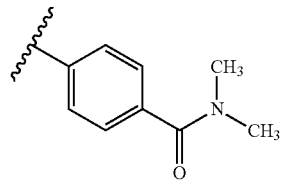 [SMILES: *c1ccc(C(=O)N(C)C)cc1] | A | 1 | 1.65 | 466.1 | B |

TABLE 3-continued

| Ex. No. | Ar Structure | Stereo. Chem. | LCMS Method | LCMS RT | (m/z): (M + H)+ | Method |
|---|---|---|---|---|---|---|
| 26 | 2-CH3, 4-Br phenyl | A | 1 | 2.43 | 487.0 | A |
| 27 | 3-Cl phenyl | A | 1 | 2.26 | 428.9 | A |
| 28 | 3-CH3, 5-F phenyl | A | 2 | 4.17 | 426.9 | A |
| 29 | 2-CH3, 4-OCF3 phenyl | A | 1 | 2.47 | 493.1 | B |
| 30 | 4-CF3 phenyl | A | 1 | 2.32 | 463.1 | B |
| 31 | 4-OC(CH3)3 phenyl | A | 1 | 2.31 | 467.1 | B |
| 32 | 4-CN phenyl | A | 1 | 1.93 | 420.1 | B |
| 33 | 2-OCF3 phenyl | A | 1 | 2.27 | 479.1 | B |
| 34 | 3-CN phenyl | A | 1 | 1.97 | 420.1 | B |
| 35 | 2-OCH3 phenyl | A | 1 | 1.98 | 425.1 | B |

TABLE 3-continued

| Ex. No. | Ar Structure | Stereo. Chem. | LCMS Method | LCMS RT | (m/z): (M + H)+ | Method |
|---|---|---|---|---|---|---|
| 36 | 2-OCH3, 5-F phenyl | A | 1 | 1.95 | 443.0 | B |
| 37 | 4-isopropyl phenyl | A | 1 | 2.47 | 437.1 | B |
| 38 | 3-Cl, 4-CN phenyl | A | 1 | 2.16 | 454.0 | B |
| 39 | 3-OCH3, 4-Cl phenyl | A | 1 | 2.27 | 459.1 | B |
| 40 | 3-Cl, 4-CH3 phenyl | A | 1 | 2.49 | 443.1 | B |
| 41 | 2-Cl, 4-OCF3 phenyl | A | 1 | 2.46 | 513.1 | B |
| 42 | 3-Cl, 4-OCF3 phenyl | A | 1 | 2.49 | 513.0 | B |
| 43 | 2-CN phenyl | A | 1 | 1.86 | 420.0 | B |
| 44 | 2-F phenyl | A | 1 | 2.07 | 413.1 | B |
| 45 | 3-F phenyl | A | 1 | 2.08 | 413.1 | B |

TABLE 3-continued

| Ex. No. | Ar Structure | Stereo. Chem. | LCMS Method | LCMS RT | (m/z): (M + H)+ | Method |
|---|---|---|---|---|---|---|
| 46 | ![phenyl] | A | 1 | 2.07 | 395.1 | B |

Example 47

6-Bromo-1-methyl-2-oxo-4-(4-(4-(trifluoromethoxy)phenoxy)piperidin-1-yl)-1,2-dihydro-1,5-naphthyridine-3-carbonitrile

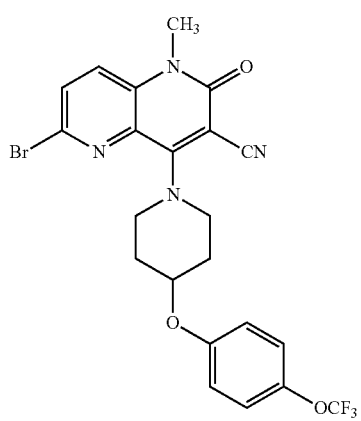

(47)

To a solution of 6-bromo-4-chloro-1-methyl-2-oxo-1,2-dihydro-1,5-naphthyridine-3-carbonitrile (50 mg, 0.167 mmol) in DMF (4 mL), 4-(4-(trifluoromethoxy)phenoxy)piperidine (48.1 mg, 0.184 mmol) and triethylamine (0.093 mL, 0.670 mmol) were added. The reaction mixture was stirred at room temperature for 2 h and was then quenched by the addition of water. A white colored solid separated and was collected by filtration, 85 mg. 20 mg of this material was dissolved in a 1:1 mixture of DMF and methanol, and this solution was purified via preparative LC/MS with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 41-81% B over 15 minutes, then a 5-minute hold at 100% B; Flow: 20 mL/min. Fractions containing the product were combined and dried via centrifugal evaporation. The yield of the product was 9.5 mg, and its estimated purity by LCMS analysis was 99%. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 98.7%; Observed Mass: 523.02; Retention Time: 2.34 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 98.8%; Observed Mass: 523.03; Retention Time: 2.36 min. $^1$H NMR (500 MHz, DMSO-$d_6$) δ 7.97-7.92 (m, 1H), 7.91-7.87 (m, 1H), 7.30 (br d, J=8.5 Hz, 2H), 7.14 (br d, J=8.9 Hz, 2H), 4.80 (br d, J=3.4 Hz, 1H), 4.12-3.99 (m, 2H), 3.72 (br t, J=10.1 Hz, 1H), 2.19 (br s, 2H), 1.95-1.80 (m, 2H). The full spectrum was not assigned due to the water suppression technique used in the acquisition of the spectrum.

Example 48

6-methoxy-1-methyl-2-oxo-4-(4-(4-(trifluoromethoxy)phenoxy)piperidin-1-yl)-1,2-dihydro-1,5-naphthyridine-3-carbonitrile

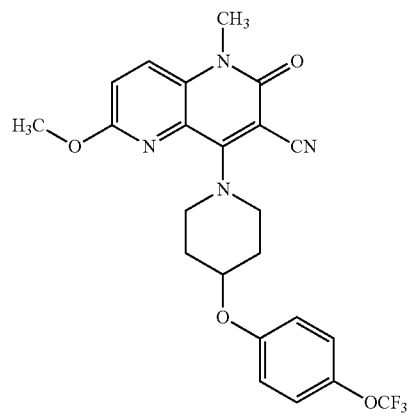

(48)

6-Bromo-1-methyl-2-oxo-4-(4-(4-(trifluoromethoxy)phenoxy)piperidin-1-yl)-1,2-dihydro-1,5-naphthyridine-3-carbonitrile (30 mg, 0.057 mmol), 5-[di(1-adamantyl)phosphino]-1',3',5'-triphenyl-1'h-[1,4']bipyrazole (3.80 mg, 5.73 μmol), cesium carbonate (18.68 mg, 0.057 mmol) and Pd(OAc)$_2$ (0.644 mg, 2.87 μmol) were loaded into a dry vial that was subsequently sealed, evacuated and flushed with nitrogen. Acetonitrile (2 mL) and methanol (0.1 mL) were then added and the reaction mixture was heated at 80° C. overnight. The crude material was purified via preparative LC/MS with the following conditions: Column: XBridge C18, 200 mm×19 mm, 5-μm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 41% B, 41-81% B over 25 minutes, then a 4-minute hold at 100% B; Flow Rate: 20 mL/min; Column Temperature: 25° C. Fraction collection was triggered by MS and UV signals. Fractions containing the product were combined and dried via centrifugal evaporation. The yield of the product was 14.4 mg, and its estimated purity by LCMS analysis was 100%. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 475.04; Retention Time: 2.24 min. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 475.05; Retention Time: 2.18 min. $^1$H NMR (500 MHz, DMSO-$d_6$) δ 8.02 (br d, J=9.2 Hz, 1H), 7.31 (br d, J=8.5 Hz, 2H), 7.25 (d, J=9.2 Hz, 1H), 7.15 (br d, J=8.9 Hz, 2H), 4.78 (br s, 1H), 4.14 (br d, J=12.5 Hz, 2H), 3.92 (s, 3H), 3.79 (br t, J=9.6 Hz, 2H), 2.22 (br s, 2H), 1.91 (br d, J=8.2 Hz, 2H).

Example 50

5-methyl-6-oxo-8-(4-(4-(trifluoromethoxy)phenoxy) piperidin-1-yl)-5,6-dihydro-1,5-naphthyridine-2,7-dicarbonitrile

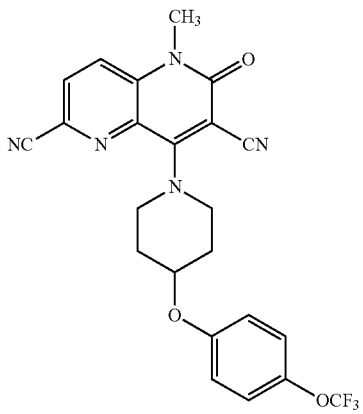

(50)

6-Bromo-1-methyl-2-oxo-4-(4-(4-(trifluoromethoxy)phenoxy)piperidin-1-yl)-1,2-dihydro-1,5-naphthyridine-3-carbonitrile (50 mg, 0.096 mmol), zinc (1.249 mg, 0.019 mmol), zinc cyanide (6.73 mg, 0.057 mmol) and 1,1'-bis(diphenylphosphino)ferrocene-palladium(II)dichloride dichloromethane complex (7.80 mg, 9.55 μmol) were loaded into a dry microwave vial that was sealed, evacuated and then flushed with nitrogen. NMP (4 mL) was added and the resultant mixture was irradiated in the microwave at 75° C. for 4.5 hr. The reaction mixture was then cooled to room temperature, diluted with acetonitrile and filtered. The filtrate was fractionated using reverse phase preparative HPLC using a $CH_3CN$—$H_2O$-TFA system. Homogeneous fractions were combined, neutralized with saturated $NaHCO_3$ solution and then concentrated in vacuo. The product was obtained as a yellow solid, (22.5 mg, 0.048 mmol, 50.2% yield). LCMS: (m/z) (method 2) RT=4.39 min. (m/z): (M+H)$^+$=470.1. $^1$H NMR (400 MHz, DMSO-$d_6$) δ 8.28 (d, J=8.8 Hz, 1H), 8.17 (d, J=8.8 Hz, 1H), 7.31 (br d, J=8.8 Hz, 2H), 7.16 (d, J=9.0 Hz, 2H), 4.83 (dt, 4.0 Hz, 1H), 4.18-4.02 (m, 2H), 3.78 (br t, J=9.5 Hz, 2H), 3.55 (s, 3H), 2.29-2.16 (m, 2H), 2.02-1.84 (m, 2H).

Example 51

5-methyl-7-nitro-6-oxo-8-(4-(4-(trifluoromethoxy) phenoxy)piperidin-1-yl)-5,6-dihydro-1,5-naphthyridine-2-carbonitrile

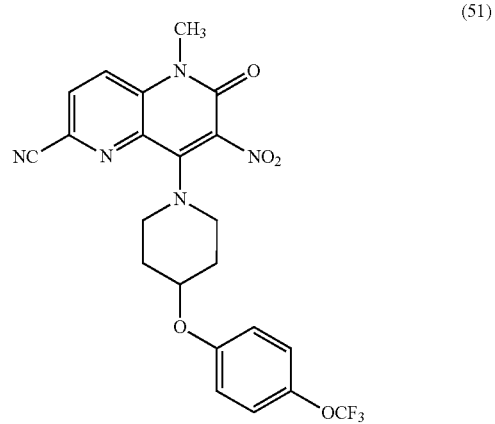 [SMILES: Cn1c(=O)c([N+](=O)[O-])c(N2CCC(Oc3ccc(OC(F)(F)F)cc3)CC2)c2nc(C#N)ccc21]

(51)

To a solution of 8-chloro-5-methyl-7-nitro-6-oxo-5,6-dihydro-1,5-naphthyridine-2-carbonitrile (15 mg, 0.057 mmol) in DMF (1.5 mL), 4-(4-(trifluoromethoxy)phenoxy) piperidine (16.29 mg, 0.062 mmol) and triethylamine (0.024 mL, 0.170 mmol) were added. The reaction mixture was stirred at room temperature for over the weekend. The resultant solution was purified via preparative HPLC with the following conditions: Column: XBridge C18, 19×200 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 38-78% B over 20 minutes, then a 4-minute hold at 100% B; Flow: 20 mL/min. Fractions containing the product were combined and dried via centrifugal evaporation. The yield of the product was 19.1 mg, and its estimated purity by LCMS analysis was 99%. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 490.09; Retention Time: 2.3 min. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 99.1%; Observed Mass: 490.1; Retention Time: 2.25 min. $^1$H NMR (500 MHz, DMSO-$d_6$) δ 8.43-8.12 (m, 1H), 7.43-7.03 (m, 2H), 4.90-4.59 (m, 1H), 3.70-3.48 (m, 2H), 2.25-2.12 (m, 1H), 1.97-1.85 (m, 1H). The full spectrum was not assigned due to the water suppression technique used in the acquisition of the spectrum.

The following method (Method A) was used to prepare a number of the following examples of the current invention.

Example 52

5-methyl-6-oxo-8-(4-(4-(trifluoromethoxy)phenoxy)piperidin-1-yl)-5,6-dihydro-1,5-naphthyridine-2-carbonitrile

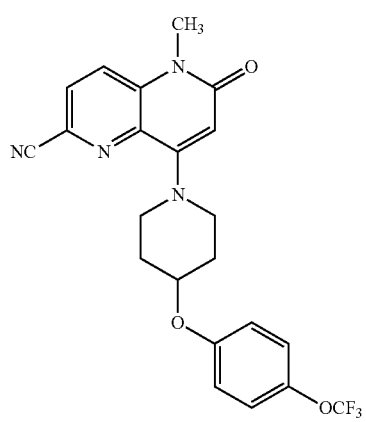

(52)

8-Chloro-5-methyl-6-oxo-5,6-dihydro-1,5-naphthyridine-2-carbonitrile (22 mg, 0.100 mmol) was dissolved in DMF (1 mL) contained in a one dram pressure vial. 4-[4-Trifluoromethoxy)phenoxy]piperidine (32 mg, 0.122 mmol) was added together with potassium carbonate (40 mg, 0.289 mmol) and the reaction vessel was evacuated, flushed with nitrogen, sealed and then heated in an oil bath at 90° C. for 5 h. The reaction mixture was allowed to cool before being diluted to a volume of 2 mL by the addition of acetonitrile and two drops of water. This mixture was filtered, and the crude solution was purified via preparative LC/MS with the following conditions: Column: XBridge C18, 200 mm×19 mm, 5-μm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 33% B, 33-73% B over 25 minutes, then a 4-minute hold at 100% B; Flow Rate: 20 mL/min; Column Temperature: 25° C. Fraction collection was triggered by MS and UV signals. Fractions containing the product were combined and dried via centrifugal evaporation. The yield of the product was 26.1 mg, and its estimated purity by LCMS analysis was 100%. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 445.12; Retention Time: 2.19 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 445.14; Retention Time: 2.12 min. $^1$H NMR (500 MHz, DMSO-$d_6$) δ 8.10-7.96 (m, 1.9H), 7.25 (br d, J=8.2 Hz, 1.9H), 7.08 (br d, J=8.9 Hz, 2.0H), 6.12 (s, 0.9H), 4.65 (br s, 0.9H), 3.75 (br d, J=7.6 Hz, 1.2H), 3.51 (s, 2.6H), 3.33 (br t, J=9.2 Hz, 1.9H), 2.09 (br s, 2.1H), 1.83-1.68 (m, 2.0H). Reported chemical shifts are uncorrected for the effects of water suppression The following method (Method B) was used to prepare a number of the following examples of the current invention.

Example 53

4-(4-(4-(tert-butyl)phenoxy)piperidin-1-yl)-1-methyl-2-oxo-1,2-dihydroquinoline-6-carbonitrile

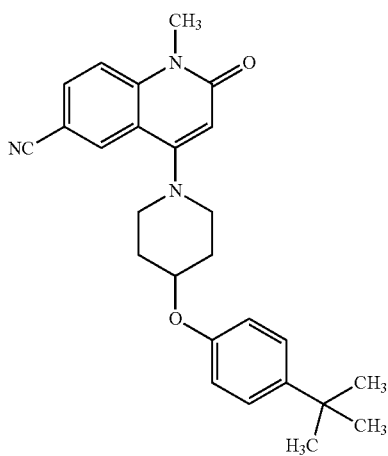

(53)

Triphenylphosphine resin (56.6 mg, 0.217 mmol) (70 mg @ ~3 mmol/g) was placed in an oven dried, vacuum cooled one dram vial, charge) and suspended in NMP (0.5 mL) under nitrogen, and the mixture was left to stand for 2 min. 4-Tert-butylphenol (23.0 mg, 0.153 mmol) and di-tert-butyl azodicarboxylate (43 mg, 0.187 mmol) were then added and the mixture was shaken for a further 5 min. A solution of 8-(4-hydroxypiperidin-1-yl)-5-methyl-6-oxo-5,6-dihydro-1,5-naphthyridine-2-carbonitrile in N-Methyl-2-pyrrolidinone (1.0 mL, 28 mg, 0.098 mmol) was added and the resultant suspension was maintained under nitrogen and agitated at room temperature overnight. The mixture was then filtered and the volume of filtrate was adjusted to 2 mL by the addition of more NMP. The crude material was purified via preparative LC/MS with the following conditions: Column: XBridge C18, 200 mm×19 mm, 5-μm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 42% B, 42-82% B over 20 minutes, then a 7-minute hold at 100% B; Flow Rate: 20 mL/min; Column Temperature: 25° C. Fraction collection was triggered by MS and UV signals. Fractions containing the product were combined and dried via centrifugal evaporation. The yield of the product was 0.6 mg and its estimated purity by LCMS analysis was 96%. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min; Detection: MS and UV (220 nm). Injection 1 results: Purity: 100.0%; Observed Mass: 417.18; Retention Time: 2.31 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). Injection 2 results: Purity: 96.4%; Observed Mass: 417.06; Retention Time: 2.27 min. $^1$H NMR (500 MHz, DMSO-d$_6$) δ 8.16 (d, J=8.9 Hz, 1.0H), 8.08 (d, J=8.9 Hz, 1.0H), 7.29 (br d, J=8.5 Hz, 1.9H), 6.92 (br d, J=8.5 Hz, 1.9H), 6.14 (s, 1.0H), 4.66-4.55 (m, 1.0H), 3.82-3.71 (m, 2.0H), 3.54 (s, 1.8H), 2.16-2.02 (m, 2.0H), 1.88-1.73 (m, 1.9H), 1.25 (s, 9.0H).

In a similar fashion, the following examples can be prepared.

TABLE 4

| Ex. No. | Ar Structure | Stereo. Chem. | LCMS Method | LCMS RT | (m/z): (M + H)⁺ | Method |
|---|---|---|---|---|---|---|
| 54 | | A | 1 | 2.51 | 431.1 | B |
| 55 | | A | 1 | 2.26 | 451.2 | B |
| 56 | | A | 1 | 2.40 | 417.1 | B |
| 57 | | A | 1 | 2.33 | 403.3 | B |
| 58 | | A | 1 | 2.54 | 429.1 | B |
| 59 | | A | 1 | 2.10 | 401.0 | B |
| 60 | | A | 1 | 2.38 | 417.0 | B |
| 61 | | A | 1 | 2.27 | 415.0 | B |

TABLE 4-continued

| Ex. No. | Ar Structure | Stereo. Chem. | LCMS Method | LCMS RT | (m/z): (M + H)+ | Method |
|---|---|---|---|---|---|---|
| 62 | 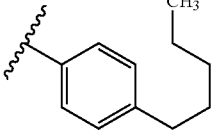 | A | 1 | 2.57 | 431.1 | B |
| 63 | 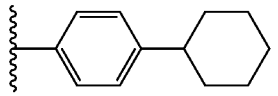 | A | 1 | 2.55 | 443.1 | B |
| 64 | 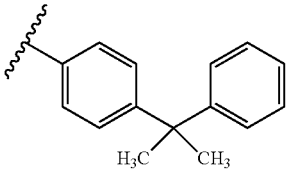 [SMILES: *c1ccc(C(C)(C)c2ccccc2)cc1] | A | 1 | 2.48 | 479.1 | B |
| 65 | 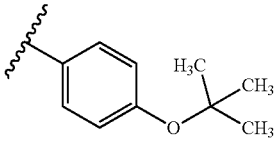 | A | 1 | 2.18 | 433.3 | B |

The following method (Method A) was used to prepare a number of the following examples of the current invention.

Example 66

8-(4-((5-isopropoxypyridin-2-yl)oxy)piperidin-1-yl)-5-methyl-6-oxo-5,6-dihydro-1,5-naphthyridine-2-carbonitrile

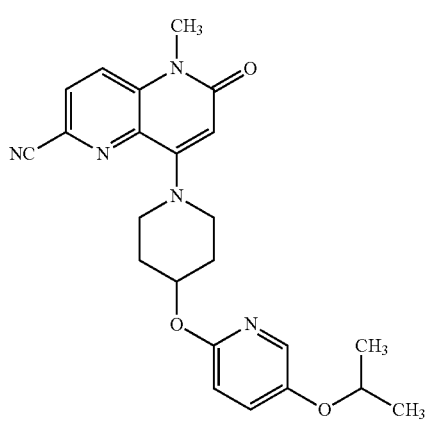

(66)

In a dried one dram vial, 8-(4-hydroxypiperidin-1-yl)-5-methyl-6-oxo-5,6-dihydro-1,5-naphthyridine-2-carbonitrile (29 mg, 0.102 mmol) was dissolved in NMP (1.0 ml) under nitrogen. Sodium hydride (10.6 mg, 0.265 mmol) was then added and the mixture was stirred for 3 min, after which 2-fluoro-5-isopropoxypyridine (17 μL, 0.142 mmol) was added. Stirring was continued at room temperature overnight. The reaction was then quenched by the addition of acetic acid, and the volume was adjusted to 1.8 mL by the addition of NMP. This mixture was filtered and then purified by preparative LC/MS with the following conditions: Column: XBridge C18, 200 mm×19 mm, 5-μm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 30% B, 30-70% B over 20 minutes, then a 4-minute hold at 100% B; Flow Rate: 20 mL/min; Column Temperature: 25° C. Fraction collection was triggered by MS signals. Fractions containing the product were combined and dried via centrifugal evaporation. The yield of the product was 9.3 mg, and its estimated purity by LCMS analysis was 97%. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min; Detection: MS and UV (220 nm). Injection 1 results: Purity: 97.3%; Observed Mass: 420.07; Retention Time: 1.95 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). Injection 2 results: Purity: 98.8%; Observed Mass: 420.32; Retention Time: 1.85 min. $^1$H NMR (500 MHz, DMSO-$d_6$) δ 8.11 (s, 1.0H), 8.07-8.00 (m, 1.0H), 7.79 (d, J=3.1 Hz, 1.0H), 7.36 (dd, J=8.9, 3.1 Hz, 1.0H), 6.74 (d, J=9.2 Hz, 1.0H), 6.13 (s, 1.0H), 5.18-5.04 (m, 1.0H), 4.49 (dt, J=12.1, 6.0 Hz, 1.0H), 3.85-3.71 (m, 1.7H), 3.30 (br t, J=9.6 Hz, 1.8H), 2.18-2.04 (m, 2.0H), 1.87-1.71 (m, 2.0H), 1.23 (d, J=5.8 Hz, 6.0H). Water suppression at 3.57 ppm diminishes the intensity of adjacent signals.

In a similar fashion the following examples can be prepared.
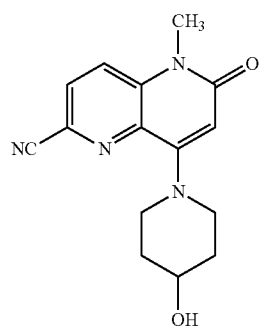
Heteroaryl halide, NaH/NMP →
-continued
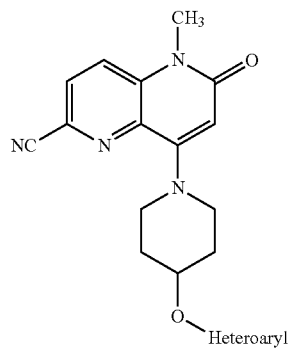
TABLE 5
| Ex. No. | Heteroaryl Structure | Stereo. Chem. | LCMS Method | LCMS RT | (m/z): (M + H)+ | Method |
|---|---|---|---|---|---|---|
| 67 | pyridine-Cl | A | 1 | 1.97 | 396.0 | A |
| 68 | pyridazine-C(CH₃)₃ | A | 1 | 1.64 | 419.3 | A |
| 69 | quinoxaline | A | 1 | 1.92 | 413.3 | A |
| 70 | 2,6-dimethylpyrimidine | A | 1 | 1.14 | 391.1 | A |
| 71 | quinazoline | A | 1 | 1.46 | 413.0 | A |
| 72 | 2-methylpyrimidine | A | 1 | 1.10 | 377.1 | A |

TABLE 5-continued
| Ex. No. | Heteroaryl Structure | Stereo. Chem. | LCMS Method | LCMS RT | (m/z): (M + H)+ | Method |
|---|---|---|---|---|---|---|
| 73 | 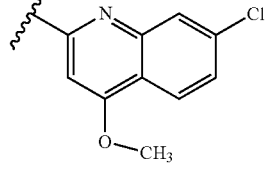 | A | 1 | 2.30 | 476.1 | A |
| 74 | 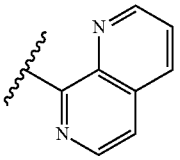 [SMILES: *c1nccc2cccnc12] | A | 1 | 1.46 | 413.0 | A |
| 75 | 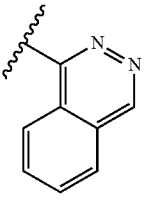 [SMILES: *c1nncc2ccccc12] | A | 1 | 1.28 | 412.9 | A |
| 76 | 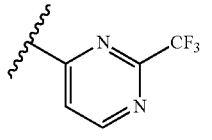 [SMILES: *c1ccnc(C(F)(F)F)n1] | A | 1 | 1.80 | 431.3 | A |
| 77 | 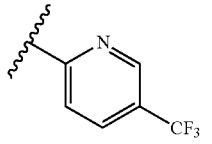 [SMILES: *c1ccc(C(F)(F)F)cn1] | A | 1 | 2.11 | 430.2 | A |
| 78 | 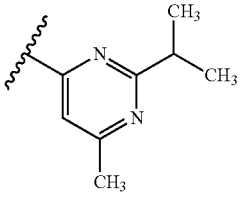 | A | 1 | 1.34 | 419.3 | A |

Example 79

(+/−) 6-cyano-1-methyl-4-(trans-3-methyl-4-(4-(trifluoromethoxy)phenoxy)piperidin-1-yl)-1,5-naphthyridin-2(1H)-one (79)

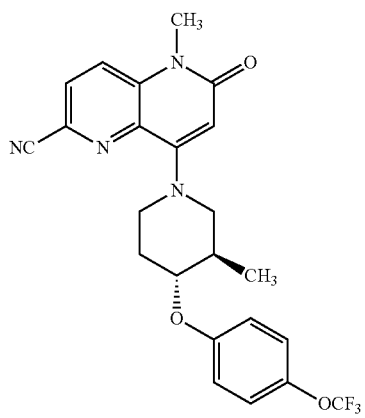

A dry 20 mL scintillation vial fitted with a septum was charged with triphenylphosphane (polymer supported) 3 mmol/g (2.212 mL, 0.664 mmol) and then evacuated and flushed with nitrogen. THF (2 mL) was then added, followed after ~1 min. by 4-(trifluoromethoxy)phenol (0.039 mL, 0.302 mmol). The resultant mixture was mixed briefly, after which a solution of di-tert-butyl (E)-diazene-1,2-dicarboxylate (111 mg, 0.483 mmol) in THF (1 mL) was added via syringe in a single portion. The mixture was agitated on an orbital shaker for 3 min., after which a solution of 8-(cis-4-hydroxy-3-methylpiperidin-1-yl)-5-methyl-6-oxo-5,6-dihydro-1,5-naphthyridine-2-carbonitrile (90 mg, 0.302 mmol)) in THF (2 mL) was added in a single portion. The vail was then shaken at room temperature overnight. The reaction mixture was subsequently filtered and evaporated to dryness. The residue was dissolved in 2 mL of DMF and the resultant solution fractionated via preparative LC/MS under the following conditions: Column: XBridge C18, 200 mm×19 mm, 5-μm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 31% B, 31-71% B over 25 minutes, then a 5-minute hold at 100% B; Flow Rate: 20 mL/min; Column Temperature: 25° C. Fraction collection was triggered by UV signals. Fractions containing the product were combined and dried via centrifugal evaporation. The yield of the product was 13.3 mg, and its estimated purity by LCMS analysis was 100%. Analytical LC/MS was used to determine purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min; Detection: MS and UV (220 nm). Injection 1 results: Purity: 100.0%; Observed Mass: 459.09; Retention Time: 2.44 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). Injection 2 results: Purity: 100.0%; Observed Mass: 459.08; Retention Time: 2.28 min. $^1$H NMR (500 MHz, DMSO-$d_6$) δ 8.21-8.13 (m, 1H), 8.18-8.04 (m, 2H), 8.12-8.04 (m, 1H), 7.33-7.24 (m, 2H), 7.15-7.08 (m, 2H), 6.17-6.11 (m, 1H), 4.27 (br d, J=3.7 Hz, 1H), 4.04-3.87 (m, 2H), 3.59-3.51 (m, 3H), 3.39 (br d, J=4.9 Hz, 1H), 3.23-3.12 (m, 1H), 3.00 (br t, J=11.3 Hz, 1H), 2.24-1.99 (m, 2H), 1.73-1.58 (m, 1H), 1.07 (br d, J=6.4 Hz, 3H).

The above racemic mixture was resolved by a chiral SFC separation method. Approximately 10.1 mg of racemate were resolved into two peaks collected in IPA w/0.1% DEA. The chiral purity for the isolates were estimated based on the prep chromatogram below.

| Isolate | Chiral Purity |
|---|---|
| 1st Eluting Peak | >95% |
| 2nd Eluting Peak | >95% |
| Preparative Chromatographic Conditions: | |
| Instrument: | Waters 100 Prep SFC |
| Column: | Chiral AD, 30 × 250 mm. 5 micron |
| Mobile Phase: | 75% CO$_2$/25% IPA w/0.1% DEA |
| Flow Conditions: | 100 mL/min |
| Detector Wavelength: | 220 nm |
| Injection Details: | 1500 μL 10.1 mg dissolved in 4 mL MeOH |
| Analytical Chromatographic Conditions(Before Prep): | |
| Instrument: | Shimadzu Nexera UC SFC |
| Column: | Chiralpak AD, 4.6 × 100 mm, 5 micron |
| Mobile Phase: | 75% CO$_2$/25% IPA w/0.1% DEA |
| Flow Conditions: | 2 mL/min |
| Detector Wavelength: | 220 nm |
| Example 80: Isolate 1: | First eluting peak |
| Example 81: Isolate 2: | Second eluting peak |

Example 80

6-cyano-1-methyl-4-(trans-3-methyl-4-(4-(trifluoromethoxy)phenoxy)piperidin-1-yl)-1,5-naphthyridin-2(1H)-one (rel)

(80)

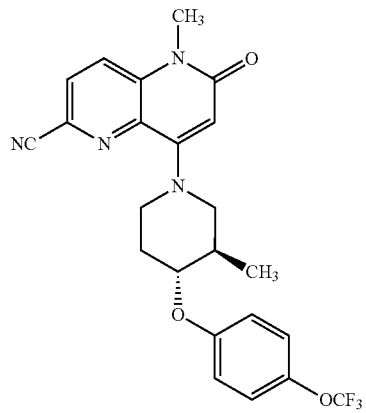

Analytical LC/MS was used to determine purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min; Detection: MS and UV (220 nm). Injection 1 results: Purity: 98.7%; Observed Mass: 458.95; Retention Time: 2.2 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). Injection 2 results: Purity: 96.3%; Observed Mass: 459.1; Retention Time: 2.26 min. $^1$H NMR (500 MHz, DMSO-$d_6$) δ 8.32-7.90 (m, 2H), 7.33-7.02 (m, 4H), 6.13 (s, 1H), 4.31-4.18 (m, 1H), 4.03-3.88 (m, 2H), 3.57-3.51 (m, 3H), 3.21-3.12 (m, 1H), 3.04-2.93 (m, 1H), 2.24-2.15 (m, 1H), 2.11-2.00 (m, 1H), 1.74-1.55 (m, 1H), 1.10-1.02 (m, 3H).

Example 81

6-cyano-1-methyl-4-(trans-3-methyl-4-(4-(trifluoromethoxy)phenoxy)piperidin-1-yl)-1,5-naphthyridin-2(1H)-one (rel)

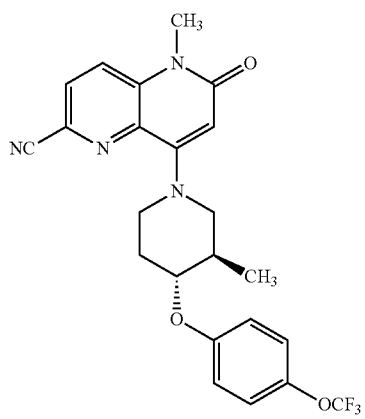

(81)

Analytical LC/MS was used to determine purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min; Detection: MS and UV (220 nm). Injection 1 results: Purity: 99.3%; Observed Mass: 459.08; Retention Time: 2.2 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). Injection 2 results: Purity: 97.8%; Observed Mass: 459.24; Retention Time: 2.26 min. $^1$H NMR (500 MHz, DMSO-$d_6$) δ 8.19-8.00 (m, 2H), 7.32-7.05 (m, 4H), 6.13 (s, 1H), 4.32-4.20 (m, 1H), 4.02-3.88 (m, 2H), 3.57-3.52 (m, 3H), 3.21-3.10 (m, 1H), 3.05-2.90 (m, 1H), 2.24-2.14 (m, 1H), 2.11-2.00 (m, 1H), 1.72-1.57 (m, 1H), 1.09-1.02 (m, 3H).

Using similar methodology and purification techniques, the following examples were prepared.

TABLE 6

| Ex. No. | Aryl Structure | Stereo. Chem. | LCMS Method | LCMS RT | (m/z): (M + H)$^+$ | Method |
|---|---|---|---|---|---|---|
| 82 | 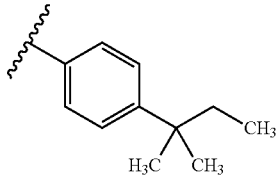 [SMILES: *c1ccc(C(C)(C)CC)cc1] | R | 1 | 2.60 | 445.2 | A |
| 83 | 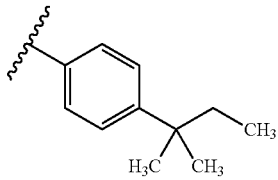 [SMILES: *c1ccc(C(C)(C)CC)cc1] | H | 1 | 2.60 | 445.3 | A |
| 84 | 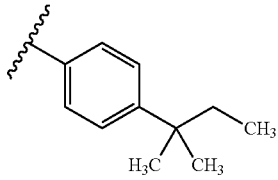 [SMILES: *c1ccc(C(C)(C)CC)cc1] | H | 1 | 2.60 | 445.3 | A |

TABLE 6-continued

| Ex. No. | Aryl Structure | Stereo. Chem. | LCMS Method | LCMS RT | (m/z): (M + H)+ | Method |
|---|---|---|---|---|---|---|
| 85 | 4-OC(CH3)3-phenyl | R | 1 | 2.27 | 447.1 | A |
| 86 | 4-OC(CH3)3-phenyl | H | 3 | 2.23 | 447.1 | A |
| 87 | 4-OC(CH3)3-phenyl | H | 3 | 2.23 | 447.1 | A |
| 88 | 4-C(CH3)3-phenyl | R | 1 | 2.46 | 431.0 | A |
| 89 | 4-C(CH3)3-phenyl | H | 3 | 2.40 | 431.1 | A |
| 90 | 4-C(CH3)3-phenyl | H | 3 | 2.40 | 431.1 | A |
| 91 | 3-cyclopropyl-phenyl | R | 3 | 2.25 | 415.2 | A |
| 92 | 3-cyclopropyl-phenyl | H | 3 | 2.22 | 415.3 | A |
| 93 | 3-cyclopropyl-phenyl | H | 3 | 2.22 | 415.3 | A |
| 94 | 4-iPr-phenyl | R | 1 | 2.53 | 417.2 | A |
| 95 | 4-iPr-phenyl | H | 1 | 2.405 | 417.3 | A |

TABLE 6-continued
| Ex. No. | Aryl Structure | Stereo. Chem. | LCMS Method | LCMS RT | (m/z): (M + H)+ | Method |
|---|---|---|---|---|---|---|
| 96 | 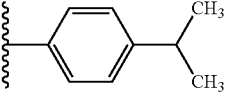 | H | 1 | 2.40 | 417.3 | A |
| 97 | 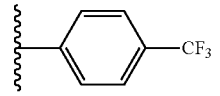 [SMILES: *c1ccc(C(F)(F)F)cc1] | R | 1 | 2.44 | 443.1 | A |
| 98 | 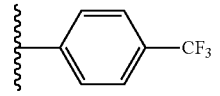 [SMILES: *c1ccc(C(F)(F)F)cc1] | H | 1 | 2.26 | 443.2 | A |
| 99 | 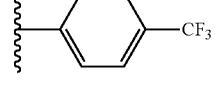 | H | 1 | 2.25 | 443.2 | A |
| 100 | 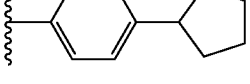 | R | 1 | 2.60 | 443.3 | A |
| 101 | 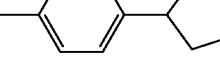 | H | 3 | 2.57 | 443.4 | A |
| 102 | 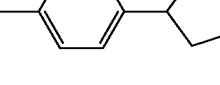 | H | 3 | 2.57 | 443.3 | A |
| 103 | 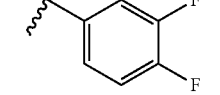 | R | 1 | 2.11 | 411.1 | A |
| 104 | 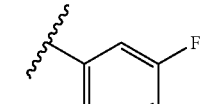 | H | 1 | 2.10 | 411.1 | A |
| 105 | 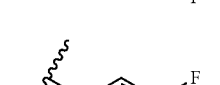 | H | 1 | 2.10 | 411.1 | A |
| 106 | 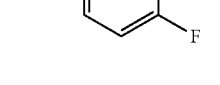 | R | 3 | 2.69 | 457.1 | A |
| 107 | 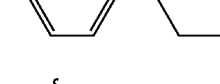 | R | 3 | 2.14 | 389.2 | A |

TABLE 6-continued

| Ex. No. | Aryl Structure | Stereo. Chem. | LCMS Method | LCMS RT | (m/z): (M + H)+ | Method |
|---|---|---|---|---|---|---|
| 108 | 3-CH3-phenyl | H | 4 | 2.13 | 389.1 | A |
| 109 | 3-CH3-phenyl | H | 4 | 2.107 | 389.3 | A |
| 110 | 4-ethyl-phenyl | R | 1 | 2.26 | 403.2 | A |
| 111 | 4-cyclopropyl-phenyl | R | 1 | 2.24 | 415.2 | A |
| 112 | 2-F-4-CF3-phenyl | R | 1 | 2.27 | 461.1 | A |
| 113 | 2,4-diF-phenyl | R | 1 | 2.06 | 411.1 | A |
| 114 | 2,4-diF-phenyl | H | 1 | 2.05 | 411.1 | A |
| 115 | 2,4-diF-phenyl | H | 1 | 2.05 | 411.1 | A |
| 116 | 2-CF3-4-F-phenyl | R | 1 | 2.24 | 461.1 | A |
| 117 | 2-CF3-4-F-phenyl | H | 3 | 2.20 | 461.2 | A |

TABLE 6-continued

| Ex. No. | Aryl Structure | Stereo. Chem. | LCMS Method | LCMS RT | (m/z): (M + H)+ | Method |
|---|---|---|---|---|---|---|
| 118 | 2-CF3, 4-F phenyl | H | 3 | 2.20 | 461.2 | A |
| 119 | 4-CH3 phenyl | R | 3 | 2.12 | 389.2 | A |
| 120 | 4-CH3 phenyl | H | 3 | 2.08 | 389.4 | A |
| 121 | 4-CH3 phenyl | H | 3 | 2.07 | 389.3 | A |
| 122 | 3-isopropyl phenyl | R | 1 | 2.35 | 417.2 | A |
| 123 | 3-tert-butyl phenyl | R | 1 | 2.42 | 431.2 | A |
| 124 | 2-CF3, 6-F phenyl | R | 1 | 2.22 | 461.1 | A |
| 125 | 2,6-diF phenyl | R | 1 | 2.06 | 411.1 | A |
| 126 | 2,6-diF phenyl | H | 3 | 2.01 | 411.1 | A |
| 127 | 2,6-diF phenyl | H | 3 | 2.01 | 411.2 | A |
| 128 | 4-F phenyl | R | 1 | 2.00 | 393.3 | A |

TABLE 6-continued

| Ex. No. | Aryl Structure | Stereo. Chem. | LCMS Method | LCMS RT | (m/z): (M + H)+ | Method |
|---|---|---|---|---|---|---|
| 129 | (4-F phenyl) | H | 3 | 1.96 | 393.0 | A |
| 130 | (4-F phenyl) | H | 3 | 1.96 | 393.4 | A |
| 131 | (2,3,5-triF phenyl) | R | 1 | 2.12 | 429.1 | A |
| 132 | (benzodioxepine) | R | 1 | 1.91 | 447.2 | A |

Using methodology related to that presented in the preceeding scheme and table and employing (+/−) 8-(cis-4-hydroxy-3-methylpiperidin-1-yl)-5-methyl-6-oxo-5,6-dihydro-1,5-naphthyridine-2,7-dicarbonitrile as a coupling partner with appropriately functionalized phenols in the Mitsunobu reaction, the following examples can be prepared. Isolation of specific enantiomers can be achieved using preparative HPLC techniques as described above.

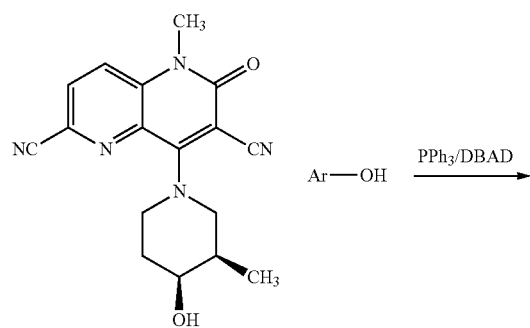

TABLE 7

| Ex. No. | Aryl Structure | Stereo. Chem. | LCMS Method | LCMS RT | (m/z): (M + H)+ | Method |
|---|---|---|---|---|---|---|
| 136 | (3-CH3 phenyl) | R | 1 | 2.12 | 414.2 | A |

Using related methodology and employing (+/−) 8-(cis-3-ethyl-4-hydroxypiperidin-1-yl)-5-methyl-6-oxo-5,6-dihydro-1,5-naphthyridine-2-carbonitrile as a coupling partner with appropriately functionalized phenols in the Mitsunobu reaction, the following examples can be prepared. Isolation of specific enantiomers can be achieved using preparative HPLC techniques as described above.

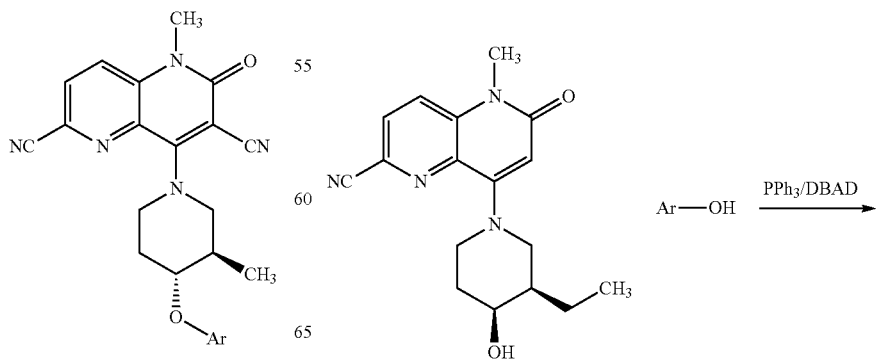

-continued
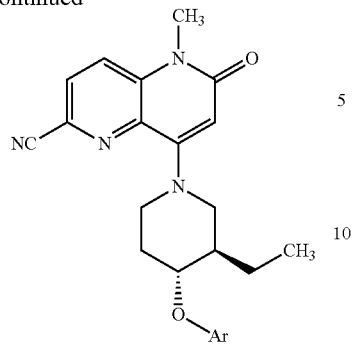
TABLE 8
| Ex. No. | Aryl Structure | Stereo. Chem. | LCMS Method | LCMS RT | (m/z): (M + H)+ | Method |
|---|---|---|---|---|---|---|
| 137 | 3-isopropylphenyl | R | 3 | 2.44 | 431.2 | A |
| 138 | 3-isopropylphenyl | H | 5 | 2.48 | 431.1 | A |
| 139 | 3-isopropylphenyl | H | 5 | 2.48 | 431.1 | A |
| 140 | 3-CF3-phenyl | R | 3 | 2.41 | 457.1 | A |
| 141 | 3-CF3-phenyl | H | 3 | 2.31 | 457.3 | A |
| 142 | 3-CF3-phenyl | H | 3 | 2.30 | 457.2 | A |
| 143 | 4-isopropylphenyl | R | 1 | 2.53 | 431.1 | A |
| 144 | 4-isopropylphenyl | H | 3 | 2.48 | 431.0 | A |

TABLE 8-continued

| Ex. No. | Aryl Structure | Stereo. Chem. | LCMS Method | LCMS RT | (m/z): (M + H)+ | Method |
|---|---|---|---|---|---|---|
| 145 | 4-isopropylphenyl | H | 3 | 2.48 | 431.4 | A |
| 146 | 4-CF3-phenyl | R | 1 | 2.38 | 457.0 | A |
| 147 | 4-CF3-phenyl | H | 3 | 2.39 | 457.3 | A |
| 148 | 4-CF3-phenyl | H | 3 | 2.39 | 457.3 | A |
| 149 | 4-tert-butylphenyl | R | 1 | 2.73 | 459.1 | A |
| 150 | 4-tert-butylphenyl | H | 3 | 2.73 | 459.1 | A |
| 151 | 4-tert-butylphenyl | H | 3 | 2.74 | 459.1 | A |
| 152 | 4-isopropylphenyl (gem-diMe) | R | 3 | 2.54 | 445.1 | A |
| 153 | 4-isopropylphenyl (gem-diMe) | H | 3 | 2.61 | 445.1 | A |
| 154 | 4-isopropylphenyl (gem-diMe) | H | 3 | 2.62 | 445.1 | A |
| 155 | 3-cyclopropylphenyl | R | 3 | 2.32 | 429.2 | A |
| 156 | 3-cyclopropylphenyl | H | 1 | 2.35 | 429.2 | A |

TABLE 8-continued

| Ex. No. | Aryl Structure | Stereo. Chem. | LCMS Method | LCMS RT | (m/z): (M + H)+ | Method |
|---|---|---|---|---|---|---|
| 157 | 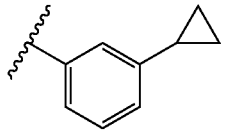 [SMILES: *c1cccc(C2CC2)c1] | H | 1 | 2.35 | 428.9 | A |
| 158 | 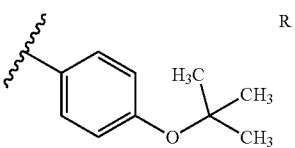 | R | 1 | 2.36 | 460.9 | A |
| 159 | 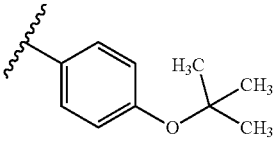 | H | 3 | 2.40 | 461.1 | A |
| 160 | 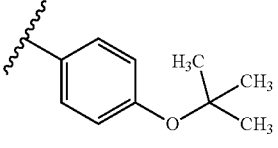 [SMILES: *c1ccc(OC(C)(C)C)cc1] | H | 3 | 2.39 | 461.2 | A |
| 161 | 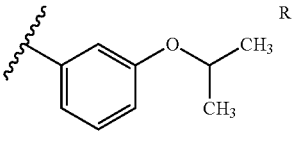 | R | 3 | 2.38 | 447.1 | A |
| 162 | 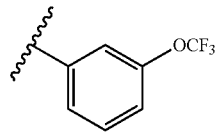 [SMILES: *c1cccc(OC(F)(F)F)c1] | H | 3 | 2.35 | 472.9 | A |
| 163 | 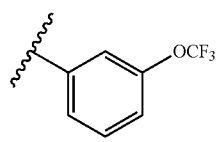 [SMILES: *c1cccc(OC(F)(F)F)c1] | H | 3 | 2.35 | 473.3 | A |

Using methodology related to that presented in the preceeding table and employing (+/−) 8-(trans-3-ethyl-4-hydroxypiperidin-1-yl)-5-methyl-6-oxo-5,6-dihydro-1,5-naphthyridine-2-carbonitrile as a coupling partner with appropriately functionalized phenols in the Mitsunobu reaction, the following examples can be prepared. Isolation of specific enantiomers was achieved using preparative HPLC techniques as described above.

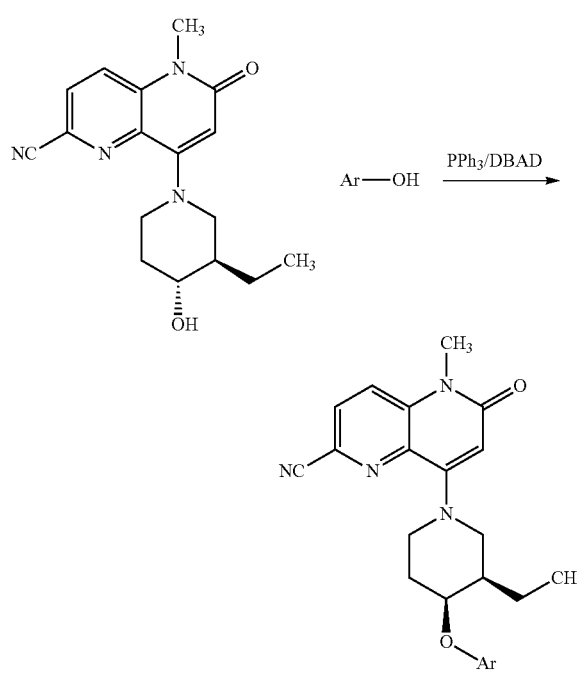

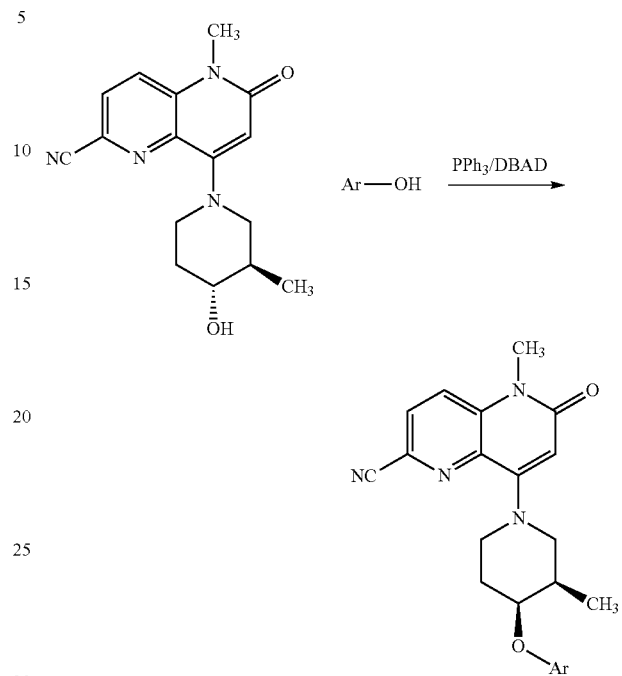

tion, the following examples can be prepared. Isolation of specific enantiomers was achieved using preparative HPLC techniques as described above.

TABLE 9

| Ex. No. | Aryl Structure | Stereo. Chem. | LCMS Method | LCMS RT | (m/z): (M + H)+ |
|---|---|---|---|---|---|
| 164 | 3-isopropylphenyl | R | 3 | 2.58 | 431.1 |
| 165 | 3-tert-butylphenyl (H3C, CH3, CH3) | R | 3 | 2.54 | 445.3 |
| 166 | H3C,CH3,CH3 substituted phenyl | H | 3 | 2.54 | 445.0 |
| 167 | H3C,CH3,CH3 substituted phenyl | H | 3 | 2.66 | 445.1 |
| 168 | 3-CF3-phenyl | R | 1 | 2.37 | 457.1 |

Using methodology related to that presented in the preceeding table and employing (+/−) 8-(trans-4-hydroxy-3-methylpiperidin-1-yl)-5-methyl-6-oxo-5,6-dihydro-1,5-naphthyridine-2-carbonitrile as a coupling partner with appropriately functionalized phenols in the Mitsunobu reac-

TABLE 10

| Ex. No. | Aryl Structure | Stereo. Chem. | LCMS Method | LCMS RT | (m/z): (M + H)+ |
|---|---|---|---|---|---|
| 169 | 4-(2-methylbutan-2-yl)phenyl | R | 1 | 2.64 | 444.9 |
| 170 | 4-(2-methylbutan-2-yl)phenyl | H | 3 | 2.62 | 445.0 |
| 171 | 4-(2-methylbutan-2-yl)phenyl | H | 3 | 2.62 | 445.2 |
| 172 | 4-(2-methylpropan-2-yloxy)phenyl | R | 1 | 2.28 | 446.9 |

TABLE 10-continued

| Ex. No. | Aryl Structure | Stereo. Chem. | LCMS Method | LCMS RT | (m/z): (M + H)+ |
|---|---|---|---|---|---|
| 173 | 4-(2-methoxypropan-2-yl... ) phenyl (H3C-C(CH3)(CH3)-O-C6H4-) | H | 3 | 2.31 | 447.1 |
| 174 | 4-(2-methoxypropan-2-yl) phenyl | H | 3 | 2.32 | 447.1 |
| 175 | 4-tert-butylphenyl | R | 1 | 2.52 | 431.0 |
| 176 | 3-(1-methylethyl)phenyl | R | 1 | 2.40 | 417.3 |
| 177 | 3-(1-methylethyl)phenyl | H | 3 | 2.43 | 417.0 |
| 178 | 3-(1-methylethyl)phenyl | H | 3 | 2.43 | 417.3 |
| 179 | 3-cyclopropylphenyl | R | 3 | 2.24 | 415.0 |
| 180 | 3-cyclopropylphenyl | H | 1 | 2.26 | 415.3 |
| 181 | 3-cyclopropylphenyl | H | 1 | 2.26 | 415.3 |
| 182 | 4-(1-methylethyl)phenyl | R | 1 | 2.43 | 417.3 |
| 183 | 4-(1-methylethyl)phenyl | H | 3 | 2.46 | 417.1 |
| 184 | 4-(1-methylethyl)phenyl | H | 3 | 2.46 | 417.3 |

Example 185

(+/−) 5-methyl-8-(cis-3-methyl-4-(4-(trifluoromethyl)phenoxy)piperidin-1-yl)-6-oxo-5,6-dihydro-1,5-naphthyridine-2-carboxamide

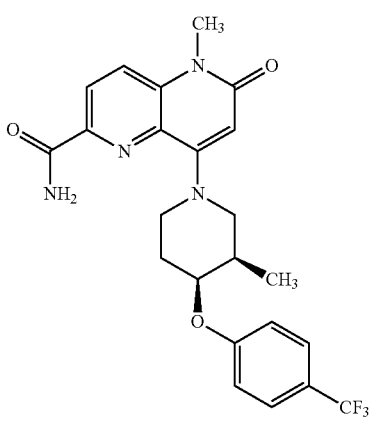

(185)

A suspension of sodium hydride (3.54 mg, 0.074 mmol) and (+/−) 8-(cis-4-hydroxy-3-methylpiperidin-1-yl)-5-methyl-6-oxo-5,6-dihydro-1,5-naphthyridine-2-carbonitrile (20 mg, 0.067 mmol) in DMF (2 mL) was heated at 80° C. under nitrogen for 15 mins. 1-fluoro-4-(trifluoromethyl)benzene (9.36 μL, 0.074 mmol) was then added in a single portion and heating was continued overnight, and the reaction mixture was left at room temperature for 48 h. The crude material was purified via preparative LC/MS with the following conditions: Column: XBridge C18, 200 mm×19 mm, 5-μm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 24% B, 24-64% B over 20 minutes, then a 5-minute hold at 100% B; Flow Rate: 20 mL/min; Column Temperature: 25° C. Fraction collection was triggered by UV signals. Fractions containing the product were combined and dried via centrifugal evaporation. The yield of the product was 14.1 mg, and its estimated purity by LCMS analysis was 92%. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0%

B to 100% B over 3 min, then a 0.50 min hold at 100% B; Flow: 1 mL/min; Detection: MS and UV (220 nm). Injection 1 results: Purity: 98.2%; Observed Mass: 317.13; Retention Time: 1.29 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). Injection 2 results: Purity: 91.8%; Observed Mass: 317.14; Retention Time: 1.12 min. $^1$H NMR (500 MHz, DMSO-$d_6$) δ 8.21-8.14 (m, 1H), 8.08-8.01 (m, 1H), 7.82-7.74 (m, 1H), 7.51-7.46 (m, 1H), 6.07-6.02 (m, 1H), 3.84-3.75 (m, 1H), 3.57-3.50 (m, 1H), 3.19-3.07 (m, 1H), 2.06-1.95 (m, 1H), 1.90-1.71 (m, 2H), 0.97-0.85 (m, 3H). Not all signals were assigned due to water suppression. Racemic.

Example 186

(+/−) 5-methyl-8-(cis-3-methyl-4-(4-(trifluoromethyl)phenoxy)piperidin-1-yl)-6-oxo-5,6-dihydro-1,5-naphthyridine-2-carbonitrile

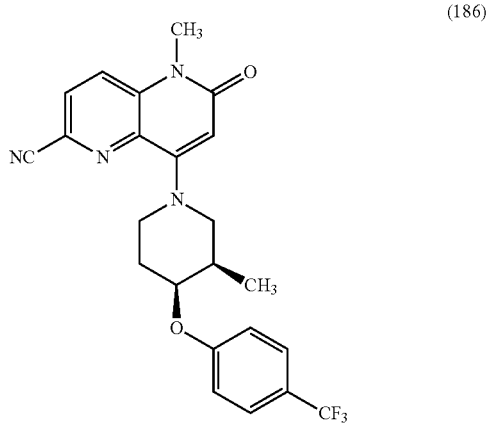 [SMILES: C[C@@H]1CN(c2cc(=O)n(C)c3ccc(C#N)nc23)CC[C@@H]1Oc1ccc(C(F)(F)F)cc1]

(186)

The TFA salt of (+/−) cis-3-methyl-4-(4-(trifluoromethyl)phenoxy)piperidine, (40.3 mg, 0.108 mmol) was added to a solution of 6-cyano-1-methyl-2-oxo-1,2-dihydro-1,5-naphthyridin-4-yl trifluoromethanesulfonate (30 mg, 0.090 mmol) and Hunig's base (0.047 mL, 0.270 mmol) in DMF (1.5 mL) and the reaction mixture was heated at 85° C. overnight. The crude material was purified via preparative LC/MS with the following conditions: Column: XBridge C18, 200 mm×19 mm, 5-μm particles; Mobile Phase A: 5:95 acetonitrile:water with 0.1% trifluoroacetic acid; Mobile Phase B: 95:5 acetonitrile: water with 0.1% trifluoroacetic acid; Gradient: a 0-minute hold at 40% B, 40-80% B over 20 minutes, then a 4-minute hold at 100% B; Flow Rate: 20 mL/min; Column Temperature: 25° C. Fraction collection was triggered by MS signals. Fractions containing the product were combined and dried via centrifugal evaporation. Analytical LC/MS was used to determine the final purity. Injection 1 conditions: Column: Waters) XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min; Detection: MS and UV (220 nm). Injection 1 results: Purity: 99.3%; Observed Mass: 4-((2.98; Retention Time: 2.3 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). Injection 2 results: Purity: 100.0%; Observed Mass: 443.21; Retention Time: 2.33 min. $^1$H NMR (500 MHz, DMSO-$d_6$) δ 8.20-8.11 (m, 1H), 8.11-8.02 (m, 1H), 7.72-7.57 (m, 2H), 7.32-7.12 (m, 2H), 6.21-6.06 (m, 1H), 4.84-4.63 (m, 1H), 2.36-2.21 (m, 1H), 2.10-1.90 (m, 2H), 1.12-0.91 (m, 3H). The full spectrum was not assigned due to the water suppression technique employed.

The racemic product was further fractionated using SFC-chiral chromatography. The following two enantiomers were obtained and characterized.

Example 187

5-methyl-8-(cis-3-methyl-4-(4-(trifluoromethyl)phenoxy)piperidin-1-yl)-6-oxo-5,6-dihydro-1,5-naphthyridine-2-carbonitrile (rel)

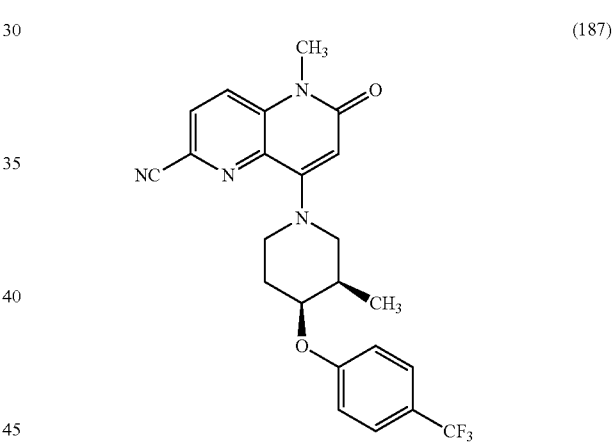

(187)

Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min; Detection: MS and UV (220 nm). Injection 1 results: Purity: 97.5%; Observed Mass: 4-((2.84; Retention Time: 2.25 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). Injection 2 results: Purity: 99.4%; Observed Mass: 443.07; Retention Time: 2.25 min. $^1$H NMR (500 MHz, DMSO-$d_6$) δ 8.22-8.12 (m, 1H), 8.12-8.01 (m, 1H), 7.69-7.58 (m, 2H), 7.28-7.17 (m, 2H), 6.23-6.09 (m, 1H), 4.84-4.66 (m, 1H), 2.39-2.19

(m, 1H), 2.13-1.92 (m, 2H), 1.12-0.88 (m, 3H). The full spectrum was not assigned due to the water suppression technique employed.

Example 188

5-methyl-8-(cis-3-methyl-4-(4-(trifluoromethyl)phenoxy)piperidin-1-yl)-6-oxo-5,6-dihydro-1,5-naphthyridine-2-carbonitrile (rel)

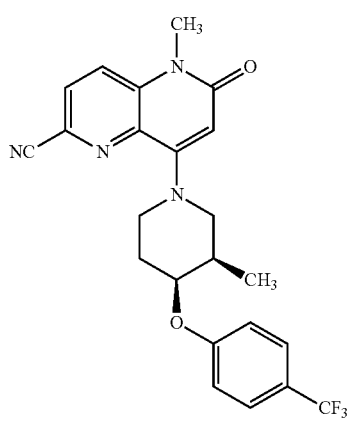
(188)

Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min; Detection: MS and UV (220 nm). Injection 1 results: Purity: 96.4%; Observed Mass: 443.09; Retention Time: 2.26 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). Injection 2 results: Purity: 98.6%; Observed Mass: 443.07; Retention Time: 2.25 min. $^1$H NMR (500 MHz, DMSO-d$_6$) δ 8.23-8.11 (m, 1H), 8.11-8.02 (m, 1H), 7.78-7.55 (m, 2H), 7.31-7.15 (m, 2H), 6.21-6.05 (m, 1H), 4.82-4.62 (m, 1H), 2.37-2.12 (m, 1H), 2.06-1.92 (m, 2H), 1.06-0.92 (m, 3H). The full spectrum was not assigned due to the water suppression technique employed.

Using methodology related to that presented in the preceeding table and employing 3,6-dicyano-1-methyl-2-oxo-1,2-dihydro-1,5-naphthyridin-4-yl trifluoromethanesulfonate as a coupling partner with appropriately functionalized (+/−) cis-3-methyl-4-aryloxypiperidine intermediates, the following examples were be prepared. Isolation of specific enantiomers was achieved using preparative HPLC techniques as described above.

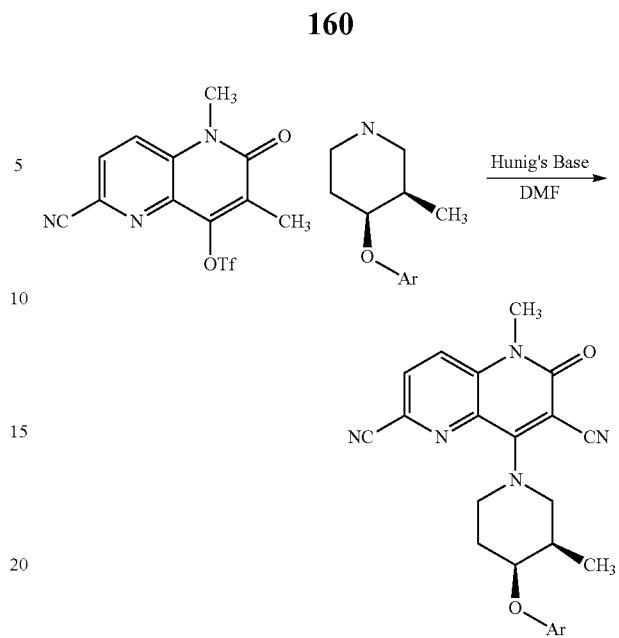

TABLE 11

| Ex. No. | Aryl | Stereo. Chem. | LCMS Method | LCMS RT | (m/z): (M + H)$^+$ |
|---|---|---|---|---|---|
| 189 | ![CF3-phenyl] | R | 3 | 2.31 | 468.0 |
| 190 | ![CF3-phenyl] | H | 1 | 2.25 | 468.1 |
| 191 | ![CF3-phenyl] | H | 1 | 2.25 | 468.1 |

Using methodology related to that presented in the preceeding table and employing 6-cyano-1-methyl-2-oxo-1,2-dihydro-1,5-naphthyridin-4-yl trifluoromethanesulfonate as a coupling partner with appropriately functionalized (+/−) trans-3-ethyl-4-aryloxypiperidine intermediates, the following examples were prepared. Isolation of specific enantiomers can be achieved using preparative HPLC techniques as described above.

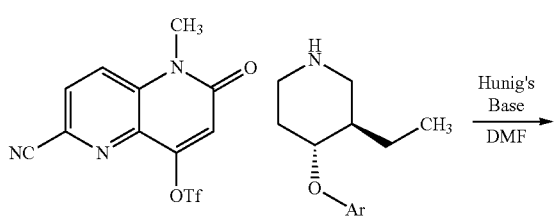

-continued

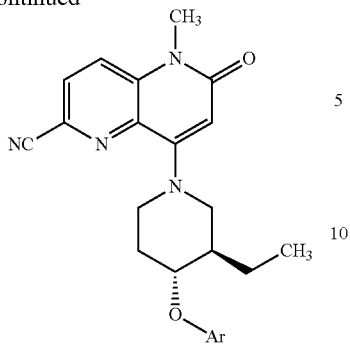

TABLE 12

| Ex. No. | Aryl Structure | Stereo. Chem. | LCMS Method | LCMS RT | (m/z): (M + H)+ |
|---|---|---|---|---|---|
| 192 | pyridyl-O-iPr | R | 1 | 2.17 | 447.9 |
| 193 | pyridyl-O-iPr | H | 1 | 2.13 | 448.3 |
| 194 | pyridyl-O-iPr | H | 1 | 2.13 | 448.1 |
| 195 | 4-F-3-propyl-phenyl | R | 1 | 2.50 | 449.2 |
| 196 | 3-(2-methyl-2-propyl)phenyl | R | 3 | 2.62 | 445.3 |

TABLE 12-continued

| Ex. No. | Aryl Structure | Stereo. Chem. | LCMS Method | LCMS RT | (m/z): (M + H)+ |
|---|---|---|---|---|---|
| 197 | 3-(2-methyl-2-propyl)phenyl | H | 3 | 2.62 | 445.2 |
| 198 | 3-(2-methyl-2-propyl)phenyl | H | 3 | 2.62 | 445.2 |

Using methodology related to that presented in the preceeding table and employing 6-cyano-1-methyl-2-oxo-1,2-dihydro-1,5-naphthyridin-4-yl trifluoromethanesulfonate as a coupling partner with appropriately functionalized (+/−) trans-3-methyl-4-aryloxypiperidine intermediates, the following examples were prepared. Isolation of specific enantiomers can be achieved using preparative HPLC techniques as described above.

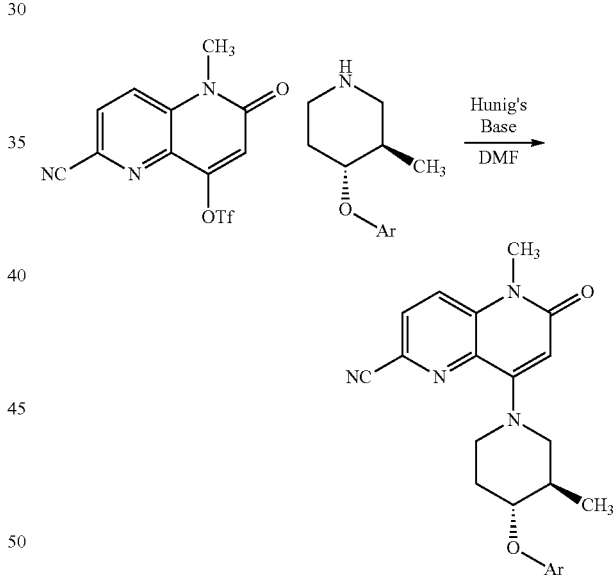

TABLE 13

| Ex. No. | Aryl Structure | Stereo. Chem. | LCMS Method | LCMS RT | (m/z): (M + H)+ |
|---|---|---|---|---|---|
| 199 | pyridyl-O-iPr | Diastereomeric mixture | 3 | 2.00 | 434.1 |

TABLE 13-continued

| Ex. No. | Aryl Structure | Stereo. Chem. | LCMS Method | LCMS RT | (m/z): (M + H)+ |
|---|---|---|---|---|---|
| 200 | (pyridine with OCH(CH3)2) | H | 1 | 2.12 | 434.3 |
| 201 | (pyridine with OCH(CH3)2) | H | 1 | 2.12 | 434.3 |

Using methodology related to that presented in the preceeding table and 6-cyano-1-methyl-2-oxo-1,2-dihydro-1,5-naphthyridin-4-yl trifluoromethanesulfonate as a coupling partner with appropriately functionalized (+/−) cis-3-ethyl-4-aryloxypiperidine intermediates in an SNAr reaction, the following examples can be prepared. Isolation of specific enantiomers can be achieved using preparative HPLC techniques as described above.

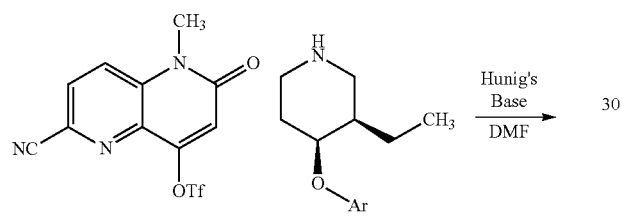

Hunig's Base
DMF

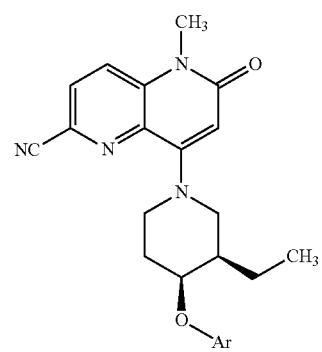

TABLE 14

| Ex. No. | Aryl | Stereo. Chem. | LCMS Method | LCMS RT | (m/z): (M + H)+ |
|---|---|---|---|---|---|
| 202 | (pyridine with OCH(CH3)2) | R | 3 | 2.18 | 448.1 |
| 203 | (pyridine with OCH(CH3)2) | H | 3 | 2.04 | 448.2 |
| 204 | (pyridine with OCH(CH3)2) | H | 3 | 2.04 | 448.4 |

Using methodology related to that presented in the preceeding table and 6-cyano-1-methyl-2-oxo-1,2-dihydro-1,5-naphthyridin-4-yl trifluoromethanesulfonate as a coupling partner with appropriately functionalized (+/−) cis-3-methyl-4-aryloxypiperidine intermediates, the following examples were prepared. Isolation of specific enantiomers can be achieved using preparative HPLC techniques as described above.

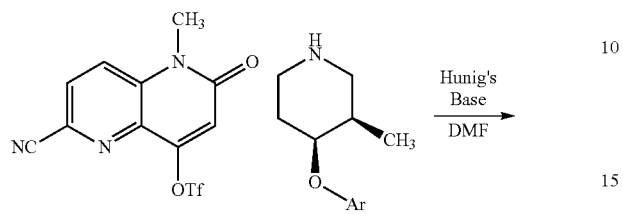

Hunig's Base
DMF

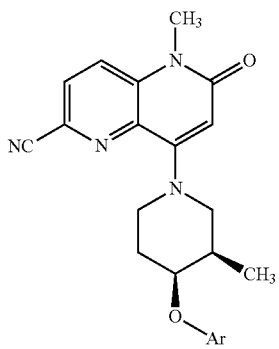

TABLE 15

| Ex. No. | Aryl Structure | Stereo. Chem. | LCMS Method | LCMS RT | (m/z): (M + H)+ |
|---|---|---|---|---|---|
| 205 | pyridine-CH(CH3)2 | R | 3 | 1.88 | 418.1 |
| 206 | pyridine-CH(CH3)2 | H | 3 | 1.78 | 418.2 |
| 207 | pyridine-CH(CH3)2 | H | 3 | 1.79 | 418.2 |
| 208 | pyridine-CHF2 | R | 3 | 2.01 | 426.3 |
| 209 | pyridine-CHF2 | H | 1 | 1.99 | 426.1 |
| 210 | pyridine-CHF2 | H | 1 | 1.99 | 426.0 |
| 211 | pyridine-CH(CH3)2 | R | 1 | 1.74 | 418.3 |

TABLE 15-continued

| Ex. No. | Aryl Structure | Stereo. Chem. | LCMS Method | LCMS RT | (m/z): (M + H)+ |
|---|---|---|---|---|---|
| 212 | | H | 3 | 1.73 | 418.1 |
| 213 | | H | 3 | 1.73 | 418.1 |
| 214 | | R | 3 | 2.12 | 418.1 |
| 215 | | H | 3 | 1.92 | 418.1 |
| 216 | | H | 3 | 1.92 | 418.1 |
| 217 | | R | 1 | 1.46 | 377.1 |
| 218 | | R | 3 | 1.39 | 407.1 |
| 219 | | R | 1 | 1.86 | 419.1 |
| 220 | | R | 1 | 1.18 | 391.1 |
| 221 | | R | 1 | 1.71 | 405.1 |

TABLE 15-continued

| Ex. No. | Aryl Structure | Stereo. Chem. | LCMS Method | LCMS RT | (m/z): (M + H)+ |
|---|---|---|---|---|---|
| 222 | 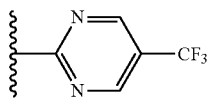 | R | 1 | 1.88 | 445.1 |
| 223 | 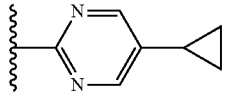 [SMILES: *c1ncc(C2CC2)cn1] | R | 1 | 1.81 | 417.0 |
| 224 | 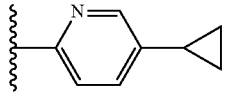 [SMILES: *c1ccc(C2CC2)cn1] | R | 3 | 1.84 | 416.1 |
| 225 | 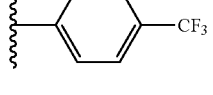 | R | 3 | 2.23 | 444.0 |
| 226 | 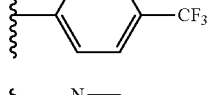 | H | 3 | 2.17 | 443.9 |
| 227 | 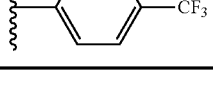 | H | 3 | 2.17 | 444.2 |

Example 228

(+/−) 8-(cis-4-((5-isopropoxypyridin-2-yl)oxy)-3-methylpiperidin-1-yl)-5-methyl-6-oxo-5,6-dihydro-1,5-naphthyridine-2-carbonitrile

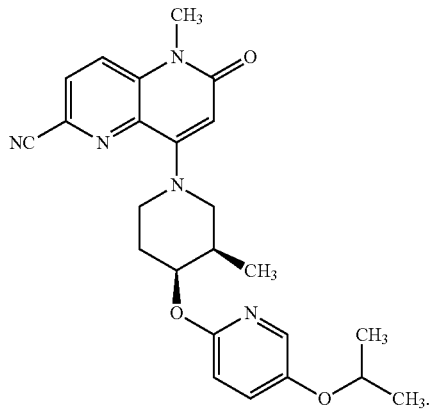

(228)

Sodium hydride (60% in mineral oil, 10.05 mg, 0.251 mmol) was added to a solution of (+/−) 8-(cis-4-hydroxy-3-methylpiperidin-1-yl)-5-methyl-6-oxo-5,6-dihydro-1,5-naphthyridine-2-carbonitrile (30 mg, 0.101 mmol) in anhydrous N-methyl-2-pyrrolidinone (1.0 ml). The reaction mixture was stirred at room temperature for 5 minutes and then 2-fluoro-5-isopropoxypyridine (0.018 ml, 0.151 mmol) was added and stirring was continued at room temperature overnight. The reaction was quenched by the addition of acetic acid (0.014 ml, 0.251 mmol), diluted with acetonitrile and then filtered. The filtrate was purified via preparative LC/MS with the following conditions: Column: XBridge C18, 200 mm×19 mm, 5-μm particles; Mobile Phase A: 5:95 acetonitrile:water with ammonium acetate; Mobile Phase B: 95:5 acetonitrile:water with ammonium acetate; Gradient: a 0-minute hold at 26% B, 26-66% B over 30 minutes, then a 0-minute hold at 100% B; Flow Rate: 20 mL/min; Column Temperature: 25° C. Fraction collection was triggered by MS and UV signals. Fractions containing the product were combined and dried via centrifugal evaporation. The yield of the product was 6.8 mg, and its estimated purity by LCMS analysis was 100%. Analytical LC/MS was used to determine the purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min; Detection: MS and UV (220 nm). Injection 1 results: Purity: 100%; Observed Mass: 434.20; Retention Time: 2.08 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). Injection 2 results: Purity: 100%; Observed Mass: 434.13; Retention Time: 2.04 min. $^1$H NMR (500 MHz, DMSO-d$_6$) δ 8.23-8.15 (m, 1H), 8.14-8.03 (m, 1H), 7.88-7.78 (m, 1H), 7.46-7.35 (m, 1H), 6.88-6.70 (m, 1H), 6.19-6.08 (m, 1H), 5.28-5.18 (m, 1H), 4.60-4.47 (m, 1H), 3.64-3.45 (m, 3H), 2.40-2.28

(m, 1H), 2.11-2.01 (m, 1H), 2.01-1.89 (m, 1H), 1.35-1.23 (m, 6H), 1.10-0.94 (m, 3H). Racemic. The spectrum was not fully assigned due to the water suppression technique employed.

Example 229

(+/−) 5-methyl-8-(trans-3-methyl-4-(4-(tert-pentyl) phenoxy)piperidin-1-yl)-6-oxo-5,6-dihydro-1,5-naphthyridine-2,7-dicarbonitrile

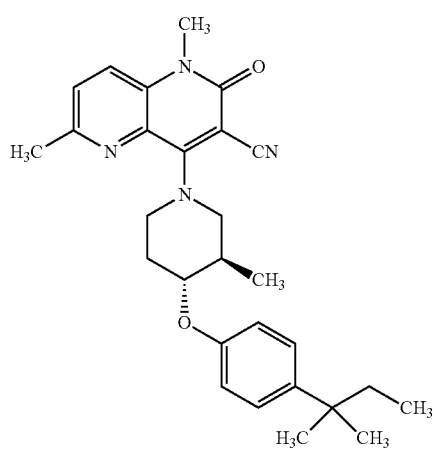

(229)

In a microwave tube, the TFA salt of (+/−) 6-bromo-1-methyl-4-(trans-3-methyl-4-(4-(tert-pentyl)phenoxy)piperidin-1-yl)-2-oxo-1,2-dihydro-1,5-naphthyridine-3-carbonitrile (31 mg, 0.049 mmol), zinc (0.636 mg, 9.73 μmol), zinc cyanide (3.43 mg, 0.029 mmol) and 1,1'-bis(diphenylphosphino)ferrocene-palladium(II)dichloride dichloromethane complex (3.97 mg, 4.86 μmol) were added. The tube was sealed, evacuated and then flushed with nitrogen. NMP (1.5 mL) was then added and the reaction mixture was heated at 80° C. for 4 h. The mixture was then allowed to cool before being diluted to a volume of 2 mL by the addition of acetonitrile. The resultant mixture was filtered, and the crude solution was purified by preparative LC/MS with the following conditions: Column: XBridge C18, 200 mm×19 mm, 5-μm particles; Mobile Phase A: 5:95 acetonitrile:water with 10-mM ammonium acetate; Mobile Phase B: 95:5 acetonitrile:water with 10-Mm ammonium acetate; Gradient: a 0-minute hold at 52% B, 52-92% B over 20 minutes, then a 4-minute hold at 100% B; Flow Rate: 20 mL/min; Column Temperature: 25° C. Fraction collection was triggered by MS and UV signals. Fractions containing the product were combined and dried via centrifugal evaporation. The yield of the product was 10.2 mg, and its estimated purity by LCMS analysis was 98%. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min; Detection: MS and UV (220 nm). Injection 1 results: Purity: 98.5%; Observed Mass: 469.88; Retention Time: 2.62 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). Injection 2 results: Purity: 98.8%; Observed Mass: 470.17; Retention Time: 2.61 min. $^1$H NMR (500 MHz, DMSO-$d_6$) δ 8.26 (d, J=8.9 Hz, 1H), 8.15 (d, J=9.2 Hz, 1H), 7.24 (br d, J=8.5 Hz, 2H), 6.96 (br d, J=8.5 Hz, 2H), 4.32 (br dd, J=7.5, 4.4 Hz, 1H), 4.26-4.14 (m, 1H), 4.26-4.11 (m, 1H), 3.77-3.60 (m, 1H), 2.36-2.25 (m, 1H), 2.23-2.11 (m, 1H), 1.78-1.63 (m, 1H), 1.62-1.53 (m, 2H), 1.22 (s, 6H), 1.04 (br d, J=6.7 Hz, 3H), 0.64 (br t, J=7.2 Hz, 3H). Racemic. Not all signals were assigned due to the water suppression techniques used.

The racemic material was further purified using SFC-chiral chromatography. Two enantiomers were obtained.

Example 230

5-methyl-8-(trans-3-methyl-4-(4-(tert-pentyl)phenoxy)piperidin-1-yl)-6-oxo-5,6-dihydro-1,5-naphthyridine-2,7-dicarbonitrile (rel)

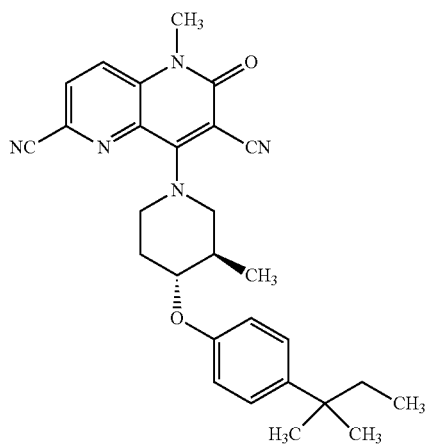

(230)

Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min; Detection: MS and UV (220 nm). Injection 1 results: Purity: 96.6%; Observed Mass: 470.36; Retention Time: 2.61 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). Injection 2 results: Purity: 95.8%; Observed Mass: 470.33; Retention Time: 2.60 min. $^1$H NMR (500 MHz, DMSO-$d_6$) δ 8.26 (d, J=8.9 Hz, 1H), 8.15 (d, J=9.2 Hz, 1H), 7.24 (br d, J=8.9 Hz, 2H), 6.96 (br d, J=8.5 Hz, 2H), 4.32 (td, J=8.7, 4.0 Hz, 1H), 4.25-4.12 (m, 2H), 3.78-3.62 (m, 1H), 2.31 (br dd, J=12.5, 2.7 Hz, 1H), 2.20 (br d, J=5.5 Hz, 1H), 1.76-1.66 (m, 1H), 1.58 (q, J=7.3 Hz, 2H), 1.22 (s, 6H), 1.03 (br d, J=6.4 Hz,

Example 231

5-methyl-8-(trans-3-methyl-4-(4-(tert-pentyl)phenoxy)piperidin-1-yl)-6-oxo-5,6-dihydro-1,5-naphthyridine-2,7-dicarbonitrile (rel)

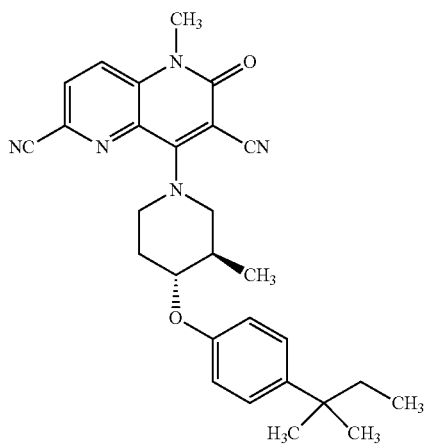

(231)

Analytical LC/MS was used to determine the final purity. Injection 1 conditions: Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min; Detection: MS and UV (220 nm). Injection 1 results: Purity: 98.2%; Observed Mass: 470.34; Retention Time: 2.61 min. Injection 2 conditions: Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). Injection 2 results: Purity: 95.6%; Observed Mass: 470.32; Retention Time: 2.6 min. $^1$H NMR (500 MHz, DMSO-$d_6$) δ 8.25 (d, J=8.9 Hz, 1H), 8.14 (d, J=9.2 Hz, 1H), 7.23 (br d, J=8.5 Hz, 2H), 6.96 (br d, J=8.5 Hz, 2H), 4.32 (dt, 4.5 Hz, 1H), 4.25-4.11 (m, 2H), 3.77-3.61 (m, 1H), 2.31 (br d, J=9.8 Hz, 1H), 2.22-2.08 (m, 1H), 1.76-1.64 (m, 1H), 1.58 (br d, J=7.3 Hz, 2H), 1.21 (s, 6H), 1.03 (br d, J=6.4 Hz, 3H), 0.63 (t, J=7.3 Hz, 3H). Full spectral assignment was not made due to water suppression technique employed.

Example 232

(+/−) 8-(4-((5-isopropoxypyridin-2-yl)oxy)-3,3-dimethylpiperidin-1-yl)-5-methyl-6-oxo-5,6-dihydro-1,5-naphthyridine-2-carbonitrile

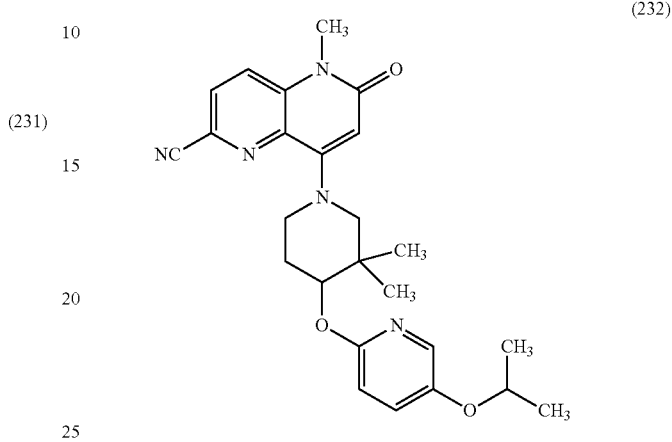

(232)

6-Cyano-1-methyl-2-oxo-1,2-dihydro-1,5-naphthyridin-4-yl trifluoromethanesulfonate (19.21 mg, 0.058 mmol) was added to a solution of the TFA salt of (+/−) 2-((3,3-dimethylpiperidin-4-yl)oxy)-5-isopropoxypyridine (24 mg, 0.063 mmol) and N-ethyl-N-isopropylpropan-2-amine (0.040 mL, 0.231 mmol) in DMF (1.5 mL) and the reaction mixture was heated at 70° C. overnight. The mixture was allowed to cool to room temperature and was then diluted with acetonitrile to a volume of 2 mL. This solution was filtered and then fractionated using preparative LC/MS with the following conditions: Column: XBridge C18, 200 mm×19 mm, 5-µm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 40% B, 40-80% B over 20 minutes, then a 0-minute hold at 100% B; Flow Rate: 20 mL/min; Column Temperature: 25° C. Fraction collection was triggered by MS signals. Fractions containing the product were combined and dried via centrifugal evaporation. The yield of the product was 16.4 mg, and its estimated purity by LCMS analysis was 100%. Analytical LC/MS was used to determine the final purity. Injection 1 conditions: Column: Waters XBridge C18, 2.1 mm×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min; Detection: MS and UV (220 nm). Injection 1 results: Purity: 100%; Observed Mass: 448.32; Retention Time: 2.33 min. Injection 2 conditions: Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). Injection 2 results: Purity: 100%; Observed Mass: 448.17; Retention Time: 2.17 min. $^1$H NMR (500 MHz, DMSO-$d_6$) δ 8.20-8.13 (m, 1H), 8.08 (d, J=8.8 Hz, 1H), 7.82 (d, J=3.1 Hz, 1H), 7.39 (dd, J=9.0, 2.9 Hz, 1H), 6.79 (d, J=8.9 Hz, 1H), 6.14 (s, 1H), 4.90 (br dd, J=9.2, 3.7 Hz, 1H), 4.52 (dt, J=12.0, 6.1 Hz, 1H), 3.80 (br d, J=12.5 Hz, 1H), 3.23-3.15 (m, 1H), 3.05 (br d, J=13.1 Hz, 1H), 2.16-2.06 (m, 1H), 1.86 (br dd, J=9.0, 4.1 Hz, 1H), 1.26 (d, J=5.8 Hz, 5H), 1.16 (s, 3H), 1.03 (s, 3H). Full spectral assignment was not made due to water suppression technique employed.

The racemic material was further purified by SCP using SFC-chiral chromatography. Two enantiomers were obtained. Example 232 was the first eluting isomer.

Example 233

8-(4-((5-isopropoxypyridin-2-yl)oxy)-3,3-dimethylpiperidin-1-yl)-5-methyl-6-oxo-5,6-dihydro-1,5-naphthyridine-2-carbonitrile (rel)

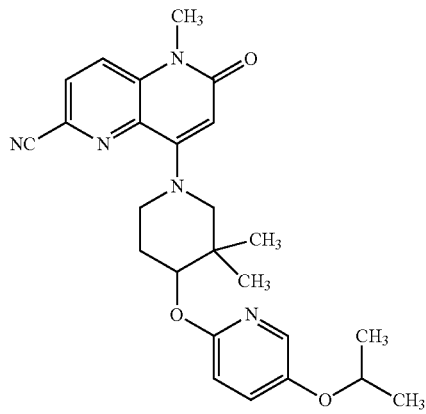

(233)

The yield of the product was 4.2 mg, and its purity was 96%. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min; Detection: MS and UV (220 nm). Injection 1 results: Purity: 99.3%; Observed Mass: 448.36; Retention Time: 2.19 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). Injection 2 results: Purity: 96.4%; Observed Mass: 447.92; Retention Time: 2.04 min. $^1$H NMR (500 MHz, DMSO-$d_6$) δ 8.18-8.14 (m, 1H), 8.08 (d, J=8.9 Hz, 1H), 7.82 (d, J=3.1 Hz, 1H), 7.39 (dd, J=9.2, 3.1 Hz, 1H), 6.79 (d, J=8.9 Hz, 1H), 6.14 (s, 1H), 4.90 (dd, J=8.7, 3.8 Hz, 1H), 4.52 (dt, J=12.0, 6.1 Hz, 1H), 3.80 (br d, J=11.9 Hz, 1H), 3.55 (s, 1H), 3.23-3.12 (m, 1H), 3.05 (br d, J=12.2 Hz, 1H), 2.17-2.09 (m, 1H), 1.85 (br dd, J=9.0, 4.1 Hz, 1H), 1.26 (d, J=6.1 Hz, 6H), 1.16 (s, 3H), 1.03 (s, 3H). Full spectral assignment was not made due to water suppression technique employed. Example 233 was the second eluting isomer.

Example 234

8-(4-((5-isopropoxypyridin-2-yl)oxy)-3,3-dimethylpiperidin-1-yl)-5-methyl-6-oxo-5,6-dihydro-1,5-naphthyridine-2-carbonitrile (rel)

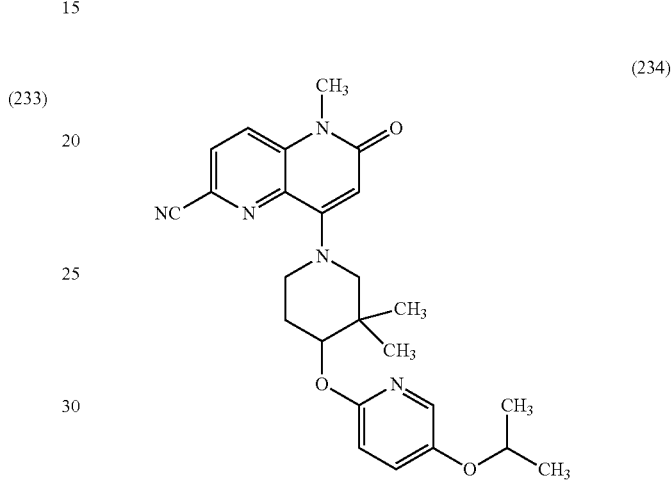

(234)

The yield of the product was 3.6 mg, and its purity was 98%. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min; Detection: MS and UV (220 nm). Injection 1 results: Purity: 100%; Observed Mass: 448.38; Retention Time: 2.19 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). Injection 2 results: Purity: 97.5%; Observed Mass: 447.90; Retention Time: 2.04 min. $^1$H NMR (500 MHz, DMSO-$d_6$) δ 8.21-8.13 (m, 1H), 8.08 (d, J=8.9 Hz, 1H), 7.82 (d, J=2.7 Hz, 1H), 7.39 (dd, J=8.9, 3.1 Hz, 1H), 6.78 (d, J=9.2 Hz, 1H), 6.14 (s, 1H), 4.90 (dd, J=8.9, 4.0 Hz, 1H), 4.52 (dt, J=12.1, 6.0 Hz, 1H), 3.80 (br d, J=12.2 Hz, 1H), 3.55 (s, 1H), 3.25-3.13 (m, 1H), 3.05 (br d, J=12.2 Hz, 1H), 2.15-2.09 (m, 1H), 1.90-1.80 (m, 1H), 1.26 (d, J=5.8 Hz, 6H), 1.16 (s, 3H), 1.03 (s, 3H). Full spectral assignment was not made due to water suppression technique employed.

Example 235

(+/−) 5-methyl-8-(cis-3-methyl-4-((4-(trifluoromethoxy)benzyl)oxy)piperidin-1-yl)-6-oxo-5,6-dihydro-1,5-naphthyridine-2-carbonitrile

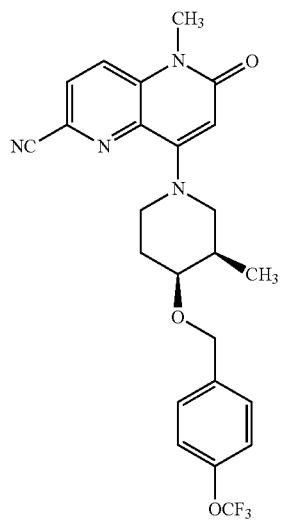

(235)

Sodium hydride (4.02 mg, 0.084 mmol) was added to a suspension of (+/−) 8-(cis-4-hydroxy-3-methylpiperidin-1-yl)-5-methyl-6-oxo-5,6-dihydro-1,5-naphthyridine-2-carbonitrile (25 mg, 0.084 mmol) in THF (5 mL). The reaction mixture was stirred at room temperature under nitrogen for 10 min. 1-(Bromomethyl)-4-(trifluoromethoxy) benzene (0.013 mL, 0.084 mmol) was added in a single portion and the reaction mixture was stirred at room temperature overnight. Two drops of glacial acetic acid were added and the mixture was filtered and then purified using preparative LC/MS with the following conditions: Column: XBridge C18, 200 mm×19 mm, 5-μm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 40% B, 40-80% B over 20 minutes, then a 5-minute hold at 100% B; Flow Rate: 20 mL/min; Column Temperature: 25° C. Fraction collection was triggered by UV signals. Fractions containing the product were combined and dried via centrifugal evaporation. The yield of the product was 1.8 mg, and its estimated purity by LCMS analysis was 99%. Analytical LC/MS was used to determine the final purity. Injection 1 conditions: Column: Waters) XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min; Detection: MS and UV (220 nm). Injection 1 results: Purity: 99.3%; Observed Mass: 473.15; Retention Time: 2.49 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). Injection 2 results: Purity: 99.1%; Observed Mass: 473.09; Retention Time: 2.38 min. $^1$H NMR (500 MHz, DMSO-$d_6$) δ 8.16-8.11 (m, 1H), 8.08-8.03 (m, 1H), 7.51 (br d, J=8.2 Hz, 2H), 7.38-7.32 (m, 2H), 6.10-6.07 (m, 1H), 4.64 (br d, J=12.2 Hz, 1H), 4.52 (br d, J=12.5 Hz, 1H), 3.71-3.64 (m, 1H), 2.17 (br s, 1H), 1.99 (br s, 1H), 1.86-1.74 (m, 2H), 1.03 (br d, J=6.7 Hz, 3H). All the protons of the piperidine were not assigned due to the water suppression technique used in the spectra's acquisition.

An additional component, Example 236, was isolated from the same crude material.

Example 236

(+/−) 5-methyl-8-(cis-3-methyl-4-((4-(trifluoromethoxy)benzyl)oxy)piperidin-1-yl)-6-oxo-5,6-dihydro-1,5-naphthyridine-2-carboxamide

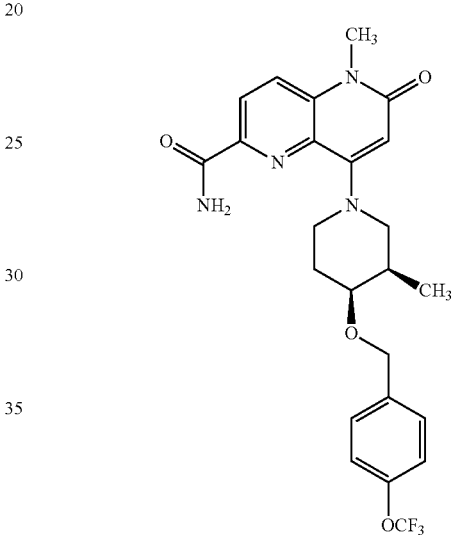

(236)

The crude material of Example 235 was purified via preparative LC/MS with the following conditions: Column: XBridge C18, 200 mm×19 mm, 5-μm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 40% B, 40-80% B over 20 minutes, then a 5-minute hold at 100% B; Flow Rate: 20 mL/min; Column Temperature: 25° C. Fraction collection was triggered by UV signals. Fractions containing the product were combined and dried via centrifugal evaporation. The yield of the product was 6.9 mg, and its estimated purity by LCMS analysis was 94%. Analytical LC/MS was used to determine the final purity. Injection 1 conditions: Column: Waters) XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). Injection 1 results: Purity: 96.2%; Observed Mass: 491.12; Retention Time: 2.03 min. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min; Detection: MS and UV (220 nm). Injection 2 results: Purity: 93.9%; Observed Mass: 491.15; Retention Time: 2.12 min. $^1$H NMR (500 MHz, DMSO-$d_6$) δ 8.22-8.14 (m, 1H), 8.09-8.01 (m, 1H), 7.83-7.74 (m, 1H), 7.55-7.47 (m, 3H), 7.41-7.30 (m, 2H), 6.11-6.03 (m, 1H), 4.73-4.62 (m, 1H), 4.53-4.47 (m, 1H), 3.73-3.64 (m, 1H), 3.59-3.50 (m, 1H), 3.43-3.32 (m, 1H), 3.32-3.22 (m, 1H), 2.27-2.15 (m, 1H), 2.11-2.00 (m, 1H), 1.03-0.93 (m, 3H). All the protons of the piperidine were not assigned due to the water suppression technique used in the acquisition of the spectra.

Example 237

7-fluoro-5-methyl-6-oxo-8-(4-(4-(trifluoromethoxy) phenoxy)piperidin-1-yl)-5,6-dihydro-1,5-naphthyridine-2-carbonitrile

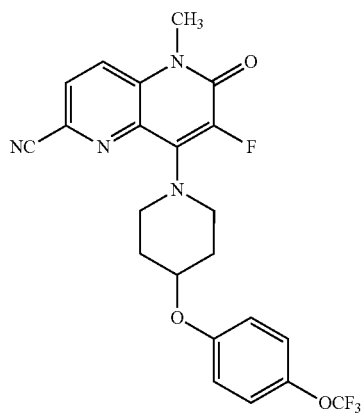

(237)

5-methyl-6-oxo-8-(4-(4-(trifluoromethoxy)phenoxy)piperidin-1-yl)-5,6-dihydro-1,5-naphthyridine-2-carbonitrile, (25 mg, 0.056 mmol) was dissolved in a mixture of acetonitrile (0.4 mL) and THF (0.2 mL) and the resultant mixture was cooled to 0° C. under a nitrogen atmosphere. 1-Chloromethyl-4-fluoro-1,4-diazoniabicyclo[2.2.2]octane bis(tetrafluoroborate) (22.4 mg, 0.063 mmol) dissolved in a 1:1 mixture of water and THF (0.3 mL) was added and the mixture was allowed to warm to room temperature and stirring was continued for 2 h. The mixture was diluted to a volume of 1.8 mL by the addition of DMF and the crude solution was purified via preparative LC/MS with the following conditions: Column: XBridge C18, 200 mm×19 mm, 5-μm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 40% B, 40-80% B over 20 minutes, then a 5-minute hold at 100% B; Flow Rate: 20 mL/min; Column Temperature: 25° C. Fraction collection was triggered by MS and UV signals. Fractions containing the product were combined and dried via centrifugal evaporation. The yield of the product was 12.6 mg, and its estimated purity by LCMS analysis was 100%. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 463.11; Retention Time: 2.26 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 463.11; Retention Time: 2.25 min. $^1$H NMR (500 MHz, DMSO-$d_6$) δ 8.18-8.13 (m, 1.0H), 8.12-8.08 (m, 1.0H), 7.28 (br d, J=8.2 Hz, 2.0H), 7.11 (br d, J=8.9 Hz, 2.0H), 4.69 (dt, J=7.6, 3.5 Hz, 1.0H), 3.71 (br d, J=13.7 Hz, 1.3H), 3.60 (s, 0.5H), 3.42 (br J=9.9 Hz, 1.1H), 2.18-2.07 (m, 2.0H), 1.87-1.75 (m, 1.9H). Signals adjacent to the water suppression frequency exhibit reduced intensity. Report values are uncorrected for the effects of water suppression: $^{19}$F signals observed in proton decoupled spectra: $^{19}$F NMR (471 MHz, DMSO-$d_6$) δ −57.23, −140.76 ppm.

Example 238

7-chloro-5-methyl-6-oxo-8-(4-(4-(trifluoromethoxy) phenoxy)piperidin-1-yl)-5,6-dihydro-1,5-naphthyridine-2-carbonitrile

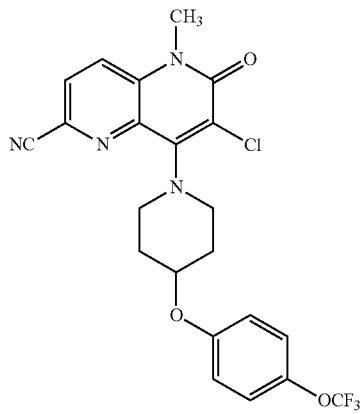

(238)

5-methyl-6-oxo-8-(4-(4-(trifluoromethoxy)phenoxy)piperidin-1-yl)-5,6-dihydro-1,5-naphthyridine-2-carbonitrile (20 mg, 0.045 mmol) was dissolved in anhydrous DMF (0.4 ml) and the solution was cooled to 0° C. under nitrogen. NCS (9.4 mg, 0.070 mmol) was then added and the mixture was stirred for 5 min and then heated to 50° C. for 2 h. The crude solution was purified via preparative LC/MS with the following conditions: Column: XBridge C18, 200 mm×19 mm, 5-μm particles; Mobile Phase A: 5:95 acetonitrile:water with 10-mM ammonium acetate; Mobile Phase B: 95:5 acetonitrile: water with 10-mM ammonium acetate; Gradient: a 0-minute hold at 41% B, 41-81% B over 25 minutes, then a 4-minute hold at 100% B; Flow Rate: 20 mL/min; Column Temperature: 25° C. Fraction collection was triggered by MS and UV signals. Fractions containing the product were combined and dried via centrifugal evaporation. The yield of the product was 11.8 mg, and its estimated purity by LCMS analysis was 100%. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 1 results: Purity: 100.0%; Observed Mass: 479.08; Retention Time: 2.35 min. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 2 results: Purity: 100.0%; Observed Mass: 479.09; Retention Time: 2.39 min. $^1$H NMR (400 MHz, CHLOROFORM-d) δ 7.86-7.78 (m, 1.0H), 7.76-7.70 (m, 1.0H), 7.22-7.13 (m, 2.0H), 7.03-6.93 (m, 2.0H), 4.61 (tt, J=7.2, 3.6 Hz, 1.0H), 3.90-3.78 (m, 2.1H), 3.74 (s, 3.0H), 3.57 (ddd, J=13.1, 7.7, 3.4 Hz, 2.1H), 2.28-2.18 (m, 2.0H), 2.11-1.99 (m, 2.0H).

Example 239

7-bromo-5-methyl-6-oxo-8-(4-(4-(trifluoromethoxy)phenoxy)piperidin-1-yl)-5,6-dihydro-1,5-naphthyridine-2-carbonitrile

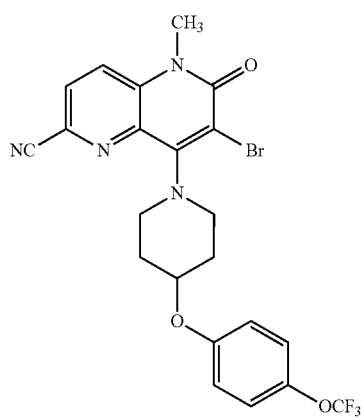

(239)

5-methyl-6-oxo-8-(4-(4-(trifluoromethoxy)phenoxy)piperidin-1-yl)-5,6-dihydro-1,5-naphthyridine-2-carbonitrile (20 mg, 0.045 mmol) was dissolved in DMF (0.45 mL) in a dry one dram vial. NBS (9.1 mg, 0.051 mmol) was added and the mixture was stirred under nitrogen at room temperature for 4 h. One drop of water was then added and the reaction mixture was diluted to 1.8 mL by the addition of acetonitrile. This crude solution was purified via preparative LC/MS with the following conditions: Column: XBridge C18, 200 mm×19 mm, 5-μm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 45% B, 45-85% B over 20 minutes, then a 5-minute hold at 100% B; Flow Rate: 20 mL/min; Column Temperature: 25° C. Fraction collection was triggered by MS and UV signals. Fractions containing the product were combined and dried via centrifugal evaporation. The yield of the product was 14.3 mg, and its estimated purity by LCMS analysis was 95%. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 95.1%; Observed Mass: 523.03; Retention Time: 2.4 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 96.2%; Observed Mass: 523.01; Retention Time: 2.4 min. $^1$H NMR (500 MHz, DMSO-d$_6$) δ 8.20-8.15 (m, 1.0H), 8.15-8.09 (m, 1.0H), 7.28 (br d, J=8.5 Hz, 2.0H), 7.13 (br d, J=8.9 Hz, 2.0H), 4.72 (dt, J=7.8, 4.0 Hz, 1.0H), 3.72-3.60 (m, 1.6H), 3.53-3.43 (m, 0.4H), 2.14 (br d, J=10.1 Hz, 2.0H), 1.92-1.78 (m, 2.0H). The signals adjacent to the water suppression frequency of 3.57 ppm exhibited reduced intensities.

Example 240

7-(6-methoxypyridin-3-yl)-5-methyl-6-oxo-8-(4-(4-(trifluoromethoxy)phenoxy)piperidin-1-yl)-5,6-dihydro-1,5-naphthyridine-2-carbonitrile

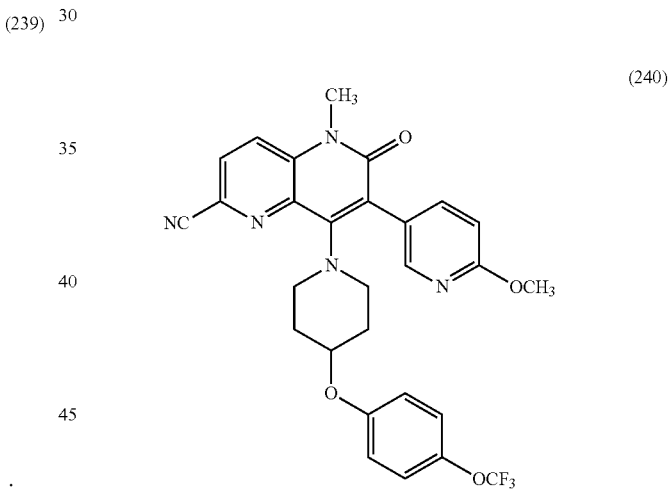

(240)

In a dry one dram vial were placed bis(triphenylphosphine)palladium(ii) dichloride (3.9 mg, 5.56 μmol), copper (I) chloride (19.1 mg, 0.193 mmol), lithium chloride (13 mg, 0.307 mmol) and 7-bromo-5-methyl-6-oxo-8-(4-(4-(trifluoromethoxy)phenoxy)piperidin-1-yl)-5,6-dihydro-1,5-naphthyridine-2-carbonitrile (25 mg, 0.048 mmol) and 2-methoxy-5-(tributylstannyl)pyridine (34 mg, 0.085 mmol). Anhydrous DMSO (0.48 mL) was added and the vial was sealed, evacuated and then flushed with nitrogen. The reaction mixture was then heated at 100° C. overnight. It was then cooled and filtered and the volume adjusted to 1.8 mL by the addition of DMF. The crude solution was purified via preparative LC/MS with the following conditions: Column: XBridge C18, 200 mm×19 mm, 5-μm particles; Mobile Phase A: 5:95 acetonitrile:water with 10-mM ammonium acetate; Mobile Phase B: 95:5 acetonitrile: water with 10-mM ammonium acetate; Gradient: a 0-minute hold at 45% B, 45-85% B over 20 minutes, then a 4-minute hold at 100% B; Flow Rate: 20 mL/min; Column Temperature: 25° C. Fraction collection was triggered by MS and UV signals. Fractions containing the product were combined and dried via centrifugal evaporation. The yield of the product was 15.1 mg, and its estimated purity by LCMS analysis was 96%. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 97.1%; Observed Mass: 552.13; Retention Time: 2.4 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 96.0%; Observed Mass: 552.15; Retention Time: 2.28 min. $^1$H NMR (500 MHz, DMSO-$d_6$) δ 8.19-8.13 (m, 1.1H), 8.12-8.07 (m, 1.0H), 8.05 (s, 1.0H), 7.65 (br d, J=9.2 Hz, 1.1H), 7.23 (br d, J=8.2 Hz, 2.1H), 7.04 (br d, J=8.9 Hz, 2.1H), 6.91 (d, J=8.5 Hz, 1.0H), 4.53 (br s, 1.0H), 3.89 (s, 2.9H), 3.59 (s, 0.3H), 3.23 (br d, J=12.8 Hz, 1.5H), 2.82 (br t, J=10.2 Hz, 1.9H), 1.96 (br d, J=11.3 Hz, 2.0H), 1.76-1.64 (m, 2.1H). Reported values are uncorrected for the effects of water suppression.

Example 241

7-(2-methoxypyridin-4-yl)-5-methyl-6-oxo-8-(4-(4-(trifluoromethoxy)phenoxy)piperidin-1-yl)-5,6-dihydro-1,5-naphthyridine-2-carbonitrile

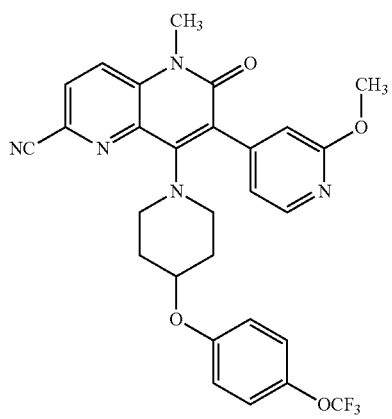

(241)

In a dry one dram vial were loaded bis(triphenylphosphine)palladium(ii) dichloride (3.7 mg, 5.27 μmol), copper (I) chloride (19.0 mg, 0.192 mmol), lithium chloride (13.2 mg, 0.311 mmol), 3-bromo-1-methyl-2-oxo-4-(4-(4-(trifluoromethoxy) phenoxy)piperidin-1-yl)-1,2-dihydroquinoline-6-carbonitrile (25 mg, 0.048 mmol) and 2-methoxy-4-(tributylstannyl)pyridine (32 mg, 0.080 mmol). Anhydrous DMSO (0.48 ml) was added and the vial was sealed, evacuated and then flushed with nitrogen. The reaction mixture was then heated at 100° C. overnight. It was then cooled and filtered and the volume adjusted to 1.8 mL by the addition of DMF. The crude solution was purified by preparative LC/MS with the following conditions: Column: XBridge C18, 200 mm×19 mm, 5-μm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 44% B, 44-84% B over 20 minutes, then a 4-minute hold at 100% B; Flow Rate: 20 mL/min; Column Temperature: 25° C. Fraction collection was triggered by MS and UV signals. Fractions containing the product were combined and dried via centrifugal evaporation. The yield of the product was 12.7 mg, and its estimated purity by LCMS analysis was 97%. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.75 min hold at 100% B; Flow: 1 mL/min; Detection: MS and UV (220 nm). Injection 1 results: Purity: 97.8%; Observed Mass: 552.14; Retention Time: 2.37 min. Injection 2 conditions: Column: Waters) XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm). Injection 2 results: Purity: 96.6%; Observed Mass: 552.15; Retention Time: 2.14 min. $^1$H NMR (500 MHz, DMSO-$d_6$) δ 8.24-8.15 (m, 2.0H), 8.13-8.07 (m, 1.0H), 7.23 (br d, J=8.5 Hz, 2.0H), 7.04 (br d, J=8.9 Hz, 2.1H), 6.88 (br d, J=4.9 Hz, 1.0H), 6.74 (s, 1.0H), 4.62-4.50 (m, 1.0H), 3.88 (s, 2.7H), 3.59-3.56 (m, 0.3H), 3.25 (br d, J=13.7 Hz, 1.3H), 2.84 (br t, J=10.1 Hz, 1.8H), 1.97 (br d, J=10.7 Hz, 2.0H), 1.77-1.65 (m, 2.0H). Reported values were uncorrected for the effects of water suppression.

Example 242

(+/−) 6-bromo-1-methyl-4-(trans-3-methyl-4-(4-(tert-pentyl)phenoxy)piperidin-1-yl)-2-oxo-1,2-dihydro-1,5-naphthyridine-3-carbonitrile

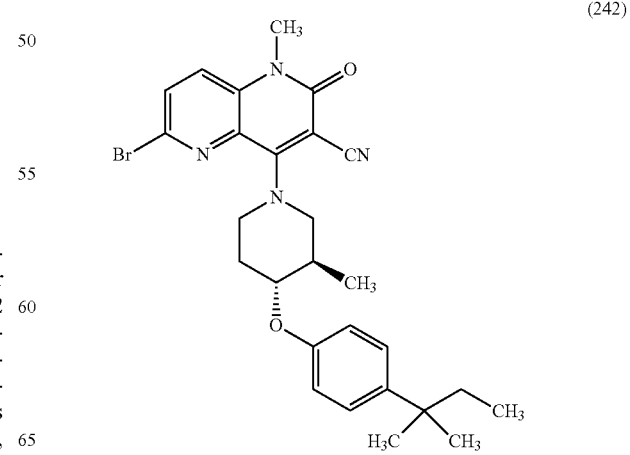

(242)

To a solution of 4-(tert-pentyl)phenol (65.3 mg, 0.398 mmol) in THF (8 mL), triphenylphosphine (194 mg, 0.583 mmol) on solid support was added. The reaction mixture was stirred at room temperature for 5 min. Then, di-tert-butyl (E)-diazene-1,2-dicarboxylate (98 mg, 0.424 mmol) and (+/−) 6-bromo-4-(cis-4-hydroxy-3-methylpiperidin-1-yl)-1-methyl-2-oxo-1,2-dihydro-1,5-naphthyridine-3-carbonitrile (100 mg, 0.265 mmol) were added. The reaction mixture was stirred at room temperature for 6 days. The reaction mixture was then filtered and the filtrate concentrated under vacuum to give a yellow solid. The product was purified using reverse phase preparative HPLC column using a $CH_3CN$—$H_2O$-TFA solvent system as eluent. Homogeneous fractions were collected and concentrated in vacuo to give the TFA salt of the title compound as a light-yellow colored solid, (31 mg, 0.049 mmol, 18.34% yield). LCMS: (m/z): (M+H)$^+$=523.0. $^1$H NMR (400 MHz, acetone) δ 7.98 (d, J=9.0 Hz, 1H), 7.86 (d, J=9.0 Hz, 1H), 7.30 (d, J=8.8 Hz, 2H), 7.01 (d, J=8.8 Hz, 2H), 4.40-4.32 (m, 2H), 4.31-4.23 (m, 1H), 3.77 (ddd, J=13.4, 10.9, 2.8 Hz, 1H), 3.63 (s, 3H), 3.35 (dd, J=13.2, 9.8 Hz, 1H), 2.54-2.42 (m, 1H), 2.37 (ddd, J=12.6, 6.2, 2.9 Hz, 1H), 1.97-1.78 (m, 1H), 1.15 (d, J=6.6 Hz, 3H), 0.69 (t, J=7.5 Hz, 3H). A full assignment was not made due to obfuscation of certain compound associated peaks by solvent impurities.

LCMS Methods Employed in Preceeding Tables:

Method 1: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm).

Method 2: Start % B=0, Final % B=100, Gradient Time=4 min, Flow Rate=0.8 ml/min, Wavelength=220, Solvent Pair=Water-Methanol-0.1% TFA, Solvent A=90% Water–10% Methanol-0.1% TFA, Solvent B=10% Water–90% Methanol-0.1% TFA, Column 2=(2) PHENOMENEX-LUNA 2.0×50 mm 3 μm, Method 3: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm).

Method 4: Column: Waters Acquity UPLC BEH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1%, trifluoroacetic acid; Temperature: 50° C.; Gradient: 0-100% B over 3 minutes, then a 0.75-minute hold at 100% B; Flow: 1.0 mL/min; Detection: UV at 220 nm.

Method 5: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min; Detection: MS and UV (220 nm).

LCMS Conditions:

Method A: Column: Waters Acquity UPLC BEH C18 (2.1×50 mm) 1.7 μm, Mobile phase A: 10 mM NH$_4$OAc: acetonitrile (95:5); Mobile phase B: 10 mM NH$_4$OAc: acetonitrile (5:95), Gradient=20-90% B over 1.1 minute, then a 0.6 minute hold at 90% B; Temperature: 50° C.; Flow rate: 0.7 mL/min; Detection: UV at 220 nm.

Method B: Column: Ascentis Express C18 (2.1×50 mm), 2.7 μm; Mobile phase A: 10 mM NH$_4$OAc:acetonitrile (95:5), Mobile phase B: 10 mM NH$_4$OAc: acetonitrile (5:95), Gradient=0-100% B over 3 minutes; Temperature: 50° C.; Flow rate: 1.1 mL/min; Detection: UV at 220 nm.

Method C: Column: XBridge BEH XP C18 (50×2.1 mm), 2.5 μm; Mobile phase A: 95% water: 5% acetonitrile; 10 mM ammonium acetate; Mobile phase B: 5% Water: 95% acetonitrile; 10 mM ammonium acetate; Flow: 1.1 mL/min; Temp: 50° C.; Time (min): 0-3; % B: 0-100%)

Method D: Column: Kinetex XB-C18 (3×75 mm) 2.6 μm; Mobile phase A: 10 mM ammonium formate: acetonitrile (98:2), Mobile phase B: 10 mM ammonium formate: acetonitrile (2:98), Gradient=20-100% B over 4 minutes, then a 0.6 minute hold at 100% B; Temperature: 27° C.; Flow rate: 1.0 mL/min; Detection: UV at 220 nm.

Intermediate 73

Ethyl 3-((3-methoxy-2-methyl-3-oxopropyl)amino)butanoate

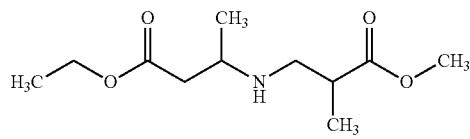

(I-73)

A mixture of ethyl 3-aminobutanoate (25 g, 191 mmol), methyl methacrylate (50 mL, 191 mmol), acetic acid (1.5 mL, 26.2 mmol and ethanol (40 mL) were heated at reflux for 16 h. The reaction mixture was cooled to room temperature and was poured into a beaker containing ether (300 mL). The solid was separated and was washed with ether (50 mL). The organic phase was washed with a saturated solution of NaHCO$_3$ (2×50 mL), brine (30 mL), dried over Na$_2$SO$_4$ and evaporated under reduced pressure to yield ethyl 3-((3-methoxy-2-methyl-3-oxopropyl)amino)butanoate as a yellow liquid. LCMS: m/z, 232.2 (M+H); rt 1.42 min; LCMS Method: Column-Kinetex XB-C18 (75×3 mm-2.6 μm); Mobile phase A: 10 mM NH$_4$COOH in water:acetonitrile (98:2), Mobile phase B: 10 mM NH$_4$COOH in water:acetonitrile (2:98), Gradient=20-100% B over 4.0 minutes, Flow rate: 1.0 mL; then 0.6 minute hold at 100% B, Flow rate: 1.5 mL; then 100-20% B over 0.1 min, Flow rate: 1.5 mL; then 0.3 minute hold at 20% B, Flow rate: 1.5 mL; Detection: ELSD.

Intermediates 73A and 73B (±)-Cis tert-butyl-2,5-dimethyl-4-oxopiperidine-1-carboxylate and (±)-Trans tert-butyl-2,5-dimethyl-4-oxopiperidine-1-carboxylate

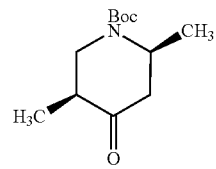

(I-73A)

-continued (I-73B)

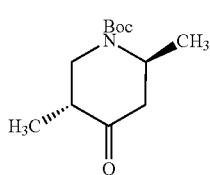

Sodium (2.98 g, 130 mmol) metal was taken in xylene (100 mL) and was heated to 100° C. and a mixture of ethyl 3-aminobutyrate and ethyl 3-((3-methoxy-2-methyl-3-oxopropyl) amino) butanoate (30 g, 130 mmol) in xylene (30 mL) was slowly added to the solution. The heating was continued at 140° C. for 2 h. The reaction mixture was cooled to room temperature, and the xylenes were removed under reduced pressure to afford the crude 3-(ethoxycarbonyl)-2,5-dimethyl-4-piperidone as a brown solid. To this crude mixture was added 20% HCl (100 mL) slowly at 0° C. in 2 h. Reaction mixture stirred for 2 h at room temperature and was reflux at 100° C. for 16 h. The reaction mixture was cooled to room temperature and was evaporated under reduced pressure to afford the crude as a brown solid. The residue was dissolved in methanol (450 mL) and added TEA (50 mL, 359 mmol), and Boc-anhydride (50 mL, 215 mmol). The reaction mixture was heated to reflux for 2 h, cooled to room temperature and the solvents were evaporated under reduced pressure. The residue was dissolved in ether (400 mL), washed with water (2×50 mL), brine (2×50 mL), dried over and evaporated under reduced pressure to afford a brown liquid, was purified by chromatography (ELSD method) on silica gel using hexanes/ethyl acetate (80:20) as eluents to afford cis-piperidone and the trans-piperidone.

Intermediate 73A: (±)-Cis Piperidone isomer (Solid): LCMS: m/z, [(M-Boc)+H] 172.2; rt 2.29 min; LCMS Method: Column-Kinetex XB-C18 (75×3 mm-2.6 μm); Mobile phase A: 10 mM $NH_4COOH$ in water:acetonitrile (98:2), Mobile phase B: 10 mM $NH_4COOH$ in water:acetonitrile (02:98), Gradient=20-100% B over 4.0 minutes, Flow rate: 1.0 mL; then 0.6 minute hold at 100% B, Flow rate: 1.5 mL; then 100-20% B over 0.1 min, Flow rate: 1.5 mL; then 0.3 minute hold at 20% B, Flow rate: 1.5 mL; Detection: ELSD. $^1$H NMR ($CDCl_3$) δ ppm 4.87-4.52 (m, 1H), 4.38-4.15 (m, 1H), 2.84-2.82 (m, 1H), 2.68 (dd, J=6.8 Hz, J=13.6 Hz, 1H), 2.54-2.52 (m, 1H), 2.25 (dd, J=2.0 Hz, J=13.6 Hz, 1H), 1.51 (s, 9H), 1.15 (d, J=6.8 Hz, 3H), 1.02 (d, J=6.4 Hz, 3H).

Intermediate 73B: (±)-Trans Piperidone isomer (Yellow liquid): LCMS: m/z, [[(M-Boc)+H] 172.2; rt 2.19 min. LCMS Method: Column-Kinetex XB-C18 (75×3 mm-2.6 μm); Mobile phase A: 10 mM $NH_4COOH$ in water:acetonitrile (98:02), Mobile phase B: 10 mM $NH_4COOH$ in water:acetonitrile (2:98), Gradient=20-100% B over 4.0 minutes, Flow rate: 1.0 mL; then 0.6 minute hold at 100% B, Flow rate: 1.5 mL; then 100-20% B over 0.1 min, Flow rate: 1.5 mL; then 0.3 minute hold at 20% B, Flow rate: 1.5 mL; Detection: ELSD. $^1$H NMR ($CDCl_3$) δ ppm 4.60-4.56 (m, 1H), 3.77 (dd, J=4.6 Hz, J=13.8 Hz, 1H), 3.64 (dd, J=4.4 Hz, J=13.8 Hz, 1H), 2.64 (dd, J=6.8 Hz, J=15.2 Hz, 1H), 2.53-2.48 (m, 1H), 2.09 (dd, J=3.6 Hz, J=15.2 Hz, 1H), 1.47 (s, 9H), 1.14 (d, J=7.2 Hz, 3H), 1.05 (d, J=6.4 Hz, 3H).

Intermediate 74

(±)-Cis-tert-butyl-4-hydroxy-2,5-dimethylpiperidine-1-carboxylate

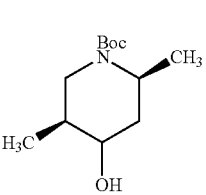

(I-74)

To a stirred solution of (±)-cis-tert-butyl-2,5-dimethyl-4-oxopiperidine-1-carboxylate (800 mg, 3.52 mmol) in dry MeOH (6.0 mL) at 0° C., was added sodium borohydride (333 mg, 8.80 mmol) and stirred for 2 h at room temperature. The reaction was quenched with saturated sodium bicarbonate solution. Ethyl acetate was added to the mixture and the mixture was stirred for 10 minutes. The organic layer was separated and the aqueous layer was extracted with ethyl acetate (2×50 mL). The combined organic layer dried over sodium sulphate and evaporated under reduced pressure to afford a diastereomeric mixture of (±)-cis-tert-butyl-4-hydroxy-2,5-dimethylpiperidine-1-carboxylate. LCMS: m/z, 230.2 [M+H]; rt 2.0 min. LCMS Method: Column-Kinetex XB-C18 (75×3 mm-2.6 μm); Mobile phase A: 10 mM $NH_4COOH$ in water:acetonitrile (98:02), Mobile phase B: 10 mM $NH_4COOH$ in water:acetonitrile (02:98), Gradient=20-100% B over 4.0 minutes, Flow rate: 1.0 mL; then 0.6 minute hold at 100% B, Flow rate: 1.5 mL; then 100-20% B over 0.1 min, Flow rate: 1.5 mL; then 0.3 minute hold at 20% B, Flow rate: 1.5 mL; Detection: ELSD.

Intermediate 75

(±)-Cis-Tert-butyl-4-((5-isopropoxypyridin-2-yl)oxy)-2,5-dimethylpiperidine-1-carboxylate

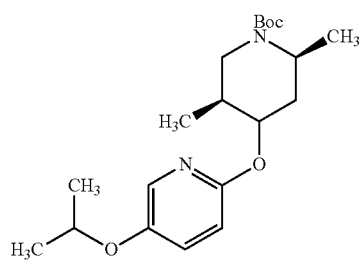

(I-75)

To a mixture of (±)-cis-tert-butyl-4-((5-isopropoxypyridin-2-yl)oxy)-2,5-dimethylpiperidine-1-carboxylate (500 mg, 2.18 mmol) and 2-fluoro-5-isopropoxypyridine (338 mg, 2.18 mmol) in DMSO (15 mL), potassium tert-butoxide (294 mg, 2.62 mmol) was added under a nitrogen atmosphere. The reaction mixture was stirred for 16 h at room temperature. The reaction mixture diluted with ether, washed with water, dried over sodium sulphate and evaporated under reduced pressure to afford crude product which was purified by chromatography (ELSD method) on silica gel using hexanes/ethyl acetate (80:20) as eluents to afford (±)-cis-tert-butyl (2S,5S)-4-((5-isopropoxypyridin-2-yl)

oxy)-2,5-dimethylpiperidine-1-carboxylate. LCMS: m/z, 365.2 [M+H]; rt 4.0 min. LCMS Method: Column-Kinetex XB-C18 (75×3 mm-2.6 μm); Mobile phase A: 10 mM NH$_4$COOH in water:acetonitrile (98:02), Mobile phase B: 10 mM NH$_4$COOH in water:acetonitrile (2:98), Gradient=20-100% B over 4.0 minutes, Flow rate: 1.0 mL; then 0.6 minute hold at 100% B, Flow rate: 1.5 mL; then 100-20% B over 0.1 min, Flow rate: 1.5 mL; then 0.3 minute hold at 20% B, Flow rate: 1.5 mL; Detection: ELSD.

Intermediate 76

(±)-cis-2-(2,5)-dimethylpiperidin-4-yl)oxy)-5-isopropoxypyridine

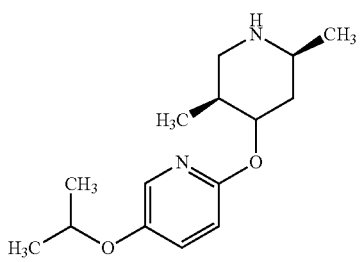

(I-76)

To a solution of (±)-cis-tert-butyl-4-((5-isopropoxypyridin-2-yl)oxy)-2,5-dimethylpiperidine-1-carboxylate (350 mg, 0.96 mmol) in DCM (5.0 mL), TFA (0.370 mL, 4.80 mmol) was added at room temperature. The reaction mixture was stirred for 4 h. The reaction mixture was evaporated under reduced pressure to afford the light yellow liquid of (±)-cis-2-(2,5)-dimethylpiperidin-4-yl)oxy)-5-isopropoxypyridine. LCMS: m/z, 265.2 [M+H]; rt 1.58 min. LCMS Method: Column-Kinetex XB-C18 (75×3 mm-2.6 μm); Mobile phase A: 10 mM NH$_4$COOH in water:acetonitrile (98:2), Mobile phase B: 10 mM NH$_4$COOH in water:acetonitrile (2:98), Gradient=20-100% B over 4.0 minutes, Flow rate: 1.0 mL; then 0.6 minute hold at 100% B, Flow rate: 1.5 mL; then 100-20% B over 0.1 min, Flow rate: 1.5 mL; then 0.3 minute hold at 20% B, Flow rate: 1.5 mL; Detection: ELSD.

Examples 243 to 246

(±)-Cis-(-4-((5-isopropoxypyridin-2-yl)oxy)-2,5-dimethylpiperidin-1-yl)-1-methyl-2-oxo-1,2-dihydropyrido[3,2-d]pyrimidine-6-carbonitrile

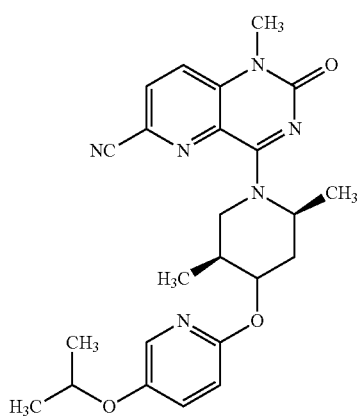

(243)

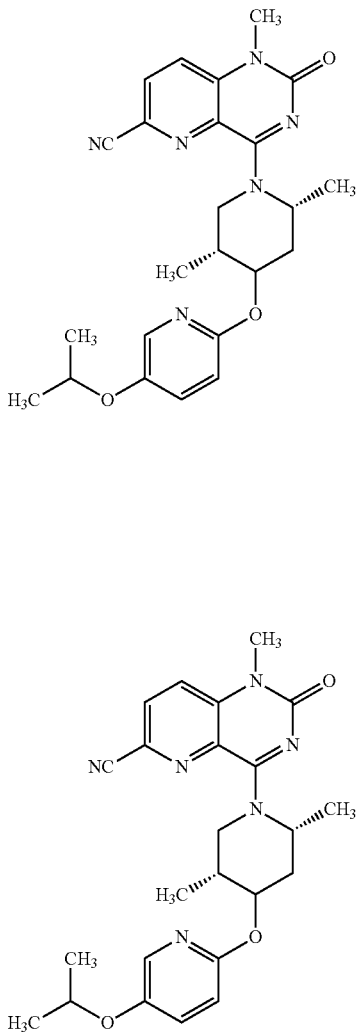

(244)

(245)

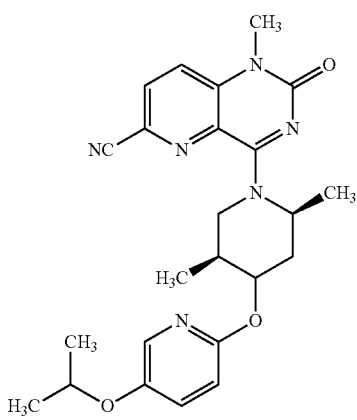 [SMILES: CC(C)Oc1ccc(OC2C[C@H](C)N(c3nc(=O)n(C)c4ccc(C#N)nc34)C[C@H]2C)nc1]

(246)

To a stirred solution of (±)-Cis-6-chloro-4-(~4-((5-isopropoxypyridin-2-yl)oxy)-2,5-dimethylpiperidin-1-yl)-1-methylpyrido[3,2-d]pyrimidin-2(1H)-one (50 mg, 0.11 mmol) in THF (2.0 mL) and water (1.0 mL), was added zinc cyanide (25.6 mg, 0.22 mmol). The mixture was purged with argon for 5 minutes and chloro[2-(di-tert-butylphosphino)-2',4',6'-triisopropyl-1,1'-biphenyl][2-(2-aminoethyl)phenyl)] palladium(II), [2-(di-tert-butylphosphino)-2',4',6'-triisopropyl-1,1'-biphenyl][2-(2-aminoethyl)phenyl)] palladium(II) chloride (tBuXPhos-Pd-G1) (0.750 mg, 1.09 µmol) was added at room temperature. The reaction mixture was heated at 40° C. for 24 h. The reaction mixture was cooled to room temperature, concentrated under reduced pressure, diluted with dichloromethane, washed with water, dried over sodium sulphate, evaporated under reduced pressure to yield the crude product which was purified by preparative HPLC to afford Racemate Mixture 1 and Racemate Mixture 2. Prep-HPLC Method: Column: Sunfire C-18 (150 mm×21.2 mm ID, 5 µm), Mobile phase A=10 mM ammonium acetate in water, Mobile phase B=acetonitrile: MeOH (1:1) Gradient: a 0-minute hold at 60% B, 72% B over 25 minutes, Flow Rate: 20 mL/min.

Chiral separation of Racemate Mixture 1 afforded Example 243 (rt=8.24 min) and Example 244 (rt=9.22 min). Chiral HPLC method: Cellulose-5 (250×21.2) mm-5 µm, Mobile phase A: 0.1% DEA in acetonitrile: MeOH (90:10), Mobile phase B: Flow: 22 mL/min.

Chiral separation of above Racemate Mixture 2 afforded Example 245 (rt=16.2 min) and Example 246 (rt=20.0 min). Chiral HPLC method: Cellulose-5 (250×21.2) mm-5 µm, Mobile phase A: 0.1% DEA in acetonitrile: MeOH (90:10), Mobile phase B: Flow: 22 mL/min.

Example 243: LCMS: m/z, 449.2 [M+H]; rt 2.86 min. LCMS method: Column: Kinetex XB-C18 (3×75 mm) 2.6 µm; Mobile phase A: 10 mM ammonium formate: acetonitrile (98:2), Mobile phase B: 10 mM ammonium formate: acetonitrile (2:98), Gradient=20-100% B over 4 minutes, then a 0.6 minute hold at 100% B; Temperature: 27° C.; Flow rate: 1.0 mL/min; Detection: UV at 220 nm.

Example 244: LCMS: m/z, 449.2 [M+H]; rt 2.85 min. LCMS method: Column: Kinetex XB-C18 (3×75 mm) 2.6 µm; Mobile phase A: 10 mM ammonium formate: acetonitrile (98:2), Mobile phase B: 10 mM ammonium formate: acetonitrile (2:98), Gradient=20-100% B over 4 minutes, then a 0.6 minute hold at 100% B; Temperature: 27° C.; Flow rate: 1.0 mL/min; Detection: UV at 220 nm.

Example 245: LCMS: m/z, 449.2 [M+H]; rt 2.91 min. LCMS method: Column: Kinetex XB-C18 (3×75 mm) 2.6 µm; Mobile phase A: 10 mM ammonium formate: acetonitrile (98:2), Mobile phase B: 10 mM ammonium formate: acetonitrile (2:98), Gradient=20-100% B over 4 minutes, then a 0.6 minute hold at 100% B; Temperature: 27° C.; Flow rate: 1.0 mL/min; Detection: UV at 220 nm.

Example 246: LCMS: m/z, 449.2 [M+H]; rt 2.91 min. LCMS method: Column: Kinetex XB-C18 (3×75 mm) 2.6 µm; Mobile phase A: 10 mM ammonium formate: acetonitrile (98:2), Mobile phase B: 10 mM ammonium formate: acetonitrile (2:98), Gradient=20-100% B over 4 minutes, then a 0.6 minute hold at 100% B; Temperature: 27° C.; Flow rate: 1.0 mL/min; Detection: UV at 220 nm.

The examples in the Table 16 were prepared according to the same general procedure for Examples 243 to 246 by substituting (±)-cis-tert-butyl-4-hydroxy-2,5-dimethylpiperidine-1-carboxylate with the appropriate piperidine isomer. When the reaction provided a mixture of diastereomers, the mixture was separated at the final stage using preparative chiral chromatography. The absolute stereochemistry was not assigned at the newly formed carbon-oxygen bond.

TABLE 16

| Ex. No. | Structure | Stereochemistry | LCMS Method | LCMS RT | M + H |
|---|---|---|---|---|---|
| 247 | 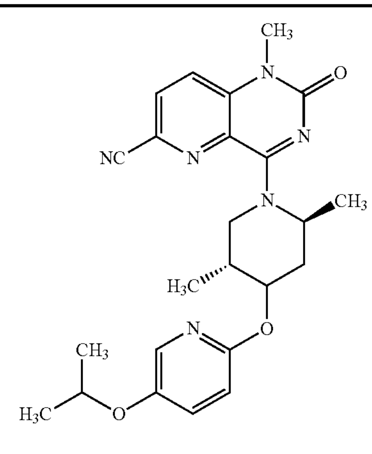 | H | D | 2.85 | 449.3 |

TABLE 16-continued

| Ex. No. | Structure | Stereo-chemistry | LCMS Method | LCMS RT | M + H |
|---|---|---|---|---|---|
| 248 | 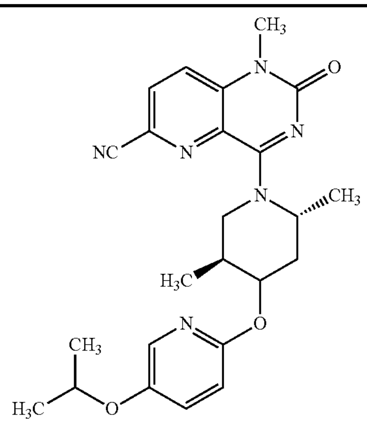 | H | D | 2.87 | 449.3 |
| 249 | 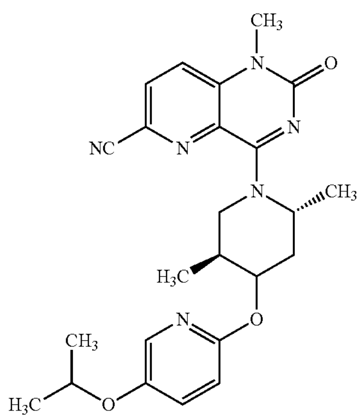 [SMILES: CC(C)Oc1ccc(OC2C[C@@H](C)N(c3nc(=O)n(C)c4ccc(C#N)nc34)C[C@@H]2C)nc1] | H | D | 2.90 | 449.3 |
| 250 | 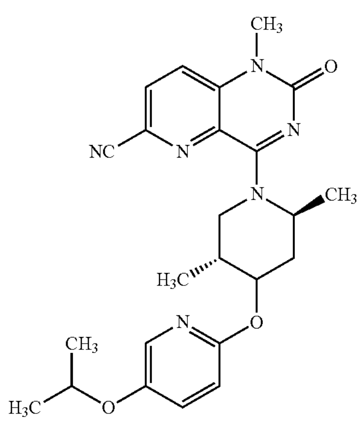 [SMILES: CC(C)Oc1ccc(OC2C[C@H](C)N(c3nc(=O)n(C)c4ccc(C#N)nc34)C[C@H]2C)nc1] | H | D | 2.90 | 449.3 |

The examples in the Table 17 were prepared according to the general procedure for Examples 243-246 by substituting 2-fluoro-5-isopropoxypyridine with the 1-fluoro-3-(trifluoromethyl)benzene and the appropriate piperidine. When the reaction provided a mixture of diastereomers, the mixture was separated at the final stage using preparative chiral chromatography. The absolute stereochemistry was not assigned at the newly formed carbon-oxygen bond.

TABLE 17

| Ex. No. | Structure | Stereo. chem. | LCMS Method | LCMS RT | M + H |
|---|---|---|---|---|---|
| 251 | 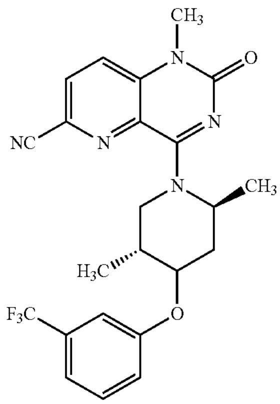 [SMILES: C[C@@H]1CN(c2nc(=O)n(C)c3ccc(C#N)nc23)[C@@H](C)CC1Oc1cccc(C(F)(F)F)c1] | H | D | 3.07 | 458.3 |
| 252 | 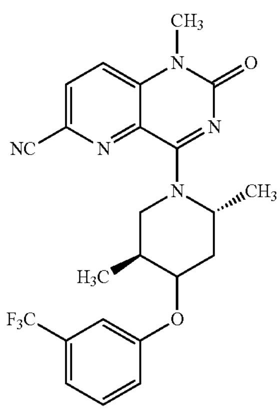 [SMILES: C[C@@H]1CC(Oc2cccc(C(F)(F)F)c2)[C@@H](C)CN1c1nc(=O)n(C)c2ccc(C#N)nc12] | H | D | 3.07 | 458.3 |
| 253 | 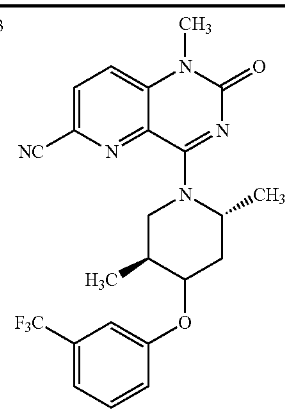 | H | D | 3.12 | 458.3 |
| 254 | 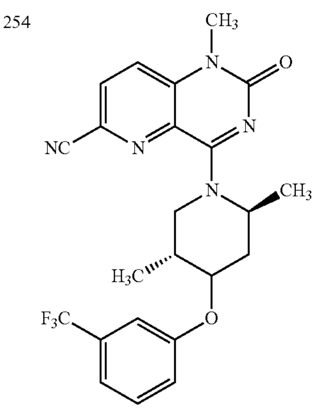 | H | D | 3.12 | 458.3 |

The examples in the Table 18 were prepared according to the general procedure for Examples 243-246 by substituting 2-fluoro-5-isopropoxypyridine with 1-fluoro-3-(trifluoromethyl)benzene. When the reaction provided a mixture of diastereomers, the mixture was separated at the final stage using preparative chiral chromatography. The absolute stereochemistry was not assigned at the newly formed carbon-oxygen bond.

TABLE 18

| Ex. No. | Structure | Stereo. chem. | LCMS Method | LCMS RT | M + H |
|---|---|---|---|---|---|
| 255 | 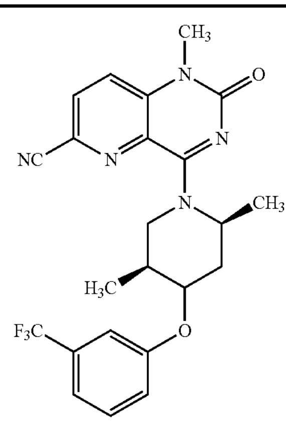 | H | D | 3.09 | 458.3 |

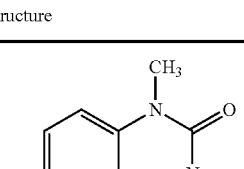

TABLE 18-continued

| Ex. No. | Structure | Stereo. chem. | LCMS Method | LCMS RT | M + H |
|---|---|---|---|---|---|
| 256 | 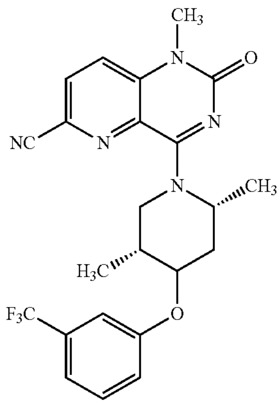 [SMILES: C[C@@H]1CN(c2nc(=O)n(C)c3ccc(C#N)nc23)[C@H](C)CC1Oc1cccc(C(F)(F)F)c1] | H | D | 3.09 | 458.3 |
| 257 | 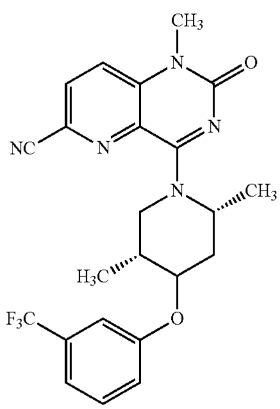 [SMILES: C[C@@H]1CN(c2nc(=O)n(C)c3ccc(C#N)nc23)[C@H](C)CC1Oc1cccc(C(F)(F)F)c1] | H | D | 3.18 | 458.3 |
| 258 | 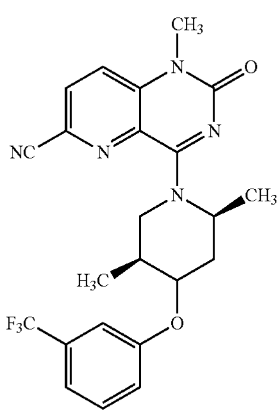 [SMILES: C[C@H]1CN(c2nc(=O)n(C)c3ccc(C#N)nc23)[C@@H](C)CC1Oc1cccc(C(F)(F)F)c1] | H | D | 3.18 | 458.3 |

Intermediates 77 and 78

(±)-trans-tert-butyl-3-hydroxy-4-(3-(trifluoromethyl)phenoxy)piperidine-1-carboxylate (I-78) and (±)-trans-tert-butyl-4-hydroxy-3-(3-(trifluoromethyl)phenoxy)piperidine-1-carboxylate (I-79)

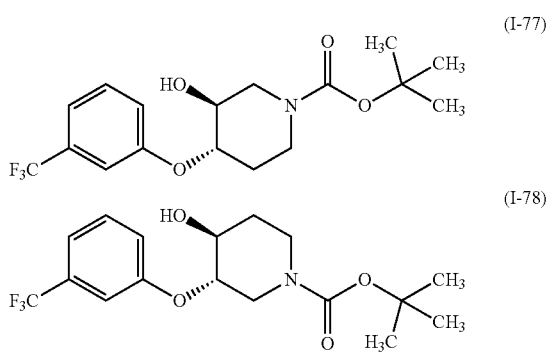

To a stirred solution of tert-butyl-7-oxa-3-azabicyclo[4.1.0]heptane-3-carboxylate (1.5 g, 7.53 mmol) in ethanol (15 mL) were added $K_2CO_3$ (1.04 g, 7.53 mmol) and 3-(trifluoromethyl)phenol (1.22 g, 7.53 mmol) at room temperature. The reaction mixture was heated to 80° C. for 3 h. The reaction mixture was cooled to room temperature, filtered through Celite pad, washed with excess EtOH and the filtrate was concentrated under reduced pressure to give crude product. The crude residue was purified via flash chromatography using a 24 g silica gel column and eluted with 30% EtOAc in petroleum ether to afford (±)-trans-tert-butyl-4-hydroxy-3-(3-(trifluoromethyl)phenoxy)piperidine-1-carboxylate and (±)-tert-butyl-3-hydroxy-4-(3-(trifluoromethyl)phenoxy) piperidine-1-carboxylate.

Intermediate 77: LCMS: m/z, 262.2 (M-100); rt 1.76 min. (LCMS Method: Column: Waters Acquity UPLC BEH C18 (2.1×50 mm) 1.7 μm, Mobile phase A: 10 mM NH$_4$OAc: acetonitrile (95:5); Mobile phase B: 10 mM NH$_4$OAc: acetonitrile (5:95), Gradient=20-100% B over 2 minute, then a 0.3 minute hold at 100% B; Temperature: 50° C.; Flow rate: 0.7 mL/min; Detection: UV at 220 nm).

Intermediate 78: LCMS: m/z, 262.2 (M-100); rt 1.82 min. (LCMS Method: Column: Waters Acquity UPLC BEH C18 (2.1×50 mm) 1.7 μm, Mobile phase A: 10 mM NH$_4$OAc: acetonitrile (95:5); Mobile phase B: 10 mM NH$_4$OAc: acetonitrile (5:95), Gradient=20-100% B over 2 minute, then a 0.3 minute hold at 100% B; Temperature: 50° C.; Flow rate: 0.7 mL/min; Detection: UV at 220 nm).

Intermediate 79

(±)-trans-4-(3-(trifluoromethyl)phenoxy)piperidin-3-ol, HCl

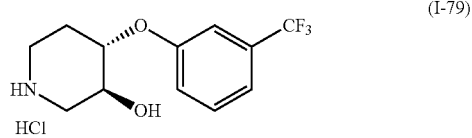 [SMILES: O[C@H]1CNCC[C@@H]1Oc1cccc(C(F)(F)F)c1 ; Cl]

To a stirred solution of (±)-trans-tert-butyl-3-hydroxy-4-(3-(trifluoromethyl) phenoxy)piperidine-1-carboxylate (170 mg, 0.47 mmol) in DCM (5 mL) was added HCl (4 M in dioxane) (0.6 mL, 2.36 mmol) at 0° C. The reaction mixture was stirred for 3 h at room temperature. The solvent was evaporated under reduced pressure to afford (±)-trans-4-(3-(trifluoromethyl)phenoxy)piperidin-3-ol, HCl. LCMS: m/z, 262.2 (M+1); rt 1.01 min. (LCMS Method: Column: Waters Acquity UPLC BEH C18 (2.1×50 mm) 1.7 μm, Mobile phase A: 10 mM NH$_4$OAc: acetonitrile (95:5); Mobile phase B: 10 mM NH$_4$OAc: acetonitrile (5:95), Gradient=20-100% B over 2 minute, then a 0.3 minute hold at 100% B; Temperature: 50° C.; Flow rate: 0.7 mL/min; Detection: UV at 220 nm).

Examples 259 and 260

(+/−)-trans-8-(3-hydroxy-4-(3-(trifluoromethyl)phenoxy)piperidin-1-yl)-5-methyl-6-oxo-5,6-dihydro-1,5-naphthyridine-2-carbonitrile

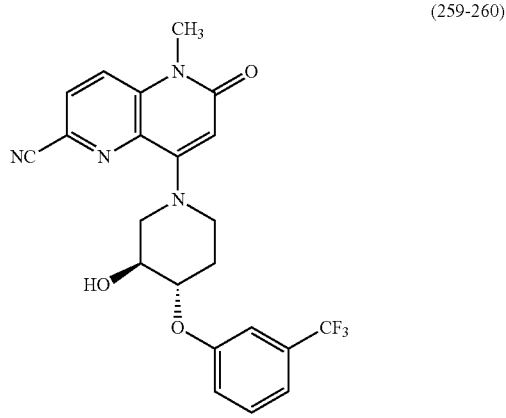 [SMILES: Cn1c(=O)cc(N2CC[C@H](Oc3cccc(C(F)(F)F)c3)[C@@H](O)C2)c2nc(C#N)ccc21]

To a stirred solution of (±)-trans-4-(3-(trifluoromethyl) phenoxy)piperidin-3-ol, HCl (140 mg, 0.47 mmol) in acetonitrile (5 mL) was added DIPEA (0.4 mL, 2.35 mmol), followed by the addition of 6-cyano-1-methyl-2-oxo-1,2-dihydro-1,5-naphthyridin-4-yl trifluoromethanesulfonate (188 mg, 0.56 mmol). The reaction mixture was heated at 85° C. overnight. The reaction mixture was cooled to room temperature and the solvent was removed under reduced pressure to yield the crude product which was purified by preparative HPLC (Column: DAD-1-Cellulose-5 (250×4.6 mm), 5 μm Mobile Phase: 10 mM Ammonium acetate in MeOH, flow rate: 1.5 mL/min Injection vol: 8.0 μL, Run time: 25 min).

Example 259: LCMS: m/z=445.2 (M+H); rt 1.75 min; (LCMS method: Waters) XBridge C18, 19×150 mm, 5-μm particles; Mobile Phase A: 10-mM ammonium acetate; Mobile Phase B: acetonitrile; Gradient: 20-65% B over 20 minutes, then a 5-minute hold at 100% B; Flow: 15 mL/min). $^1$H NMR (400 MHz, DMSO-d$_6$) δ 8.22-8.13 (m, 1H), 8.11-7.98 (m, 1H), 7.59-7.47 (m, 1H), 7.36 (br d, J=4.9 Hz, 2H), 7.28 (d, J=7.8 Hz, 1H), 6.16 (s, 1H), 4.50-4.46 (m, 2H), 4.08 (br dd, J=3.8, 12.8 Hz, 1H), 3.94-3.87 (m, 1H), 3.81 (dt, J=4.4, 8.3 Hz, 1H), 3.54 (s, 3H), 3.34-3.22 (m, 1H), 3.12 (dd, J=9.0, 12.7 Hz, 1H), 2.26-2.17 (m, 1H).

Example 260: LCMS: m/z=445.2 (M+H); rt 1.75 min; (LCMS method: Waters) XBridge C18, 19×150 mm, 5-μm particles; Mobile Phase A: 10-mM ammonium acetate; Mobile Phase B: acetonitrile; Gradient: 20-65% B over 20 minutes, then a 5-minute hold at 100% B; Flow: 15 mL/min. $^1$H NMR (400 MHz, DMSO-$d_6$) δ 8.22-8.14 (m, 1H), 8.12-8.03 (m, 1H), 7.58-7.47 (m, 1H), 7.42-7.32 (m, 2H), 7.28 (d, J=8.1 Hz, 1H), 6.16 (s, 1H), 5.60-5.34 (m, 1H), 4.53-4.42 (m, 1H), 4.15-4.05 (m, 1H), 3.96-3.86 (m, 1H), 3.84-3.77 (m, 1H), 3.54 (s, 3H), 3.28 (br s, 1H), 3.12 (dd, J=9.4, 12.6 Hz, 1H), 2.26-2.18 (m, 1H).

Intermediate 80

(±)-trans-tert-butyl-3-methoxy-4-(3-(trifluoromethyl)phenoxy)piperidine-1-carboxylate

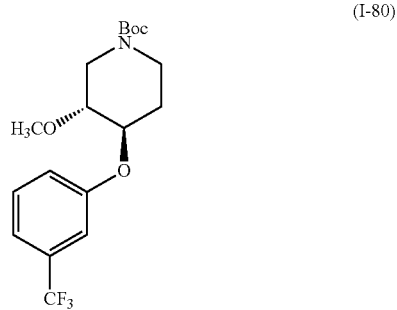 [SMILES: CO[C@@H]1CN(C(=O)OC(C)(C)C)CC[C@H]1Oc1cccc(C(F)(F)F)c1]

(I-80)

To a stirred solution of (±)-trans-tert-butyl-3-hydroxy-4-(3-(trifluoromethyl) phenoxy)piperidine-1-carboxylate (100 mg, 0.28 mmol) in THF (5 mL) was added NaH (60% in mineral oil) (44.3 mg, 1.11 mmol, 60% w/w) at 0° C. After 5 minutes, a solution of iodomethane (0.04 mL, 0.55 mmol) in THF (2 mL) was added and the reaction mixture was stirred for 2 h at room temperature. The reaction mixture was cooled to 0° C. The reaction was quenched with ice cold water. The mixture was extracted with EtOAc (2×50 mL). The combined organic extracts were washed with brine, dried over $Na_2SO_4$ and concentrated to afford (±)-trans-tert-butyl-3-methoxy-4-(3-(trifluoromethyl) phenoxy)piperidine-1-carboxylate. LCMS: m/z, 276.1 (M-100); rt 2.24 min. (LCMS Method: Column: Waters Acquity UPLC BEH C18 (2.1×50 mm) 1.7 μm, Mobile phase A: 10 mM $NH_4$OAc:acetonitrile (95:5); Mobile phase B: 10 mM $NH_4$OAc: acetonitrile (5:95), Gradient=20-100% B over 2 minute, then a 0.3 minute hold at 100% B; Temperature: 50° C.; Flow rate: 0.7 mL/min; Detection: UV at 220 nm).

Intermediate 81

(±)-trans-3-methoxy-4-(3-(trifluoromethyl)phenoxy)piperidine hydrochloride

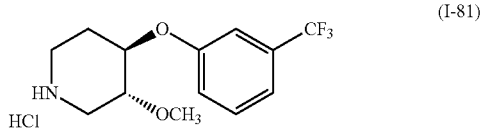 [SMILES: CO[C@@H]1CNCC[C@H]1Oc1cccc(C(F)(F)F)c1 ; Cl]

(I-81)

To a stirred solution of (±)-trans-tert-butyl-3-methoxy-4-(3-(trifluoromethyl) phenoxy)piperidine-1-carboxylate (100 mg, 0.27 mmol) in DCM (5 mL) was added HCl (4 M in dioxane) (0.6 mL, 2.6 mmol) at 0° C. The reaction mixture was stirred at room temperature for 3 h. The solvent was evaporated under reduced pressure to afford (±)-trans-3-methoxy-4-(3-(trifluoromethyl)phenoxy)piperidine, HCl. LCMS: m/z, 276.1 (M+1); rt 1.16 min. (LCMS Method: Column: Waters Acquity UPLC BEH C18 (2.1×50 mm) 1.7μ, Mobile phase A: 10 mM $NH_4$OAc: acetonitrile (95:5); Mobile phase B: 10 mM $NH_4$OAc: acetonitrile (5:95), Gradient=20-100% B over 2 minute, then a 0.3 minute hold at 100% B; Temperature: 50° C.; Flow rate: 0.7 mL/min; Detection: UV at 220 nm).

Examples 261 and 262

(±)-trans-8-(3-methoxy-4-(3-(trifluoromethyl)phenoxy)piperidin-1-yl)-5-methyl-6-oxo-5,6-dihydro-1,5-naphthyridine-2-carbonitrile

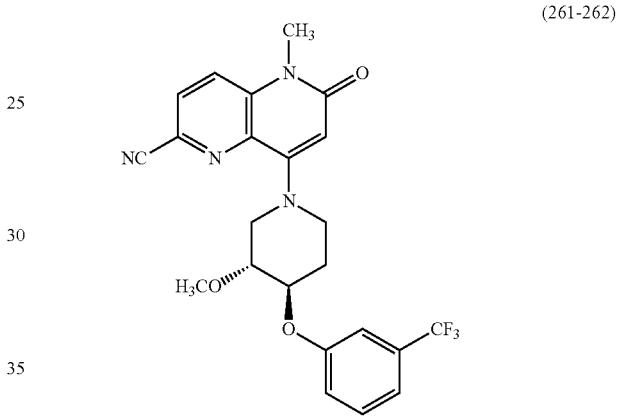

(261-262)

To a stirred solution of (±)-trans-3-methoxy-4-(3-(trifluoromethyl)phenoxy) piperidine, HCl (80 mg, 0.26 mmol) in acetonitrile (5 mL) was added DIPEA (0.23 mL, 1.28 mmol). The reaction mixture was stirred for 5 min at room temperature. Next, 6-cyano-1-methyl-2-oxo-1,2-dihydro-1,5-naphthyridin-4-yl trifluoromethanesulfonate (103 mg, 0.31 mmol) was added and the reaction mixture was heated at 85° C. for 4 h. The reaction mixture was cooled to room temperature and the solvent was removed under reduced pressure to yield the crude product, which was purified by preparative HPLC [Method: Column: DAD-1-Cellulose-5 (250×4.6 mm), 5 micron Mobile Phase: 10 mM Ammonium acetate in MeOH, flow rate: 1.5 mL/min, Injection vol: 4.0 μL, Run time: 20 min).

Example 261: LCMS: m/z, 459.2 (M+H); rt 2.04 min; LC/MS Method: Column: Waters XBridge C18, 19×150 mm, 5-μm particles; Mobile Phase A: 10-mM ammonium acetate; Mobile Phase B: acetonitrile; Gradient: 20-65% B over 20 minutes, then a 5-minute hold at 100% B; Flow: 15 mL/min. $^1$H NMR (400 MHz, DMSO-$d_6$) δ=8.23-8.16 (m, 1H), 8.13-8.07 (m, 1H), 7.59-7.47 (m, 1H), 7.44-7.34 (m, 2H), 7.30 (d, J=7.8 Hz, 1H), 6.17 (s, 1H), 4.71-4.58 (m, 1H), 4.32-4.22 (m, 1H), 3.75-3.65 (m, 1H), 3.62-3.53 (m, 4H), 3.41 (s, 3H), 3.27-3.19 (m, 2H), 2.27-2.16 (m, 1H), 1.82-1.66 (m, 1H).

Example 262: LCMS: m/z, 459.2 (M+H); rt 2.04 min; LC/MS Method: Column: Waters XBridge C18, 19×150 mm, 5-μm particles; Mobile Phase A: 10-mM ammonium acetate; Mobile Phase B: acetonitrile; Gradient: 20-65% B over 20 minutes, then a 5-minute hold at 100% B; Flow: 15 mL/min. $^1$H NMR (400 MHz, DMSO-$d_6$): δ ppm 8.23-8.15 (m, 1H), 8.14-8.07 (m, 1H), 7.60-7.48 (m, 1H), 7.46-7.34 (m, 2H), 7.30 (d, J=8.3 Hz, 1H), 6.17 (s, 1H), 4.72-4.60 (m, 1H), 4.32-4.20 (m, 1H), 3.74-3.65 (m, 1H), 3.64-3.55 (m, 1H), 3.54 (s, 3H), 3.41 (s, 3H), 3.27-3.16 (m, 2H), 2.27-2.16 (m, 1H), 1.80-1.69 (m, 1H).

The Examples in Table 19 were prepared from the appropriate alkyl halide according to the general procedures disclosed in Examples 259 and 260.

TABLE 19

| Ex. No. | Structure | Stereochemistry | LCMS Method | LCMS RT | M + H |
|---|---|---|---|---|---|
| 263 | 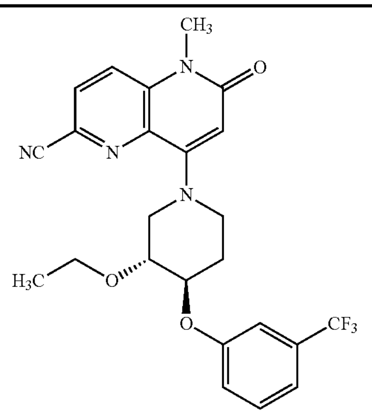 | H | C | 2.15 | 473.3 |
| 264 | | H | C | 2.15 | 473.3 |

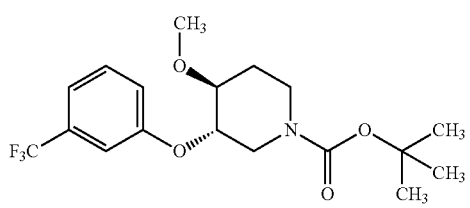

4-methoxy-3-(3-(trifluoromethyl) phenoxy)piperidine-1-carboxylate. LCMS: m/z, 276.1 (M-100); rt 2.10 min. (LCMS Method: Column: Waters Acquity UPLC BEH C18 (2.1×50 mm) 1.7 μm, Mobile phase A: 10 mM NH$_4$OAc: acetonitrile (95:5); Mobile phase B: 10 mM NH$_4$OAc: acetonitrile (5:95), Gradient=20-100% B over 2 minute, then a 0.3 minute hold at 100% B; Temperature: 50° C.; Flow rate: 0.7 mL/min; Detection: UV at 220 nm).

Intermediate 82

(±)-trans-tert-butyl-4-methoxy-3-(3-(trifluoromethyl) phenoxy)piperidine-1-carboxylate (I-82)

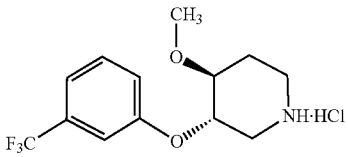

To a stirred solution of (±)-trans-tert-butyl-4-hydroxy-3-(3-(trifluoromethyl) phenoxy)piperidine-1-carboxylate (75 mg, 0.21 mmol) in THF (3 mL) was added NaH (60% in mineral oil) (34 mg, 0.83 mmol) at 0° C. After 5 minutes, a solution of iodomethane (0.03 mL, 0.41 mmol) in THF (1 mL) was added and the reaction mixture was stirred for 2 h at room temperature. The reaction mixture was cooled to 0° C. The reaction was quenched with ice cold water and the reaction mixture was extracted with EtOAc (2×50 mL). The combined organic extracts were washed with brine, dried over Na$_2$SO$_4$ and concentrated to give (±)-trans-tert-butyl- Intermediate 83

(±)-trans-4-methoxy-3-(3-(trifluoromethyl)phenoxy) piperidine, HCl (I-83)

To a stirred solution of (±)-trans-tert-butyl-4-methoxy-3-(3-(trifluoromethyl) phenoxy)piperidine-1-carboxylate (75 mg, 0.20 mmol) in DCM (5 mL) was added HCl (4 M in dioxane) (0.25 mL, 1.00 mmol) at 0° C. The reaction mixture was allowed to warm to room temperature and stirred for 3 h. The solvent was evaporated under reduced pressure to afford (±)-trans-4-methoxy-3-(3-(trifluoromethyl)phenoxy)piperidine, HCl. LCMS: m/z, 276.1 (M+1); rt 1.13 min. (LCMS Method: Column: Waters Acquity UPLC BEH C18 (2.1×50 mm) 1.7 μm, Mobile phase A: 10 mM NH$_4$OAc:acetonitrile (95:5); Mobile phase B: 10 mM NH$_4$OAc: acetonitrile (5:95), Gradient=20-100% B over 2 minute, then a 0.3 minute hold at 100% B; Temperature: 50° C.; Flow rate: 0.7 mL/min; Detection: UV at 220 nm).

Examples 265 and 266

(±)-cis-8-(3-fluoro-4-(3-(trifluoromethyl)phenoxy) piperidin-1-yl)-5-methyl-6-oxo-5,6-dihydro-1,5-naphthyridine-2-carbonitrile

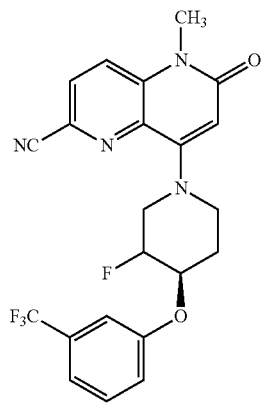

(265-266)

To a stirred solution of (±)-trans-8-(3-hydroxy-4-(3-(trifluoromethyl)phenoxy) piperidin-1-yl)-5-methyl-6-oxo-5,6-dihydro-1,5-naphthyridine-2-carbonitrile (130 mg, 0.29 mmol) in DCM (2 mL) was added DAST (0.05 mL, 0.35 mmol) at −78° C. The reaction mixture was stirred at room temperature for 16 h. The reaction was quenched with saturated $NaHCO_3$ solution. The reaction mixture was extracted with DCM (2×50 mL). The combined organic extracts were washed with water, brine, dried over $Na_2SO_4$ and concentrated to give crude product which was purified by preparative HPLC [Method: Column: Waters XBridge C18, 19×150 mm, 5-μm particles; Mobile Phase A: 10-mM ammonium acetate; Mobile Phase B: acetonitrile; Gradient: 17-52% B over 19 minutes, then a 5-minute hold at 20% B; Flow: 20 mL/min].

Example 265: LCMS: m/z, 447.2 (M+H); rt 1.92 min; LC/MS Method: Column: Waters XBridge C18, 19×150 mm, 5-μm particles; Mobile Phase A: 10-mM ammonium acetate; Mobile Phase B: acetonitrile; Gradient: 20-65% B over 20 minutes, then a 5-minute hold at 100% B; Flow: 15 mL/min. $^1$H NMR (400 MHz, DMSO-$d_6$) δ=8.21-8.11 (m, 1H), 8.05 (d, J=9.0 Hz, 1H), 7.62-7.46 (m, 1H), 7.37-7.19 (m, 3H), 5.83 (s, 1H), 5.53-5.42 (m, 1H), 5.30 (d, J=4.2 Hz, 1H), 4.95-4.72 (m, 1H), 4.66-4.45 (m, 1H), 3.79-3.68 (m, 1H), 3.64-3.54 (m, 1H), 3.52 (s, 3H), 2.55-2.45 (m, 1H) 2.26-2.12 (m, 1H).

Example 266: LCMS: m/z, 447.2 (M+H); rt 2.01 min; LC/MS Method: Column: Waters XBridge C18, 19×150 mm, 5-μm particles; Mobile Phase A: 10-mM ammonium acetate; Mobile Phase B: acetonitrile; Gradient: 20-65% B over 20 minutes, then a 5-minute hold at 100% B; Flow: 15 mL/min. $^1$H NMR (400 MHz, DMSO-$d_6$) δ ppm 8.24-8.17 (m, 1H), 8.14-8.07 (m, 1H), 7.61-7.50 (m, 1H), 7.46-7.37 (m, 2H), 7.33 (d, J=7.6 Hz, 1H), 6.25 (s, 1H), 4.99-4.77 (m, 1H), 4.32-4.19 (m, 1H), 3.83-3.70 (m, 1H), 3.55 (s, 3H), 3.48 (br dd, J=5.1, 13.4 Hz, 1H), 3.40-3.27 (m, 2H), 2.35-2.19 (m, 1H), 1.86-1.72 (m, 1H).

Intermediate 84

(±)-trans-tert-butyl-3-hydroxy-4-((5-isopropoxypyridin-2-yl)oxy)piperidine-1-carboxylate

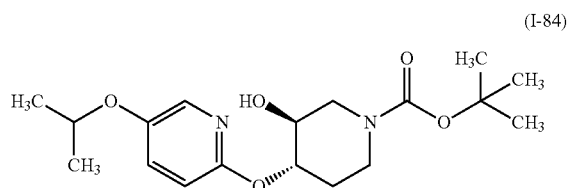

(I-84)

To a stirred solution of tert-butyl 7-oxa-3-azabicyclo[4.1.0]heptane-3-carboxylate (250 mg, 1.25 mmol) in EtOH (3 mL) were added $K_2CO_3$ (173 mg, 1.25 mmol) and 5-isopropoxypyridin-2-ol (192 mg, 1.25 mmol) at room temperature. The reaction mixture was heated at 80° C. for 16 h. The reaction mixture was cooled to room temperature, filtered through Celite pad, washed with excess EtOH and the filtrate was concentrated under reduced pressure to give crude product. The crude residue was purified via flash chromatography 24 g silica gel column and eluted with 30% EtOAc in petroleum ether to afford (±)-trans-tert-butyl-3-hydroxy-4-((5-isopropoxypyridin-2-yl)oxy)piperidine-1-carboxylate. LCMS: m/z, 353.2 (M+1); rt 1.71 min. (LCMS Method: Column: Waters Acquity UPLC BEH C18 (2.1×50 mm) 1.7 μm, Mobile phase A: 10 mM $NH_4OAc$: acetonitrile (95:5); Mobile phase B: 10 mM $NH_4OAc$: acetonitrile (5:95), Gradient=20-100% B over 2 minute, then a 0.3 minute hold at 100% B; Temperature: 50° C.; Flow rate: 0.7 mL/min; Detection: UV at 220 nm).

Intermediate 85

(±)-trans-4-((5-isopropoxypyridin-2-yl)oxy)piperidin-3-ol, HCl

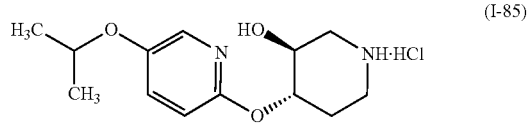

(I-85)

To a stirred solution of (±)-trans-tert-butyl-3-hydroxy-4-((5-isopropoxypyridin-2-yl)oxy)piperidine-1-carboxylate (100 mg, 0.28 mmol) in DCM (5 mL) was added HCl (4 M in dioxane) (0.35 mL, 1.42 mmol) at 0° C. The reaction mixture was stirred at room temperature for 3 h. The solvent was evaporated under reduced pressure to afford (±)-trans-4-((5-isopropoxypyridin-2-yl)oxy)piperidin-3-ol, HCl. LCMS: m/z, 253.2 (M+1); rt 0.76 min. (LCMS Method: Column: Waters Acquity UPLC BEH C18 (2.1×50 mm) 1.7 μm, Mobile phase A: 10 mM $NH_4OAc$:acetonitrile (95:5); Mobile phase B: 10 mM $NH_4OAc$: acetonitrile (5:95), Gradient=20-100% B over 2 minute, then a 0.3 minute hold at 100% B; Temperature: 50° C.; Flow rate: 0.7 mL/min; Detection: UV at 220 nm).

Examples 267 and 268

(±)-trans-8-(3-hydroxy-4-((5-isopropoxypyridin-2-yl)oxy)piperidin-1-yl)-5-methyl-6-oxo-5,6-dihydro-1,5-naphthyridine-2-carbonitrile

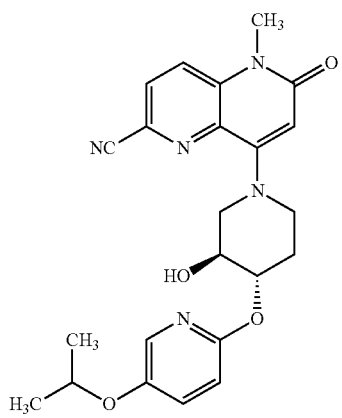

(267-268)

To a stirred solution of (±)-trans-4-((5-isopropoxypyridin-2-yl)oxy)piperidin-3-ol, HCl (80 mg, 0.277 mmol) in acetonitrile (5 mL) was added DIPEA (0.25 mL, 1.38 mmol) followed by the addition of 6-cyano-1-methyl-2-oxo-1,2-dihydro-1,5-naphthyridin-4-yl trifluoromethanesulfonate (111 mg, 0.33 mmol). The reaction mixture was heated at 85° C. for 3 h. The reaction mixture was cooled to room temperature and the solvent was removed under reduced pressure to yield the crude product, which was purified by preparative HPLC [Column: Column: DAD-1-Cellulose-5 (250×4.6 mm), 5 micron Mobile Phase: 10 mM ammonium acetate in MeOH, Flow: 1.5 mL/min, Injection vol: 2.0 µL, Run time: 30 min].

Example 267: LCMS: m/z=436.3 (M+H); rt 1.57 min; (LCMS method: Waters) XBridge C18, 19×150 mm, 5-µm particles; Mobile Phase A: 10-mM ammonium acetate; Mobile Phase B: acetonitrile; Gradient: 20-65% B over 20 minutes, then a 5-minute hold at 100% B; Flow: 15 mL/min). $^1$H NMR (400 MHz, DMSO-$d_6$) δ=8.22-8.15 (m, 1H), 8.12-8.03 (m, 1H), 7.82 (d, J=3.2 Hz, 1H), 7.39 (dd, J=3.1, 8.9 Hz, 1H), 6.77 (d, J=8.8 Hz, 1H), 6.15 (s, 1H), 5.41-5.19 (m, 1H), 4.93 (dt, J=4.5, 8.4 Hz, 1H), 4.52 (td, J=6.0, 12.2 Hz, 1H), 4.12-3.99 (m, 1H), 3.90-3.76 (m, 2H), 3.54 (s, 3H), 3.23 (brs, 1H), 3.11 (dd, J=8.9, 12.6 Hz, 1H), 2.31-2.22 (m, 1H), 1.70-1.54 (m, 1H), 1.24 (d, J=6.1 Hz, 6H).

Example 268: LCMS: m/z=436.2 (M+H); rt 1.57 min; (LCMS method: Waters) XBridge C18, 19×150 mm, 5-µm particles; Mobile Phase A: 10-mM ammonium acetate; Mobile Phase B: acetonitrile; Gradient: 20-65% B over 20 minutes, then a 5-minute hold at 100% B; Flow: 15 mL/min). $^1$H NMR (400 MHz, DMSO-$d_6$): δ ppm 8.22-8.14 (m, 1H), 8.12-8.02 (m, 1H), 7.82 (d, J=3.2 Hz, 1H), 7.39 (dd, J=3.1, 8.9 Hz, 1H), 6.77 (d, J=9.0 Hz, 1H), 6.15 (s, 1H), 5.38-5.23 (m, 1H), 4.98-4.86 (m, 1H), 4.52 (td, J=6.0, 12.2 Hz, 1H), 4.12-4.00 (m, 1H), 3.90-3.74 (m, 2H), 3.54 (s, 3H), 3.23 (br s, 1H), 3.11 (dd, J=8.9, 12.6 Hz, 1H), 2.32-2.21 (m, 1H), 1.70-1.56 (m, 1H), 1.24 (d, J=6.1 Hz, 6H).

Intermediate 86

(±)-trans-tert-butyl-4-((5-isopropoxypyridin-2-yl)oxy)-3-methoxypiperidine-1-carboxylate

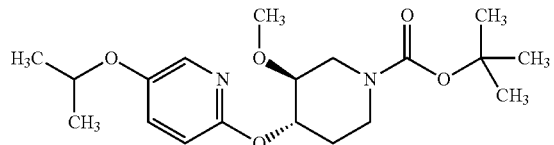

(I-86)

To a stirred solution of (±)-trans-tert-butyl-3-hydroxy-4-((5-isopropoxypyridin-2-yl)oxy)piperidine-1-carboxylate (100 mg, 0.28 mmol) in THF (3 mL) was added NaH (60% in mineral oil) (45.4 mg, 1.14 mmol) at 0° C. After 5 minutes, a solution of iodomethane (0.035 mL, 0.57 mmol) in THF (1 mL) was added and the reaction mixture was stirred for 3 h at room temperature. The reaction mixture was cooled to 0° C. The reaction was quenched with ice cold water and the reaction mixture was extracted with EtOAc (2×50 mL). The combined organic extracts were washed with brine, dried over $Na_2SO_4$ and concentrated to give (±)-trans-tert-butyl-4-((5-isopropoxypyridin-2-yl)oxy)-3-methoxypiperidine-1-carboxylate. LCMS: m/z, 367.3 (M+1); rt 2.08 min. (LCMS Method: Column: Waters Acquity UPLC BEH C18 (2.1×50 mm) 1.7 µm, Mobile phase A: 10 mM $NH_4OAc$:acetonitrile (95:5); Mobile phase B: 10 mM $NH_4OAc$:acetonitrile (5:95), Gradient=20-100% B over 2 minute, then a 0.3 minute hold at 100% B; Temperature: 50° C.; Flow rate: 0.7 mL/min; Detection: UV at 220 nm).

Intermediate 87

(±)-trans-5-isopropoxy-2-((3-methoxypiperidin-4-yl)oxy)pyridine, HCl

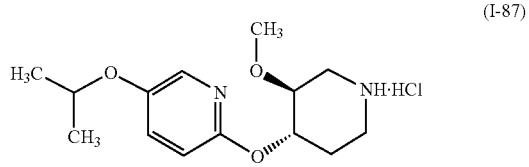

(I-87)

To a stirred solution of (±)-trans-tert-butyl-4-((5-isopropoxypyridin-2-yl)oxy)-3-methoxypiperidine-1-carboxylate (100 mg, 0.273 mmol) in DCM (15 mL) was added HCl (4 M in dioxane) (0.35 mL, 1.364 mmol) at 0° C. The reaction mixture was stirred at room temperature for 3 h. The solvent was evaporated under reduced pressure to afford (±)-trans-5-isopropoxy-2-((3-methoxypiperidin-4-yl)oxy)pyridine, HCl. LCMS: m/z, 267.2 (M+1); rt 0.86 min. (LCMS Method: Column: Waters Acquity UPLC BEH C18 (2.1×50 mm) 1.7 µm, Mobile phase A: 10 mM $NH_4OAc$: acetonitrile (95:5); Mobile phase B: 10 mM $NH_4OAc$: acetonitrile (5:95); Gradient=20-100% B over 2 minute, then a 0.3 minute hold at 100% B; Temperature: 50° C.; Flow rate: 0.7 mL/min; Detection: UV at 220 nm).

Examples 269 and 270

(±)-trans-8-(4-((5-isopropoxypyridin-2-yl)oxy)-3-methoxypiperidin-1-yl)-5-methyl-6-oxo-5,6-dihydro-1,5-naphthyridine-2-carbonitrile

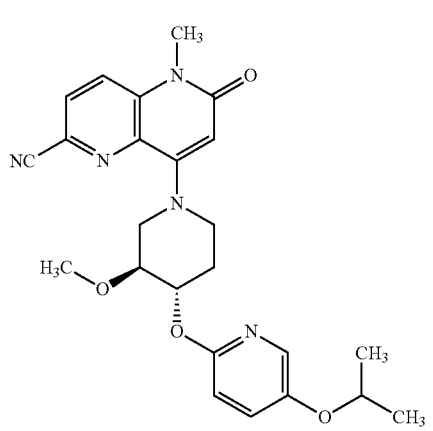

(269-270)

To a stirred solution of (±)-trans-5-isopropoxy-2-((3-methoxypiperidin-4-yl) oxy)pyridine, HCl (80 mg, 0.26 mmol) in acetonitrile (5 mL) was added DIPEA (0.23 mL, 1.32 mmol). The reaction mixture was stirred for 5 min at room temperature and then 6-cyano-1-methyl-2-oxo-1,2-dihydro-1,5-naphthyridin-4-yl trifluoromethanesulfonate (106 mg, 0.31 mmol) was added. The reaction mixture was heated at 85° C. for 4 h. The reaction mixture was cooled to room temperature and the solvent was removed under reduced pressure to yield the crude product, which was purified by preparative HPLC (Method: Column: DAD-1: Cellulose-2 (250×4.6 mm), 5 micron DAD-2: Cellulose-4 (250×4.6 mm), 5 micron Mobile Phase: 10 mM ammonium acetate in MeOH, FLOW: 2.0 mL\min Injection vol: 6.0 μL, Run time: 20 min).

Example 269: LCMS: m/z, 450.2 (M+H); rt 1.82; LC/MS Method: Column: Waters XBridge C18, 19×150 mm, 5-μm particles; Mobile Phase A: 10-mM ammonium acetate; Mobile Phase B: acetonitrile; Gradient: 20-65% B over 20 minutes, then a 5-minute hold at 100% B; Flow: 15 mL/min. $^1$H NMR (400 MHz, DMSO-$d_6$) δ=8.22-8.16 (m, 1H), 8.13-8.05 (m, 1H), 7.83 (d, J=2.9 Hz, 1H), 7.39 (dd, J=3.1, 8.9 Hz, 1H), 6.79 (d, J=8.8 Hz, 1H), 6.16 (s, 1H), 5.12-5.04 (m, 1H), 4.53 (quin, J=6.0 Hz, 1H), 4.21-4.11 (m, 1H), 3.58 (br d, J=3.2 Hz, 1H), 3.54 (s, 3H), 3.41 (s, 3H), 3.33-3.27 (m, 3H), 2.31-2.22 (m, 1H), 1.72 (br dd, J=4.3, 8.4 Hz, 1H), 1.25 (d, J=6.1 Hz, 6H).

Example 270: LCMS 450.3 (M+H); rt 1.82 min; LC/MS Method: Column: Waters) XBridge C18, 19×150 mm, 5-μm particles; Mobile Phase A: 10-mM ammonium acetate; Mobile Phase B: acetonitrile; Gradient: 20-65% B over 20 minutes, then a 5-minute hold at 100% B; Flow: 15 mL/min. $^1$H NMR (400 MHz, DMSO-$d_6$): δ ppm 8.23-8.15 (m, 1H), 8.14-8.06 (m, 1H), 7.83 (d, J=2.9 Hz, 1H), 7.39 (dd, J=3.1, 8.9 Hz, 1H), 6.79 (d, J=8.8 Hz, 1H), 6.16 (s, 1H), 5.14-5.01 (m, 1H), 4.52 (td, J=6.1, 12.0 Hz, 1H), 4.24-4.08 (m, 1H), 3.70-3.51 (m, 4H), 3.41 (s, 3H), 3.26 (br dd, J=5.4, 13.2 Hz, 3H), 2.31-2.18 (m, 1H), 1.76-1.65 (m, 1H), 1.25 (d, J=5.9 Hz, 6H).

Examples 271 and 272

(+/−)-trans-6-chloro-4-(3-hydroxy-4-(3-(trifluoromethyl)phenoxy)piperidin-1-yl)-1-methylpyrido[3,2-d]pyrimidin-2(1H)-one

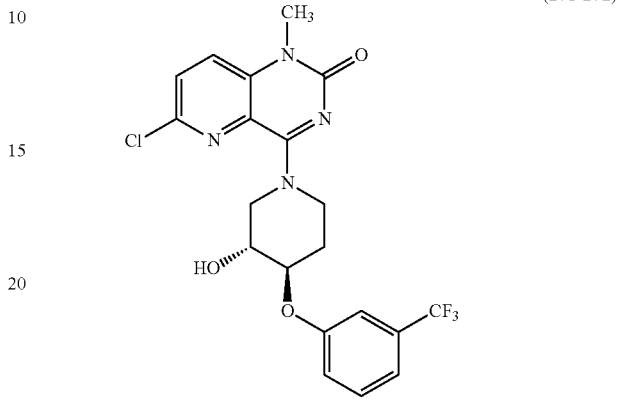

(271-272)

To a stirred solution of (±)-trans-4-(3-(trifluoromethyl)phenoxy)piperidin-3-ol, HCl (600 mg, 2.02 mmol) in acetonitrile (15 mL) was added DIPEA (1.8 mL, 10.08 mmol). The reaction mixture was stirred for 5 min at room temperature. Next, 4,6-dichloro-1-methylpyrido[3,2-d]pyrimidin-2(1H)-one (556 mg, 2.42 mmol) was added and the reaction mixture was heated at 85° C. for 4 h. The reaction mixture was cooled to room temperature and the solvent was removed under reduced pressure to yield the crude product, which was purified by flash chromatography 24 g silica gel column and eluted with 3% MeOH in DCM to afford (±)-trans-6-chloro-4-(3-hydroxy-4-(3-(trifluoromethyl) phenoxy)piperidin-1-yl)-1-methylpyrido[3,2-d]pyrimidin-2 (1H)-one. The product was purified by preparative HPLC [Method: Column: DAD-1: Cellulose-2 (250×4.6 mm), 5 micron DAD-2: Cellulose-4 (250×4.6 mm), 5 micron Mobile Phase: 10 mM ammonium acetate in MeOH, Flow: 2.0 mL\min Injection vol: 6.0 μL, Run time: 20 min.

Example 271: LCMS: m/z, 455.1 (M+H); rt 1.82 min; LC/MS Method: Column: Waters XBridge C18, 19×150 mm, 5-μm particles; Mobile Phase A: 10-mM ammonium acetate; Mobile Phase B: acetonitrile; Gradient: 20-65% B over 20 minutes, then a 5-minute hold at 100% B; Flow: 15 mL/min. $^1$H NMR (400 MHz, DMSO-$d_6$) δ=7.95 (d, J=9.0 Hz, 1H), 7.81 (d, J=8.8 Hz, 1H), 7.52 (d, J=8.1 Hz, 1H), 7.38-7.32 (m, 2H), 7.29 (d, J=7.8 Hz, 1H), 5.53-5.44 (m, 1H), 4.85-4.72 (m, 1H), 4.57-4.48 (m, 1H), 3.87-3.76 (m, 1H), 3.76-3.65 (m, 1H), 3.45 (s, 3H), 2.27-2.17 (m, 1H), 1.68-1.56 (m, 1H), Example 272: LCMS: m/z, 455.1 (M+H); rt 1.82 min; LC/MS Method: Column: Waters XBridge C18, 19×150 mm, 5-μm particles; Mobile Phase A: 10-mM ammonium acetate; Mobile Phase B: acetonitrile; Gradient: 20-65% B over 20 minutes, then a 5-minute hold at 100% B; Flow: 15 mL/min. $^1$H NMR (400 MHz, DMSO-$d_6$): δ ppm 7.95 (d, J=9.0 Hz, 1H), 7.81 (d, J=9.0 Hz, 1H), 7.57-7.43 (m, 1H), 7.40-7.32 (m, 2H), 7.32-7.23 (m, 1H), 5.54-5.45 (m, 1H), 4.85-4.70 (m, 1H), 4.57-4.48 (m, 1H), 3.85-3.76 (m, 1H), 3.74-3.69 (m, 1H), 3.45 (s, 3H), 2.27-2.18 (m, 1H), 1.68-1.57 (m, 1H).

Examples 273 and 274

(+/−)-trans-4-(3-hydroxy-4-(3-(trifluoromethyl)phenoxy)piperidin-1-yl)-1-methyl-2-oxo-1,2-dihydropyrido[3,2-d]pyrimidine-6-carbonitrile

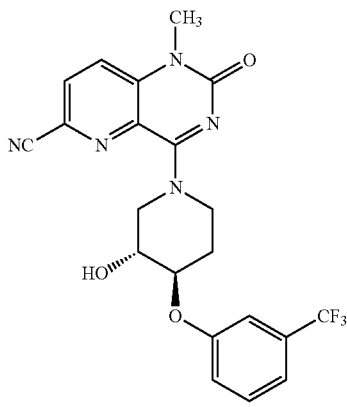

(273-274)

To a stirred solution of (±)-trans-6-chloro-4-(3-hydroxy-4-(3-(trifluoromethyl) phenoxy)piperidin-1-yl)-1-methylpyrido[3,2-d]pyrimidin-2(1H)-one (100 mg, 0.22 mmol) in DMF (5 mL) were added zinc (22 mg, 0.33 mmol), zinc cyanide (77 mg, 0.66 mmol) and TEA (0.12 mL, 0.88 mmol). The reaction mixture was degassed for 5 min and dichloro[9,9-dimethyl-4,5-bis(diphenylphosphino)xanthene]palladium(II) (33.2 mg, 0.04 mmol) was added. The reaction mixture was heated at 90° C. overnight. The reaction mixture was cooled to room temperature, diluted with ethyl acetate and filtered through Celite pad. The filtrate was washed with water, brine and the organic layer was dried over anhydrous $Na_2SO_4$ filtered and evaporated under reduced pressure to get crude compound. The crude product was purified by preparative HPLC [Method: Column: DAD-1: Cellulose-2 (250×4.6 mm), 5 micron DAD-2: Cellulose-4 (250×4.6 mm), 5 micron Mobile Phase: 10 mM ammonium acetate in MeOH; Flow: 2.0 mL\min, Injection vol: 6.0 µL, Run time: 20 min.

Example 273: LCMS: m/z, 446.2 (M+H); rt 1.65 min; LC/MS Method: Column: Waters XBridge C18, 19×150 mm, 5-µm particles; Mobile Phase A: 10-mM ammonium acetate; Mobile Phase B: acetonitrile; Gradient: 20-65% B over 20 minutes, then a 5-minute hold at 100% B; Flow: 15 mL/min. $^1$H NMR (400 MHz, DMSO-$d_6$) δ=8.26 (d, J=8.8 Hz, 1H), 8.01 (d, J=8.8 Hz, 1H), 7.58-7.49 (m, 1H), 7.40-7.32 (m, 2H), 7.29 (d, J=7.3 Hz, 1H), 5.61-5.43 (m, 1H), 4.94-4.66 (m, 1H), 4.61-4.10 (m, 2H), 3.97-3.81 (m, 1H), 3.78-3.66 (m, 1H), 3.46 (s, 3H), 2.30-2.19 (m, 1H), 1.79-1.48 (m, 1H).

Example 274: LCMS: m/z, 446.2 (M+H); rt 1.66 min; LC/MS Method: Column: Waters XBridge C18, 19×150 mm, 5-µm particles; Mobile Phase A: 10-mM ammonium acetate; Mobile Phase B: acetonitrile; Gradient: 20-65% B over 20 minutes, then a 5-minute hold at 100% B; Flow: 15 mL/min. $^1$H NMR (400 MHz, DMSO-$d_6$): δ ppm 8.26 (d, J=8.8 Hz, 1H), 8.01 (d, J=8.8 Hz, 1H), 7.58-7.49 (m, 1H), 7.40-7.32 (m, 2H), 7.29 (d, J=7.3 Hz, 1H), 5.61-5.43 (m, 1H), 4.94-4.66 (m, 1H), 4.61-4.10 (m, 2H), 3.97-3.81 (m, 1H), 3.78-3.66 (m, 1H), 3.46 (s, 3H), 2.30-2.19 (m, 1H), 1.79-1.48 (m, 1H).

Example 275

6-chloro-4-((3R,4R)-3-methoxy-4-(3-(trifluoromethyl)phenoxy)piperidin-1-yl)-1-methylpyrido[3,2-d]pyrimidin-2(1H)-one

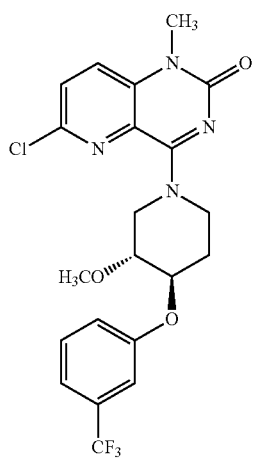

(275)

To a stirred solution of (±)-trans-6-chloro-4-(3-hydroxy-4-(3-(trifluoromethyl) phenoxy)piperidin-1-yl)-1-methylpyrido[3,2-d]pyrimidin-2(1H)-one (125 mg, 0.275 mmol) in DMF (3 mL) was added NaH (60% in mineral oil) (44.0 mg, 1.10 mmol) at 0° C. The reaction mixture was stirred for 5 minutes. Iodomethane (0.04 mL, 0.55 mmol) was added. The reaction mixture was allowed to warm to room temperature and stirred for 3 h at room temperature. The reaction mixture was cooled to 0° C. The reaction was quenched with ice cold water. The reaction mixture was extracted with EtOAc (2×50 mL). The combined organic extracts were washed with brine, dried over $Na_2SO_4$ and concentrated to give crude product which was purified by flash chromatography using silica gel 12 g column and eluted with 5% MeOH\CHCl$_3$ to afford (±)-trans-6-chloro-4-(3-methoxy-4-(3-(trifluoromethyl)phenoxy)piperidin-1-yl)-1-methylpyrido[3,2-d] pyrimidin-2(1H)-one. LCMS: m/z, 469.2 (M+1); rt 1.84 min. (LCMS Method: Column: Waters Acquity UPLC BEH C18 (2.1×50 mm) 1.7 µm, Mobile phase A: 10 mM NH$_4$OAc: acetonitrile (95:5); Mobile phase B: 10 mM NH$_4$OAc: acetonitrile (5:95), Gradient=20-100% B over 2 minute, then a 0.3 minute hold at 100% B; Temperature: 50° C.; Flow rate: 0.7 mL/min; Detection: UV at 220 nm).

Examples 276 and 277

(±)-trans-4-(3-hydroxy-4-(3-(trifluoromethyl)phenoxy)piperidin-1-yl)-1-methyl-2-oxo-1,2-dihydropyrido[3,2-d]pyrimidine-6-carbonitrile

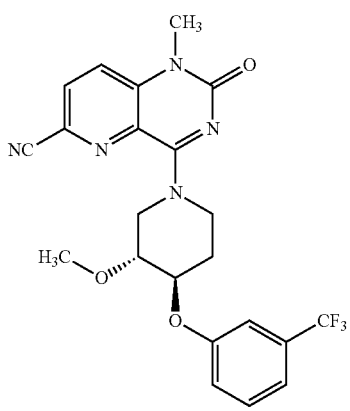
(276-277)

To a stirred solution of (±)-trans-6-chloro-4-(3-methoxy-4-(3-(trifluoromethyl) phenoxy)piperidin-1-yl)-1-methylpyrido[3,2-d]pyrimidin-2(1H)-one (70 mg, 0.15 mmol) in DMF (5 mL) were added zinc (15 mg, 0.22 mmol), zinc cyanide (53 mg, 0.45 mmol) and TEA (0.08 mL, 0.60 mmol). The reaction mixture was degassed with argon for 5 min and dichloro[9,9-dimethyl-4,5-bis(diphenylphosphino)xanthene]palladium(II) (23 mg, 0.03 mmol) was added. The reaction mixture was heated at 90° C. overnight. The reaction mixture was cooled to room temperature, diluted with ethyl acetate and filtered through Celite pad. The filtrate was washed with water, brine and the organic layer was dried over anhydrous Na$_2$SO$_4$, filtered and evaporated under reduced pressure to afford the crude compound. The crude product was purified by preparative HPLC (Method: Column: DAD-1-Cellulose-5 (250×4.6 mm), 5 micron Mobile Phase: 10 mM ammonium acetate in MeOH; Flow: 1.5 mL\min, Injection vol: 2.0 µL, Run time: 20 min].

Example 276: LCMS: m/z, 460.2 (M+1); rt 2.71 min. Column: Kinetex XB-C18 (3×75 mm) 2.6 µm; Mobile phase A: 10 mM ammonium formate: acetonitrile (98:2), Mobile phase B: 10 mM ammonium formate: acetonitrile (2:98), Gradient=20-100% B over 4 minutes, then a 0.6 minute hold at 100% B; Temperature: 27° C.; Flow rate: 1.0 mL/min; Detection: UV at 220 nm. $^1$H NMR (400 MHz, DMSO-d$_6$) δ=8.28 (d, J=9.0 Hz, 1H), 8.04 (d, J=9.0 Hz, 1H), 7.61-7.46 (m, 1H), 7.40-7.29 (m, 3H), 5.24-4.87 (m, 1H), 4.78-4.50 (m, 1H), 4.26 (br s, 1H), 3.60-3.50 (m, 3H), 3.47 (s, 3H), 3.39-3.35 (m, 3H), 2.32-2.12 (m, 1H), 1.73-1.60 (m, 1H).

Example 277: LCMS: m/z, 460.2 (M+1); rt 2.71 min. Column: Kinetex XB-C18 (3×75 mm) 2.6 µm; Mobile phase A: 10 mM ammonium formate: acetonitrile (98:2), Mobile phase B: 10 mM ammonium formate: acetonitrile (2:98), Gradient=20-100% B over 4 minutes, then a 0.6 minute hold at 100% B; Temperature: 27° C.; Flow rate: 1.0 mL/min; Detection: UV at 220 nm. $^1$H NMR (400 MHz, DMSO-d$_6$): δ ppm 8.27 (d, J=8.8 Hz, 1H), 8.03 (d, J=9.0 Hz, 1H), 7.58-7.45 (m, 1H), 7.40-7.35 (m, 2H), 7.31 (br d, J=8.1 Hz, 1H), 5.24-4.87 (m, 1H), 4.78-4.69 (m, 1H), 4.26 (br s, 3H), 3.64-3.51 (m, 1H), 3.46 (s, 3H), 3.39-3.35 (m, 3H), 2.32-2.06 (m, 1H), 1.74 (br d, J=13.4 Hz, 1H).

The Examples in Table 20 were prepared from the appropriate alkyl halide according to the general procedure disclosed in Examples 276 and 277.

TABLE 20

| Ex. No. | Structure | Stereo-chemistry | LCMS Method | LCMS RT | M + H |
|---|---|---|---|---|---|
| 278 | 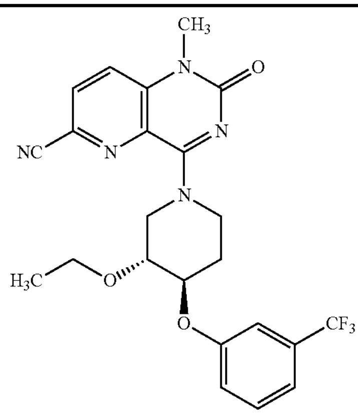 | H | D | 2.91 | 474.2 |
| 279 | | H | D | 2.91 | 474.2 |

LCMS Methods Employed in Tables:

Method 1: Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.75 min hold at 100% B; Flow: 1 mL/min; Detection: MS and UV (220 nm).

Method 2: Start % B=0, Final % B=100, Gradient Time=4 min, Flow Rate=0.8 ml/min, Wavelength=220 nm, Solvent Pair=Water-Methanol-0.1% TFA, Solvent A=90% Water–10% Methanol-0.1% TFA, Solvent B=10% Water–90% Methanol-0.1% TFA, Column 2=(2) PHENOMENEX-LUNA 2.0×50 mm 3 µm, Method 3: Column: Waters XBridge C18, 2.1 mm×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm).

Method 4: Column: Waters Acquity UPLC BEH C18, 2.1×50 mm, 1.7-μm particles; Mobile Phase A: 5:95 acetonitrile:water with 0.1% trifluoroacetic acid; Mobile Phase B: 95:5 acetonitrile:water with 0.1%, trifluoroacetic acid; Temperature: 50° C.; Gradient: 0-100% B over 3 minutes, then a 0.75-minute hold at 100% B; Flow: 1.0 mL/min; Detection: UV at 220 nm.

Method 5: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min; Detection: MS and UV (220 nm).

Intermediates 88 and 89

N-(2,5-dimethylpiperidin-4-yl)-5-methoxypyridin-2-amine (88) and N-(2,5-dimethylpiperidin-4-yl)-5-methoxypyridin-2-amine (89)

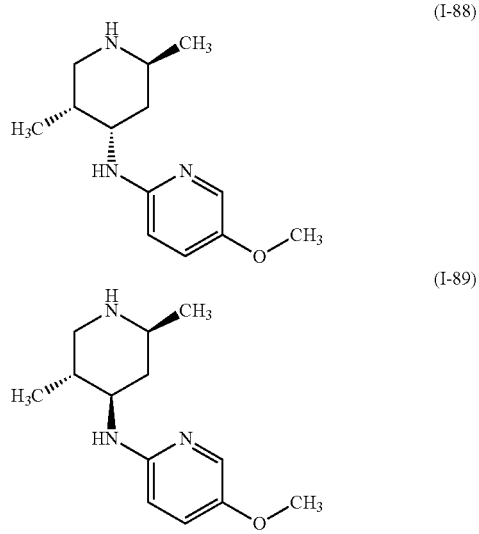

To a solution of (+/−) tert-butyl (2,5-trans)-2,5-dimethyl-4-oxopiperidine-1-carboxylate (100 mg, 0.440 mmol) in 1,2-dichloroethane (5 mL), 5-methoxypyridin-2-amine (54.6 mg, 0.440 mmol) and acetic acid (0.025 mL, 0.440 mmol) were added. The reaction mixture was stirred at room temperature for 15 min, after which sodium triacetoxyborohydride (112 mg, 0.528 mmol) was added. The reaction mixture was stirred at room temperature for 7 days. The reaction was quenched with saturated NaHCO₃ solution. The mixture was extracted with dichloromethane. The organic layers were combined, washed with brine, dried over MgSO₄, filtered and evaporated under reduced pressure to give the crude product as a yellow colored viscous oil. The crude product was purified using preparative HPLC using an CH₃CN—H₂O-ammonium acetate system as eluent. Homogeneous fractions were combined and lyophilized under reduced pressure to give a mixture of two diastereomeric materials. The mixture was dissolved in dichloromethane (2 mL) and treated with TFA (1 mL). The reaction mixture was stirred at room temperature for 3 h. The mixture was concentrated under reduced pressure to give the bis-TFA salts of the two title compounds as viscous yellow colored oils (25 mg, 0.054 mmol, 12.26% yield). The absolute stereochemistry of Intermediates 88 and 89 was not determined. The structures represent the relative orientations of the substituents attached to the piperidinyl rings.

Examples 280 and 281

8-((2S,5R)-4-((5-methoxypyridin-2-yl)amino)-2,5-dimethylpiperidin-1-yl)-5-methyl-6-oxo-5,6-dihydro-1,5-naphthyridine-2-carbonitrile (rel)

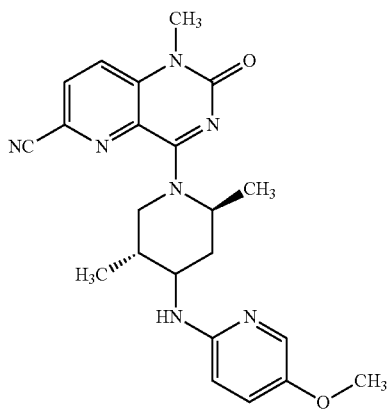

6-Cyano-1-methyl-2-oxo-1,2-dihydro-1,5-naphthyridin-4-yl trifluoromethanesulfonate (14.98 mg, 0.045 mmol) was added to a solution of N-((2,5-trans)-2,5-dimethylpiperidin-4-yl)-5-methoxypyridin-2-amine, bis-trifluoroacetate (25 mg, 0.054 mmol) and Hunig's base (0.039 mL, 0.225 mmol) in acetonitrile (1.5 mL). The reaction mixture was heated at 60° C. The crude reaction mixture was then fractionated using preparative LC/MS with the following conditions: Column: XBridge C18, 200 mm×19 mm, 5-μm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 19% B, 19-59% B over 20 minutes, then a 5-minute hold at 100% B; Flow Rate: 20 mL/min; Column Temperature: 25° C. Fraction collection was triggered by MS and UV signals. Fractions containing the products were combined and dried via centrifugal evaporation.

Example 280 (1st eluting product): The yield of the product was 1.4 mg, and its estimated purity by LCMS analysis was 100%. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min; Detection: MS and UV (220 nm). Injection 1 results: Purity: 100%; Observed Mass: 419.05; Retention Time: 1.7 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). Injection 2 results: Purity: 100%; Observed Mass: 419.07; Retention Time: 1.13 min. ¹H NMR (600 MHz, DMSO-d₆) δ 7.98-7.94 (m, 1H), 7.91-7.87 (m, 1H), 7.50 (d, J=2.9 Hz, 1H), 6.91 (dd, J=8.8, 2.9 Hz, 1H), 6.25 (d, J=9.2 Hz, 1H), 6.10 (s, 1H), 5.86 (d, J=8.4 Hz, 1H), 3.56 (dd, J=12.5, 4.0 Hz, 1H), 3.47 (s, 3H), 3.35 (s, 1H), 3.34-3.32 (m, 1H), 3.39-3.25 (m, 1H), 2.33 (br dd, J=12.1, 10.3 Hz, 1H), 1.95 (dt, J=12.8, 3.7 Hz, 1H), 1.73 (br dd, J=6.2, 3.7 Hz, 1H), 1.56 (s, 1H), 1.23-1.11 (m, 1H), 0.86 (d, J=5.9 Hz, 3H), 0.67 (d, J=6.6 Hz, 3H). Some peaks are obscured due to the water suppression technique employed.

Example 281 (2nd eluting product): The yield of the product was 3.2 mg, and its estimated purity by LCMS analysis was 98%. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min; Detection: MS and UV (220 nm). Injection 1 results: Purity: 99.1%; Observed Mass: 419.06; Retention Time: 1.74 min. Injection 2 conditions: column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). Injection 2 results: Purity: 98.3%; Observed Mass: 419.05; Retention Time: 1.16 min. ¹H NMR (600 MHz, DMSO-d₆) δ 8.17 (d, J=8.8 Hz, 1H), 8.07 (d, J=8.8 Hz, 1H), 7.73 (d, J=3.3 Hz, 1H), 7.13 (dd, J=8.8, 2.9 Hz, 1H), 6.53 (d, J=9.2 Hz, 1H), 6.10 (d, J=7.7 Hz, 1H), 6.07 (s, 1H), 4.81 (br s, 1H), 4.27 (ddt, J=12.4, 8.2, 4.2 Hz, 1H), 3.69 (s, 2H), 3.53 (s, 2H), 2.55 (s, 6H), 2.39 (br d, J=1.5 Hz, 1H), 2.18-2.07 (m, 1H), 1.54 (br d, J=12.8 Hz, 1H), 1.18 (d, J=6.6 Hz, 4H), 0.96 (d, J=7.0 Hz, 3H). Some peaks are obscured due to the water suppression technique employed.

Intermediate 90 tert-Butyl 3-methyl-4-(methylamino)piperidine-1-carboxylate

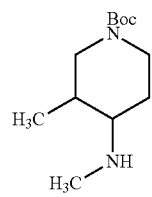

(I-90)

To a solution of tert-butyl 3-methyl-4-oxopiperidine-1-carboxylate (1 g, 4.69 mmol) in methanol (10 mL) was added methanamine (0.88 mL, 9.38 mmol, 33% wt. solution in MeOH). The reaction mixture was heated to 65° C. for 2 h. The reaction mixture was cooled to room temperature. Sodium borohydride (0.36 g, 9.38 mmol) was added and the reaction mixture stirred for 12 h. The reaction was quenched with saturated NH₄Cl. The reaction mixture was dissolved in EtOAc (100 mL), washed with saturated. NaHCO₃ (20 mL), water (20 mL), brine (20 mL), dried over Na₂SO₄ and concentrated under reduced pressure to afford tert-butyl 3-methyl-4-(methylamino)piperidine-1-carboxylate (0.95 g, 89% yield). LCMS: m/z=229.3 (M+H); retention time 0.64 and 0.92 min. LC-MS Method: Column—Aquity UPLC BEH C18 (3.0×50 mm) 1.7 μm; Mobile phase A: Buffer: acetonitrile (95:5); Mobile phase B: Buffer:acetonitrile (5:95), Buffer: 10 mM ammonium acetate; Gradient: 20-100% B over 2.0 minutes, then a 0.2 minute hold at 100% B, flow rate 0.7 mL/min.

Intermediate 91 tert-Butyl 4-(4-fluoro-N-methylbenzamido)-3-methylpiperidine-1-carboxylate

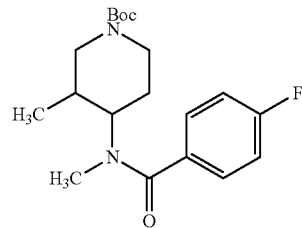

(I-92)

To a solution of 4-fluorobenzoic acid (295 mg, 2.1 mmol) and tert-butyl 3-methyl-4-(methylamino)piperidine-1-carboxylate (400 mg, 1.75 mmol) in DMF (5 mL) was added HATU (799 mg, 2.1 mmol), followed by addition of DIPEA (0.92 mL, 5.26 mmol). The reaction mixture was stirred at room temperature for 12 h. The reaction was quenched with saturated NH₄Cl. The reaction mixture was dissolved in EtOAc (100 mL), washed with saturated NaHCO₃ (20 mL), water (20 mL), brine (20 mL), dried over Na₂SO₄ and concentrated under reduced pressure to afford the crude product which was purified by silica gel chromatography by using 0-10% MeOH/CHCl₃ as eluent. Pure fractions were collected and concentrated to obtain tert-butyl 4-(4-fluoro-N-methylbenzamido)-3-methylpiperidine-1-carboxylate (500 mg, 81% yield) as yellow liquid. LCMS: m/z=295.1 [(M-ᵗBu)+H)]; retention time 1.54 min. LC-MS Method: Column-Aquity UPLC BEH C18 (3.0×50 mm) 1.7 μm; Mobile phase A: Buffer: acetonitrile (95:5); Mobile phase B: Buffer:acetonitrile (5:95), Buffer: 10 mM ammonium acetate; Gradient: 20-100% B over 2.0 minutes, then a 0.2 minute hold at 100% B, flow rate 0.7 mL/min.

Intermediate 93

4-Fluoro-N-methyl-N-(3-methylpiperidin-4-yl)benzamide, TFA

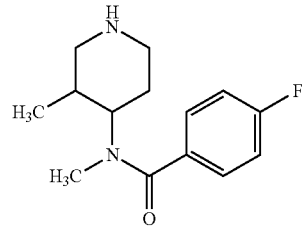

(I-94)

To a solution of tert-butyl 4-(4-fluoro-N-methylbenzamido)-3-methylpiperidine-1-carboxylate (200 mg, 0.57 mmol) in DCM (2 mL) was added TFA (0.44 mL, 5.71 mmol). The reaction mixture was stirred for 2 h. The reaction mixture was concentrated under reduced pressure and co-distilled with DCM (2×5 mL) to afford 4-fluoro-N-methyl-N-(3-methylpiperidin-4-yl)benzamide, TFA (200 mg, 96% yield). LCMS: m/z=251.2 (M+H); retention time 0.56 and 0.58 min. LC-MS Method: Column-Aquity UPLC BEH C18 (3.0×50 mm) 1.7 μm; Mobile phase A: Buffer: acetonitrile (95:5); Mobile phase B: Buffer:acetonitrile (5:95), Buffer: 10 mM ammonium acetate; Gradient: 20-100% B over 2.0 minutes, then a 0.2 minute hold at 100% B, flow rate 0.7 mL/min.

Example 284-287

N-(1-(6-Cyano-1-methyl-2-oxo-1,2-dihydro-1,5-naphthyridin-4-yl)-3-methylpiperidin-4-yl)-4-fluoro-N-methylbenzamide (284-287)

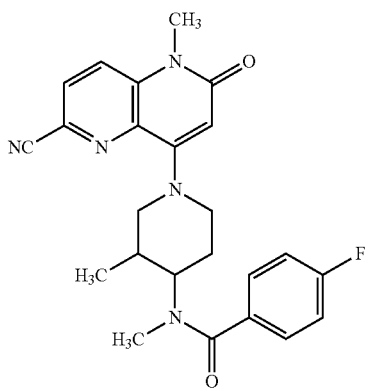

To a solution of 4-fluoro-N-methyl-N-(3-methylpiperidin-4-yl)benzamide, TFA (200 mg, 0.549 mmol) in acetonitrile (3 mL) were added DIPEA (0.29 mL, 1.65 mmol) and 6-cyano-1-methyl-2-oxo-1,2-dihydro-1,5-naphthyridin-4-yl trifluoromethanesulfonate (220 mg, 0.66 mmol). The reaction mixture was heated to 85° C. and was stirred for 16 h. The reaction mixture was cooled to room temperature, concentrated under reduced pressure and was purified by silica gel chromatography by using 0-10% MeOH/CHCl$_3$ as eluent. Pure fractions were collected and concentrated to afford a yellow liquid which was separated by LC (LC Column: YMC EXRS (250×19 ID) 5 micron; Mobile Phase A: 10 mM ammonium acetate in water-4.5 pH; Mobile Phase B: Acetonitrile Flow: 18 mL/min; Grad: 45 to 69.8% B over 10 min, then 100% B over 0.01 min and hold at 100% B over 3 min. to obtain diastereomeric mixture 1 and diastereomeric mixture 2. Diastereomeric mixture 1 and 2 were separated using SFC to get enantiomers.

Diastereomeric mixture 1 was separated by chiral SFC (Column/dimensions: ChiralCel OJ-H (250×21) mm, 5% CO$_2$: 90%; % co-solvent: 10% of methanol; Total Flow: 100.0 g/min; Back Pressure: 100 bar; Temperature: 35° C.; UV: 220 nm) to obtain Isomer 1: Example 284, retention time=6.9 min; and Isomer 2: Example 285, retention time=10.5 min.

Diastereomeric mixture 2 was separated by chiral SFC (Column/dimensions: Chiralpak AS-H (250×30) mm, 5% CO$_2$: 80%; % co-solvent: 20% of methanol; Total Flow: 100.0 g/min; Back Pressure: 100 bar; Temperature: 35° C.; UV: 220 nm) to obtain Isomer 3: Example 286, retention time=9 min; and Isomer 4: Example 287, retention time=11 min Example 284: (3.7 mg, 1% yield); LCMS: m/z=434.3 (M+H); retention time=1.51 min. LCMS Method: XBridge BEH XP C18 (50×2.1) mm, 2.5 μm; Mobile phase A: 10 mM ammonium acetate, acetonitrile (95:5); Mobile phase B: 10 mM ammonium acetate:acetonitrile (5:95); Gradient=0-100% B over 3 minutes; Temperature: 50° C.; Flow rate: 1.1 mL/min; Detection: UV at 220 nm. $^1$H NMR (400 MHz, DMSO-d$_6$) δ ppm 8.23-8.12 (m, 1H), 8.12-7.98 (m, 1H), 7.55-7.38 (m, 2H), 7.34-7.19 (m, 2H), 6.21-5.99 (m, 1H), 4.39-3.96 (m, 3H), 3.53 (d, J=9.3 Hz, 3H), 3.26-2.98 (m, 1H), 2.92-2.76 (m, 3H), 2.73-2.67 (m, 1H), 2.41-2.31 (m, 1H), 2.20-1.90 (m, 2H), 1.88-1.70 (m, 1H), 0.97-0.65 (m, 3H).

Example 285: (4.2 mg, 1% yield); LCMS: m/z=434.2 (M+H); retention time=1.51 min. LCMS Method: XBridge BEH XP C18 (50×2.1) mm, 2.5 μm; Mobile phase A: 10 mM ammonium acetate, acetonitrile (95:5); Mobile phase B: 10 mM ammonium acetate:acetonitrile (5:95); Gradient=0-100% B over 3 minutes; Temperature: 50° C.; Flow rate: 1.1 mL/min; Detection: UV at 220 nm. $^1$H NMR (400 MHz, DMSO-d$_6$) δ ppm 8.22-8.13 (m, 1H), 8.12-7.99 (m, 1H), 7.55-7.38 (m, 2H), 7.35-7.17 (m, 2H), 6.20-6.02 (m, 1H), 4.40-4.11 (m, 2H), 4.08-3.95 (m, 1H), 3.53 (d, J=9.0 Hz, 3H), 3.27-3.04 (m, 1H), 2.90-2.74 (m, 3H), 2.74-2.61 (m, 1H), 2.40-2.29 (m, 1H), 2.19-1.91 (m, 2H), 1.87-1.68 (m, 1H), 0.96-0.63 (m, 3H).

Example 286: (1.9 mg, 1% yield); LCMS: m/z=434.2 (M+H); retention time=1.58 min. LCMS Method: XBridge BEH XP C18 (50×2.1) mm, 2.5 μm; Mobile phase A: 10 mM ammonium acetate, acetonitrile (95:5); Mobile phase B: 10 mM ammonium acetate:acetonitrile (5:95); Gradient=0-100% B over 3 minutes; Temperature: 50° C.; Flow rate: 1.1 mL/min; Detection: UV at 220 nm.

Example 287: (2.0 mg, 1% yield); LCMS: m/z=434.2 (M+H); retention time=1.55 min. LCMS Method: XBridge BEH XP C18 (50×2.1) mm, 2.5 μm; Mobile phase A: 10 mM ammonium acetate, acetonitrile (95:5); Mobile phase B: 10 mM ammonium acetate:acetonitrile (5:95); Gradient=0-100% B over 3 minutes; Temperature: 50° C.; Flow rate: 1.1 mL/min; Detection: UV at 220 nm. $^1$H NMR (400 MHz, DMSO-d$_6$) δ ppm 8.21-8.14 (m, 1H), 8.11-8.04 (m, 1H), 7.53-7.43 (m, 2H), 7.33-7.20 (m, 2H), 6.12 (s, 1H), 4.47-4.26 (m, 1H), 4.16-4.07 (m, 1H), 3.93-3.83 (m, 1H), 3.53 (s, 3H), 2.93-2.90 (m, 5H), 2.39-2.26 (m, 2H), 1.88-1.77 (m, 1H), 1.58-1.56 (m, 1H), 1.24-1.21 (m, 4H).

The Examples in Table 21 were prepared from appropriate piperidine, benzoic acid, naphthyridine derivatives according to the general procedures disclosed in Examples 284-287.

TABLE 21

| Ex. No | Structure | Stereo-chemistry | LCMS Method | LCMS RT | M + H |
|---|---|---|---|---|---|
| 282 | 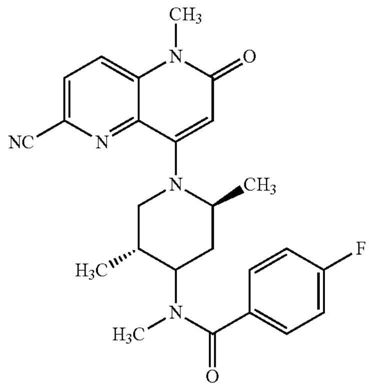 [SMILES: C[C@@H]1CN(c2cc(=O)n(C)c3ccc(C#N)nc23)[C@@H](C)CC1N(C)C(=O)c1ccc(F)cc1] | Homochiral | C | 2.32 | 448.2 |
| 283 | 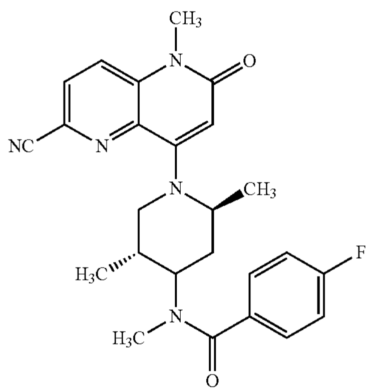 [SMILES: C[C@@H]1CN(c2cc(=O)n(C)c3ccc(C#N)nc23)[C@@H](C)CC1N(C)C(=O)c1ccc(F)cc1] | Homochiral | C | 2.40 | 448.2 |
| 283A | 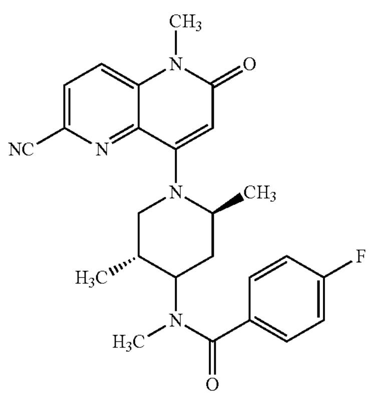 [SMILES: C[C@@H]1CN(c2cc(=O)n(C)c3ccc(C#N)nc23)[C@@H](C)CC1N(C)C(=O)c1ccc(F)cc1] | Homochiral | C | 2.38 | 448.2 |
| 283B | 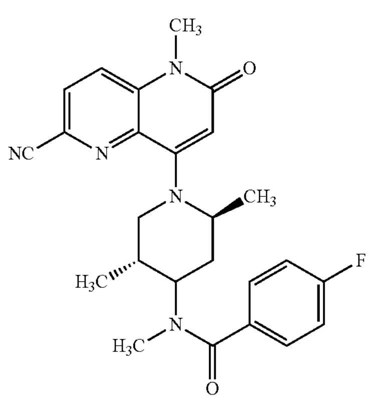 [SMILES: C[C@@H]1CN(c2cc(=O)n(C)c3ccc(C#N)nc23)[C@@H](C)CC1N(C)C(=O)c1ccc(F)cc1] | Homochiral | C | 2.30 | 448.2 |

TABLE 21-continued

| Ex. No | Structure | Stereo-chemistry | LCMS Method | LCMS RT | M + H |
|---|---|---|---|---|---|
| 288 | 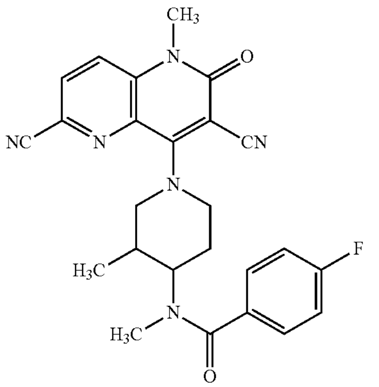 [SMILES: CC1CN(c2c(C#N)c(=O)n(C)c3ccc(C#N)nc23)CCC1N(C)C(=O)c1ccc(F)cc1] | Homochiral | C | 2.25 | 459.2 |
| 289 | 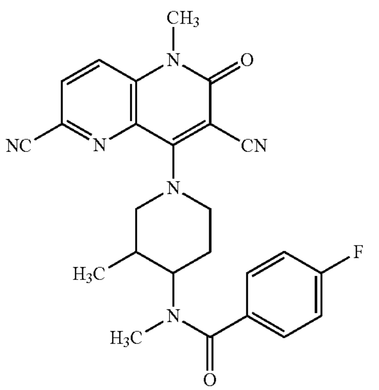 [SMILES: CC1CN(c2c(C#N)c(=O)n(C)c3ccc(C#N)nc23)CCC1N(C)C(=O)c1ccc(F)cc1] | Homochiral | C | 2.28 | 459.2 |
| 290 | 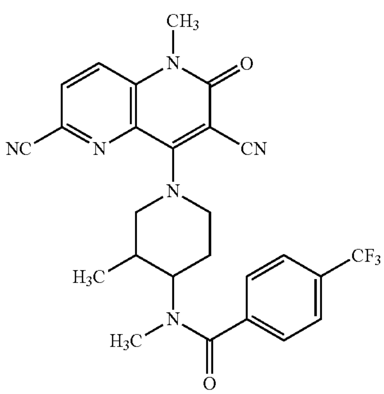 [SMILES: CC1CN(c2c(C#N)c(=O)n(C)c3ccc(C#N)nc23)CCC1N(C)C(=O)c1ccc(C(F)(F)F)cc1] | Homochiral | C | 2.61 | 509.2 |
| 291 | 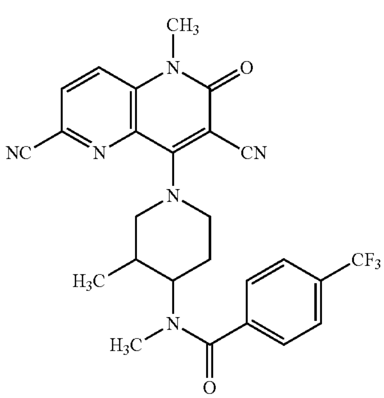 [SMILES: CC1CN(c2c(C#N)c(=O)n(C)c3ccc(C#N)nc23)CCC1N(C)C(=O)c1ccc(C(F)(F)F)cc1] | Homochiral | C | 2.61 | 509.2 |

TABLE 21-continued

| Ex. No | Structure | Stereo-chemistry | LCMS Method | LCMS RT | M + H |
|---|---|---|---|---|---|
| 292 | 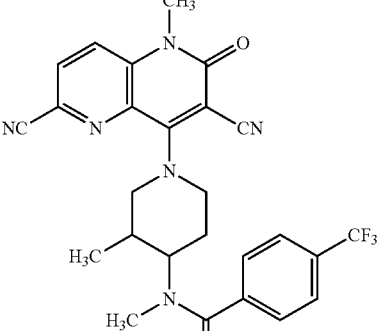 | Homochiral | C | 2.64 | 509.3 |
| 293 | 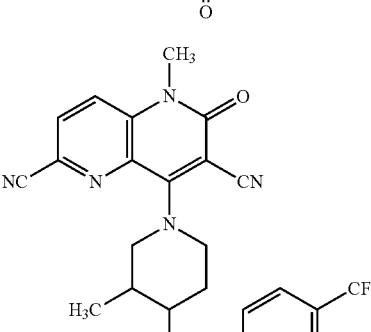 | Homochiral | C | 2.64 | 509.3 |

Intermediate 95

(R)-4-benzyl-3-butyloxazolidin-2-one

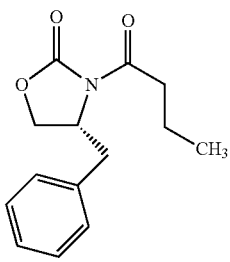

(I-95)

n-Butyl lithium (33.9 mL, 67.7 mmol) was added dropwise to a stirred solution of (R)-4-benzyloxazolidin-2-one (10 g, 56.4 mmol) in THF (120 mL) at −78° C. under nitrogen. An orange color developed during the addition of the base. On addition, stirring was maintained for 30 min, after which butyryl chloride (8.76 mL, 85 mmol) was added dropwise. During this process, the color changed to pale yellow. The reaction mixture was allowed to warm to room temperature and stirring was continued overnight. The reaction was then quenched using saturated NH₄Cl solution. The resultant mixture was extracted using EtOAc (3×). The combined extracts were washed with brine, dried over sodium sulfate, filtered and evaporated to give a very pale-yellow oil, 15 g. The crude product was fractionated using flash chromatography on silica get using 20% ethyl acetate in hexanes as eluent. Homogeneous fractions were combined and evaporated in vacuo to give the product as a colorless oil, (12.9 g., 92%). ¹H NMR (500 MHz, CHLOROFORM-d) δ 7.43-7.12 (m, 5H), 4.75-4.64 (m, 1H), 4.26-4.12 (m, 2H), 3.32 (dd, J=13.4, 3.3 Hz, 1H), 3.05-2.84 (m, 2H), 2.79 (dd, J=13.4, 9.6 Hz, 1H), 1.76 (ddd, J=14.7, 7.4, 2.6 Hz, 2H), 1.04 (t, J=7.5 Hz, 3H).

Intermediate 96

(R)-4-benzyl-3-((2R,3S)-2-ethyl-3-hydroxy-4-(2-methyl-1,3-dioxolan-2-yl)butanoyl) oxazolidin-2-one

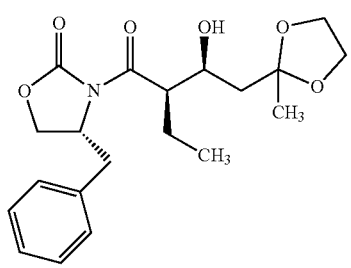

(I-96)

To a stirred solution of (R)-4-benzyl-3-butyloxazolidin-2-one (4.95 g, 20 mmol) in DCM (40 mL) at −78° C. under argon was slowly added dibutyl(((trifluoromethyl)sulfonyl)oxy)borane (26.0 mL, 26.0 mmol) followed by triethylamine (3.90 mL, 28.0 mmol) and stirring was continued for 30 min. The reaction mixture was warmed to 0° C. for 1 h and then re-cooled to −78° C. 2-(2-methyl-1,3-dioxolan-2-yl)acetaldehyde (2.86 g, 22.00 mmol) in DCM (10 mL) was added dropwise. After 30 min the reaction mixture was warmed to 0° C. and stirred for 3 h. Next, pH 7 buffer solution (100 mL), methanol (30 mL) and $H_2O_2$ (30 mL, 30% aqueous) were added and the mixture was stirred for 1.5 h at room temperature. The layers were separated and the aqueous layer was extracted with DCM, and the combined organic layers were dried over $MgSO_4$, filtered and the solvent was evaporated in vacuo to give 10.2 g of a colorless, viscous oil. This crude product was purified by column chromatography using 30-50% EtOAc:Hexane mixtures as eluant. Homogeneous fractions were combined and evaporated in vacuo to give the purified product as a colorless, viscous oil, (5.97 g, 75%). LCMS (Method A*): $R_T$=1.321 min. $(M+Na)^+$ =399.95. $^1$H NMR (500 MHz, CHLOROFORM-d) δ 7.40-7.22 (m, 5H), 4.74 (ddt, J=10.3, 7.2, 3.1 Hz, 1H), 4.23-4.13 (m, 3H), 4.05-3.92 (m, 4H), 3.62 (d, J=1.5 Hz, 1H), 3.37 (dd, J=13.2, 3.3 Hz, 1H), 2.72 (dd, J=13.2, 10.1 Hz, 1H), 1.99-1.86 (m, 3H), 1.75 (ddd, J=13.7, 7.5, 4.5 Hz, 1H), 1.39 (s, 3H), 1.00 (t, J=7.5 Hz, 3H).

Intermediate 97

(2R,3S)-1-((R)-4-benzyl-2-oxooxazolidin-3-yl)-2-ethyl-3-hydroxyhexane-1,5-dione

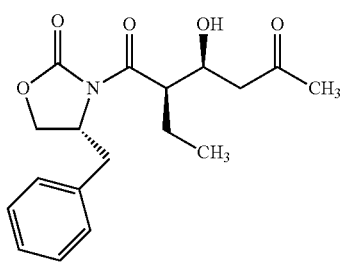

(I-97)

To a solution of (R)-4-benzyl-3-((2R,3S)-2-ethyl-3-hydroxy-4-(2-methyl-1,3-dioxolan-2-yl)butanoyl)oxazolidin-2-one (276 mg, 0.731 mmol) in acetone (14 mL) was added iron(III) chloride 5% by weight on silica (60 mg, 0.018 mmol). The reaction mixture was stirred at 25° C. under nitrogen for 30 min, and was then filtered, added to water and the product extracted with ethyl acetate. The combined extracts were dried over $MgSO_4$, filtered and concentrated in vacuo to give the product as a colorless oil, (220 mg, 90%). LCMS: (Method A*) $R_T$=1.242 min, 95%. $(M+Na)^+$=355.9. $^1$H NMR (500 MHz, CHLOROFORM-d) δ 7.39-7.24 (m, 5H), 4.75 (ddt, J=10.3, 7.3, 3.1 Hz, 1H), 4.41 (ddt, J=9.5, 5.5, 2.8 Hz, 1H), 4.26-4.15 (m, 2H), 4.10 (dt, J=9.5, 4.8 Hz, 1H), 3.37 (dd, J=13.2, 3.3 Hz, 1H), 3.23 (d, J=3.0 Hz, 1H), 2.83-2.61 (m, 3H), 2.21 (s, 3H), 1.99-1.86 (m, 1H), 1.77-1.66 (m, 1H), 1.00 (t, J=7.5 Hz, 3H).

Intermediates 98A and 98B (R)-4-benzyl-3-((2R,3S,5R)-5-(benzyl amino)-2-ethyl-3-hydroxyhexanoyl)oxazolidin-2-one and (R)-4-benzyl-3-((2R,3S,5S)-5-(benzylamino)-2-ethyl-3-hydroxyhexanoyl)oxazolidin-2-one

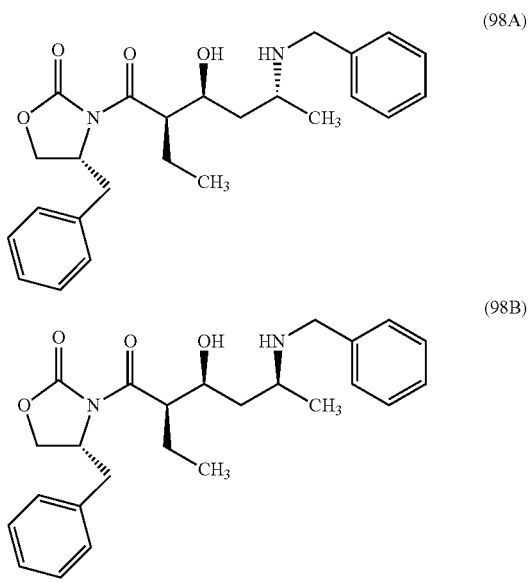

Benzylamine (1.350 ml, 12.36 mmol) was added to a solution of (2R,3S)-1-((R)-4-benzyl-2-oxooxazolidin-3-yl)-2-ethyl-3-hydroxyhexane-1,5-dione (4 g, 12.00 mmol) in DCE (40.0 ml) under nitrogen at room temperature and the mixture was stirred for 30 min. It was then cooled to 0° C., and sodium triacetoxyborohydride (2.54 g, 12.00 mmol) was added in portions over ~10 min. The mixture was then allowed to warm to room temperature and stirring was continued overnight. The reaction was quenched by the addition of saturated aqueous $NaHCO_3$, and the resulting mixture was stirred at room temperature for 15 mins. This mixture was then extracted with EtOAc (3×) and the combined extracts were washed successively with saturated aqueous $NaHCO_3$ and brine, and then dried over $MgSO_4$, filtered and concentrated in vacuo to give the crude product as a yellow colored oil.

Intermediates 99a and 99B (3R,4S,6R)-1-benzyl-3-ethyl-4-hydroxy-6-methylpiperidin-2-one and (3R,4S,6S)-1-benzyl-3-ethyl-4-hydroxy-6-methylpiperidin-2-one (99A)

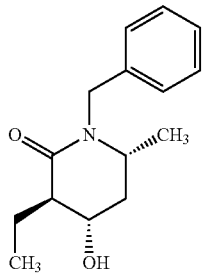

(99B)

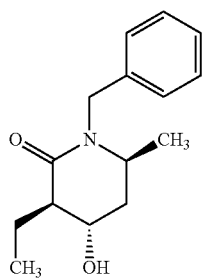

A mixture of (R)-4-benzyl-3-((2R,3S,5R)-5-(benzylamino)-2-ethyl-3-hydroxyhexanoyl)oxazolidin-2-one and (R)-4-benzyl-3-((2R,3S,5S)-5-(benzylamino)-2-ethyl-3-hydroxyhexanoyl)oxazolidin-2-one (1 g) was dissolved in MeOH (18 mL) and irradiated at 90° C. for 3 h in a microwave reactor. The resultant solution was then evaporated under reduced pressure to give an oil that was fractionated using preparative reverse phase chromatography under the following conditions: Column: Biotage Sfar C18 D 120 g. Eluants: A: 95% Water+0.05% TFA, 5% ACN+0.05% TFA; B: 5% Water–0.05% TFA, 95% ACN+0.05% TFA. Equilibration: 0% B 3 CV, Gradient: 0-80% B 10 CV, 80-100% 5CV, 100-100% 3 CV. Fractions containing the piperidinone products were combined and concentrated in vacuo to remove ACN. The resultant mixture was basified by the addition of saturated NaHCO$_3$ solution and the products were extracted using DCM (3×). The combined extracts were dried over MgSO$_4$, filtered and concentrated in vacuo to give a colorless oil. This material was further fractionated by flash chromatography using 20-25% acetone in hexanes as eluant. Homogeneous fractions were combined and evaporated under reduced pressure to give the following products. Higher Rf fraction: LCMS (Method A); $R_T$=1.380 min, m/z=247.90 (M+H)$^+$. $^1$H NMR (500 MHz, CHLOROFORM-d) δ 7.43-7.04 (m, 6H), 5.35 (d, J=15.3 Hz, 1H), 4.14 (d, J=15.3 Hz, 1H), 3.96-3.81 (m, 1H), 3.39 (dt, J=9.9, 5.8 Hz, 1H), 2.39 (dt, J=9.1, 4.6 Hz, 1H), 2.19 (dt, J=13.1, 4.4 Hz, 1H), 2.08 (td, J=6.9, 4.7 Hz, 1H), 1.95-1.85 (m, 1H), 1.69-1.62 (m, 1H), 1.26 (d, J=6.4 Hz, 3H), 1.01 (t, J=7.5 Hz, 3H). Lower Rf fraction: LCMS (Method A); $R_T$=1.326 min, m/z=247.95 (M+H)$^+$. $^1$H NMR (500 MHz, CHLOROFORM-d) δ 7.42-7.13 (m, 5H), 5.25 (d, J=15.3 Hz, 1H), 4.22-4.02 (m, 2H), 3.63-3.52 (m, 1H), 3.70-3.47 (m, 1H), 2.50-2.28 (m, 1H), 2.00-1.84 (m, 4H), 1.22 (d, J=6.6 Hz, 3H), 1.02 (t, J=7.4 Hz, 3H).

Intermediate 100

(2S,4S,5S)-1-benzyl-5-ethyl-2-methylpiperidin-4-ol (I-100)

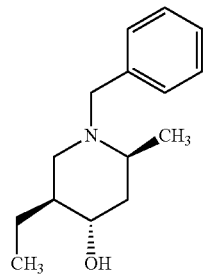

BH$_3$.THF (6.87 ml, 6.87 mmol) was added to a solution of (3R,4S,6S)-1-benzyl-3-ethyl-4-hydroxy-6-methylpiperidin-2-one (425 mg, 1.718 mmol) in THF (6 ml) and the resulting solution was heated at 66° C. in a sealed vial for 3.5 h. The reaction mixture was cooled to room temperature. The reaction was quenched by the sequential addition of water (5 mL) followed by 1 M NaOH (9 mL). The resultant mixture was extracted with EtOAc (3×5 mL) and the combined organic layers were dried over MgSO$_4$, filtered and and then concentrated in vacuo to give 273 mg of the crude product. This material was dissolved in MeOH and heated under reflux for 45 min. LCMS (Method A); RT=0.958 min, m/z=233.95 (M+H)$^+$.

Intermediate 101 tert-butyl (2S,4S,5S)-5-ethyl-4-hydroxy-2-methylpiperidine-1-carboxylate (I-101)

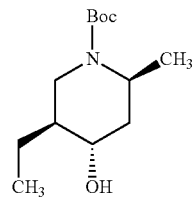

Pd—C (100 mg, 0.094 mmol) was added to a solution of (2S,4S,5S)-1-benzyl-5-ethyl-2-methylpiperidin-4-ol (400 mg, 1.714 mmol) and di-tert-butyl dicarbonate (0.438 mL, 1.886 mmol) in ethyl acetate (20 mL). The resultant mixture was sequentially subjected to reduced pressure and flushed with nitrogen (3×). The mixture was evacuated once more and then flushed with hydrogen. The resultant suspension was stirred vigorously at room temperature overnight. The reaction mixture was then filtered under a blanket of nitrogen and the filtrate was concentrated under reduced pressure (water bath temperature 50° C.) to give the crude product as a colorless oil. This was adsorbed onto silica gel and fractionated using flash chromatography employing 20-40% EtOAc in hexanes and eluant. Homogeneous fractions were combined and evaporated under reduced pressure to give a colorless oil, 93 mg. LCMS (Method A): $R_T$=1.668 min, m/z=166.00, (M-CO$_2$-t-Bu+Na)$^+$.

Intermediate 102 tert-butyl (2S,4S,5S)-5-ethyl-4-((5-isopropoxypyridin-2-yl)oxy)-2-methylpiperidine-1-carboxylate

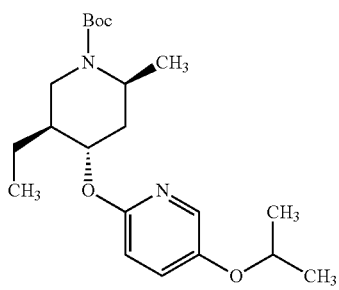

(I-102)

Sodium hydride (27.8 mg, 0.660 mmol) was added to a solution of tert-butyl (2S,4S,5S)-5-ethyl-4-hydroxy-2-methylpiperidine-1-carboxylate (146 mg, 0.600 mmol) in THF (6 mL) and the resultant suspension was stirred at room temperature for 10 min. 2-Fluoro-5-isopropoxypyridine (93 mg, 0.600 mmol) was then added and the mixture was stirred at 63° C. overnight. The crude product was fractionated using preparative reverse phase HPLC. Homogeneous fractions were combined and evaporated in vacuo to give the product as a colorless oil, 21 mg. LCMS (Method A): RT=1.370 min, m/z=279.20, (M-CO2-t-Bu+H)$^+$.

Intermediate 103

2-(((2S,4S,5S)-5-ethyl-2-methylpiperidin-4-yl)oxy)-5-isopropoxypyridine

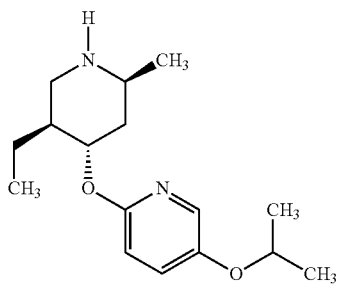

(I-103)

Trifluoroacetic acid (5 mL, 64.9 mmol) was added to a solution of tert-butyl (2S,4S,5S)-5-ethyl-4-((5-isopropoxypyridin-2-yl)oxy)-2-methylpiperidine-1-carboxylate (60 mg, 0.159 mmol) in DCM (5 mL) and the resultant mixture was stirred at room temperature for 30 min. The solution was then concentrated in vacuo.

Intermediate 104

(2R,4S,5S)-1-benzyl-5-ethyl-2-methylpiperidin-4-ol

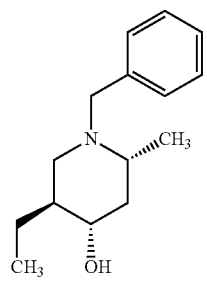

(I-104)

BH$_3$.THF (4738 µL, 4.74 mmol) was added to a solution of (3R,4S,6R)-1-benzyl-3-ethyl-4-hydroxy-6-methylpiperidin-2-one (293 mg, 1.185 mmol) in THF (5.9 mL). The resulting solution was heated at 66° C. in a sealed vial for 3.5 h. The reaction mixture was cooled to room temperature. The reaction was quenched by the sequential addition of water (1 mL) and 1 M NaOH (3 mL). The mixture was extracted with EtOAc (3×5 mL) and the combined organic layers were dried over MgSO$_4$, filtered and concentrated in vacuo to give 80 mg of a crude product. This was dissolved in MeOH and the resultant solution was heated under reflux for 45 min. It was then evaporated under reduced pressure and the residue was partitioned between water and ethyl acetate. The organic layer was collected and the aqueous layer basified with 1 N NaOH solution and extracted (2×) with ethyl acetate. The combined extracts were dried over MgSO$_4$, filtered and evaporated in vacuo to give the product as a colorless oil, 71 mg. LCMS (Method A): RT=0.995 min, m/e=234.00 (M+H)$^+$. $^1$H NMR (500 MHz, CHLOROFORM-d) δ 7.74 (d, J=7.0 Hz, 4H), 7.49-7.22 (m, 11H), 3.99 (d, J=13.6 Hz, 1H), 3.38 (br dd, J=9.7, 5.5 Hz, 1H), 3.15 (br d, J=13.6 Hz, 1H), 2.86 (dd, J=11.0, 2.7 Hz, 1H), 2.17-2.00 (m, 1H), 1.91-1.77 (m, 1H), 1.69-1.46 (m, 4H), 1.11-1.03 (m, 11H), 1.02-0.86 (m, 4H), 0.73 (t, J=7.5 Hz, 3H).

Intermediate 105 tert-butyl (2R,4S,5S)-5-ethyl-4-hydroxy-2-methylpiperidine-1-carboxylate

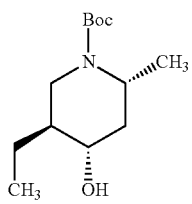

(I-105)

Pd—C (113 mg, 1.058 mmol) was added to a solution of (2R,4S,5S)-1-benzyl-5-ethyl-2-methylpiperidin-4-ol (247 mg, 1.058 mmol) and di-tert-butyl dicarbonate (0.270 mL, 1.164 mmol) in ethyl acetate (10 mL). The resultant mixture was sequentially subjected to reduced pressure and flushed with nitrogen (3×). The mixture was evacuated once more and then flushed with hydrogen and the resultant suspension was stirred vigorously at room temperature overnight. The reaction mixture was then filtered under a blanket of nitrogen and the filtrate was concentrated under reduced pressure (water bath temperature 50° C.) to give a crude product as a colorless oil.

Intermediate 106 tert-butyl (2R,4S,5S)-5-ethyl-4-((5-isopropoxypyridin-2-yl)oxy)-2-methylpiperidine-1-carboxylate

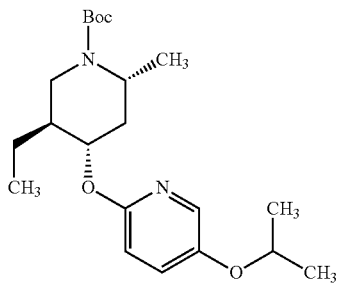

(I-106)

Sodium hydride (51.8 mg, 1.230 mmol) was added to a solution of tert-butyl (2R,4S,5S)-5-ethyl-4-((5-isopropoxypyridin-2-yl)oxy)-2-methylpiperidine-1-carboxylate (52 mg, 0.137 mmol, 12.29% yield) in THF (10 mL). The mixture was stirred at room temperature for 10 min. 2-Fluoro-5-isopropoxypyridine (173 mg, 1.118 mmol) was added and the resultant mixture was heated at 63° C. for 24 h. The crude product was fractionated using preparative reverse phase HPLC. Homogeneous fractions were combined and evaporated in vacuo to give the product as a colorless oil, 52 mg. LCMS (Method A): RT=1.364 min, m/z=279.15, (M-CO₂-t-Bu+H)⁺.

Intermediate 107

2-(((2R,4S,5S)-5-ethyl-2-methylpiperidin-4-yl)oxy)-5-isopropoxypyridine

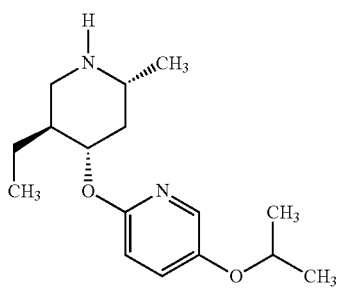

(I-107)

Trifluoroacetic acid (5 mL, 64.9 mmol) was added to a solution of tert-butyl (2R,4S,5S)-5-ethyl-4-((5-isopropoxypyridin-2-yl)oxy)-2-methylpiperidine-1-carboxylate (75 mg, 0.198 mmol) in DCM (5 mL). The resultant mixture was stirred at room temperature for 30 min. The solution was then concentrated in vacuo.

Intermediate 108

Tert-butyl (2R,4S,5R)-5-ethyl-2-methyl-4-((4-nitrobenzoyl)oxy)piperidine-1-carboxylate

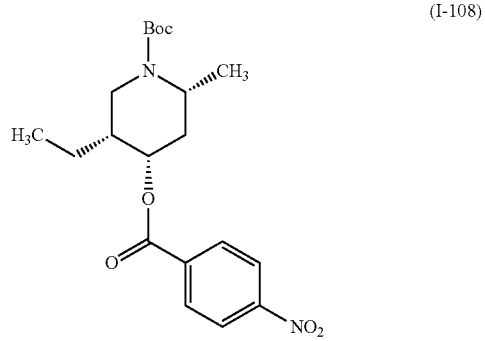 [SMILES: CC[C@@H]1CN(C(=O)OC(C)(C)C)[C@H](C)C[C@@H]1OC(=O)c1ccc([N+](=O)[O-])cc1]

(I-108)

To a solution of tert-butyl (2R,4R,5R)-5-ethyl-4-hydroxy-2-methylpiperidine-1-carboxylate (550 mg, 2.260 mmol) in THF (15 mL), triphenylphosphine (830 mg, 3.16 mmol) and 4-nitrobenzoic acid (529 mg, 3.16 mmol) were added. Di-tert-butyl (E)-diazene-1,2-dicarboxylate (729 mg, 3.16 mmol) was then added in portions at 0° C., after which the reaction mixture was warmed to room temperature and then stirred for 48 h. The resultant mixture was then concentrated in vacuo and the residue purified by silica gel flash chromatography using 15% ethyl acetate in hexanes as eluent. Homogeneous fractions were collected and concentrated under reduced pressure to give the product as a white solid, (450 mg, 1.147 mmol, 50.7% yield). LC/MS (Method A) 2.423 min, the molecular ion was not present. ¹H NMR (400 MHz, CHLOROFORM-d) δ 8.38-8.29 (m, 2H), 8.27-8.16 (m, 2H), 5.54-5.32 (m, 1H), 4.64-4.32 (m, 1H), 4.16-3.84 (m, 1H), 3.13-2.85 (m, 1H), 2.10-1.89 (m, 2H), 1.78-1.61 (m, 1H), 1.50 (s, 9H), 1.44-1.30 (m, 2H), 1.23 (d, J=7.1 Hz, 3H), 0.97 (t, J=7.4 Hz, 3H).

Intermediate 109 tert-butyl (2R,4S,5R)-5-ethyl-4-hydroxy-2-methylpiperidine-1-carboxylate

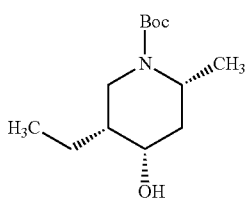 [SMILES: CC[C@@H]1CN(C(=O)OC(C)(C)C)[C@H](C)C[C@@H]1O]

Sodium hydroxide (227 mg, 5.67 mmol) was added to a solution of tert-butyl (2R,4S,5R)-5-ethyl-2-methyl-4-((4-nitrobenzoyl)oxy)piperidine-1-carboxylate (445 mg, 1.134 mmol) in MeOH (20 mL) and the resultant mixture was stirred at room temperature for 3 hr. The reaction mixture was then concentrated in vacuo and the residue was partitioned between ethyl acetate and water. The organic layer was then collected, washed with brine, dried over MgSO₄, filtered and evaporated to dryness under reduced pressure to give the crude product as a white solid. This was purified by using silica gel flash chromatography using 5%-40% ethyl acetate in hexanes as eluent. Homogeneous fractions were collected and concentrated in vacuo to give the title compound as a white solid (225 mg, 0.925 mmol, 82% yield). LC/MS (Method B) 1.719 min, the molecular ion was not present. $^1$H NMR (400 MHz, CHLOROFORM-d) δ 4.44-4.26 (m, 1H), 4.10-4.01 (m, 1H), 3.89-3.74 (m, 1H), 2.97-2.80 (m, 1H), 1.89-1.72 (m, 2H), 1.51-1.25 (m, 16H), 0.99 (t, J=7.4 Hz, 3H).

Intermediate 110

8-((2S,4R,5R)-5-ethyl-4-hydroxy-2-methylpiperidin-1-yl)-5-methyl-6-oxo-5,6-dihydro-1,5-naphthyridine-2-carbonitrile

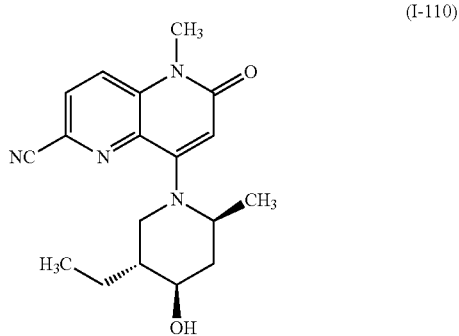 [SMILES: CC[C@@H]1CN(c2cc(=O)n(C)c3ccc(C#N)nc23)[C@@H](C)C[C@H]1O]
(I-110)

TFA (1 mL) was added to a solution of tert-butyl (2S,4R,5R)-5-ethyl-4-hydroxy-2-methylpiperidine-1-carboxylate (50 mg, 0.205 mmol) in dichloromethane (2 mL) and the mixture was stirred for 2 h at room temperature. It was then concentrated in vacuo to give an viscous oil that was dissolved in acetonitrile (3 mL). To this solution were added 6-cyano-1-methyl-2-oxo-1,2-dihydro-1,5-naphthyridin-4-yl trifluoromethanesulfonate (65.2 mg, 0.196 mmol) and DIPEA (0.137 mL, 0.783 mmol) and the resultant mixture was heated at 65° C. under nitrogen overnight. The reaction mixture was then concentrated in vacuo, and the residue was fractionated using preparative HPLC using an acetonitrile: water: ammonium acetate solution eluent system. Homogeneous fractions were collected, combined and then concentrated under reduced pressure to give the product as a light yellow-colored solid (35.8 mg, 0.110 mmol, 56.1% yield). LC/MS (Method A) 1.289 min, 327.05 (MW). $^1$H NMR (400 MHz, CHLOROFORM-d) δ 7.81 (d, J=8.7 Hz, 1H), 7.72 (d, J=8.8 Hz, 1H), 6.29 (s, 1H), 4.13-3.98 (m, 1H), 3.98-3.87 (m, 1H), 3.78-3.70 (m, 1H), 3.67 (s, 3H), 2.99-2.73 (m, 1H), 2.37-2.19 (m, 1H), 1.86-1.63 (m, 3H), 1.41-1.20 (m, 5H), 0.97 (t, J=7.4 Hz, 3H).

Using the above methodologies employing (R)-4-benzyl-3-butyryloxazolidin-2-one as a starting material, the following intermediates were prepared.

TABLE 22

| Intermediate Number | Structure | LCMS Method | LCMS RT (min) | M + H |
|---|---|---|---|---|
| I-111 | ![structure] | A | 1.767 | 247.9 |
| I-112 | ![structure] | A | 1.763 | 377.9 |

TABLE 22-continued

| Intermediate Number | Structure | LCMS Method | LCMS RT (min) | M + H |
|---|---|---|---|---|
| I-113 | 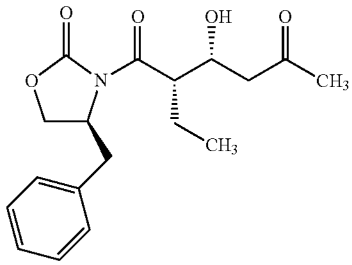 [SMILES: CC[C@H](C(=O)N1C(=O)OC[C@@H]1Cc1ccccc1)[C@H](O)CC(C)=O] | A | 1.592 | 333.9 |
| I-114 | 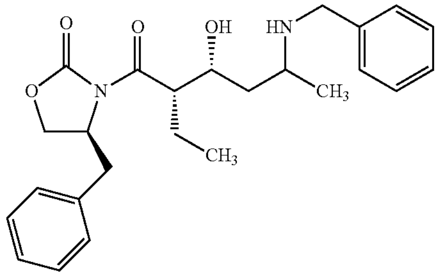 [SMILES: CC[C@H](C(=O)N1C(=O)OC[C@@H]1Cc1ccccc1)[C@H](O)CC(C)NCc1ccccc1] | A | 1.546, 1.573 | 425.1, 425.1 |
| I-115 | 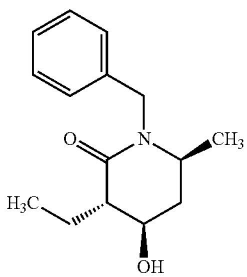 [SMILES: CC[C@@H]1C(=O)N(Cc2ccccc2)[C@@H](C)C[C@H]1O] | A | 1.428 | 248.2 |
| I-116 | 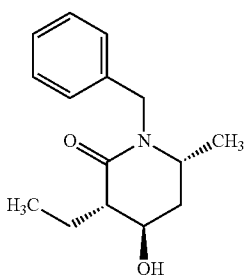 [SMILES: CC[C@@H]1C(=O)N(Cc2ccccc2)[C@H](C)C[C@H]1O] | A | 1.415 | 248.0 |
| I-117 | 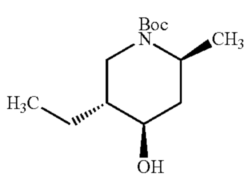 [SMILES: CC[C@@H]1CN(C(=O)OC(C)(C)C)[C@@H](C)C[C@H]1O] | A | 1.661 | The molecular ion was not present |
| I-118 | 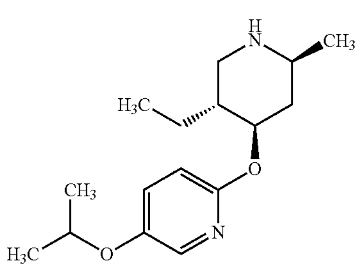 [SMILES: CC[C@@H]1CN[C@@H](C)C[C@H]1Oc1ccc(OC(C)C)cn1] | A | 1.335 | 279.0 |

TABLE 22-continued

| Intermediate Number | Structure | LCMS Method | LCMS RT (min) | M + H |
|---|---|---|---|---|
| I-119 | 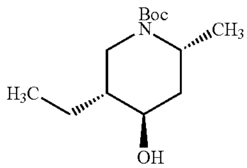 [SMILES: CC[C@@H]1CN(C(=O)OC(C)(C)C)[C@H](C)C[C@H]1O] | A | 1.682 | The molecular ion was not present. |
| I-120 | 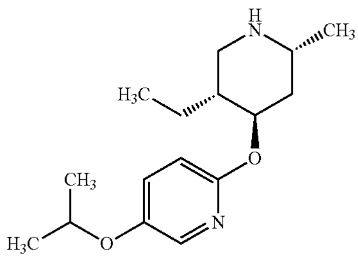 [SMILES: CC[C@@H]1CN[C@H](C)C[C@H]1Oc1ccc(OC(C)C)cn1] | A | 1.303 | 279.1 |
| I-121 | 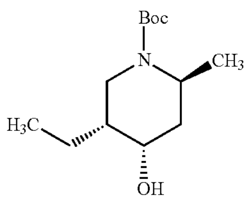 [SMILES: CC[C@@H]1CN(C(=O)OC(C)(C)C)[C@@H](C)C[C@@H]1O] | A | 1.522 | The molecular ion was not present |
| I-122 | 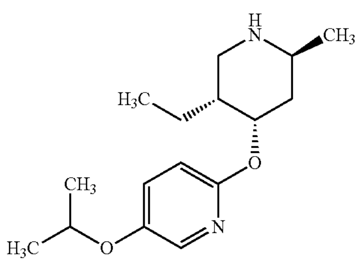 [SMILES: CC[C@@H]1CN[C@@H](C)C[C@@H]1Oc1ccc(OC(C)C)cn1] | B | 1.413 | 279.1 |
| I-123 | 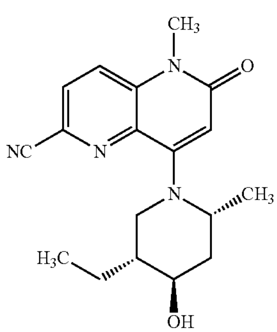 [SMILES: CC[C@@H]1CN(c2cc(=O)n(C)c3ccc(C#N)nc23)[C@H](C)C[C@H]1O] | B | 1.318 | 327.1 |
| I-124 | 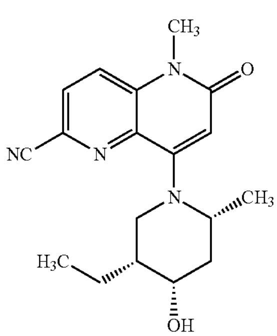 [SMILES: CC[C@@H]1CN(c2cc(=O)n(C)c3ccc(C#N)nc23)[C@H](C)C[C@@H]1O] | B | 1.600 | 327.0 |

TABLE 22-continued

| Intermediate Number | Structure | LCMS Method | LCMS RT (min) | M + H |
|---|---|---|---|---|
| I-125 | | A | 1.602 | 364.0 |
| I-126 | 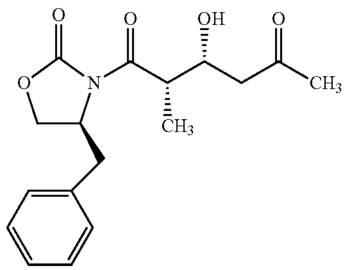 [SMILES: CC(=O)C[C@@H](O)[C@H](C)C(=O)N1C(=O)OC[C@@H]1Cc1ccccc1] | A | 1.457 | 319.9 |
| I-127 | 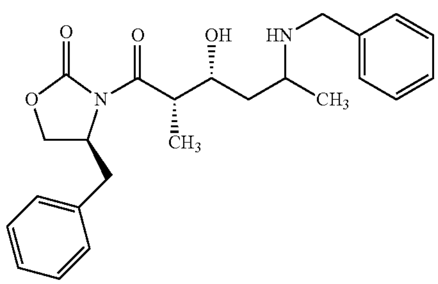 [SMILES: CC(C[C@@H](O)[C@H](C)C(=O)N1C(=O)OC[C@@H]1Cc1ccccc1)NCc1ccccc1] | A | 1.388, 1.422 | 411.0, 411.0 |
| I-128 | 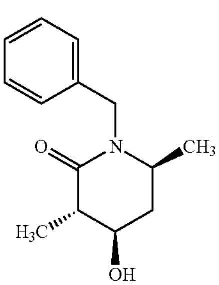 [SMILES: C[C@@H]1C(=O)N(Cc2ccccc2)[C@@H](C)C[C@H]1O] | A | 1.285 | 234.1 |
| I-129 | 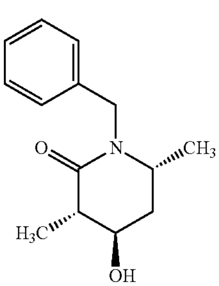 [SMILES: C[C@@H]1C(=O)N(Cc2ccccc2)[C@H](C)C[C@H]1O] | A | 1.308 | 233.9 |

TABLE 22-continued

| Intermediate Number | Structure | LCMS Method | LCMS RT (min) | M + H |
|---|---|---|---|---|
| I-130 | 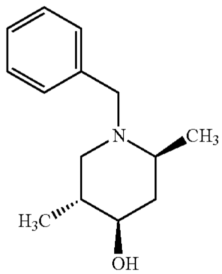 [SMILES: C[C@@H]1CN(Cc2ccccc2)[C@@H](C)C[C@H]1O] | A | 0.966 | 220.0 |
| I-131 | 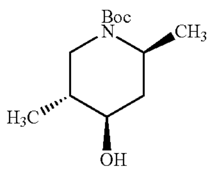 | A | 1.492 | The molecular ion was not present. |
| I-132 | 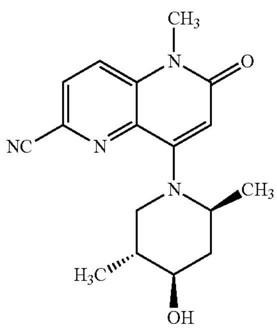 [SMILES: C[C@@H]1CN(c2cc(=O)n(C)c3ccc(C#N)nc23)[C@@H](C)C[C@H]1O] | A | 1.075 | 313.0 |
| I-133 | 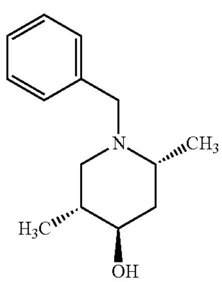 [SMILES: C[C@@H]1CN(Cc2ccccc2)[C@H](C)C[C@H]1O] | A | 0.890 | 220.0 |
| I-134 | 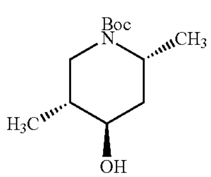 | A | 1.541 | The molecular ion was not present. |
| I-135 | 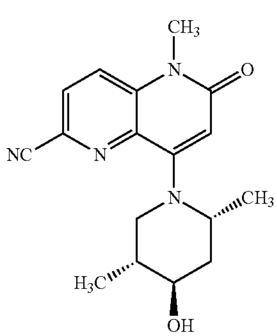 [SMILES: C[C@@H]1CN(c2cc(=O)n(C)c3ccc(C#N)nc23)[C@H](C)C[C@H]1O] | A | 1.305 | 313.0 |

TABLE 22-continued

| Intermediate Number | Structure | LCMS Method | LCMS RT (min) | M + H |
|---|---|---|---|---|
| I-136 | (Boc-piperidine with 2-CH₃, 5-CH₃, 4-O-C(O)-C₆H₄-4-NO₂) | A | 2.355 | The molecular ion was not present. |
| I-137 | (Boc-piperidine with 2-CH₃, 5-CH₃, 4-OH) | A | 1.502 | The molecular ion was not present. |
| I-138 | (Boc-piperidine with 2-CH₃, 5-CH₃, 4-O-C(O)-C₆H₄-4-NO₂, different stereochem) | A | 2.378 | The molecular ion was not present. |
| I-139 | (Boc-piperidine with 2-CH₃, 5-CH₃, 4-OH, different stereochem) | A | 1.430 | The molecular ion was not present. |

Using the above methodologies with (R)-4-benzyl-3-butyryloxazolidin-2-one and propanoyl chloride as starting material, the following intermediates were prepared.

TABLE 23

| Intermediate Number | Structure | LCMS Method | LCMS RT (min) | M + H |
|---|---|---|---|---|
| I-140 | (R)-4-benzyl-oxazolidinone-N-C(O)-CH(CH₃)-CH(OH)-CH₂-dioxolane (CH₃) | — | — | — |

TABLE 23-continued

| Intermediate Number | Structure | LCMS Method | LCMS RT (min) | M + H |
|---|---|---|---|---|
| I-141 | 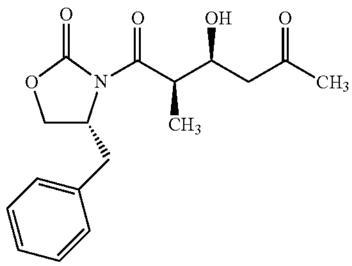 [SMILES: CC(=O)C[C@H](O)[C@@H](C)C(=O)N1C(=O)OC[C@H]1Cc1ccccc1] | B | 1.889 | 302 (Loss of water) |
| I-142 | 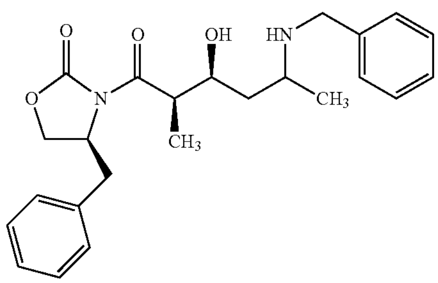 [SMILES: CC(C[C@H](O)[C@@H](C)C(=O)N1C(=O)OC[C@@H]1Cc1ccccc1)NCc1ccccc1] | B | 1.546, 1.597 | 411.10, 411.03 |
| I-143 | 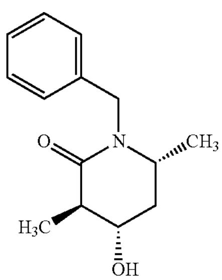 [SMILES: C[C@@H]1C[C@H](O)[C@@H](C)C(=O)N1Cc1ccccc1] | B | 1.256 | 233.9 |
| I-144 | 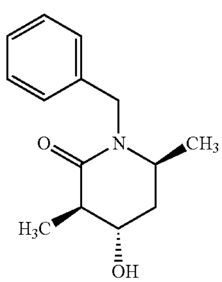 [SMILES: C[C@H]1C(=O)N(Cc2ccccc2)[C@@H](C)C[C@@H]1O] | B | 1.232 | 233.9 |
| I-145 | 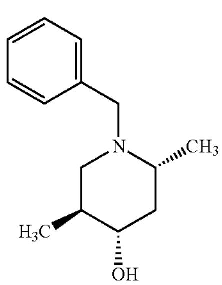 [SMILES: C[C@@H]1C[C@H](O)[C@@H](C)CN1Cc1ccccc1] | B | 1.128 | 219.9 |

TABLE 23-continued

| Intermediate Number | Structure | LCMS Method | LCMS RT (min) | M + H |
|---|---|---|---|---|
| I-146 | 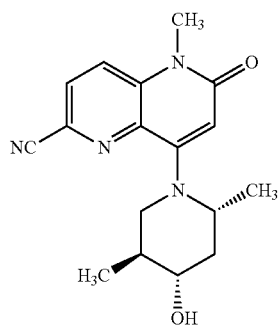 | B | 1.107 | 219.9 |

Intermediate 147

8-((2R,4S,5S)-4-hydroxy-2,5-dimethylpiperidin-1-yl)-5-methyl-6-oxo-5,6-dihydro-1,5-naphthyridine-2-carbonitrile

Intermediate 148

8-((2S,4S,5S)-4-hydroxy-2,5-dimethylpiperidin-1-yl)-5-methyl-6-oxo-5,6-dihydro-1,5-naphthyridine-2-carbonitrile

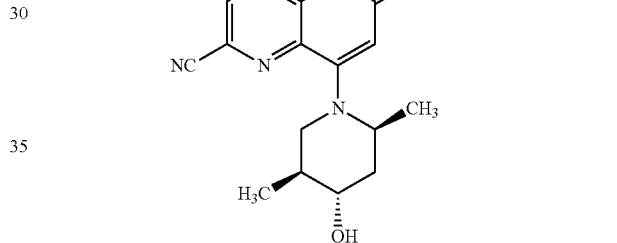

(I-147)                                                        (I-148)

In a round bottom flask, (2R,4S,5S)-1-benzyl-2,5-dimethylpiperidin-4-ol (400 mg, 1.824 mmol) and palladium on carbon (194 mg, 1.824 mmol) were combined under nitrogen and dissolved in MeOH (6 mL). The reaction mixture was placed under 1 atm of hydrogen and stirred overnight at room temperature. LC/MS analysis showed no remaining starting material. The reaction mixture was diluted with ethyl acetate, filtered through celite and concentrated at the rotary evaporator. In a reaction vial, the crude reduction product was combined with Hunig's base (0.956 mL, 5.47 mmol) and 6-cyano-1-methyl-2-oxo-1,2-dihydro-1,5-naphthyridin-4-yl trifluoromethanesulfonate (729 mg, 2.189 mmol) in acetonitrile (10 mL) and heated overnight at 80° C. The solvent was removed and the crude redissolved in 4 mL of DMF and chromatographed on a redi-sep column with acetonitrile and water buffered with TFA. Homogeneous fractions were combined and evaporated to give the title compound, (300 mg, 0.960 mmol, 52.7% yield). LCMS: (Method A*) $R_T$=1.455 min, 94%. (M+2H$_2$O+H)$^+$=348.95. NMR: $^1$H NMR (400 MHz, CHLOROFORM-d) δ 7.96-7.78 (m, 2H), 6.56 (s, 1H), 4.34-4.21 (m, 1H), 3.95-3.84 (m, 1H), 3.82-3.68 (m, 3H), 3.53 (dd, J=13.0, 6.0 Hz, 1H), 2.39-2.27 (m, 1H), 2.17-1.96 (m, 1H), 1.84-1.69 (m, 1H), 1.41 (d, J=6.5 Hz, 3H), 1.15 (d, J=7.0 Hz, 3H).

In a round bottom flask, (2R,4S,5S)-1-benzyl-2,5-dimethylpiperidin-4-ol (670 mg, 3.05 mmol) and palladium on carbon (194 mg, 1.824 mmol) were combined under nitrogen and dissolved in MeOH (6 mL). The reaction mixture was placed under 1 atm of hydrogen and stirred overnight at room temperature. LC/MS analysis showed no remaining starting material. The reaction mixture was diluted with ethyl acetate, filtered through celite and concentrated at the rotary evaporator. In a reaction vial, the crude reduction product was combined with Hunig's base (1.601 mL, 9.16 mmol) and 6-cyano-1-methyl-2-oxo-1,2-dihydro-1,5-naphthyridin-4-yl trifluoromethanesulfonate (1222 mg, 3.67 mmol) in acetonitrile (15 mL) and heated overnight at 80° C. The solvent was removed and the crude redissolved in 4 mL of DMF and chromatographed on a redi-sep column with acetonitrile and water buffered with TFA. Homogeneous fractions were combined and evaporated to give the title compound. LCMS: (Method A*) $R_T$=1.719 min, 87%. (M+H)$^+$=312.95. NMR: $^1$H NMR (400 MHz, DMSO-d$_6$) δ 8.21-8.11 (m, 1H), 8.09-8.00 (m, 1H), 6.02 (s, 1H), 4.78 (br s, 1H), 4.61 (d, J=5.9 Hz, 1H), 3.53 (s, 3H), 3.48-3.38 (m, 2H), 2.92 (t, J=12.5 Hz, 1H), 1.79 (ddd, J=12.7, 4.6, 2.0 Hz, 1H), 1.72-1.52 (m, 2H), 1.18 (d, J=7.0 Hz, 3H), 1.01 (d, J=6.5 Hz, 3H).

Example 294

8-((2S,4S,5S)-5-ethyl-4-((5-isopropoxypyridin-2-yl)oxy)-2-methylpiperidin-1-yl)-5-methyl-6-oxo-5,6-dihydro-1,5-naphthyridine-2-carbonitrile

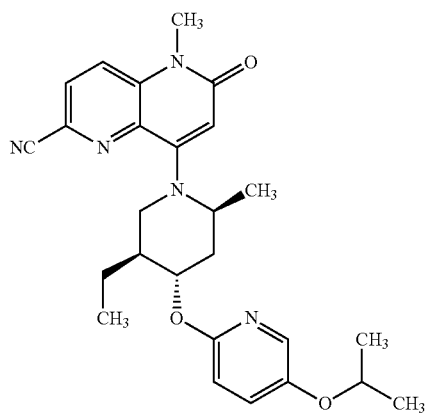

(294)

A solution of Hunig's base (0.033 mL, 0.191 mmol), 2-((2S,4S,5S)-5-ethyl-2-methylpiperidin-4-yl)oxy)-5-isopropoxypyridine 2,2,2-trifluoroacetate (25 mg, 0.064 mmol) and 6-cyano-1-methyl-2-oxo-1,2-dihydro-1,5-naphthyridin-4-yl trifluoromethanesulfonate (21.23 mg, 0.064 mmol) in DMF (2 mL) was heated at 65° C. overnight. The crude reaction mixture was cooled to room temperature, filtered and then fractionated using preparative LC/MS using the following conditions: Column: XBridge C18, 200 mm×19 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: a 0-minute hold at 30% B, 30-70% B over 25 minutes, then a 0-minute hold at 100% B; Flow Rate: 20 mL/min; Column Temperature: 25° C. Fraction collection was triggered by MS and UV signals. Fractions containing the product were combined and dried via centrifugal evaporation. The yield of the product was 14.4 mg, and its estimated purity by LCMS analysis was 100%. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min; Detection: MS and UV (220 nm). Injection 1 results: Purity: 100%; Observed Mass: 462.09; Retention Time: 2.4 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). Injection 2 results: Purity: 100%; Observed Mass: 462.05; Retention Time: 2.01 min. Proton NMR was acquired in deuterated DMSO. $^1$H NMR (500 MHz, DMSO-$d_6$) δ 8.16 (d, J=8.9 Hz, 1H), 8.10-8.05 (m, 1H), 7.82 (d, J=3.0 Hz, 1H), 7.36 (dd, J=8.9, 2.8 Hz, 1H), 6.73 (d, J=8.9 Hz, 1H), 6.07 (s, 1H), 5.28-5.06 (m, 1H), 4.71-4.57 (m, 1H), 4.55-4.46 (m, 1H), 4.04-3.86 (m, 1H), 3.11-2.90 (m, 2H), 2.10 (br d, J=11.8 Hz, 1H), 1.98-1.87 (m, 1H), 1.82-1.57 (m, 2H), 1.29 (d, J=7.0 Hz, 3H), 1.25 (br d, J=6.0 Hz, 6H), 0.97 (t, J=7.5 Hz, 3H).

Example 295

8-((2R,4S,5S)-5-ethyl-4-((5-isopropoxypyridin-2-yl)oxy)-2-methylpiperidin-1-yl)-5-methyl-6-oxo-5,6-dihydro-1,5-naphthyridine-2-carbonitrile

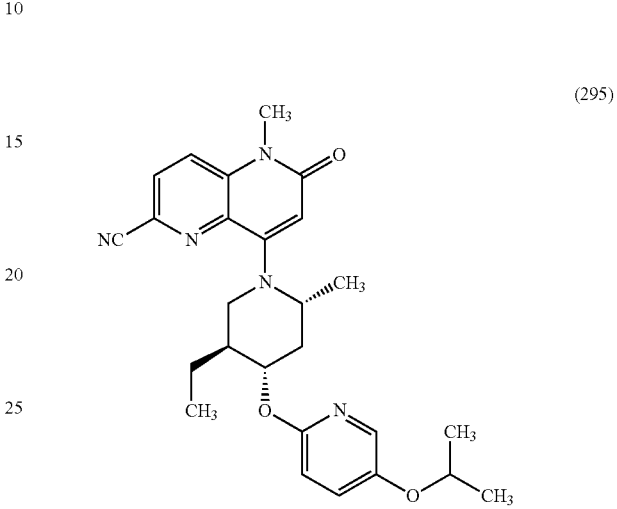

(295)

A solution of Hunig's base (0.069 mL, 0.398 mmol), 2-((2R,4S,5S)-5-ethyl-2-methylpiperidin-4-yl)oxy)-5-isopropoxypyridine 2,2,2-trifluoroacetate (52 mg, 0.133 mmol) and 6-cyano-1-methyl-2-oxo-1,2-dihydro-1,5-naphthyridin-4-yl trifluoromethanesulfonate (44.2 mg, 0.133 mmol) in DMF (2 mL) was heated at 65° C. overnight. The crude reaction mixture was cooled to room temperature, filtered and then fractionated using preparative LC/MS with the following conditions: Column: XBridge C18, 200 mm×19 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: a 0-minute hold at 30% B, 30-70% B over 25 minutes, then a 0-minute hold at 100% B; Flow Rate: 20 mL/min; Column Temperature: 25° C. Fraction collection was triggered by MS and UV signals. Fractions containing the product were combined and dried via centrifugal evaporation. The yield of the product was 14.4 mg, and its estimated purity by LCMS analysis was 100%. Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min; Detection: MS and UV (220 nm). Injection 1 results: Purity: 100%; Observed Mass: 462.09; Retention Time: 2.4 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). Injection 2 results: Purity: 100%; Observed Mass: 462.05; Retention Time: 2.01 min. Proton NMR was acquired in deuterated DMSO. $^1$H NMR (500 MHz, DMSO-$d_6$) δ 8.18-8.12 (m, 1H), 8.11-8.05 (m, 1H), 7.83 (br d, J=1.2 Hz, 1H), 7.41-7.34 (m, 1H), 6.81-6.70 (m, 1H), 6.26-6.19 (m, 1H), 4.98 (br d, J=3.6 Hz, 1H), 4.60-4.47 (m, 1H), 4.15 (br d, J=4.1 Hz, 1H), 3.91-3.77 (m, 1H), 3.10-2.88 (m, 2H), 1.91 (br d, J=2.0 Hz, 1H), 1.68 (dt, J=13.5, 6.8 Hz, 1H), 1.61-1.46 (m, 1H), 1.40-1.30 (m, 1H), 1.27-1.23 (m, 6H), 1.18-1.13 (m, 3H), 0.92-0.83 (m, 3H).

Using the above methodologies and intermediates, the following examples can be prepared in an analogous manner.

| Ex. No. | Structure | LCMS Method | LCMS RT (min) | M+H |
|---|---|---|---|---|
| 296 | 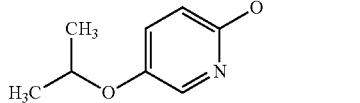 | C | 2.39 | 462.1 |
| 297 | 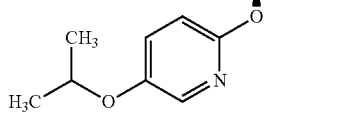 | C | 2.39 | 462.1 |
| 298 | 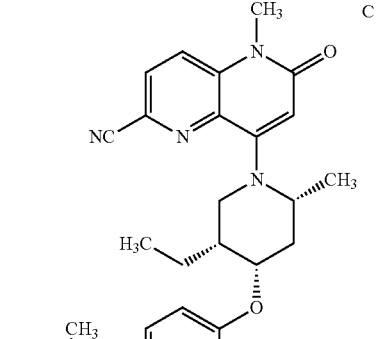 | C | 2.44 | 462.2 |
| 299 | 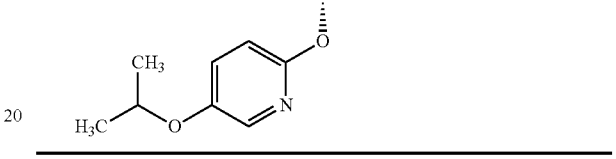 | C | 2.364 | 462.1 |

Example 300

6-chloro-4-((2S,4R,5R)-5-ethyl-4-((5-isopropoxy-pyridin-2-yl)oxy)-2-methylpiperidin-1-yl)-1-methylpyrido[3,2-d]pyrimidin-2(1H)-one

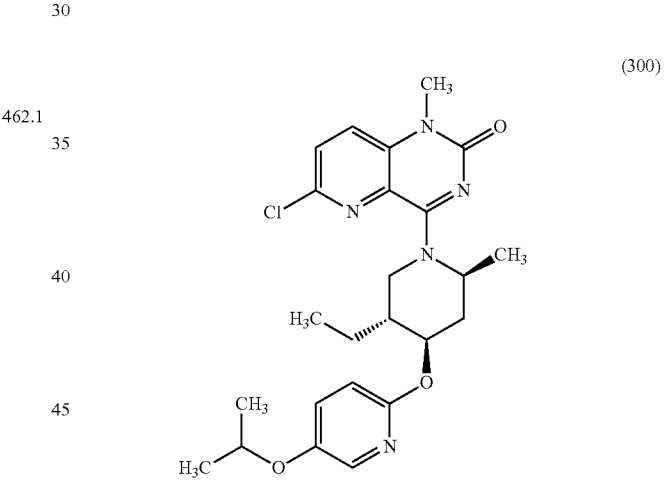

(300)

To a solution of 2-(((2S,4R,5R)-5-ethyl-2-methylpiperidin-4-yl)oxy)-5-isopropoxypyridine 2 TFA (37 mg, 0.073 mmol) in acetonitrile (5 mL), 4,6-dichloro-1-methylpyrido[3,2-d]pyrimidin-2(1H)-one (24.01 mg, 0.073 mmol) and DIPEA (0.051 mL, 0.292 mmol) were added. The reaction mixture was heated at 70° C. for 1 hr. The reaction mixture was then concentrate under reduced pressure and the residue was dissolved in a mixture of acetonitrile and DMF. The solution was filtered and then fractionated using preparative reverse phase HPLC under the following conditions: Column: XBridge C18, 200 mm×19 mm, 5-μm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 42% B, 42-82% B over 20 minutes, then a 0-minute hold at 100% B; Flow Rate: 20 mL/min; Column Temperature: 25° C. Fraction collection was triggered by MS and UV signals. Fractions containing the product were combined and dried via centrifugal evaporation to give 6-chloro-4-((2S,4R,5R)-5-ethyl-4-((5-isopropoxypyridin-2-yl)oxy)-2-methylpiperidin-1-yl)-1-methylpyrido[3,2-d]pyrimidin-2(1H)-one (27.6 mg, 80% yield). Analytical LC/MS was used to determine the final purity. Injection 1 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). Injection 1 results: Purity: 100%; Observed Mass: 472.02; Retention Time: 2.11 min. Injection 2 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min; Detection: MS and UV (220 nm). Injection 2 results: Purity: 100%; Observed Mass: 472.07; Retention Time: 2.34 min. $^1$H NMR (500 MHz, DMSO-$d_6$) δ 7.99-7.89 (m, 1H), 7.86-7.75 (m, 2H), 7.47-7.28 (m, 1H), 6.93 (d, J=5.3 Hz, 1H), 5.49-5.29 (m, 1H), 5.07-4.89 (m, 1H), 4.66-4.34 (m, 1H), 3.79-3.59 (m, 1H), 3.44 (s, 3H), 3.13-2.86 (m, 1H), 2.24-2.05 (m, 1H), 1.98-1.69 (m, 2H), 1.50-1.33 (m, 5H), 1.26 (d, J=5.8 Hz, 6H), 0.97 (t, J=7.1 Hz, 3H).

Example 301

4-((2S,4R,5R)-5-ethyl-4-((5-isopropoxypyridin-2-yl)oxy)-2-methylpiperidin-1-yl)-1-methyl-2-oxo-1,2-dihydropyrido[3,2-d]pyrimidine-6-carbonitrile

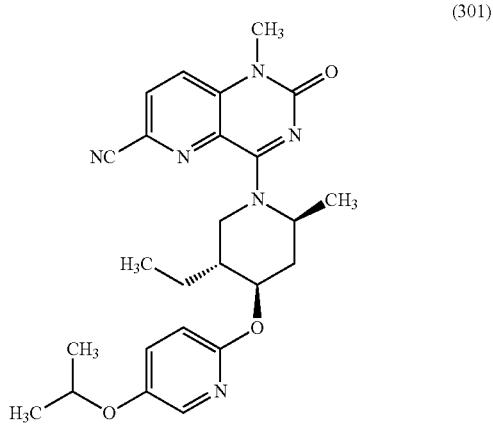 [SMILES: CC[C@@H]1CN(c2nc(=O)n(C)c3ccc(C#N)nc23)[C@@H](C)C[C@H]1Oc1ccc(OC(C)C)cn1]

(301)

In a microwave tube, 6-chloro-4-((2S,4R,5R)-5-ethyl-4-((5-isopropoxypyridin-2-yl) oxy)-2-methylpiperidin-1-yl)-1-methylpyrido[3,2-d]pyrimidin-2(1H)-one (25 mg, 0.053 mmol), zinc (3.46 mg, 0.053 mmol), zinc cyanide (7.46 mg, 0.064 mmol) and 1,1'-bis(diphenylphosphino)ferrocene-palladium(II)dichloride dichloromethane complex (4.33 mg, 5.30 μmol) were added. The reaction vessel was subjected to sequential evacuation and nitrogen flushing (3x) before being placed under a nitrogen atmosphere. NMP (1.5 mL) was then added and the reaction vial was irradiated under microwave conditions at 80° C. for 3 hr. The reaction mixture was then diluted with CH$_3$CN to a volume of 2 mL, filtered and the filtrate was fractionated using preparative reverse phase HPLC under the following conditions: Column: XBridge C18, 200 mm×19 mm, 5-μm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 33% B, 33-73% B over 20 minutes, then a 0-minute hold at 100% B; Flow Rate: 20 mL/min; Column Temperature: 25 C. Fraction collection was triggered by MS and UV signals. Fractions containing the product were combined and dried via centrifugal evaporation to give 4-((2S,4R,5R)-5-ethyl-4-((5-isopropoxypyridin-2-yl)oxy)-2-methylpiperidin-1-yl)-1-methyl-2-oxo-1,2-dihydropyrido[3,2-d]pyrimidine-6-carbonitrile (14.2 mg, 58.0% yield). Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min; Detection: MS and UV (220 nm). Injection 1 results: Purity: 100%; Observed Mass: 463.11; Retention Time: 2.23 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). Injection 2 results: Purity: 100%; Observed Mass: 463.12; Retention Time: 1.87 min. $^1$H NMR (500 MHz, DMSO-$d_6$) δ 8.08-7.92 (m, 1H), 7.80-7.66 (m, 1H), 7.65-7.51 (m, 1H), 7.25-7.08 (m, 1H), 6.56 (d, J=8.9 Hz, 1H), 5.29-4.99 (m, 1H), 4.81-4.58 (m, 1H), 4.39-4.19 (m, 1H), 3.67 (s, 3H), 3.55-3.39 (m, 1H), 2.89-2.64 (m, 1H), 1.96-1.88 (m, 1H), 1.75-1.63 (m, 1H), 1.63-1.51 (m, 1H), 1.29-1.10 (m, 5H), 1.02 (d, J=6.0 Hz, 6H), 0.81-0.68 (m, 3H).

Using the above methodologies and intermediates, the following examples were prepared in an analogous manner.

| Ex. No. | Structure | LCMS Method | LCMS RT (min) | M + H |
|---|---|---|---|---|
| 302 | 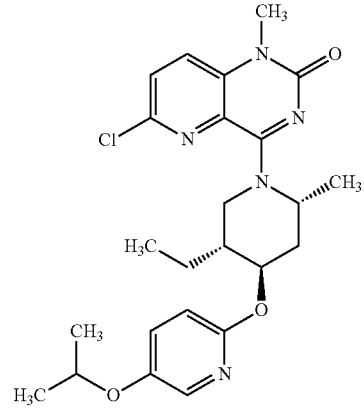 [SMILES: CC[C@@H]1CN(c2nc(=O)n(C)c3ccc(Cl)nc23)[C@H](C)C[C@H]1Oc1ccc(OC(C)C)cn1] | A | 2.229 | 472.1 |

-continued
| Ex. No. | Structure | LCMS Method | LCMS RT (min) | M + H |
|---|---|---|---|---|
| 303 | 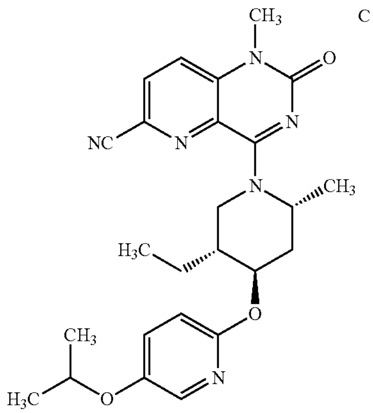 | C | 2.23 | 463.1 |
| 304 | 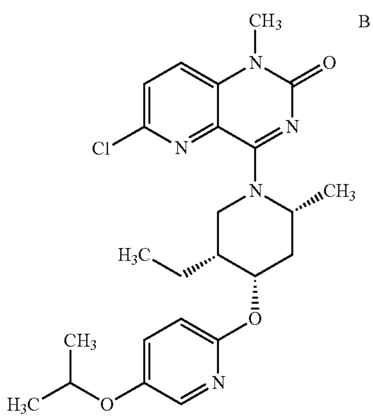 | B | 3.193 | 472.1 |
| 305 | 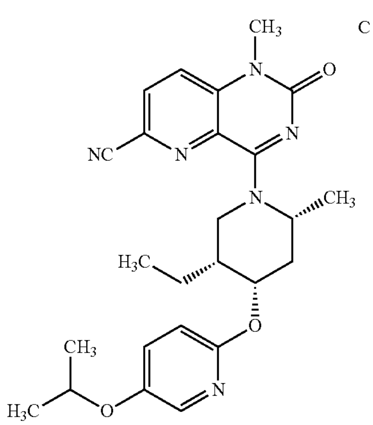 | C | 2.27 | 463.1 |
-continued
| Ex. No. | Structure | LCMS Method | LCMS RT (min) | M + H |
|---|---|---|---|---|
| 306 | 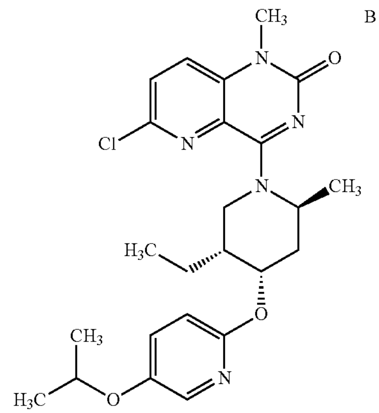 | B | 2.305 | 472.1 |
| 307 | 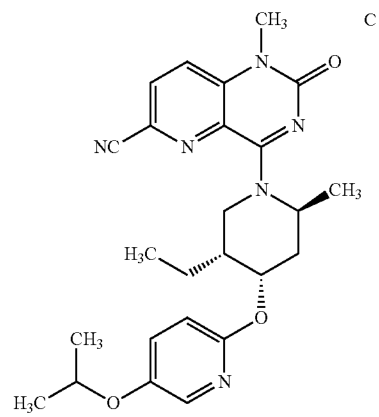 | C | 2.192 | 463.1 |
Example 308
8-((2S,4S,5R)-5-ethyl-2-methyl-4-(3-(trifluoromethyl)phenoxy)piperidin-1-yl)-5-methyl-6-oxo-5,6-dihydro-1,5-naphthyridine-2-carbonitrile
(308)
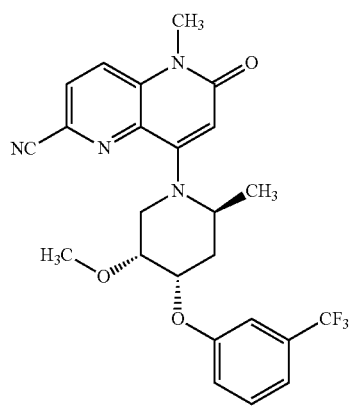 [SMILES: CC[C@@H]1CN(c2cc(=O)n(C)c3ccc(C#N)nc23)[C@H](C)C[C@@H]1Oc1cccc(C(F)(F)F)c1]
To a solution of 3-(trifluoromethyl)phenol (23.84 mg, 0.147 mmol) in THF (4 mL), triphenylphosphine (71.9 mg, 0.216 mmol) on solid support was added. The reaction mixture was stirred at room temperature for 5 min after which di-tert-butyl (E)-diazene-1,2-dicarboxylate (36.1 mg, 0.157 mmol) and 8-((2S,4R,5R)-5-ethyl-4-hydroxy-2-methylpiperidin-1-yl)-5-methyl-6-oxo-5,6-dihydro-1,5-naphthyridine-2-carbonitrile (32 mg, 0.098 mmol) were added. The reaction mixture was stirred at room temperature under nitrogen overnight. It was then filtered and concentrated in vacuo and the residue was dissolved in DMF/CH$_3$CN and the resultant solution was filtered and then fractionated using preparative reverse phase HPLC under the following conditions: Column: XBridge C18, 200 mm×19 mm, 5-μm particles; Mobile Phase A: 5:95 acetonitrile:water with 10-mM ammonium acetate; Mobile Phase B: 95:5 acetonitrile: water with 10-mM ammonium acetate; Gradient: a 0-minute hold at 43% B, 43-83% B over 20 minutes, then a 0-minute hold at 100% B; Flow Rate: 20 mL/min; Column Temperature: 25° C. Fraction collection was triggered by MS signals. Fractions containing the product were combined and dried via centrifugal evaporation to give 8-((2S,4S,5R)-5-ethyl-2-methyl-4-(3-(trifluoromethyl) phenoxy)piperidin-1-yl)-5-methyl-6-oxo-5,6-dihydro-1,5-naphthyridine-2-carbonitrile (0.8 mg, 1.700 μmol, 1.734% yield). Analytical LC/MS was used to determine the final purity. Injection 1 conditions: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min; Detection: MS and UV (220 nm). Injection 1 results: Purity: 100%; Observed Mass: 471.09; Retention Time: 2.52 min. Injection 2 conditions: Column: Waters XBridge C18, 2.1 mm×50 mm, 1.7 μm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0% B to 100% B over 3 min, then a 0.50 min hold at 100% B; Flow: 1 mL/min; Detection: MS and UV (220 nm). Injection 2 results: Purity: 100%; Observed Mass: 471.06; Retention Time: 2.28 min. $^1$H NMR (500 MHz, DMSO-d$_6$) δ 8.23-8.03 (m, 2H), 7.64-7.46 (m, 1H), 7.43-7.23 (m, 3H), 6.19 (s, 1H), 5.13-4.88 (m, 1H), 4.67-4.51 (m, 1H), 3.61-3.52 (m, 4H), 3.12-2.89 (m, 1H), 2.27-2.14 (m, 1H), 1.91-1.75 (m, 1H), 1.59-1.31 (m, 3H), 1.19 (d, J=6.6 Hz, 3H), 0.80 (t, J=7.2 Hz, 3H).

Using the above Mitsunobu conditions with appropriate intermediates the following examples were prepared.

| Ex. No. | Structure | LCMS Method | LCMS RT (min) | M + H |
|---|---|---|---|---|
| 309 | | C | 2.41 | 471.1 |
| 310 | 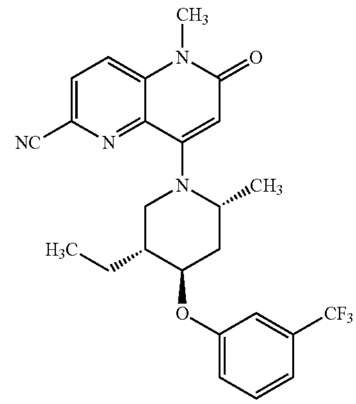 [SMILES: CC[C@@H]1CN(c2cc(=O)n(C)c3ccc(C#N)nc23)[C@H](C)C[C@H]1Oc1cccc(C(F)(F)F)c1] | C | 2.53 | 471.1 |
| 311 | 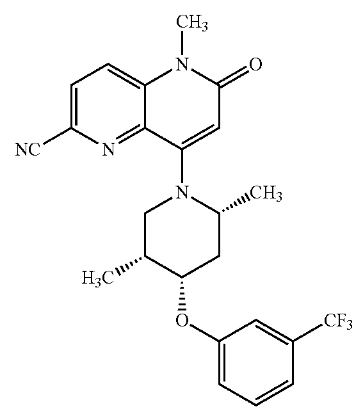 [SMILES: C[C@@H]1CN(c2cc(=O)n(C)c3ccc(C#N)nc23)[C@H](C)C[C@@H]1Oc1cccc(C(F)(F)F)c1] | C | 2.44 | 457.0 |
| 312 | 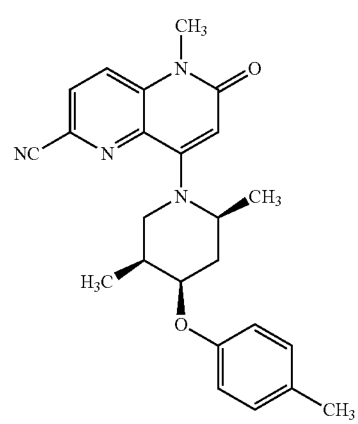 [SMILES: Cc1ccc(O[C@@H]2C[C@H](C)N(c3cc(=O)n(C)c4ccc(C#N)nc34)C[C@@H]2C)cc1] | A* | 1.49 | 407.0 |

-continued

| Ex. No. | Structure | LCMS Method | LCMS RT (min) | M+H |
|---|---|---|---|---|
| 313 | 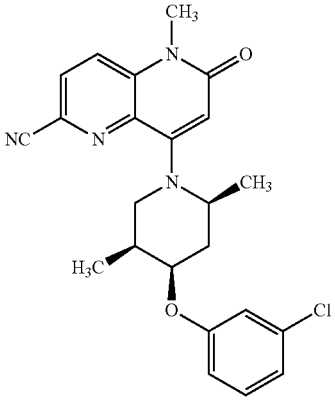 [SMILES: C[C@H]1CN(c2cc(=O)n(C)c3ccc(C#N)nc23)[C@@H](C)C[C@H]1Oc1cccc(Cl)c1] | A* | 1.60 | 402.9 |
| 314 | 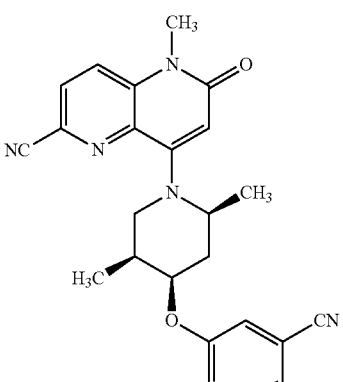 | A* | 1.42 | 408.9 |
| 315 | 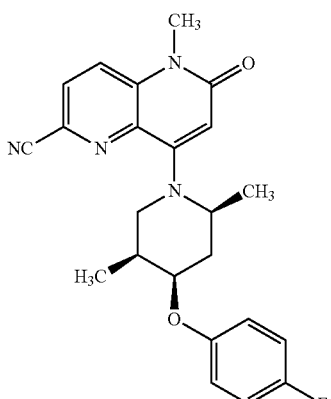 | A* | 1.62 | 423.0 |

Method A: Column: Waters Acquity BEH C18, 2.1×50 mm, 1.7-μm particles; Mobile Phase A: 5:95 acetonitrile:water with 0.05% TFA; Mobile Phase B: 95:5 acetonitrile:water with 0.05% TFA; Gradient: 0-100% B over 3 minutes, then a 0.50-minute hold at 100% B; Flow: 1.0 mL/min; Detection: UV at 220 nm.

Method A*: Column: Waters Acquity BEH C18, 2.1×50 mm, 1.7-μm particles; Mobile Phase A: 5:95 acetonitrile:water with 0.05% TFA; Mobile Phase B: 95:5 acetonitrile:water with 0.05% TFA; Gradient: 0-100% B over 1.8 minutes, then a 0.2-minute hold at 100% B; Flow: 1.0 mL/min; Detection: UV at 220 nm.

Method B: Column: Waters Acquity BEH C18, 2.1×50 mm, 1.7-μm particles; Mobile Phase A: 5:95 acetonitrile:water with 10 mM ammonium acetate; Mobile Phase B: 95:5 acetonitrile:water with 10 mM ammonium acetate; Gradient: 0-100% B over 3 minutes, then a 0.50-minute hold at 100% B; Flow: 1.0 mL/min; Detection: UV at 220 nm.

Method C: Column: Waters XBridge C18, 2.1 mm×50 mm, 1.7 μm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0% B to 100% B over 3 min, then a 0.50 min hold at 100% B; Flow: 1 mL/min; Detection: MS and UV (220 nm).

Intermediate 149

(+/−) tert-butyl-2,5-Dimethyl-4-((4-(trifluoromethyl)phenyl)amino)piperidine-1-carboxylate

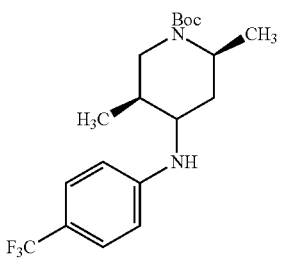

(I-149)

To a mixture of (+/−) tert-butyl-2,5-dimethyl-4-oxopiperidine-1-carboxylate (600 mg, 2.64 mmol), 4-(trifluoromethyl)aniline (425 mg, 2.64 mmol) in THF (10 mL) was added TiCl$_4$ (1.32 mL, 1.32 mmol, 1 M solution in THF) in drop wise manner at room temperature. Reaction mixture was stirred for another 30 min and sodium triacetoxyborohydride (727 mg, 3.43 mmol) was added and stirred for 12 h. The reaction was quenched with saturated NH$_4$Cl solution. The reaction mixture was extracted with EtOAc (100 mL), washed with water (20 mL), brine (20 mL), dried over Na$_2$SO$_4$ and concentrated under reduced pressure to obtain crude product. The crude product was purified via silica gel chromatography (0-100% EtOAc/petroleum ether) to afford (+/−) tert-butyl-2,5-dimethyl-4-((4-(trifluoromethyl)phenyl)amino)piperidine-1-carboxylate (800 mg, 81% yield). LCMS: m/z=317.3 [(M-$^t$Bu)+H)]; retention time 2.22 min. LCMS Method: Column: Waters Acquity UPLC BEH C18 (3×50 mm) 1.7 μm, Mobile phase A: 2.5 mM ammonium acetate:acetonitrile (95:5); Mobile phase B: 2.5 mM ammonium acetate:acetonitrile (5:95), Gradient=60-98% B over 1.1 minute, then a 0.6 minute hold at 98% B; Temperature: 50° C.; Flow rate: 0.7 mL/min; Detection: UV at 220 nm.

Intermediate 150

(+/−) 2,5-Dimethyl-N-(4-(trifluoromethyl)phenyl)piperidin-4-amine

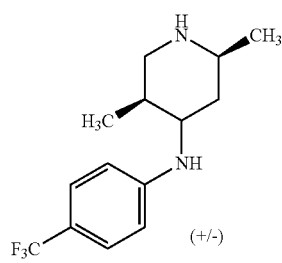

(I-150)

To a solution of (+/−)-tert-butyl-2,5-dimethyl-4-((4-(trifluoromethyl)phenyl)amino) piperidine-1-carboxylate (800 mg, 2.15 mmol) in DCM (2 mL) was added TFA (1.66 mL, 21.48 mmol). The reaction mixture was stirred at room temperature for 2 h, concentrated under reduced pressure to afford (+/−)-2,5-dimethyl-N-(4-(trifluoromethyl)phenyl)piperidin-4-amine, TFA (800 mg, 96% yield). LCMS: m/z=273.2 (M+H); retention time 1.16 and 1.21 min. LCMS Method: Column: Waters Acquity UPLC BEH C18 (3×50 mm) 1.7 μm, Mobile phase A: 2.5 mM Ammonium acetate:acetonitrile (95:5); Mobile phase B: 2.5 mM Ammonium acetate:acetonitrile (5:95), Gradient=60-98% B over 1.1 minute, then a 0.6 minute hold at 98% B; Temperature: 50° C.; Flow rate: 0.7 mL/min; Detection: UV at 220 nm.

Example 316A (+/−) 8-(2,5)-Dimethyl-4-((4-(trifluoromethyl)phenyl)amino)piperidin-1-yl)-5-methyl-6-oxo-5,6-dihydro-1,5-naphthyridine-2-carbonitrile

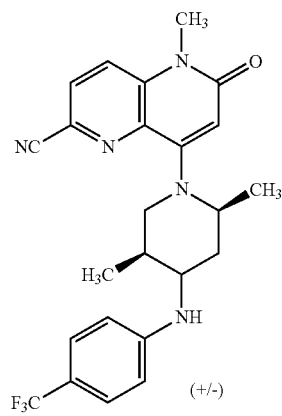

(I-151)

To a solution of 2,5-dimethyl-N-(4-(trifluoromethyl)phenyl)piperidin-4-amine, TFA (800 mg, 2.07 mmol) in acetonitrile (6 mL) were added DIPEA (1.09 mL, 6.21 mmol) and 6-cyano-1-methyl-2-oxo-1,2-dihydro-1,5-naphthyridin-4-yl trifluoromethanesulfonate (828 mg, 2.49 mmol). The reaction mixture was stirred at 85° C. for 16 h, concentrated under reduced pressure to obtain crude product. The crude product was purified by silica gel chromatography (0-20% MeOH/CHCl₃). Pure fractions were collected and concentrated to obtain 8-(2,5)-dimethyl-4-((4-(trifluoromethyl)phenyl)amino)piperidin-1-yl)-5-methyl-6-oxo-5,6-dihydro-1,5-naphthyridine-2-carbonitrile (700 mg, 74% yield) as yellow liquid. LCMS: m/z=456.2 (M+H); retention time=1.91 min. LCMS Method: Column: Waters Acquity UPLC BEH C18 (3×50 mm) 1.7 μm, Mobile phase A: 2.5 mM ammonium acetate:acetonitrile (95:5); Mobile phase B: 2.5 mM ammonium acetate:acetonitrile (5:95), Gradient=90-98% B over 1.1 minute, then a 0.6 minute hold at 98% B; Temperature: 50° C.; Flow rate: 0.7 mL/min; Detection: UV at 220 nm.

Examples 316-319

8-(2,5)-Dimethyl-4-(methyl(4-(trifluoromethyl)phenyl)amino)piperidin-1-yl)-5-methyl-6-oxo-5,6-dihydro-1,5-naphthyridine-2-carbonitrile (homochiral)

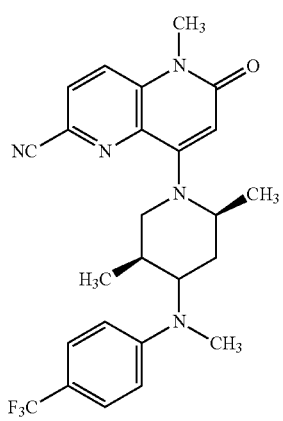

(316-319)

To a mixture of 8-(2,5)-dimethyl-4-((4-(trifluoromethyl)phenyl)amino)piperidin-1-yl)-5-methyl-6-oxo-5,6-dihydro-1,5-naphthyridine-2-carbonitrile (150 mg, 0.33 mmol), formaldehyde (9.89 mg, 0.33 mmol) in THF (2 mL) was added TiCl₄ (0.17 mL, 0.17 mmol, 1 M solution in THF) at room temperature. The stirring was continued for 30 min at the same temperature. Sodium triacetoxyborohydride (91 mg, 0.428 mmol) was then added and the resulting mixture was stirred at room temperature for overnight. The reaction was quenched with saturated NH₄Cl solution. The reaction mixture was dissolved in EtOAc (100 mL), washed with water (20 mL), brine (20 mL), dried over Na₂SO₄ and concentrated under reduced pressure to obtain crude product as light yellow liquid. The crude was purified by silica gel chromatography by using 0-10% MeOH/CHCl₃ as eluent. Pure fractions were collected and concentrated to obtain mixture of isomers, which was purified via preparative SFC (Chiral SFC method: Column/dimensions: Whelk (R,R) (250×30) mm, 5 um, % CO₂: 70%; Co-Solvent: 15% of MeOH, Total Flow: 140.0 g/min, Temperature: 40° C., Pressure: 100 bar; UV: 220 nm).

First eluting isomer, Example 294: retention time=5.33 min; second eluting isomer, Example 295: retention time=6.58 min; Third Eluting Isomer, Example 296: retention time=9.48 min; Fourth Eluting Isomer, Example 297: retention time=11.44 min.

Example 294: (1.5 mg, 1% yield); LCMS: m/z=470.2 (M+H); retention time=3.43 min. LCMS Method: Column: Kinetex XB-C18 (3×75 mm) 2.6 μm; Mobile phase A: 10 mM ammonium formate:acetonitrile (98:2), Mobile phase B: 10 mM ammonium formate:acetonitrile (2:98), Gradient=20-100% B over 4 minutes, then a 0.6 minute hold at 100% B; Temperature: 27° C.; Flow rate: 1.0 mL/min; Detection: UV at 220 nm.

Example 295: (1.32 mg, 1% yield); LCMS: m/z=470.2 (M+H); retention time=3.42 min. LCMS Method: Column: Kinetex XB-C18 (3×75 mm) 2.6 μm; Mobile phase A: 10 mM ammonium formate:acetonitrile (98:2), Mobile phase B: 10 mM ammonium formate:acetonitrile (2:98), Gradient=20-100% B over 4 minutes, then a 0.6 minute hold at 100% B; Temperature: 27° C.; Flow rate: 1.0 mL/min; Detection: UV at 220 nm.

Example 296: (2.0 mg, 1% yield); LCMS: m/z=470.2 (M+H); retention time=3.44 min. LCMS Method: Column: Kinetex XB-C18 (3×75 mm) 2.6 μm; Mobile phase A: 10 mM ammonium formate:acetonitrile (98:2), Mobile phase B: 10 mM ammonium formate:acetonitrile (2:98), Gradient=20-100% B over 4 minutes, then a 0.6 minute hold at 100% B; Temperature: 27° C.; Flow rate: 1.0 mL/min; Detection: UV at 220 nm.

Example 297: (2.1 mg, 1.3% yield); LCMS: m/z=470.2 (M+H); retention time=3.44 min. LCMS Method: Column: Kinetex XB-C18 (3×75 mm) 2.6 μm; Mobile phase A: 10 mM ammonium formate:acetonitrile (98:2), Mobile phase B: 10 mM ammonium formate:acetonitrile (2:98), Gradient=20-100% B over 4 minutes, then a 0.6 minute hold at 100% B; Temperature: 27° C.; Flow rate: 1.0 mL/min; Detection: UV at 220 nm.

The Examples in Table 24 were prepared from 3-(trifluoromethyl)aniline according to the general procedures disclosed in Examples 294-297.

TABLE 24

| Ex. No | Structure | Stereochemistry | LCMS Method | LCMS RT | M + H |
|---|---|---|---|---|---|
| 320 | 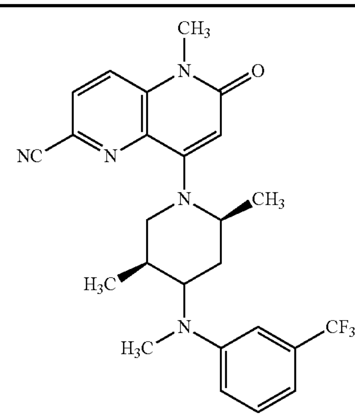 | Diastereomeric mixture | C | 3.53 | 470.2 |
| 321 | 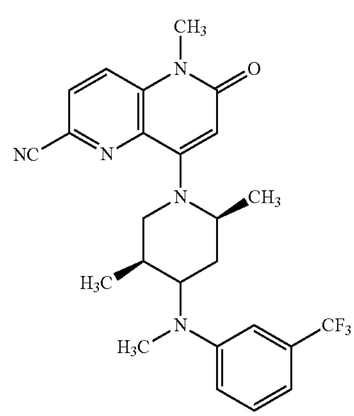 [SMILES: C[C@H]1CN(c2cc(=O)n(C)c3ccc(C#N)nc23)[C@@H](C)CC1N(C)c1cccc(C(F)(F)F)c1] | Diastereomeric mixture | C | 3.55 | 470.2 |

Intermediate 152 t-Butyl 3-methyl-4-(methylamino)piperidine-1-carboxylate

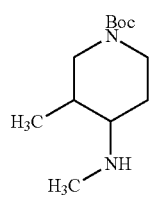

(I-152)

To a solution of tert-butyl 3-methyl-4-oxopiperidine-1-carboxylate (500 mg, 2.344 mmol) in methanol (10 mL) was added methyl amine (0.44 mL, 33% in MeOH, 4.69 mmol) and the reaction mixture was heated to 85° C. for 2 h. The reaction mixture was cooled to room temperature. Sodium borohydride (177 mg, 4.69 mmol) was added and the reaction mixture was stirred for 12 h. The reaction was quenched with saturated NH$_4$Cl. The reaction mixture was dissolved in EtOAc (100 mL), washed with saturated NaHCO$_3$ (20 mL), water (20 mL), brine (20 mL), dried over Na$_2$SO$_4$ and concentrated under reduced pressure to afford tert-butyl 3-methyl-4-(methylamino)piperidine-1-carboxylate (330 mg, 62% yield). LCMS: m/z=229.2 (M+H); retention time 1.07 min. LC-MS Method: Column-Aquity UPLC BEH C18 (3.0×50 mm) 1.7 μm; Mobile phase A: Buffer: acetonitrile (95:5); Mobile phase B: Buffer:acetonitrile (5:95), Buffer: 10 mM ammonium acetate; Gradient: 20-100% B over 2.0 minutes, then a 0.2 minute hold at 100% B, flow rate 0.7 mL/min.

Intermediate 153 tert-Butyl 4-((4-fluorobenzyl)(methyl)amino)-3-methylpiperidine-1-carboxylate

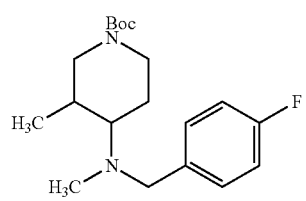

(I-153)

To a solution of tert-butyl 3-methyl-4-(methylamino)piperidine-1-carboxylate (330 mg, 1.45 mmol) in acetonitrile (5 mL) were added 1-(chloromethyl)-4-fluorobenzene (313 mg, 2.17 mmol), DIPEA (0.505 mL, 2.89 mmol) and sodium iodide (217 mg, 1.45 mmol) and heated 85° C. for 4 h. The reaction mixture was cooled to room temperature, diluted with EtOAc (100 mL) and washed with water (20 mL), brine (20 mL), dried over Na$_2$SO$_4$ and concentrated under reduced pressure to obtain crude product, which was purified by silica gel chromatography by using 0-10% MeOH/CHCl$_3$ as eluent. Pure fractions were collected and concentrated to obtain tert-butyl 4-((4-fluorobenzyl)(methyl)amino)-3-methylpiperidine-1-carboxylate (420 mg, 86% yield) as yellow liquid. LCMS: m/z=337.2 (M+H); retention time 2.12 min. LC-MS Method: Column-Aquity UPLC BEH C18 (3.0×50 mm) 1.7 μm; Mobile phase A: Buffer: acetonitrile (95:5); Mobile phase B: Buffer:acetonitrile (5:95), Buffer: 10 mM ammonium acetate; Gradient: 20-100% B over 2.0 minutes, then a 0.2 minute hold at 100% B, flow rate 0.7 mL/min.

Intermediate 154

N-(4-Fluorobenzyl)-N,3-dimethylpiperidin-4-amine, TFA

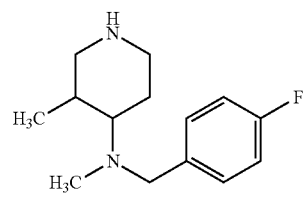

(I-154)

To a solution of tert-butyl 4-((4-fluorobenzyl)(methyl)amino)-3-methylpiperidine-1-carboxylate (400 mg, 1.19 mmol) in CH$_2$Cl$_2$ (4 mL) was added TFA (0.916 mL, 11.89 mmol) and stirred for 2 h. The reaction mixture was concentrated under reduced pressure to yield N-(4-fluorobenzyl)-N,3-dimethylpiperidin-4-amine, TFA (400 mg, 96% yield). LCMS: m/z=237.2 (M+H); retention time 1.15 min. LC-MS Method: Column-Aquity UPLC BEH C18 (3.0×50 mm) 1.7 μm; Mobile phase A: Buffer:acetonitrile (95:5); Mobile phase B: Buffer:acetonitrile (5:95), Buffer: 10 mM ammonium acetate; Gradient: 20-100% B over 2.0 minutes, then a 0.2 minute hold at 100% B, flow rate 0.7 mL/min.

Examples 322-325

8-(4-((4-Fluorobenzyl)(methyl)amino)-3-methylpiperidin-1-yl)-5-methyl-6-oxo-5,6-dihydro-1,5-naphthyridine-2,7-dicarbonitrile

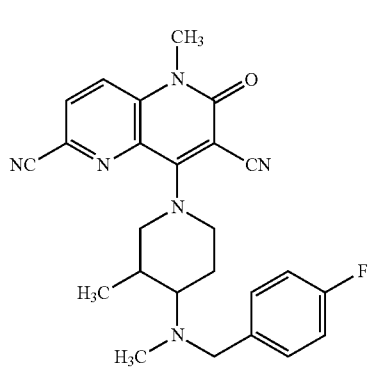

(322-325)

To a solution of N-(4-fluorobenzyl)-N,3-dimethylpiperidin-4-amine, TFA (200 mg, 0.57 mmol) in acetonitrile (3 mL) were added DIPEA (0.3 mL, 1.71 mmol) and 8-chloro-5-methyl-6-oxo-5,6-dihydro-1,5-naphthyridine-2,7-dicarbonitrile (209 mg, 0.856 mmol). The reaction mixture was heated at 85° C. for 16 h. The reaction mixture was cooled to room temperature, concentrated under reduced pressure and was purified by silica gel chromatography by using 0-10% MeOH/CHCl₃ as eluent. Pure fractions were collected and concentrated to afford a yellow liquid which was separated by Prep HPLC (Column: Sunfire C-18 (150 mm×21.2 mm ID, 5 µm); Mobile Phase A: 10 mM ammonium acetate in water-4.5 pH; Mobile Phase B: Acetonitrile, Flow: 20 mL/min; Grad: 25 to 45% B over 20 min) to obtain diastereomeric mixture 1 and diastereomeric mixture 2.

Diastereomeric mixture 1 was separated by chiral SFC (Column/dimensions: Chiralpak IG (250×4.6) mm, 5 µm; Co-Solvent %: 40%; Co solvent: 0.2% DEA in IPA+acetonitrile (1+1); Total Flow: 4 g/min; Back Pressure: 100 bar; Temperature: 30° C.) to afford Isomer 1: Example 322, retention time=2.5 min; and Isomer 2: Example 323, retention time=3.49 min.

Diastereomeric mixture 2 was separated by chiral SFC (Column/dimensions: Cellulose 4 (250×4.6) mm, 5 µm; Co-Solvent %: 50%; Co solvent: 0.2% of 4 M methanolic ammonia in methanol; Total Flow: 4 g/min; Back Pressure: 100 bar; Temperature: 30° C.;) to obtain Isomer 3: Example 324, retention time=2.09 min; and Isomer 4: Example 325, retention time=2.82 min Example 322: (9 mg, 3.5% yield); LCMS: m/z=445.2 (M+H); retention time=1.33 min. LCMS Method: Column: Kinetex XB-C18 (3×75 mm) 2.6 µm; Mobile phase A: 10 mM ammonium formate: acetonitrile (98:2), Mobile phase B: 10 mM ammonium formate:acetonitrile (2:98), Gradient=20-100% B over 4 minutes, then a 0.6 minute hold at 100% B; Temperature: 27° C.; Flow rate: 1.0 mL/min; Detection: UV at 220 nm.

Example 323: (10 mg, 4% yield); LCMS: m/z=445.4 (M+H); retention time=1.24 min. LCMS Method: Column: Kinetex XB-C18 (3×75 mm) 2.6 µm; Mobile phase A: 10 mM ammonium formate: acetonitrile (98:2), Mobile phase B: 10 mM ammonium formate:acetonitrile (2:98), Gradient=20-100% B over 4 minutes, then a 0.6 minute hold at 100% B; Temperature: 27° C.; Flow rate: 1.0 mL/min; Detection: UV at 220 nm.

Example 324: (11 mg, 4% yield); LCMS: m/z=445.4 (M+H); retention time=1.24 min. LCMS Method: Column: Kinetex XB-C18 (3×75 mm) 2.6 µm; Mobile phase A: 10 mM ammonium formate: acetonitrile (98:2), Mobile phase B: 10 mM ammonium formate: acetonitrile (2:98), Gradient=20-100% B over 4 minutes, then a 0.6 minute hold at 100% B; Temperature: 27° C.; Flow rate: 1.0 mL/min; Detection: UV at 220 nm.

Example 325: (6 mg, 2.5% yield); LCMS: m/z=445.3 (M+H); retention time=1.32 min. LCMS Method: Column: Kinetex XB-C18 (3×75 mm) 2.6 µm; Mobile phase A: 10 mM ammonium formate: acetonitrile (98:2), Mobile phase B: 10 mM ammonium formate:acetonitrile (2:98), Gradient=20-100% B over 4 minutes, then a 0.6 minute hold at 100% B; Temperature: 27° C.; Flow rate: 1.0 mL/min; Detection: UV at 220 nm.

The Examples in Table 25 were prepared from 6-cyano-1-methyl-2-oxo-1,2-dihydro-1,5-naphthyridin-4-yl trifluoromethanesulfonate, according to the general procedures disclosed in Examples 322-325.

TABLE 25

| Ex. No | Structure | Stereochemistry | LCMS Method | LCMS RT | M + H |
|---|---|---|---|---|---|
| 326 | 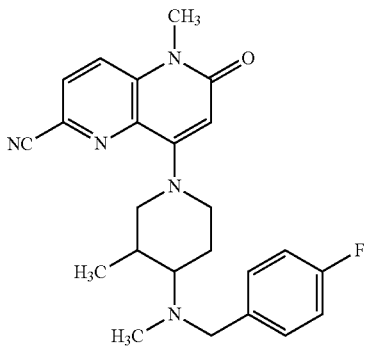 [SMILES: CC1CN(c2cc(=O)n(C)c3ccc(C#N)nc23)CCC1N(C)Cc1ccc(F)cc1] | Homochiral | A | 2.17 | 420.3 |
| 327 | 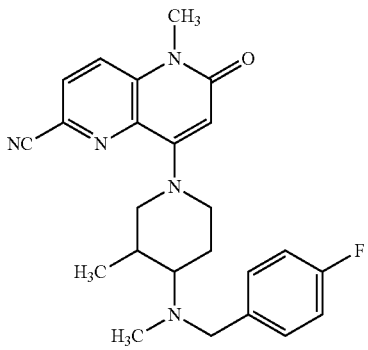 [SMILES: CC1CN(c2cc(=O)n(C)c3ccc(C#N)nc23)CCC1N(C)Cc1ccc(F)cc1] | Homochiral | A | 2.17 | 420.3 |

TABLE 25-continued

| Ex. No | Structure | Stereochemistry | LCMS Method | LCMS RT | M + H |
|---|---|---|---|---|---|
| 328 | 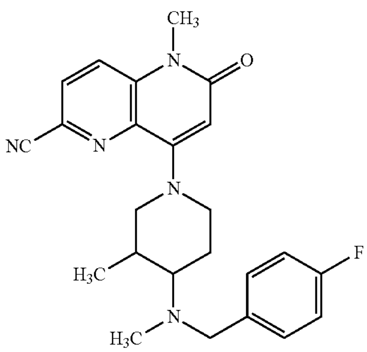 [SMILES: CC1CN(c2cc(=O)n(C)c3ccc(C#N)nc23)CCC1N(C)Cc1ccc(F)cc1] | Homochiral | A | 2.31 | 420.3 |
| 329 | 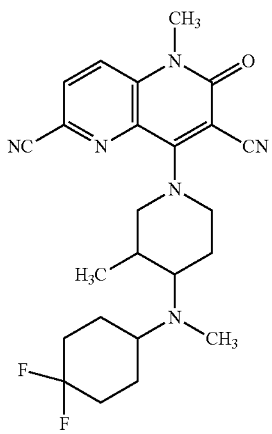 [SMILES: CC1CN(c2c(C#N)c(=O)n(C)c3ccc(C#N)nc23)CCC1N(C)C1CCC(F)(F)CC1] | Homochiral | C | 2.30 | 455.2 |
| 330 | 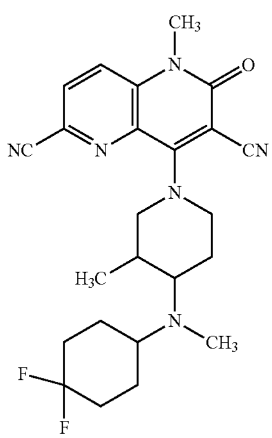 [SMILES: CC1CN(c2c(C#N)c(=O)n(C)c3ccc(C#N)nc23)CCC1N(C)C1CCC(F)(F)CC1] | Homochiral | C | 2.29 | 455.2 |
| 331 | 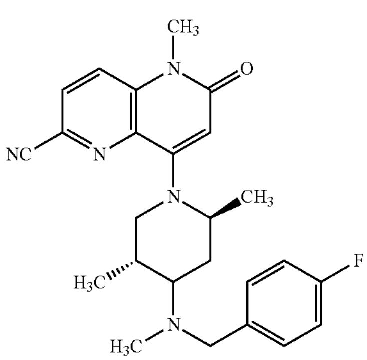 [SMILES: C[C@@H]1CN(c2cc(=O)n(C)c3ccc(C#N)nc23)[C@@H](C)CC1N(C)Cc1ccc(F)cc1] | Homochiral | C | 1.31 | 434.4 |

TABLE 25-continued

| Ex. No | Structure | Stereochemistry | LCMS Method | LCMS RT | M + H |
|---|---|---|---|---|---|
| 332 | 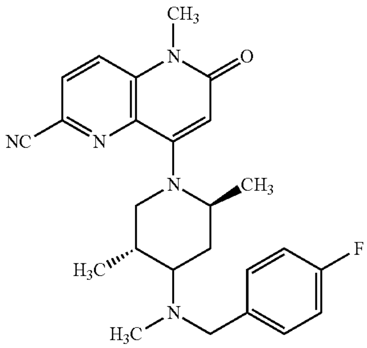 [SMILES: C[C@@H]1CN(c2cc(=O)n(C)c3ccc(C#N)nc23)[C@@H](C)CC1N(C)Cc1ccc(F)cc1] | Homochiral | C | 1.21 | 434.4 |
| 333 | 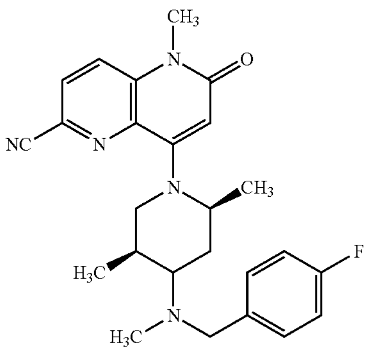 [SMILES: C[C@H]1CN(c2cc(=O)n(C)c3ccc(C#N)nc23)[C@@H](C)CC1N(C)Cc1ccc(F)cc1] | Homochiral | C | 1.20 | 434.4 |
| 334 | 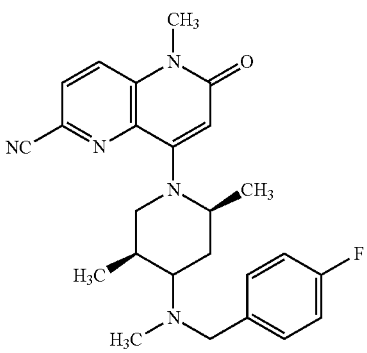 [SMILES: C[C@H]1CN(c2cc(=O)n(C)c3ccc(C#N)nc23)[C@@H](C)CC1N(C)Cc1ccc(F)cc1] | Homochiral | C | 1.23 | 434.4 |

Intermediate 155

(±)-tert-Butyl (2S,5S)-4-hydroxy-2,4,5-trimethylpiperidine-1-carboxylate

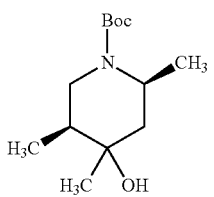

(I-155)

To a stirred solution of tert-butyl (2S,5S)-2,5-dimethyl-4-oxopiperidine-1-carboxylate (500 mg, 2.20 mmol) in tetrahydrofuran (10 mL) at −30° C. was added methylmagnesium bromide in diethyl ether (3.7 mL, 11.00 mmol) dropwise under nitrogen over 3 min. The reaction mixture was slowly warmed to room temperature and was stirred for 16 h. The reaction was quenched with saturated aqueous ammonium chloride solution (100 mL). The reaction mixture was diluted with ethylacetate (3×100 mL). The combined organic layer was dried over anhydrous sodium sulfate, filtered and evaporated under reduced pressure to obtain crude product, which was purified by silica gel chromatography (using 15%-20% ethylacetate/Pet. ether) to get tert-butyl-4-hydroxy-2,4,5-trimethylpiperidine-1-carboxylate (420 mg, 78% yield). $^1$H NMR (300 MHz, CDCl$_3$) δ 4.42-4.23 (m, 1H), 3.81-3.59 (m, 1H), 2.92-2.77 (m, 1H), 1.78-1.66 (m, 1H), 1.58-1.50 (m, 1H), 1.49-1.44 (m, 10H), 1.28 (d, J=7.2 Hz, 3H), 1.21-1.17 (m, 3H), 0.95-0.87 (m, 3H) ppm.

Intermediate 156

(±) tert-Butyl (2S,5S)-4-((5-isopropoxypyridin-2-yl)oxy)-2,4,5-trimethylpiperidine-1-carboxylate

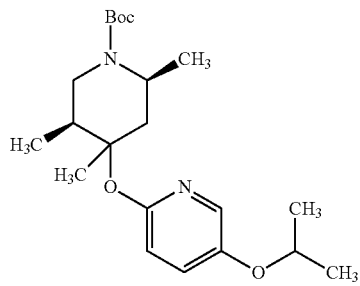

(I-156)

To a stirred solution of tert-butyl-4-hydroxy-2,4,5-trimethylpiperidine-1-carboxylate (200 mg, 0.82 mmol) in DMSO (8 mL) was added NaH (60% w/w, 99 mg, 2.47 mmol) at 0° C. and 2-fluoro-5-isopropoxypyridine (191 mg, 1.23 mmol). The reaction mixture was heated at 65° C. for 20 h. The reaction was quenched with water (50 mL). The reaction mixture was extracted with ethyl acetate (3×100 mL). The combined organic layer was dried over anhydrous sodium sulfate, filtered and evaporated under reduced pressure to obtain crude product, which was purified by silica gel column (10%-20% ethyl acetate/Pet. ether) to afford tert-butyl (2S,5S)-4-((5-isopropoxypyridin-2-yl)oxy)-2,4,5-trimethylpiperidine-1-carboxylate (110 mg, 0.17 mmol, 20.86% yield). LCMS: m/z=379.2 (M+H); retention time 4.18 min; LCMS Method: Column: Kinetex XB-C18 (3×75 mm) 2.6µ; Mobile phase A: 10 mM ammonium formate:acetonitrile (98:2), Mobile phase B: 10 mM ammonium formate:acetonitrile (2:98), Gradient=20-100% B over 4 minutes, then a 0.6 minute hold at 100% B; Temperature: 27° C.; Flow rate: 1.0 mL/min; Detection: UV at 220 nm.

Intermediate 157

(±) 5-Isopropoxy-2-(((2S,5S)-2,4,5-trimethylpiperidin-4-yl)oxy)pyridine hydrochloride

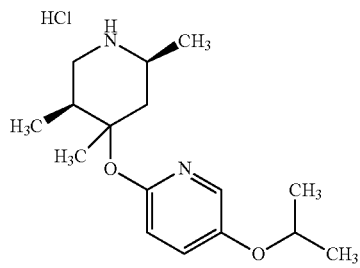

(I-157)

To a stirred solution of (±)tert-butyl (2S,5S)-4-((5-isopropoxypyridin-2-yl)oxy)-2,4,5-trimethylpiperidine-1-carboxylate (120 mg, 0.317 mmol) in DCM (5 mL) was added HCl in dioxane (0.05 mL, 1.59 mmol). The reaction mixture was stirred at room temperature for 2 h. The reaction mixture was concentrated under reduced pressure to afford (±) 5-isopropoxy-2-(((2S,5S)-2,4,5-trimethylpiperidin-4-yl)oxy)pyridine (80 mg, 91% yield). LCMS: m/z=279.2 (M+H); retention time 1.932 min. LCMS Method: Column: Kinetex XB-C18 (3×75 mm) 2.6 µm; Mobile phase A: 10 mM ammonium formate:acetonitrile (98:2), Mobile phase B: 10 mM ammonium formate:acetonitrile (2:98), Gradient=20-100% B over 4 minutes, then a 0.6 minute hold at 100% B; Temperature: 27° C.; Flow rate: 1.0 mL/min; Detection: UV at 220 nm.

Examples 335 and 336

8-((2S,5S)-4-((5-Isopropoxypyridin-2-yl)oxy)-2,4,5-trimethylpiperidin-1-yl)-5-methyl-6-oxo-5,6-dihydro-1,5-naphthyridine-2-carbonitrile

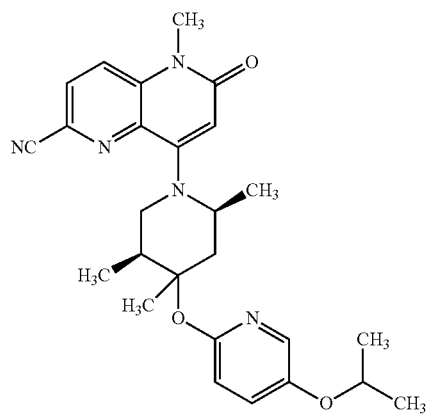

(335-336)

To a stirred solution of 6-cyano-1-methyl-2-oxo-1,2-dihydro-1,5-naphthyridin-4-yl trifluoromethanesulfonate (100 mg, 0.30 mmol) in acetonitrile (8 mL) were added DIPEA (0.16 mL, 0.90 mmol) and 5-isopropoxy-2-(((2S,5S)-2,4,5-trimethylpiperidin-4-yl)oxy) pyridine, HCl (113 mg, 0.36 mmol). The reaction mixture was heated at 85° C. for 16 h. The reaction was quenched with water (20 mL). The reaction mixture was extracted with ethyl acetate (3×20 mL). The combined organic layer was dried over anhydrous sodium sulfate, filtered and evaporated under reduced pressure to obtain the crude product, which was purified by preparative SFC [SFC condition: Column/dimensions: ChiralCel OJ-H (250×30) mm, 5 µm; % CO$_2$: 85%; % Co solvent: 15% MEOH; Total Flow: 100.0 g/min; Back Pressure: 100 bar; Temperature: 35° C.; UV: 227 nm] to give Example 362 (14 mg, 10% yield) and Example 363 (13 mg, 10% yield).

Example 362: LCMS: m/z=462.3 (M+H); retention time 2.416 min; [LCMS Method: Column: XBridge BEH XP C18 (50×2.1) mm, 2.5 µm; Mobile phase A: 10 mM ammonium acetate, acetonitrile (95:5); Mobile phase B: 10 mM ammonium acetate: acetonitrile (5:95); Gradient=0-100% B over 3 minutes; Temperature: 50° C.; Flow rate: 1.1 mL/min; Detection: UV at 220 nm]. $^1$H NMR (400 MHz, DMSO-d$_6$) δ 8.18-8.10 (m, 1H), 8.09-7.99 (m, 1H), 7.79 (d, J=2.9 Hz, 1H), 7.33-7.36 (m, 1H), 6.72 (d, J=9.0 Hz, 1H), 6.04 (s, 1H), 4.73-4.63 (m, 1H), 4.49-4.54 (m, 1H), 3.52 (s, 3H), 3.39-3.44 (m, 2H), 3.07-3.11 (m, 1H), 2.01-1.90 (m, 1H), 1.80-1.85 (m, 1H), 1.51 (s, 3H), 1.23-1.25 (m, 6H), 1.09 (d, J=6.8 Hz, 3H), 1.03 (d, J=7.1 Hz, 3H).

Example 363: LCMS: m/z=462.3 (M+H); retention time 2.417 min [LCMS Method: Column: XBridge BEH XP C18 (50×2.1) mm, 2.5 μm; Mobile phase A: 10 mM ammonium acetate, acetonitrile (95:5); Mobile phase B: 10 mM ammonium acetate: acetonitrile (5:95); Gradient=0-100% B over 3 minutes; Temperature: 50° C.; Flow rate: 1.1 mL/min; Detection: UV at 220 nm]. $^1$H NMR (400 MHz, DMSO-$d_6$) δ 8.19-8.08 (m, 1H), 8.08-7.96 (m, 1H), 7.84-7.74 (m, 1H), 7.32-7.35 (m, 1H), 6.79-6.65 (m, 1H), 6.10-5.97 (m, 1H), 4.76-4.61 (m, 1H), 4.48-4.54 (m, 1H), 3.52 (s, 3H), 3.42-3.36 (m, 2H), 3.08-3.11 (m, 1H), 2.01-1.90 (m, 1H), 1.87-1.77 (m, 1H), 1.51 (d, J=2.4 Hz, 3H), 1.27-1.21 (m, 6H), 1.08-1.10 (m, 3H), 1.02-1.08 (m, 3H).

The Examples in Table 26 were prepared from appropriate starting material according to the general procedures disclosed in Example 335 and 336.

TABLE 26

| Ex. No. | Structure | LCMS Method | LCMS RT | M + H | Stereo-chemistry |
|---|---|---|---|---|---|
| 337 | 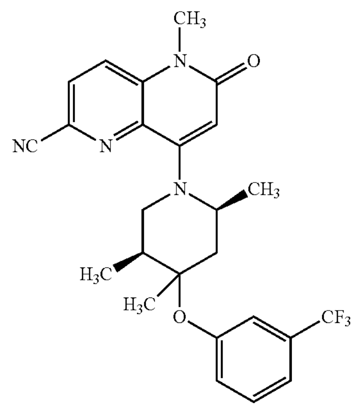 [SMILES: C[C@H]1CC(C)(Oc2cccc(C(F)(F)F)c2)[C@@H](C)CN1c1cc(=O)n(C)c2ccc(C#N)nc12] | A | 2.44 | 471.3 | Homochiral |
| 338 | 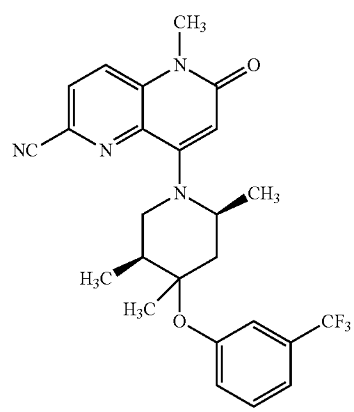 [SMILES: C[C@H]1CC(C)(Oc2cccc(C(F)(F)F)c2)[C@@H](C)CN1c1cc(=O)n(C)c2ccc(C#N)nc12] | A | 2.44 | 471.3 | Homochiral |
| 339 | 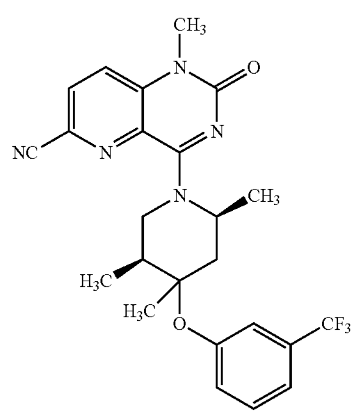 [SMILES: C[C@H]1CC(C)(Oc2cccc(C(F)(F)F)c2)[C@@H](C)CN1c1nc(=O)n(C)c2ccc(C#N)nc12] | A | 2.17 | 472.2 | Homochiral |

TABLE 26-continued

| Ex. No. | Structure | LCMS Method | LCMS RT | M + H | Stereo-chemistry |
|---|---|---|---|---|---|
| 340 | 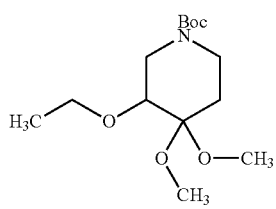 | A | 2.18 | 472.4 | Homochiral |

Intermediate 158

(±)-tert-Butyl 3-ethoxy-4,4-dimethoxypiperidine-1-carboxylate (I-158)

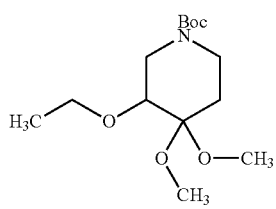

To a stirred solution of (±)-tert-butyl 3-hydroxy-4,4-dimethoxypiperidine-1-carboxylate (8 g, 30.6 mmol) in THF (80 mL) was added NaH (60% in mineral oil) (1.71 g, 42.9 mmol, 60% w/w) at 0° C. After 5 minutes, a solution of iodoethane (4.95 mL, 61.2 mmol) was added and the reaction mixture was stirred for overnight at room temperature. The reaction mixture was cooled to 0° C. The reaction was quenched with ice cold water. The mixture was extracted with EtOAc (2×50 mL). The combined organic extracts were washed with brine, dried over $Na_2SO_4$ and concentrated to afford crude product, which was purified via flash chromatography using a 120 g silica gel column and eluted with 30%-50% EtOAc in petroleum ether to afford (±)-tert-butyl 3-ethoxy-4,4-dimethoxypiperidine-1-carboxylate (5 g, 56% yield). $^1$H NMR (400 MHz, DMSO-$d_6$) δ ppm 4.02-4.21 (m, 1H), 3.59-3.90 (m, 2H), 3.11 (s, 3H), 3.09 (s, 3H), 2.54-2.93 (m, 3H), 1.63-1.73 (m, 1H), 1.46-1.61 (m, 1H), 1.39 (s, 9H), 1.02-1.18 (m, 3H).

Intermediate 159

(±)-tert-butyl 3-ethoxy-4-oxopiperidine-1-carboxylate (I-159)

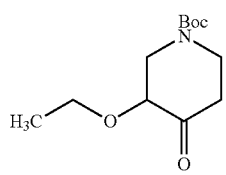

To a stirred solution of tert-butyl 3,4,4-triethoxypiperidine-1-carboxylate (9 g, 28.4 mmol) in dichloromethane (70 mL) was added TFA (10.9 mL, 142 mmol) dropwise and reaction mixture was heated at 50° C. for 16 h. The reaction mixture was cooled to room temperature and solvent was removed under reduced pressure to obtain crude product, which was dissolved in DCM (50 mL). TEA (19.8 mL, 142 mmol), $BOC_2O$ (9.9 mL, 42.5 mmol) were added sequentially at room temperature and stirred for overnight. The reaction mixture was extracted with DCM (2×100 mL). The combined organic extracts were washed with brine, dried over $Na_2SO_4$ and concentrated to afford crude product, which was purified via flash chromatography using a 120 g silica gel column and eluted with 10-15% EtOAc in petroleum ether to afford (±)-tert-butyl 3-ethoxy-4-oxopiperidine-1-carboxylate (5 g, 72% yield). $^1$H NMR (400 MHz, CHLOROFORM-d) δ ppm 3.96-4.42 (m, 2H), 3.64-3.89 (m, 2H), 3.19-3.59 (m, 3H), 2.47-2.65 (m, 2H), 1.50 (s, 9H), 1.25 (t, J=7.0 Hz, 3H).

Intermediate 160 tert-Butyl 3-ethoxy-4-oxopiperidine-1-carboxylate

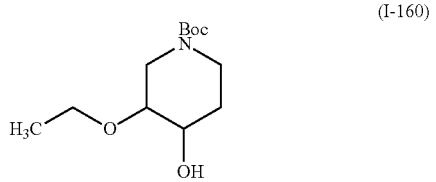 [SMILES: CCOC1CN(C(=O)OC(C)(C)C)CCC1O]

(I-160)

A sodium borohydride (0.93 g, 24.66 mmol) was added in a portion wise to a solution of (±)-tert-butyl 3-ethoxy-4-oxopiperidine-1-carboxylate (3 g, 12.3 mmol) in MeOH (20 mL) at 0° C. under nitrogen. The reaction mixture was allowed to warm to room temperature and stirred for 2 h. The reaction mixture was cooled to 0° C. The reaction was quenched with a dropwise solution of saturated aqueous NH$_4$Cl. The reaction mixture was extracted with EtOAc (3×100 mL). The combined organic extracts were washed with brine, dried over Na$_2$SO$_4$ and concentrated to afford tert-butyl-3-ethoxy-4-hydroxypiperidine-1-carboxylate (2.5 g, 83% yield). $^1$H NMR 300 MHz, DMSO-d$_6$) δ ppm 4.50-4.95 (m, 1H), 3.38-3.74 (m, 5H), 2.97-3.29 (m, 3H), 1.42-1.80 (m, 2H), 1.38 (s, 9H), 1.04-1.16 (m, 3H).

Intermediate 161

3-ethoxypiperidin-4-ol, HCl Salt

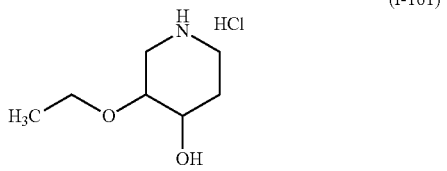

(I-161)

A 4M HCl in dioxane (3.72 mL, 122 mmol) was added to a solution of tert-butyl 3-ethoxy-4-hydroxypiperidine-1-carboxylate (3 g, 12.23 mmol) in DCM (15 mL) at 0° C. The reaction mixture was stirred at room temperature for 2 h, after which it was concentrated under reduced pressure to afford 3-ethoxypiperidin-4-ol HCl salt (1.5 g, 84% yield). $^1$H NMR (300 MHz, DMSO-d$_6$) δ ppm 9.16-9.37 (m, 1H), 8.47-8.70 (m, 1H), 3.81-3.96 (m, 1H), 3.42-3.76 (m, 5H), 2.93-3.11 (m, 3H), 1.53-1.86 (m, 2H), 1.14 (t, J=7.0 Hz, 3H)

Intermediates 161 and 162

(±)cis-8-(3-Ethoxy-4-hydroxypiperidin-1-yl)-5-methyl-6-oxo-5,6-dihydro-1,5-naphthyridine-2-carbonitrile and (±) trans-8-(3-Ethoxy-4-hydroxypiperidin-1-yl)-5-methyl-6-oxo-5,6-dihydro-1,5-naphthyridine-2-carbonitrile

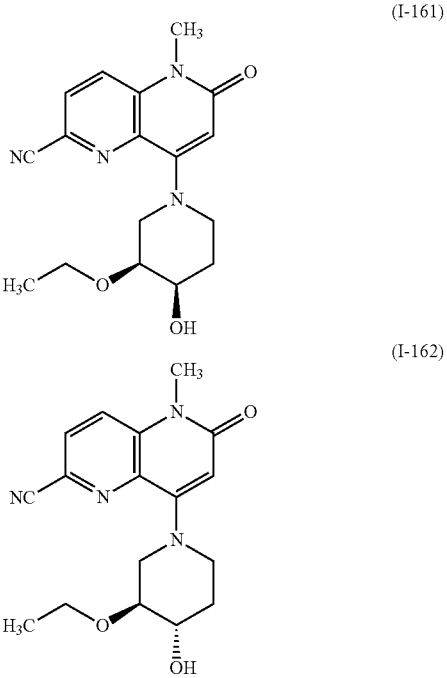

To a stirred solution of 3-ethoxypiperidin-4-ol. HCl salt (1.4 g, 9.64 mmol) in acetonitrile (15 mL) were added DIPEA (5.1 mL, 28.9 mmol) and 6-cyano-1-methyl-2-oxo-1,2-dihydro-1,5-naphthyridin-4-yl trifluoromethanesulfonate (3.21 g, 9.64 mmol) at room temperature. The reaction mixture was heated at 80° C. for 12 h. The reaction mixture was cooled to room temperature and the solvent was removed under reduced pressure to yield the crude product, which was purified by silica gel chromatography (80-100% EtOAc in petroleum ether) to afford diastereomeric mixture of 8-(3-ethoxy-4-hydroxypiperidin-1-yl)-5-methyl-6-oxo-5,6-dihydro-1,5-naphthyridine-2-carbonitrile. LCMS: m/z, 329.2 (M+1); retention time: 0.79 and 0.82 min. (LCMS Method: Column: Waters Acquity UPLC BEH C18 (2.1×50 mm) 1.7 μm, Mobile phase A: 10 mM ammonium acetate: acetonitrile (95:5); Mobile phase B: 10 mM Ammonium acetate: acetonitrile (5:95), Gradient=20-100% B over 2 minute, then a 0.3 minute hold at 100% B; Temperature: 50° C.; Flow rate: 0.7 mL/min; Detection: UV at 220 nm).

The cis/trans diastereomers were further purified by prep-SFC [Column: Princeton Diol (250×30) mm, 5% CO$_2$: 90%; % Co solvent: 10% of Methanol; Total Flow: 150.0 g/min; Back Pressure: 100 bar; Temperature: 40° C.; UV: 226 nm].

Intermediate 136: (±)cis-8-(3-Ethoxy-4-hydroxypiperidin-1-yl)-5-methyl-6-oxo-5,6-dihydro-1,5-naphthyridine-2-carbonitrile; Peak-1: (1.7 g, 52.1% yield); LCMS: m/z, 329.2 (M+1); retention time: 1.02 min. (LCMS Method: Column: Kinetex XB-C18 (3×75 mm) 2.6 μm; Mobile phase A: 10 mM ammonium formate: acetonitrile (98:2), Mobile phase B: 10 mM ammonium formate: acetonitrile (2:98), Gradient=20-100% B over 4 minutes, then a 0.6 minute hold at 100% B; Temperature: 27° C.; Flow rate: 1.0 mL/min; Detection: UV at 220 nm).

Intermediate 137: (±)trans-8-(3-Ethoxy-4-hydroxypiperidin-1-yl)-5-methyl-6-oxo-5,6-dihydro-1,5-naphthyridine-2-carbonitrile: Peak-2 (trans-isomer/racemate): (0.7 g, 20% yield); LCMS: m/z, 329.2 (M+1); retention time: 1.25 min. (LCMS Method: Column: Kinetex XB-C18 (3×75 mm) 2.6 μm; Mobile phase A: 10 mM ammonium formate: acetonitrile (98:2), Mobile phase B: 10 mM ammonium formate: acetonitrile (2:98), Gradient=20-100% B over 4 minutes, then a 0.6 minute hold at 100% B; Temperature: 27° C.; Flow rate: 1.0 mL/min; Detection: UV at 220 nm).

Examples 341 and 342 trans-8-(3-Ethoxy-4-phenoxypiperidin-1-yl)-5-methyl-6-oxo-5,6-dihydro-1,5-naphthyridine-2-carbonitrile

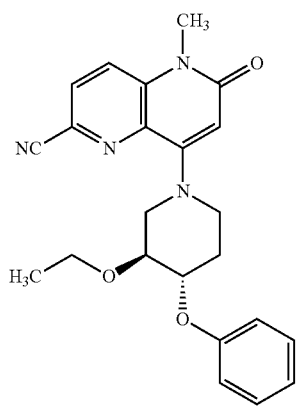

(341-342)

To a stirred solution of (±)-cis-8-(3-ethoxy-4-hydroxypiperidin-1-yl)-5-methyl-6-oxo-5,6-dihydro-1,5-naphthyridine-2-carbonitrile (100 mg, 0.30 mmol) in THF (5 mL), triphenylphosphine (176 mg, 0.67 mmol), DIAD (0.12 mL, 0.61 mmol) and phenol (57.3 mg, 0.61 mmol) were added sequentially at room temperature. The reaction mixture was heated at 60° C. for 2 h. The reaction mixture was cooled to room temperature and the solvent was removed under reduced pressure to yield the crude product, which was purified by preparative SFC (Column: Luxcellulose-4 (250× 21.5) mm, 5% $CO_2$: 70%; % Co solvent: 30% of 4 M methanolic ammonia in MeOH; Total Flow: 80.0 g/min; Back Pressure: 100 bar; Temperature: 30° C.; UV: 226 nm).

Example 341: (homochiral): (6.2 mg, 5% yield); LCMS: m/z, 405.2 (M+H); retention time: 1.91; LC/MS Method: Column: Waters XBridge C18, 19×150 mm, 5-μm particles; Mobile Phase A: 10-mM ammonium acetate; Mobile Phase B: acetonitrile; Gradient: 20-65% B over 20 minutes, then a 5-minute hold at 100% B; Flow: 15 mL/min. $^1$H NMR (400 MHz, DMSO-$d_6$) δ 8.22-8.14 (m, 1H), 8.12-8.01 (m, 1H), 7.37-7.23 (m, 2H), 7.04 (d, J=7.8 Hz, 2H), 6.94 (t, J=7.3 Hz, 1H), 6.14 (s, 1H), 4.52-4.40 (m, 1H), 4.21-4.11 (m, 1H), 3.79-3.57 (m, 4H), 3.54 (s, 3H), 3.30-3.15 (m, 2H), 2.27-2.15 (m, 1H), 1.80-1.66 (m, 1H), 1.07 (t, J=7.0 Hz, 3H).

Example 342: (homochiral): (3.2 mg, 2.5% yield); LCMS 405.3 (M+H); retention time: 1.91 min; LC/MS Method: Column: Waters XBridge C18, 19×150 mm, 5-μm particles; Mobile Phase A: 10-mM ammonium acetate; Mobile Phase B: acetonitrile; Gradient: 20-65% B over 20 minutes, then a 5-minute hold at 100% B; Flow: 15 mL/min. $^1$H NMR (400 MHz, DMSO-$d_6$): δ ppm 8.22-8.14 (m, 1H), 8.12-8.03 (m, 1H), 7.36-7.24 (m, 2H), 7.04 (d, J=7.8 Hz, 2H), 6.94 (t, J=7.3 Hz, 1H), 6.15 (s, 1H), 4.47 (td, J=7.7, 4.4 Hz, 1H), 4.20-4.10 (m, 1H), 3.78-3.56 (m, 4H), 3.54 (s, 3H), 3.29-3.17 (m, 2H), 2.27-2.18 (m, 1H), 1.81-1.68 (m, 1H), 1.07 (t, J=7.0 Hz, 3H).

The Examples in Table 27 were prepared from appropriate starting material according to the general procedures disclosed in Examples 341 and 342.

TABLE 27

| Ex. No. | Structure | Stereochemistry | LCMS Method | LCMS RT | M + H |
|---|---|---|---|---|---|
| 343 | 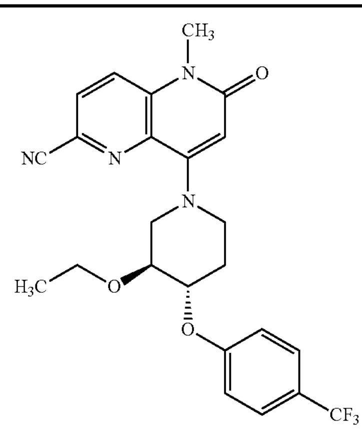 | Homochiral | A | 2.19 | 473.2 |

TABLE 27-continued

| Ex. No. | Structure | Stereochemistry | LCMS Method | LCMS RT | M + H |
|---|---|---|---|---|---|
| 344 | 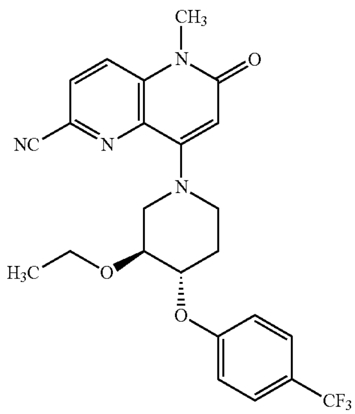 [SMILES: CCO[C@H]1CN(c2cc(=O)n(C)c3ccc(C#N)nc23)CC[C@@H]1Oc1ccc(C(F)(F)F)cc1] | Homochiral | A | 2.19 | 473.2 |
| 345 | 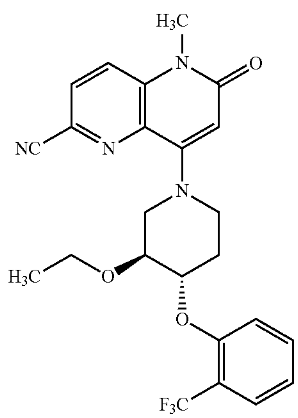 [SMILES: CCO[C@H]1CN(c2cc(=O)n(C)c3ccc(C#N)nc23)CC[C@@H]1Oc1ccccc1C(F)(F)F] | Homochiral | A | 2.12 | 473.3 |
| 346 | 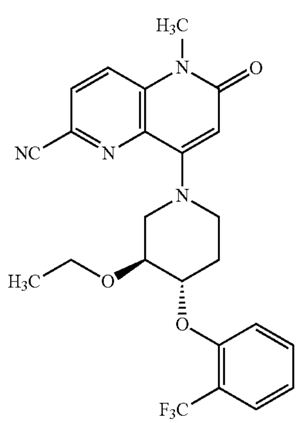 [SMILES: CCO[C@H]1CN(c2cc(=O)n(C)c3ccc(C#N)nc23)CC[C@@H]1Oc1ccccc1C(F)(F)F] | Homochiral | A | 2.12 | 473.2 |

TABLE 27-continued
| Ex. No. | Structure | Stereo-chemistry | LCMS Method | LCMS RT | M + H |
|---|---|---|---|---|---|
| 347 | 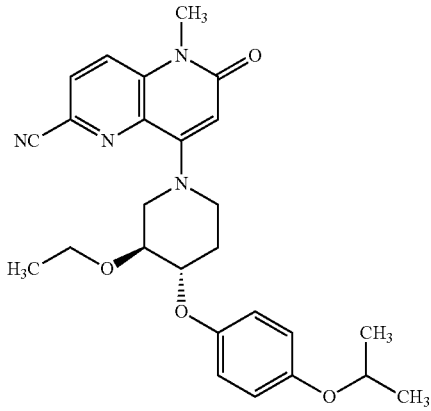 [SMILES: CCO[C@H]1CN(c2cc(=O)n(C)c3ccc(C#N)nc23)CC[C@@H]1Oc1ccc(OC(C)C)cc1] | Homochiral | A | 2.24 | 463.3 |
| 348 | 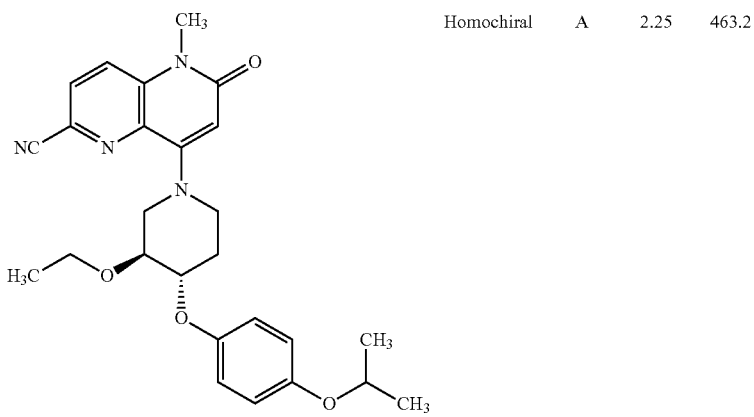 | Homochiral | A | 2.25 | 463.2 |
| 349 | 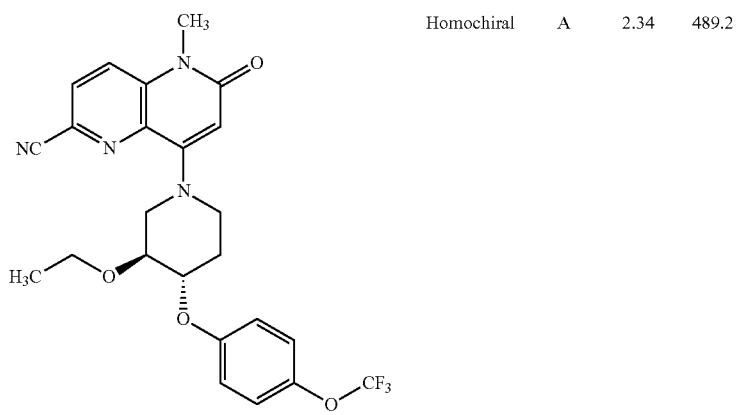 | Homochiral | A | 2.34 | 489.2 |

TABLE 27-continued

| Ex. No. | Structure | Stereo- chemistry | LCMS Method | LCMS RT | M + H |
|---|---|---|---|---|---|
| 350 | 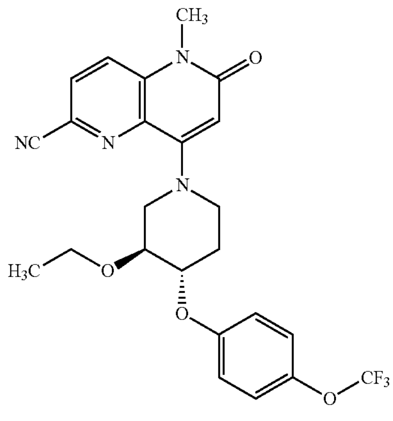 [SMILES: CCO[C@H]1CN(c2cc(=O)n(C)c3ccc(C#N)nc23)CC[C@@H]1Oc1ccc(OC(F)(F)F)cc1] | Homochiral | A | 2.33 | 489.2 |
| 351 | 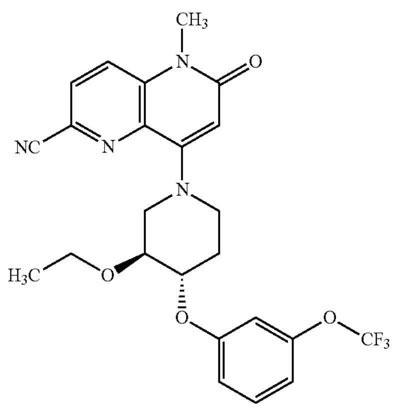 [SMILES: CCO[C@H]1CN(c2cc(=O)n(C)c3ccc(C#N)nc23)CC[C@@H]1Oc1cccc(OC(F)(F)F)c1] | Homochiral | A | 2.37 | 489.2 |
| 352 | 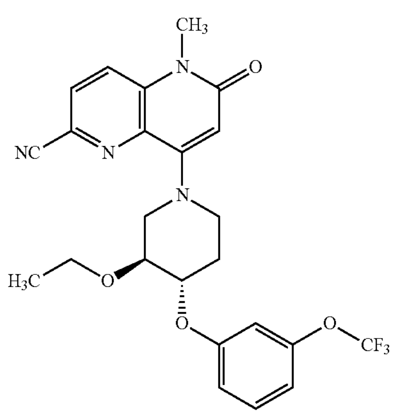 [SMILES: CCO[C@H]1CN(c2cc(=O)n(C)c3ccc(C#N)nc23)CC[C@@H]1Oc1cccc(OC(F)(F)F)c1] | Homochiral | A | 2.37 | 489.2 |

TABLE 27-continued

| Ex. No. | Structure | Stereo-chemistry | LCMS Method | LCMS RT | M + H |
|---|---|---|---|---|---|
| 353 | 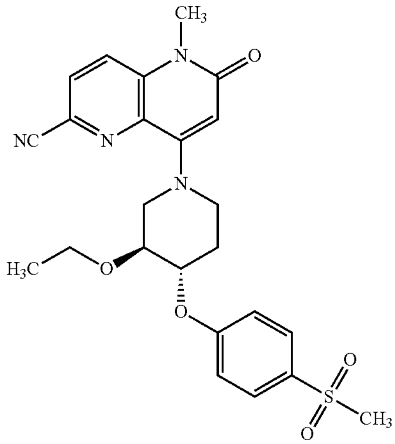 [SMILES: CCO[C@H]1CN(c2cc(=O)n(C)c3ccc(C#N)nc23)CC[C@@H]1Oc1ccc(S(C)(=O)=O)cc1] | Homochiral | A | 1.55 | 483.2 |
| 354 | 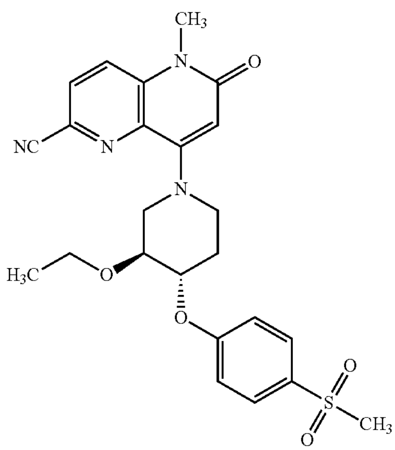 [SMILES: CCO[C@H]1CN(c2cc(=O)n(C)c3ccc(C#N)nc23)CC[C@@H]1Oc1ccc(S(C)(=O)=O)cc1] | Homochiral | A | 1.55 | 483.2 |
| 355 | 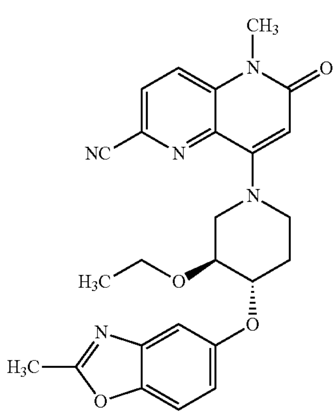 [SMILES: CCO[C@H]1CN(c2cc(=O)n(C)c3ccc(C#N)nc23)CC[C@@H]1Oc1ccc2oc(C)nc2c1] | Homochiral | A | 1.59 | 460.1 |

TABLE 27-continued

| Ex. No. | Structure | Stereo-chemistry | LCMS Method | LCMS RT | M + H |
|---|---|---|---|---|---|
| 356 | 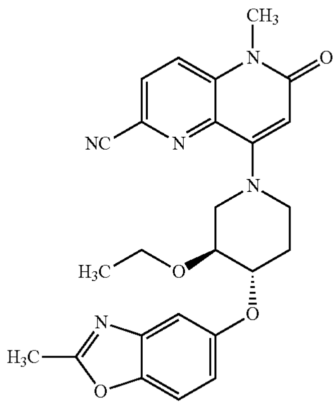 [SMILES: CCO[C@H]1CN(c2cc(=O)n(C)c3ccc(C#N)nc23)CC[C@@H]1Oc1ccc2oc(C)nc2c1] | Homochiral | A | 1.66 | 460.1 |
| 357 | 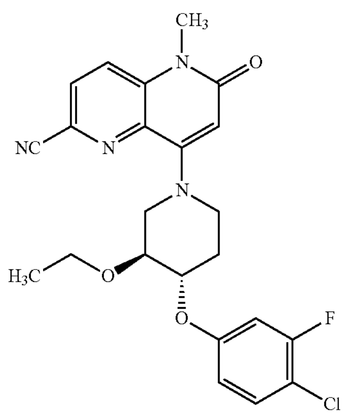 [SMILES: CCO[C@H]1CN(c2cc(=O)n(C)c3ccc(C#N)nc23)CC[C@@H]1Oc1ccc(Cl)c(F)c1] | Homochiral | A | 2.08 | 457.1 |
| 358 | 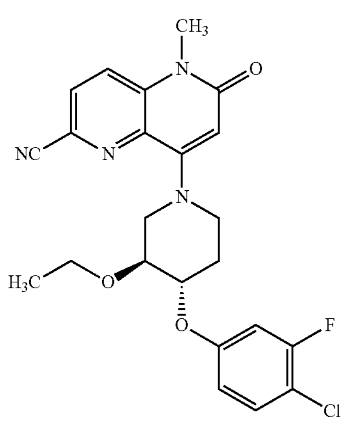 [SMILES: CCO[C@H]1CN(c2cc(=O)n(C)c3ccc(C#N)nc23)CC[C@@H]1Oc1ccc(Cl)c(F)c1] | Homochiral | A | 2.07 | 457.1 |

TABLE 27-continued

| Ex. No. | Structure | Stereo-chemistry | LCMS Method | LCMS RT | M + H |
|---|---|---|---|---|---|
| 359 | 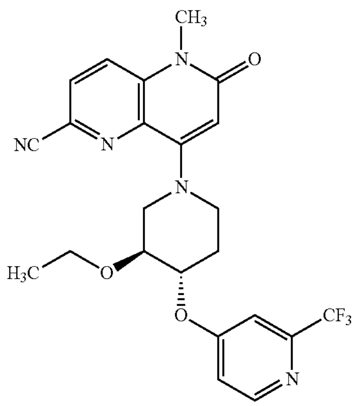 [SMILES: CCO[C@H]1CN(c2cc(=O)n(C)c3ccc(C#N)nc23)CC[C@@H]1Oc1ccnc(C(F)(F)F)c1] | Homochiral | A | 2.04 | 474.3 |
| 360 | 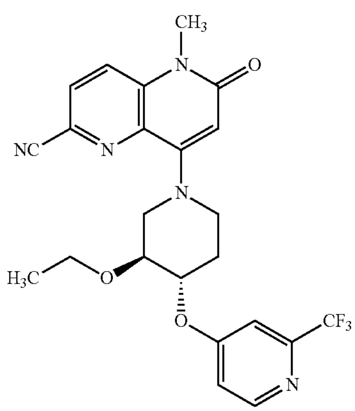 [SMILES: CCO[C@H]1CN(c2cc(=O)n(C)c3ccc(C#N)nc23)CC[C@@H]1Oc1ccnc(C(F)(F)F)c1] | Homochiral | A | 2.03 | 474.2 |
| 361 | 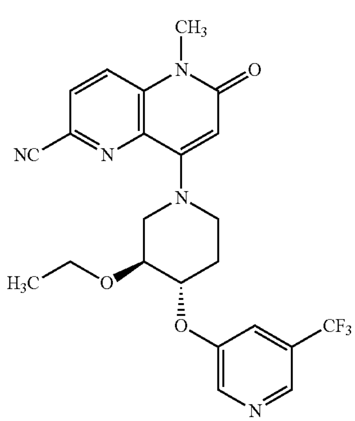 [SMILES: CCO[C@H]1CN(c2cc(=O)n(C)c3ccc(C#N)nc23)CC[C@@H]1Oc1cncc(C(F)(F)F)c1] | Homochiral | A | 2.07 | 474.2 |

TABLE 27-continued

| Ex. No. | Structure | Stereo-chemistry | LCMS Method | LCMS RT | M + H |
|---|---|---|---|---|---|
| 362 | 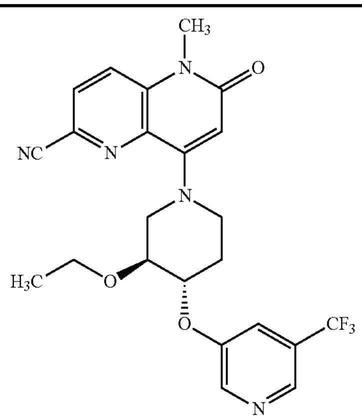 | Homochiral | A | 2.07 | 474.2 |

Examples 363 and 364 trans-8-(3-Ethoxy-4-((6-(trifluoromethyl)pyridin-2-yl)oxy)piperidin-1-yl)-5-methyl-6-oxo-5,6-dihydro-1,5-naphthyridine-2-carbonitrile

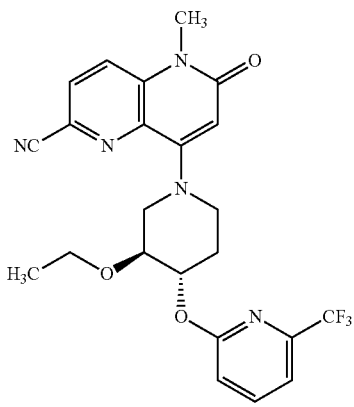

(363-364)

To a stirred solution of (±)-trans-8-(3-ethoxy-4-hydroxypiperidin-1-yl)-5-methyl-6-oxo-5,6-dihydro-1,5-naphthyridine-2-carbonitrile (100 mg, 0.30 mmol) in DMSO (3 mL) were added potassium tert-butoxide (68.3 mg, 0.61 mmol) and 2-fluoro-6-(trifluoromethyl) pyridine (75 mg, 0.46 mmol) at room temperature and stirred for 2 h. The reaction was quenched with ice cold water. The reaction mixture was extracted with EtOAc (2×10 mL). The combined organic extracts were washed with brine, dried over $Na_2SO_4$ and concentrated to afford crude product, which was purified by preparative SFC (Column: Luxcellulose-4 (250×30) mm, 5 μm; % $CO_2$: 65%; % co-solvent: 35% of 0.2% ammonia in MeOH; Total Flow: 70.0 g/min; Back Pressure: 100 bar; Temperature: 30° C.; UV: 225 nm).

Example 363: (11 mg, 8% yield); LCMS: m/z, 474.2 (M+H); retention time: 2.06; LC/MS Method: Column: Waters XBridge C18, 19×150 mm, 5-μm particles; Mobile Phase A: 10-mM ammonium acetate; Mobile Phase B: acetonitrile; Gradient: 20-65% B over 20 minutes, then a 5-minute hold at 100% B; Flow: 15 mL/min. $^1$H NMR (400 MHz, DMSO-$d_6$) δ ppm 8.16-8.21 (m, 1H), 8.07-8.13 (m, 1H), 7.95-8.01 (m, 1H), 7.48-7.53 (m, 1H), 7.16-7.21 (m, 1H), 6.17 (s, 1H), 5.13-5.20 (m, 1H), 4.12-4.19 (m, 1H), 3.54-3.78 (7H), 2.28-2.37 (m, 1H), 1.75-1.85 (m, 1H), 1.07 (t, J=7.0 Hz, 3H).

Example 364: (10 mg, 7% yield); LCMS 474.2 (M+H); retention time: 2.07 min; LC/MS Method: Column: Waters XBridge C18, 19×150 mm, 5-μm particles; Mobile Phase A: 10-mM ammonium acetate; Mobile Phase B: acetonitrile; Gradient: 20-65% B over 20 minutes, then a 5-minute hold at 100% B; Flow: 15 mL/min. $^1$H NMR (400 MHz, DMSO-$d_6$) δ ppm 8.15-8.21 (m, 1H), 8.06-8.13 (m, 1H), 7.96-8.03 (m, 1H), 7.46-7.53 (m, 1H), 7.19 (d, J=8.3 Hz, 1H), 6.16 (s, 1H), 5.11-5.20 (m, 1H), 4.11-4.18 (m, 1H), 3.52-3.79 (m, 7H), 2.27-2.38 (m, 1H), 1.73-1.85 (m, 1H), 1.07 (t, J=7.0 Hz, 3H).

The Examples in Table 28 were prepared from appropriate starting material according to the general procedures disclosed in Example 363 and 364.

TABLE 28

| Ex. No. | Structure | Stereo-chemistry | LCMS Method | LCMS RT | M + H |
|---|---|---|---|---|---|
| 365 | 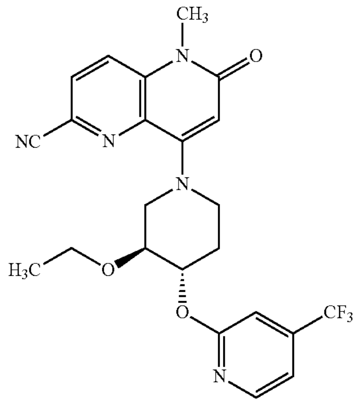 [SMILES: CCO[C@H]1CN(c2cc(=O)n(C)c3ccc(C#N)nc23)CC[C@@H]1Oc1cc(C(F)(F)F)ccn1] | Homochiral | A | 2.07 | 474.2 |
| 366 | 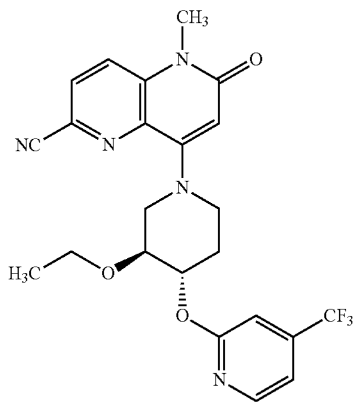 [SMILES: CCO[C@H]1CN(c2cc(=O)n(C)c3ccc(C#N)nc23)CC[C@@H]1Oc1cc(C(F)(F)F)ccn1] | Homochiral | A | 2.07 | 474.2 |

Examples 367 and 368 trans-8-(3-Ethoxy-4-((5-(trifluoromethyl)pyridin-2-yl)oxy)piperidin-1-yl)-5-methyl-6-oxo-5,6-dihydro-1,5-naphthyridine-2-carbonitrile

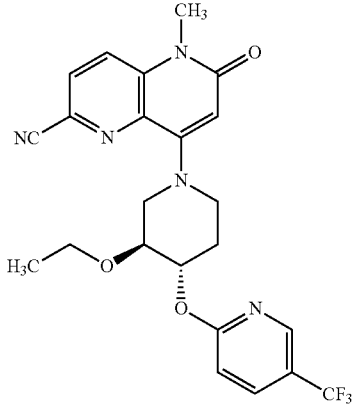

(367-368)

To a stirred solution of (±)-trans-8-(3-ethoxy-4-hydroxypiperidin-1-yl)-5-methyl-6-oxo-5,6-dihydro-1,5-naphthyridine-2-carbonitrile (60 mg, 0.18 mmol) in DMF (3 mL) were added $Cs_2CO_3$ (179 mg, 0.55 mmol) and 2-chloro-5-(trifluoromethyl)pyridine (43.1 mg, 0.24 mmol) at room temperature. The reaction mixture was heated at 100° C. for 6 h. The reaction mixture was cooled to room temperature, diluted with water and extracted with EtOAc (2×10 mL). The combined organic extracts were washed with brine, dried over $Na_2SO_4$ and concentrated to afford crude product, which was purified by preparative SFC (Column: Cellulose-4 (250×30) mm, 5 μm; % $CO_2$: 50%; % co-solvent: 50% of MeOH; Total Flow: 70.0 g/min; Back Pressure: 100 bar; Temperature: 30° C.; UV: 225 nm).

Example 367: (3.4 mg, 4% yield); LCMS: m/z, 474.2 (M+H); retention time: 2.05; LC/MS Method: Column: Waters XBridge C18, 19×150 mm, 5-μm particles; Mobile Phase A: 10-mM ammonium acetate; Mobile Phase B: acetonitrile; Gradient: 20-65% B over 20 minutes, then a 5-minute hold at 100% B; Flow: 15 mL/min. $^1$H NMR (400 MHz, DMSO-$d_6$) δ ppm 8.59-8.64 (m, 1H), 8.18-8.24 (m, 1H), 8.08-8.13 (m, 2H), 7.07 (d, J=8.6 Hz, 1H), 6.18 (s, 1H), 5.26-5.33 (m, 1H), 4.21-4.29 (m, 1H), 3.68-3.79 (m, 3H), 3.54-3.63 (m, 4H), 3.17-3.24 (m, 2H), 2.29-2.36 (m, 1H), 1.72-1.87 (m, 1H), 1.07 (t, J=7.0 Hz, 3H).

Example 368: (2 mg, 4% yield); LCMS 474.2 (M+H); retention time: 2.14 min; LC/MS Method: Column: Waters XBridge C18, 19×150 mm, 5-μm particles; Mobile Phase A: 10-mM ammonium acetate; Mobile Phase B: acetonitrile; Gradient: 20-65% B over 20 minutes, then a 5-minute hold at 100% B; Flow: 15 mL/min. $^1$H NMR (400 MHz, DMSO-$d_6$) δ ppm 8.59-8.62 (m, 1H), 8.19 (d, J=9.0 Hz, 1H), 8.08-8.13 (m, 2H), 7.06 (d, J=9.0 Hz, 1H), 6.18 (s, 1H), 5.26-5.33 (m, 1H), 4.22-4.29 (m, 1H), 3.69-3.78 (m, 3H), 3.54-3.63 (m, 4H), 3.16-3.23 (m, 2H), 2.27-2.32 (m, 1H), 1.74-1.85 (m, 1H), 1.07 (t, J=7.0 Hz, 3H).

Examples 369 and 370 cis-8-(3-Ethoxy-4-(3-(trifluoromethyl)phenoxy)piperidin-1-yl)-5-methyl-6-oxo-5,6-dihydro-1,5-naphthyridine-2-carbonitrile

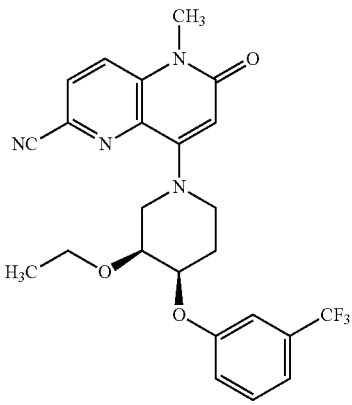

(369-370)

To a stirred solution of (±)-trans-8-(3-ethoxy-4-hydroxypiperidin-1-yl)-5-methyl-6-oxo-5,6-dihydro-1,5-naphthyridine-2-carbonitrile (70 mg, 0.21 mmol) in THF (3 mL), triphenylphosphine (123 mg, 0.47 mmol), DIAD (0.08 mL, 0.43 mmol) and 3-(trifluoromethyl)phenol (69 mg, 0.43 mmol) were added sequentially at room temperature. The reaction mixture was heated at 60° C. for 2 h, then cooled to room temperature and the solvent was removed under reduced pressure to yield the crude product, which was purified by preparative SFC (Column: Luxcellulose-4(250× 30) mm, 5 u; % CO₂: 65%; % Co solvent: 35% of MeOH; Total Flow: 130.0 g/min; Back Pressure: 100 bar; Temperature: 40° C.; UV: 226 nm).

Example 369: (12 mg, 12% yield); LCMS: m/z, 473.3 (M+H); retention time: 2.20; LC/MS Method: Column: Waters XBridge C18, 19×150 mm, 5-μm particles; Mobile Phase A: 10-mM ammonium acetate; Mobile Phase B: acetonitrile; Gradient: 20-65% B over 20 minutes, then a 5-minute hold at 100% B; Flow: 15 mL/min. ¹H NMR (400 MHz, DMSO-d₆) δ ppm 8.18 (d, J=8.8 Hz, 1H), 8.06-8.11 (m, 1H), 7.48-7.55 (m, 1H), 7.33-7.40 (m, 2H), 7.29 (d, J=7.6 Hz, 1H), 6.16 (s, 1H), 4.59-4.65 (m, 1H), 4.24-4.30 (m, 1H), 3.64-3.77 (m, 3H), 3.52-3.60 (m, 4H), 3.12-3.23 (m, 2H), 2.19-2.27 (m, 1H), 1.72-1.82 (m, 1H), 1.04 (t, J=7.0 Hz, 3H).

Example 370: (10 mg, 10% yield); LCMS 473.2 (M+H); retention time: 2.23 min; LC/MS Method: Waters XBridge C18, 19×150 mm, 5-μm particles; Mobile Phase A: 10-mM ammonium acetate; Mobile Phase B: acetonitrile; Gradient: 20-65% B over 20 minutes, then a 5-minute hold at 100% B; Flow: 15 mL/min. ¹H NMR (400 MHz, DMSO-d₆) δ ppm 8.44 (d, J=8.8 Hz, 1H), 8.33-8.38 (m, 1H), 7.75-7.82 (m, 1H), 7.54-7.68 (m, 3H), 6.42 (s, 1H), 4.84-4.93 (m, 1H), 4.50-4.58 (m, 1H), 3.91-4.02 (m, 3H), 3.79-3.86 (m, 4H), 3.41-3.50 (m, 2H), 2.46-2.55 (m, 1H), 1.98-2.09 (m, 1H), 1.30 (t, J=7.1 Hz, 3H).

Intermediate 163

(±)-cis-tert-Butyl-3-ethoxy-4-hydroxypiperidine-1-carboxylate

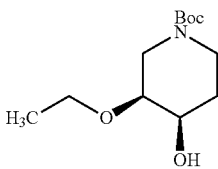

(I-163)

A solution of L-selectride (38.8 mL, 38.8 mmol, 1M in THF) was added dropwise to a solution of (±)-tert-butyl 3-ethoxy-4-oxopiperidine-1-carboxylate (6.3 g, 25.9 mmol) in THF (60 mL) at −78° C. The reaction mixture was allowed to warm to room temperature and stirred for overnight. The reaction mixture was cooled to 0° C. The reaction was quenched with dropwise solution of saturated aqueous NH₄Cl. The reaction mixture was extracted with EtOAc (3×100 mL). The combined organic extracts were washed with brine, dried over Na₂SO₄ and concentrated to afford crude product, which was purified via flash chromatography using a 120 g silica gel column and eluted with 10-15% EtOAc in petroleum ether to afford (±)-cis-tert-butyl-3-ethoxy-4-hydroxypiperidine-1-carboxylate (5.3 g, 83% yield). ¹H NMR (400 MHz, CHLOROFORM-d) δ ppm 3.86 (br s, 1H), 3.63-3.74 (m, 1H), 3.20-3.61 (m, 6H), 2.37 (br s, 1H), 1.75-1.85 (m, 1H), 1.57-1.70 (m, 1H), 1.45 (s, 9H), 1.20 (br t, J=6.9 Hz, 3H).

Intermediate 164

(±)-cis-tert-butyl-3-ethoxy-4-((5-isopropoxypyridin-2-yl)oxy)piperidine-1-carboxylate

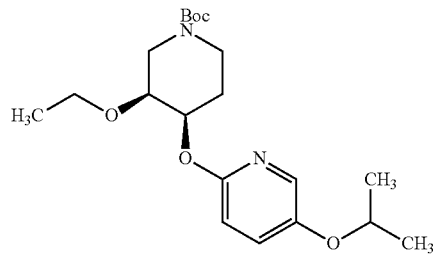

(I-164)

To a stirred solution of (±)-cis-tert-butyl-3-ethoxy-4-hydroxypiperidine-1-carboxylate (100 mg, 0.41 mmol) in DMSO (2 mL) were added potassium tert-butoxide (60 mg, 0.82 mmol) and 2-fluoro-5-isopropoxypyridine (95 mg, 0.61 mmol) at room temperature and stirred for 2 h. The reaction was quenched with ice cold water. The reaction mixture was extracted with EtOAc (2×10 mL). The combined organic extracts were washed with brine, dried over Na₂SO₄ and concentrated to afford crude product, which was purified via flash chromatography (60-80% EtOAc in petroleum ether) to afford (±)-cis-tert-butyl-3-ethoxy-4-((5-isopropoxypyridin-2-yl)oxy)piperidine-1-carboxylate (120 mg, 80% yield). LCMS: m/z, 381.3 (M+1); retention time: 2.07 min. (LCMS Method: Column: Waters Acquity UPLC BEH C18 (2.1×50

Intermediate 165

(±)-cis-2-((3-Ethoxypiperidin-4-yl)oxy)-5-isopropoxypyridine, TFA

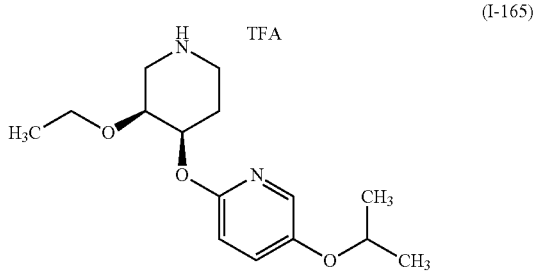 [SMILES: CCO[C@H]1CNCC[C@H]1Oc1ccc(OC(C)C)cn1]

(I-165)

To a stirred solution of (±)-cis-tert-butyl 3-ethoxy-4-((5-isopropoxypyridin-2-yl)oxy) piperidine-1-carboxylate (0.1 g, 0.26 mmol) in DCM (15 mL) was cooled to 0° C. and added TFA (0.1 mL, 1.31 mmol). The reaction mixture was stirred at room temperature for 2 h, and concentrated under reduced pressure to afford (±)-cis-2-((3-ethoxypiperidin-4-yl)oxy)-5-isopropoxypyridine (90 mg, 90% yield). LCMS: m/z, 281.3 (M+1); retention time: 1.01 min. (LCMS Method: Column: Waters Acquity UPLC BEH C18 (2.1×50 mm) 1.7 μm, Mobile phase A: 10 mM ammonium acetate: acetonitrile (95:5); Mobile phase B: 10 mM ammonium acetate:acetonitrile (5:95), Gradient=20-100% B over 2 minute, then a 0.3 minute hold at 100% B; Temperature: 50° C.; Flow rate: 0.7 mL/min; Detection: UV at 220 nm).

Examples 371 and 372 cis-8-(3-Ethoxy-4-((5-isopropoxypyridin-2-yl)oxy) piperidin-1-yl)-5-methyl-6-oxo-5,6-dihydro-1,5-naphthyridine-2-carbonitrile

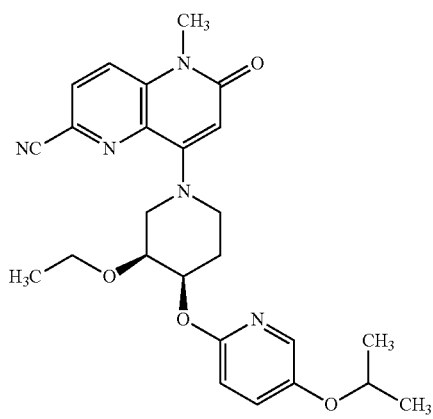

(371-372)

To a stirred solution of (±)-cis-2-((3-ethoxypiperidin-4-yl)oxy)-5-isopropoxypyridine.TFA (70 mg, 0.25 mmol) in acetonitrile (3 mL) were added DIPEA (0.13 mL, 0.75 mmol) and 6-cyano-1-methyl-2-oxo-1,2-dihydro-1,5-naphthyridin-4-yl trifluoromethanesulfonate (83 mg, 0.25 mmol) at room temperature. The reaction mixture was heated at 80° C. for 12 h. The reaction mixture was cooled to room temperature and the solvent was removed under reduced pressure to yield the crude product, which was purified by prep-SFC[Column: Luxcellulose-4 (250×30) mm, 5 μm; % $CO_2$: 60%; % Cosolvent: 40% of MeOH; Total Flow: 140.0 g/min; Back Pressure: 100 bar; Temperature: 40° C.; UV: 226 nm].

Example 371: (8.7 mg, 7% yield); LCMS: m/z, 464.2 (M+H); retention time: 1.81; LC/MS Method: Column: Waters XBridge C18, 19×150 mm, 5-μm particles; Mobile Phase A: 10-mM ammonium acetate; Mobile Phase B: acetonitrile; Gradient: 20-65% B over 20 minutes, then a 5-minute hold at 100% B; Flow: 15 mL/min. $^1$H NMR (400 MHz, DMSO-$d_6$) δ ppm 8.14-8.22 (m, 1H), 8.06-8.12 (m, 1H), 7.79-7.85 (m, 1H), 7.35-7.42 (m, 1H), 6.78 (d, J=8.8 Hz, 1H), 6.15 (s, 1H), 5.29-5.37 (m, 1H), 4.52 (dt, J=12.0, 6.1 Hz, 1H), 3.98-4.07 (m, 1H), 3.82-3.87 (m, 1H), 3.52-3.66 (m, 5H), 3.34-3.50 (m, 3H), 2.08-2.17 (m, 1H), 1.85-1.95 (m, 1H), 1.24 (d, J=6.1 Hz, 6H), 0.95 (t, J=6.8 Hz, 3H).

Example 372: (12 mg, 11% yield); LCMS: m/z, 464.2 (M+H); retention time: 1.81; LC/MS Method: Column: Waters XBridge C18, 19×150 mm, 5-μm particles; Mobile Phase A: 10-mM ammonium acetate; Mobile Phase B: acetonitrile; Gradient: 20-65% B over 20 minutes, then a 5-minute hold at 100% B; Flow: 15 mL/min. $^1$H NMR (400 MHz, DMSO-$d_6$) δ ppm 8.15-8.21 (m, 1H), 8.05-8.12 (m, 1H), 7.78-7.84 (m, 1H), 7.34-7.43 (m, 1H), 6.78 (d, J=9.0 Hz, 1H), 6.15 (s, 1H), 5.29-5.39 (m, 1H), 4.48-4.56 (m, 1H), 3.98-4.08 (m, 1H), 3.81-3.89 (m, 1H), 3.52-3.68 (m, 5H), 3.35-3.49 (m, 3H), 2.06-2.19 (m, 1H), 1.85-1.96 (m, 1H), 1.24 (d, J=6.1 Hz, 6H), 0.95 (t, J=7.0 Hz, 3H).

Intermediate 166

(±)-trans-tert-Butyl-3-ethoxy-4-((4-nitrobenzoyl)oxy)piperidine-1-carboxylate

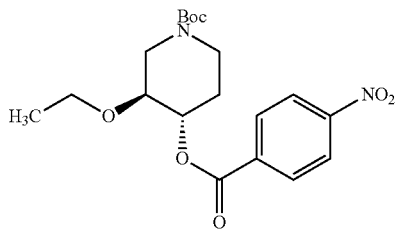

(I-166)

To a stirred solution of (±)-cis-tert-butyl-3-ethoxy-4-hydroxypiperidine-1-carboxylate (2.0 g, 8.15 mmol) in THF (20 mL), 4-nitrobenzoic acid (2.04 g, 12.2 mmol) and triphenylphosphine (3.21 g, 12.23 mmol) were added sequentially at room temperature. The reaction mixture was cooled to 0° C. and DIAD (3.2 mL, 16.31 mmol) was added dropwise. The reaction mixture was allowed to warm to room temperature and stirred for overnight. Solvent was removed under reduced pressure to give crude product, which was purified via flash chromatography using a 40 g silica gel column and eluted with 10-15% EtOAc in petroleum ether to afford (±)-trans-tert-butyl-3-ethoxy-4-((4-nitrobenzoyl)oxy)piperidine-1-carboxylate (2.3 g, 71% yield). LCMS: m/z, 417.2 (M+23); retention time: 3.39 min. (LCMS Method: Column: Kinetex XB-C18 (3×75 mm) 2.6 µm; Mobile phase A: 10 mM ammonium formate: acetonitrile (98:2), Mobile phase B: 10 mM ammonium formate: acetonitrile (2:98), Gradient=20-100% B over 4 minutes, then a 0.6 minute hold at 100% B; Temperature: 27° C.; Flow rate: 1.0 mL/min; Detection: UV at 220 nm).

Intermediate 167

(±)-trans-tert-Butyl 3-ethoxy-4-oxopiperidine-1-carboxylate

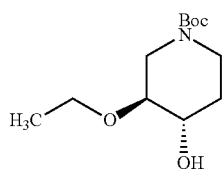

(I-167)

To a stirred solution of (±)-trans-tert-butyl-3-ethoxy-4-((4-nitrobenzoyl)oxy) piperidine-1-carboxylate (2.3 g, 5.83 mmol) in THF (20 mL)/Water (5 mL), NaOH (1.17 g, 29.2 mmol) was added at 0° C. The reaction mixture was allowed to warm to room temperature and stirred for overnight. The reaction mixture was extracted with EtOAc (3×70 mL), washed with water, brine, dried over sodium sulphate and concentrated under reduced pressure to give crude product, which was purified via flash chromatography using a 40 g silica gel column and eluted with 20-30% EtOAc in petroleum ether to afford (±)-trans-tert butyl-3-ethoxy-4-hydroxypiperidine-1-carboxylate (1.1 g, 77% yield). $^1$H NMR (400 MHz, CHLOROFORM-d) δ ppm 4.16-4.49 (m, 1H), 3.95-4.13 (m, 1H), 3.67-3.83 (m, 1H), 3.50-3.58 (m, 2H), 3.01-3.14 (m, 1H), 2.72-2.86 (m, 1H), 2.39-2.62 (m, 2H), 1.90-2.01 (m, 1H), 1.49-1.53 (m, 1H), 1.47 (s, 9H), 1.23 (t, J=7.0 Hz, 3H).

Intermediate 168

(±)-trans-tert-Butyl 4-(benzo[d]thiazol-2-yloxy)-3-ethoxypiperidine-1-carboxylate

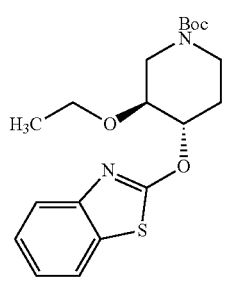

(I-168)

To a stirred solution of (±)-trans-tert butyl-3-ethoxy-4-hydroxypiperidine-1-carboxylate (100 mg, 0.41 mmol) in THF or DMF (5 mL) was added NaH (60% in mineral oil, 33 mg, 0.82 mmol, 60% w/w) at 0° C. After 5 minutes, a solution of 2-bromobenzo[d]thiazole (131 mg, 0.611 mmol) in THF (2 mL). The reaction mixture was allowed to warm to room temperature and stirred for 3 h. The reaction was quenched with ice cold water. The mixture was extracted with EtOAc (2×50 mL). The combined organic extracts were washed with brine, dried over $Na_2SO_4$ and concentrated to afford crude product, which was purified via flash chromatography using a 12 g silica gel column and eluted with 30%-40% EtOAc in petroleum ether to afford (±)-trans-tert-butyl-4-(benzo[d]thiazol-2-yloxy)-3-ethoxypiperidine-1-carboxylate (120 mg, 78% yield). LCMS: m/z, 379.2 (M+1); retention time: 3.16 min. (LCMS Method: Column: Kinetex XB-C18 (3×75 mm) 2.6 µm; Mobile phase A: 10 mM ammonium formate: acetonitrile (98:2), Mobile phase B: 10 mM ammonium formate: acetonitrile (2:98), Gradient=20-100% B over 4 minutes, then a 0.6 minute hold at 100% B; Temperature: 27° C.; Flow rate: 1.0 mL/min; Detection: UV at 220 nm).

Intermediate 169

(±)-trans-2-((3-Ethoxypiperidin-4-yl)oxy)benzo[d]thiazole, HCl

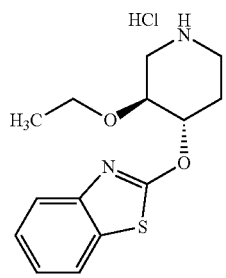

(I-169)

A 4 M HCl in dioxane (0.4 mL, 1.6 mmol) was added to a solution of (±)-trans-tert-butyl-4-(benzo[d]thiazol-2-yloxy)-3-ethoxypiperidine-1-carboxylate (0.12 g, 0.32 mmol) in DCM (5 mL) at 0° C. The reaction mixture was stirred at room temperature for 2 h, after which it was concentrated under reduced pressure to afford (±)-trans-2-((3-ethoxypiperidin-4-yl)oxy)benzo[d]thiazole, HCl (100 mg, quantitative). LCMS: m/z, 279.2 (M+1); retention time: 1.28 min. (LCMS Method: Column: Kinetex XB-C18 (3×75 mm) 2.6 µm; Mobile phase A: 10 mM ammonium formate: acetonitrile (98:2), Mobile phase B: 10 mM ammonium formate: acetonitrile (2:98), Gradient=20-100% B over 4 minutes, then a 0.6 minute hold at 100% B; Temperature: 27° C.; Flow rate: 1.0 mL/min; Detection: UV at 220 nm).

Examples 373 and 374 trans-8-4-(Benzo[d]thiazol-2-yloxy)-3-ethoxypiperidin-1-yl)-5-methyl-6-oxo-5,6-dihydro-1,5-naphthyridine-2-carbonitrile

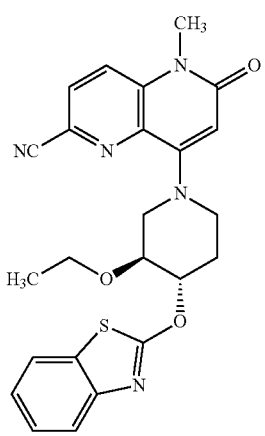

(373-374)

To a stirred solution of (±)-trans-2-(3-ethoxypiperidin-4-yl)oxy)benzo[d]thiazole.HCl salt (100 mg, 0.36 mmol) in acetonitrile (3 mL) were added DIPEA (0.2 mL, 1.1 mmol) and 6-cyano-1-methyl-2-oxo-1,2-dihydro-1,5-naphthyridin-4-yl trifluoromethanesulfonate (180 mg, 0.54 mmol) at room temperature. The reaction mixture was heated at 80° C. for 12 h. The reaction mixture was cooled to room temperature and the solvent was removed under reduced pressure to yield the crude product, which was purified by prep-SFC [Column/dimensions: Chiralpak IC (250×21) mm, 5 μm; % CO$_2$: 70%; % Co solvent: 30% ACN:IPA (50:50); Total Flow: 90.0 g/min; Back Pressure: 100 bar; Temperature: 35° C.; UV: 220 nm]

Example 373: (2.3 mg, 1% yield); LCMS: m/z, 462.2 (M+H); retention time: 1.92; LC/MS Method: Column: Waters XBridge C18, 19×150 mm, 5-μm particles; Mobile Phase A: 10-mM ammonium acetate; Mobile Phase B: acetonitrile; Gradient: 20-65% B over 20 minutes, then a 5-minute hold at 100% B; Flow: 15 mL/min. $^1$H NMR (400 MHz, DMSO-d$_6$) δ 8.17-8.22 (m, 1H), 8.11 (d, J=9.0 Hz, 1H), 7.88-7.92 (m, 1H), 7.70 (d, J=8.0 Hz, 1H), 7.38-7.45 (m, 1H), 7.26-7.32 (m, 1H), 6.20 (s, 1H), 5.24-5.32 (m, 1H), 4.29-4.36 (m, 1H), 3.73-3.86 (m, 3H), 3.59-3.67 (m, 1H), 3.56 (s, 3H), 3.21-3.30 (m, 1H), 3.13-3.20 (m, 1H), 2.40-2.47 (m, 1H), 1.86-1.99 (m, 1H), 1.10 (t, J=7.0 Hz, 3H)

Example 374: (3 mg, 2% yield); LCMS 462.0 (M+H); retention time: 1.98 min; LC/MS Method: Column: Waters XBridge C18, 19×150 mm, 5-μm particles; Mobile Phase A: 10-mM ammonium acetate; Mobile Phase B: acetonitrile; Gradient: 20-65% B over 20 minutes, then a 5-minute hold at 100% B; Flow: 15 mL/min. $^1$H NMR (400 MHz, DMSO-d$_6$): 8.17-8.22 (m, 1H), 8.11 (d, J=9.0 Hz, 1H), 7.88-7.92 (m, 1H), 7.70 (d, J=8.0 Hz, 1H), 7.38-7.45 (m, 1H), 7.26-7.32 (m, 1H), 6.20 (s, 1H), 5.24-5.32 (m, 1H), 4.29-4.36 (m, 1H), 3.73-3.86 (m, 3H), 3.59-3.67 (m, 1H), 3.56 (s, 3H), 3.21-3.30 (m, 1H), 3.13-3.20 (m, 1H), 2.40-2.47 (m, 1H), 1.86-1.99 (m, 1H), 1.10 (t, J=7.0 Hz, 3H).

The Examples in Table 29 were prepared from appropriate starting material according to the general procedures disclosed in Example 373 and 374.

TABLE 29

| Ex. No. | Structure | Stereo-chemistry | LCMS Method | LCMS RT | M + H |
|---|---|---|---|---|---|
| 375 | | Homochiral | A | 1.77 | 465.2 |
| 376 | | Homochiral | A | 1.77 | 465.1 |

TABLE 29-continued

| Ex. No. | Structure | Stereo-chemistry | LCMS Method | LCMS RT | M + H |
|---|---|---|---|---|---|
| 377 | | Homochiral | A | 1.98 | 465.2 |
| 378 | | Homochiral | A | 1.98 | 465.1 |
| 379 | | Homochiral | A | 1.65 | 465.2 |
| 380 | | Homochiral | A | 1.65 | 465.2 |
| 381 | | Homochiral | A | 2.07 | 487.1 |
| 382 | | Homochiral | A | 2.07 | 487.2 |
| 383 | | Homochiral | A | 1.71 | 478.2 |
| 384 | | Homochiral | A | 1.72 | 478.2 |

The Examples in Table 30 were prepared from appropriate alkyl halide according to the general procedures disclosed in Examples 259 and 260.
TABLE 30
| Ex. No. | Structure | Stereo- chemistry | LCMS Method | LCMS RT | M + H |
|---|---|---|---|---|---|
| 385 | | H | A | 1.61 | 516.3 |
| 386 | 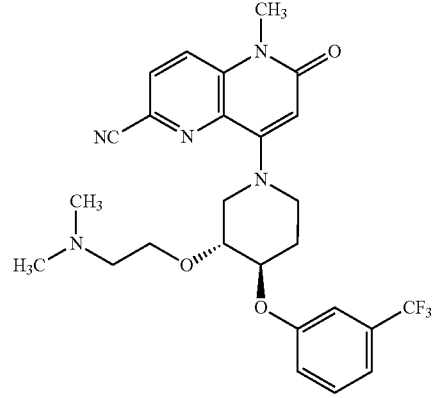 [SMILES: CN(C)CCO[C@@H]1CN(c2cc(=O)n(C)c3ccc(C#N)nc23)CC[C@H]1Oc1cccc(C(F)(F)F)c1] | H | A | 1.61 | 516.3 |
| 387 | | H | A | 2.26 | 499.3 |
| 388 | 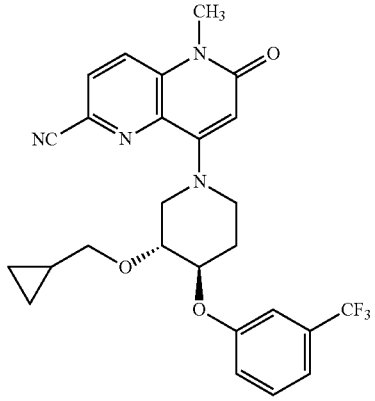 [SMILES: Cn1c(=O)cc(N2CC[C@@H](Oc3cccc(C(F)(F)F)c3)[C@H](OCC3CC3)C2)c2nc(C#N)ccc21] | H | A | 2.26 | 499.3 |
| 389 | | H | A | 2.02 | 503.3 |
| 390 | 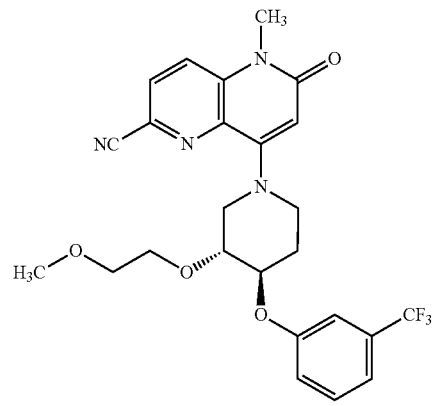 [SMILES: COCCO[C@@H]1CN(c2cc(=O)n(C)c3ccc(C#N)nc23)CC[C@H]1Oc1cccc(C(F)(F)F)c1] | H | A | 2.02 | 503.2 |

TABLE 30-continued

| Ex. No. | Structure | Stereo-chemistry | LCMS Method | LCMS RT | M + H |
|---|---|---|---|---|---|
| 391 |  | H | A | 1.90 | 558.2 |
| 392 |  | H | A | 1.90 | 558.2 |
| 393 |  | H | A | 2.27 | 527.2 |
| 394 |  | H | A | 2.27 | 527.2 |

Intermediate 170

(±)-trans-tert-butyl (3-acetoxy-4-(3-(trifluoromethyl)phenoxy)piperidine-1-carboxylate

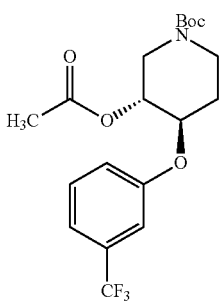
(I-170)

To a stirred solution of (±)-trans-tert-butyl 3-hydroxy-4-(3(trifluoromethyl) phenoxy)piperidine-1-carboxylate (650 mg, 1.80 mmol) in pyridine (7 mL) was added Ac$_2$O (0.8 mL, 9.0 mmol) at 0° C. The reaction mixture was allowed to reach room temperature and stirred for 16 h. The solvent was evaporated under reduced pressure to afford crude product. The mixture was extracted with EtOAc (2×50 mL). The combined organic extracts were washed with brine, dried over Na$_2$SO$_4$ and concentrated to afford (±)-trans-tert-butyl (3-acetoxy-4-(3-(trifluoromethyl)phenoxy)piperidine-1-carboxylate (600 mg, 83% yield). LCMS: m/z, 421.2 (M+18); retention time: 1.20 min. (LCMS Method: Column: Waters Acquity UPLC BEH C18 (2.1×50 mm) 1.7 μm, Mobile phase A: 10 mM ammonium acetate:acetonitrile (95:5); Mobile phase B: 10 mM Ammonium acetate:acetonitrile (5:95), Gradient=20-100% B over 2 minute, then a 0.3 minute hold at 100% B; Temperature: 50° C.; Flow rate: 0.7 mL/min; Detection: UV at 220 nm).

Intermediate 171

(±)-trans-tert-butyl 3-(prop-1-en-2-yloxy)-4-(3-(trifluoromethyl)phenoxy)piperidine-1-carboxylate

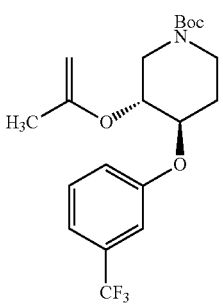
(I-171)

315

To a stirred solution of (±)-trans-tert-butyl-3-acetoxy-4-(3-(trifluoromethyl) phenoxy)piperidine-1-carboxylate (600 mg, 1.49 mmol) in THF (12 mL) was added pyridine (0.7 mL, 8.92 mmol) followed by Tebbe's reagent (8.92 mL, 4.46 mmol, 0.5 M solution in toluene) at −40° C. The reaction mixture was allowed to reach room temperature and stirred for overnight. The reaction mixture was cooled to 0° C. The reaction was quenched with aqueous 1 M NaOH. The reaction mixture was extracted with EtOAc (2×100 mL). The combined organic extracts were washed with brine, dried over $Na_2SO_4$ and concentrated to give crude product, which was purified via flash chromatography using a 12 g silica gel column and eluted with 25%-30% EtOAc in petroleum ether to afford (±)-trans tert-butyl 3-(prop-1-en-2-yloxy)-4-(3-(trifluoromethyl)phenoxy)piperidine-1-carboxylate (300 mg, 50% yield). $^1H$ NMR (300 MHz, CHLOROFORM-d) δ ppm 7.36-7.44 (m, 1H), 7.20-7.26 (m, 2H), 7.10-7.16 (m, 1H), 4.43-4.59 (m, 1H), 4.05-4.12 (m, 1H), 3.98 (s, 2H), 3.76-3.92 (m, 1H), 3.39-3.69 (m, 3H), 2.07-2.20 (m, 1H), 1.78-1.93 (m, 1H), 1.75 (s, 3H), 1.48 (s, 9H).

Intermediate 172

(+/−)-trans-tert-butyl trans-4-hydroxy-3-methylpiperidine-1-carboxylate

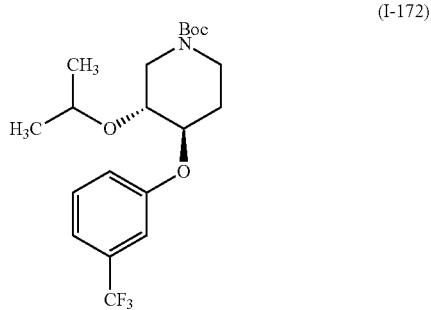 [SMILES: CC(C)O[C@@H]1CN(C(=O)OC(C)(C)C)CC[C@H]1Oc1cccc(C(F)(F)F)c1]

(I-172)

A solution of (±)-trans tert-butyl 3-(prop-1-en-2-yloxy)-4-(3-(trifluoromethyl) phenoxy)piperidine-1-carboxylate (350 mg, 0.87 mmol) in methanol (10 mL) was degassed and flushed with nitrogen (2×). Next, 10% Pd—C (37.1 mg, 0.35 mmol) was added and the mixture again evacuated and flushed with nitrogen (2×) before being evacuated and filled with hydrogen at 1 atmosphere (balloon). The reaction mixture was stirred vigorously under the hydrogen atmosphere overnight. The reaction mixture was filtered through celite, and the filtrate was washed with methanol and the washings combined with the original filtrate. The combined solutions were concentrated under vacuum to afford (±)-trans-tert-butyl 3-isopropoxy-4-(3-(trifluoromethyl)phenoxy)piperidine-1-carboxylate (350 mg, 68% yield). LCMS: m/z, 304.2 (M-100+H); retention time: 1.52 min. (LCMS Method: Column: Waters Acquity UPLC BEH C18 (2.1×50 mm) 1.7 μm, Mobile phase A: 10 mM ammonium acetate: acetonitrile (95:5); Mobile phase B: 10 mM ammonium acetate:acetonitrile (5:95), Gradient=20-100% B over 2 minute, then a 0.3 minute hold at 100% B; Temperature: 50° C.; Flow rate: 0.7 mL/min; Detection: UV at 220 nm).

316

Intermediate 173

(±)-trans-3-Isopropoxy-4-(3-(trifluoromethyl)phenoxy)piperidine

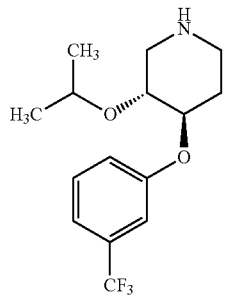

(I-173)

To a stirred solution of (±)-trans-tert-butyl-3-isopropoxy-4-(3-(trifluoromethyl) phenoxy)piperidine-1-carboxylate (300 mg, 0.74 mmol) in DCM (5 mL) was added HCl (4 M in dioxane) (1.9 mL, 7.44 mmol) at 0° C. The reaction mixture was stirred at room temperature for 3 h. The solvent was evaporated under reduced pressure to give crude product, which was diluted with DCM (50 mL) and neutralized with aqueous $NaHCO_3$ solution. The aqueous layer was separated and re-extracted with DCM (2×50 mL). The combined organic extracts were washed with water, brine, dried over sodium sulphate and concentrated under reduced pressure to afford (±)-trans-3-isopropoxy-4-(3-(trifluoromethyl) phenoxy)piperidine (200 mg, 89% yield). LCMS: m/z, 304.2 (M+1); retention time: 1.63 min. (LCMS Method: Column: Waters Acquity UPLC BEH C18 (2.1×50 mm) 1.7 μm, Mobile phase A: 10 mM ammonium acetate: acetonitrile (95:5); Mobile phase B: 10 mM Ammonium acetate:acetonitrile (5:95), Gradient=20-100% B over 2 minute, then a 0.3 minute hold at 100% B; Temperature: 50° C.; Flow rate: 0.7 mL/min; Detection: UV at 220 nm).

Examples 395 and 396 trans-8-(3-Isopropoxy-4-(3-(trifluoromethyl)phenoxy)piperidin-1-yl)-5-methyl-6-oxo-5,6-dihydro-1,5-naphthyridine-2-carbonitrile

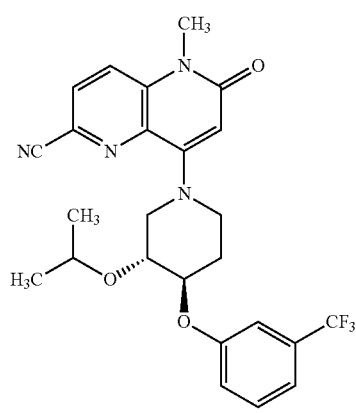

(395-396)

To a stirred solution of (±)-trans-3-isopropoxy-4-(3-(trifluoromethyl)phenoxy) piperidine (150 mg, 0.5 mmol) in acetonitrile (5 mL) was added DIPEA (0.4 mL, 2.47 mmol). The reaction mixture was stirred for 5 min at room temperature. Next, 6-cyano-1-methyl-2-oxo-1,2-dihydro-1,5-naphthyridin-4-yl trifluoromethanesulfonate (330 mg, 0.989 mmol) was added and the reaction mixture was heated at 85° C. for 4 h. The reaction mixture was cooled to room temperature and the solvent was removed under reduced pressure to yield the crude product, which was purified by preparative SFC (Column: Luxcellulose-4(250×21.5) mm, 5 μm; % $CO_2$: 65%; % Co solvent: 35% of MeOH; Total Flow: 85.0 g/min; Back Pressure: 100 bar; Temperature: 35° C.; UV: 273 nm).

Example 396: LCMS: m/z, 487.2 (M+H); retention time: 2.46 min; LC/MS Method: Column: Waters XBridge C18, 19×150 mm, 5-μm particles; Mobile Phase A: 10-mM ammonium acetate; Mobile Phase B: acetonitrile; Gradient: 20-65% B over 20 minutes, then a 5-minute hold at 100% B; Flow: 15 mL/min. $^1$H NMR (400 MHz, DMSO-$d_6$) δ ppm 8.15-8.22 (m, 1H), 8.10 (d, J=9.0 Hz, 1H), 7.49-7.55 (m, 1H), 7.33-7.41 (m, 2H), 7.26-7.31 (m, 1H), 6.14 (s, 1H), 4.53-4.62 (m, 1H), 4.32-4.40 (m, 1H), 3.80-3.88 (m, 1H), 3.66-3.78 (m, 2H), 3.55 (s, 3H), 3.11-3.21 (m, 1H), 2.98 (dd, J=12.3, 9.3 Hz, 1H), 2.19-2.29 (m, 1H), 1.71-1.85 (m, 1H), 1.09 (d, J=6.0 Hz, 3H), 0.96 (d, J=6.0 Hz, 3H).

Example 397: LCMS: m/z, 487.2 (M+H); retention time: 2.46 min; LC/MS Method: Column: Waters XBridge C18, 19×150 mm, 5-μm particles; Mobile Phase A: 10-mM ammonium acetate; Mobile Phase B: acetonitrile; Gradient: 20-65% B over 20 minutes, then a 5-minute hold at 100% B; Flow: 15 mL/min. $^1$H NMR (400 MHz, DMSO-$d_6$) δ ppm 8.16-8.20 (m, 1H), 8.08-8.11 (m, 1H), 7.49-7.55 (m, 1H), 7.33-7.39 (m, 2H), 7.28 (d, J=7.6 Hz, 1H), 6.15 (s, 1H), 4.53-4.61 (m, 1H), 4.31-4.39 (m, 1H), 3.83 (dt, J=12.2, 6.1 Hz, 1H), 3.65-3.76 (m, 2H), 3.54 (s, 3H), 3.11-3.20 (m, 1H), 2.98 (dd, J=12.3, 9.7 Hz, 1H), 2.20-2.27 (m, 1H), 1.72-1.83 (m, 1H), 1.09 (d, J=6.1 Hz, 3H), 0.95 (d, J=6.1 Hz, 3H).

Intermediate 174

(±)-trans-tert-Butyl-4-((5-isopropoxypyridin-2-yl)oxy)-3-ethoxypiperidine-1-carboxylate

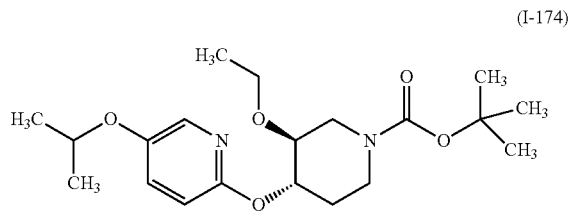 [SMILES: CCO[C@H]1CN(C(=O)OC(C)(C)C)CC[C@@H]1Oc1ccc(OC(C)C)cn1]

(I-174)

To a stirred solution of (±)-trans-tert-butyl-3-hydroxy-4-((5-isopropoxypyridin-2-yl) oxy)piperidine-1-carboxylate (200 mg, 0.56 mmol) in THF (5 mL) was added NaH (60% in mineral oil) (68.1 mg, 1.70 mmol) at 0° C. After 5 minutes, a solution of iodoethane (0.1 mL, 1.13 mmol) in THF (1 mL) was added and the reaction mixture was stirred for 3 h at room temperature. The reaction mixture was cooled to 0° C. The reaction was quenched with ice cold water. The reaction mixture was extracted with EtOAc (2×50 mL). The combined organic extracts were washed with brine, dried over $Na_2SO_4$ and concentrated to give (±)-trans-tert-butyl-4-((5-isopropoxypyridin-2-yl)oxy)-3-ethoxypiperidine-1-carboxylate. LCMS: m/z, 381.3 (M+1); retention time: 1.23 min. (LCMS Method: Column: Waters Acquity UPLC BEH C18 (2.1×50 mm) 1.7 μm, Mobile phase A: 10 mM ammonium acetate:acetonitrile (95:5); Mobile phase B: 10 mM ammonium acetate:acetonitrile (5:95), Gradient=20-100% B over 2 minute, then a 0.3 minute hold at 100% B; Temperature: 50° C.; Flow rate: 0.7 mL/min; Detection: UV at 220 nm).

Intermediate 175

(±)-trans-5-Isopropoxy-2-((3-ethoxypiperidin-4-yl)oxy)pyridine.HCl

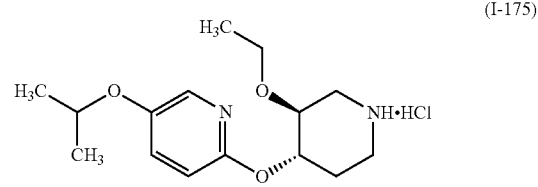

(I-175)

To a stirred solution of (±)-trans-tert-butyl-4-((5-isopropoxypyridin-2-yl)oxy)-3-methoxypiperidine-1-carboxylate (200 mg, 0.53 mmol) in DCM (5 mL) was added HCl (4 M in dioxane) (0.7 mL, 2.63 mmol) at 0° C. The reaction mixture was stirred at room temperature for 3 h. The solvent was evaporated under reduced pressure to afford (±)-trans-5-isopropoxy-2-((3-ethoxypiperidin-4-yl)oxy)pyridine, HCl. LCMS: m/z, 281.2 (M+1); retention time: 1.28 min. (LCMS Method: Column: Waters Acquity UPLC BEH C18 (2.1×50 mm) 1.7 μm, Mobile phase A: 10 mM ammonium acetate:acetonitrile (95:5); Mobile phase B: 10 mM ammonium acetate:acetonitrile (5:95), Gradient=20-100% B over 2 minute, then a 0.3 minute hold at 100% B; Temperature: 50° C.; Flow rate: 0.7 mL/min; Detection: UV at 220 nm).

Examples 397 and 398 trans-8-(4-((5-Isopropoxypyridin-2-yl)oxy)-3-ethoxypiperidin-1-yl)-5-methyl-6-oxo-5,6-dihydro-1,5-naphthyridine-2-carbonitrile

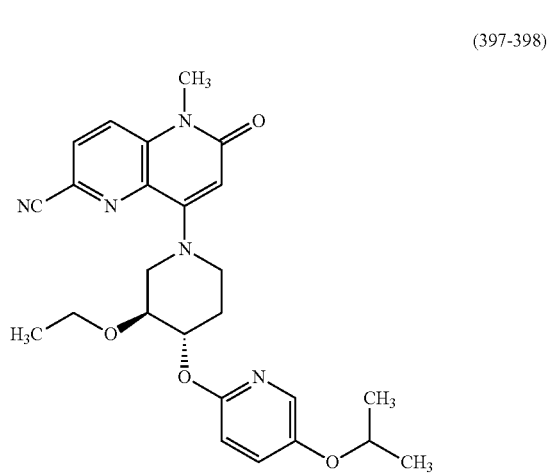 [SMILES: CCO[C@H]1CN(c2cc(=O)n(C)c3ccc(C#N)nc23)CC[C@@H]1Oc1ccc(OC(C)C)cn1]

(397-398)

To a stirred solution of (±)-trans-5-isopropoxy-2-((3-ethoxypiperidin-4-yl)oxy) pyridine, HCl (190 mg, 0.60 mmol) in acetonitrile (5 mL) was added DIPEA (0.5 mL, 2.63 mmol). The reaction mixture was stirred for 5 min at room temperature and then 6-cyano-1-methyl-2-oxo-1,2-dihydro-1,5-naphthyridin-4-yl trifluoromethanesulfonate (175 mg, 0.52 mmol) was added. The reaction mixture was heated at 85° C. for 4 h. The reaction mixture was cooled to room temperature and the solvent was removed under reduced pressure to yield the crude product, which was purified by preparative SFC (Column: Cellulose-4(250×30) mm, 5% $CO_2$: 50%; % Cosolvent: 50% of MeOH; Total Flow: 70.0 g/min; Back Pressure: 100 bar; Temperature: 30° C.; UV: 300 nm).

Examples 397: LCMS: m/z, 464.3 (M+H); retention time: 1.92; LC/MS Method: Column: Waters XBridge C18, 19×150 mm, 5-μm particles; Mobile Phase A: 10-mM ammonium acetate; Mobile Phase B: acetonitrile; Gradient: 20-65% B over 20 minutes, then a 5-minute hold at 100% B; Flow: 15 mL/min. $^1$H NMR (400 MHz, DMSO-$d_6$) δ=8.22-8.14 (m, 1H), 8.13-8.06 (m, 1H), 7.83 (d, J=3.2 Hz, 1H), 7.39 (dd, J=3.1, 8.9 Hz, 1H), 6.78 (d, J=8.8 Hz, 1H), 6.15 (s, 1H), 5.05 (dt, J=4.4, 7.9 Hz, 1H), 4.52 (td, J=6.1, 12.0 Hz, 1H), 4.20-4.09 (m, 1H), 3.77-3.55 (m, 4H), 3.54 (s, 3H), 3.29-3.15 (m, 2H), 2.31-2.20 (m, 1H), 1.76-1.63 (m, 1H), 1.25 (d, J=5.9 Hz, 6H), 1.06 (t, J=7.0 Hz, 3H).

Examples 398: LCMS 464.3 (M+H); retention time: 1.92 min; LC/MS Method: Column: Waters XBridge C18, 19×150 mm, 5-μm particles; Mobile Phase A: 10-mM ammonium acetate; Mobile Phase B: acetonitrile; Gradient: 20-65% B over 20 minutes, then a 5-minute hold at 100% B; Flow: 15 mL/min. $^1$H NMR (400 MHz, DMSO-$d_6$): δ ppm 8.21-8.12 (m, 1H), 8.11-8.05 (m, 1H), 7.82 (d, J=3.2 Hz, 1H), 7.39 (dd, J=3.2, 8.8 Hz, 1H), 6.78 (d, J=8.8 Hz, 1H), 6.15 (s, 1H), 5.09-4.99 (m, 1H), 4.52 (td, J=6.1, 12.0 Hz, 1H), 4.21-4.10 (m, 1H), 3.78-3.55 (m, 4H), 3.54 (s, 3H), 3.28-3.18 (m, 2H), 2.34-2.18 (m, 1H), 1.76-1.63 (m, 1H), 1.25 (d, J=6.1 Hz, 6H), 1.06 (t, J=7.0 Hz, 3H).

Example 399

(±)-trans-6-Chloro-4-(3-ethoxy-4-((5-isopropoxy-pyridin-2-yl)oxy)piperidin-1-yl)-1-methylpyrido[3,2-d]pyrimidin-2(1H)-one

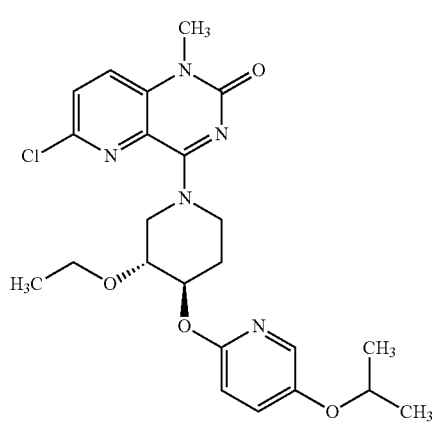

(399)

To a stirred solution of (±)-trans-2-(3-ethoxypiperidin-4-yl)oxy)-5-isopropoxypyridine (150 mg, 0.54 mmol) in acetonitrile (15 mL) was added DIPEA (0.5 mL, 2.68 mmol). The reaction mixture was stirred for 5 min at room temperature. Next, 4,6-dichloro-1-methylpyrido[3,2-d]pyrimidin-2(1H)-one (246 mg, 1.07 mmol) was added and the reaction mixture was heated at 85° C. for 4 h. The reaction mixture was cooled to room temperature and the solvent was removed under reduced pressure to yield the crude product, which was purified by silica gel chromatography (3% MeOH in DCM) to afford (±)-trans-6-chloro-4-(3-ethoxy-4-((5-isopropoxypyridin-2-yl)oxy)piperidin-1-yl)-1-methylpyrido[3,2-d]pyrimidin-2(1H)-one. LCMS: m/z, 474.3 (M+1); retention time: 1.77 min. (LCMS Method: Column: Waters Acquity UPLC BEH C18 (2.1×50 mm) 1.7 μm, Mobile phase A: 10 mM ammonium acetate:acetonitrile (95:5); Mobile phase B: 10 mM Ammonium acetate:acetonitrile (5:95), Gradient=20-100% B over 2 minute, then a 0.3 minute hold at 100% B; Temperature: 50° C.; Flow rate: 0.7 mL/min; Detection: UV at 220 nm).

Examples 400 and 401 trans-4-(3-Ethoxy-4-((5-isopropoxypyridin-2-yl)oxy) piperidin-1-yl)-1-methyl-2-oxo-1,2-dihydropyrido[3,2-d]pyrimidine-6-carbonitrile

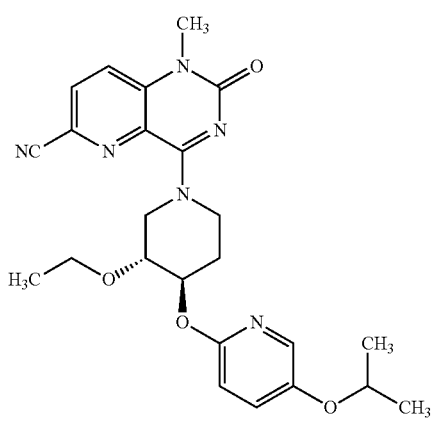

(400-401)

To a stirred solution of (±)-trans-6-chloro-4-(3-ethoxy-4-((5-isopropoxypyridin-2-yl) oxy)piperidin-1-yl)-1-methylpyrido[3,2-d]pyrimidin-2(1H)-one (180 mg, 0.38 mmol) in DMF (5 mL) were added zinc (37 mg, 0.57 mmol), zinc cyanide (134 mg, 1.14 mmol) and TEA (0.2 mL, 1.52 mmol). The reaction mixture was degassed for 5 min and dichloro[9,9-dimethyl-4,5-bis(diphenylphosphino)xanthene]palladium(II) (115 mg, 0.15 mmol) was added. The reaction mixture was heated at 90° C. overnight. The reaction mixture was cooled to room temperature, diluted with ethyl acetate and filtered through Celite pad. The filtrate was washed with water, brine and the organic layer was dried over anhydrous $Na_2SO_4$ filtered and evaporated under reduced pressure to obtain crude product. The crude product was purified by preparative SFC [Method: Column: Chiralpak IG (250×30) mm, 5 u; % $CO_2$: 60%; % Co solvent: 40% of 4 M methanolic ammonia in MeOH; Total flow: 100 g/min; Back Pressure: 100 bar; Temperature: 35° C.; UV: 220 nm].

Example 400: LCMS: m/z, 465.3 (M+H); retention time: 1.97 min; LC/MS Method: Column: Waters XBridge C18, 19×150 mm, 5-μm particles; Mobile Phase A: 10-mM ammonium acetate; Mobile Phase B: acetonitrile; Gradient: 20-65% B over 20 minutes, then a 5-minute hold at 100% B; Flow: 15 mL/min. $^1$H NMR (400 MHz, DMSO-$d_6$) δ=8.26 (d, J=9.0 Hz, 1H), 8.02 (d, J=9.0 Hz, 1H), 7.83 (d, J=3.2 Hz, 1H), 7.40 (dd, J=9.0, 3.2 Hz, 1H), 6.78 (d, J=9.0 Hz, 1H), 5.16-5.07 (m, 1H), 4.94-4.70 (m, 1H), 4.53 (dt, J=12.0, 6.1 Hz, 1H), 4.43-3.81 (m, 3H), 3.68-3.49 (m, 3H), 3.46 (s, 3H), 2.29-2.17 (m, 1H), 1.74-1.62 (m, 1H), 1.25 (d, J=6.1 Hz, 6H), 1.05-0.87 (m, 3H).

Example 401: LCMS: m/z, 465.2 (M+H); retention time: 1.97 min; LC/MS Method: Column: Waters XBridge C18, 19×150 mm, 5-μm particles; Mobile Phase A: 10-mM ammonium acetate; Mobile Phase B: acetonitrile; Gradient: 20-65% B over 20 minutes, then a 5-minute hold at 100% B; Flow: 15 mL/min. $^1$H NMR (400 MHz, DMSO-$d_6$): δ ppm 8.27 (d, J=9.0 Hz, 1H), 8.03 (d, J=8.8 Hz, 1H), 7.84 (d, J=2.9 Hz, 1H), 7.41 (dd, J=8.9, 3.1 Hz, 1H), 6.79 (d, J=9.0 Hz, 1H), 5.17-5.09 (m, 1H), 4.96-4.81 (m, 1H), 4.58-4.09 (m, 3H), 3.91 (br s, 1H), 3.67-3.51 (m, 3H), 3.47 (s, 3H), 2.28-2.20 (m, 1H), 1.76-1.63 (m, 1H), 1.26 (d, J=6.1 Hz, 6H), 0.97 (br s, 3H).

Intermediate 176

(+/−) cis-3-Ethoxypiperidin-4-ol, HCl Salt

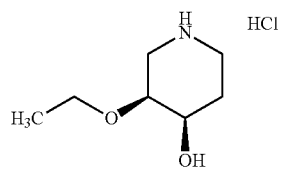

(I-176)

A 4 N solution of HCl in dioxane (2.5 mL, 82 mmol) was added to a solution of tert-butyl-cis-3-ethoxy-4-hydroxypiperidine-1-carboxylate (2 g, 8.15 mmol) in DCM (15 mL). The reaction mixture was stirred at room temperature for 2 h, after which it was concentrated under reduced pressure to afford cis-3-ethoxypiperidin-4-ol HCl salt. $^1$H NMR (300 MHz, DMSO-$d_6$) δ ppm 8.58 (br s, 1H), 8.28 (br s, 1H), 3.77-3.90 (m, 1H), 3.50-3.65 (m, 3H), 2.88-3.18 (m, 4H), 1.61-1.90 (m, 2H), 1.14 (t, J=7.0 Hz, 3H).

Intermediate 177

(±)-cis-6-Chloro-4-(3-ethoxy-4-hydroxypiperidin-1-yl)-1-methylpyrido[3,2-d]pyrimidin-2(1H)-one

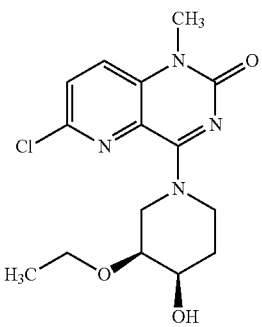

(I-177)

To a stirred solution of (±)-cis-3-ethoxypiperidin-4-ol (0.7 g, 4.82 mmol) in acetonitrile (15 mL) was added DIPEA (2.5 mL, 14.5 mmol). The reaction mixture was stirred for 5 min at room temperature. Next, 4,6-dichloro-1-methylpyrido[3,2-d]pyrimidin-2(1H)-one (1.1 g, 4.82 mmol) was added and the reaction mixture was heated at 85° C. for 4 h. The reaction mixture was cooled to room temperature and the solvent was removed under reduced pressure to yield the crude product, which was purified by silica gel chromatography (3% MeOH in DCM) to afford (±)-cis-6-chloro-4-(3-ethoxy-4-hydroxypiperidin-1-yl)-1-methylpyrido[3,2-d]pyrimidin-2(1H)-one. LCMS: m/z, 339.2 (M+1); retention time: 0.83 min. (LCMS Method: Column: Waters Acquity UPLC BEH C18 (2.1×50 mm) 1.7 μm, Mobile phase A: 10 mM ammonium acetate:acetonitrile (95:5); Mobile phase B: 10 mM ammonium acetate:acetonitrile (5:95), Gradient=20-100% B over 2 minute, then a 0.3 minute hold at 100% B; Temperature: 50° C.; Flow rate: 0.7 mL/min; Detection: UV at 220 nm).

Intermediate 178

(±)-cis-4-(3-Ethoxy-4-hydroxypiperidin-1-yl)-1-methyl-2-oxo-1,2-dihydropyrido[3,2-d] pyrimidine-6-carbonitrile

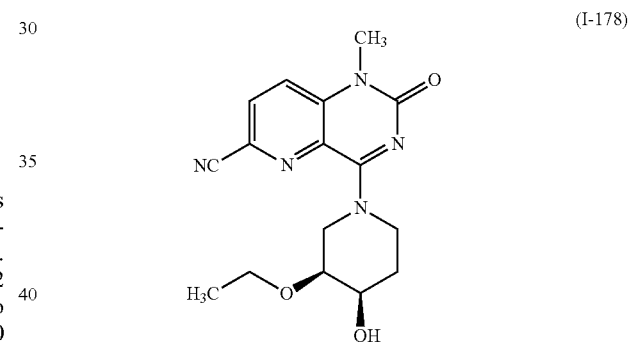

(I-178)

To a stirred solution of (±)-cis-6-chloro-4-(3-ethoxy-4-hydroxypiperidin-1-yl)-1-methylpyrido[3,2-d]pyrimidin-2(1H)-one (0.5 g, 1.48 mmol) in DMF (5 mL) were added zinc (0.15 g, 2.21 mmol), zinc cyanide (0.26 g, 2.21 mmol) and TEA (0.6 mL, 4.43 mmol). The reaction mixture was degassed for 5 min and dichloro[9,9-dimethyl-4,5-bis(diphenylphosphino)xanthene]palladium(II) (0.11 g, 0.15 mmol) was added. The reaction mixture was heated at 90° C. overnight. The reaction mixture was cooled to room temperature, diluted with ethyl acetate and filtered through Celite pad. The filtrate was washed with water, brine and the organic layer was dried over anhydrous $Na_2SO_4$ filtered and evaporated under reduced pressure to obtain crude product, which was purified by silica gel chromatography (3% MeOH in DCM) to afford (±)-cis-4-(3-ethoxy-4-hydroxypiperidin-1-yl)-1-methyl-2-oxo-1,2-dihydropyrido[3,2-d]pyrimidine-6-carbonitrile. LCMS: m/z, 329.2 (M+1); retention time: 0.71 min. (LCMS Method: Column: Waters Acquity UPLC BEH C18 (2.1×50 mm) 1.7 μm, Mobile phase A: 10 mM ammonium acetate:acetonitrile (95:5); Mobile phase B: 10 mM $NH_4$OAc:acetonitrile (5:95), Gradient=20-100% B over 2 minute, then a 0.3 minute hold at 100% B; Temperature: 50° C.; Flow rate: 0.7 mL/min; Detection: UV at 220 nm).

Examples 402 and 403 trans-4-(3-Ethoxy-4-phenoxypiperidin-1-yl)-1-methyl-2-oxo-1,2-dihydropyrido[3,2-d] pyrimidine-6-carbonitrile

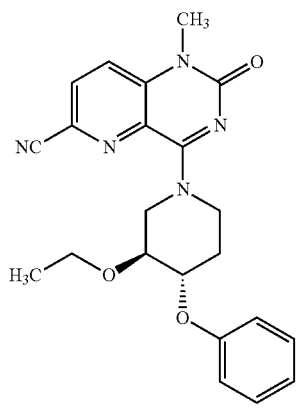

(402-403)

To a stirred solution of (±)-cis-4-(3-ethoxy-4-hydroxypiperidin-1-yl)-1-methyl-2-oxo-1,2-dihydropyrido[3,2-d]pyrimidine-6-carbonitrile (100 mg, 0.30 mmol) in THF (5 mL), triphenylphosphine (120 mg, 0.45 mmol), DIAD (0.12 mL, 0.61 mmol) and phenol (43 mg, 0.45 mmol) were added sequentially at room temperature. The reaction mixture was heated at 60° C. for 2 h. The reaction mixture was cooled to room temperature and the solvent was removed under reduced pressure to yield the crude product, which was purified by preparative SFC (Column: Luxcellulose-4 (250× 21.5) mm, 5 μm; % CO$_2$:

55%; % Co solvent: 45% of MeOH; Total Flow: 140.0 g/min; Back Pressure: 100 bar; Temperature: 40° C.; UV: 220 nm).

Example 402: LCMS: m/z, 406.1 (M+H); retention time: 1.69; LC/MS Method: Column: Waters XBridge C18, 19×150 mm, 5-μm particles; Mobile Phase A: 10-mM ammonium acetate; Mobile Phase B: acetonitrile; Gradient: 20-65% B over 20 minutes, then a 5-minute hold at 100% B; Flow: 15 mL/min. $^1$H NMR (400 MHz, DMSO-d$_6$) δ 8.27 (d, J=9.0 Hz, 1H), 8.02 (d, J=9.0 Hz, 1H), 7.37-7.23 (m, 2H), 7.08-6.99 (m, 2H), 6.93-7.00 (m, 1H), 4.53-4.59 (m, 1H), 3.53-3.67 (m, 3H), 3.47 (s, 3H), 2.16-2.26 (m, 1H), 1.65-1.77 (m, 1H), 0.89-1.05 (m, 3H).

Example 403: LCMS 406.1 (M+H); retention time: 1.69 min; LC/MS Method: Column: Waters XBridge C18, 19×150 mm, 5-μm particles; Mobile Phase A: 10-mM ammonium acetate; Mobile Phase B: acetonitrile; Gradient: 20-65% B over 20 minutes, then a 5-minute hold at 100% B; Flow: 15 mL/min. $^1$H NMR (400 MHz, DMSO-d$_6$): δ ppm 8.27 (d, J=8.8 Hz, 1H), 8.02 (d, J=9.0 Hz, 1H), 7.37-7.24 (m, 2H), 7.10-6.99 (m, 2H), 6.99-6.88 (m, 1H), 5.01-4.70 (m, 1H), 4.61-4.51 (m, 1H), 4.45-4.03 (m, 2H), 3.92 (s, 1H), 3.67-3.52 (m, 3H), 3.46 (s, 3H), 2.24-2.16 (m, 1H), 1.76-1.63 (m, 1H), 1.10-0.90 (m, 3H).

The examples in Table 31 were prepared from appropriate phenol according to the general procedures disclosed in Examples 402 and 403.

TABLE 31

| Ex. No. | Structure | Stereochemistry | LCMS Method | LCMS RT | M + H |
|---|---|---|---|---|---|
| 404 | 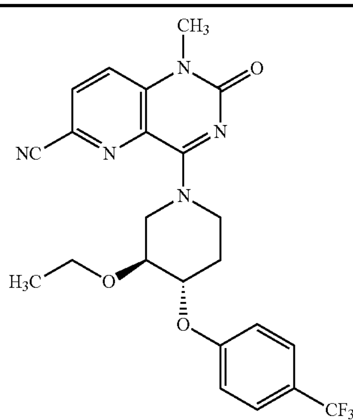 | Homochiral | A | 1.96 | 474.1 |
| 405 |  | Homochiral | A | 1.86 | 474.1 |

Biological Assays

The pharmacological properties of the compounds of this invention may be confirmed by a number of biological assays. The exemplified biological assays, which follow, have been carried out with compounds of the invention.

Assay 1: In Vitro DGK Inhibition Assays—Method A

The DGKα and DGKζ reactions were performed using extruded liposomes (DGKα and DGKζ LIPGLO assays). The reactions were carried out in 50 mM MOPS pH 7.5, 100 mM NaCl, 10 mM MgCl$_2$, 1 μM CaCl$_2$), and 1 mM DTT (assay buffer). The lipid substrates were 2 mM PS, 0.25 mM DAG, and 2.75 mM PC for the extruded liposome reactions. The reactions were carried out in 150 μM ATP. The enzyme concentrations for the DGKα and DGKζ were 5 nM.

The compound inhibition studies were carried out as follows: 50 nL droplets of each test compound (top concentration 10 mM with 11 point, 3-fold dilution series for each compound) solubilized in DMSO were transferred to wells of a white 1536 well plate (Corning 3725). A 5 mL enzyme/substrate solution at 2× final reaction concentration was prepared by combining 2.5 mL 4× enzyme solution (20 nM DGKα or DGKζ (prepared as described below) in assay buffer) and 2.5 mL of 4× liposome solution (compositions described below) and incubated at room temperature for 10 minutes. Next, 1 μL 2× enzyme/substrate solution was added to wells containing the test compound and reactions were initiated with the addition of 1 μL 300 uM ATP. The reactions were allowed to proceed for 1 hr, after which 2 μL Glo Reagent (Promega V9101) was added and incubated for 40 minutes. Next, 4 μL Kinase Detection Reagent was added and incubated for 30 minutes. Luminescence was recorded using an EnVision microplate reader. The percent inhibition was calculated from the ATP conversion generated by no enzyme control reactions for 100% inhibition and vehicle-only reactions for 0% inhibition. The compounds were evaluated at 11 concentrations to determine $IC_{50}$.

4× Liposome Preparation

The lipid composition was 5 mol % DAG (Avanti 8008110), 40 mol % PS (Avanti 840035P), and 55 mol % PC (Avanti 850457) at a total lipid concentration of 15.2 mg/mL for the 4× liposome solution. The PC, DAG, and PS were dissolved in chloroform, combined, and dried in vacuo to a thin film. The lipids were hydrated to 20 mM in 50 mM MOPS pH 7.5, 100 mM NaCl, 5 mM $MgCl_2$, and were freeze-thawed five times. The lipid suspension was extruded through a 100 nm polycarbonate filter eleven times. Dynamic light scattering was carried out to confirm liposome size (50-60 nm radius). The liposome preparation was stored at 4° C. for as long as four weeks.

Baculovirus Expression of Human DGKα and DGKζ

Human DGK-alpha-TVMV-His-pFBgate and human DGK-zeta-transcript variant-2-TVMV-His-pFBgate baculovirus samples were generated using the Bac-to-Bac baculovirus expression system (Invitrogen) according to the manufacturer's protocol. The DNA used for expression of DGK-alpha and DGK-zeta have SEQ ID NOs: 1 and 3, respectively. Baculovirus amplification was achieved using infected Sf9 cells at 1:1500 virus/cell ratios, and grown for 65 hours at 27° C. post-transfection.

The expression scale up for each protein was carried out in the Cellbag 50L WAVE-Bioreactor System 20/50 from GE Healthcare Bioscience. 12 L of 2×10⁶ cells/mL Sf9 cells (Expression System, Davis, Calif.) grown in ESF921 insect medium (Expression System) were infected with virus stock at 1:200 virus/cell ratios, and grown for 66-68 hours at 27° C. post-infection. The infected cell culture was harvested by centrifugation at 2000 rpm for 20 min 4° C. in a SOR-VALL® RC12BP centrifuge. The cell pellets were stored at −70° C. until purification.

Purification of Human DGK-Alpha and DGK-Zeta

Full length human DGKα and DGKζ, each expressed containing a TVMV-cleavable C-terminal Hexa-His tag sequence (SEQ ID NOs: 2 and 4, respectively) and produced as described above, were purified from Sf9 baculovirus-infected insect cell paste. The cells were lysed using nitrogen cavitation method with a nitrogen bomb (Parr Instruments), and the lysates were clarified by centrifugation. The clarified lysates were purified to ~90% homogeneity, using three successive column chromatography steps on an ÄKTA Purifier Plus system. The three steps column chromatography included nickel affinity resin capture (i.e. HisTrap FF crude, GE Healthcare), followed by size exclusion chromatography (i.e. HiLoad 26/600 Superdex×200 prep grade, GE Healthcare for DGK-alpha, and HiPrep 26/600 Sephacryl S 300_HR, GE Healthcare for DGK-zeta). The third step was ion exchange chromatography, and differed for the two isoforms. DGKα was polished using Q-Sepharose anion exchange chromatography (GE Healthcare). DGKζ was polished using SP Sepharose cation exchange chromatography (GE Healthcare). The proteins were delivered at concentrations of >2 mg/mL. The formulation buffers were identical for both proteins: 50 mM Hepes, pH 7.2, 500 mM NaCl, 10% v/v glycerol, 1 mM TCEP, and 0.5 mM EDTA.

Assay 2: In Vitro DGK Inhibition Assays—Method B

The DGKα and DGKζ reactions were performed using either extruded liposome (DGKα and DGKζ LIPGLO assays). The reactions were carried out in 50 mM MOPS pH 7.5, 100 mM NaCl, 10 mM $MgCl_2$, 1 μM $CaCl_2$), and 1 mM DTT (assay buffer). The lipid substrate concentrations were 2 mM PS, 0.25 mM DAG, and 2.75 mM PC for the extruded liposome reactions (5 mM total lipid). The reactions were carried out in 150 μM ATP. The enzyme concentrations for the DGKα and DGKζ were 5 nM.

The compound inhibition studies were carried out as follows: 25 nL droplets of each test compound (top concentration 10 mM with 11 point, 3-fold dilution series for each compound) solubilized in DMSO were transferred to wells of a white 1536 well plate (Corning 3725). A 5 mL enzyme/lipid substrate solution at 2× final reaction concentration was prepared by combining 2.5 mL 4× enzyme solution (20 nM DGKα or DGKζ (prepared as described below) in assay buffer) and 2.5 mL of 4× detergent/lipid micelle solution (compositions described below) and incubated at room temperature for 10 minutes. Next, 1 μL 2× enzyme/lipid substrate solution was added to wells containing the test compound and reactions were initiated with the addition of 1 μL 300 uM ATP. The reactions were allowed to proceed for 2 hr, after which 2 μL Glo Reagent (Promega V9101) was added and incubated for 40 minutes. Next, 4 μL Kinase Detection Reagent was added and incubated for 30 minutes. Luminescence was recorded using an EnVision microplate reader. The percent inhibition was calculated from the ATP conversion generated by no enzyme control reactions for 100% inhibition and vehicle-only reactions for 0% inhibition. The compounds were evaluated at 11 concentrations to determine $IC_{50}$.

2× Liposome Preparation

The lipid composition was 5 mol % DAG (Avanti 8008110), 40 mol % PS (Avanti 840035P), and 55 mol % PC (Avanti 850457) at a total lipid concentration of 7-8 mg/mL for the liposome solution. The PC, DAG, and PS were dissolved in chloroform, combined, and dried in vacuo to a thin film. The lipids were hydrated to 20 mM in 50 mM MOPS pH 7.5, 100 mM NaCl, 5 mM $MgCl_2$, and were freeze-thawed five times. The lipid suspension was extruded through a 100 nm polycarbonate filter 10-12 times. Dynamic light scattering was carried out to confirm liposome size (50-60 nm radius). The liposome preparation was stored at 4° C. for as long as four weeks.

Baculovirus Expression of Near Full Length Human DGKα and Full Length DGKζ

Human MA-hDGKα-(59-5727)-Ct-TVMV-His-pFBgate and full length human DGK-C-transcript variant-2-TVMV-His-pFBgate baculovirus samples were generated using the Bac-to-Bac baculovirus expression system (Invitrogen) according to the manufacturer's protocol (note: MA—in name of DGKα reagents indicates two extra amino acids added prior to Ser-9). The DNA used for expression of the DGK-α(9-727) and DGK-C have SEQ ID NOs: 5 and 3, respectively. Baculovirus amplification was achieved using infected Sf9 cells at 1:1500 virus/cell ratios, and grown for 65 hours at 27° C. post-transfection.

The expression scale up for the near full length DGK-α (9-727) protein was carried out in 2 L flasks, and the full length DGKζ was done using a Cellbag 50 L WAVE-Bioreactor System 20/50 from GE Healthcare Bioscience. The proteins were expressed at different volumes using similar conditions. For expression of DGKα(9-727), 2×2 L flasks each containing 0.8 L final volume of culture media were used, and DGKζ was grown at 12 L scale in a 50 L Cellbag. For each, an initial density of $2\times10^6$ cells/mL 519 cells (Expression System, Davis, Calif.) was seeded in ESF921 insect medium (Expression System), infected with virus stock at 1:200 virus/cell ratios, and grown for 66-68 hours at 27° C. post-infection. The infected cell cultures were harvested by centrifugation at 2000 rpm for 20 min 4° C. in a SORVALL® RC12BP centrifuge. The cell pellets were stored at −80° C. until purification.

Purification of Human DGK-Alpha and DGK-Zeta

Human DGKα(9-727) and full length DGKζ, each expressed containing a TVMV-cleavable C-terminal Hexa-His tag sequence (SEQ ID NOs: 2 and 4, respectively) and produced as described above, were purified from Sf9 baculovirus-infected insect cell paste. The cell pastes were thawed and suspended in buffer (50 mM HEPES, pH 7.2, 300 mM NaCl, 10% v/v glycerol, 1 mM TCEP containing benzonase and protease inhibitors), to 1:10 v/v of original culture volume. Lysis was accomplished using the nitrogen cavitation method with a nitrogen bomb (Parr Instruments), and the lysates were clarified by high speed centrifugation. The clarified lysates were purified to ~90% homogeneity, using two or three successive column chromatography steps, respectively, on an AKTA Purifier Plus system. Both isoforms were purified by nickel affinity purification with imidazole gradient elution (i.e. HisTrap FF, GE Healthcare), followed by size exclusion chromatography (i.e. HiLoad 26/600 Superdex200 prep grade, GE Healthcare, for DGKα (9-727), and HiPrep 26/600 Sephacryl S 300_HR, GE Healthcare, for DGKζ). These two steps yielded DGKα(9-727) at >90% purity. Achieving similar purity for full length DGKζ required a third step, employing cation exchange chromatography (SP Sepharose FF, GE Healthcare), and eluting with a NaCl gradient. The final formulation buffers were similar for both proteins, with DGKα(9-727) prepared in 50 mM Hepes, pH 7.3, 300 mM NaCl, 10% v/v glycerol, and 1 mM TCEP, and full length DGKζ prepared in 50 mM Hepes, pH 7.3, 500 mM NaCl, 5% v/v glycerol, and 1 mM TCEP. The proteins were concentrated to 1-2 mg/mL, flash frozen, and kept at −80° C. for long term storage.

Assay 3: Raji CD4 T Cell IL2 Assay

A 1536-well IL-2 assay was performed in 4 μL volume using pre-activated CD4 T cells and Raji cells. Prior to the assay, CD4 T cells were pre-activated by treatment with α-CD3, α-CD28 and PHA at 1.5 μg/mL, 1 μg/mL, and 10 μg/mL, respectively. Raji cells were treated with Staphylococcal enterotoxin B (SEB) at 10,000 ng/mL. Serially diluted compounds were first transferred to 1536-well assay plate (Corning, #3727), followed by addition of 2 μL of pre-activated CD4 T cells (final density at 6000 cells/well) and 2 μL of SEB-treated Raji cells (2000 cells/well). After 24 hours incubation at a 37° C./5% $CO_2$ incubator, 4 μl of IL-2 detection reagents were added to the assay plate (Cisbio, #64IL2PEC). The assay plates were read on an Envision reader. To assess compound cytotoxicity, either Raji or CD4 T cells were incubated with the serially diluted compounds. After 24 hours incubation, 4 μL of Cell Titer Glo (Promega, #G7572) were added, and the plates were read on an Envision reader. The 50% effective concentration ($IC_{50}$) was calculated using the four-parameter logistic formula $y=A+((B-A)/(1+((C/x)^{\wedge}D)))$, where A and B denote minimal and maximal % activation or inhibition, respectively, C is the $IC_{50}$, D is hill slope and x represent compound concentration.

Assay 4: CellTiter-Glo CD8 T Cell Proliferation Assay

Frozen naïve human CD8 T cells were thawed in RPMI+ 10% FBS, incubated for 2 h in 37° C., and counted. The 384-well tissue culture plate was coated overnight at 4° C. with 20 μl anti-human CD3 at 0.1 μg/mL in plain RPMI, which was removed off the plate before 20 k/40 μL CD8 T cells with 0.5 μg/ml soluble anti-human CD28 were added to each well. The compounds were echoed to the cell plate immediately after the cells were plated. After 72 h incubation at 37° C. incubator, 10 μL CellTiter-glo reagent (Promega catalog number G7570) was added to each well. The plate was vigorously shaken for 5 mins, incubated at room temperature for another 15 mins and read on Envision for CD8 T cell proliferation. In analysis, 0.1 μg/mL anti-CD3 and 0.5 μg/mL anti-CD28 stimulated CD8 T cell signal was background. The reference compound, 8-(4-(bis(4-fluorophenyl)methyl) piperazin-1-yl)-5-methyl-7-nitro-6-oxo-5,6-dihydro-1,5-naphthyridine-2-carbonitrile, at 3 μM was used to set the 100% range and $EC_{50}$ was at absolute 50% to normalize the data.

Assay 5: DGK AP1-Reporter Assay

The Jurkat AP1-luciferase Reporter was generated using the Cignal Lenti AP1 Reporter (luc) Kit from SABiosciences (CLS-011L).

The compounds were transferred from an Echo LDV plate to individual wells of a 384-well plate (white, solid-bottom, opaque PE CulturPlate 6007768) using an Echo550 instrument. The sample size was 30 nL per well; and one destination plate per source plate. The cell suspensions were prepared by transferring 40 mL cells (2×20 mL) to clean 50 mL conical tubes. The cells were concentrated by centrifugation (1200 rpm; 5 mins; ambient temperature). The supernatant was removed and all cells were suspended in RPMI (Gibco 11875)+10% FBS to make a $1.35\times10^6$ cells/ml concentration. The cells were added manually using a multichannel pipette, 30 μL/well of cell suspension to a 384-well TC plate containing the compounds, $4.0\times10^4$ cells per well. The cell plates were incubated for 20 minutes at 37° C. and 5% $CO_2$.

During the incubation, anti-CD3 antibody (αCD3) solutions were prepared by mixing 3 μL aCD3 (1.3 mg/mL) with 10 mL medium [final conc=0.4 μg/mL]. Next, 1.5 μl aCD3 (1.3 mg/mL) was mixed with 0.5 mL medium [final conc=4 μg/ml]. After 20 minutes, 10 μL medium was added to all wells in column 1, wells A to M, and 10 μL αCD3 (4 ug/mL) per well was added in column 1, rows N to P for reference. Then using a multi-channel pipette, 10 μL αCD3 (0.4 ug/mL) per well was added. The αCD3 stimulated +/−compound-treated cells were incubated at 37° C., 5% $CO_2$ for 6 hours.

During this incubation period, Steady-Glo (Promega E2520) reagent was slowly thawed to ambient temperature. Next, 20 μL Steady-Glo reagent per well was added using a multi-drop Combi-dispenser. Bubbles were removed by centrifugation (2000 rpm, ambient temperature, 10 secs). The cells were incubated at room temperature for 5 minutes. Samples were characterized by measuring the Relative Light Units (RLU) with an using Envision Plate Reader Instrument on a luminescence protocol. The data was analyzed using the reference compound, 8-(4-(bis(4-fluorophenyl)methyl)piperazin-1-yl)-5-methyl-7-nitro-6-oxo-5,6-dihydro-1,5-naphthyridine-2-carbonitrile, to normalize 100% inhibition.

Assay 6: Murine Cytotoxic T Lymphocyte Assay

An antigen-specific cytolytic T-cell (CTL) assay was developed to evaluate functionally the ability of DGKα and DGKζ inhibitors to enhance effector T cell mediated tumor cell killing activity. CD8+ T-cells isolated from the OT-1 transgenic mouse recognize antigen presenting cells, MC38, that present the ovalbumin derived peptide SIINFEKL. Recognition of the cognate antigen initiates the cytolytic activity of the OT-1 antigen-specific CD8+ T cells.

Functional CTL cells were generated as follows: OT-1 splenocytes from 8-12 week old mice were isolated and expanded in the presence of the SIINFEKL peptide at 1 µg/mL and mIL2 at 10 U/mL. After three days, fresh media with mIL2 U/ml was added. On day 5 of the expansion, the CD8+ T cells were isolated and ready for use. Activated CTL cells may be stored frozen for 6 months. Separately, one million MC38 tumor cells were pulsed with 1 µg/mL of SIINFEKL-OVA peptide for 3 hours at 37° C. The cells were washed (3×) with fresh media to remove excess peptide. Finally, CTL cells that were pretreated with DGK inhibitors for 1 hour in a 96-well U bottom plate were combined with the antigen loaded MC38 tumor cells at a 1:10 ratio. The cells were then spun at 700 rpm for 5 min and placed in an incubator overnight at 37° C. After 24 hours, the supernatant was collected for analysis of IFN-γ cytokine levels by AlphaLisa purchased from Perkin Elmer.

Assay 7: PHA Proliferation Assay

Phytohaemagglutinin (PHA)-stimulated blast cells from frozen stocks were incubated in RPMI medium (Gibco, ThermoFisher Scientific, Waltham, Mass.) supplemented with 10% fetal bovine serum (Sigma Aldrich, St. Louis, Mo.) for one hour prior to adding to individual wells of a 384-well plate (10,000 cells per well). The compounds were transferred to individual wells of a 384-well plate and the treated cells are maintained at 37° C., 5% $CO_2$ for 72 h in culture medium containing human IL2 (20 ng/mL) prior to measuring growth using MTS reagent [3-(4,5-dimethyl-2-yl)-5-(3-carboxymethoxyphenyl)-2-(4-sulfophenyl)-2H-tetrazolium] following manufacturer's instructions (Promega, Madison, Wis.). Percent inhibition was calculated comparing values between IL2 stimulated (0% inhibition) and unstimulated control (100% inhibition). Inhibition concentration ($IC_{50}$) determinations were calculated based on 50% inhibition on the fold-induction between IL2 stimulated and unstimulated treatments.

Assay 8: Human CD8 T Cells IFN-γ Assay

Frozen naïve human CD8 T cells were thawed in AIM-V media, incubated for 2 h in 37° C., and counted. The 384-well tissue culture plate was coated overnight at 4° C. with 20 µL anti-human CD3 at 0.05 µg/mL in PBS, which was removed off the plate before 40,000 cells per 40 microliters CD8 T cells with 0.1 µg/mL soluble anti-human CD28 were added to each well. The compounds were transferred using an Echo liquid handler to the cell plate immediately after the cells were plated. After 20 h incubation at 37° C. incubator, 3 microliters per well supernatants transferred into a new 384-well white assay plate for cytokine measurement.

Interferon-γ (IFN-γ) was quantitated using the AlphLISA kit (Cat #AL217) as described by the manufacturer manual (Perkin Elmer). The counts from each well were converted to IFN-γ concentration (pg/mL). The compound $EC_{50}$ values were determined by setting 0.05 µg/mL anti-CD3 plus 0.1 µg/mL anti-CD28 as the baseline, and co-stimulation of 3 µM of the reference compound, 8-(4-(bis(4-fluorophenyl)methyl) piperazin-1-yl)-5-methyl-7-nitro-6-oxo-5,6-dihydro-1,5-naphthyridine-2-carbonitrile, with anti-CD3 plus anti-CD28 as 100% activation.

Assay 9: Human CD8 T Cells pERK Assay

Frozen naïve human CD8 T cells were thawed in AIM-V media, incubated for 2 h in 37° C., and counted. The CD8 positive T cells were added to 384-well tissue culture plate at 20,000 cells per well in AIM-V media. One compound was added to each well, then bead bound anti-human CD3 and anti-CD28 mAb were added at final concentration of 0.3 µg/mL. The cells were incubated at 37° C. for 10 minutes. The reaction was stopped by adding lysis buffer from the AlphaLISA Surefire kit. (Perkin Elmer, cat # ALSU-PERK-A). Lysate (5 µL per well) was transferred into a new 384-well white assay plate for pERK activation measurement.

Compound $EC_{50}$ was determined as setting anti-CD3 plus anti-CD28 as baseline, and co-stimulation of 3 µM 8-(4-(bis (4-fluorophenyl)methyl)piperazin-1-yl)-5-methyl-7-nitro-6-oxo-5,6-dihydro-1,5-naphthyridine-2-carbonitrile with anti-CD3 plus anti-CD28 as 100% activation.

Assay 10: Human Whole Blood IFN-γ Assay

Human venous whole blood (22.5 µL per well), obtained from healthy donors, was pre-treated with compounds for one hour at 37° C. in a humidified 95% air/5% $CO_2$ incubator. The blood was stimulated with 2.5 µL anti-human CD3 and anti-CD28 mAb at a final concentration of 1 µg/mL each for 24 hours at 37° C. IFN-γ in the supernatants was measured using AlphLISA kit (Cat #AL217).

Compound $EC_{50}$ determined as setting anti-CD3 plus anti-CD28 as baseline, and co-stimulation of 3 µM of the reference compound, 8-(4-(bis(4-fluorophenyl)methyl) piperazin-1-yl)-5-methyl-7-nitro-6-oxo-5,6-dihydro-1,5-naphthyridine-2-carbonitrile, with anti-CD3 plus anti-CD28 as 100% activation.

Assay 11: DGK Human Whole Blood pERK Assay

Human whole blood ERK phosphorylation assay was performed with human venous whole blood obtained from healthy donors (drawn with Heparin as anti-coagulant). Serial dilutions of compounds (11 points, 3-fold) in DMSO were added to 384 well plates at 20 nL/well using an ECHO 550 acoustic dispenser (Labcyte) to achieve final starting concentration of 20 µM in assay. Heparinized human whole blood was added to the compound plate at 9 µL per well and incubated for one hour at 37° C. in a humidified 95%, air/5% $CO_2$ incubator. After one hour of compound incubation, 1 µL of human anti-CD3 antibody (in-house) in the presence of cross-linking antibody goat anti-mouse IgG (4 µg/mL) was added to the well at 1 µg/mL final concentration for stimulation of pathway and additionally incubated for 15 minutes at 37° C. Stimulation was stopped by adding 90 µL Fix/Lyse buffer (BD 558049). Cells were washed and stained with anti-CD8 PE (BD 555635) antibodies for 60 minutes at room temperature, washed again, and permeabilized on ice using Perm III buffer (BD 558050) for 30 minutes. Cells were then stained with an Alexa Fluor® 647 anti-ERK1/2 Phospho (Thr202/Tyr204) Antibody (Bioleged 675504) for 60 minutes at 1:50 dilution. Samples were washed and resuspended in dPBS containing 1% BSA (dPBS, Gibco 14190136; BSA, Sigma-Aldrich A9205). Samples analyzed using the Intellicyt® iQue Screener PLUS. The pERK activation was quantitated by the percentage of pERK positive population within CD8 positive population. Calculations of compound potencies were based on internal compound at 20 µM concentration as a 100% activation, and anti-CD3 control as a 0% activation.

TABLE A

Activity Data

| Ex. No. | DGKα LIPGLO $IC_{50}$ (μM) | DGKα ADPGLO $IC_{50}$ (μM) | DGKζ LIPGLO $IC_{50}$ (μM) | HuCD8 INFG Normalized $EC_{50}$ (μM) | msCTL INFg $IC_{50}$ (μM) | INFg Whole Blood Normalized Agonist $EC_{50}$ (μM) | DGK HWB pERK $IC_{50}$ (μM) | CD8 GLO Normalized $EC_{50}$ (μM) |
|---|---|---|---|---|---|---|---|---|
| 1 | 0.24 | — | 100 | — | 5.2 | 10 | — | 1.6 |
| 2 | — | — | — | — | — | — | — | 0.34 |
| 3 | 0.11 | — | 240 | — | 1.5 | 10 | — | 0.49 |
| 4 | — | — | — | — | — | — | — | 0.44 |
| 5 | — | — | — | — | — | — | — | 10 |
| 6 | — | — | — | — | — | — | — | 10 |
| 7 | — | — | — | — | — | — | — | 2.3 |
| 8 | — | — | — | — | — | — | — | 0.32 |
| 9 | — | — | — | — | — | — | — | 0.79 |
| 10 | 0.15 | — | 2.8 | — | 4.5 | 5.0 | — | 0.14 |
| 11 | 12 | — | 150 | — | 0.83 | 10 | — | 10 |
| 12 | 3.2 | — | 27 | — | 3.8 | 5.0 | — | 2.3 |
| 13 | 2.0 | — | 240 | — | 1.5 | 5.0 | — | 1.2 |
| 14 | 0.25 | — | 13 | — | 0.83 | 7.0 | — | 0.28 |
| 15 | 0.51 | — | 7.4 | 0.87 | 0.29 | 7.6 | — | 0.32 |
| 16 | 1.7 | — | — | — | 1.1 | 10 | — | 0.093 |
| 17 | 1.1 | — | 240 | — | 1.1 | 10 | — | 0.47 |
| 18 | 2.6 | — | 13 | 0.19 | 1.5 | 10 | — | 0.079 |
| 19 | 0.32 | — | — | — | 0.21 | 10 | — | 0.28 |
| 20 | 0.43 | — | 16 | — | — | — | — | 0.87 |
| 21 | 0.77 | — | 7.8 | 0.16 | 1.7 | — | — | 0.092 |
| 22 | 0.15 | — | 5.7 | — | — | — | — | 0.62 |
| 23 | 66 | — | 58 | — | 10 | — | — | — |
| 24 | 2.0 | — | 27 | — | 1.5 | — | — | 0.75 |
| 25 | 0.73 | — | 240 | — | 10 | — | — | 1.2 |
| 26 | — | — | — | — | 10 | — | — | 2.7 |
| 27 | — | — | — | — | 7.4 | — | — | 0.073 |
| 28 | 1.6 | — | 5.4 | — | 10 | — | — | — |
| 29 | 3.8 | — | 240 | — | 10 | — | — | 5.9 |
| 30 | 0.98 | — | 240 | — | 3.5 | — | — | 10 |
| 31 | 0.28 | — | 11 | — | 10 | — | — | 0.044 |
| 32 | — | — | — | — | 10 | — | — | — |
| 33 | 2.8 | — | 240 | — | 3.8 | — | — | 10 |
| 34 | 1.1 | — | 9.0 | — | 8.5 | — | — | 4.1 |
| 35 | 0.29 | — | 12 | — | — | — | — | 0.21 |
| 36 | 1.6 | — | 32 | — | — | — | — | — |
| 37 | 0.49 | — | 240 | — | — | — | — | 1.1 |
| 38 | 1.8 | — | 9.0 | — | 10 | — | — | 1.6 |
| 39 | 0.35 | — | 14 | — | 3.7 | — | — | 0.13 |
| 40 | 0.74 | — | 9.0 | — | 10 | — | — | 1.2 |
| 41 | 1.1 | — | 23 | — | 10 | — | — | 0.21 |
| 42 | 5.4 | — | 240 | — | 10 | — | — | 0.70 |
| 43 | 1.5 | — | 27 | — | 10 | — | — | 10 |
| 44 | 1.7 | — | 59 | — | — | — | — | 1.5 |
| 45 | — | — | — | — | 10 | — | — | 0.098 |
| 46 | 0.15 | — | 27 | — | 8.5 | — | — | 1.2 |
| 47 | 0.45 | — | 240 | — | 0.68 | — | — | 0.49 |
| 48 | 2.7 | — | 3.4 | — | 0.27 | 6.4 | — | 0.13 |
| 49 | — | — | — | — | — | — | — | — |
| 50 | 1.6 | — | 12 | — | 0.99 | 5.0 | — | 0.055 |
| 51 | 0.23 | — | 3.0 | — | 0.18 | 1.7 | 2.5 | 0.14 |
| 52 | 0.80 | — | 3.8 | 1.0 | 0.15 | 2.7 | — | — |
| 53 | 0.77 | — | 2.0 | — | — | 1.8 | 2.8 | — |
| 54 | 0.54 | — | 2.1 | — | — | 2.3 | — | — |
| 55 | 0.95 | — | 3.8 | — | — | 3.7 | — | — |
| 56 | 0.84 | — | 13 | — | — | 3.8 | — | — |
| 57 | 0.73 | — | 6.1 | — | — | 4.3 | — | — |
| 58 | 0.34 | — | 2.9 | — | — | 5.9 | — | — |
| 59 | 1.0 | — | 3.7 | — | — | 6.4 | — | — |
| 60 | 0.24 | — | 5.5 | — | — | 7.9 | — | — |
| 61 | 0.73 | — | 4.7 | — | — | 8.5 | — | — |
| 62 | 1.5 | — | 5.2 | — | — | 20 | — | — |
| 63 | 0.74 | — | 38 | — | — | — | — | — |
| 64 | 0.76 | — | 20 | — | — | — | 2.9 | — |
| 65 | 0.56 | — | 3.3 | — | — | 6.8 | — | — |
| 66 | 1.2 | — | 4.0 | — | — | 0.82 | 2.7 | — |
| 67 | 1.6 | — | 7.1 | — | — | 2.7 | — | — |
| 68 | 1.7 | — | 1.7 | — | — | 9.6 | — | — |

TABLE A-continued

Activity Data

| Ex. No. | DGKα LIPGLO IC$_{50}$ (μM) | DGKα ADPGLO IC$_{50}$ (μM) | DGKζ LIPGLO IC$_{50}$ (μM) | HuCD8 INFG Normalized EC$_{50}$ (μM) | msCTL INFg IC$_{50}$ (μM) | INFg Whole Blood Normalized Agonist EC$_{50}$ (μM) | DGK HWB pERK IC$_{50}$ (μM) | CD8 GLO Normalized EC$_{50}$ (μM) |
|---|---|---|---|---|---|---|---|---|
| 69 | 5.7 | — | 1.4 | — | — | 17 | — | — |
| 70 | 12 | — | 11 | — | — | 20 | — | — |
| 71 | 2.3 | — | 3.0 | — | — | 20 | — | — |
| 72 | 4.2 | — | 39 | — | — | 20 | 20 | — |
| 73 | 2.2 | — | 8.3 | — | — | 20 | — | — |
| 74 | 2.8 | — | 3.3 | — | — | 20 | — | — |
| 75 | 27 | — | 18 | — | — | 20 | — | — |
| 76 | 11 | — | 34 | — | — | 20 | 20 | — |
| 77 | 3.0 | — | 3.0 | — | — | — | — | — |
| 78 | 0.81 | — | 16 | — | — | — | 20 | — |
| 79 | 0.17 | — | 4.7 | — | — | 2.2 | — | — |
| 80 | 0.11 | — | 39 | — | — | 2.4 | — | — |
| 81 | 0.85 | — | 7.7 | — | — | 2.0 | — | — |
| 82 | 0.030 | — | 3.9 | — | — | 0.65 | — | — |
| 83 | 0.28 | — | 5.8 | 0.0025 | — | 0.36 | — | — |
| 84 | 0.048 | — | 23 | — | — | 1.2 | — | — |
| 85 | 0.080 | — | 3.0 | 0.61 | — | 2.2 | — | — |
| 86 | 0.72 | — | 2.9 | — | — | 0.69 | — | — |
| 87 | 0.050 | — | 2.5 | — | — | 2.0 | — | — |
| 88 | 0.12 | — | 8.3 | — | — | 0.88 | — | — |
| 89 | 0.037 | — | 5.6 | — | — | 0.98 | — | — |
| 90 | 0.047 | — | 50 | — | — | 5.6 | — | — |
| 91 | 0.065 | — | 14 | — | — | 4.4 | — | — |
| 92 | 0.028 | 0.00051 | 16 | — | — | 0.91 | — | — |
| 93 | 0.30 | — | 18 | — | — | 5.9 | — | — |
| 94 | 0.080 | — | 6.1 | — | — | 1.1 | 3.9 | — |
| 95 | 0.40 | — | 5.0 | — | — | 1.0 | — | — |
| 96 | 0.057 | — | 20 | — | — | 2.6 | — | — |
| 97 | 0.0042 | — | 11 | — | — | 1.9 | 3.0 | — |
| 98 | 0.22 | — | 43 | — | — | 1.2 | — | — |
| 99 | 2.5 | — | 21 | — | — | 2.9 | — | — |
| 100 | 0.11 | — | 28 | — | — | 2.7 | — | — |
| 101 | 0.43 | — | 6.8 | — | — | 1.4 | — | — |
| 102 | 0.068 | — | 83 | — | — | 3.3 | — | — |
| 103 | 0.33 | — | 7.7 | — | — | 1.5 | 5.5 | — |
| 104 | 0.076 | — | 15 | — | — | 1.8 | 1.1 | — |
| 105 | 2.6 | — | 11 | — | — | 2.0 | — | — |
| 106 | 0.081 | — | 83 | — | — | 2.2 | — | — |
| 107 | 0.13 | — | 24 | — | — | 13 | — | — |
| 108 | 0.91 | — | 11 | — | — | 3.0 | — | — |
| 109 | 0.12 | — | 29 | — | — | 4.2 | — | — |
| 110 | 0.24 | — | 27 | — | — | 3.0 | — | — |
| 111 | 0.17 | — | 25 | — | — | 3.3 | — | — |
| 112 | 0.34 | — | 7.5 | — | — | 4.1 | — | — |
| 113 | 0.31 | — | 12 | — | — | 4.1 | — | — |
| 114 | 0.51 | — | 60 | — | — | — | — | — |
| 115 | 2.7 | — | 15 | — | — | — | — | — |
| 116 | 0.45 | — | 13 | — | — | 4.7 | — | — |
| 117 | 2.0 | — | 20 | — | — | 4.6 | — | — |
| 118 | 0.25 | — | 52 | — | — | 4.7 | — | — |
| 119 | 0.24 | — | 20 | — | — | 6.6 | — | — |
| 120 | 0.35 | — | 73 | — | — | 4.7 | — | — |
| 121 | 1.8 | — | 9.9 | — | — | 6.7 | — | — |
| 122 | 0.017 | — | 28 | — | — | 5.8 | — | — |
| 123 | 0.028 | 0.003 | — | — | — | 19 | — | — |
| 124 | 1.4 | — | 28 | — | — | 20 | — | — |
| 125 | 0.83 | — | 17 | — | — | 20 | — | — |
| 126 | 6.5 | — | 250 | — | — | 20 | — | — |
| 127 | 0.45 | — | 250 | — | — | 20 | — | — |
| 128 | 0.39 | — | 45 | — | — | 20 | — | — |
| 129 | 3.4 | — | 13 | — | — | 20 | — | — |
| 130 | 0.13 | — | 100 | — | — | — | — | — |
| 131 | 3.1 | — | 250 | — | — | — | — | — |
| 132 | 0.011 | — | 4.3 | — | — | — | — | — |
| 136 | 0.81 | — | 250 | — | — | 20 | — | — |
| 137 | 0.036 | — | 0.92 | — | — | — | — | — |
| 138 | 0.024 | 0.0052 | 0.80 | — | — | 0.34 | — | — |
| 139 | 0.10 | — | 1.7 | — | — | 1.5 | 5.3 | — |
| 140 | 0.13 | — | — | — | — | 1.2 | — | — |
| 141 | 0.068 | — | 0.26 | — | — | 0.50 | 1.0 | — |
| 142 | 4.7 | — | 1.1 | — | — | 3.0 | — | — |

TABLE A-continued

Activity Data

| Ex. No. | DGKα LIPGLO IC$_{50}$ (µM) | DGKα ADPGLO IC$_{50}$ (µM) | DGKζ LIPGLO IC$_{50}$ (µM) | HuCD8 INFG Normalized EC$_{50}$ (µM) | msCTL INFg IC$_{50}$ (µM) | INFg Whole Blood Normalized Agonist EC$_{50}$ (µM) | DGK HWB pERK IC$_{50}$ (µM) | CD8 GLO Normalized EC$_{50}$ (µM) |
|---|---|---|---|---|---|---|---|---|
| 143 | 0.27 | — | 1.5 | — | — | 2.2 | — | — |
| 144 | 0.096 | — | 2.1 | — | — | 0.80 | 0.88 | — |
| 145 | 0.70 | — | 3.1 | — | — | 7.8 | — | — |
| 146 | 0.44 | — | 1.6 | — | — | 1.7 | — | — |
| 147 | 0.38 | — | 1.8 | — | — | 1.2 | 0.61 | — |
| 148 | 5.6 | — | 6.0 | — | — | 12 | — | — |
| 149 | 0.23 | — | 2.1 | — | — | 1.4 | — | — |
| 150 | 0.10 | — | 3.8 | — | — | 1.4 | — | — |
| 151 | 1.1 | — | 5.3 | — | — | 2.4 | — | — |
| 152 | 0.14 | — | 1.7 | — | — | 1.5 | — | — |
| 153 | 0.050 | — | 2.1 | — | — | 1.7 | — | — |
| 154 | 0.89 | — | 6.3 | — | — | 11 | — | — |
| 155 | 0.34 | — | 1.9 | — | — | 20 | — | — |
| 156 | 0.024 | — | 0.71 | — | — | 1.8 | — | — |
| 157 | 0.049 | — | 1.1 | — | — | 2.8 | — | — |
| 158 | 0.36 | — | 1.9 | — | — | 2.0 | — | — |
| 159 | 0.13 | — | 2.3 | — | — | 4.2 | — | — |
| 160 | 1.7 | — | 3.3 | — | — | 4.5 | — | — |
| 161 | 0.011 | — | 0.54 | — | — | 2.4 | — | — |
| 162 | 1.7 | — | 1.1 | — | — | — | — | — |
| 163 | 0.042 | — | 0.36 | — | — | — | — | — |
| 164 | — | — | — | — | — | 0.79 | 5.1 | — |
| 165 | 0.096 | — | 1.2 | — | — | 0.84 | — | — |
| 166 | 0.046 | — | 1.6 | — | — | 0.79 | — | — |
| 167 | 0.12 | — | 1.0 | — | — | 1.6 | 2.0 | — |
| 168 | 1.0 | — | 0.89 | — | — | 1.6 | 3.7 | — |
| 169 | 0.60 | — | 1.4 | — | — | 1.7 | — | — |
| 170 | 0.37 | — | 1.1 | — | — | 0.86 | 0.54 | — |
| 171 | 1.4 | — | 3.7 | — | — | 3.0 | — | — |
| 172 | 0.62 | — | 1.2 | — | — | 1.5 | — | — |
| 173 | 0.74 | — | 0.89 | — | — | 1.1 | — | — |
| 174 | 1.6 | — | 5.1 | — | — | 3.6 | — | — |
| 175 | 0.43 | — | 0.98 | — | — | 1.4 | 0.80 | — |
| 176 | 0.041 | — | 1.3 | — | — | 2.3 | — | — |
| 177 | 0.14 | — | 1.1 | — | — | 3.5 | — | — |
| 178 | 0.062 | — | 0.53 | — | — | 4.6 | 2.3 | — |
| 179 | 0.069 | — | 1.2 | — | — | 2.4 | — | — |
| 180 | 0.045 | — | 1.0 | — | — | — | — | — |
| 181 | 0.061 | — | 1.4 | — | — | — | — | — |
| 182 | 1.1 | — | 1.8 | — | — | 2.8 | — | — |
| 183 | 0.71 | — | 0.94 | — | — | 2.6 | — | — |
| 184 | 1.4 | — | 6.0 | — | — | 4.0 | — | — |
| 185 | 77 | — | 250 | — | — | — | — | — |
| 186 | 0.61 | — | 0.62 | — | — | 1.6 | — | — |
| 187 | 1.7 | — | 1.5 | — | — | 1.7 | 1.8 | — |
| 188 | 1.8 | — | 8.7 | — | — | 6.4 | — | — |
| 189 | 1.4 | — | 4.1 | — | — | 20 | — | — |
| 190 | 2.2 | — | 3.1 | — | — | 20 | — | — |
| 191 | 1.8 | — | 8.6 | — | — | 20 | — | — |
| 192 | 0.049 | — | 0.42 | — | — | 0.29 | — | — |
| 193 | 0.28 | 0.040 | 2.2 | — | — | 0.37 | 0.40 | — |
| 194 | 1.4 | 0.75 | 1.8 | — | — | 1.8 | 3.0 | — |
| 195 | 0.0042 | — | 0.58 | — | — | 0.33 | — | — |
| 196 | 0.037 | — | 1.0 | — | — | 0.29 | — | — |
| 197 | 0.011 | 0.0054 | 0.25 | — | — | 0.57 | 0.60 | — |
| 198 | 0.16 | — | 1.3 | — | — | 3.1 | — | — |
| 199 | 0.051 | — | 1.7 | — | — | 2.1 | — | — |
| 200 | 0.039 | — | 1.6 | — | — | 1.5 | 3.3 | — |
| 201 | 0.32 | — | 0.30 | — | — | 0.92 | 3.9 | — |
| 202 | 0.11 | — | 0.70 | — | — | 2.0 | — | — |
| 203 | 0.25 | — | 0.23 | — | — | — | — | — |
| 204 | 0.20 | — | 0.33 | — | — | — | — | — |
| 205 | 0.16 | — | 0.071 | — | — | 0.37 | — | — |
| 206 | 0.62 | — | 0.23 | — | — | 0.41 | 3.6 | — |
| 207 | 0.73 | — | 1.7 | — | — | 1.3 | 12 | — |
| 208 | 0.28 | — | 0.30 | — | — | 2.1 | — | — |
| 209 | 0.26 | — | 3.1 | — | — | 1.8 | 18 | — |
| 210 | 0.35 | — | 0.50 | — | — | 1.2 | 13 | — |
| 211 | 0.093 | — | 0.50 | — | — | 3.9 | — | — |
| 212 | 0.46 | — | 13 | — | — | 1.9 | — | — |
| 213 | 0.031 | — | 0.14 | — | — | 4.9 | — | — |

TABLE A-continued

Activity Data

| Ex. No. | DGKα LIPGLO IC$_{50}$ (μM) | DGKα ADPGLO IC$_{50}$ (μM) | DGKζ LIPGLO IC$_{50}$ (μM) | HuCD8 INFG Normalized EC$_{50}$ (μM) | msCTL INFg IC$_{50}$ (μM) | INFg Whole Blood Normalized Agonist EC$_{50}$ (μM) | DGK HWB pERK IC$_{50}$ (μM) | CD8 GLO Normalized EC$_{50}$ (μM) |
|---|---|---|---|---|---|---|---|---|
| 214 | 0.044 | — | 3.6 | — | — | 5.0 | — | — |
| 215 | 0.025 | — | 0.99 | — | — | 2.1 | — | — |
| 216 | 0.30 | — | 1.2 | — | — | 1.4 | 14 | — |
| 217 | 0.95 | — | 7.1 | — | — | 20 | — | — |
| 218 | 0.43 | — | 0.82 | — | — | 20 | — | — |
| 219 | 0.48 | — | 2.6 | — | — | — | — | — |
| 220 | 0.41 | — | 4.0 | — | — | — | — | — |
| 221 | 0.35 | — | 1.8 | — | — | — | — | — |
| 222 | 0.85 | — | 1.6 | — | — | 3.9 | — | — |
| 223 | 0.26 | — | 1.3 | — | — | 17 | — | — |
| 224 | 0.63 | — | 1.0 | — | — | 5.8 | — | — |
| 225 | 0.94 | — | 2.9 | — | — | 1.8 | — | — |
| 226 | 1.2 | — | 0.37 | — | — | 2.4 | — | — |
| 227 | 0.88 | — | 3.7 | — | — | 4.2 | — | — |
| 228 | 0.94 | — | 1.9 | — | — | 1.1 | 1.5 | — |
| 229 | 0.28 | — | 250 | — | — | — | — | — |
| 230 | 3.3 | — | 250 | — | — | — | — | — |
| 231 | 0.49 | 1.6 | 83 | — | — | 0.51 | 0.40 | — |
| 232 | 0.016 | — | 4.3 | — | — | 7.0 | — | — |
| 233 | 0.018 | — | 0.39 | — | — | 3.3 | — | — |
| 234 | 0.31 | — | 0.62 | — | — | 9.3 | — | — |
| 235 | 0.44 | — | 4.8 | — | — | 5.2 | — | — |
| 236 | 2.2 | — | 250 | — | — | 20 | — | — |
| 237 | 0.56 | — | 4.0 | 0.34 | 0.20 | 3.3 | — | — |
| 238 | 0.70 | — | 12 | 0.16 | — | — | — | — |
| 239 | 0.78 | — | 27 | 0.82 | — | — | — | — |
| 240 | 0.30 | — | 41 | 1.0 | 0.58 | 5.3 | — | — |
| 241 | 0.058 | — | 22 | 1.3 | 0.57 | 10 | — | — |
| 243 | — | 0.59 | 0.36 | — | — | — | 0.59 | — |
| 244 | — | 0.32 | 0.92 | — | — | 0.78 | 3.1 | — |
| 245 | — | 0.43 | 0.050 | — | — | 0.41 | 0.80 | — |
| 246 | — | 0.069 | 0.87 | — | — | 0.45 | 0.83 | — |
| 247 | — | 1.9 | 0.081 | — | — | — | 0.74 | — |
| 248 | — | 0.080 | 0.081 | — | — | — | 0.74 | — |
| 249 | — | 2.0 | 0.050 | — | — | — | 0.49 | — |
| 250 | — | 0.098 | 1.8 | — | — | — | 2.1 | — |
| 251 | — | 31 | 0.056 | — | — | — | 1.8 | — |
| 252 | — | 10 | 2.0 | — | — | — | 3.5 | — |
| 253 | — | 4.3 | 0.33 | — | — | — | 2.3 | — |
| 254 | — | 22 | 0.98 | — | — | — | 2.3 | — |
| 255 | — | 17 | 0.81 | — | — | — | 2.2 | — |
| 256 | — | 24 | 2.7 | — | — | — | 4.7 | — |
| 257 | — | 5.2 | 0.029 | — | — | — | 0.80 | — |
| 258 | — | 16 | 0.68 | — | — | — | 1.2 | — |
| 259 | — | 1.1 | 150 | — | — | 20 | — | — |
| 260 | — | 1.9 | 140 | — | — | — | — | — |
| 261 | — | 0.20 | 1.4 | — | — | 0.91 | 1.5 | — |
| 262 | — | 3.7 | 15 | — | — | 12 | — | — |
| 263 | — | 0.21 | 0.11 | — | — | 0.18 | 0.20 | — |
| 264 | — | 4.0 | 17 | — | — | 6.5 | — | — |
| 265 | — | 8.5 | 250 | — | — | 20 | — | — |
| 266 | — | 0.21 | 8.1 | — | — | 4.4 | — | — |
| 267 | — | 0.26 | 10 | — | — | 17 | — | — |
| 268 | — | 1.3 | 17 | — | — | 13 | — | — |
| 269 | — | 0.047 | 1.5 | — | — | 1.6 | 2.1 | — |
| 270 | — | 2.4 | 12 | — | — | 5.4 | — | — |
| 271 | — | 10 | 28 | — | — | 20 | — | — |
| 272 | — | 19 | 24 | — | — | 16 | — | — |
| 273 | — | — | 4.7 | — | — | — | — | — |
| 274 | — | 14 | 15 | — | — | 8.2 | — | — |
| 276 | — | 1.0 | 2.0 | — | — | 1.0 | — | — |
| 277 | — | 4.9 | 3.9 | — | — | 4.5 | — | — |
| 278 | — | 2.4 | 1.2 | — | — | 0.64 | — | — |
| 279 | — | 6.5 | 3.6 | — | — | 8.7 | — | — |
| 280 | — | 0.38 | 170 | — | — | 20 | — | — |
| 281 | — | 2.7 | 2.8 | — | — | 9.8 | — | — |
| 282 | — | 12 | 14 | — | — | — | — | — |
| 283 | — | 0.78 | 22 | — | — | — | — | — |
| 284 | — | 23 | 120 | — | — | — | 20 | — |
| 285 | — | 30 | 130 | — | — | — | 20 | — |
| 286 | — | 5.2 | 9.2 | — | — | — | 8.7 | — |

TABLE A-continued

Activity Data

| Ex. No. | DGKα LIPGLO IC$_{50}$ (µM) | DGKα ADPGLO IC$_{50}$ (µM) | DGKζ LIPGLO IC$_{50}$ (µM) | HuCD8 INFG Normalized EC$_{50}$ (µM) | msCTL INFg IC$_{50}$ (µM) | INFg Whole Blood Normalized Agonist EC$_{50}$ (µM) | DGK HWB pERK IC$_{50}$ (µM) | CD8 GLO Normalized EC$_{50}$ (µM) |
|---|---|---|---|---|---|---|---|---|
| 287 | — | 3.2 | 7.4 | — | — | — | — | — |
| 288 | — | 4.3 | 130 | — | — | — | 20 | — |
| 289 | — | 4.0 | 130 | — | — | — | 20 | — |
| 290 | — | 8.7 | 130 | — | — | — | — | — |
| 291 | — | 1.4 | 130 | — | — | — | — | — |
| 292 | — | 10 | 130 | — | — | — | 20 | — |
| 293 | — | 5.3 | 85 | — | — | — | 20 | — |
| 294 | — | 2.3 | 19 | — | — | — | — | — |
| 295 | — | 11 | 0.96 | — | — | — | — | — |
| 296 | — | 0.058 | 5.0 | — | — | — | 13 | — |
| 297 | — | 0.41 | 0.46 | — | — | — | 0.68 | — |
| 298 | — | 0.19 | 0.41 | — | — | — | 0.91 | — |
| 299 | — | 0.24 | 1.9 | — | — | — | 0.78 | — |
| 300 | — | 0.49 | 47 | — | — | — | 8.3 | — |
| 301 | — | 0.19 | 6.1 | — | — | — | 11 | — |
| 302 | — | — | — | — | — | — | — | — |
| 303 | — | 0.68 | 0.13 | — | — | — | 0.38 | — |
| 304 | — | — | — | — | — | — | — | — |
| 305 | — | 0.94 | 0.25 | — | — | — | 0.73 | — |
| 307 | — | 0.029 | 0.92 | — | — | — | 0.17 | — |
| 308 | — | 4.3 | 3.1 | — | — | — | — | — |
| 309 | — | 2.8 | 7.8 | — | — | — | 4.0 | — |
| 310 | — | 3.8 | 4.6 | — | — | — | 9.9 | — |
| 312 | — | 6.6 | 10 | — | — | — | 6.0 | — |
| 313 | — | 11 | 11 | — | — | — | 7.1 | — |
| 314 | — | 21 | 13 | — | — | — | 16 | — |
| 315 | — | 2.9 | 21 | — | — | — | — | — |
| 316 | — | — | — | — | — | — | — | — |
| 317 | — | — | — | — | — | — | — | — |
| 318 | — | 130 | 130 | — | — | — | 20 | — |
| 319 | — | 61 | 130 | — | — | — | — | — |
| 320 | — | 5.0 | 120 | — | — | — | — | — |
| 321 | — | 11 | 9.9 | — | — | — | — | — |
| 322 | — | 6.8 | 78 | — | — | — | 20 | — |
| 323 | — | 3.5 | 18 | — | — | — | 12 | — |
| 324 | — | 130 | 130 | — | — | — | 20 | — |
| 325 | — | 49 | 50 | — | — | — | 20 | — |
| 326 | — | 12 | 40 | — | — | — | — | — |
| 327 | — | 1.3 | 3.8 | — | — | — | 1.9 | — |
| 328 | — | 0.17 | — | — | — | — | — | — |
| 329 | — | 5.9 | 83 | — | — | — | 13 | — |
| 330 | — | 6.3 | 77 | — | — | — | 20 | — |
| 331 | — | 14 | 19 | — | — | — | 11 | — |
| 332 | — | 13 | 9.1 | — | — | — | 16 | — |
| 333 | — | 8.7 | 28 | — | — | — | 5.5 | — |
| 334 | — | 24 | 7.8 | — | — | — | 20 | — |
| 335 | — | 2.0 | 13 | — | — | — | — | — |
| 336 | — | 4.5 | 0.56 | — | — | — | — | — |
| 337 | — | 24 | 1.9 | — | — | — | — | — |
| 338 | — | 3.8 | 7.4 | — | — | — | — | — |
| 339 | — | 38 | 1.2 | — | — | — | — | — |
| 340 | — | 0.35 | 1.5 | — | — | — | — | — |
| 341 | — | 0.28 | 0.53 | — | — | — | 0.59 | — |
| 342 | — | 0.58 | 0.96 | — | — | — | 0.84 | — |
| 343 | — | 0.11 | 0.13 | — | — | — | 0.32 | — |
| 344 | — | 6.5 | 85 | — | — | — | 20 | — |
| 345 | — | 0.85 | 0.89 | — | — | — | 0.82 | — |
| 346 | — | 38 | 40 | — | — | — | 20 | — |
| 347 | — | 0.044 | 0.12 | — | — | — | 0.35 | — |
| 348 | — | — | 36 | — | — | — | — | — |
| 349 | — | 0.077 | 0.11 | — | — | — | — | — |
| 350 | — | 0.33 | 0.58 | — | — | — | — | — |
| 351 | — | 0.13 | 0.16 | — | — | — | 0.21 | — |
| 352 | — | 2.4 | 12 | — | — | — | 12 | — |
| 353 | — | 0.61 | 2.0 | — | — | — | — | — |
| 354 | — | — | — | — | — | — | 20 | — |
| 355 | — | 13 | 13 | — | — | — | 20 | — |
| 356 | — | 1.8 | 0.62 | — | — | — | 3.9 | — |
| 357 | — | 68 | 63 | — | — | — | 20 | — |
| 358 | — | 1.4 | 6.9 | — | — | — | 7.0 | — |
| 359 | — | 10 | — | — | — | — | 20 | — |

TABLE A-continued

Activity Data

| Ex. No. | DGKα LIPGLO IC$_{50}$ (μM) | DGKα ADPGLO IC$_{50}$ (μM) | DGKζ LIPGLO IC$_{50}$ (μM) | HuCD8 INFG Normalized EC$_{50}$ (μM) | msCTL INFg IC$_{50}$ (μM) | INFg Whole Blood Normalized Agonist EC$_{50}$ (μM) | DGK HWB pERK IC$_{50}$ (μM) | CD8 GLO Normalized EC$_{50}$ (μM) |
|---|---|---|---|---|---|---|---|---|
| 360 | — | 0.26 | 0.28 | — | — | — | 0.70 | — |
| 361 | — | 0.96 | 0.21 | — | — | — | 3.0 | — |
| 362 | — | 11 | 3.5 | — | — | — | 20 | — |
| 363 | — | 0.56 | 0.58 | — | — | — | 1.1 | — |
| 364 | — | 3.2 | 3.4 | — | — | — | 20 | — |
| 365 | — | 0.20 | 0.21 | — | — | — | 0.60 | — |
| 366 | — | 13 | 14 | — | — | — | 20 | — |
| 367 | — | 0.45 | 0.18 | — | — | — | 0.64 | — |
| 368 | — | 4.0 | 10 | — | — | — | — | — |
| 369 | — | 0.25 | 0.19 | — | — | — | 0.62 | — |
| 370 | — | 5.1 | 5.6 | — | — | — | 6.7 | — |
| 371 | — | 9.1 | 4.0 | — | — | — | 3.6 | — |
| 372 | — | 24 | 9.8 | — | — | — | 18 | — |
| 373 | — | 0.52 | 2.4 | — | — | — | 1.6 | — |
| 374 | — | 25 | 97 | — | — | — | 20 | — |
| 375 | — | 0.48 | 1.8 | — | — | — | 2.3 | — |
| 376 | — | 4.3 | 14 | — | — | — | 20 | — |
| 377 | — | 0.13 | 0.075 | — | — | — | 0.45 | — |
| 378 | — | 7.7 | 5.2 | — | — | — | 10 | — |
| 379 | — | 0.58 | 3.1 | — | — | — | 7.0 | — |
| 380 | — | 1.3 | 14 | — | — | — | 20 | — |
| 381 | — | 0.31 | 7.4 | — | — | — | 0.24 | — |
| 382 | — | 17 | 130 | — | — | — | 20 | — |
| 383 | — | 6.1 | 8.6 | — | — | — | 20 | — |
| 384 | — | 0.82 | 0.75 | — | — | — | 4.0 | — |
| 385 | — | 100 | 130 | — | — | — | — | — |
| 386 | — | 130 | 42 | — | — | — | 20 | — |
| 387 | — | 2.1 | 0.097 | — | — | — | 0.65 | — |
| 388 | — | — | — | — | — | — | 20 | — |
| 389 | — | 2.5 | 0.27 | — | — | — | 3.0 | — |
| 390 | — | 2.2 | 1.9 | — | — | — | 20 | — |
| 391 | — | — | — | — | — | — | 17 | — |
| 392 | — | 42 | 24 | — | — | — | 13 | — |
| 393 | — | 1.1 | 0.38 | — | — | — | 0.68 | — |
| 394 | — | 14 | 51 | — | — | — | 6.2 | — |
| 395 | — | 0.32 | 0.069 | — | — | — | 0.91 | — |
| 396 | — | 38 | 3.6 | — | — | — | 14 | — |
| 397 | — | — | 0.42 | — | — | — | 0.14 | — |
| 398 | — | — | 1.2 | — | — | — | 2.8 | — |
| 400 | — | 6.1 | 0.70 | — | — | — | 9.2 | — |
| 401 | — | 0.83 | 0.39 | — | — | — | 2.3 | — |
| 402 | — | 2.1 | 0.90 | — | — | — | 2.8 | — |
| 403 | — | 19 | 5.3 | — | — | — | 11 | — |
| 404 | — | 5.6 | 1.2 | — | — | — | 1.3 | — |
| 405 | — | 7.3 | 14 | — | — | — | — | — |
| 283A | — | 26 | 14 | — | — | — | — | — |
| 283B | — | 42 | 42 | — | — | — | — | — |

Table A lists in vitro DGK inhibition IC$_{50}$ activity values measured in the DGKα and DGKζ liposome (LIPGLO) assays.

The compounds of the present invention possess activity as an inhibitor(s) of one or both of the DGKα and DGKζ enzymes, and therefore, may be used in the treatment of diseases associated with the inhibition of DGKα and DGKζ activity.

Nucleotide sequence encoding hDGKα-(M1-S735)-Ct-TVMV-His:

(SEQ ID NO: 1)

```
  1 ATGGCCAAGG AGAGGGGCCT AATAAGCCCC AGTGATTTTG CCCAGCTGCA

51 AAAATACATG GAATACTCCA CCAAAAAGGT CAGTGATGTC CTAAAGCTCT

101 TCGAGGATGG CGAGATGGCT AAATATGTCC AAGGAGATGC CATTGGGTAC

151 GAGGGATTCC AGCAATTCCT GAAAATCTAT CTCGAAGTGG ATAATGTTCC
```

-continued

```
 201 CAGACACCTA AGCCTGGCAC TGTTTCAATC CTTTGAGACT GGTCACTGCT
 251 TAAATGAGAC AAATGTGACA AAAGATGTGG TGTGTCTCAA TGATGTTTCC
 301 TGCTACTTTT CCCTTCTGGA GGGTGGTCGG CCAGAAGACA AGTTAGAATT
 351 CACCTTCAAG CTGTACGACA CGGACAGAAA TGGGATCCTG ACAGCTCAG
 401 AAGTGGACAA AATTATCCTA CAGATGATGC GAGTGGCTGA ATACCTGGAT
 451 TGGGATGTGT CTGAGCTGAG GCCGATTCTT CAGGAGATGA TGAAAGAGAT
 501 TGACTATGAT GGCAGTGGCT CTGTCTCTCA AGCTGAGTGG GTCCGGGCTG
 551 GGGCCACCAC CGTGCCACTG CTAGTGCTGC TGGGTCTGGA GATGACTCTG
 601 AAGGACGACG GACAGCACAT GTGGAGGCCC AAGAGGTTCC CCAGACCAGT
 651 CTACTGCAAT CTGTGCGAGT CAAGCATTGG TCTTGGCAAA CAGGGACTGA
 701 GCTGTAACCT CTGTAAGTAC ACTGTTCACG ACCAGTGTGC CATGAAAGCC
 751 CTGCCTTGTG AAGTCAGCAC CTATGCCAAG TCTCGGAAGG ACATTGGTGT
 801 CCAATCACAT GTGTGGGTGC GAGGAGGCTG TGAGTCCGGG CGCTGCGACC
 851 GCTGTCAGAA AAAGATCCGG ATCTACCACA GTCTGACCGG GCTGCATTGT
 901 GTATGGTGCC ACCTAGAGAT CCACGATGAC TGCCTGCAAG CGGTGGGCCA
 951 TGAGTGTGAC TGTGGGCTGC TCCGGGATCA CATCCTGCCT CCATCTTCCA
1001 TCTATCCCAG TGTCCTGGCC TCTGGACCGG ATCGTAAAAA TAGCAAAACA
1051 AGCCAGAAGA CCATGGATGA TTTAAATTTG AGCACCTCTG AGGCTCTGCG
1101 GATTGACCCT GTTCCTAACA CCCACCCACT TCTCGTCTTT GTCAATCCTA
1151 AGAGTGGCGG GAAGCAGGGG CAGAGGGTGC TCTGGAAGTT CCAGTATATA
1201 TTAAACCCTC GACAGGTGTT CAACCTCCTA AAGGATGGTC CTGAGATAGG
1251 GCTCCGATTA TTCAAGGATG TTCCTGATAG CCGGATTTTG GTGTGTGGTG
1301 GAGACGGCAC AGTAGGCTGG ATTCTAGAGA CCATTGACAA AGCTAACTTG
1351 CCAGTTTTGC CTCCTGTTGC TGTGTTGCCC CTGGGTACTG GAAATGATCT
1401 GGCTCGATGC CTAAGATGGG GAGGAGGTTA TGAAGGACAG AATCTGGCAA
1451 AGATCCTCAA GGATTTAGAG ATGAGTAAAG TGGTACATAT GGATCGATGG
1501 TCTGTGGAGG TGATACCTCA ACAAACTGAA GAAAAAGTG ACCCAGTCCC
1551 CTTTCAAATC ATCAATAACT ACTTCTCTAT TGGCGTGGAT GCCTCTATTG
1601 CTCATCGATT CCACATCATG CGAGAGAAAT ATCCGGAGAA GTTCAACAGC
1651 AGAATGAAGA ACAAGCTATG GTACTTCGAA TTTGCCACAT CTGAATCCAT
1701 CTTCTCAACA TGCAAAAAGC TGGAGGAGTC TTTGACAGTT GAGATCTGTG
1751 GGAAACCGCT GGATCTGAGC AACCTGTCCC TAGAAGGCAT CGCAGTGCTA
1801 AACATCCCTA GCATGCATGG TGGCTCCAAC CTCTGGGGTG ATACCAGGAG
1851 ACCCCATGGG GATATCTATG GGATCAACCA GGCCTTAGGT GCTACAGCTA
1901 AAGTCATCAC CGACCCTGAT ATCCTGAAAA CCTGTGTACC AGACCTAAGT
1951 GACAAGAGAC TGGAAGTGGT TGGGCTGGAG GGTGCAATTG AGATGGGCCA
2001 AATCTATACC AAGCTCAAGA ATGCTGGACG TCGGCTGGCC AAGTGCTCTG
2051 AGATCACCTT CCACACCACA AAAACCCTTC CCATGCAAAT TGACGGAGAA
2101 CCCTGGATGC AGACGCCCTG TACAATCAAG ATCACCCACA AGAACCAGAT
2151 GCCCATGCTC ATGGGCCCAC CCCCCCGCTC CACCAATTTC TTTGGCTTCT
```

-continued

```
2201 TGAGCGGATC CTCGGAGACA GTGCGGTTTC AGGGACACCA CCACCATCAC

2251 CACTGA
```

Amino acid sequence of hDGKα-(M1-S735)-Ct-TVMV-His:

(SEQ ID NO: 2)

```
0001 MAKERGLISP SDFAQLQKYM EYSTKKVSDV LKLFEDGEMA KYVQGDAIGY EGFQQFLKIY 0060
0061 LEVDNVPRHL SLALFQSFET GHCLNETNVT KDVVCLNDVS CYFSLLEGGR PEDKLEFTFK 0120
0121 LYDTDRNGIL DSSEVDKIIL QMMRVAEYLD WDVSELRPIL QEMMKEIDYD GSGSVSQAEW 0180
0181 VRAGATTVPL LVLLGLEMTL KDDGQHMWRP KRFPRPVYCN LCESSIGLGK QGLSCNLCKY 0240
0241 TVHDQCAMKA LPCEVSTYAK SRKDIGVQSH VWVRGGCESG RCDRCQKKIR IYHSLTGLHC 0300
0301 VWCHLEIHDD CLQAVGHECD CGLLRDHILP PSSIYPSVLA SGPDRKNSKT SQKTMDDLNL 0360
0361 STSEALRIDP VPNTHPLLVF VNPKSGGKQG QRVLWKFQYI LNPRQVENLL KDGPEIGLRL 0420
0421 FKDVPDSRIL VCGGDGTVGW ILETIDKANL PVLPPVAVLP LGTGNDLARC LRWGGGYEGQ 0480
0481 NLAKILKDLE MSKVVHMDRW SVEVIPQQTE EKSDPVPFQI INNYFSIGVD ASIAHRFHIM 0540
0541 REKYPEKFNS RMKNKLWYFE FATSESIFST CKKLEESLTV EICGKPLDLS NLSLEGIAVL 0600
0601 NIPSMHGGSN LWGDTRRPHG DIYGINQALG ATAKVITDPD ILKTCVPDLS DKRLEVVGLE 0660
0661 GAIEMGQIYT KLKNAGRRLA KCSEITFHTT KTLPMQIDGE PWMQTPCTIK ITHKNQMPML 0720
0721 MGPPPRSTNF FGFLSGSSET VRFQGHHHHH H 0751
```

Nucleotide sequence encoding hDGKζ-(M1-A928)-transcript variant-2 Ct-TVMV-His:

(SEQ ID NO: 3)

```
   1 ATGGAGCCGC GGGACGGTAG CCCCGAGGCC CGGAGCAGCG ACTCCGAGTC

51 GGCTTCCGCC TCGTCCAGCG GCTCCGAGCG CGACGCCGGT CCCGAGCCGG

101 ACAAGGCGCC GCGGCGACTC AACAAGCGGC GCTTCCCGGG GCTGCGGCTC

151 TTCGGGCACA GGAAAGCCAT CACGAAGTCG GGCCTCCAGC ACCTGGCCCC

201 CCCTCCGCCC ACCCCTGGGG CCCCGTGCAG CGAGTCAGAG CGGCAGATCC

251 GGAGTACAGT GGACTGGAGC GAGTCAGCGA CATATGGGGA GCACATCTGG

301 TTCGAGACCA ACGTGTCCGG GGACTTCTGC TACGTTGGGG AGCAGTACTG

351 TGTAGCCAGG ATGCTGCAGA AGTCAGTGTC TCGAAGAAAG TGCGCAGCCT

401 GCAAGATTGT GGTGCACACG CCCTGCATCG AGCAGCTGGA GAAGATAAAT

451 TTCCGCTGTA AGCCGTCCTT CCGTGAATCA GGCTCCAGGA ATGTCCGCGA

501 GCCAACCTTT GTACGGCACC ACTGGGTACA CAGACGACGC CAGGACGGCA

551 AGTGTCGGCA CTGTGGGAAG GGATTCCAGC AGAAGTTCAC CTTCCACAGC

601 AAGGAGATTG TGGCCATCAG CTGCTCGTGG TGCAAGCAGG CATACCACAG

651 CAAGGTGTCC TGCTTCATGC TGCAGCAGAT CGAGGAGCCG TGCTCGCTGG

701 GGGTCCACGC AGCCGTGGTC ATCCCGCCCA CCTGGATCCT CCGCGCCCGG

751 AGGCCCCAGA ATACTCTGAA AGCAAGCAAG AAGAAGAAGA GGGCATCCTT

801 CAAGAGGAAG TCCAGCAAGA AAGGGCCTGA GGAGGGCCGC TGGAGACCCT

851 TCATCATCAG GCCCACCCCC TCCCCGCTCA TGAAGCCCCT GCTGGTGTTT

901 GTGAACCCCA AGAGTGGGGG CAACCAGGGT GCAAAGATCA TCCAGTCTTT

951 CCTCTGGTAT CTCAATCCCC GACAAGTCTT CGACCTGAGC CAGGGAGGGC

1001 CCAAGGAGGC GCTGGAGATG TACCGCAAAG TGCACAACCT GCGGATCCTG

1051 GCGTGCGGGG GCGACGGCAC GGTGGGCTGG ATCCTCTCCA CCCTGGACCA

1101 GCTACGCCTG AAGCCGCCAC CCCCTGTTGC CATCCTGCCC CTGGGTACTG
```

```
-continued
1151 GCAACGACTT GGCCCGAACC CTCAACTGGG GTGGGGGCTA CACAGATGAG

1201 CCTGTGTCCA AGATCCTCTC CCACGTGGAG GAGGGGAACG TGGTACAGCT

1251 GGACCGCTGG GACCTCCACG CTGAGCCCAA CCCCGAGGCA GGGCCTGAGG

1301 ACCGAGATGA AGGCGCCACC GACCGGTTGC CCCTGGATGT CTTCAACAAC

1351 TACTTCAGCC TGGGCTTTGA CGCCCACGTC ACCCTGGAGT TCCACGAGTC

1401 TCGAGAGGCC AACCCAGAGA AATTCAACAG CCGCTTTCGG AATAAGATGT

1451 TCTACGCCGG GACAGCTTTC TCTGACTTCC TGATGGGCAG CTCCAAGGAC

1501 CTGGCCAAGC ACATCCGAGT GGTGTGTGAT GGAATGGACT TGACTCCCAA

1551 GATCCAGGAC CTGAAACCCC AGTGTGTTGT TTTCCTGAAC ATCCCCAGGT

1601 ACTGTGCGGG CACCATGCCC TGGGGCCACC CTGGGGAGCA CCACGACTTT

1651 GAGCCCCAGC GGCATGACGA CGGCTACCTC GAGGTCATTG GCTTCACCAT

1701 GACGTCGTTG GCCGCGCTGC AGGTGGGCGG ACACGGCGAG CGGCTGACGC

1751 AGTGTCGCGA GGTGGTGCTC ACCACATCCA AGGCCATCCC GGTGCAGGTG

1801 GATGGCGAGC CCTGCAAGCT TGCAGCCTCA CGCATCCGCA TCGCCCTGCG

1851 CAACCAGGCC ACCATGGTGC AGAAGGCCAA GCGGCGGAGC GCCGCCCCCC

1901 TGCACAGCGA CCAGCAGCCG GTGCCAGAGC AGTTGCGCAT CCAGGTGAGT

1951 CGCGTCAGCA TGCACGACTA TGAGGCCCTG CACTACGACA AGGAGCAGCT

2001 CAAGGAGGCC TCTGTGCCGC TGGGCACTGT GGTGGTCCCA GGAGACAGTG

2051 ACCTAGAGCT CTGCCGTGCC ACATTGAGA GACTCCAGCA GGAGCCCGAT

2101 GGTGCTGGAG CCAAGTCCCC GACATGCCAG AAACTGTCCC CCAAGTGGTG

2151 CTTCCTGGAC GCCACCACTG CCAGCCGCTT CTACAGGATC GACCGAGCCC

2201 AGGAGCACCT CAACTATGTG ACTGAGATCG CACAGGATGA GATTTATATC

2251 CTGGACCCTG AGCTGCTGGG GGCATCGGCC CGGCCTGACC TCCCAACCCC

2301 CACTTCCCCT CTCCCCACCT CACCCTGCTC ACCCACGCCC CGGTCACTGC

2351 AAGGGGATGC TGCACCCCCT CAAGGTGAAG AGCTGATTGA GGCTGCCAAG

2401 AGGAACGACT TCTGTAAGCT CCAGGAGCTG CACCGAGCTG GGGGCGACCT

2451 CATGCACCGA GACGAGCAGA GTCGCACGCT CCTGCACCAC GCAGTCAGCA

2501 CTGGCAGCAA GGATGTGGTC CGCTACCTGC TGGACCACGC CCCCCCAGAG

2551 ATCCTTGATG CGGTGGAGGA AAACGGGGAG ACCTGTTTGC ACCAAGCAGC

2601 GGCCCTGGGC CAGCGCACCA TCTGCCACTA CATCGTGGAG GCCGGGGCCT

2651 CGCTCATGAA GACAGACCAG CAGGGCGACA CTCCCCGGCA GCGGGCTGAG

2701 AAGGCTCAGG ACACCGAGCT GGCCGCCTAC CTGGAGAACC GGCAGCACTA

2751 CCAGATGATC CAGCGGGAGG ACCAGGAGAC GGCTGTGGGA TCCTCGGAGA

2801 CAGTGCGGTT TCAGGGACAC CACCACCATC ACCACTGA

Amino acid sequence of hDGKζ-(M1-A928)-transcript variant-2 Ct-TVMV-His:
                                                             (SEQ ID NO: 4)
0001 MEPRDGSPEA RSSDSESASA SSSGSERDAG PEPDKAPRRL NKRRFPGIRL FGHRKAITKS 0060

0061 GLQHLAPPPP TPGAPCSESE RQIRSTVDWS ESATYGEHIW FETNVSGDFC YVGEQYCVAR 0120

0121 mLQKSVSRRK CAACKIVVHT PCIEQLEKIN FRCKPSFRES GSRNVREPTF VRHHWVHRRR 0180

0181 QDGKCRHCGK GFQQKFTFHS KEIVAISCSW CKQAYHSKVS CFMLQQIEEP CSLGVHAAVV 0240

0241 IPPTWILRAR RPQNTLKASK KKRASFKRK SSKKGPEEGR WRPFIIRPTP SPLMKPLLVF 0300

0301 VNPKSGGNQG AKIIQSFLWY LNPRQVEDLS QGGPKEALEM YRKVHNLRIL ACGGDGTVGW 0360
```

```
0361 ILSTLDQLRL KPPPPVAILP LGTGNDLART LNWGGGYTDE PVSKILSHVE EGNVVQLDRW 0420

0421 DLHAEPNPEA GPEDRDEGAT DRLPLDVENN YFSLGFDAHV TLEFHESREA NPEKFNSRFR 0480

0481 NKMFYAGTAF SDFLMGSSKD LAKHIRVVCD GMDLTPKIQD LKPQCVVFLN IPRYCAGTMP 0540

0541 WGHPGEHHDF EPQRHDDGYL EVIGFTMTSL AALQVGGHGE RLTQCREVVL TTSKAIPVQV 0600

0601 DGEPCKLAAS RIRIALRNQA TMVQKAKRRS AAPLHSDQQP VPEQLRIQVS RVSMHDYEAL 0660

0661 HYDKEQLKEA SVPLGTVVVP GDSDLELCRA HIERLQQEPD GAGAKSPTCQ KLSPKWCFLD 0720

0721 ATTASRFYRI DRAQEHLNYV TEIAQDEIYI LDPELLGASA RPDLPTPTSP LPTSPCSPTP 0780

0781 RSLQGDAAPP QGEELIEAAK RNDFCKLQEL HRAGGDLMHR DEQSRTLLHH AVSTGSKDVV 0840

0841 RYLLDHAPPE ILDAVEENGE TCLHQAAALG QRTICHYIVE AGASLMKTDQ QGDTPRQRAE 0900

0901 KAQDTELAAY LENRQHYQMI QREDQETAVG SSETVRFQGH HHHHH 0945
```

Nucleotide sequence encoding MA-hDGKα-(S9-S727)-Ct-TVMV-His:
(SEQ ID NO: 5)

```
0001 ATGGCTTCCC CAAGCGACTT CGCCCAGCTG CAGAAGTACA TGGAATACAG CACCAAGAAG 0060

0061 GTGTCTGACG TCCTGAAGCT GTTCGAGGAC GGTGAAATGG CTAAGTACGT CCAGGGCGAC 0120

0121 GCTATCGGAT ACGAGGGATT CCAGCAGTTC TGAAGATCT ACCTGGAAGT GGACAACGTC 0180

0181 CCCAGGCACC TGTCACTGGC TCTGTTCCAG TCCTTCGAGA CTGGCCACTG CCTGAACGAA 0240

0241 ACCAACGTCA CTAAGGACGT GGTCTGCCTG AACGACGTGA GCTGCTACTT CTCTCTGCTG 0300

0301 GAGGGTGGCA GACCAGAGGA CAAGCTGGAA TTCACCTTCA GCTGTACGA CACTGACCGC 0360

0361 AACGGAATCC TGGACTCCAG CGAAGTGGAC AAGATCATCC TGCAGATGAT GCGTGTCGCT 0420

0421 GAGTACCTGG ACTGGGACGT GAGCGAACTG AGGCCTATCC TGCAGGAGAT GATGAAGGAA 0480

0481 ATCGACTACG ACGGCTCTGG ATCAGTGTCC CAGGCTGAGT GGGTCCGCGC TGGTGCTACC 0540

0541 ACTGTGCCAC TGCTGGTCCT GCTGGGACTG GAAATGACCC TGAAGGACGA CGGTCAGCAC 0600

0601 ATGTGGCGCC CAAAGCGTTT CCCCAGGCCA GTCTACTGCA ACCTGTGCGA GTCTTCAATC 0660

0661 GGTCTGGGCA AGCAGGGCCT GTCATGCAAC CTGTGCAAGT ACACCGTGCA CGACCAGTGC 0720

0721 GCTATGAAGG CCCTGCCCTG CGAGGTCTCA ACTTACGCTA AGTCCCGTAA GGACATCGGA 0780

0781 GTGCAGTCAC ACGTGTGGGT CAGGGGAGGT TGCGAATCCG GTAGATGCGA CCGCTGCCAG 0840

0841 AAGAAGATCC GTATCTACCA CTCCCTGACC GGACTGCACT GCGTCGGTG CCACCTGGAG 0900

0901 ATCCACGACG ACTGCCTGCA GGCCGTGGGA CACGAATGCG ACTGCGGTCT GCTGCGTGAC 0960

0961 CACATCCTGC CTCCCTCCAG CATCTACCCT TCAGTCCTGG CTTCCGGTCC GACAGGAAG 1020

1021 AACAGCAAGA CCTCTCAGAA GACTATGGAC GACCTGAACC TGAGCACCTC TGAGGCCCTG 1080

1081 CGCATCGACC TGTGCCCAA CACTCACCCA CTGCTGGTGT TCGTCAACCC TAAGAGCGGC 1140

1141 GGAAAGCAGG GTCAGAGAGT CCTGTGGAAG TTCCAGTACA TCCTGAACCC ACGCCAGGTG 1200

1201 TTCAACCTGC TGAAGGACGG CCCTGAGATC GGACTGAGAC TGTTCAAGGA CGTGCCCGAC 1260

1261 TCTCGCATCC TCGTCTGCGG TGGCGACGGT ACTGTGGGAT GGATCCTGGA AACTATCGAC 1320

1321 AAGGCTAACC TGCCAGTGCT GCCACCTGTG CTGTCCTGC CACTGGGAAC CGGTAACGAC 1380

1381 CTGGCTCGTT GCCTGCGTTG GGGAGGTGGC TACGAGGGAC AGAACCTGGC CAAGATCCTG 1440

1441 AAGGACCTGG AAATGAGCAA GGTGGTCCAC ATGGACAGAT GGTCTGTGGA GGTCATCCCA 1500

1501 CAGCAGACTG AGGAAAAGTC AGACCCAGTC CCTTTCCAGA TCATCAACAA CTACTTCAGC 1560

1561 ATCGGTGTGG ACGCTTCTAT CGCCCACAGA TTCCACATCA TGCGCGAGAA GTACCCTGAA 1620

1621 AAGTTCAACT CCCGCATGAA GAACAAGCTG TGGTACTTCG AGTTCGCTAC CTCAGAATCC 1680

1681 ATCTTCTCAA CTTGCAAGAA GCTGGAGGAA TCCCTGACCG TCGAGATCTG CGGCAAGCCT 1740
```

-continued

```
1741 CTGGACCTGT CAAACCTGTC CCTGGAAGGC ATCGCTGTGC TGAACATCCC AAGCATGCAC 1800

1801 GGAGGTTCTA ACCTCTGGGG CGACACTAGG AGGCCTCACG GTGACATCTA CGGCATCAAC 1860

1861 CAGGCCCTGG GAGCTACCGC CAAGGTCATC ACTGACCCCG ACATCCTGAA GACCTGCGTG 1920

1921 CCAGACCTGA GCGACAAGCG TCTGGAGGTG GTCGGACTGG AGGGTGCCAT CGAAATGGGC 1980

1981 CAGATCTACA CTAAGCTGAA GAACGCTGGA AGGAGACTGG CCAAGTGCTC TGAGATCACC 2040

2041 TTCCACACCA CTAAGACTCT GCCTATGCAG ATCGACGGTG AACCCTGGAT GCAGACCCCA 2100

2101 TGCACTATCA AGATCACCCA CAAGAACCAG ATGCCCATGC TGATGGGTCC TCCTCCTCGC 2160

2161 TCTGGATCTT CAGAAACTGT GAGGTTCCAG GGCCACCACC ACCACCACCA CTGA 2214
```

Amino acid sequence of MA-hDGKα-(S9-S727)-Ct-TVMV-His:

(SEQ ID NO: 6)
```
0001 MASPSDFAQL QKYMEYSTKK VSDVLKLFED GEMAKYVQGD AIGYEGFQQF LKIYLEVDNV 0060

0061 PRHLSLALFQ SFETGHCLNE TNVTKDVVCL NDVSCYFSLL EGGRPEDKLE FTFKLYDTDR 0120

0121 NGILDSSEVD KIILQMMRVA EYLDWDVSEL RPILQEMMKE IDYDGSGSVS QAEWVRAGAT 0180

0181 TVPLLVLLGL EMTLKDDGQH MWRPKRFPRP VYCNLCESSI GLGKQGLSCN LCKYTVHDQC 0240

0241 AMKALPCEVS TYAKSRKDIG VQSHVWVRGG CESGRCDRCQ KKIRIYHSLT GLHCVWCHLE 0300

0301 IHDDCLQAVG HECDCGLLRD HILPPSSIYP SVLASGPDRK NSKTSQKTMD DLNLSTSEAL 0360

0361 RIDPVPNTHP LLVFVNPKSG GKQGQRVLWK FQYILNPRQV FNLLKDGPEI GLRLFKDVPD 0420

0421 SRILVCGGDG TVGWILETID KANLPVLPPV AVLPLGTGND LARCLRWGGG YEGQNLAKIL 0480

0481 KDLEMSKVVH MDRWSVEVIP QQTEEKSDPV PFQIINNYFS IGVDASIAHR FHIMREKYPE 0540

0541 KFNSRMKNKL WYFEFATSES IFSTCKKLEE SLTVEICGKP LDLSNLSLEG IAVLNIPSMH 0600

0601 GGSNLWGDTR RPHGDIYGIN QALGATAKVI TDPDILKTCV PDLSDKRLEV VGLEGAIEMG 0660

0661 QIYTKLKNAG RRLAKCSEIT FHTTKTLPMQ IDGEPWMQTP CTIKITHKNQ MPMLMGPPPR 0720

0721 SGSSETVRFQ GHHHHHH 0737
```

---

What is claimed is:

1. A compound of Formula (I):

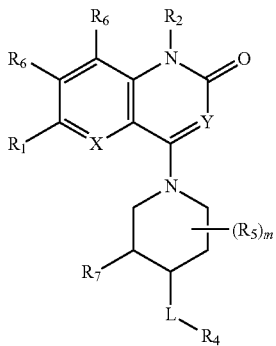

or a salt thereof, wherein:

X is or N;

Y is $CR_3$ or N;

L is —O—, —S—, —S(O)$_2$—, —NR$_{4c}$—, or —NR$_{4d}$C(O)—;

$R_1$ is H, F, Cl, Br, —CN, $C_{1-3}$ alkyl substituted with zero to 4 $R_{1a}$, $C_{3-4}$ cycloalkyl substituted with zero to 4 $R_{1a}$, $C_{1-3}$ alkoxy substituted with zero to 4 $R_{1a}$, —C(O)NR$_a$R$_a$, —NR$_a$R$_a$, —S(O)$_n$R$_e$, or —P(O)R$_e$R$_e$;

each $R_{1a}$ is independently F, Cl, —CN, —OH, —OCH$_3$, or —NR$_a$R$_a$;

each $R_a$ is independently H or $C_{1-3}$ alkyl;

each $R_e$ is independently $C_{3-4}$ cycloalkyl or $C_{1-3}$ alkyl substituted with zero to 4 $R_{1a}$;

$R_2$ is H, $C_{1-3}$ alkyl substituted with zero to 4 $R_{2a}$, $C_{2-3}$ alkenyl substituted with zero to 4 $R_{2a}$, or $C_{3-4}$ cycloalkyl substituted with zero to 4 $R_{2a}$;

each $R_{2a}$ is independently F, Cl, —CN, —OH, —O($C_{1-2}$ alkyl), $C_{3-4}$ cycloalkyl, $C_{3-4}$ alkenyl, or $C_{3-4}$ alkynyl;

$R_3$ is H, F, Cl, Br, —CN, $C_{1-3}$ alkyl, $C_{1-2}$ fluoroalkyl, $C_{3-4}$ cycloalkyl, $C_{3-4}$ fluorocycloalkyl, —NO$_2$, or pyridinyl substituted with zero to 2 $R_{3a}$;

each $R_{3a}$ is halo, —CN, $C_{1-3}$ alkyl, or $C_{1-3}$ alkoxy;

$R_4$ is $R_{4a}$, —CH$_2$R$_{4a}$, or —CH$_2$CH$_2$R$_{4a}$;

$R_{4a}$ is $C_{3-6}$ cycloalkyl, $C_{5-14}$ heterocyclyl, $C_{6-10}$ aryl, or $C_{5-14}$ heteroaryl, each substituted with zero to 4 $R_{4b}$;

each $R_{4b}$ is independently F, Cl, Br, —CN, —OH, $C_{1-6}$ alkyl, $C_{1-3}$ fluoroalkyl, $C_{1-4}$ hydroxyalkyl, —(CH$_2$)$_{1-2}$O($C_{1-3}$ alkyl), $C_{1-4}$ alkoxy, —O($C_{1-4}$ hydroxyalkyl), $C_{1-3}$ fluoroalkoxy, —OCH$_2$CH=CH$_2$, —OCH$_2$C≡CH, —C(O)($C_{1-4}$ alkyl), —C(O)OH, —C(O)O($C_{1-4}$ alkyl), —C(O)NH$_2$, —C(O)NH($C_{1-4}$ alkyl), —C(O)N($C_{1-4}$ alkyl)$_2$, —NR$_c$R$_c$, —NR$_a$S(O)$_2$($C_{1-3}$ alkyl), —NR$_a$C(O)($C_{1-3}$ alkyl), —NR$_a$C(O)O($C_{1-4}$ alkyl), —P(O)($C_{1-3}$ alkyl)$_2$, —S(O)$_2$($C_{1-3}$ alkyl), —O(CH$_2$)$_{1-2}$($C_{3-6}$ cycloalkyl), —O(CH$_2$)$_{1-2}$(morpholinyl), $C_{3-6}$ cycloalkyl, cyanocyclopropyl, methylazetidinyl, acetylazetidinyl, triazolyl, tetrahydropyranyl, morpholinyl, thiophenyl, methylpiperidinyl, or —CR$_c$R$_c$(phenyl);

each $R_c$ is independently H or $C_{1-2}$ alkyl;

$R_{4c}$ is H, $C_{1-6}$ alkyl, or $R_{4a}$;

$R_{4d}$ is H or $C_{1-6}$ alkyl;

each R$_5$ is independently F, Cl, —CN, —OH, C$_{1-6}$ alkyl substituted with zero to 4 R$_g$, C$_{1-3}$ alkoxy substituted with zero to 4 R$_g$, C$_{2-4}$ alkenyl substituted with zero to 4 R$_g$, C$_{2-4}$ alkynyl substituted with zero to 4 R$_g$, —(CH$_2$)$_{1-2}$(C$_{3-4}$ cycloalkyl substituted with zero to 4 R$_g$), phenyl substituted with zero to 4 R$_g$, oxadiazolyl substituted with zero to 3 R$_g$, pyridinyl substituted with zero to 4 R$_g$, —(CH$_2$)$_{1-2}$(heterocyclyl substituted with zero to 4 R$_g$), —(CH$_2$)$_{1-2}$NR$_c$C(O)(C$_{1-4}$ alkyl), —(CH$_2$)$_{1-2}$NR$_c$C(O)O(C$_{1-4}$ alkyl), —O(CH$_2$)$_{1-2}$(heterocyclyl substituted with zero to 4 R$_g$), —(CH$_2$)$_{1-2}$NR$_c$S(O)$_2$(C$_{1-4}$ alkyl), —C(O)(C$_{1-4}$ alkyl), —C(O)OH, —C(O)O(C$_{1-4}$ alkyl), —C(O)O(C$_{3-4}$ cycloalkyl), —C(O)NR$_a$R$_a$, or —C(O)NR$_a$(C$_{3-4}$ cycloalkyl), or two R$_5$ attached to the same carbon atom form =O;

each R$_g$ is independently F, Cl, —CN, —OH, C$_{1-3}$ alkoxy, C$_{1-3}$ fluoroalkoxy, —O(CH$_2$)$_{1-2}$O(C$_{1-2}$ alkyl), C$_{3-5}$ cycloalkyl, or —NR$_c$R$_c$;

each R$_6$ is H, F, Cl, —CN, —CH$_3$, —CH$_2$F, —CHF$_2$, —CF$_3$, or —OCH$_3$;

R$_7$ is H or —CH$_3$;

m is zero, 1, 2, or 3; and n is zero, 1, or 2.

2. The compound according to claim 1 or a salt thereof, wherein:

R$_1$ is H, F, Cl, Br, —CN, C$_{1-3}$ alkyl substituted with zero to 4 R$_{1a}$, cyclopropyl substituted with zero to 3 R$_{1a}$, C$_{1-3}$ alkoxy substituted with zero to 3 R$_{1a}$, —C(O)NR$_a$R$_a$, —NR$_a$R$_a$, —S(O)$_n$CH$_3$, or —P(O)(CH$_3$)$_2$;

each R$_{1a}$ is independently F, Cl, or —CN;

each R$_a$ is independently H or C$_{1-3}$ alkyl;

R$_2$ is H, C$_{1-2}$ alkyl substituted with zero to 2 R$_{2a}$, or C$_{2-3}$ alkenyl substituted with zero to 2 R$_{2a}$;

each R$_{2a}$ is independently F, Cl, —CN, —OH, —O(C$_{1-2}$ alkyl), cyclopropyl, C$_{3-4}$ alkenyl, or C$_{3-4}$ alkynyl;

R$_3$ is H, F, Cl, Br, —CN, C$_{1-2}$ alkyl, C$_{1-2}$ fluoroalkyl, C$_{3-4}$ cycloalkyl, —NO$_2$, or pyridinyl substituted with zero to 1 R$_{3a}$;

R$_{4a}$ is C$_{3-6}$ cycloalkyl, oxetanyl, tetrahydrofuranyl, tetrahydropyranyl, piperidinyl, piperazinyl, morpholinyl, phenyl, naphthalenyl, furanyl, pyranyl, pyrrolyl, pyrazolyl, imidazolyl, isoxazolyl, oxazolyl, oxadiazolyl, triazolyl, indolyl, indazolyl, phthalazinyl, pyridazinyl, pyridinyl, pyrimidinyl, pyrazinyl, triazinyl, benzooxazolyl, benzothiazolyl, benzoimidazolyl, quinolinyl, isoquinolinyl, quinoxalinyl, quinazolinyl, naphthyridinyl, or dihydrobenzo[b][1,4]dioxepinyl, each substituted with zero to 3 R$_{4b}$;

each R$_{4b}$ is independently F, Cl, Br, —CN, —OH, C$_{1-6}$ alkyl, C$_{1-2}$ fluoroalkyl, C$_{1-3}$ hydroxyalkyl, —(CH$_2$)$_{1-2}$O(C$_{1-3}$ alkyl), C$_{1-4}$ alkoxy, —O(C$_{1-3}$ hydroxyalkyl), C$_{1-2}$ fluoroalkoxy, —C(O)(C$_{1-3}$ alkyl), —C(O)OH, —C(O)O(C$_{1-3}$ alkyl), —C(O)NH$_2$, —C(O)NH(C$_{1-3}$ alkyl), —C(O)N(C$_{1-3}$ alkyl)$_2$, —NR$_c$R$_c$, —S(O)$_2$(C$_{1-2}$ alkyl), C$_{3-6}$ cycloalkyl, or —CR$_c$R$_c$(phenyl);

R$_{4c}$ is H, C$_{1-4}$ alkyl, or R$_{4a}$;

R$_{4d}$ is H or C$_{1-4}$ alkyl;

each R$_5$ is independently F, —CN, —OH, C$_{1-5}$ alkyl substituted with zero to 4 R$_g$, C$_{1-3}$ alkoxy substituted with zero to 3 R$_g$, C$_{2-3}$ alkenyl substituted with zero to 4 R$_g$, C$_{2-3}$ alkynyl substituted with zero to 4 R$_g$, —(CH$_2$)$_{1-2}$(C$_{3-4}$ cycloalkyl substituted with zero to 4 R$_g$), phenyl substituted with zero to 3 R$_g$, oxadiazolyl substituted with zero to 3 R$_g$, pyridinyl substituted with zero to 3 R$_g$, —(CH$_2$)$_{1-2}$ (heterocyclyl substituted with zero to 4 R$_g$), —O(CH$_2$)$_{1-2}$(heterocyclyl substituted with zero to 4 R$_g$), —(CH$_2$)$_{1-2}$NR$_c$C(O)(C$_{1-4}$ alkyl), —(CH$_2$)$_{1-2}$NR$_c$C(O)O(C$_{1-4}$ alkyl), —(CH$_2$)$_{1-2}$NR$_c$S(O)$_2$(C$_{1-4}$ alkyl), —C(O)(C$_{1-4}$ alkyl), —C(O)OH, —C(O)O(C$_{1-4}$ alkyl), —C(O)O(C$_{3-4}$ cycloalkyl), —C(O)NR$_a$R$_a$, or —C(O)NR$_a$(C$_{3-4}$ cycloalkyl); and each R$_6$ is H, F, or —CH$_3$.

3. The compound according to claim 1 or a salt thereof, wherein:

L is —O—, —NH—, —N(CH$_3$)—, or —N(CH$_3$)C(O)—;

R$_1$ is F, Cl, Br, —CN, —OCH$_3$, or —C(O)NH$_2$;

R$_2$ is —CH$_3$;

R$_3$ is H, F, Cl, Br, —CN, —CH$_3$, —NO$_2$, methylpyridinyl, or methoxypyridinyl;

R$_4$ is R$_{4a}$ or —CH$_2$R$_{4a}$;

R$_{4a}$ is cyclohexyl, phenyl, indazolyl, phthalazinyl, pyridazinyl, pyridinyl, pyrimidinyl, pyrazinyl, benzooxazolyl, benzothiazolyl, quinolinyl, quinoxalinyl, quinazolinyl, 1,7-naphthyridinyl, or dihydrobenzo[b][1,4] dioxepinyl, each substituted with zero to 3 R$_{4b}$;

each R$_{4b}$ is independently F, Cl, Br, —CN, —CH$_3$, —CH$_2$CH$_3$, —CH$_2$CH$_2$CH$_3$, —CH(CH$_3$)$_2$, —CH$_2$CH$_2$CH$_2$CH$_3$, —C(CH$_3$)$_3$, —CH$_2$CH$_2$CH$_2$CH$_2$CH$_3$, —C(CH$_3$)$_2$CH$_2$CH$_3$, —CHF$_2$, —CF$_3$, —OCH$_3$, —OCH(CH$_3$)$_2$, —OC(CH$_3$)$_3$, —OCF$_3$, —C(O)N(CH$_3$)$_2$, —S(O)$_2$CH$_3$, —CH$_2$(phenyl), —C(CH$_3$)$_2$(phenyl), cyclopropyl, cyclopentyl, or cyclohexyl;

each R$_5$ is independently hydrogen, F, —OH, C$_{1-2}$ alkyl, C$_{1-3}$ alkoxy, —CH$_2$CF$_3$, —OCH$_2$CH$_2$OCH$_3$, —OCH$_2$CH$_2$N(CH$_3$)$_2$, —OCH$_2$(cyclopropyl), or —OCH$_2$CH$_2$(morpholinyl); and each R$_6$ is H.

4. The compound according to claim 1 or a salt thereof, wherein:

Y is CR$_3$.

5. The compound according to claim 1 or a salt thereof, wherein:

Y is N.

6. The compound according to claim 1 or a salt thereof, wherein L is —O—.

7. The compound according to claim 1 or a salt thereof, wherein L is —NR$_{4c}$—.

8. The compound according to claim 1 or a salt thereof, wherein L is —NR$_{4d}$C(O)—.

9. The compound according to claim 1 or a salt thereof, having a structure selected from:

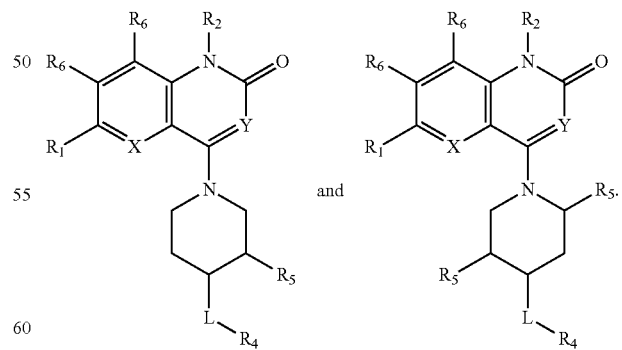

and

10. A compound or a salt thereof, wherein said compound is:

6-chloro-4-(4-(3-methoxyphenoxy)piperidin-1-yl)-1-methyl-2-oxo-1,2-dihydro-1,5-naphthyridine-3-carbonitrile;

6-chloro-1-methyl-2-oxo-4-(4-(2-(trifluoromethyl)phenoxy)piperidin-1-yl)-1,2-dihydro-1,5-naphthyridine-3-carbonitrile;
6-chloro-4-(4-(3,4-difluorophenoxy)piperidin-1-yl)-1-methyl-2-oxo-1,2-dihydro-1,5-naphthyridine-3-carbonitrile;
6-chloro-1-methyl-2-oxo-4-(4-(3-(trifluoromethoxy)phenoxy)piperidin-1-yl)-1,2-dihydro-1,5-naphthyridine-3-carbonitrile;
6-chloro-4-(4-(4-methoxyphenoxy)piperidin-1-yl)-1-methyl-2-oxo-1,2-dihydro-1,5-naphthyridine-3-carbonitrile;
4-(4-(4-(tert-butyl)phenoxy)piperidin-1-yl)-6-chloro-1-methyl-2-oxo-1,2-dihydro-1,5-naphthyridine-3-carbonitrile;
6-chloro-4-(4-(4-chlorophenoxy)piperidin-1-yl)-1-methyl-2-oxo-1,2-dihydro-1,5-naphthyridine-3-carbonitrile;
6-chloro-4-(4-(3-fluoro-4-(trifluoromethoxy)phenoxy)piperidin-1-yl)-1-methyl-2-oxo-1,2-dihydro-1,5-naphthyridine-3-carbonitrile;
6-chloro-4-(4-(2-chlorophenoxy)piperidin-1-yl)-1-methyl-2-oxo-1,2-dihydro-1,5-naphthyridine-3-carbonitrile;
6-chloro-1-methyl-2-oxo-4-(4-(4-(trifluoromethoxy)phenoxy)piperidin-1-yl)-1,2-dihydro-1,5-naphthyridine-3-carbonitrile;
6-chloro-4-(4-(4-fluorophenoxy)piperidin-1-yl)-1-methyl-2-oxo-1,2-dihydro-1,5-naphthyridine-3-carbonitrile;
6-chloro-1-methyl-2-oxo-4-(4-(p-tolyloxy)piperidin-1-yl)-1,2-dihydro-1,5-naphthyridine-3-carbonitrile;
6-chloro-1-methyl-2-oxo-4-(4-(m-tolyloxy)piperidin-1-yl)-1,2-dihydro-1,5-naphthyridine-3-carbonitrile;
6-chloro-4-(4-(2-chloro-5-fluorophenoxy)piperidin-1-yl)-1-methyl-2-oxo-1,2-dihydro-1,5-naphthyridine-3-carbonitrile;
6-chloro-1-methyl-2-oxo-4-(4-(3-(trifluoromethyl)phenoxy)piperidin-1-yl)-1,2-dihydro-1,5-naphthyridine-3-carbonitrile;
4-((1-(6-chloro-3-cyano-1-methyl-2-oxo-1,2-dihydro-1,5-naphthyridin-4-yl)piperidin-4-yl)oxy)-N,N-dimethylbenzamide;
4-(4-(4-bromo-2-methylphenoxy)piperidin-1-yl)-6-chloro-1-methyl-2-oxo-1,2-dihydro-1,5-naphthyridine-3-carbonitrile;
6-chloro-4-(4-(3-chlorophenoxy)piperidin-1-yl)-1-methyl-2-oxo-1,2-dihydro-1,5-naphthyridine-3-carbonitrile;
6-chloro-4-(4-(3-chloro-5-fluorophenoxy)piperidin-1-yl)-1-methyl-2-oxo-1,2-dihydro-1,5-naphthyridine-3-carbonitrile;
6-chloro-1-methyl-4-(4-(2-methyl-4-(trifluoromethoxy)phenoxy)piperidin-1-yl)-2-oxo-1,2-dihydro-1,5-naphthyridine-3-carbonitrile;
6-chloro-1-methyl-2-oxo-4-(4-(4-(trifluoromethyl)phenoxy)piperidin-1-yl)-1,2-dihydro-1,5-naphthyridine-3-carbonitrile;
4-(4-(4-(tert-butoxy)phenoxy)piperidin-1-yl)-6-chloro-1-methyl-2-oxo-1,2-dihydro-1,5-naphthyridine-3-carbonitrile;
6-chloro-4-(4-(4-cyanophenoxy)piperidin-1-yl)-1-methyl-2-oxo-1,2-dihydro-1,5-naphthyridine-3-carbonitrile;
6-chloro-1-methyl-2-oxo-4-(4-(2-(trifluoromethoxy)phenoxy)piperidin-1-yl)-1,2-dihydro-1,5-naphthyridine-3-carbonitrile;
6-chloro-4-(4-(3-cyanophenoxy)piperidin-1-yl)-1-methyl-2-oxo-1,2-dihydro-1,5-naphthyridine-3-carbonitrile;
6-chloro-4-(4-(2-methoxyphenoxy)piperidin-1-yl)-1-methyl-2-oxo-1,2-dihydro-1,5-naphthyridine-3-carbonitrile;
6-chloro-4-(4-(4-fluoro-2-methoxyphenoxy)piperidin-1-yl)-1-methyl-2-oxo-1,2-dihydro-1,5-naphthyridine-3-carbonitrile;
6-chloro-4-(4-(4-isopropylphenoxy)piperidin-1-yl)-1-methyl-2-oxo-1,2-dihydro-1,5-naphthyridine-3-carbonitrile;
6-chloro-4-(4-(3-chloro-4-cyanophenoxy)piperidin-1-yl)-1-methyl-2-oxo-1,2-dihydro-1,5-naphthyridine-3-carbonitrile;
6-chloro-4-(4-(4-chloro-3-methoxyphenoxy)piperidin-1-yl)-1-methyl-2-oxo-1,2-dihydro-1,5-naphthyridine-3-carbonitrile;
6-chloro-4-(4-(3-chloro-4-methylphenoxy)piperidin-1-yl)-1-methyl-2-oxo-1,2-dihydro-1,5-naphthyridine-3-carbonitrile;
6-chloro-4-(4-(2-chloro-4-(trifluoromethoxy)phenoxy)piperidin-1-yl)-1-methyl-2-oxo-1,2-dihydro-1,5-naphthyridine-3-carbonitrile;
6-chloro-4-(4-(3-chloro-4-(trifluoromethoxy)phenoxy)piperidin-1-yl)-1-methyl-2-oxo-1,2-dihydro-1,5-naphthyridine-3-carbonitrile;
6-chloro-4-(4-(2-cyanophenoxy)piperidin-1-yl)-1-methyl-2-oxo-1,2-dihydro-1,5-naphthyridine-3-carbonitrile;
6-chloro-4-(4-(2-fluorophenoxy)piperidin-1-yl)-1-methyl-2-oxo-1,2-dihydro-1,5-naphthyridine-3-carbonitrile;
6-chloro-4-(4-(3-fluorophenoxy)piperidin-1-yl)-1-methyl-2-oxo-1,2-dihydro-1,5-naphthyridine-3-carbonitrile;
6-chloro-1-methyl-2-oxo-4-(4-phenoxypiperidin-1-yl)-1,2-dihydro-1,5-naphthyridine-3-carbonitrile;
6-bromo-1-methyl-2-oxo-4-(4-(4-(trifluoromethoxy)phenoxy)piperidin-1-yl)-1,2-dihydro-1,5-naphthyridine-3-carbonitrile;
6-methoxy-1-methyl-2-oxo-4-(4-(4-(trifluoromethoxy)phenoxy)piperidin-1-yl)-1,2-dihydro-1,5-naphthyridine-3-carbonitrile;
1-methyl-2,6-dioxo-4-(4-(4-(trifluoromethoxy)phenoxy)piperidin-1-yl)-1,2,5,6-tetrahydro-1,5-naphthyridine-3-carbonitrile;
5-methyl-6-oxo-8-(4-(4-(trifluoromethoxy)phenoxy)piperidin-1-yl)-5,6-dihydro-1,5-naphthyridine-2,7-dicarbonitrile;
5-methyl-7-nitro-6-oxo-8-(4-(4-(trifluoromethoxy)phenoxy)piperidin-1-yl)-5,6-dihydro-1,5-naphthyridine-2-carbonitrile;
5-methyl-6-oxo-8-(4-(4-(trifluoromethoxy)phenoxy)piperidin-1-yl)-5,6-dihydro-1,5-naphthyridine-2-carbonitrile;
4-(4-(4-(tert-butyl)phenoxy)piperidin-1-yl)-1-methyl-2-oxo-1,2-dihydroquinoline-6-carbonitrile;
5-methyl-6-oxo-8-(4-(4-(tert-pentyl)phenoxy)piperidin-1-yl)-5,6-dihydro-1,5-naphthyridine-2-carbonitrile;
8-(4-(4-benzylphenoxy)piperidin-1-yl)-5-methyl-6-oxo-5,6-dihydro-1,5-naphthyridine-2-carbonitrile;
8-(4-(4-butylphenoxy)piperidin-1-yl)-5-methyl-6-oxo-5,6-dihydro-1,5-naphthyridine-2-carbonitrile;
5-methyl-6-oxo-8-(4-(4-propylphenoxy)piperidin-1-yl)-5,6-dihydro-1,5-naphthyridine-2-carbonitrile;

8-(4-(4-cyclopentylphenoxy)piperidin-1-yl)-5-methyl-6-oxo-5,6-dihydro-1,5-naphthyridine-2-carbonitrile;

8-(4-(4-cyclopropylphenoxy)piperidin-1-yl)-5-methyl-6-oxo-5,6-dihydro-1,5-naphthyridine-2-carbonitrile;

8-(4-(4-isopropyl-3-methylphenoxy)piperidin-1-yl)-5-methyl-6-oxo-5,6-dihydro-1,5-naphthyridine-2-carbonitrile;

5-methyl-6-oxo-8-(4-((5,6,7,8-tetrahydronaphthalen-2-yl)oxy)piperidin-1-yl)-5,6-dihydro-1,5-naphthyridine-2-carbonitrile;

5-methyl-6-oxo-8-(4-(4-pentylphenoxy)piperidin-1-yl)-5,6-dihydro-1,5-naphthyridine-2-carbonitrile;

8-(4-(4-cyclohexylphenoxy)piperidin-1-yl)-5-methyl-6-oxo-5,6-dihydro-1,5-naphthyridine-2-carbonitrile;

8-(4-(4-(2-cyclohexylpropan-2-yl)phenoxy)piperidin-1-yl)-5-methyl-6-oxo-5,6-dihydro-1,5-naphthyridine-2-carbonitrile;

8-(4-(4-(tert-butoxy)phenoxy)piperidin-1-yl)-5-methyl-6-oxo-5,6-dihydro-1,5-naphthyridine-2-carbonitrile;

8-(4-((5-isopropoxypyridin-2-yl)oxy)piperidin-1-yl)-5-methyl-6-oxo-5,6-dihydro-1,5-naphthyridine-2-carbonitrile;

8-(4-((5-chloropyridin-2-yl)oxy)piperidin-1-yl)-5-methyl-6-oxo-5,6-dihydro-1,5-naphthyridine-2-carbonitrile;

8-(4-((6-(tert-butyl)pyridazin-3-yl)oxy)piperidin-1-yl)-5-methyl-6-oxo-5,6-dihydro-1,5-naphthyridine-2-carbonitrile;

5-methyl-6-oxo-8-(4-(quinoxalin-2-yloxy)piperidin-1-yl)-5,6-dihydro-1,5-naphthyridine-2-carbonitrile;

8-(4-((2,6-dimethylpyrimidin-4-yl)oxy)piperidin-1-yl)-5-methyl-6-oxo-5,6-dihydro-1,5-naphthyridine-2-carbonitrile;

5-methyl-6-oxo-8-(4-(quinazolin-4-yloxy)piperidin-1-yl)-5,6-dihydro-1,5-naphthyridine-2-carbonitrile;

5-methyl-8-(4-((2-methylpyrimidin-4-yl)oxy)piperidin-1-yl)-6-oxo-5,6-dihydro-1,5-naphthyridine-2-carbonitrile;

8-(4-((7-chloro-4-methoxyquinolin-2-yl)oxy)piperidin-1-yl)-5-methyl-6-oxo-5,6-dihydro-1,5-naphthyridine-2-carbonitrile;

8-(4-((1,7-naphthyridin-8-yl)oxy)piperidin-1-yl)-5-methyl-6-oxo-5,6-dihydro-1,5-naphthyridine-2-carbonitrile;

5-methyl-6-oxo-8-(4-(phthalazin-1-yloxy)piperidin-1-yl)-5,6-dihydro-1,5-naphthyridine-2-carbonitrile;

5-methyl-6-oxo-8-(4-((2-(trifluoromethyl)pyrimidin-4-yl)oxy)piperidin-1-yl)-5,6-dihydro-1,5-naphthyridine-2-carbonitrile;

5-methyl-6-oxo-8-(4-((5-(trifluoromethyl)pyridin-2-yl)oxy)piperidin-1-yl)-5,6-dihydro-1,5-naphthyridine-2-carbonitrile;

8-(4-(2-isopropyl-6-methylpyrimidin-4-yl)oxy)piperidin-1-yl)-5-methyl-6-oxo-5,6-dihydro-1,5-naphthyridine-2-carbonitrile;

(+/−) 6-cyano-1-methyl-4-((3R,4R)-3-methyl-4-(4-(trifluoromethoxy)phenoxy)piperidin-1-yl)-1,5-naphthyridin-2(1H)-one;

6-cyano-1-methyl-4-((3R,4R)-3-methyl-4-(4-(trifluoromethoxy)phenoxy)piperidin-1-yl)-1,5-naphthyridin-2(1H)-one;

6-cyano-1-methyl-4-((3R,4R)-3-methyl-4-(4-(trifluoromethoxy)phenoxy)piperidin-1-yl)-1,5-naphthyridin-2(1H)-one;

5-methyl-8-((3R,4R)-3-methyl-4-(4-(tert-pentyl)phenoxy)piperidin-1-yl)-6-oxo-5,6-dihydro-1,5-naphthyridine-2-carbonitrile;

8-((3R,4R)-4-(4-(tert-butoxy)phenoxy)-3-methylpiperidin-1-yl)-5-methyl-6-oxo-5,6-dihydro-1,5-naphthyridine-2-carbonitrile;

8-((3R,4R)-4-(4-(tert-butyl)phenoxy)-3-methylpiperidin-1-yl)-5-methyl-6-oxo-5,6-dihydro-1,5-naphthyridine-2-carbonitrile;

8-((3R,4R)-4-(3-cyclopropylphenoxy)-3-methylpiperidin-1-yl)-5-methyl-6-oxo-5,6-dihydro-1,5-naphthyridine-2-carbonitrile;

8-((3R,4R)-4-(4-isopropylphenoxy)-3-methylpiperidin-1-yl)-5-methyl-6-oxo-5,6-dihydro-1,5-naphthyridine-2-carbonitrile;

5-methyl-8-((3R,4R)-3-methyl-4-(4-(trifluoromethyl)phenoxy)piperidin-1-yl)-6-oxo-5,6-dihydro-1,5-naphthyridine-2-carbonitrile;

8-((3R,4R)-4-(4-cyclopentylphenoxy)-3-methylpiperidin-1-yl)-5-methyl-6-oxo-5,6-dihydro-1,5-naphthyridine-2-carbonitrile;

8-((3R,4R)-4-(3,4-difluorophenoxy)-3-methylpiperidin-1-yl)-5-methyl-6-oxo-5,6-dihydro-1,5-naphthyridine-2-carbonitrile;

8-((3R,4R)-4-(4-cyclohexylphenoxy)-3-methylpiperidin-1-yl)-5-methyl-6-oxo-5,6-dihydro-1,5-naphthyridine-2-carbonitrile;

5-methyl-8-((3R,4R)-3-methyl-4-(m-tolyloxy)piperidin-1-yl)-6-oxo-5,6-dihydro-1,5-naphthyridine-2-carbonitrile;

8-((3R,4R)-4-(4-ethylphenoxy)-3-methylpiperidin-1-yl)-5-methyl-6-oxo-5,6-dihydro-1,5-naphthyridine-2-carbonitrile;

8-((3R,4R)-4-(4-cyclopropylphenoxy)-3-methylpiperidin-1-yl)-5-methyl-6-oxo-5,6-dihydro-1,5-naphthyridine-2-carbonitrile;

8-((3R,4R)-4-(2-fluoro-4-(trifluoromethyl)phenoxy)-3-methylpiperidin-1-yl)-5-methyl-6-oxo-5,6-dihydro-1,5-naphthyridine-2-carbonitrile;

8-((3R,4R)-4-(2,4-difluorophenoxy)-3-methylpiperidin-1-yl)-5-methyl-6-oxo-5,6-dihydro-1,5-naphthyridine-2-carbonitrile;

8-((3R,4R)-4-(4-fluoro-2-(trifluoromethyl)phenoxy)-3-methylpiperidin-1-yl)-5-methyl-6-oxo-5,6-dihydro-1,5-naphthyridine-2-carbonitrile;

5-methyl-8-((3R,4R)-3-methyl-4-(p-tolyloxy)piperidin-1-yl)-6-oxo-5,6-dihydro-1,5-naphthyridine-2-carbonitrile;

8-((3R,4R)-4-(3-isopropylphenoxy)-3-methylpiperidin-1-yl)-5-methyl-6-oxo-5,6-dihydro-1,5-naphthyridine-2-carbonitrile;

8-((3R,4R)-4-(3-(tert-butyl)phenoxy)-3-methylpiperidin-1-yl)-5-methyl-6-oxo-5,6-dihydro-1,5-naphthyridine-2-carbonitrile;

8-((3R,4R)-4-(2-fluoro-6-(trifluoromethyl)phenoxy)-3-methylpiperidin-1-yl)-5-methyl-6-oxo-5,6-dihydro-1,5-naphthyridine-2-carbonitrile;

8-((3R,4R)-4-(2,6-difluorophenoxy)-3-methylpiperidin-1-yl)-5-methyl-6-oxo-5,6-dihydro-1,5-naphthyridine-2-carbonitrile;

8-((3R,4R)-4-(4-fluorophenoxy)-3-methylpiperidin-1-yl)-5-methyl-6-oxo-5,6-dihydro-1,5-naphthyridine-2-carbonitrile;

5-methyl-8-((3R,4R)-3-methyl-4-(2,4,6-trifluorophenoxy)piperidin-1-yl)-6-oxo-5,6-dihydro-1,5-naphthyridine-2-carbonitrile;

8-((3R,4R)-4-((3,4-dihydro-2H-benzo[b][1,4]dioxepin-6-yl)oxy)-3-methylpiperidin-1-yl)-5-methyl-6-oxo-5,6-dihydro-1,5-naphthyridine-2-carbonitrile;

5-methyl-8-((3R,4R)-3-methyl-4-(m-tolyloxy)piperidin-1-yl)-6-oxo-5,6-dihydro-1,5-naphthyridine-2,7-dicarbonitrile;

8-((3R,4R)-3-ethyl-4-(3-isopropylphenoxy)piperidin-1-yl)-5-methyl-6-oxo-5,6-dihydro-1,5-naphthyridine-2-carbonitrile;

8-((3R,4R)-3-ethyl-4-(3-(trifluoromethyl)phenoxy)piperidin-1-yl)-5-methyl-6-oxo-5,6-dihydro-1,5-naphthyridine-2-carbonitrile;

8-((3R,4R)-3-ethyl-4-(4-isopropylphenoxy)piperidin-1-yl)-5-methyl-6-oxo-5,6-dihydro-1,5-naphthyridine-2-carbonitrile;

8-((3R,4R)-3-ethyl-4-(4-(trifluoromethyl)phenoxy)piperidin-1-yl)-5-methyl-6-oxo-5,6-dihydro-1,5-naphthyridine-2-carbonitrile;

8-((3R,4R)-3-ethyl-4-(4-(tert-pentyl)phenoxy)piperidin-1-yl)-5-methyl-6-oxo-5,6-dihydro-1,5-naphthyridine-2-carbonitrile;

8-((3R,4R)-4-(4-(tert-butyl)phenoxy)-3-ethylpiperidin-1-yl)-5-methyl-6-oxo-5,6-dihydro-1,5-naphthyridine-2-carbonitrile;

8-((3R,4R)-4-(3-cyclopropylphenoxy)-3-ethylpiperidin-1-yl)-5-methyl-6-oxo-5,6-dihydro-1,5-naphthyridine-2-carbonitrile;

8-((3R,4R)-4-(4-(tert-butoxy)phenoxy)-3-ethylpiperidin-1-yl)-5-methyl-6-oxo-5,6-dihydro-1,5-naphthyridine-2-carbonitrile;

8-((3R,4R)-3-ethyl-4-(4-isopropoxyphenoxy)piperidin-1-yl)-5-methyl-6-oxo-5,6-dihydro-1,5-naphthyridine-2-carbonitrile;

8-((3R,4R)-3-ethyl-4-(3-(trifluoromethoxy)phenoxy)piperidin-1-yl)-5-methyl-6-oxo-5,6-dihydro-1,5-naphthyridine-2-carbonitrile;

8-((3R,4S)-3-ethyl-4-(3-isopropylphenoxy)piperidin-1-yl)-5-methyl-6-oxo-5,6-dihydro-1,5-naphthyridine-2-carbonitrile;

8-((3R,4S)-4-(3-(tert-butyl)phenoxy)-3-ethylpiperidin-1-yl)-5-methyl-6-oxo-5,6-dihydro-1,5-naphthyridine-2-carbonitrile;

5-methyl-8-((3R,4S)-3-methyl-4-(4-(tert-pentyl)phenoxy)piperidin-1-yl)-6-oxo-5,6-dihydro-1,5-naphthyridine-2-carbonitrile;

8-((3R,4S)-4-(4-(tert-butoxy)phenoxy)-3-methylpiperidin-1-yl)-5-methyl-6-oxo-5,6-dihydro-1,5-naphthyridine-2-carbonitrile;

8-((3R,4S)-4-(4-(tert-butyl)phenoxy)-3-methylpiperidin-1-yl)-5-methyl-6-oxo-5,6-dihydro-1,5-naphthyridine-2-carbonitrile;

8-((3R,4S)-4-(4-isopropylphenoxy)-3-methylpiperidin-1-yl)-5-methyl-6-oxo-5,6-dihydro-1,5-naphthyridine-2-carbonitrile;

8-((3R,4S)-4-(3-cyclopropylphenoxy)-3-methylpiperidin-1-yl)-5-methyl-6-oxo-5,6-dihydro-1,5-naphthyridine-2-carbonitrile;

8-((3R,4S)-4-(4-isopropylphenoxy)-3-methylpiperidin-1-yl)-5-methyl-6-oxo-5,6-dihydro-1,5-naphthyridine-2-carbonitrile;

(+/−) 5-methyl-8-((3R,4S)-3-methyl-4-(4-(trifluoromethyl)phenoxy)piperidin-1-yl)-6-oxo-5,6-dihydro-1,5-naphthyridine-2-carboxamide;

(+/−) 5-methyl-8-((3R,4S)-3-methyl-4-(4-(trifluoromethyl)phenoxy)piperidin-1-yl)-6-oxo-5,6-dihydro-1,5-naphthyridine-2-carbonitrile;

5-methyl-8-((3R,4S)-3-methyl-4-(4-(trifluoromethyl)phenoxy)piperidin-1-yl)-6-oxo-5,6-dihydro-1,5-naphthyridine-2-carbonitrile;

5-methyl-8-((3R,4S)-3-methyl-4-(4-(trifluoromethyl)phenoxy)piperidin-1-yl)-6-oxo-5,6-dihydro-1,5-naphthyridine-2,7-dicarbonitrile;

8-((3R,4R)-3-ethyl-4-((5-isopropoxypyridin-2-yl)oxy)piperidin-1-yl)-5-methyl-6-oxo-5,6-dihydro-1,5-naphthyridine-2-carbonitrile;

8-((3R,4R)-3-ethyl-4-(4-fluoro-3-propylphenoxy)piperidin-1-yl)-5-methyl-6-oxo-5,6-dihydro-1,5-naphthyridine-2-carbonitrile;

8-((3R,4R)-4-(3-(tert-butyl)phenoxy)-3-ethylpiperidin-1-yl)-5-methyl-6-oxo-5,6-dihydro-1,5-naphthyridine-2-carbonitrile;

8-((3R,4R)-4-((5-isopropoxypyridin-2-yl)oxy)-3-methylpiperidin-1-yl)-5-methyl-6-oxo-5,6-dihydro-1,5-naphthyridine-2-carbonitrile;

8-((3R,4S)-3-ethyl-4-((5-isopropoxypyridin-2-yl)oxy)piperidin-1-yl)-5-methyl-6-oxo-5,6-dihydro-1,5-naphthyridine-2-carbonitrile;

8-((3R,4S)-4-((5-isopropylpyridin-2-yl)oxy)-3-methylpiperidin-1-yl)-5-methyl-6-oxo-5,6-dihydro-1,5-naphthyridine-2-carbonitrile;

8-((3R,4S)-4-((5-(difluoromethyl)pyridin-2-yl)oxy)-3-methylpiperidin-1-yl)-5-methyl-6-oxo-5,6-dihydro-1,5-naphthyridine-2-carbonitrile;

8-((3R,4S)-4-(4-isopropylpyridin-2-yl)oxy)-3-methylpiperidin-1-yl)-5-methyl-6-oxo-5,6-dihydro-1,5-naphthyridine-2-carbonitrile;

8-((3R,4S)-4-(6-isopropylpyridin-2-yl)oxy)-3-methylpiperidin-1-yl)-5-methyl-6-oxo-5,6-dihydro-1,5-naphthyridine-2-carbonitrile;

5-methyl-8-((3R,4S)-3-methyl-4-(pyrimidin-2-yloxy)piperidin-1-yl)-6-oxo-5,6-dihydro-1,5-naphthyridine-2-carbonitrile;

8-((3R,4S)-4-((4-methoxypyrimidin-2-yl)oxy)-3-methylpiperidin-1-yl)-5-methyl-6-oxo-5,6-dihydro-1,5-naphthyridine-2-carbonitrile;

5-methyl-8-((3R,4S)-3-methyl-4-((5-propylpyrimidin-2-yl)oxy)piperidin-1-yl)-6-oxo-5,6-dihydro-1,5-naphthyridine-2-carbonitrile;

5-methyl-8-((3R,4S)-3-methyl-4-((2-methylpyrimidin-4-yl)oxy)piperidin-1-yl)-6-oxo-5,6-dihydro-1,5-naphthyridine-2-carbonitrile;

8-((3R,4S)-4-((5-ethylpyrimidin-2-yl)oxy)-3-methylpiperidin-1-yl)-5-methyl-6-oxo-5,6-dihydro-1,5-naphthyridine-2-carbonitrile;

5-methyl-8-((3R,4S)-3-methyl-4-((5-(trifluoromethyl)pyrimidin-2-yl)oxy)piperidin-1-yl)-6-oxo-5,6-dihydro-1,5-naphthyridine-2-carbonitrile;

8-((3R,4S)-4-((5-cyclopropylpyrimidin-2-yl)oxy)-3-methylpiperidin-1-yl)-5-methyl-6-oxo-5,6-dihydro-1,5-naphthyridine-2-carbonitrile;

8-((3R,4S)-4-((5-cyclopropylpyridin-2-yl)oxy)-3-methylpiperidin-1-yl)-5-methyl-6-oxo-5,6-dihydro-1,5-naphthyridine-2-carbonitrile;

5-methyl-8-((3R,4S)-3-methyl-4-((5-(trifluoromethyl)pyridin-2-yl)oxy)piperidin-1-yl)-6-oxo-5,6-dihydro-1,5-naphthyridine-2-carbonitrile;

(+/−) 8-((3R,4S)-4-((5-isopropoxypyridin-2-yl)oxy)-3-methylpiperidin-1-yl)-5-methyl-6-oxo-5,6-dihydro-1,5-naphthyridine-2-carbonitrile;

(+/−) 5-methyl-8-((3R,4R)-3-methyl-4-(4-(tert-pentyl)phenoxy)piperidin-1-yl)-6-oxo-5,6-dihydro-1,5-naphthyridine-2,7-dicarbonitrile;

5-methyl-8-((3R,4R)-3-methyl-4-(4-(tert-pentyl)phenoxy)piperidin-1-yl)-6-oxo-5,6-dihydro-1,5-naphthyridine-2,7-dicarbonitrile;

5-methyl-8-((3R,4R)-3-methyl-4-(4-(tert-pentyl)phenoxy)piperidin-1-yl)-6-oxo-5,6-dihydro-1,5-naphthyridine-2,7-dicarbonitrile;

(+/−) 8-(4-((5-isopropoxypyridin-2-yl)oxy)-3,3-dimethylpiperidin-1-yl)-5-methyl-6-oxo-5,6-dihydro-1,5-naphthyridine-2-carbonitrile;

8-(4-((5-isopropoxypyridin-2-yl)oxy)-3,3-dimethylpiperidin-1-yl)-5-methyl-6-oxo-5,6-dihydro-1,5-naphthyridine-2-carbonitrile;

8-(4-((5-isopropoxypyridin-2-yl)oxy)-3,3-dimethylpiperidin-1-yl)-5-methyl-6-oxo-5,6-dihydro-1,5-naphthyridine-2-carbonitrile;

(+/−) 5-methyl-8-((3R,4S)-3-methyl-4-((4-(trifluoromethoxy)benzyl)oxy)piperidin-1-yl)-6-oxo-5,6-dihydro-1,5-naphthyridine-2-carbonitrile;

(+/−) 5-methyl-8-((3R,4S)-3-methyl-4-((4-(trifluoromethoxy)benzyl)oxy)piperidin-1-yl)-6-oxo-5,6-dihydro-1,5-naphthyridine-2-carboxamide;

7-fluoro-5-methyl-6-oxo-8-(4-(4-(trifluoromethoxy)phenoxy)piperidin-1-yl)-5,6-dihydro-1,5-naphthyridine-2-carbonitrile;

7-chloro-5-methyl-6-oxo-8-(4-(4-(trifluoromethoxy)phenoxy)piperidin-1-yl)-5,6-dihydro-1,5-naphthyridine-2-carbonitrile;

7-bromo-5-methyl-6-oxo-8-(4-(4-(trifluoromethoxy)phenoxy)piperidin-1-yl)-5,6-dihydro-1,5-naphthyridine-2-carbonitrile;

7-(6-methoxypyridin-3-yl)-5-methyl-6-oxo-8-(4-(4-(trifluoromethoxy)phenoxy)piperidin-1-yl)-5,6-dihydro-1,5-naphthyridine-2-carbonitrile;

7-(2-methoxypyridin-4-yl)-5-methyl-6-oxo-8-(4-(4-(trifluoromethoxy)phenoxy)piperidin-1-yl)-5,6-dihydro-1,5-naphthyridine-2-carbonitrile;

(+/−) 6-bromo-1-methyl-4-((3R,4R)-3-methyl-4-(4-(tert-pentyl)phenoxy)piperidin-1-yl)-2-oxo-1,2-dihydro-1,5-naphthyridine-3-carbonitrile;

8-((2S,5S)-4-((5-isopropoxypyridin-2-yl)oxy)-2,5-dimethylpiperidin-1-yl)-5-methyl-6-oxo-5,6-dihydro-1,5-naphthyridine-2-carbonitrile;

8-((2R,5R)-4-((5-isopropoxypyridin-2-yl)oxy)-2,5-dimethylpiperidin-1-yl)-5-methyl-6-oxo-5,6-dihydro-1,5-naphthyridine-2-carbonitrile;

4-((2R,5S)-4-((5-isopropoxypyridin-2-yl)oxy)-2,5-dimethylpiperidin-1-yl)-1-methyl-2-oxo-1,2-dihydropyrido[3,2-d]pyrimidine-6-carbonitrile;

4-((2S,5R)-4-((5-isopropoxypyridin-2-yl)oxy)-2,5-dimethylpiperidin-1-yl)-1-methyl-2-oxo-1,2-dihydropyrido[3,2-d]pyrimidine-6-carbonitrile;

4-((2R,5S)-2,5-dimethyl-4-(3-(trifluoromethyl)phenoxy)piperidin-1-yl)-1-methyl-2-oxo-1,2-dihydropyrido[3,2-d]pyrimidine-6-carbonitrile;

4-((2S,5R)-2,5-dimethyl-4-(3-(trifluoromethyl)phenoxy)piperidin-1-yl)-1-methyl-2-oxo-1,2-dihydropyrido[3,2-d]pyrimidine-6-carbonitrile;

4-((2R,5R)-2,5-dimethyl-4-(3-(trifluoromethyl)phenoxy)piperidin-1-yl)-1-methyl-2-oxo-1,2-dihydropyrido[3,2-d]pyrimidine-6-carbonitrile;

8-((2S,5S)-2,5-dimethyl-4-(3-(trifluoromethyl)phenoxy)piperidin-1-yl)-5-methyl-6-oxo-5,6-dihydro-1,5-naphthyridine-2-carbonitrile;

(±)-trans-8-(3-hydroxy-4-(3-(trifluoromethyl)phenoxy)piperidin-1-yl)-5-methyl-6-oxo-5,6-dihydro-1,5-naphthyridine-2-carbonitrile;

(±)-trans-8-(3-methoxy-4-(3-(trifluoromethyl)phenoxy)piperidin-1-yl)-5-methyl-6-oxo-5,6-dihydro-1,5-naphthyridine-2-carbonitrile;

8-((3R,4R)-3-ethoxy-4-(3-(trifluoromethyl)phenoxy)piperidin-1-yl)-5-methyl-6-oxo-5,6-dihydro-1,5-naphthyridine-2-carbonitrile;

(±)-cis-8-(3-fluoro-4-(3-(trifluoromethyl)phenoxy)piperidin-1-yl)-5-methyl-6-oxo-5,6-dihydro-1,5-naphthyridine-2-carbonitrile;

(±)-trans-8-(3-hydroxy-4-((5-isopropoxypyridin-2-yl)oxy)piperidin-1-yl)-5-methyl-6-oxo-5,6-dihydro-1,5-naphthyridine-2-carbonitrile;

(±)-trans-8-(4-((5-isopropoxypyridin-2-yl)oxy)-3-methoxypiperidin-1-yl)-5-methyl-6-oxo-5,6-dihydro-1,5-naphthyridine-2-carbonitrile;

(±)-trans-6-chloro-4-(3-hydroxy-4-(3-(trifluoromethyl)phenoxy)piperidin-1-yl)-1-methylpyrido[3,2-d]pyrimidin-2(1H)-one;

(±)-trans-4-(3-hydroxy-4-(3-(trifluoromethyl)phenoxy)piperidin-1-yl)-1-methyl-2-oxo-1,2-dihydropyrido[3,2-d]pyrimidine-6-carbonitrile;

6-chloro-4-((3R,4R)-3-methoxy-4-(3-(trifluoromethyl)phenoxy)piperidin-1-yl)-1-methylpyrido[3,2-d]pyrimidin-2(1H)-one;

(±)-trans-4-(3-hydroxy-4-(3-(trifluoromethyl)phenoxy)piperidin-1-yl)-1-methyl-2-oxo-1,2-dihydropyrido[3,2-d]pyrimidine-6-carbonitrile;

4-((3R,4R)-3-ethoxy-4-(3-(trifluoromethyl)phenoxy)piperidin-1-yl)-1-methyl-2-oxo-1,2-dihydropyrido[3,2-d]pyrimidine-6-carbonitrile;

8-((2S,5R)-4-((5-methoxypyridin-2-yl)amino)-2,5-dimethylpiperidin-1-yl)-5-methyl-6-oxo-5,6-dihydro-1,5-naphthyridine-2-carbonitrile;

N-((2S,5R)-1-(6-cyano-1-methyl-2-oxo-1,2-dihydro-1,5-naphthyridin-4-yl)-2,5-dimethylpiperidin-4-yl)-4-fluoro-N-methylbenzamide;

N-(1-(6-cyano-1-methyl-2-oxo-1,2-dihydro-1,5-naphthyridin-4-yl)-3-methylpiperidin-4-yl)-4-fluoro-N-methylbenzamide;

N-(1-(3,6-dicyano-1-methyl-2-oxo-1,2-dihydro-1,5-naphthyridin-4-yl)-3-methylpiperidin-4-yl)-N-methyl-4-(trifluoromethyl)benzamide;

8-((2S,4S,5S)-5-ethyl-4-((5-isopropoxypyridin-2-yl)oxy)-2-methylpiperidin-1-yl)-5-methyl-6-oxo-5,6-dihydro-1,5-naphthyridine-2-carbonitrile;

8-((2R,4S,5S)-5-ethyl-4-((5-isopropoxypyridin-2-yl)oxy)-2-methylpiperidin-1-yl)-5-methyl-6-oxo-5,6-dihydro-1,5-naphthyridine-2-carbonitrile;

8-((2S,4R,5R)-5-ethyl-4-((5-isopropoxypyridin-2-yl)oxy)-2-methylpiperidin-1-yl)-5-methyl-6-oxo-5,6-dihydro-1,5-naphthyridine-2-carbonitrile;

8-((2R,4R,5R)-5-ethyl-4-((5-isopropoxypyridin-2-yl)oxy)-2-methylpiperidin-1-yl)-5-methyl-6-oxo-5,6-dihydro-1,5-naphthyridine-2-carbonitrile;

8-((2R,4S,5R)-5-ethyl-4-((5-isopropoxypyridin-2-yl)oxy)-2-methylpiperidin-1-yl)-5-methyl-6-oxo-5,6-dihydro-1,5-naphthyridine-2-carbonitrile;

8-((2S,4S,5R)-5-ethyl-4-((5-isopropoxypyridin-2-yl)oxy)-2-methylpiperidin-1-yl)-5-methyl-6-oxo-5,6-dihydro-1,5-naphthyridine-2-carbonitrile;

6-chloro-4-((2S,4R,5R)-5-ethyl-4-((5-isopropoxypyridin-2-yl)oxy)-2-methylpiperidin-1-yl)-1-methylpyrido[3,2-d]pyrimidin-2(1H)-one;

4-((2S,4R,5R)-5-ethyl-4-((5-isopropoxypyridin-2-yl)oxy)-2-methylpiperidin-1-yl)-1-methyl-2-oxo-1,2-dihydropyrido[3,2-d]pyrimidine-6-carbonitrile;

6-chloro-4-((2R,4R,5R)-5-ethyl-4-((5-isopropoxypyridin-2-yl)oxy)-2-methylpiperidin-1-yl)-1-methylpyrido[3,2-d]pyrimidin-2(1H)-one;
4-((2R,4R,5R)-5-ethyl-4-((5-isopropoxypyridin-2-yl)oxy)-2-methylpiperidin-1-yl)-1-methyl-2-oxo-1,2-dihydropyrido[3,2-d]pyrimidine-6-carbonitrile;
6-chloro-4-((2R,4S,5R)-5-ethyl-4-((5-isopropoxypyridin-2-yl)oxy)-2-methylpiperidin-1-yl)-1-methylpyrido[3,2-d]pyrimidin-2(1H)-one;
4-((2R,4S,5R)-5-ethyl-4-((5-isopropoxypyridin-2-yl)oxy)-2-methylpiperidin-1-yl)-1-methyl-2-oxo-1,2-dihydropyrido[3,2-d]pyrimidine-6-carbonitrile;
6-chloro-4-((2S,4S,5R)-5-ethyl-4-((5-isopropoxypyridin-2-yl)oxy)-2-methylpiperidin-1-yl)-1-methylpyrido[3,2-d]pyrimidin-2(1H)-one;
4-((2S,4S,5R)-5-ethyl-4-((5-isopropoxypyridin-2-yl)oxy)-2-methylpiperidin-1-yl)-1-methyl-2-oxo-1,2-dihydropyrido[3,2-d]pyrimidine-6-carbonitrile;
8-((2S,4S,5R)-5-ethyl-2-methyl-4-(3-(trifluoromethyl)phenoxy)piperidin-1-yl)-5-methyl-6-oxo-5,6-dihydro-1,5-naphthyridine-2-carbonitrile;
8-((2R,4S,5R)-5-ethyl-2-methyl-4-(3-(trifluoromethyl)phenoxy)piperidin-1-yl)-5-methyl-6-oxo-5,6-dihydro-1,5-naphthyridine-2-carbonitrile;
8-((2R,4R,5R)-5-ethyl-2-methyl-4-(3-(trifluoromethyl)phenoxy)piperidin-1-yl)-5-methyl-6-oxo-5,6-dihydro-1,5-naphthyridine-2-carbonitrile;
8-((2R,4S,5R)-2,5-dimethyl-4-(3-(trifluoromethyl)phenoxy)piperidin-1-yl)-5-methyl-6-oxo-5,6-dihydro-1,5-naphthyridine-2-carbonitrile;
8-((2S,4R,5S)-2,5-dimethyl-4-(p-tolyloxy)piperidin-1-yl)-5-methyl-6-oxo-5,6-dihydro-1,5-naphthyridine-2-carbonitrile;
8-((2S,4R,5S)-4-(3-chlorophenoxy)-2,5-dimethylpiperidin-1-yl)-5-methyl-6-oxo-5,6-dihydro-1,5-naphthyridine-2-carbonitrile;
8-((2S,4R,5S)-4-(3-cyanophenoxy)-2,5-dimethylpiperidin-1-yl)-5-methyl-6-oxo-5,6-dihydro-1,5-naphthyridine-2-carbonitrile;
8-((2S,4R,5S)-4-(4-fluorophenoxy)-2,5-dimethylpiperidin-1-yl)-5-methyl-6-oxo-5,6-dihydro-1,5-naphthyridine-2-carbonitrile;
8-((2S,5S)-2,5-dimethyl-4-((4-(trifluoromethyl)phenyl)amino)piperidin-1-yl)-5-methyl-6-oxo-5,6-dihydro-1,5-naphthyridine-2-carbonitrile (316A);
8-(2,5)-dimethyl-4-(methyl(4-(trifluoromethyl)phenyl)amino)piperidin-1-yl)-5-methyl-6-oxo-5,6-dihydro-1,5-naphthyridine-2-carbonitrile;
8-((2S,5S)-2,5-dimethyl-4-(methyl(3-(trifluoromethyl)phenyl)amino)piperidin-1-yl)-5-methyl-6-oxo-5,6-dihydro-1,5-naphthyridine-2-carbonitrile;
8-(4-((4-fluorobenzyl)(methyl)amino)-3-methylpiperidin-1-yl)-5-methyl-6-oxo-5,6-dihydro-1,5-naphthyridine-2,7-dicarbonitrile;
8-(4-((4-fluorobenzyl)(methyl)amino)-3-methylpiperidin-1-yl)-5-methyl-6-oxo-5,6-dihydro-1,5-naphthyridine-2-carbonitrile;
8-(4-((4,4-difluorocyclohexyl)(methyl)amino)-3-methylpiperidin-1-yl)-5-methyl-6-oxo-5,6-dihydro-1,5-naphthyridine-2,7-dicarbonitrile;
8-((2S,5R)-4-((4-fluorobenzyl)(methyl)amino)-2,5-dimethylpiperidin-1-yl)-5-methyl-6-oxo-5,6-dihydro-1,5-naphthyridine-2-carbonitrile;
8-((2S,5S)-4-((4-fluorobenzyl)(methyl)amino)-2,5-dimethylpiperidin-1-yl)-5-methyl-6-oxo-5,6-dihydro-1,5-naphthyridine-2-carbonitrile;
8-((2S,5S)-4-((5-Isopropoxypyridin-2-yl)oxy)-2,4,5-trimethylpiperidin-1-yl)-5-methyl-6-oxo-5,6-dihydro-1,5-naphthyridine-2-carbonitrile;
5-methyl-6-oxo-8-((2S,5S)-2,4,5-trimethyl-4-(3-(trifluoromethyl)phenoxy)piperidin-1-yl)-5,6-dihydro-1,5-naphthyridine-2-carbonitrile;
1-methyl-2-oxo-4-((2S,5S)-2,4,5-trimethyl-4-(3-(trifluoromethyl)phenoxy)piperidin-1-yl)-1,2-dihydropyrido[3,2-d]pyrimidine-6-carbonitrile;
trans-8-(3-ethoxy-4-phenoxypiperidin-1-yl)-5-methyl-6-oxo-5,6-dihydro-1,5-naphthyridine-2-carbonitrile;
8-((3S,4S)-3-ethoxy-4-(4-(trifluoromethyl)phenoxy)piperidin-1-yl)-5-methyl-6-oxo-5,6-dihydro-1,5-naphthyridine-2-carbonitrile;
8-((3S,4S)-3-ethoxy-4-(2-(trifluoromethyl)phenoxy)piperidin-1-yl)-5-methyl-6-oxo-5,6-dihydro-1,5-naphthyridine-2-carbonitrile;
8-((3S,4S)-3-ethoxy-4-(4-isopropoxyphenoxy)piperidin-1-yl)-5-methyl-6-oxo-5,6-dihydro-1,5-naphthyridine-2-carbonitrile;
8-((3S,4S)-3-ethoxy-4-(4-(trifluoromethoxy)phenoxy)piperidin-1-yl)-5-methyl-6-oxo-5,6-dihydro-1,5-naphthyridine-2-carbonitrile;
8-((3S,4S)-3-ethoxy-4-(3-(trifluoromethoxy)phenoxy)piperidin-1-yl)-5-methyl-6-oxo-5,6-dihydro-1,5-naphthyridine-2-carbonitrile;
8-((3S,4S)-3-ethoxy-4-(4-(methylsulfonyl)phenoxy)piperidin-1-yl)-5-methyl-6-oxo-5,6-dihydro-1,5-naphthyridine-2-carbonitrile;
8-((3S,4S)-3-ethoxy-4-((2-methylbenzo[d]oxazol-5-yl)oxy)piperidin-1-yl)-5-methyl-6-oxo-5,6-dihydro-1,5-naphthyridine-2-carbonitrile;
8-((3S,4S)-4-(4-chloro-3-fluorophenoxy)-3-ethoxypiperidin-1-yl)-5-methyl-6-oxo-5,6-dihydro-1,5-naphthyridine-2-carbonitrile;
8-((3S,4S)-3-ethoxy-4-((2-(trifluoromethyl)pyridin-4-yl)oxy)piperidin-1-yl)-5-methyl-6-oxo-5,6-dihydro-1,5-naphthyridine-2-carbonitrile;
trans-8-(3-ethoxy-4-((6-(trifluoromethyl)pyridin-2-yl)oxy)piperidin-1-yl)-5-methyl-6-oxo-5,6-dihydro-1,5-naphthyridine-2-carbonitrile;
8-((3S,4S)-3-ethoxy-4-((4-(trifluoromethyl)pyridin-2-yl)oxy)piperidin-1-yl)-5-methyl-6-oxo-5,6-dihydro-1,5-naphthyridine-2-carbonitrile;
trans-8-(3-ethoxy-4-((5-(trifluoromethyl)pyridin-2-yl)oxy)piperidin-1-yl)-5-methyl-6-oxo-5,6-dihydro-1,5-naphthyridine-2-carbonitrile;
cis-8-(3-ethoxy-4-(3-(trifluoromethyl)phenoxy)piperidin-1-yl)-5-methyl-6-oxo-5,6-dihydro-1,5-naphthyridine-2-carbonitrile;
cis-8-(3-ethoxy-4-((5-isopropoxypyridin-2-yl)oxy)piperidin-1-yl)-5-methyl-6-oxo-5,6-dihydro-1,5-naphthyridine-2-carbonitrile;
trans-8-4-(benzo[d]thiazol-2-yloxy)-3-ethoxypiperidin-1-yl)-5-methyl-6-oxo-5,6-dihydro-1,5-naphthyridine-2-carbonitrile;
8-((3S,4S)-3-ethoxy-4-((6-isopropoxypyridazin-3-yl)oxy)piperidin-1-yl)-5-methyl-6-oxo-5,6-dihydro-1,5-naphthyridine-2-carbonitrile;
8-((3S,4S)-3-ethoxy-4-((5-isopropoxypyrazin-2-yl)oxy)piperidin-1-yl)-5-methyl-6-oxo-5,6-dihydro-1,5-naphthyridine-2-carbonitrile;
8-((3S,4S)-3-ethoxy-4-((5-isopropoxypyrimidin-2-yl)oxy)piperidin-1-yl)-5-methyl-6-oxo-5,6-dihydro-1,5-naphthyridine-2-carbonitrile;

8-((3S,4S)-3-ethoxy-4-((3-(trifluoromethyl)benzyl)oxy)piperidin-1-yl)-5-methyl-6-oxo-5,6-dihydro-1,5-naphthyridine-2-carbonitrile;

8-((3S,4S)-3-ethoxy-4-((5-isopropoxypyridin-2-yl)methoxy)piperidin-1-yl)-5-methyl-6-oxo-5,6-dihydro-1,5-naphthyridine-2-carbonitrile;

8-((3R,4R)-3-(2-(dimethylamino)ethoxy)-4-(3-(trifluoromethyl)phenoxy)piperidin-1-yl)-5-methyl-6-oxo-5,6-dihydro-1,5-naphthyridine-2-carbonitrile;

8-((3R,4R)-3-(cyclopropylmethoxy)-4-(3-(trifluoromethyl)phenoxy)piperidin-1-yl)-5-methyl-6-oxo-5,6-dihydro-1,5-naphthyridine-2-carbonitrile;

8-((3R,4R)-3-(2-methoxyethoxy)-4-(3-(trifluoromethyl)phenoxy)piperidin-1-yl)-5-methyl-6-oxo-5,6-dihydro-1,5-naphthyridine-2-carbonitrile;

5-methyl-8-((3R,4R)-3-(2-morpholinoethoxy)-4-(3-(trifluoromethyl)phenoxy)piperidin-1-yl)-6-oxo-5,6-dihydro-1,5-naphthyridine-2-carbonitrile;

5-methyl-6-oxo-8-((3R,4R)-3-(2,2,2-trifluoroethoxy)-4-(3-(trifluoromethyl)phenoxy) piperidin-1-yl)-5,6-dihydro-1,5-naphthyridine-2-carbonitrile;

trans-8-(3-isopropoxy-4-(3-(trifluoromethyl)phenoxy)piperidin-1-yl)-5-methyl-6-oxo-5,6-dihydro-1,5-naphthyridine-2-carbonitrile;

trans-8-(4-((5-isopropoxypyridin-2-yl)oxy)-3-ethoxypiperidin-1-yl)-5-methyl-6-oxo-5,6-dihydro-1,5-naphthyridine-2-carbonitrile;

(±)-trans-6-chloro-4-(3-ethoxy-4-((5-isopropoxypyridin-2-yl)oxy)piperidin-1-yl)-1-methylpyrido[3,2-d]pyrimidin-2(1H)-one;

trans-4-(3-ethoxy-4-((5-isopropoxypyridin-2-yl)oxy)piperidin-1-yl)-1-methyl-2-oxo-1,2-dihydropyrido[3,2-d]pyrimidine-6-carbonitrile;

trans-4-(3-ethoxy-4-phenoxypiperidin-1-yl)-1-methyl-2-oxo-1,2-dihydropyrido[3,2-d] pyrimidine-6-carbonitrile; or 4-((3S,4S)-3-ethoxy-4-(4-(trifluoromethyl)phenoxy)piperidin-1-yl)-1-methyl-2-oxo-1,2-dihydropyrido[3,2-d]pyrimidine-6-carbonitrile.

11. A pharmaceutical composition comprising a compound according to claim 1 or a pharmaceutically-acceptable salt thereof; and a pharmaceutically acceptable carrier.

* * * * *

UNITED STATES PATENT AND TRADEMARK OFFICE
CERTIFICATE OF CORRECTION

PATENT NO. : 11,964,973 B2
APPLICATION NO. : 17/130022
DATED : April 23, 2024
INVENTOR(S) : Gentles et al.

It is certified that error appears in the above-identified patent and that said Letters Patent is hereby corrected as shown below:

On the Title Page

Column 2 (Other Publications), Line 5, delete "Inhyibitors" and insert -- Inhibitors --.

Column 2 (Other Publications), Line 7, delete "Activites" and insert -- Activities --.

In the Claims

Claim 1, Column 391, Line 57 (Approx.), delete "is or" and insert -- is --.

Claim 1, Column 391, Line 61, delete "is H," and insert -- is --.

Claim 2, Column 393, Line 26, delete "is H," and insert -- is --.

Claim 2, Column 393, Lines 44-45, delete "benzooxazolyl," and insert -- benzoxazolyl, --.

Claim 2, Column 393, Line 65, delete "—CH$_2$)$_{1-2}$ (heterocyclyl" and insert -- —CH$_2$)$_{1-2}$(hetereocyclyl --.

Claim 3, Column 394, Lines 16-17 (Approx.), delete "benzooxazolyl," and insert -- benzoxazolyl, --.

Claim 3, Column 394, Line 28 (Approx.), delete "hydrogen, F," and insert -- F, --.

Claim 10, Column 396, Lines 58-59, above "5-methyl-6-oxo-8-(4-(4-(tert-pentyl)phenoxy)piperidin-" delete "4-(4-(tert-butyl)phenoxy)piperidin-1-yl)-1-methyl-2-oxo-1,2-dihydroquinoline-6-carbonitrile;".

Claim 10, Column 397, Line 53, delete "8-(4-(2-" and insert -- 8-(4-((2- --.

Signed and Sealed this
Fourteenth Day of October, 2025

John A. Squires
*Director of the United States Patent and Trademark Office*

Claim 10, Column 400, Line 29, delete "-4-(4-" and insert -- -4-((4- --.

Claim 10, Column 400, Line 32, delete "-4-(6-" and insert -- -4-((6- --.

Claim 10, Column 403, Line 46, delete "carbonitrile (316A);" and insert -- carbonitrile; --.

SEQUENCE LISTING

<160> NUMBER OF SEQ ID NOS: 6

<210> SEQ ID NO 1
<211> LENGTH: 2256
<212> TYPE: DNA
<213> ORGANISM: Homo sapiens

<400> SEQUENCE: 1

```
atggccaagg agaggggcct aataagcccc agtgattttg cccagctgca aaaatacatg      60
gaatactcca ccaaaaaggt cagtgatgtc ctaaagctct cgaggatggc gagatggct     120 aaatatgtcc aaggagatgc cattgggtac gagggattcc agcaattcct gaaaatctat    180
ctcgaagtgg ataatgttcc agacaccta agcctggcac tgtttcaatc ctttgagact     240
ggtcactgct aaatgagac aaatgtgaca aaagatgtgg tgtgtctcaa tgatgtttcc     300
tgctactttt cccttctgga gggtggtcgg ccagaagaca gttagaatt caccttcaag     360 ctgtacgaca cggacagaaa tgggatcctg gacagctcag aagtggacaa aattatccta    420
cagatgatgc gagtggctga ataccctgat tgggatgtgt ctgagctgag gccgattctt    480
caggagatga tgaaagagat tgactatgat ggcagtggct ctgtctctca agctgagtgg    540
gtccgggctg ggccaccac cgtgccactg ctagtgctgc tggtctgga gatgactctg     600 aaggacgacg gacagcacat gtggaggccc aagaggttcc ccagaccagt ctactgcaat    660
```

-continued

| | |
|---|---|
| ctgtgcgagt caagcattgg tcttggcaaa cagggactga gctgtaacct ctgtaagtac | 720 |
| actgttcacg accagtgtgc catgaaagcc ctgccttgtg aagtcagcac ctatgccaag | 780 |
| tctcggaagg acattggtgt ccaatcacat gtgtgggtgc gaggaggctg tgagtccggg | 840 |
| cgctgcgacc gctgtcagaa aaagatccgg atctaccaca gtctgaccgg gctgcattgt | 900 |
| gtatggtgcc acctagagat ccacgatgac tgcctgcaag cggtgggcca tgagtgtgac | 960 |
| tgtgggctgc tccgggatca catcctgcct ccatcttcca tctatcccag tgtcctggcc | 1020 |
| tctggaccgg atcgtaaaaa tagcaaaaca agccagaaga ccatggatga tttaaatttg | 1080 |
| agcacctctg aggctctgcg gattgaccct gttcctaaca cccacccact tctcgtcttt | 1140 |
| gtcaatccta gagtggcgg gaagcagggg cagagggtgc tctggaagtt ccagtatata | 1200 |
| ttaaaccctc gacaggtgtt caacctccta aaggatggtc ctgagatagg gctccgatta | 1260 |
| ttcaaggatg ttcctgatag ccggattttg gtgtgtggtg gagacggcac agtaggctgg | 1320 |
| attctagaga ccattgacaa agctaacttg ccagttttgc ctcctgttgc tgtgttgccc | 1380 |
| ctgggtactg gaaatgatct ggctcgatgc ctaagatggg gaggaggtta tgaaggacag | 1440 |
| aatctggcaa agatcctcaa ggatttagag atgagtaaag tggtacatat ggatcgatgg | 1500 |
| tctgtggagg tgatacctca acaaactgaa gaaaaagtg acccagtccc ctttcaaatc | 1560 |
| atcaataact acttctctat tggcgtggat gcctctattg ctcatcgatt ccacatcatg | 1620 |
| cgagagaaat atccggagaa gttcaacagc agaatgaaga acaagctatg gtacttcgaa | 1680 |
| tttgccacat ctgaatccat cttctcaaca tgcaaaaagc tggaggagtc tttgacagtt | 1740 |
| gagatctgtg ggaaaccgct ggatctgagc aacctgtccc tagaaggcat cgcagtgcta | 1800 |
| aacatcccta gcatgcatgg tggctccaac ctctggggtg ataccaggag accccatggg | 1860 |
| gatatctatg ggatcaacca ggccttaggt gctacagcta aagtcatcac cgaccctgat | 1920 |
| atcctgaaaa cctgtgtacc agacctaagt gacaagagac tggaagtggt tgggctggag | 1980 |
| ggtgcaattg agatgggcca aatctatacc aagctcaaga atgctggacg tcggctggcc | 2040 |
| aagtgctctg agatcaccct tccacaccac aaaaaccctt ccatgcaaat tgacggagaa | 2100 |
| ccctggatgc agacgccctg tacaatcaag atcacccaca gaaccagat gcccatgctc | 2160 |
| atgggcccac ccccccgctc caccaatttc tttggcttct tgagcggatc ctcggagaca | 2220 |
| gtgcggtttc agggacacca ccaccatcac cactga | 2256 |

<210> SEQ ID NO 2
<211> LENGTH: 737
<212> TYPE: PRT
<213> ORGANISM: Homo sapiens

<400> SEQUENCE: 2

Met Ala Ser Pro Ser Asp Phe Ala Gln Leu Gln Lys Tyr Met Glu Tyr
1               5                   10                  15

Ser Thr Lys Lys Val Ser Asp Val Leu Lys Leu Phe Glu Asp Gly Glu
            20                  25                  30

Met Ala Lys Tyr Val Gln Gly Asp Ala Ile Gly Tyr Glu Gly Phe Gln
        35                  40                  45

Gln Phe Leu Lys Ile Tyr Leu Glu Val Asp Asn Val Pro Arg His Leu
    50                  55                  60

Ser Leu Ala Leu Phe Gln Ser Phe Glu Thr Gly His Cys Leu Asn Glu
65                  70                  75                  80

Thr Asn Val Thr Lys Asp Val Val Cys Leu Asn Asp Val Ser Cys Tyr
                85                  90                  95

```
Phe Ser Leu Leu Glu Gly Gly Arg Pro Glu Asp Lys Leu Glu Phe Thr
            100                 105                 110

Phe Lys Leu Tyr Asp Thr Asp Arg Asn Gly Ile Leu Asp Ser Ser Glu
        115                 120                 125

Val Asp Lys Ile Ile Leu Gln Met Met Arg Val Ala Glu Tyr Leu Asp
    130                 135                 140

Trp Asp Val Ser Glu Leu Arg Pro Ile Leu Gln Glu Met Met Lys Glu
145                 150                 155                 160

Ile Asp Tyr Asp Gly Ser Gly Val Ser Gln Ala Glu Trp Val Arg
                165                 170                 175

Ala Gly Ala Thr Thr Val Pro Leu Leu Val Leu Leu Gly Leu Glu Met
            180                 185                 190

Thr Leu Lys Asp Asp Gly Gln His Met Trp Arg Pro Lys Arg Phe Pro
        195                 200                 205

Arg Pro Val Tyr Cys Asn Leu Cys Glu Ser Ser Ile Gly Leu Gly Lys
    210                 215                 220

Gln Gly Leu Ser Cys Asn Leu Cys Lys Tyr Thr Val His Asp Gln Cys
225                 230                 235                 240

Ala Met Lys Ala Leu Pro Cys Glu Val Ser Thr Tyr Ala Lys Ser Arg
            245                 250                 255

Lys Asp Ile Gly Val Gln Ser His Val Trp Val Arg Gly Gly Cys Glu
        260                 265                 270

Ser Gly Arg Cys Asp Arg Cys Gln Lys Lys Ile Arg Ile Tyr His Ser
    275                 280                 285

Leu Thr Gly Leu His Cys Val Trp Cys His Leu Glu Ile His Asp Asp
290                 295                 300

Cys Leu Gln Ala Val Gly His Glu Cys Asp Cys Gly Leu Leu Arg Asp
305                 310                 315                 320

His Ile Leu Pro Pro Ser Ser Ile Tyr Pro Ser Val Leu Ala Ser Gly
            325                 330                 335

Pro Asp Arg Lys Asn Ser Lys Thr Ser Gln Lys Thr Met Asp Asp Leu
        340                 345                 350

Asn Leu Ser Thr Ser Glu Ala Leu Arg Ile Asp Pro Val Pro Asn Thr
    355                 360                 365

His Pro Leu Leu Val Phe Val Asn Pro Lys Ser Gly Gly Lys Gln Gly
370                 375                 380

Gln Arg Val Leu Trp Lys Phe Gln Tyr Ile Leu Asn Pro Arg Gln Val
385                 390                 395                 400

Phe Asn Leu Leu Lys Asp Gly Pro Glu Ile Gly Leu Arg Leu Phe Lys
            405                 410                 415

Asp Val Pro Asp Ser Arg Ile Leu Val Cys Gly Gly Asp Gly Thr Val
        420                 425                 430

Gly Trp Ile Leu Glu Thr Ile Asp Lys Ala Asn Leu Pro Val Leu Pro
    435                 440                 445

Pro Val Ala Val Leu Pro Leu Gly Thr Gly Asn Asp Leu Ala Arg Cys
450                 455                 460

Leu Arg Trp Gly Gly Gly Tyr Glu Gly Gln Asn Leu Ala Lys Ile Leu
465                 470                 475                 480

Lys Asp Leu Glu Met Ser Lys Val His Met Asp Arg Trp Ser Val
            485                 490                 495

Glu Val Ile Pro Gln Gln Thr Glu Glu Lys Ser Asp Pro Val Pro Phe
        500                 505                 510
```

Gln Ile Ile Asn Asn Tyr Phe Ser Ile Gly Val Asp Ala Ser Ile Ala
            515                 520                 525

His Arg Phe His Ile Met Arg Glu Lys Tyr Pro Glu Lys Phe Asn Ser
        530                 535                 540

Arg Met Lys Asn Lys Leu Trp Tyr Phe Glu Phe Ala Thr Ser Glu Ser
545                 550                 555                 560

Ile Phe Ser Thr Cys Lys Lys Leu Glu Glu Ser Leu Thr Val Glu Ile
                565                 570                 575

Cys Gly Lys Pro Leu Asp Leu Ser Asn Leu Ser Leu Glu Gly Ile Ala
            580                 585                 590

Val Leu Asn Ile Pro Ser Met His Gly Gly Ser Asn Leu Trp Gly Asp
        595                 600                 605

Thr Arg Arg Pro His Gly Asp Ile Tyr Gly Ile Asn Gln Ala Leu Gly
    610                 615                 620

Ala Thr Ala Lys Val Ile Thr Asp Pro Asp Ile Leu Lys Thr Cys Val
625                 630                 635                 640

Pro Asp Leu Ser Asp Lys Arg Leu Glu Val Val Gly Leu Glu Gly Ala
                645                 650                 655

Ile Glu Met Gly Gln Ile Tyr Thr Lys Leu Lys Asn Ala Gly Arg Arg
            660                 665                 670

Leu Ala Lys Cys Ser Glu Ile Thr Phe His Thr Thr Lys Thr Leu Pro
        675                 680                 685

Met Gln Ile Asp Gly Glu Pro Trp Met Gln Thr Pro Cys Thr Ile Lys
    690                 695                 700

Ile Thr His Lys Asn Gln Met Pro Met Leu Met Gly Pro Pro Pro Arg
705                 710                 715                 720

Ser Gly Ser Ser Glu Thr Val Arg Phe Gln Gly His His His His
                725                 730                 735

His

<210> SEQ ID NO 3
<211> LENGTH: 2838
<212> TYPE: PRT
<213> ORGANISM: Homo sapiens

<400> SEQUENCE: 3

Ala Thr Gly Gly Ala Gly Cys Cys Gly Cys Gly Gly Ala Cys Gly
1               5                   10                  15

Gly Thr Ala Gly Cys Cys Cys Gly Ala Gly Gly Cys Cys Cys Gly
                20                  25                  30

Gly Ala Gly Cys Ala Gly Cys Gly Ala Cys Thr Cys Cys Gly Ala Gly
            35                  40                  45

Thr Cys Gly Gly Cys Thr Thr Cys Cys Gly Cys Thr Cys Gly Thr
    50                  55                  60

Cys Cys Ala Gly Cys Gly Gly Cys Thr Cys Gly Ala Gly Cys Gly
65                  70                  75                  80

Cys Gly Ala Cys Gly Cys Cys Gly Gly Thr Cys Cys Gly Ala Gly
                85                  90                  95

Cys Cys Gly Gly Ala Cys Ala Ala Gly Gly Cys Cys Gly Cys
            100                 105                 110

Gly Gly Cys Gly Ala Cys Thr Cys Ala Ala Cys Ala Ala Gly Cys Gly
        115                 120                 125

Gly Cys Gly Cys Thr Thr Cys Cys Gly Gly Gly Cys Thr Gly
    130                 135                 140

```
Cys Gly Gly Cys Thr Cys Thr Thr Cys Gly Gly Gly Cys Ala Cys Ala
145                 150                 155                 160

Gly Gly Ala Ala Ala Gly Cys Cys Ala Thr Cys Ala Cys Gly Ala Ala
                165                 170                 175

Gly Thr Cys Gly Gly Gly Cys Cys Thr Cys Cys Ala Gly Cys Ala Cys
            180                 185                 190

Cys Thr Gly Gly Cys Cys Cys Cys Cys Cys Cys Thr Cys Cys Gly Cys
        195                 200                 205

Cys Cys Ala Cys Cys Cys Cys Thr Gly Gly Gly Gly Cys Cys Cys Cys
    210                 215                 220

Gly Thr Gly Cys Ala Gly Cys Gly Ala Gly Thr Cys Ala Gly Ala Gly
225                 230                 235                 240

Cys Gly Gly Cys Ala Gly Ala Thr Cys Cys Gly Gly Ala Gly Thr Ala
                245                 250                 255

Cys Ala Gly Thr Gly Gly Ala Cys Thr Gly Gly Ala Gly Cys Gly Ala
            260                 265                 270

Gly Thr Cys Ala Gly Cys Gly Ala Cys Ala Thr Ala Thr Gly Gly Gly
        275                 280                 285

Gly Ala Gly Cys Ala Cys Ala Thr Cys Thr Gly Gly Thr Thr Cys Gly
    290                 295                 300

Ala Gly Ala Cys Cys Ala Ala Cys Gly Thr Gly Thr Cys Cys Gly Gly
305                 310                 315                 320

Gly Gly Ala Cys Thr Thr Cys Thr Gly Cys Thr Ala Cys Gly Thr Thr
                325                 330                 335

Gly Gly Gly Gly Ala Gly Cys Ala Gly Thr Ala Cys Thr Gly Thr Gly
            340                 345                 350

Thr Ala Gly Cys Cys Ala Gly Gly Ala Thr Gly Cys Thr Gly Cys Ala
        355                 360                 365

Gly Ala Ala Gly Thr Cys Ala Gly Thr Gly Thr Cys Thr Cys Gly Ala
    370                 375                 380

Ala Gly Ala Ala Ala Gly Thr Gly Cys Gly Cys Ala Gly Cys Cys Thr
385                 390                 395                 400

Gly Cys Ala Ala Gly Ala Thr Thr Gly Thr Gly Gly Thr Gly Cys Ala
                405                 410                 415

Cys Ala Cys Gly Cys Cys Cys Thr Gly Cys Ala Thr Cys Gly Ala Gly
            420                 425                 430

Cys Ala Gly Cys Thr Gly Gly Ala Gly Ala Ala Gly Ala Thr Ala Ala
        435                 440                 445

Ala Thr Thr Thr Cys Cys Gly Cys Thr Gly Thr Ala Ala Gly Cys Cys
    450                 455                 460

Gly Thr Cys Cys Thr Thr Cys Cys Gly Thr Gly Ala Ala Thr Cys Ala
465                 470                 475                 480

Gly Gly Cys Thr Cys Cys Ala Gly Gly Ala Ala Thr Gly Thr Cys Cys
                485                 490                 495

Gly Cys Gly Ala Gly Cys Cys Ala Ala Cys Cys Thr Thr Thr Gly Thr
            500                 505                 510

Ala Cys Gly Gly Cys Ala Cys Cys Ala Cys Thr Gly Gly Gly Thr Ala
        515                 520                 525

Cys Ala Cys Ala Gly Ala Cys Gly Ala Cys Gly Cys Cys Ala Gly Gly
    530                 535                 540

Ala Cys Gly Gly Cys Ala Ala Gly Thr Gly Thr Cys Gly Gly Cys Ala
545                 550                 555                 560

Cys Thr Gly Thr Gly Gly Gly Ala Ala Gly Gly Gly Ala Thr Thr Cys
```

```
            565                 570                 575
Cys Ala Gly Cys Ala Gly Ala Ala Gly Thr Thr Cys Ala Cys Cys Thr
            580                 585                 590
Thr Cys Cys Ala Cys Ala Gly Cys Ala Ala Gly Gly Ala Gly Ala Thr
            595                 600                 605
Thr Gly Thr Gly Gly Cys Ala Thr Cys Ala Gly Cys Thr Gly Cys
            610                 615                 620
Thr Cys Gly Thr Gly Gly Thr Gly Cys Ala Gly Cys Ala Gly Gly
625                 630                 635                 640
Cys Ala Thr Ala Cys Ala Cys Ala Gly Cys Ala Ala Gly Gly Thr
                    645                 650                 655
Gly Thr Cys Cys Thr Gly Cys Thr Thr Cys Ala Thr Gly Cys Thr Gly
            660                 665                 670
Cys Ala Gly Cys Ala Gly Ala Thr Cys Gly Ala Gly Gly Ala Gly Cys
            675                 680                 685
Cys Gly Thr Gly Cys Thr Cys Gly Cys Thr Gly Gly Gly Gly Thr
            690                 695                 700
Cys Cys Ala Cys Gly Cys Ala Gly Cys Cys Gly Thr Gly Gly Thr Cys
705                 710                 715                 720
Ala Thr Cys Cys Cys Gly Cys Cys Cys Ala Cys Cys Thr Gly Gly Ala
                    725                 730                 735
Thr Cys Cys Thr Cys Cys Gly Cys Gly Cys Cys Cys Gly Gly Ala Gly
            740                 745                 750
Gly Cys Cys Cys Ala Gly Ala Ala Thr Ala Cys Thr Cys Thr Gly
            755                 760                 765
Ala Ala Ala Gly Cys Ala Ala Gly Cys Ala Ala Gly Ala Ala Gly Ala
            770                 775                 780
Ala Gly Ala Ala Gly Ala Gly Gly Gly Cys Ala Thr Cys Cys Thr Thr
785                 790                 795                 800
Cys Ala Ala Gly Ala Gly Gly Ala Ala Gly Thr Cys Cys Ala Gly Cys
                    805                 810                 815
Ala Ala Gly Ala Ala Gly Gly Gly Cys Cys Thr Gly Ala Gly Gly
            820                 825                 830
Ala Gly Gly Gly Cys Cys Gly Cys Thr Gly Ala Gly Ala Gly Cys Cys
            835                 840                 845
Cys Thr Thr Cys Ala Thr Cys Ala Thr Cys Ala Gly Gly Cys Cys Cys
850                 855                 860
Ala Cys Cys Cys Cys Thr Cys Cys Cys Cys Gly Cys Thr Cys Ala
865                 870                 875                 880
Thr Gly Ala Ala Gly Cys Cys Cys Thr Gly Cys Thr Gly Gly Thr
            885                 890                 895
Gly Thr Thr Thr Gly Thr Gly Ala Ala Cys Cys Cys Ala Ala Gly
            900                 905                 910
Ala Gly Thr Gly Gly Gly Gly Cys Ala Ala Cys Cys Ala Gly Gly
            915                 920                 925
Gly Thr Gly Cys Ala Ala Gly Ala Thr Cys Ala Thr Cys Cys Ala
            930                 935                 940
Gly Thr Cys Thr Thr Cys Cys Thr Cys Thr Gly Gly Thr Ala Thr
945                 950                 955                 960
Cys Thr Cys Ala Ala Thr Cys Cys Cys Gly Ala Cys Ala Ala Gly
                    965                 970                 975
Thr Cys Thr Thr Cys Gly Ala Cys Cys Thr Gly Ala Gly Cys Cys Ala
            980                 985                 990
```

Gly Gly Gly Ala Gly Gly Gly Cys Cys Cys Ala Ala Gly Gly Ala Gly
             995                 1000                1005

Gly Cys Gly Cys Thr Gly Gly Ala Gly Ala Thr Gly Thr Ala Cys
        1010                1015                1020

Cys Gly Cys Ala Ala Ala Gly Thr Gly Cys Ala Cys Ala Ala Cys
        1025                1030                1035

Cys Thr Gly Cys Gly Gly Ala Thr Cys Cys Thr Gly Gly Cys Gly
        1040                1045                1050

Thr Gly Cys Gly Gly Gly Gly Cys Gly Ala Cys Gly Gly Cys
        1055                1060                1065

Ala Cys Gly Gly Thr Gly Gly Gly Cys Thr Gly Gly Ala Thr Cys
        1070                1075                1080

Cys Thr Cys Thr Cys Cys Ala Cys Cys Cys Thr Gly Gly Ala Cys
        1085                1090                1095

Cys Ala Gly Cys Thr Ala Cys Gly Cys Cys Thr Gly Ala Ala Gly
        1100                1105                1110

Cys Cys Gly Cys Cys Ala Cys Cys Cys Cys Thr Gly Thr Thr
        1115                1120                1125

Gly Cys Cys Ala Thr Cys Cys Thr Gly Cys Cys Cys Thr Gly
        1130                1135                1140

Gly Gly Thr Ala Cys Thr Gly Gly Cys Ala Ala Cys Gly Ala Cys
        1145                1150                1155

Thr Thr Gly Gly Cys Cys Cys Gly Ala Ala Cys Cys Cys Thr Cys
        1160                1165                1170

Ala Ala Cys Thr Gly Gly Gly Thr Gly Gly Gly Gly Cys
        1175                1180                1185

Thr Ala Cys Ala Cys Ala Gly Ala Thr Gly Ala Gly Cys Cys Thr
        1190                1195                1200

Gly Thr Gly Thr Cys Cys Ala Ala Gly Ala Thr Cys Cys Thr Cys
        1205                1210                1215

Thr Cys Cys Cys Ala Cys Gly Thr Gly Gly Ala Gly Gly Ala Gly
        1220                1225                1230

Gly Gly Gly Ala Ala Cys Gly Thr Gly Gly Thr Ala Cys Ala Gly
        1235                1240                1245

Cys Thr Gly Gly Ala Cys Cys Gly Cys Thr Gly Gly Ala Cys
        1250                1255                1260

Cys Thr Cys Cys Ala Cys Gly Cys Thr Gly Ala Gly Cys Cys Cys
        1265                1270                1275

Ala Ala Cys Cys Cys Cys Gly Ala Gly Gly Cys Ala Gly Gly Gly
        1280                1285                1290

Cys Cys Thr Gly Ala Gly Gly Ala Cys Cys Gly Ala Gly Ala Thr
        1295                1300                1305

Gly Ala Ala Gly Gly Cys Gly Cys Cys Ala Cys Cys Gly Ala Cys
        1310                1315                1320

Cys Gly Gly Thr Thr Gly Cys Cys Cys Cys Thr Gly Gly Ala Thr
        1325                1330                1335

Gly Thr Cys Thr Thr Cys Ala Ala Cys Ala Ala Cys Thr Ala Cys
        1340                1345                1350

Thr Thr Cys Ala Gly Cys Cys Thr Gly Gly Gly Cys Thr Thr Thr
        1355                1360                1365

Gly Ala Cys Gly Cys Cys Cys Ala Cys Gly Thr Cys Ala Cys Cys
        1370                1375                1380

```
Cys Thr Gly Gly Ala Gly Thr Thr Cys Ala Cys Gly Ala Gly
    1385                1390            1395

Thr Cys Thr Cys Gly Ala Gly Ala Gly Gly Cys Cys Ala Ala Cys
    1400                1405            1410

Cys Cys Ala Gly Ala Gly Ala Ala Ala Thr Thr Cys Ala Ala Cys
    1415                1420            1425

Ala Gly Cys Cys Gly Cys Thr Thr Thr Cys Gly Gly Ala Ala Thr
    1430                1435            1440

Ala Ala Gly Ala Thr Gly Thr Thr Cys Thr Ala Cys Gly Cys Cys
    1445                1450            1455

Gly Gly Gly Ala Cys Ala Gly Cys Thr Thr Thr Cys Thr Cys Thr
    1460                1465            1470

Gly Ala Cys Thr Thr Cys Cys Thr Gly Ala Thr Gly Gly Gly Cys
    1475                1480            1485

Ala Gly Cys Thr Cys Cys Ala Ala Gly Gly Ala Cys Cys Thr Gly
    1490                1495            1500

Gly Cys Cys Ala Ala Gly Cys Ala Cys Ala Thr Cys Cys Gly Ala
    1505                1510            1515

Gly Thr Gly Gly Thr Gly Thr Gly Thr Gly Ala Thr Gly Gly Ala
    1520                1525            1530

Ala Thr Gly Gly Ala Cys Thr Thr Gly Ala Cys Thr Cys Cys Cys
    1535                1540            1545

Ala Ala Gly Ala Thr Cys Cys Ala Gly Gly Ala Cys Cys Thr Gly
    1550                1555            1560

Ala Ala Ala Cys Cys Cys Cys Ala Gly Thr Gly Thr Gly Thr Thr
    1565                1570            1575

Gly Thr Thr Thr Thr Cys Thr Gly Ala Ala Cys Ala Thr Cys
    1580                1585            1590

Cys Cys Cys Ala Gly Gly Thr Ala Cys Thr Gly Thr Gly Cys Gly
    1595                1600            1605

Gly Gly Cys Ala Cys Cys Ala Thr Gly Cys Cys Cys Thr Gly Gly
    1610                1615            1620

Gly Gly Cys Cys Ala Cys Cys Thr Gly Gly Gly Gly Ala Gly
    1625                1630            1635

Cys Ala Cys Cys Ala Cys Gly Ala Cys Thr Thr Thr Gly Ala Gly
    1640                1645            1650

Cys Cys Cys Ala Gly Cys Gly Gly Cys Ala Thr Gly Ala Cys
    1655                1660            1665

Gly Ala Cys Gly Gly Cys Thr Ala Cys Cys Thr Cys Gly Ala Gly
    1670                1675            1680

Gly Thr Cys Ala Thr Thr Gly Gly Cys Thr Thr Cys Ala Cys Cys
    1685                1690            1695

Ala Thr Gly Ala Cys Gly Thr Cys Gly Thr Thr Gly Gly Cys Cys
    1700                1705            1710

Gly Cys Gly Cys Thr Gly Cys Ala Gly Gly Thr Gly Gly Cys
    1715                1720            1725

Gly Gly Ala Cys Ala Cys Gly Gly Cys Gly Ala Gly Cys Gly Gly
    1730                1735            1740

Cys Thr Gly Ala Cys Gly Cys Ala Gly Thr Gly Thr Cys Gly Cys
    1745                1750            1755

Gly Ala Gly Gly Thr Gly Gly Thr Gly Cys Thr Cys Ala Cys Cys
    1760                1765            1770

Ala Cys Ala Thr Cys Cys Ala Ala Gly Gly Cys Cys Ala Thr Cys
```

1775 1780 1785

Cys Cys Gly Gly Thr Gly Cys Ala Gly Gly Thr Gly Gly Ala Thr
1790 1795 1800

Gly Gly Cys Gly Ala Gly Cys Cys Cys Thr Gly Cys Ala Ala Gly
1805 1810 1815

Cys Thr Thr Gly Cys Ala Gly Cys Cys Thr Cys Ala Cys Gly Cys
1820 1825 1830

Ala Thr Cys Cys Gly Cys Ala Thr Cys Gly Cys Cys Cys Thr Gly
1835 1840 1845

Cys Gly Cys Ala Ala Cys Cys Ala Gly Gly Cys Cys Ala Cys Cys
1850 1855 1860

Ala Thr Gly Gly Thr Gly Cys Ala Gly Ala Ala Gly Gly Cys Cys
1865 1870 1875

Ala Ala Gly Cys Gly Gly Cys Gly Gly Ala Gly Cys Gly Cys Cys
1880 1885 1890

Gly Cys Cys Cys Cys Cys Cys Thr Gly Cys Ala Cys Ala Gly Cys
1895 1900 1905

Gly Ala Cys Cys Ala Gly Cys Ala Gly Cys Cys Gly Gly Thr Gly
1910 1915 1920

Cys Cys Ala Gly Ala Gly Cys Ala Gly Thr Thr Gly Cys Gly Cys
1925 1930 1935

Ala Thr Cys Cys Ala Gly Gly Thr Gly Ala Gly Thr Cys Gly Cys
1940 1945 1950

Gly Thr Cys Ala Gly Cys Ala Thr Gly Cys Ala Cys Gly Ala Cys
1955 1960 1965

Thr Ala Thr Gly Ala Gly Gly Cys Cys Cys Thr Gly Cys Ala Cys
1970 1975 1980

Thr Ala Cys Gly Ala Cys Ala Ala Gly Gly Ala Gly Cys Ala Gly
1985 1990 1995

Cys Thr Cys Ala Ala Gly Gly Ala Gly Gly Cys Cys Thr Cys Thr
2000 2005 2010

Gly Thr Gly Cys Cys Gly Cys Thr Gly Gly Gly Cys Ala Cys Thr
2015 2020 2025

Gly Thr Gly Gly Thr Gly Gly Thr Cys Cys Cys Ala Gly Gly Ala
2030 2035 2040

Gly Ala Cys Ala Gly Thr Gly Ala Cys Cys Thr Ala Gly Ala Gly
2045 2050 2055

Cys Thr Cys Thr Gly Cys Cys Gly Thr Gly Cys Cys Cys Ala Cys
2060 2065 2070

Ala Thr Thr Gly Ala Gly Ala Gly Ala Cys Thr Cys Cys Ala Gly
2075 2080 2085

Cys Ala Gly Gly Ala Gly Cys Cys Cys Gly Ala Thr Gly Gly Thr
2090 2095 2100

Gly Cys Thr Gly Gly Ala Gly Cys Cys Ala Ala Gly Thr Cys Cys
2105 2110 2115

Cys Cys Gly Ala Cys Ala Thr Gly Cys Cys Ala Gly Ala Ala Ala
2120 2125 2130

Cys Thr Gly Thr Cys Cys Cys Cys Cys Ala Ala Gly Thr Gly Gly
2135 2140 2145

Thr Gly Cys Thr Thr Cys Cys Thr Gly Gly Ala Cys Gly Cys Cys
2150 2155 2160

Ala Cys Cys Ala Cys Thr Gly Cys Cys Ala Gly Cys Cys Gly Cys
2165 2170 2175

```
Thr Thr Cys Thr Ala Cys Ala Gly Gly Ala Thr Cys Gly Ala Cys
    2180            2185                2190

Cys Gly Ala Gly Cys Cys Ala Gly Gly Ala Gly Cys Ala Cys
    2195            2200                2205

Cys Thr Cys Ala Ala Cys Thr Ala Thr Gly Thr Gly Ala Cys Thr
    2210            2215                2220

Gly Ala Gly Ala Thr Cys Gly Cys Ala Cys Ala Gly Gly Ala Thr
    2225            2230                2235

Gly Ala Gly Ala Thr Thr Thr Ala Thr Ala Thr Cys Cys Thr Gly
    2240            2245                2250

Gly Ala Cys Cys Cys Thr Gly Ala Gly Cys Thr Gly Cys Thr Gly
    2255            2260                2265

Gly Gly Gly Gly Cys Ala Thr Cys Gly Gly Cys Cys Cys Gly Gly
    2270            2275                2280

Cys Cys Thr Gly Ala Cys Cys Thr Cys Cys Cys Ala Ala Cys Cys
    2285            2290                2295

Cys Cys Cys Ala Cys Thr Thr Cys Cys Cys Cys Thr Cys Thr Cys
    2300            2305                2310

Cys Cys Cys Ala Cys Cys Thr Cys Ala Cys Cys Cys Thr Gly Cys
    2315            2320                2325

Thr Cys Ala Cys Cys Ala Cys Gly Cys Cys Cys Gly Gly
    2330            2335                2340

Thr Cys Ala Cys Thr Gly Cys Ala Ala Gly Gly Gly Ala Thr
    2345            2350                2355

Gly Cys Thr Gly Cys Ala Cys Cys Cys Cys Thr Cys Ala Ala
    2360            2365                2370

Gly Gly Thr Gly Ala Ala Gly Ala Gly Cys Thr Gly Ala Thr Thr
    2375            2380                2385

Gly Ala Gly Gly Cys Thr Gly Cys Cys Ala Ala Gly Ala Gly Gly
    2390            2395                2400

Ala Ala Cys Gly Ala Cys Thr Thr Cys Thr Gly Thr Ala Ala Gly
    2405            2410                2415

Cys Thr Cys Cys Ala Gly Gly Ala Gly Cys Thr Gly Cys Ala Cys
    2420            2425                2430

Cys Gly Ala Gly Cys Thr Gly Gly Gly Gly Cys Gly Ala Cys
    2435            2440                2445

Cys Thr Cys Ala Thr Gly Cys Ala Cys Cys Gly Ala Gly Ala Cys
    2450            2455                2460

Gly Ala Gly Cys Ala Gly Ala Gly Thr Cys Gly Cys Ala Cys Gly
    2465            2470                2475

Cys Thr Cys Cys Thr Gly Cys Ala Cys Cys Ala Cys Gly Cys Ala
    2480            2485                2490

Gly Thr Cys Ala Gly Cys Ala Cys Thr Gly Gly Cys Ala Gly Cys
    2495            2500                2505

Ala Ala Gly Gly Ala Thr Gly Thr Gly Gly Thr Cys Cys Gly Cys
    2510            2515                2520

Thr Ala Cys Cys Thr Gly Cys Thr Gly Gly Ala Cys Cys Ala Cys
    2525            2530                2535

Gly Cys Cys Cys Cys Cys Cys Ala Gly Ala Gly Ala Thr Cys
    2540            2545                2550

Cys Thr Thr Gly Ala Thr Gly Cys Gly Gly Thr Gly Gly Ala Gly
    2555            2560                2565
```

-continued

```
Gly Ala  Ala  Ala  Cys Gly Gly Gly Ala  Gly  Ala Cys Cys
    2570           2575            2580

Thr Gly  Thr  Thr  Thr Gly Cys Ala Cys  Cys  Ala Gly Cys Ala
    2585           2590            2595

Gly Cys  Gly  Gly  Cys Cys Thr Gly Gly  Cys  Cys Ala Gly
    2600           2605            2610

Cys Gly  Cys  Ala  Cys Ala Thr Cys Thr  Gly  Cys Ala Cys
    2615           2620            2625

Thr Ala  Cys  Ala  Thr Cys Gly Thr Gly  Ala  Gly Cys Cys
    2630           2635            2640

Gly Gly  Gly  Gly  Cys Cys Thr Cys Gly  Cys  Thr Ala Thr Gly
    2645           2650            2655

Ala Ala  Gly  Ala  Cys Ala Gly Ala Cys  Cys  Ala Gly Cys Ala Gly
    2660           2665            2670

Gly Gly  Cys  Gly  Ala Cys Ala Cys Thr  Cys  Cys Cys Gly Gly
    2675           2680            2685

Cys Ala  Gly  Cys  Gly Gly Gly Cys Thr  Gly  Ala Gly Ala Ala Gly
    2690           2695            2700

Gly Cys  Thr  Cys  Ala Gly Gly Ala Cys  Ala  Cys Cys Gly Ala Gly
    2705           2710            2715

Cys Thr  Gly  Gly  Cys Cys Gly Cys Cys  Thr  Ala Cys Cys Thr Gly
    2720           2725            2730

Gly Ala  Gly  Ala  Ala Cys Cys Gly Gly  Cys  Cys Ala Cys Ala Cys
    2735           2740            2745

Thr Ala  Cys  Cys  Ala Gly Ala Thr Gly  Ala  Thr Cys Cys Ala Gly
    2750           2755            2760

Cys Gly  Gly  Gly  Ala Gly Gly Ala Cys  Ala  Gly Gly Ala Gly
    2765           2770            2775

Ala Cys  Gly  Gly  Cys Thr Gly Thr Gly  Gly  Ala Thr Cys Cys
    2780           2785            2790

Thr Cys  Gly  Gly  Ala Gly Ala Cys Ala  Gly  Thr Cys Gly Gly
    2795           2800            2805

Thr Thr  Thr  Cys  Ala Gly Gly Gly Ala  Cys  Ala Cys Cys Ala Cys
    2810           2815            2820

Cys Ala  Cys  Cys  Ala Thr Cys Ala Cys  Ala  Cys Thr Gly Ala
    2825           2830            2835
```

<210> SEQ ID NO 4
<211> LENGTH: 945
<212> TYPE: PRT
<213> ORGANISM: Homo sapiens

<400> SEQUENCE: 4

```
Met Glu Pro Arg Asp Gly Ser Pro Glu Ala Arg Ser Ser Asp Ser Glu
1               5                   10                  15

Ser Ala Ser Ala Ser Ser Gly Ser Glu Arg Asp Ala Gly Pro Glu
            20                  25                  30

Pro Asp Lys Ala Pro Arg Arg Leu Asn Lys Arg Arg Phe Pro Gly Leu
        35                  40                  45

Arg Leu Phe Gly His Arg Lys Ala Ile Thr Lys Ser Gly Leu Gln His
    50                  55                  60

Leu Ala Pro Pro Pro Thr Pro Gly Ala Pro Cys Ser Glu Ser Glu
65                  70                  75                  80

Arg Gln Ile Arg Ser Thr Val Asp Trp Ser Glu Ser Ala Thr Tyr Gly
                85                  90                  95
```

```
Glu His Ile Trp Phe Glu Thr Asn Val Ser Gly Asp Phe Cys Tyr Val
            100                 105                 110

Gly Glu Gln Tyr Cys Val Ala Arg Met Leu Gln Lys Ser Val Ser Arg
            115                 120                 125

Arg Lys Cys Ala Ala Cys Lys Ile Val Val His Thr Pro Cys Ile Glu
        130                 135                 140

Gln Leu Glu Lys Ile Asn Phe Arg Cys Lys Pro Ser Phe Arg Glu Ser
145                 150                 155                 160

Gly Ser Arg Asn Val Arg Glu Pro Thr Phe Val Arg His His Trp Val
                165                 170                 175

His Arg Arg Arg Gln Asp Gly Lys Cys Arg His Cys Gly Lys Gly Phe
        180                 185                 190

Gln Gln Lys Phe Thr Phe His Ser Lys Glu Ile Val Ala Ile Ser Cys
        195                 200                 205

Ser Trp Cys Lys Gln Ala Tyr His Ser Lys Val Ser Cys Phe Met Leu
        210                 215                 220

Gln Gln Ile Glu Glu Pro Cys Ser Leu Gly Val His Ala Ala Val Val
225                 230                 235                 240

Ile Pro Pro Thr Trp Ile Leu Arg Ala Arg Pro Gln Asn Thr Leu
                245                 250                 255

Lys Ala Ser Lys Lys Lys Arg Ala Ser Phe Lys Arg Lys Ser Ser
        260                 265                 270

Lys Lys Gly Pro Glu Glu Gly Arg Trp Arg Pro Phe Ile Ile Arg Pro
        275                 280                 285

Thr Pro Ser Pro Leu Met Lys Pro Leu Leu Val Phe Val Asn Pro Lys
        290                 295                 300

Ser Gly Asn Gln Gly Ala Lys Ile Ile Gln Ser Phe Leu Trp Tyr
305                 310                 315                 320

Leu Asn Pro Arg Gln Val Phe Asp Leu Ser Gln Gly Gly Pro Lys Glu
                325                 330                 335

Ala Leu Glu Met Tyr Arg Lys Val His Asn Leu Arg Ile Leu Ala Cys
            340                 345                 350

Gly Gly Asp Gly Thr Val Gly Trp Ile Leu Ser Thr Leu Asp Gln Leu
        355                 360                 365

Arg Leu Lys Pro Pro Pro Val Ala Ile Leu Pro Leu Gly Thr Gly
370                 375                 380

Asn Asp Leu Ala Arg Thr Leu Asn Trp Gly Gly Gly Tyr Thr Asp Glu
385                 390                 395                 400

Pro Val Ser Lys Ile Leu Ser His Val Glu Glu Gly Asn Val Val Gln
                405                 410                 415

Leu Asp Arg Trp Asp Leu His Ala Glu Pro Asn Pro Glu Ala Gly Pro
                420                 425                 430

Glu Asp Arg Asp Glu Gly Ala Thr Asp Arg Leu Pro Leu Asp Val Phe
            435                 440                 445

Asn Asn Tyr Phe Ser Leu Gly Phe Asp Ala His Val Thr Leu Glu Phe
            450                 455                 460

His Glu Ser Arg Glu Ala Asn Pro Glu Lys Phe Asn Ser Arg Phe Arg
465                 470                 475                 480

Asn Lys Met Phe Tyr Ala Gly Thr Ala Phe Ser Asp Phe Leu Met Gly
                485                 490                 495

Ser Ser Lys Asp Leu Ala Lys His Ile Arg Val Val Cys Asp Gly Met
        500                 505                 510
```

```
Asp Leu Thr Pro Lys Ile Gln Asp Leu Lys Pro Gln Cys Val Val Phe
            515                 520                 525

Leu Asn Ile Pro Arg Tyr Cys Ala Gly Thr Met Pro Trp Gly His Pro
530                 535                 540

Gly Glu His His Asp Phe Glu Pro Gln Arg His Asp Asp Gly Tyr Leu
545                 550                 555                 560

Glu Val Ile Gly Phe Thr Met Thr Ser Leu Ala Ala Leu Gln Val Gly
            565                 570                 575

Gly His Gly Glu Arg Leu Thr Gln Cys Arg Glu Val Val Leu Thr Thr
                580                 585                 590

Ser Lys Ala Ile Pro Val Gln Val Asp Gly Glu Pro Cys Lys Leu Ala
            595                 600                 605

Ala Ser Arg Ile Arg Ile Ala Leu Arg Asn Gln Ala Thr Met Val Gln
        610                 615                 620

Lys Ala Lys Arg Arg Ser Ala Ala Pro Leu His Ser Asp Gln Gln Pro
625                 630                 635                 640

Val Pro Glu Gln Leu Arg Ile Gln Val Ser Arg Val Ser Met His Asp
                645                 650                 655

Tyr Glu Ala Leu His Tyr Asp Lys Glu Gln Leu Lys Glu Ala Ser Val
            660                 665                 670

Pro Leu Gly Thr Val Val Pro Gly Asp Ser Asp Leu Glu Leu Cys
        675                 680                 685

Arg Ala His Ile Glu Arg Leu Gln Gln Glu Pro Asp Gly Ala Gly Ala
        690                 695                 700

Lys Ser Pro Thr Cys Gln Lys Leu Ser Pro Lys Trp Cys Phe Leu Asp
705                 710                 715                 720

Ala Thr Thr Ala Ser Arg Phe Tyr Arg Ile Asp Arg Ala Gln Glu His
                725                 730                 735

Leu Asn Tyr Val Thr Glu Ile Ala Gln Asp Glu Ile Tyr Ile Leu Asp
            740                 745                 750

Pro Glu Leu Leu Gly Ala Ser Ala Arg Pro Asp Leu Pro Thr Pro Thr
            755                 760                 765

Ser Pro Leu Pro Thr Ser Pro Cys Ser Pro Thr Pro Arg Ser Leu Gln
770                 775                 780

Gly Asp Ala Ala Pro Pro Gln Gly Glu Glu Leu Ile Glu Ala Ala Lys
785                 790                 795                 800

Arg Asn Asp Phe Cys Lys Leu Gln Glu Leu His Arg Ala Gly Gly Asp
                805                 810                 815

Leu Met His Arg Asp Glu Gln Ser Arg Thr Leu Leu His His Ala Val
            820                 825                 830

Ser Thr Gly Ser Lys Asp Val Val Arg Tyr Leu Leu Asp His Ala Pro
            835                 840                 845

Pro Glu Ile Leu Asp Ala Val Glu Glu Asn Gly Glu Thr Cys Leu His
850                 855                 860

Gln Ala Ala Ala Leu Gly Gln Arg Thr Ile Cys His Tyr Ile Val Glu
865                 870                 875                 880

Ala Gly Ala Ser Leu Met Lys Thr Asp Gln Gln Gly Asp Thr Pro Arg
                885                 890                 895

Gln Arg Ala Glu Lys Ala Gln Asp Thr Glu Leu Ala Ala Tyr Leu Glu
            900                 905                 910

Asn Arg Gln His Tyr Gln Met Ile Gln Arg Glu Asp Gln Glu Thr Ala
            915                 920                 925

Val Gly Ser Ser Glu Thr Val Arg Phe Gln Gly His His His His
```

His
945

<210> SEQ ID NO 5
<211> LENGTH: 2214
<212> TYPE: PRT
<213> ORGANISM: Homo sapiens

<400> SEQUENCE: 5

Ala Thr Gly Gly Cys Thr Thr Cys Cys Cys Ala Ala Gly Cys Gly
1               5                   10                  15

Ala Cys Thr Thr Cys Gly Cys Cys Ala Gly Cys Thr Gly Cys Ala
                20                  25                  30

Gly Ala Ala Gly Thr Ala Cys Ala Thr Gly Gly Ala Ala Thr Ala Cys
            35                  40                  45

Ala Gly Cys Ala Cys Cys Ala Ala Gly Ala Gly Thr Gly Thr
        50                  55                  60

Cys Thr Gly Ala Cys Gly Thr Cys Cys Thr Gly Ala Ala Gly Cys Thr
65                  70                  75                  80

Gly Thr Thr Cys Gly Ala Gly Gly Ala Cys Gly Gly Thr Gly Ala Ala
                85                  90                  95

Ala Thr Gly Gly Cys Thr Ala Ala Gly Thr Ala Cys Gly Thr Cys Cys
                100                 105                 110

Ala Gly Gly Gly Cys Gly Ala Cys Gly Cys Thr Ala Thr Cys Gly Gly
            115                 120                 125

Ala Thr Ala Cys Gly Ala Gly Gly Gly Ala Thr Thr Cys Cys Ala Gly
            130                 135                 140

Cys Ala Gly Thr Thr Cys Cys Thr Gly Ala Ala Gly Ala Thr Cys Thr
145                 150                 155                 160

Ala Cys Cys Thr Gly Gly Ala Ala Gly Thr Gly Gly Ala Cys Ala Ala
                165                 170                 175

Cys Gly Thr Cys Cys Cys Ala Gly Gly Cys Ala Cys Cys Thr Gly
            180                 185                 190

Thr Cys Ala Cys Thr Gly Gly Cys Thr Cys Thr Gly Thr Thr Cys Cys
                195                 200                 205

Ala Gly Thr Cys Thr Thr Cys Gly Ala Gly Ala Cys Thr Gly Gly
            210                 215                 220

Cys Cys Ala Cys Thr Gly Cys Cys Thr Gly Ala Ala Cys Gly Ala Ala
225                 230                 235                 240

Ala Cys Cys Ala Ala Cys Gly Thr Cys Ala Cys Ala Ala Gly Gly
                245                 250                 255

Ala Cys Gly Thr Gly Gly Thr Cys Thr Gly Cys Cys Thr Gly Ala Ala
            260                 265                 270

Cys Gly Ala Cys Gly Thr Gly Ala Gly Cys Thr Gly Cys Thr Ala Cys
            275                 280                 285

Thr Thr Cys Thr Cys Thr Cys Thr Gly Cys Thr Gly Gly Ala Gly Gly
            290                 295                 300

Gly Thr Gly Gly Cys Ala Gly Ala Cys Cys Ala Gly Ala Gly Gly Ala
305                 310                 315                 320

Cys Ala Ala Gly Cys Thr Gly Ala Ala Thr Thr Cys Ala Cys Cys
            325                 330                 335

Thr Thr Cys Ala Ala Gly Cys Thr Gly Thr Ala Cys Gly Ala Cys Ala
            340                 345                 350

Cys Thr Gly Ala Cys Cys Gly Cys Ala Ala Cys Gly Gly Ala Ala Thr
355 360 365

Cys Cys Thr Gly Gly Ala Cys Thr Cys Cys Ala Gly Cys Gly Ala Ala
370 375 380

Gly Thr Gly Gly Ala Cys Ala Ala Gly Ala Thr Cys Ala Thr Cys Cys
385 390 395 400

Thr Gly Cys Ala Gly Ala Thr Gly Ala Thr Gly Cys Gly Thr Gly Thr
405 410 415

Cys Gly Cys Thr Gly Ala Gly Thr Ala Cys Cys Thr Gly Gly Ala Cys
420 425 430

Thr Gly Gly Gly Ala Cys Gly Thr Gly Ala Gly Cys Gly Ala Ala Cys
435 440 445

Thr Gly Ala Gly Gly Cys Cys Thr Ala Thr Cys Cys Thr Gly Cys Ala
450 455 460

Gly Gly Ala Gly Ala Thr Gly Ala Thr Gly Ala Ala Gly Gly Ala Ala
465 470 475 480

Ala Thr Cys Gly Ala Cys Thr Ala Cys Gly Ala Cys Gly Gly Cys Thr
485 490 495

Cys Thr Gly Gly Ala Thr Cys Ala Gly Thr Gly Thr Cys Cys Cys Ala
500 505 510

Gly Gly Cys Thr Gly Ala Gly Thr Gly Gly Gly Thr Cys Cys Gly Cys
515 520 525

Gly Cys Thr Gly Gly Thr Gly Cys Thr Ala Cys Cys Ala Cys Thr Gly
530 535 540

Thr Gly Cys Cys Ala Cys Thr Gly Cys Thr Gly Gly Thr Cys Cys Thr
545 550 555 560

Gly Cys Thr Gly Gly Gly Ala Cys Thr Gly Gly Ala Ala Ala Thr Gly
565 570 575

Ala Cys Cys Cys Thr Gly Ala Ala Gly Gly Ala Cys Gly Ala Cys Gly
580 585 590

Gly Thr Cys Ala Gly Cys Ala Cys Ala Thr Gly Thr Gly Gly Cys Gly
595 600 605

Cys Cys Cys Ala Ala Ala Gly Cys Gly Thr Thr Thr Cys Cys Cys Cys
610 615 620

Ala Gly Gly Cys Cys Ala Gly Thr Cys Thr Ala Cys Thr Gly Cys Ala
625 630 635 640

Ala Cys Cys Thr Gly Thr Gly Cys Gly Ala Gly Thr Cys Thr Thr Cys
645 650 655

Ala Ala Thr Cys Gly Gly Thr Cys Thr Gly Gly Gly Cys Ala Ala Gly
660 665 670

Cys Ala Gly Gly Gly Cys Cys Thr Gly Thr Cys Ala Thr Gly Cys Ala
675 680 685

Ala Cys Cys Thr Gly Thr Gly Cys Ala Ala Gly Thr Ala Cys Ala Cys
690 695 700

Cys Gly Thr Gly Cys Ala Cys Gly Ala Cys Cys Ala Gly Thr Gly Cys
705 710 715 720

Gly Cys Thr Ala Thr Gly Ala Ala Gly Gly Cys Cys Cys Thr Gly Cys
725 730 735

Cys Cys Thr Gly Cys Gly Ala Gly Gly Thr Cys Thr Cys Ala Ala Cys
740 745 750

Thr Thr Ala Cys Gly Cys Thr Ala Ala Gly Thr Cys Cys Cys Gly Thr
755 760 765

Ala Ala Gly Gly Ala Cys Ala Thr Cys Gly Gly Ala Gly Thr Gly Cys

-continued 770 775 780

Ala Gly Thr Cys Ala Cys Ala Cys Gly Thr Gly Thr Gly Gly Gly Thr
785 790 795 800

Cys Ala Gly Gly Gly Gly Ala Gly Gly Thr Thr Gly Cys Gly Ala Ala
805 810 815

Thr Cys Cys Gly Gly Thr Ala Gly Ala Thr Gly Cys Gly Ala Cys Cys
820 825 830

Gly Cys Thr Gly Cys Cys Ala Gly Ala Ala Gly Ala Ala Gly Ala Thr
835 840 845

Cys Cys Gly Thr Ala Thr Cys Thr Ala Cys Cys Ala Cys Thr Cys Cys
850 855 860

Cys Thr Gly Ala Cys Cys Gly Gly Ala Cys Thr Gly Cys Ala Cys Thr
865 870 875 880

Gly Cys Gly Thr Cys Thr Gly Gly Thr Gly Cys Cys Ala Cys Cys Thr
885 890 895

Gly Gly Ala Gly Ala Thr Cys Cys Ala Cys Gly Ala Cys Gly Ala Cys
900 905 910

Thr Gly Cys Cys Thr Gly Cys Ala Gly Gly Cys Cys Gly Thr Gly Gly
915 920 925

Gly Ala Cys Ala Cys Gly Ala Ala Thr Gly Cys Gly Ala Cys Thr Gly
930 935 940

Cys Gly Gly Thr Cys Thr Gly Cys Thr Gly Cys Gly Thr Gly Ala Cys
945 950 955 960

Cys Ala Cys Ala Thr Cys Cys Thr Gly Cys Cys Thr Cys Cys Cys Thr
965 970 975

Cys Cys Ala Gly Cys Ala Thr Cys Thr Ala Cys Cys Cys Thr Thr Cys
980 985 990

Ala Gly Thr Cys Cys Thr Gly Gly Cys Thr Thr Cys Cys Gly Gly Thr
995 1000 1005

Cys Cys Cys Gly Ala Cys Ala Gly Gly Ala Ala Gly Ala Ala Cys
1010 1015 1020

Ala Gly Cys Ala Ala Gly Ala Cys Cys Thr Cys Thr Cys Ala Gly
1025 1030 1035

Ala Ala Gly Ala Cys Thr Ala Thr Gly Gly Ala Cys Gly Ala Cys
1040 1045 1050

Cys Thr Gly Ala Ala Cys Cys Thr Gly Ala Gly Cys Ala Cys Cys
1055 1060 1065

Thr Cys Thr Gly Ala Gly Gly Cys Cys Cys Thr Gly Cys Gly Cys
1070 1075 1080

Ala Thr Cys Gly Ala Cys Cys Cys Thr Gly Thr Gly Cys Cys Cys
1085 1090 1095

Ala Ala Cys Ala Cys Thr Cys Ala Cys Cys Cys Ala Cys Thr Gly
1100 1105 1110

Cys Thr Gly Gly Thr Gly Thr Thr Cys Gly Thr Cys Ala Ala Cys
1115 1120 1125

Cys Cys Thr Ala Ala Gly Ala Gly Cys Gly Gly Cys Gly Gly Ala
1130 1135 1140

Ala Ala Gly Cys Ala Gly Gly Gly Thr Cys Ala Gly Ala Gly Ala
1145 1150 1155

Gly Thr Cys Cys Thr Gly Thr Gly Gly Ala Ala Gly Thr Thr Cys
1160 1165 1170

Cys Ala Gly Thr Ala Cys Ala Thr Cys Cys Thr Gly Ala Ala Cys
1175 1180 1185

-continued

```
Cys Cys Ala Cys Gly Cys Cys Ala Gly Thr Gly Thr Thr Cys
    1190            1195            1200

Ala Ala Cys Cys Thr Gly Cys Thr Gly Ala Ala Gly Gly Ala Cys
    1205            1210            1215

Gly Gly Cys Cys Cys Thr Gly Ala Gly Ala Thr Cys Gly Gly Ala
    1220            1225            1230

Cys Thr Gly Ala Gly Ala Cys Thr Gly Thr Thr Cys Ala Ala Gly
    1235            1240            1245

Gly Ala Cys Gly Thr Gly Cys Cys Cys Gly Ala Cys Thr Cys Thr
    1250            1255            1260

Cys Gly Cys Ala Thr Cys Cys Thr Cys Gly Thr Cys Thr Gly Cys
    1265            1270            1275

Gly Gly Thr Gly Gly Cys Gly Ala Cys Gly Gly Thr Ala Cys Thr
    1280            1285            1290

Gly Thr Gly Gly Gly Ala Thr Gly Gly Ala Thr Cys Cys Thr Gly
    1295            1300            1305

Gly Ala Ala Ala Cys Thr Ala Thr Cys Gly Ala Cys Ala Ala Gly
    1310            1315            1320

Gly Cys Thr Ala Ala Cys Cys Thr Gly Cys Cys Ala Gly Thr Gly
    1325            1330            1335

Cys Thr Gly Cys Cys Ala Cys Cys Thr Gly Thr Gly Gly Cys Thr
    1340            1345            1350

Gly Thr Cys Cys Thr Gly Cys Cys Ala Cys Thr Gly Gly Gly Ala
    1355            1360            1365

Ala Cys Cys Gly Gly Thr Ala Ala Cys Gly Ala Cys Cys Thr Gly
    1370            1375            1380

Gly Cys Thr Cys Gly Thr Thr Gly Cys Cys Thr Gly Cys Gly Thr
    1385            1390            1395

Thr Gly Gly Gly Gly Ala Gly Gly Thr Gly Gly Cys Thr Ala Cys
    1400            1405            1410

Gly Ala Gly Gly Gly Ala Cys Ala Gly Ala Ala Cys Cys Thr Gly
    1415            1420            1425

Gly Cys Cys Ala Ala Gly Ala Thr Cys Cys Thr Gly Ala Ala Gly
    1430            1435            1440

Gly Ala Cys Cys Thr Gly Gly Ala Ala Thr Gly Ala Gly Cys Ala
    1445            1450            1455

Ala Ala Gly Gly Thr Gly Gly Thr Cys Cys Ala Cys Ala Thr Gly
    1460            1465            1470

Gly Ala Cys Ala Gly Ala Thr Gly Gly Thr Cys Thr Gly Thr Gly
    1475            1480            1485

Gly Ala Gly Gly Thr Cys Ala Thr Cys Cys Cys Ala Cys Ala Gly
    1490            1495            1500

Cys Ala Gly Ala Cys Thr Gly Ala Gly Gly Ala Ala Ala Ala Gly
    1505            1510            1515

Thr Cys Ala Gly Ala Cys Cys Cys Ala Gly Thr Cys Cys Cys Thr
    1520            1525            1530

Thr Thr Cys Cys Ala Gly Ala Thr Cys Ala Thr Cys Ala Ala Cys
    1535            1540            1545

Ala Ala Cys Thr Ala Cys Thr Thr Cys Ala Gly Cys Ala Thr Cys
    1550            1555            1560

Gly Gly Thr Gly Thr Gly Gly Ala Cys Gly Cys Thr Thr Cys Thr
    1565            1570            1575
```

| | | | | | | | | | | | |
|---|---|---|---|---|---|---|---|---|---|---|---|
| Ala | Thr | Cys | Gly | Cys | Cys | Ala | Cys | Ala | Gly | Ala | Thr Thr Cys |
| | | 1580 | | | 1585 | | | | 1590 | | |
| Cys | Ala | Cys | Ala | Thr | Cys | Ala | Thr | Gly | Cys | Gly | Cys Gly Ala Gly |
| 1595 | | | | | 1600 | | | | | 1605 | |
| Ala | Ala | Gly | Thr | Ala | Cys | Cys | Thr | Gly | Ala | Ala | Ala Ala Gly |
| 1610 | | | | | 1615 | | | | | 1620 | |
| Thr | Thr | Cys | Ala | Ala | Cys | Thr | Cys | Cys | Gly | Cys | Ala Thr Gly |
| 1625 | | | | | 1630 | | | | | 1635 | |
| Ala | Ala | Gly | Ala | Ala | Cys | Ala | Gly | Cys | Thr | Gly | Thr Gly Gly |
| 1640 | | | | | 1645 | | | | | 1650 | |
| Thr | Ala | Cys | Thr | Thr | Cys | Gly | Ala | Gly | Thr | Thr | Cys Gly Cys Thr |
| 1655 | | | | | 1660 | | | | | 1665 | |
| Ala | Cys | Cys | Thr | Cys | Ala | Gly | Ala | Ala | Thr | Cys | Ala Thr Cys |
| 1670 | | | | | 1675 | | | | | 1680 | |
| Thr | Thr | Cys | Thr | Cys | Ala | Ala | Cys | Thr | Gly | Cys | Ala Ala Gly |
| 1685 | | | | | 1690 | | | | | 1695 | |
| Ala | Ala | Gly | Cys | Thr | Gly | Gly | Ala | Gly | Gly | Ala | Ala Thr Cys Cys |
| 1700 | | | | | 1705 | | | | | 1710 | |
| Cys | Thr | Gly | Ala | Cys | Cys | Gly | Thr | Cys | Gly | Ala | Gly Ala Thr Cys |
| 1715 | | | | | 1720 | | | | | 1725 | |
| Thr | Gly | Cys | Gly | Gly | Cys | Ala | Ala | Gly | Cys | Cys | Thr Cys Thr Gly |
| 1730 | | | | | 1735 | | | | | 1740 | |
| Gly | Ala | Cys | Cys | Thr | Gly | Thr | Cys | Ala | Ala | Ala | Cys Thr Gly |
| 1745 | | | | | 1750 | | | | | 1755 | |
| Thr | Cys | Cys | Thr | Gly | Gly | Ala | Ala | Gly | Gly | Cys | Ala Thr Cys |
| 1760 | | | | | 1765 | | | | | 1770 | |
| Gly | Cys | Thr | Gly | Thr | Gly | Cys | Thr | Gly | Ala | Ala | Cys Ala Thr Cys |
| 1775 | | | | | 1780 | | | | | 1785 | |
| Cys | Cys | Ala | Ala | Gly | Cys | Ala | Thr | Gly | Cys | Ala | Cys Gly Gly Ala |
| 1790 | | | | | 1795 | | | | | 1800 | |
| Gly | Gly | Thr | Thr | Cys | Thr | Ala | Ala | Cys | Cys | Thr | Cys Thr Gly Gly |
| 1805 | | | | | 1810 | | | | | 1815 | |
| Gly | Gly | Cys | Gly | Ala | Cys | Ala | Cys | Thr | Ala | Gly | Gly Ala Gly Gly |
| 1820 | | | | | 1825 | | | | | 1830 | |
| Cys | Cys | Thr | Cys | Ala | Cys | Gly | Gly | Thr | Gly | Ala | Cys Ala Thr Cys |
| 1835 | | | | | 1840 | | | | | 1845 | |
| Thr | Ala | Cys | Gly | Gly | Cys | Ala | Thr | Cys | Ala | Ala | Cys Cys Ala Gly |
| 1850 | | | | | 1855 | | | | | 1860 | |
| Gly | Cys | Cys | Cys | Thr | Gly | Gly | Gly | Ala | Gly | Cys | Thr Ala Cys Cys |
| 1865 | | | | | 1870 | | | | | 1875 | |
| Gly | Cys | Cys | Ala | Ala | Gly | Gly | Thr | Cys | Ala | Thr | Cys Ala Cys Thr |
| 1880 | | | | | 1885 | | | | | 1890 | |
| Gly | Ala | Cys | Cys | Cys | Cys | Gly | Ala | Cys | Ala | Thr | Cys Cys Thr Gly |
| 1895 | | | | | 1900 | | | | | 1905 | |
| Ala | Ala | Gly | Ala | Cys | Cys | Thr | Gly | Cys | Gly | Thr | Gly Cys Cys Ala |
| 1910 | | | | | 1915 | | | | | 1920 | |
| Gly | Ala | Cys | Cys | Thr | Gly | Ala | Gly | Cys | Gly | Ala | Cys Ala Ala Gly |
| 1925 | | | | | 1930 | | | | | 1935 | |
| Cys | Gly | Thr | Cys | Thr | Gly | Gly | Ala | Gly | Thr | Gly | Gly Thr Cys |
| 1940 | | | | | 1945 | | | | | 1950 | |
| Gly | Gly | Ala | Cys | Thr | Gly | Gly | Ala | Gly | Gly | Thr | Gly Cys Cys |
| 1955 | | | | | 1960 | | | | | 1965 | |
| Ala | Thr | Cys | Gly | Ala | Ala | Ala | Thr | Gly | Gly | Gly | Cys Cys Ala Gly |

-continued

```
                1970                1975                1980

Ala Thr Cys Thr Ala Cys Ala Cys Thr Ala Ala Gly Cys Thr Gly
            1985                1990                1995

Ala Ala Gly Ala Ala Cys Gly Cys Thr Gly Gly Ala Ala Gly Gly
        2000                2005                2010

Ala Gly Ala Cys Thr Gly Gly Cys Cys Ala Ala Gly Thr Gly Cys
        2015                2020                2025

Thr Cys Thr Gly Ala Gly Ala Thr Cys Ala Cys Thr Thr Cys
        2030                2035                2040

Cys Ala Cys Ala Cys Cys Ala Cys Thr Ala Ala Gly Ala Cys Thr
        2045                2050                2055

Cys Thr Gly Cys Cys Thr Ala Thr Gly Cys Ala Gly Ala Thr Cys
        2060                2065                2070

Gly Ala Cys Gly Gly Thr Gly Ala Ala Cys Cys Cys Thr Gly Gly
        2075                2080                2085

Ala Thr Gly Cys Ala Gly Ala Cys Cys Cys Cys Ala Thr Gly Cys
        2090                2095                2100

Ala Cys Thr Ala Thr Cys Ala Ala Gly Ala Thr Cys Ala Cys Cys
        2105                2110                2115

Cys Ala Cys Ala Ala Gly Ala Ala Cys Cys Ala Gly Ala Thr Gly
        2120                2125                2130

Cys Cys Cys Ala Thr Gly Cys Thr Gly Ala Thr Gly Gly Gly Thr
        2135                2140                2145

Cys Cys Thr Cys Cys Thr Cys Cys Thr Cys Gly Cys Thr Cys Thr
        2150                2155                2160

Gly Gly Ala Thr Cys Thr Thr Cys Ala Gly Ala Ala Ala Cys Thr
        2165                2170                2175

Gly Thr Gly Ala Gly Gly Thr Thr Cys Cys Ala Gly Gly Gly Cys
        2180                2185                2190

Cys Ala Cys Cys Ala Cys Cys Ala Cys Cys Ala Cys Cys Ala Cys
        2195                2200                2205

Cys Ala Cys Thr Gly Ala
        2210

<210> SEQ ID NO 6
<211> LENGTH: 737
<212> TYPE: PRT
<213> ORGANISM: Homo sapiens

<400> SEQUENCE: 6

Met Ala Ser Pro Ser Asp Phe Ala Gln Leu Gln Lys Tyr Met Glu Tyr
1               5                   10                  15

Ser Thr Lys Lys Val Ser Asp Val Leu Lys Leu Phe Glu Asp Gly Glu
            20                  25                  30

Met Ala Lys Tyr Val Gln Gly Asp Ala Ile Gly Tyr Glu Gly Phe Gln
        35                  40                  45

Gln Phe Leu Lys Ile Tyr Leu Glu Val Asp Asn Val Pro Arg His Leu
    50                  55                  60

Ser Leu Ala Leu Phe Gln Ser Phe Glu Thr Gly His Cys Leu Asn Glu
65                  70                  75                  80

Thr Asn Val Thr Lys Asp Val Val Cys Leu Asn Asp Val Ser Cys Tyr
                85                  90                  95

Phe Ser Leu Leu Glu Gly Gly Arg Pro Glu Asp Lys Leu Glu Phe Thr
            100                 105                 110
```

```
Phe Lys Leu Tyr Asp Thr Asp Arg Asn Gly Ile Leu Asp Ser Ser Glu
            115                 120                 125

Val Asp Lys Ile Ile Leu Gln Met Met Arg Val Ala Glu Tyr Leu Asp
        130                 135                 140

Trp Asp Val Ser Glu Leu Arg Pro Ile Leu Gln Glu Met Met Lys Glu
145                 150                 155                 160

Ile Asp Tyr Asp Gly Ser Gly Ser Val Ser Gln Ala Glu Trp Val Arg
                165                 170                 175

Ala Gly Ala Thr Thr Val Pro Leu Leu Val Leu Leu Gly Leu Glu Met
            180                 185                 190

Thr Leu Lys Asp Asp Gly Gln His Met Trp Arg Pro Lys Arg Phe Pro
            195                 200                 205

Arg Pro Val Tyr Cys Asn Leu Cys Glu Ser Ser Ile Gly Leu Gly Lys
        210                 215                 220

Gln Gly Leu Ser Cys Asn Leu Cys Lys Tyr Thr Val His Asp Gln Cys
225                 230                 235                 240

Ala Met Lys Ala Leu Pro Cys Glu Val Ser Thr Tyr Ala Lys Ser Arg
                245                 250                 255

Lys Asp Ile Gly Val Gln Ser His Val Trp Val Arg Gly Gly Cys Glu
            260                 265                 270

Ser Gly Arg Cys Asp Arg Cys Gln Lys Lys Ile Arg Ile Tyr His Ser
        275                 280                 285

Leu Thr Gly Leu His Cys Val Trp Cys His Leu Glu Ile His Asp Asp
        290                 295                 300

Cys Leu Gln Ala Val Gly His Glu Cys Asp Cys Gly Leu Leu Arg Asp
305                 310                 315                 320

His Ile Leu Pro Pro Ser Ser Ile Tyr Pro Ser Val Leu Ala Ser Gly
                325                 330                 335

Pro Asp Arg Lys Asn Ser Lys Thr Ser Gln Lys Thr Met Asp Asp Leu
            340                 345                 350

Asn Leu Ser Thr Ser Glu Ala Leu Arg Ile Asp Pro Val Pro Asn Thr
        355                 360                 365

His Pro Leu Leu Val Phe Val Asn Pro Lys Ser Gly Gly Lys Gln Gly
370                 375                 380

Gln Arg Val Leu Trp Lys Phe Gln Tyr Ile Leu Asn Pro Arg Gln Val
385                 390                 395                 400

Phe Asn Leu Leu Lys Asp Gly Pro Glu Ile Gly Leu Arg Leu Phe Lys
                405                 410                 415

Asp Val Pro Asp Ser Arg Ile Leu Val Cys Gly Gly Asp Gly Thr Val
            420                 425                 430

Gly Trp Ile Leu Glu Thr Ile Asp Lys Ala Asn Leu Pro Val Leu Pro
        435                 440                 445

Pro Val Ala Val Leu Pro Leu Gly Thr Gly Asn Asp Leu Ala Arg Cys
        450                 455                 460

Leu Arg Trp Gly Gly Gly Tyr Glu Gly Gln Asn Leu Ala Lys Ile Leu
465                 470                 475                 480

Lys Asp Leu Glu Met Ser Lys Val Val His Met Asp Arg Trp Ser Val
                485                 490                 495

Glu Val Ile Pro Gln Gln Thr Glu Glu Lys Ser Asp Pro Val Pro Phe
            500                 505                 510

Gln Ile Ile Asn Asn Tyr Phe Ser Ile Gly Val Asp Ala Ser Ile Ala
        515                 520                 525

His Arg Phe His Ile Met Arg Glu Lys Tyr Pro Glu Lys Phe Asn Ser
```

-continued

```
            530                 535                 540
Arg Met Lys Asn Lys Leu Trp Tyr Phe Glu Phe Ala Thr Ser Glu Ser
545                 550                 555                 560

Ile Phe Ser Thr Cys Lys Lys Leu Glu Glu Ser Leu Thr Val Glu Ile
                565                 570                 575

Cys Gly Lys Pro Leu Asp Leu Ser Asn Leu Ser Leu Glu Gly Ile Ala
                580                 585                 590

Val Leu Asn Ile Pro Ser Met His Gly Gly Ser Asn Leu Trp Gly Asp
                595                 600                 605

Thr Arg Arg Pro His Gly Asp Ile Tyr Gly Ile Asn Gln Ala Leu Gly
                610                 615                 620

Ala Thr Ala Lys Val Ile Thr Asp Pro Asp Ile Leu Lys Thr Cys Val
625                 630                 635                 640

Pro Asp Leu Ser Asp Lys Arg Leu Glu Val Val Gly Leu Glu Gly Ala
                645                 650                 655

Ile Glu Met Gly Gln Ile Tyr Thr Lys Leu Lys Asn Ala Gly Arg Arg
                660                 665                 670

Leu Ala Lys Cys Ser Glu Ile Thr Phe His Thr Thr Lys Thr Leu Pro
                675                 680                 685

Met Gln Ile Asp Gly Glu Pro Trp Met Gln Thr Pro Cys Thr Ile Lys
                690                 695                 700

Ile Thr His Lys Asn Gln Met Pro Met Leu Met Gly Pro Pro Pro Arg
705                 710                 715                 720

Ser Gly Ser Ser Glu Thr Val Arg Phe Gln Gly His His His His His
                725                 730                 735

His
```